(12) United States Patent
Tebbe et al.

(10) Patent No.: US 9,963,462 B2
(45) Date of Patent: May 8, 2018

(54) SEPIAPTERIN REDUCTASE INHIBITORS

(71) Applicants: QUARTET MEDICINE, INC., Cambridge, MA (US); ECOLE POLYTECHNIQUE FEDERALE DE LAUSANNE (EPFL), Lausanne (CH)

(72) Inventors: Mark Joseph Tebbe, Arlington, MA (US); Holly Victoria Atton, Abingdon (GB); Craig Avery, Abingdon (GB); Steven Mark Bromidge, Abingdon (GB); Mark Kerry, Abingdon (GB); Adrian Kotei Kotey, Abingdon (GB); Nathaniel J. Monck, Abingdon (GB); Mirco Meniconi, Abingdon (GB); Mark Peter Ridgill, Abingdon (GB); Heather Tye, Abingdon (GB); Eddine Saiah, Brookline, MA (US); Kai Peter Johnsson, Lausanne (CH); Katarzyna Irena Gorska, Lausanne (CH); Hairuo Peng, Needham, MA (US); John Michael McCall, Boca Grande, FL (US)

(73) Assignee: MAX-PLANCK-GESELLSCHAFT ZUR FORDERUNG DER WISSENSCHAFTEN E.V., München (DE)

( * ) Notice: Subject to any disclaimer, the term of this patent is extended or adjusted under 35 U.S.C. 154(b) by 0 days. days.

(21) Appl. No.: 15/282,000

(22) Filed: Sep. 30, 2016

(65) Prior Publication Data

US 2017/0096435 A1  Apr. 6, 2017

Related U.S. Application Data

(60) Provisional application No. 62/235,191, filed on Sep. 30, 2015.

(51) Int. Cl.

| C07D 403/04 | (2006.01) |
|---|---|
| C07D 403/14 | (2006.01) |
| C07D 495/04 | (2006.01) |
| C07D 401/14 | (2006.01) |
| C07D 471/04 | (2006.01) |
| C07D 487/08 | (2006.01) |
| C07D 491/107 | (2006.01) |
| C07D 487/10 | (2006.01) |
| C07D 487/04 | (2006.01) |
| C07D 413/14 | (2006.01) |
| C07D 451/02 | (2006.01) |

(52) U.S. Cl.
CPC ......... *C07D 495/04* (2013.01); *C07D 401/14* (2013.01); *C07D 403/04* (2013.01); *C07D 403/14* (2013.01); *C07D 413/14* (2013.01); *C07D 451/02* (2013.01); *C07D 471/04* (2013.01); *C07D 487/04* (2013.01); *C07D 487/08* (2013.01); *C07D 487/10* (2013.01); *C07D 491/107* (2013.01)

(58) Field of Classification Search
CPC .......................... C07D 403/04; C07D 403/14
See application file for complete search history.

(56) References Cited

U.S. PATENT DOCUMENTS

| 3,040,047 | A | 6/1962 | Sirakawa |
|---|---|---|---|
| 5,852,019 | A | 12/1998 | Ejima et al. |
| 6,274,581 | B1 | 8/2001 | Gross |
| 6,869,952 | B2 | 3/2005 | Bhide et al. |
| 6,933,386 | B2 | 8/2005 | Bhide et al. |
| 6,969,717 | B2 | 11/2005 | Bhide et al. |
| 7,030,118 | B2 | 4/2006 | Lombardo et al. |
| 7,160,882 | B2 | 1/2007 | Bouyssou et al. |
| 7,265,113 | B2 | 9/2007 | Bhide et al. |
| 7,306,631 | B2 | 12/2007 | Glenn, Jr. et al. |
| 7,375,104 | B2 | 5/2008 | Bouyssou et al. |
| 7,521,450 | B2 | 4/2009 | Bhide et al. |
| 7,534,882 | B2 | 5/2009 | Bhattacharya et al. |
| 7,632,834 | B2 | 12/2009 | Bouyssou et al. |
| 7,820,814 | B2 | 10/2010 | Bhide et al. |
| 7,906,520 | B2 | 3/2011 | Woolf et al. |
| 8,080,666 | B2 | 12/2011 | Berdini et al. |
| 8,198,438 | B2 | 6/2012 | Sampognaro et al. |
| 8,642,609 | B2 | 2/2014 | Makings et al. |
| 9,174,995 | B2 | 11/2015 | Dorsch et al. |
| 2002/0058816 | A1 | 5/2002 | Kordik et al. |
| 2006/0058304 | A1 | 3/2006 | Bhide et al. |
| 2008/0176744 | A1 | 7/2008 | Schwogler et al. |
| 2008/0188666 | A1 | 8/2008 | Berger et al. |
| 2012/0252791 | A1 | 10/2012 | Blagg |

(Continued)

FOREIGN PATENT DOCUMENTS

| EP | 1454897 A1 | 9/2004 |
|---|---|---|
| EP | 2844659 A1 | 3/2015 |

(Continued)

OTHER PUBLICATIONS

Ambinter Stock Screening Collection, Database Accession Nos. 1172018-24-4, 1172354-13-0, 1170845-46-1, 1172864-02-6, 1169952-04-8, 1171450-23-9, 1172540-63-4, 1171768-20-9, 1171151-28-2, and 1172397-00-2 (Sep. 15, 2014).

(Continued)

*Primary Examiner* — Bruck Kifle

(74) *Attorney, Agent, or Firm* — Marshall, Gerstein & Borun LLP

(57) ABSTRACT

Inhibitors of sepiapterin reductase and uses of sepiapterin reductase inhibitors in analgesia, treatment of acute and chronic pain, anti-inflammation, and immune cell regulation are disclosed.

27 Claims, No Drawings

(56) References Cited

U.S. PATENT DOCUMENTS

| | | |
|---|---|---|
| 2012/0322800 A1 | 12/2012 | Blagg |
| 2015/0291593 A1 | 10/2015 | Su et al. |
| 2015/0307520 A1 | 10/2015 | Su et al. |

FOREIGN PATENT DOCUMENTS

| | | |
|---|---|---|
| GB | 2388594 A | 11/2003 |
| JP | S35-3032 A | 4/1960 |
| JP | H04182636 A | 6/1992 |
| JP | H05341428 A | 12/1993 |
| WO | WO-2006/035061 A1 | 4/2006 |
| WO | WO-2008/055709 A1 | 5/2008 |
| WO | WO-2008/092861 A1 | 8/2008 |
| WO | WO-2008/107478 A1 | 9/2008 |
| WO | WO-2008/131050 A1 | 10/2008 |
| WO | WO-2008/138876 A1 | 11/2008 |
| WO | WO-2010/093727 A1 | 8/2010 |
| WO | WO-2011/035009 A1 | 3/2011 |
| WO | WO-2011/047156 A1 | 4/2011 |
| WO | WO-2011/138142 A1 | 11/2011 |
| WO | WO-2013/132253 A1 | 9/2013 |
| WO | WO-2013/164061 A1 | 11/2013 |

OTHER PUBLICATIONS

Auerbach et al., The 1.25 A crystal structure of sepiapterin reductase reveals its binding mode to pterins and brain neurotransmitters, EMBO J., 16(24):7219-30 (1997).

Badawey et al., Nonsteroidal antiinflammatory agents—Part I: Antiinflammatory, analgesic and antipyretic activity of some new 1-(pyrimidin-2-yl)-3-pyrazolin-5-ones and 2-(pyrimidin-2-yl)-1,2,4,5,6,7-hexahydro-3H-indazol-3-ones, Eur. J. Med. Chem., 33:349-61 (1998).

Bennett et al., A peripheral mononeuropathy in rat that produces disorders of pain sensation like those seen in man, Pain, 33(1):87-107 (1988).

Chemical Abstracts Service, Database Accession No. 1961:8238, "2-(1-Pyrazolyl)pyrmidines", Kenzo Shirakawa, Japanese Patent No. JPS353032B (Apr. 4, 1960).

Chen et al., A tandem copper (II)—promoted synthesis of 2-substituted pyrrolo[2,1-f][1,2,4] triazin-4(3H)-ones, Tetrahedron 69(13):2714-9 (2013).

Costigan et al., Analgesia by inhibiting tetrahydrobiopterin synthesis, Curr. Opin. Pharmacol., 12(1):92-9 (2012).

Decosterd et al., Spared nerve injury: an animal model of persistent peripheral neuropathic pain, Pain, 87(2):149-58 (2000).

El-Hawash et al., Nonsteroidal antiinflammatory agents-part 2 antiinflammatory, analgesic and antipyretic activity of some substituted 3-pyrazolin-5-ones and 1,2,4,5,6,7-3H-hexahydroindazol-3-ones, Eur. J. Med. Chem., 41(2):155-65 (2006).

EMolecules, Screening Compounds catalog, Catalog No. F5649-0081. (Jan. 3, 2017).

Haruki et al., Tetrahydrobiopterin biosynthesis as an off-target of sulfa drugs, Science, 340(6135):987-91 (2013).

International Search Report and Written Opinion, International Application No. PCT/US2016/054657, dated Jan. 9, 2017.

Konishi et al., Fungicidal Activity of Pyrazolylpyrimidines Studies on Fungicidal Pyrimidinylhydrazones (Part 5), J. Pesticide Sci., 15(1):13-22 (1990).

Ladzik et al., Regioselective synthesis of 5-ethoxycarbonyl-, 5-acetyl- and 5-trifluoroacetyl-6-trifluoromethylsalicylates by one-pot cyclizations of 1,3-bis(trimethylsilyloxy)-1,3-butadienes with 3-alkoxy-2-alken-1-ones, J. Fluorine Chem., 136:38-42 (2012).

Latremoliere et al., Reduction of Neuropathic and Inflammatory Pain through Inhibition of the Tetrahydrobiopterin Pathway, Neuron., 86:1393-406 (2015).

Sampognaro et al., Proline isosteres in a series of 2,4-disubstituted pyrrolo[1,24][1,2,4]triazine inhibitors of IGF-1 R kinase and IR kinase, Bioorg. Med. Chem. Lett., 20(17):5027-30 (2010).

Sirakawa et al., Pyrimidine derivatives. XI. 2-(1-Pyrazolyl)pyrimidines. 1, Takeda Kenkyusho Nenpo, 22:19-26 (1963).

Sirakawa et al., Pyrimidine derivatives. XII. 2-(1-Pyrazolyl)pyrimidines, Takeda Kenkyusho Nenpo, 22:27-46 (1963).

Smith et al., New inhibitors of sepiapterin reductase. Lack of an effect of intracellular tetrahydrobiopterin depletion upon in vitro proliferation of two human cell lines, J. Biol. Chem., 267(8):5599-607 (1992).

Tegeder et al., GTP cyclohydrolase and tetrahydrobiopterin regulate pain sensitivity and persistence, Nat. Med., 12(11):1269-77 (2006).

Zanatta et al., Synthesis and structural study of N-methyl-2-methylthiopyrimidine derivatives from trihalomethylated enones, J. Heterocyclic Chem., 47(5):1234-9 (2010).

SEPIAPTERIN REDUCTASE INHIBITORS

BACKGROUND

Tetrahydrobiopterin (BH4) is an enzyme cofactor for various aromatic amino acid hydroxylases, including phenylalanine, tyrosine and tryptophan hydroxylases, as well as being an important cofactor for other enzymes such as the nitric oxide synthases (inducible NOS (iNOS), endothelial NOS (eNOS), and neuronal NOS (nNOS)), and alkylglycerol monooxygenase. As such, BH4 is involved in regulating production of various neurotransmitters (e.g., serotonin and dopamine) and nitric oxide. Deficiencies in BH4 are associated with deficiencies in neurotransmitters including serotonin and dopamine. Reduced BH4 production is also associated with reduced pain sensitivity after injury.

The last step in the de novo pathway for BH4 biosynthesis is conversion of 6-pyruvoyltetrahydropterin to BH4 by the action of sepiapterin reductase. Sepiapterin reductase (SPR) is inhibited by the clinically approved drug sulfasalazine and other sulfa drugs, thereby interfering with the de novo biosynthesis of BH4.

SUMMARY

Disclosed herein are compounds of formulae I, I', II, II', III, III', IV, IV', V, and V', and pharmaceutically acceptable salts thereof:

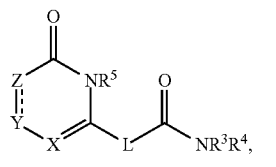

(I)

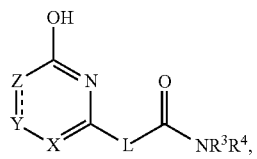

(I')

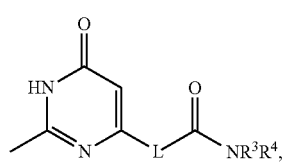

(II)

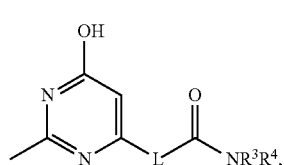

(II')

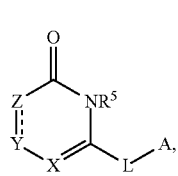

(III)

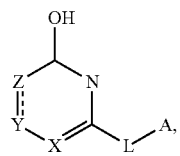

(III')

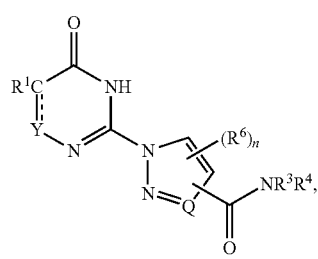

(IV)

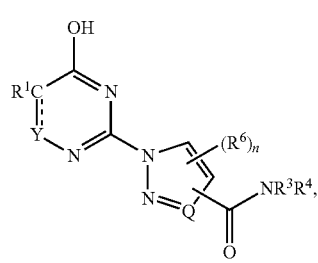

(IV')

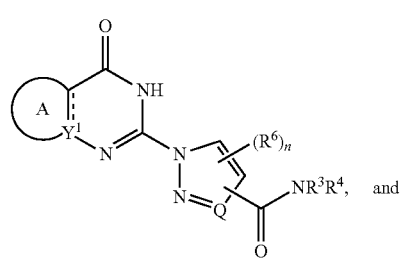

(V)

and

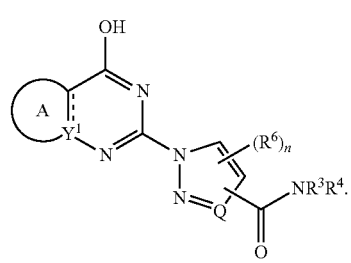

(V')

Also disclosed are compositions (e.g., pharmaceutical compositions) comprising one or more of the compounds disclosed herein and a pharmaceutically acceptable carrier.

Further disclosed are methods of using one or more of the compounds disclosed herein, or a pharmaceutical composition thereof. The methods include methods of inhibiting sepiapterin reductase (SPR), methods of treating a subject suffering from pain, methods of treating a subject suffering from inflammation, and/or methods of treating a subject suffering from an immunological disorder.

These and other embodiments and features of the present invention will become apparent from the following detailed description of the preferred embodiments.

DETAILED DESCRIPTION

Disclosed herein are inhibitors of sepiapterin reductase (SPR) and uses of sepiapterin reductase inhibitors in analgesia, treatment of acute and chronic pain, anti-inflammation, and immune cell regulation. In mouse models, administration of an SPR inhibitor reduced pain hypersensitivity and BH4 levels in target tissues (Latremoliere et al., Neuron, 86:1393-1406 (2015)).

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term $C_{m-n}$ means the alkyl group has "m" to "n" carbon atoms. The term "alkylene" refers to an alkyl group having a substituent. An alkyl (e.g., methyl), or alkylene (e.g., —$CH_2$—), group can be substituted with one or more, and typically one to three, of independently selected halo, trifluoromethyl, trifluoromethoxy, hydroxy, alkoxy, nitro, cyano, alkylamino, or amino groups, for example.

As used herein, the term "halo" refers to fluoro, chloro, bromo, and iodo. The term "hydroxy" is defined as —OH. The term "alkoxy" is defined as —OR, wherein R is alkyl. The term "amino" is defined as —$NH_2$, and the term "alkylamino" is defined as —$NR_2$, wherein at least one R is alkyl and the second R is alkyl or hydrogen. The term "carbamoyl" is defined as —C(=O)$NR_2$. The term "carboxy" is defined as —C(=O)OH or a salt thereof. The term "nitro" is defined as —$NO_2$. The term "cyano" is defined as —CN. The term "trifluoromethyl" is defined as —$CF_3$. The term "trifluoromethoxy" is defined as —$OCF_3$.

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, alkyl, alkenyl, —$OCF_3$, —$NO_2$, —CN, —NC, —OH, alkoxy, amino, alkylamino, —$CO_2H$, —$CO_2$alkyl, —OCOalkyl, aryl, and heteroaryl.

As used herein, the term "benzyl" refers to —$CH_2$-phenyl. Unless otherwise indicated, a benzyl group can be unsubstituted or substituted with one or more, and in particular one to four, groups independently selected from, for example, halo, alkyl, alkenyl, —$OCF_3$, —$NO_2$, —CN, —NC, —OH, alkoxy, amino, alkylamino, —$CO_2H$, —$CO_2$alkyl, —OCOalkyl, aryl, and heteroaryl.

As used herein, the term "heterocyclic" refers to a heteroaryl or heterocycloalkyl ring system. As used herein, the term "carbocyclic" refers to an aryl or cycloalkyl ring system.

As used herein, the term "heteroaryl" refers to a monocyclic or polycyclic ring system (for example, bicyclic) containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —$OCF_3$, —$NO_2$, —CN, —NC, —OH, alkoxy, amino, alkylamino, —$CO_2H$, —$CO_2$alkyl, —OCOalkyl, aryl, and heteroaryl.

As used herein, the term "cycloalkyl" means a monocyclic or polycyclic (e.g., bicyclic), saturated or partially unsaturated, ring system containing three or more (e.g., three to twelve or three to eight) carbon atoms, including cyclopropyl, cyclobutyl, cyclopentyl, cyclohexyl, cycloheptyl, and cyclooctyl, optionally substituted with one or more, and typically one to three, of independently selected halo, trifluoromethyl, trifluoromethoxy, hydroxy, alkoxy, nitro, cyano, alkylamino, or amino groups, for example.

As used herein, the term "heterocycloalkyl" means a monocyclic or polycyclic (e.g., bicyclic), saturated or partially unsaturated, ring system containing 3 or more (e.g., 4 to 12) total atoms, of which one to five of the atoms are independently selected from nitrogen, oxygen, and sulfur and the remaining atoms are carbon. Nonlimiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of independently selected halo, $C_{1-6}$ alkyl, $C_{1-6}$ alkoxy, cyano, amino, carbamoyl, nitro, carboxy, $C_{2-7}$ alkenyl, $C_{2-7}$ alkynyl, or the like on an atom of the ring.

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature, examples of which include isotopes of hydrogen, such as $^2H$ and $^3H$. In some cases, one or more hydrogen atoms of the compounds disclosed herein are specifically $^2H$ (deuterium). Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

In one aspect, the disclosure provides a compound of formula I or I', or a pharmaceutically acceptable salt thereof:

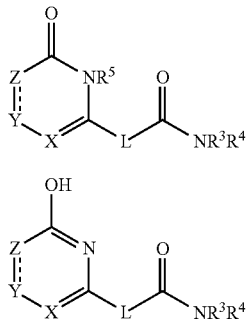

wherein:
=== is an optional double bond;
Z is $CR^1$ or $NR^1$, or if the double bond is present, then Z is $CR^1$ or N;
Y is $NR^2$ or $CR^2$, or if the double bond is present, then Y is N or $CR^2$;
X is N or $CR^{5a}$;
$R^1$ and $R^2$, taken together with the atoms to which they are attached form a 4-, 5-, 6-, or 7-membered ring; or
$R^1$ and $R^2$ are independently selected from the group consisting of H, $C_{1-5}$alkyl, $C_{3-5}$cycloalkyl, $C_{1-5}$haloalkyl, and halo;
$R^5$ and $R^{5a}$ are independently selected from the group consisting of H and $C_{1-5}$alkyl;
L is heteroaryl-$C_{0-5}$alkylene-, aryl-$C_{0-5}$alkylene-, —S—$C_{1-5}$alkylene-aryl, —S—$C_{1-5}$alkylene-heteroaryl, —$C_{1-5}$alkylene-S-aryl, or —$C_{1-5}$alkylene-S-heteroaryl;
$R^3$ and $R^4$, taken together with nitrogen atom to which they are attached form a 3-, 4-, 5-, 6-, or 7-membered monocyclic ring or 6-, 7-, 8-, 9-, 10-, 11-, 12-, 13-, or 14-membered spiro, fused, and/or bridged polycyclic (e.g., bicyclic) ring; or
$R^3$ is selected from the group consisting of H, $C_{1-5}$alkyl, $C_{3-10}$cycloalkyl, $C_{1-5}$haloalkyl, aryl, heteroaryl, and $C_{1-5}$alkylene-G,
$R^4$ is selected from the group consisting of $C_{1-5}$alkyl, $C_{3-10}$cycloalkyl, $C_{1-5}$haloalkyl, aryl, heteroaryl, and $C_{1-5}$alkylene-G; and
each G is independently selected from the group consisting of CN, aryl, heteroaryl, cycloalkyl, and heterocycloalkyl.

In some embodiments, the compound of formula I does not include a compound having a structure as recited in Table D, below.

In some embodiments, the disclosure provides a compound having a formula IA or IA':

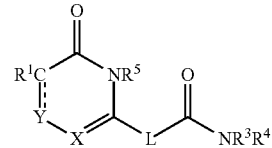

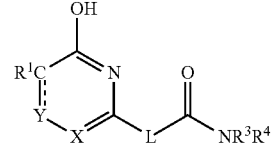

wherein:
Y is $NR^2$ or $CR^2$, or if the double bond is present, then Y is $CR^2$; and
$R^1$ and $R^2$, taken together with the atoms to which they are attached form a 4-, 5-, 6-, or 7-membered ring.

Compounds of formula IA or IA' include, but are not limited to, compounds having a structure selected from the group consisting of:

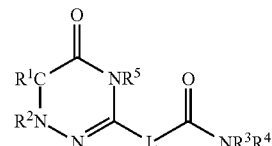

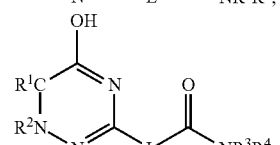

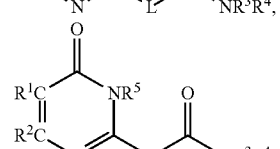

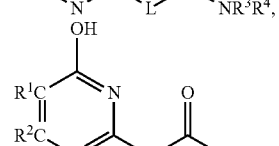

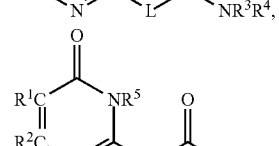, and

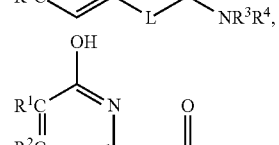.

Compounds of formula IA or IA' also include, but are not limited to, compounds having a structure:

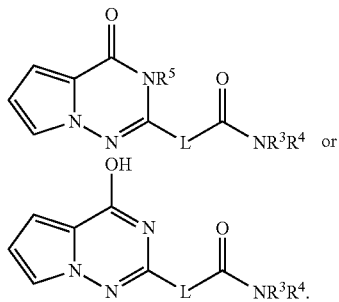

In some embodiments, $R^1$ and $R^2$, taken together with the atoms to which they are attached form a heteroaryl ring, an aryl ring, a heterocycloalkyl ring, or a cycloalkyl ring. In some embodiments, $R^1$ and $R^2$, taken together with the atoms to which they are attached form a pyrrole ring, a cyclopentene ring, a thiophene ring, a dihydrofuran ring, a cyclohexene ring, a pyrazole ring, a thiazole ring, a benzene ring, an imidazole ring, or a cyclobutene ring.

In some embodiments, the disclosure provides a compound having a formula IB or IB':

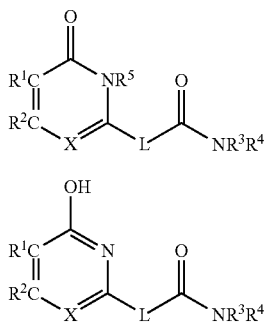

wherein $R^1$ and $R^2$ are independently selected from the group consisting of H, $C_{1-5}$alkyl, $C_{3-5}$cycloalkyl, $C_{1-5}$haloalkyl, and halo.

In some embodiments,

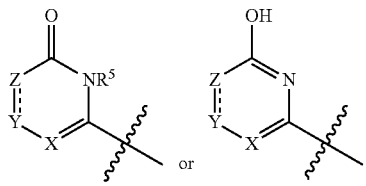

is selected from the group consisting of:

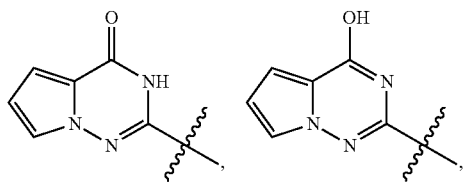

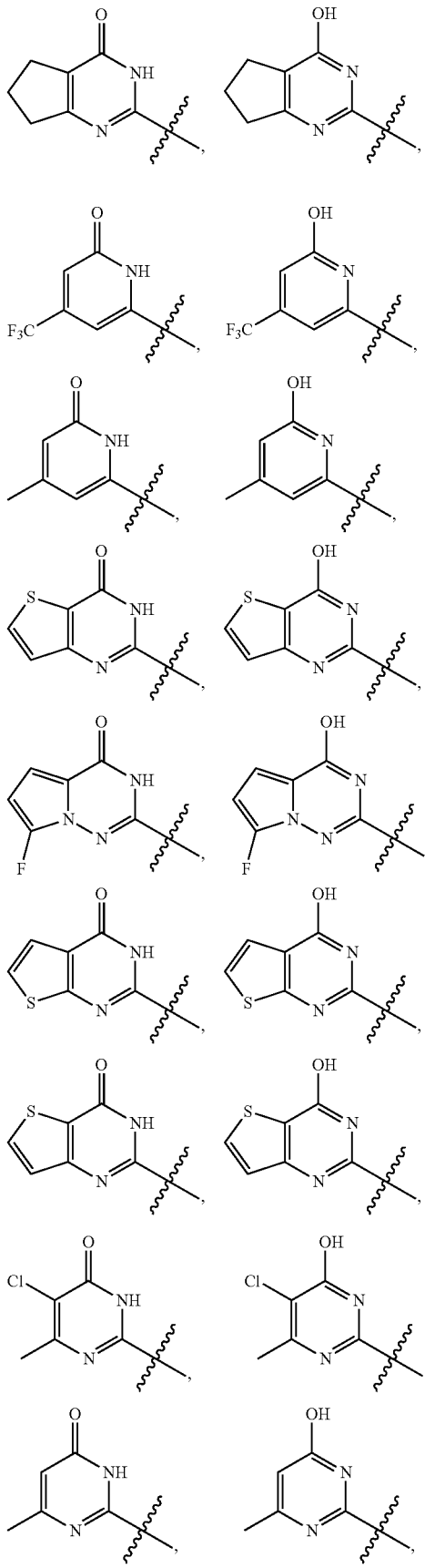

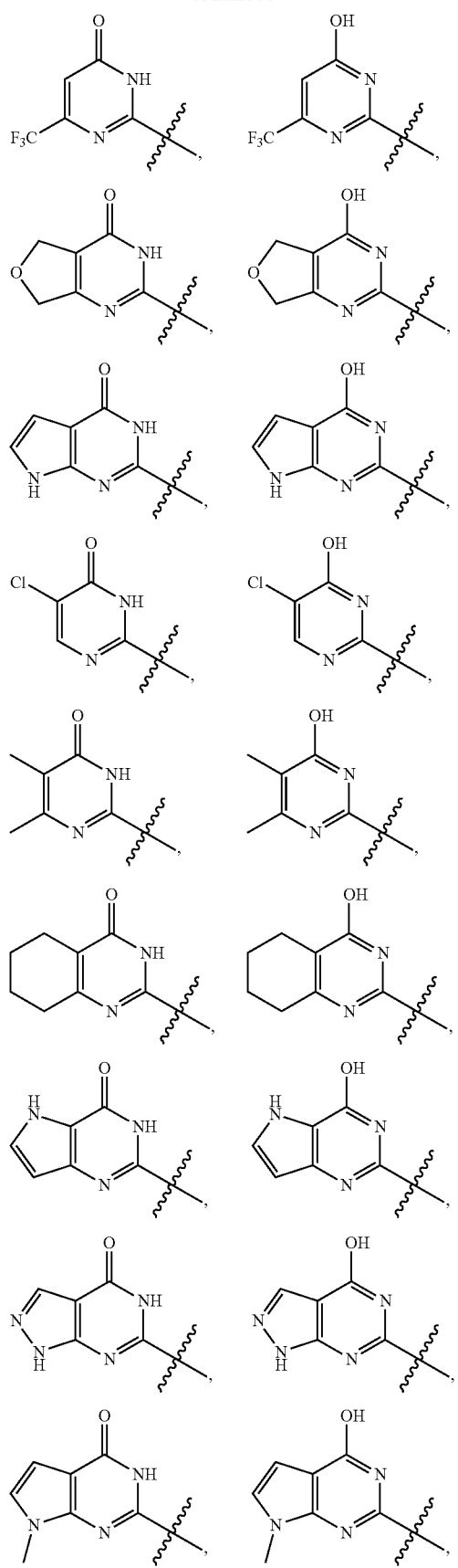
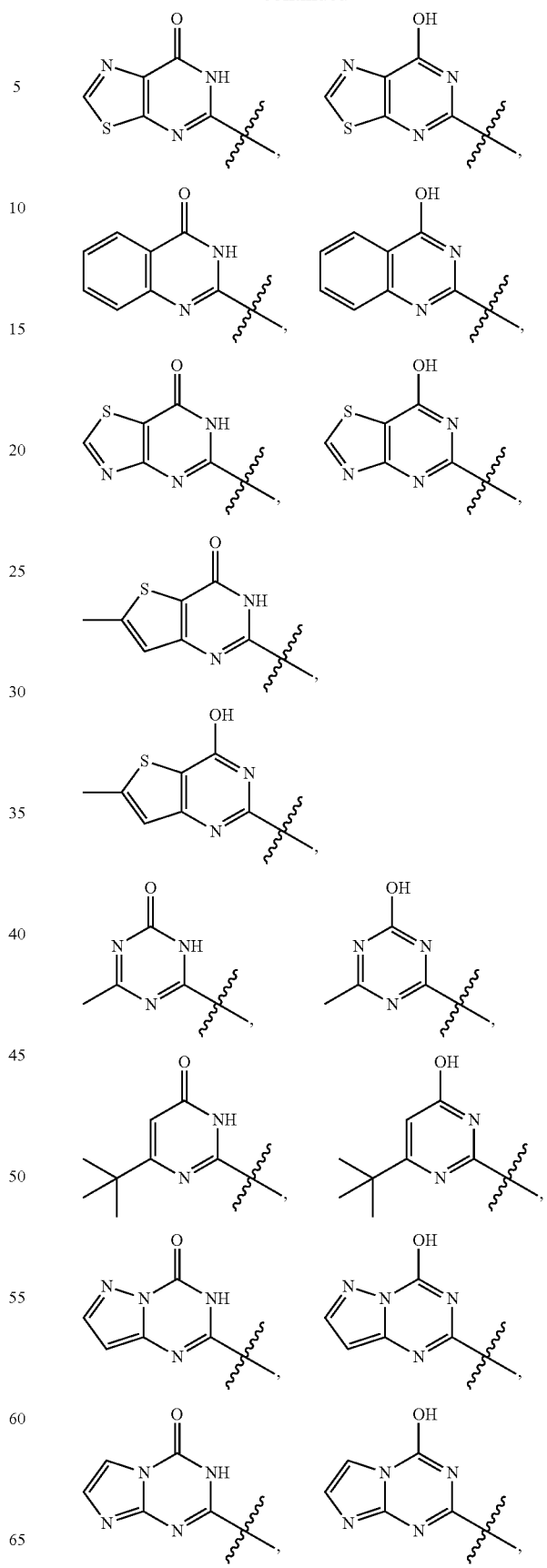

-continued
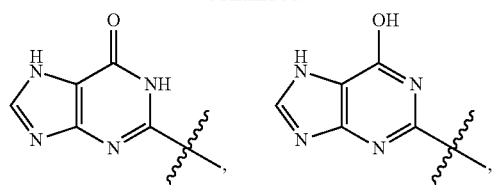
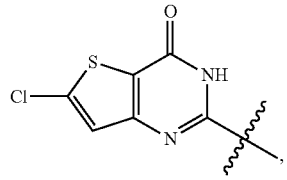
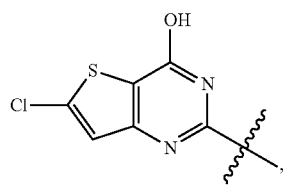
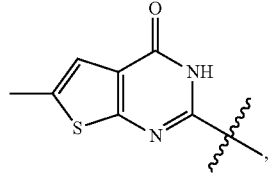
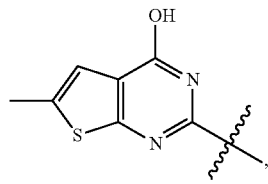
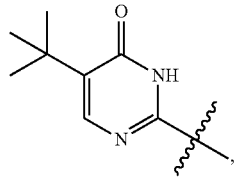
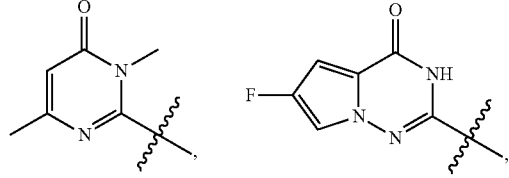
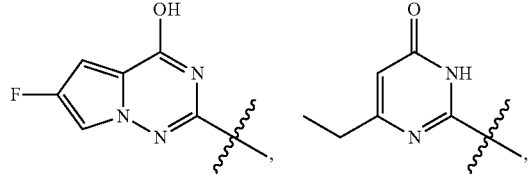
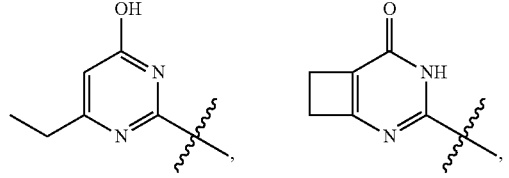
-continued
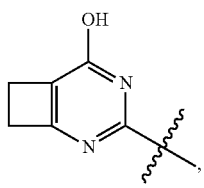 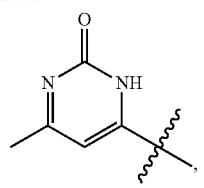
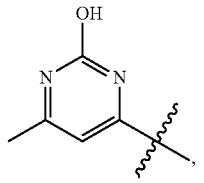 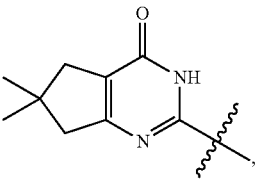
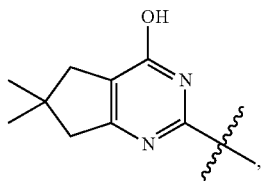
, and
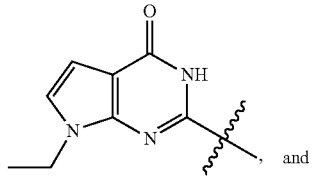
. In some cases,
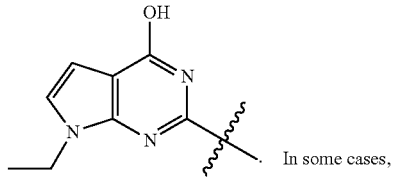 or 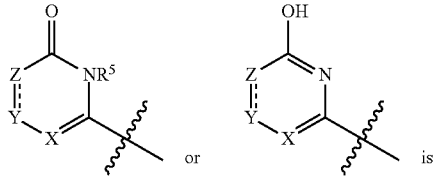 is
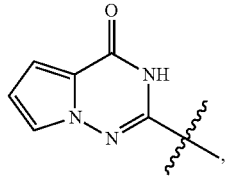
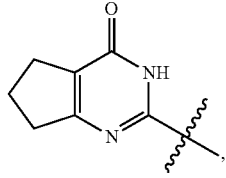
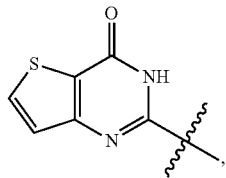

-continued

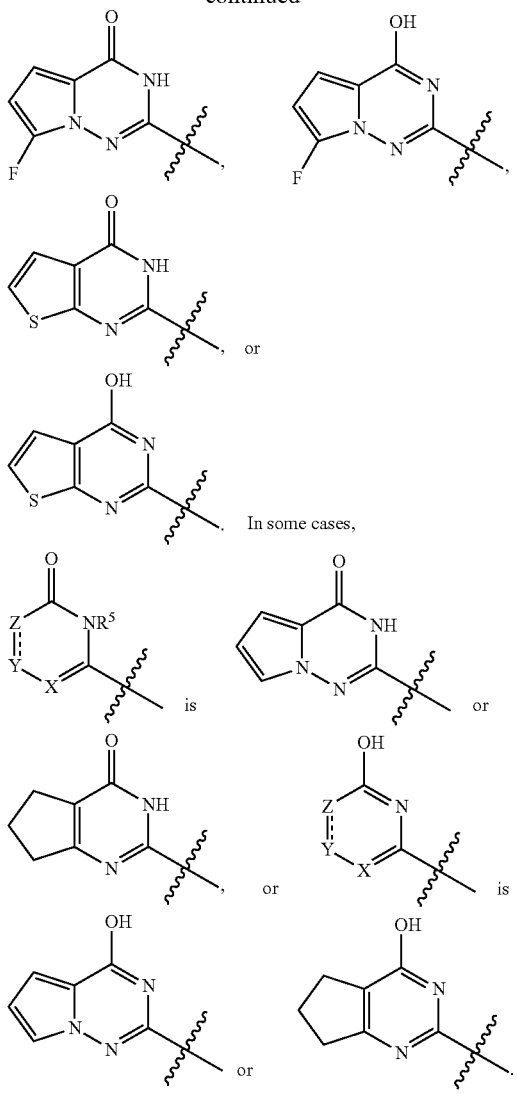

In some embodiments, L is —S—$C_{1-5}$ alkylene-aryl, —S—$C_{1-5}$ alkylene-heteroaryl, —$C_{1-5}$alkylene-S-aryl, or —$C_{1-5}$alkylene-S-heteroaryl. In other embodiments, L is aryl-$C_{1-5}$alkylene- or heteroaryl-$C_{1-5}$alkylene-. In still other embodiments, L is heteroaryl or aryl, such as, but not limited to a 5- or 6-membered heteroaryl ring. Suitable L groups include, but are not limited to, pyrazolyl, triazolyl, thiazolyl, pyridinyl, imidazolyl, phenyl, thiophenyl, pyrrolyl, and indolyl.

In some embodiments, L is

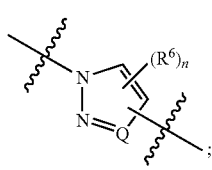

n is 0 or 1;
Q is CH, $CR^6$, or N;
each $R^6$ is selected from the group consisting of $C_{1-5}$alkyl, $C_{3-5}$cycloalkyl, heterocycloalkyl, $C_{1-5}$haloalkyl, halo, benzyl, $C_{1-5}$haloalkylene-OH, $C_{1-5}$alkylene-CN, $C_{1-5}$alkoxy, $C_{1-5}$haloalkoxy, aryloxy, heteroaryloxy, CN, OH, —$NHR^{11}$, —$NR^{11}CO_2R^{11a}$, —$SO_2R^{11}$, —$SO_2NHR^{11}$, —$SOR^{11}$, —$CO_2R^{11}$, —$CONHR^{11}$, aryl, and heteroaryl; and $R^{11}$ and $R^{11a}$ are each independently selected from the group consisting of H, $C_{1-5}$alkyl, $C_{1-5}$haloalkyl, —$C_{0-5}$alkylene-$C_{3-6}$cycloalkyl, —$C_{0-5}$alkylene-heterocycloalkyl, —$C_{0-5}$alkylene-aryl, and —$C_{0-5}$alkylene-heteroaryl. In some cases,

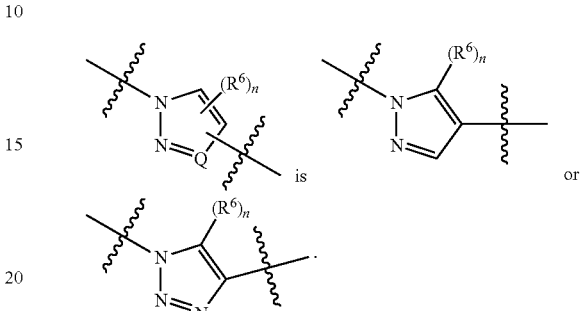

is or

In some embodiments, L is

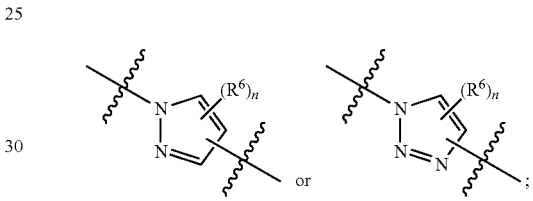

or ;

n is 0, 1, or 2;
$R^6$ is selected from the group consisting of $C_{1-5}$alkyl, $C_{3-5}$cycloalkyl, heterocycloalkyl, $C_{1-5}$haloalkyl, halo, benzyl, $C_{1-5}$haloalkylene-OH, $C_{1-5}$alkylene-CN, $C_{1-5}$alkoxy, $C_{1-5}$haloalkoxy, aryloxy, heteroaryloxy, CN, OH, —$NHR^{11}$, —$NR^{11}CO_2R^{11a}$, —$SO_2R^{11}$, —$SO_2NHR^{11}$, —$SOR^{11}$, —$CO_2R^{11}$, —$CONHR^{11}$, aryl, and heteroaryl; and $R^{11}$ and $R^{11a}$ are each independently selected from the group consisting of H, $C_{1-5}$alkyl, $C_{1-5}$haloalkyl, —$C_{0-5}$alkylene-$C_{3-6}$cycloalkyl, —$C_{0-5}$alkylene-heterocycloalkyl, —$C_{0-5}$alkylene-aryl, and —$C_{0-5}$alkylene-heteroaryl. Suitable L groups include, but are not limited to,

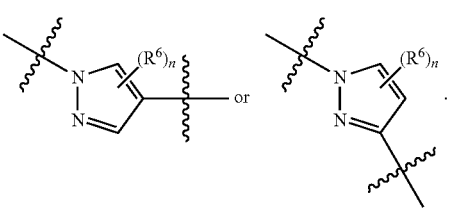

or .

In some embodiments, L has a structure selected from

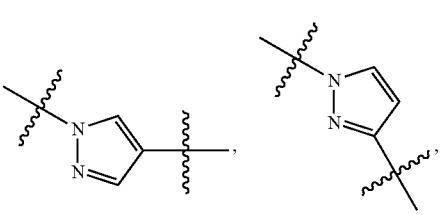

, and is substituted with 0, 1, or 2 $R^6$ substituents.

In some cases, L is selected from the group consisting of

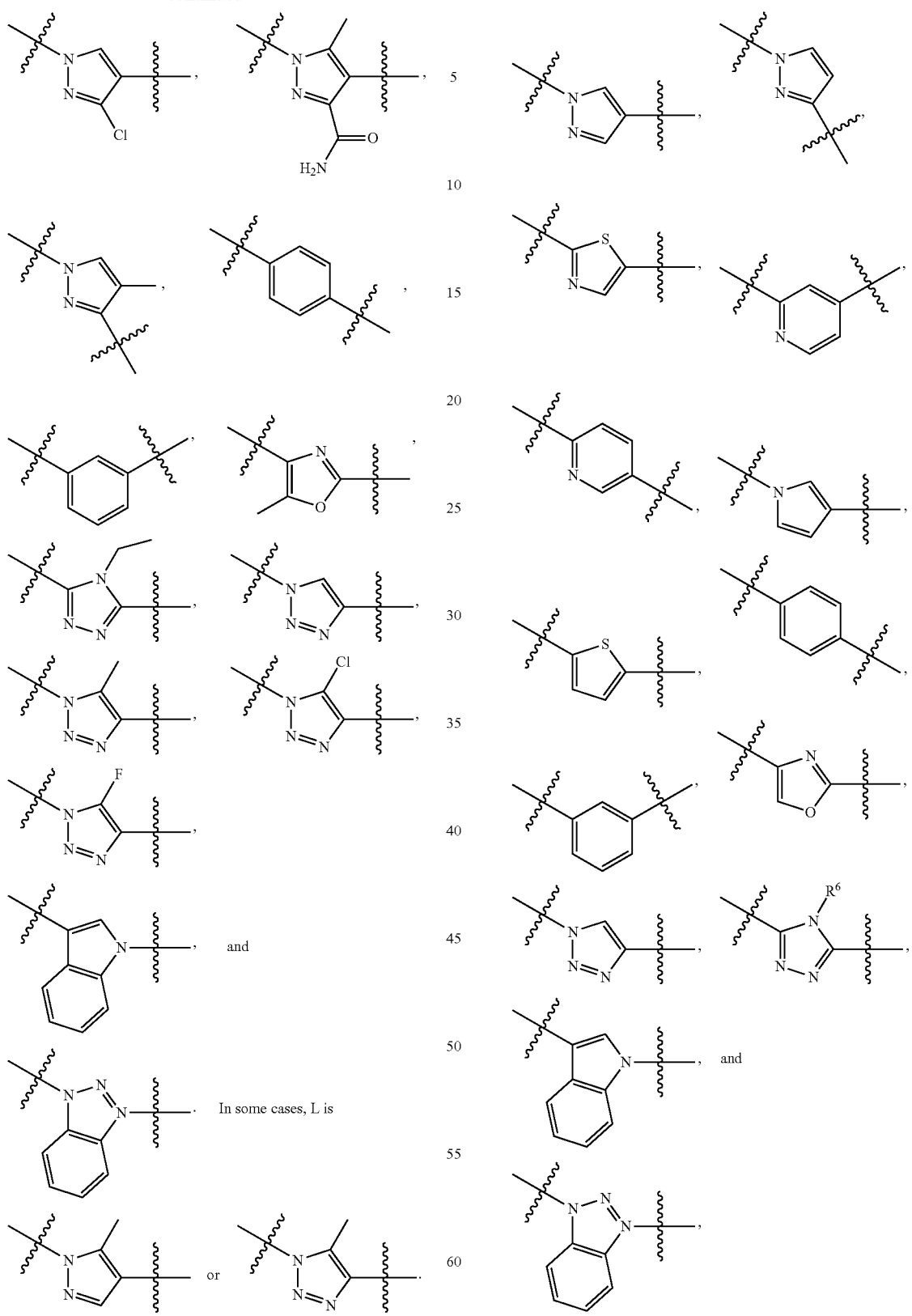
In some cases, one or more hydrogen atoms of the L groups disclosed herein are replaced with ²H (deuterium). In some cases, L has a structure selected from and is substituted with 1 or 2 deutero C₁₋₅alkyl substituents, such as CH₂D, CHD₂, or CD₃. In some cases, L has a structure selected from

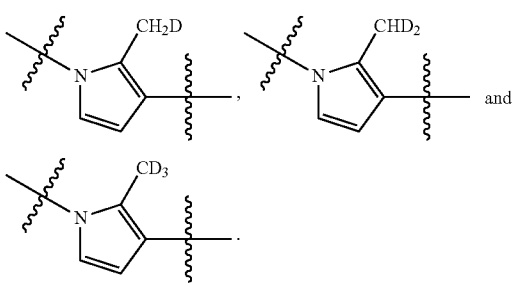

In some embodiments, $R^3$ and $R^4$, taken together with the nitrogen atom to which they are attached form a 3-, 4-, 5-, 6-, or 7-membered ring, including, but not limited to, piperidinyl, pyrrolidinyl, azetidinyl, piperazinyl, morpholinyl, thiomorpholinyl, aziridinyl, oxaziridinyl, imidazolidinyl, pyrazolidinyl, oxazolidinyl, isoxazolidinyl, thiazolidinyl, isothiazolidinyl, azepanyl, diazepanyl, or diazabicycloheptane.

In some embodiments,

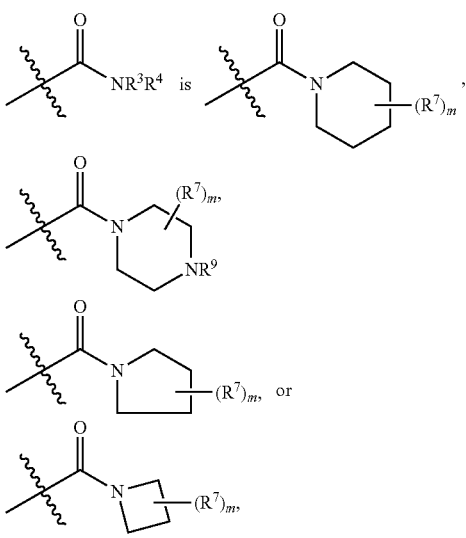

m is 0, 1, 2, or 3;

$R^7$ and $R^9$ are each independently selected from the group consisting of halo, $C_{1-5}$alkyl, $C_{3-5}$cycloalkyl, heterocycloalkyl, $C_{1-5}$haloalkyl, $C_{1-5}$haloalkylene-OH, $C_{1-5}$alkylene-CN, $C_{1-5}$alkoxy, $C_{1-5}$haloalkoxy, aryloxy, heteroaryloxy, CN, OH, —$NHR^8$, —$NR^8CO_2R^{8a}$, —$SO_2R^8$, —$CO_2R^8$, —$CONHR^8$, aryl, and heteroaryl, or two $R^7$ groups, together with the carbon atom(s) to which they are attached, form a 3-, 4-, 5-, 6-, 7-, or 8-membered cycloalkyl, a 3-, 4-, 5-, 6-, 7-, or 8-membered heterocycloalkyl, aryl, or a 5- or 6-membered heteroaryl ring; and $R^8$ and $R^{8a}$ are each independently selected from the group consisting of H, $C_{1-5}$alkyl, $C_{1-5}$haloalkyl, —$C_{0-5}$alkylene-$C_{3-6}$cycloalkyl, —$C_{0-5}$alkylene-heterocycloalkyl, —$C_{0-5}$alkylene-aryl, and —$C_{0-5}$alkylene-heteroaryl; or one $R^7$ group and $R^9$, together with the atoms to which they are attached, form a 5- or 6-membered heterocycloalkyl or heteroaryl ring.

In some embodiments,

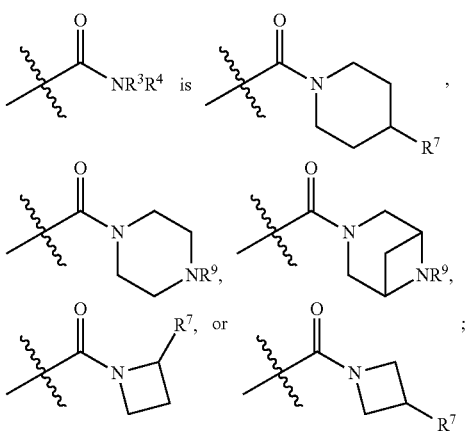

$R^7$ and $R^9$ are each independently selected from the group consisting of halo, $C_{1-5}$alkyl, $C_{3-5}$ cycloalkyl, heterocycloalkyl, $C_{1-5}$haloalkyl, $C_{1-5}$haloalkylene-OH, $C_{1-5}$alkylene-CN, $C_{1-5}$alkoxy, $C_{1-5}$haloalkoxy, aryloxy, heteroaryloxy, CN, OH, —$NHR^8$, —$NR^8CO_2R^{8a}$, —$SO_2R^8$, —$CO_2R^8$, —$CONHR^8$, aryl, and heteroaryl; and $R^8$ and $R^{8a}$ are each independently selected from the group consisting of H, $C_{1-5}$alkyl, $C_{1-5}$haloalkyl, —$C_{0-5}$alkylene-$C_{3-6}$cycloalkyl, —$C_{0-5}$alkylene-heterocycloalkyl, —$C_{0-5}$alkylene-aryl, and —$C_{0-5}$alkylene-heteroaryl.

In some embodiments, $R^7$ or $R^9$ is selected from the group consisting of $C_{3-5}$cycloalkyl, heterocycloalkyl, aryloxy, heteroaryloxy, aryl, and heteroaryl. In some embodiments, $R^7$ is oxazolyl or pyridinyl, each of which is optionally substituted with CN or F. In some embodiments, $R^7$ is selected from the group consisting of

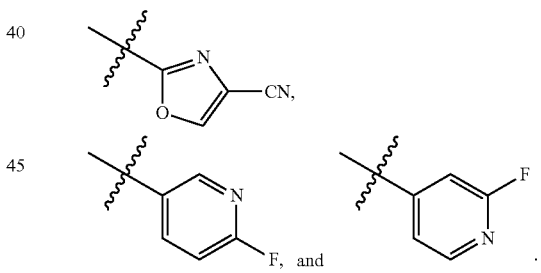

In some embodiments, $R^9$ is $C_{3-5}$cycloalkyl. In some embodiments, $R^9$ is cyclopropyl or cyclobutyl, each of which is optionally substituted with 1, 2, 3, or 4 F atoms. In some embodiments, wherein $R^9$ is selected from the group consisting of

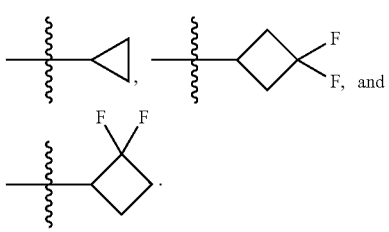

In some embodiments,

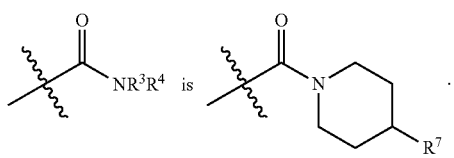

In some embodiments,

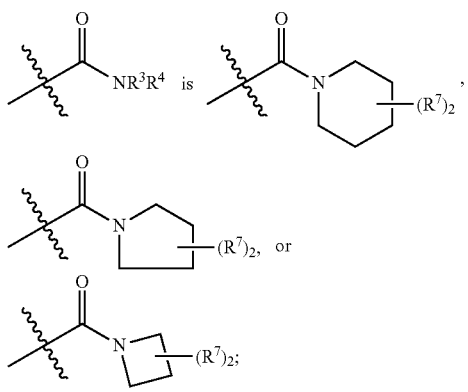

and the two $R^7$ groups are present on adjacent carbon atoms, and in some cases, the two $R^7$ groups form a 4-, 5-, 6-, or 7-membered heterocyclic group or carbocyclic group with the carbon atoms to which they are attached. In some embodiments,

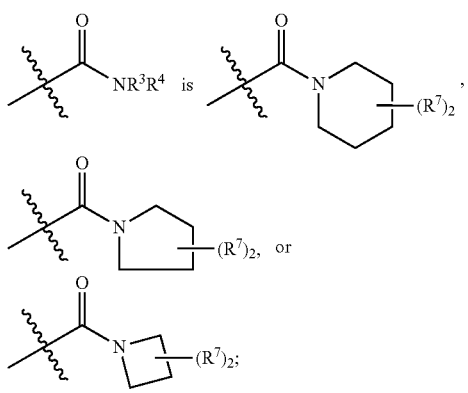

and the two $R^7$ groups are present on the same carbon atom, and in some cases, the two $R^7$ groups form a 3-, 4-, 5-, 6-, or 7-membered heterocycloalkyl group or cycloalkyl group with the carbon atom to which they are attached.

In some embodiments, at least one $R^7$ or $R^9$ is F, $CF_3$, $CH_3$, $CH_2CH_3$, —$CH_2CF_3$, cyclopropyl, 1-cyano-cyclopropyl, CN, —$C(CH_3)_2CN$, —$CH(CN)CH_2CH_3$, 3,3-difluoropyrrolidine, —OH, —$OCH_3$, —$OCH_2CH_3$, —$OCH_2CF_3$, —$C(OH)(CF_3)_2$, —$C(OH)CH_3CF_3$, —$CO_2C(CH_3)_3$, —$CONHC(CH_3)_3$, —$N(CH_3)CO_2C(CH_3)_3$, phenoxy, phenylsulfonyl, 3,4-difluorobenzenesulfonyl, phenyl, fluorophenyl, difluorophenyl, cyanophenyl, indolyl, difluoropyrrolidinyl, or benzothiazolyl, or two $R^7$ groups, together with the carbon atoms to which they are attached, form a fused benzene ring. In some embodiments, at least one $R^7$ is 3-indolyl, 6-fluoro-3-indolyl, N-methyl-3-indolyl, 4-indolyl, 2-benzothiazolyl, or 5-fluoro-2-benzothiazolyl.

In some embodiments, $R^9$ is —$C_{0-5}$alkylene-aryl. In some embodiments, $R^9$ is 2,4-difluorophenyl, 5-fluorophenyl, phenyl, or 2-chlorophenyl.

In some embodiments, $R^3$ and $R^4$, taken together with the nitrogen atom to which they are attached form a 6-, 7-, 8-, 9-, 10-, 11-, 12-, 13-, or 14-membered spiro, fused, or bridged polycyclic (e.g., bicyclic ring). Suitable 6- to 14-membered spiro, fused, or bridged bicyclic rings include, but are not limited to, 10-azabicyclodecane, 9-azabicyclononane, 8-azabicyclooctane (e.g., 8-azabicyclo[3.2.1]octane), azabicycloheptane (e.g., 7-azabicycloheptane), 3-azabicyclohexane (e.g., 3-azabicyclo[3.1.0]hexane), diazabicyclononane (e.g., 1,4-diazabicyclo[4.3.0]nonane), diazabicyclooctane, diazabicycloheptane, diazaspirononane, azaspirononane, diazaspirooctane, azaspirooctane, spiroksobenzofuran-piperidine, diazaspiroheptane, azaspiroheptane, octahydrocyclopenta[b]pyrrole, or octahydrocyclopenta[c]pyrrole. In some embodiments, the 6- to 14-membered spiro, fused, or bridged polycyclic (e.g, bicyclic) ring is substituted with one or two substituents independently selected from the group consisting of halo, $C_{1-5}$alkyl, $C_{1-5}$haloalkyl, $C_{1-5}$alkoxy, aryloxy, heteroaryloxy, CN, OH, —$SO_2R^{10}$, $CO_2R^{10}$, $CONHR^{10}$, $C_{3-5}$cycloalkyl, oxo, aryl, and heteroaryl; and $R^{10}$ is selected from the group consisting of H, $C_{1-5}$alkyl, —$C_{0-5}$alkylene-aryl, and —$C_{0-5}$alkylene-heteroaryl. In some embodiments, at least one substituent of the 6- to 14-membered spiro, fused, or bridged polycyclic (e.g., bicyclic) ring is cyclopropyl, F, —$CO_2C(CH_3)_3$, —$CH_2CF_3$, $CF_3$, fluorophenyl, cyanophenyl, OH, or phenyl.

In some embodiments, $R^3$ is selected from the group consisting H, $CH_3$, —$CH_2CH_3$, —$CH_2CH_2CH_3$, —$CH(CH_3)_2$, —$CH_2CF_3$, —$CH_2CH_2CN$, —$CH_2CH(OH)CF_3$, and benzyl; and $R^4$ is selected from the group consisting of $CH_3$, —$CH_2CH_3$, —$CH_2CH_2CH_3$, —$CH_2CH_2CF_3$, —$CH_2CF_2CF_3$, cyclohexyl, cyclopentyl, benzyl,

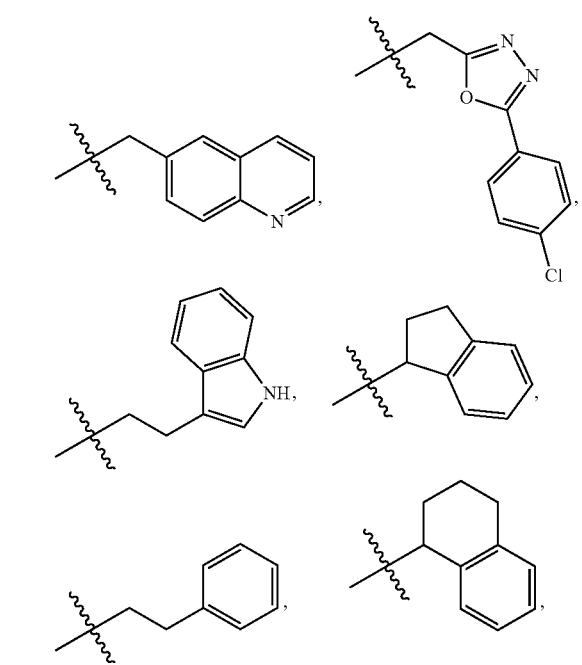

-continued

In some embodiments, —C(=O)NR³R⁴ is

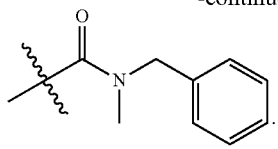
Suitable
groups also include, but are not limited to, the following:
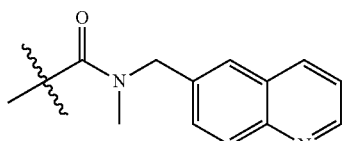
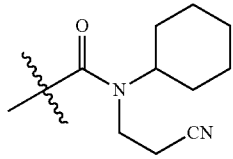
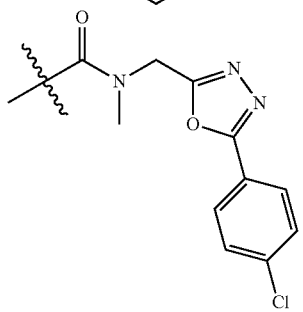
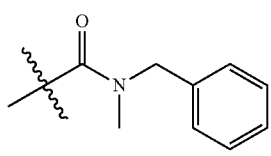
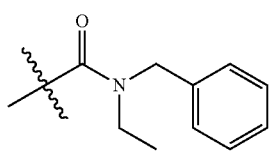
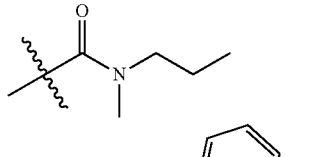
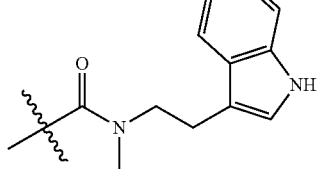
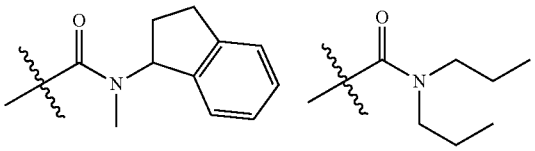
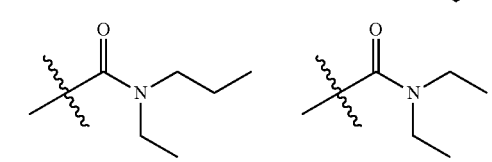
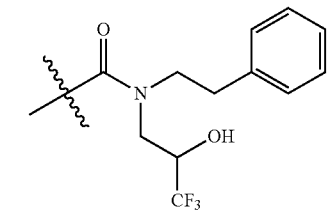
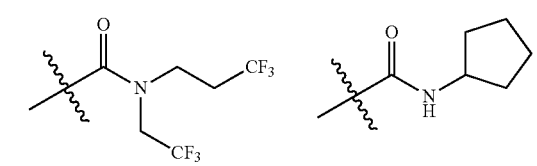
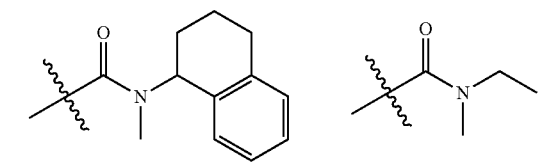
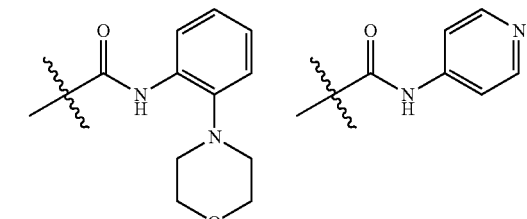
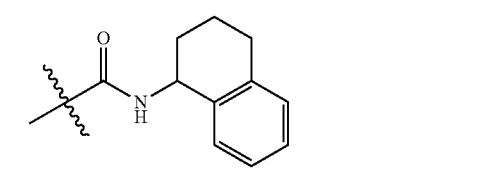
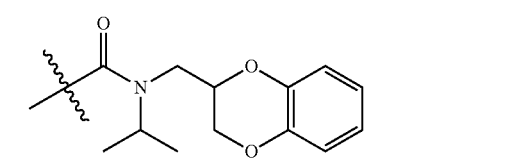
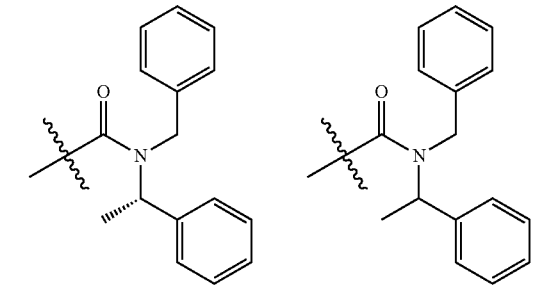

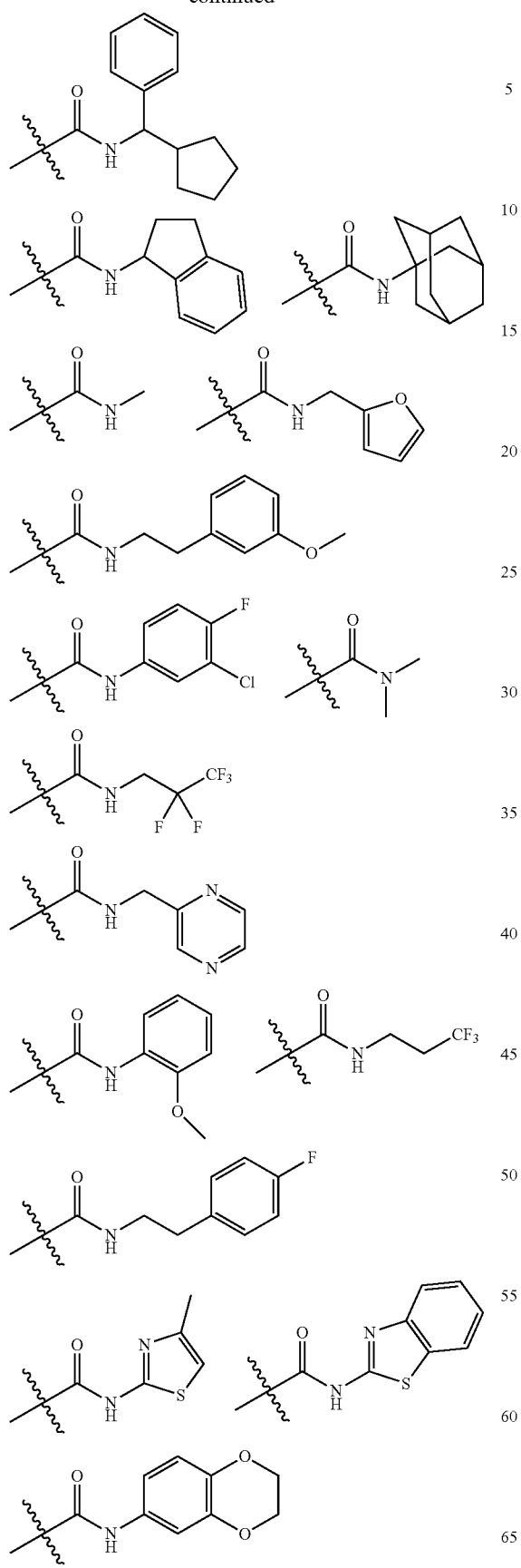
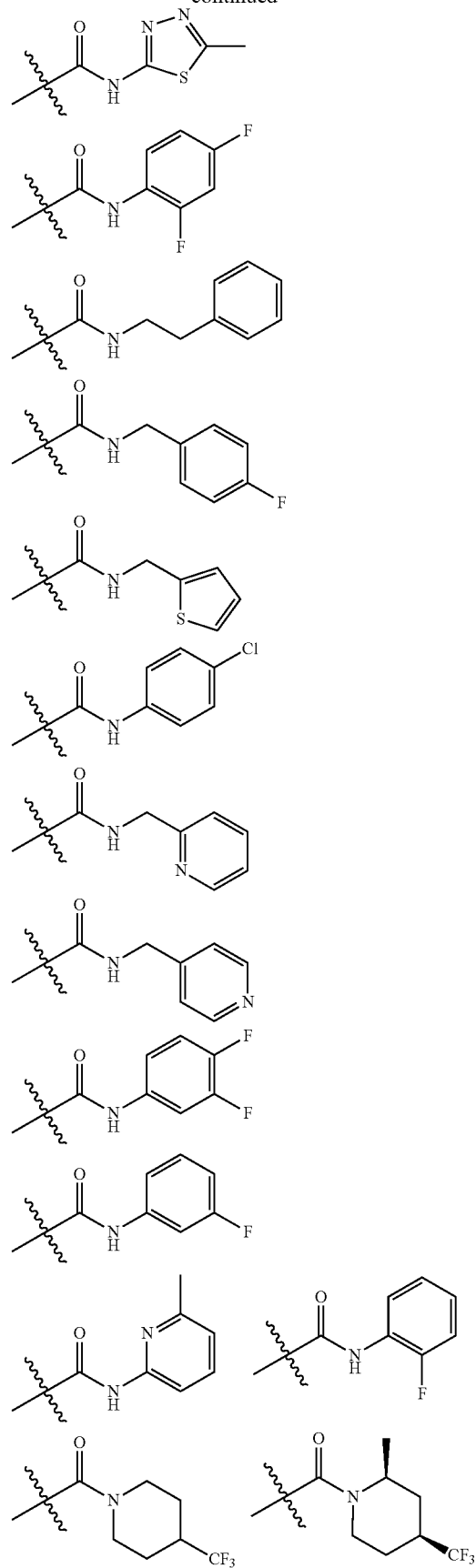

-continued
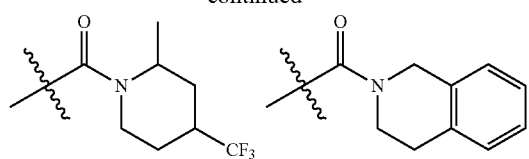
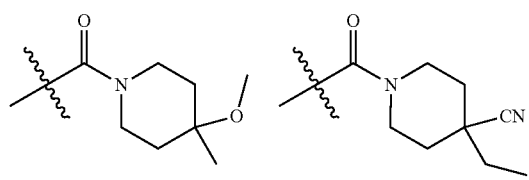
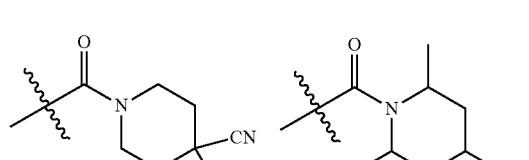
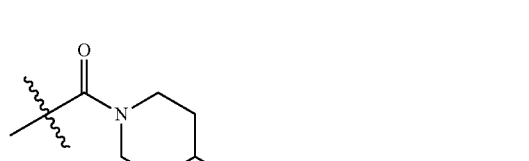
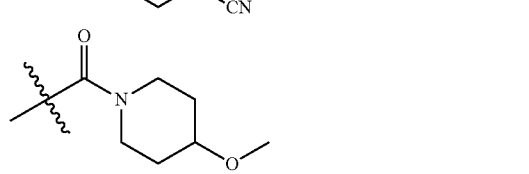
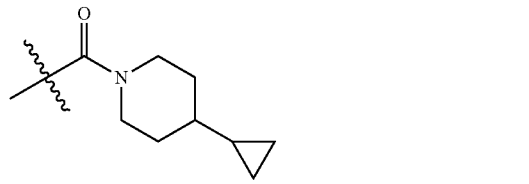

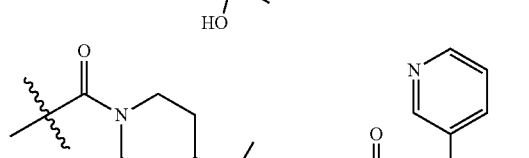
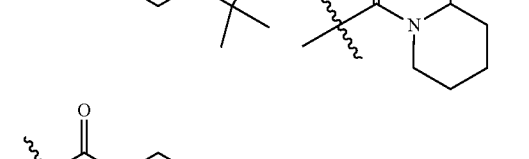
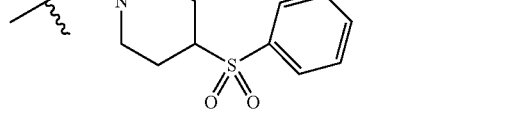
-continued
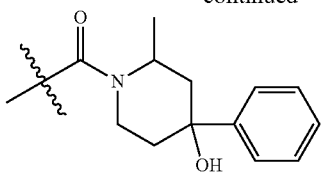
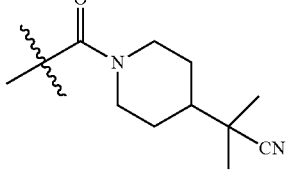
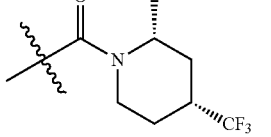
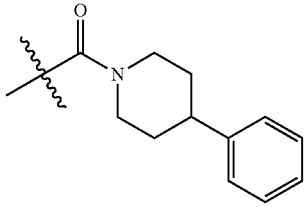
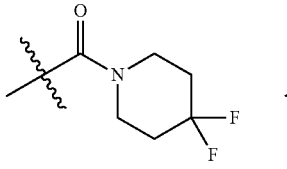
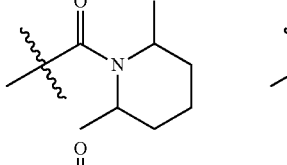

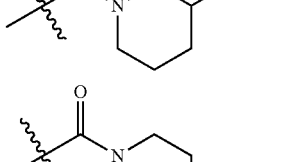
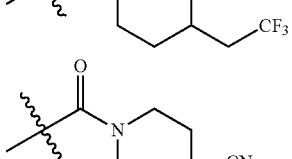
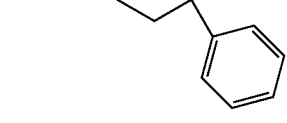

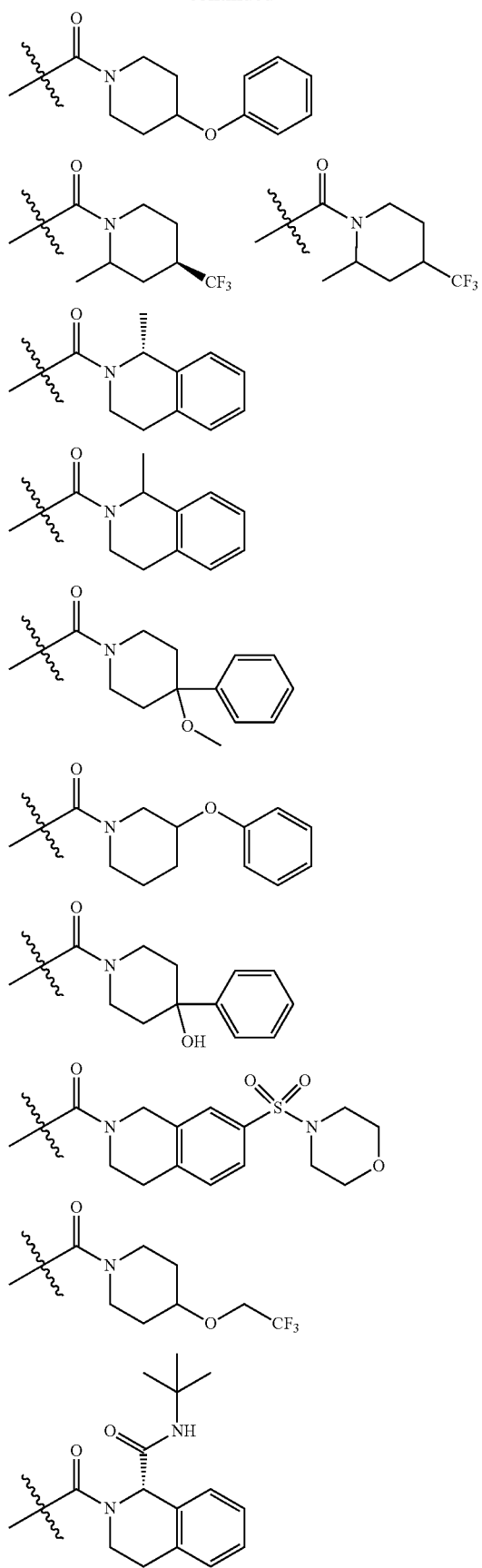
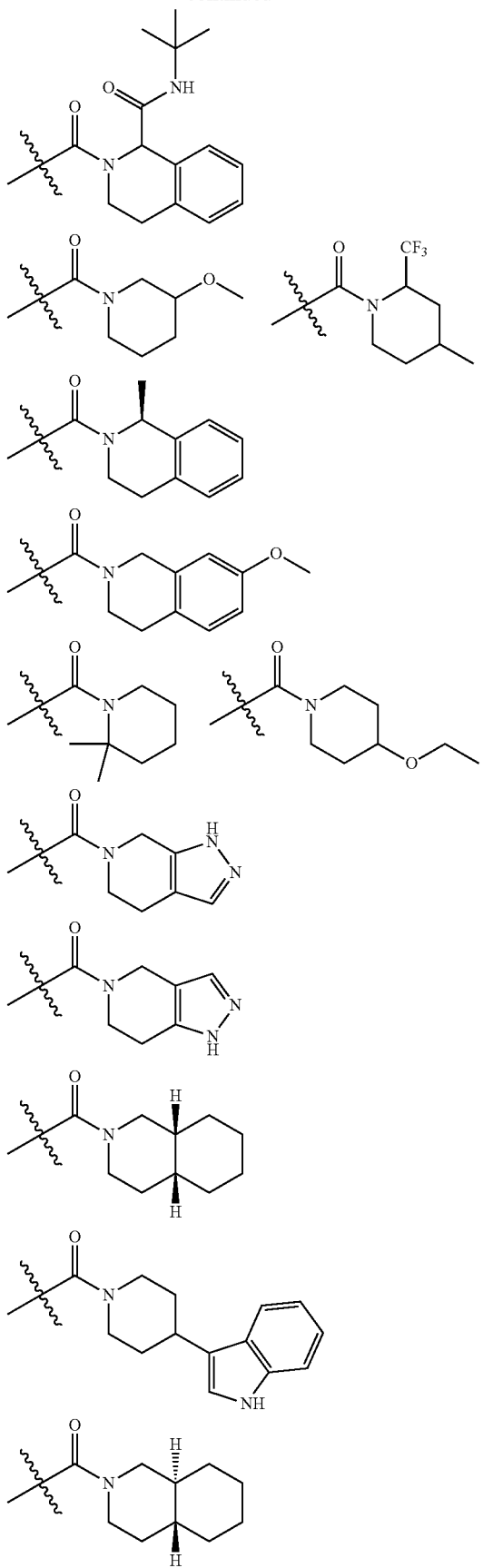

33
-continued
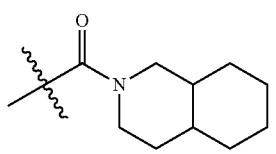
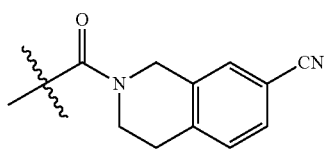
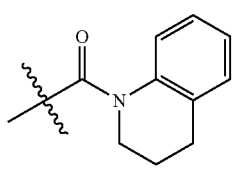
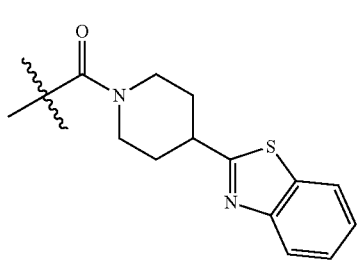
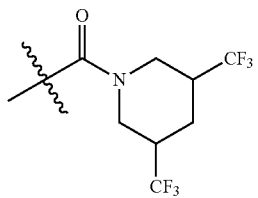
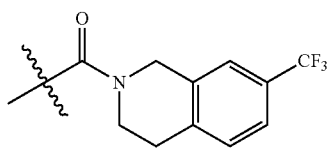
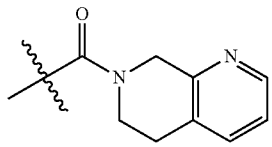 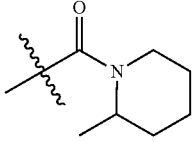
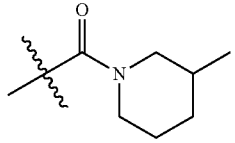
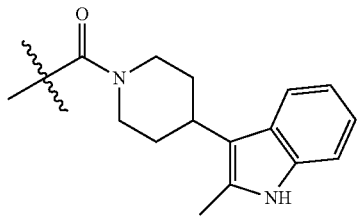
34
-continued
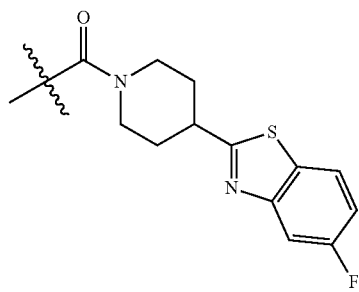
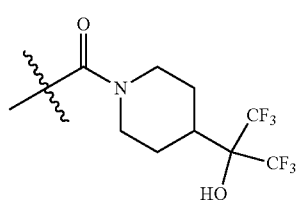
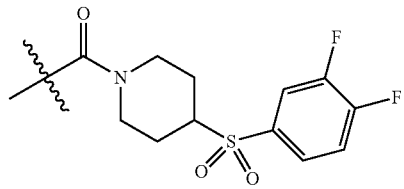
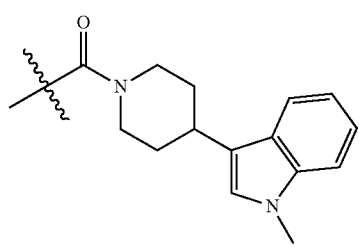
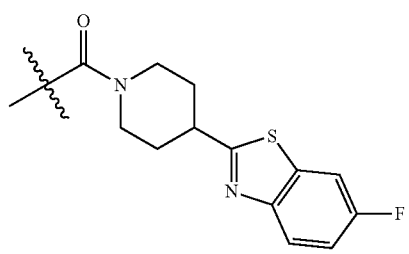
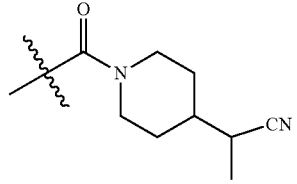
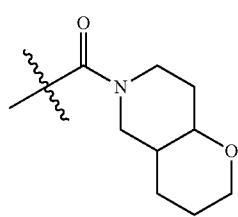

-continued
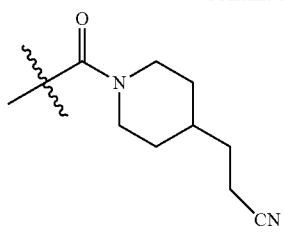
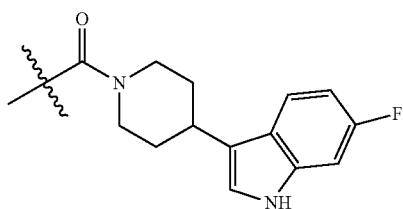
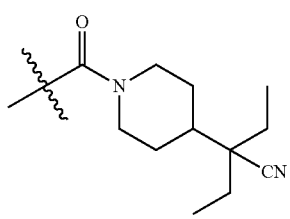
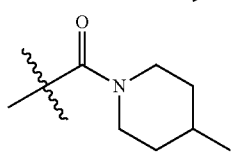
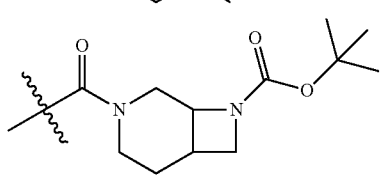
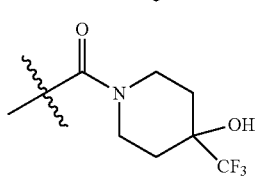
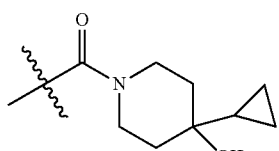
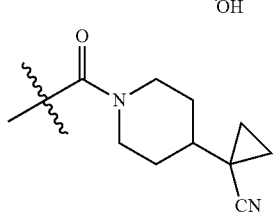
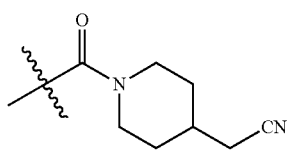
-continued
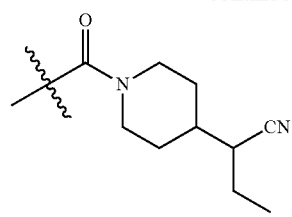
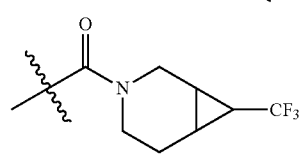
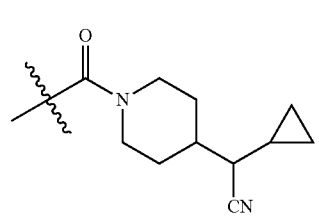
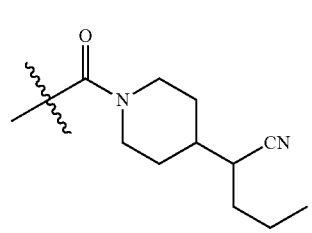
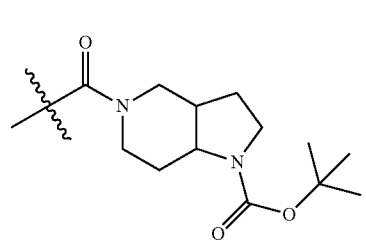
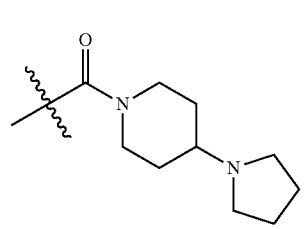
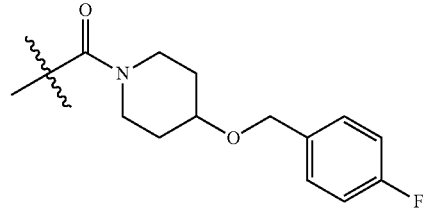
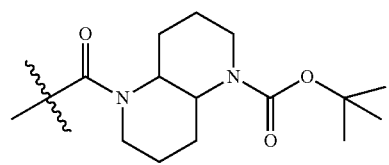

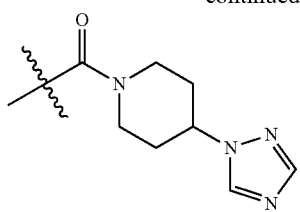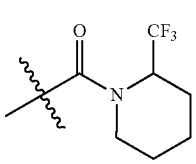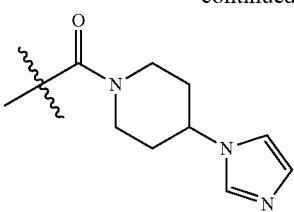
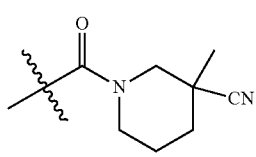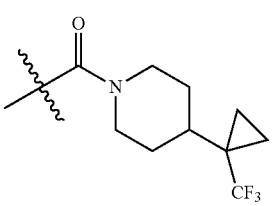
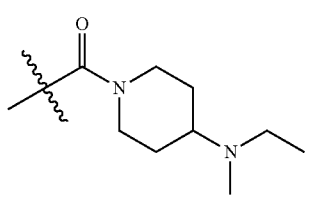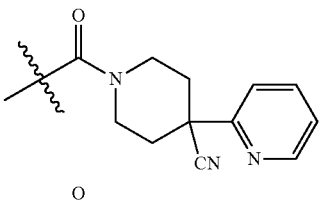
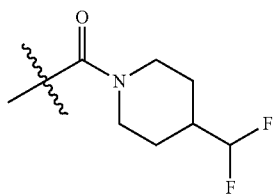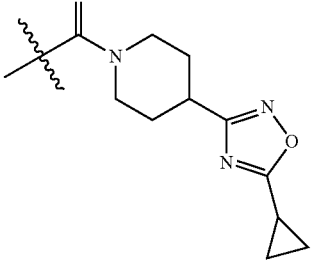
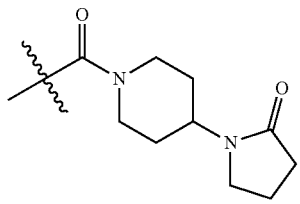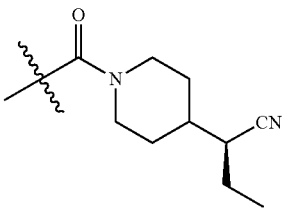
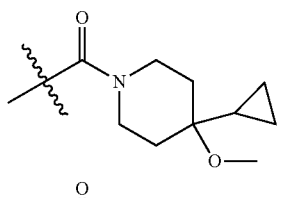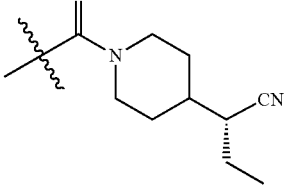
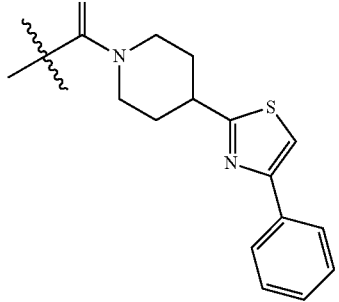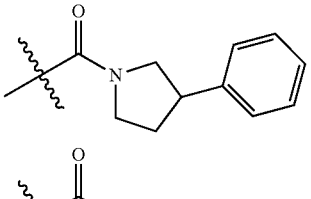
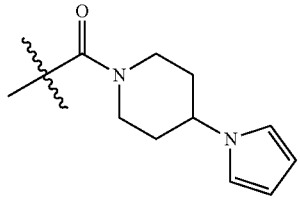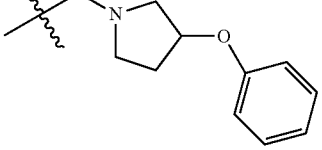

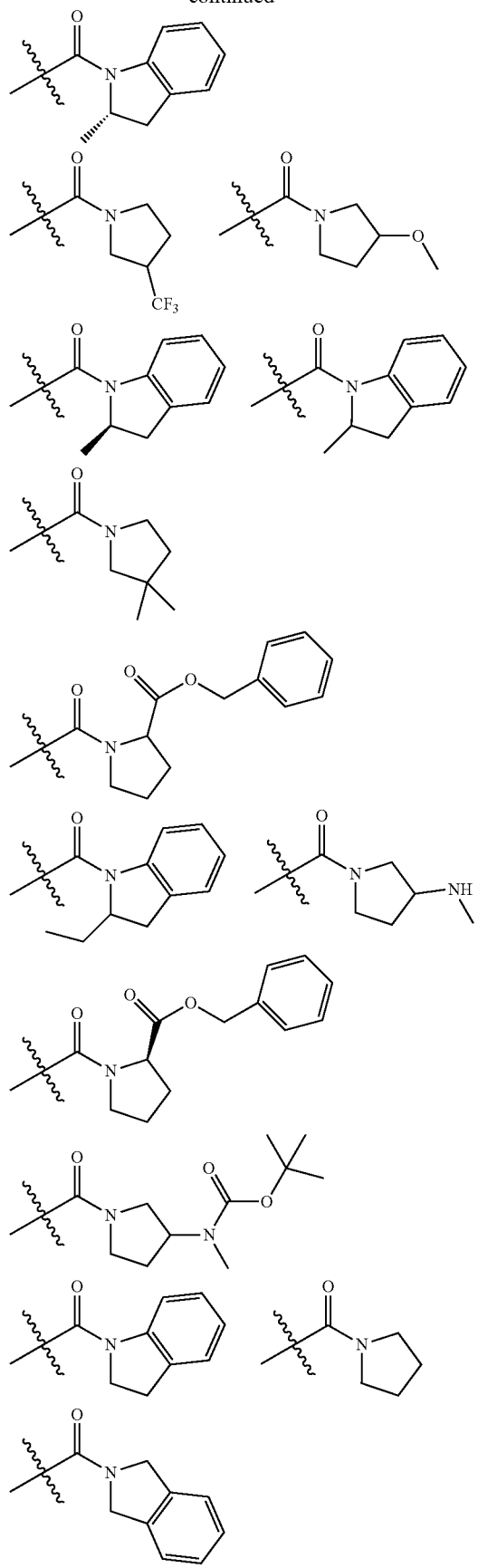
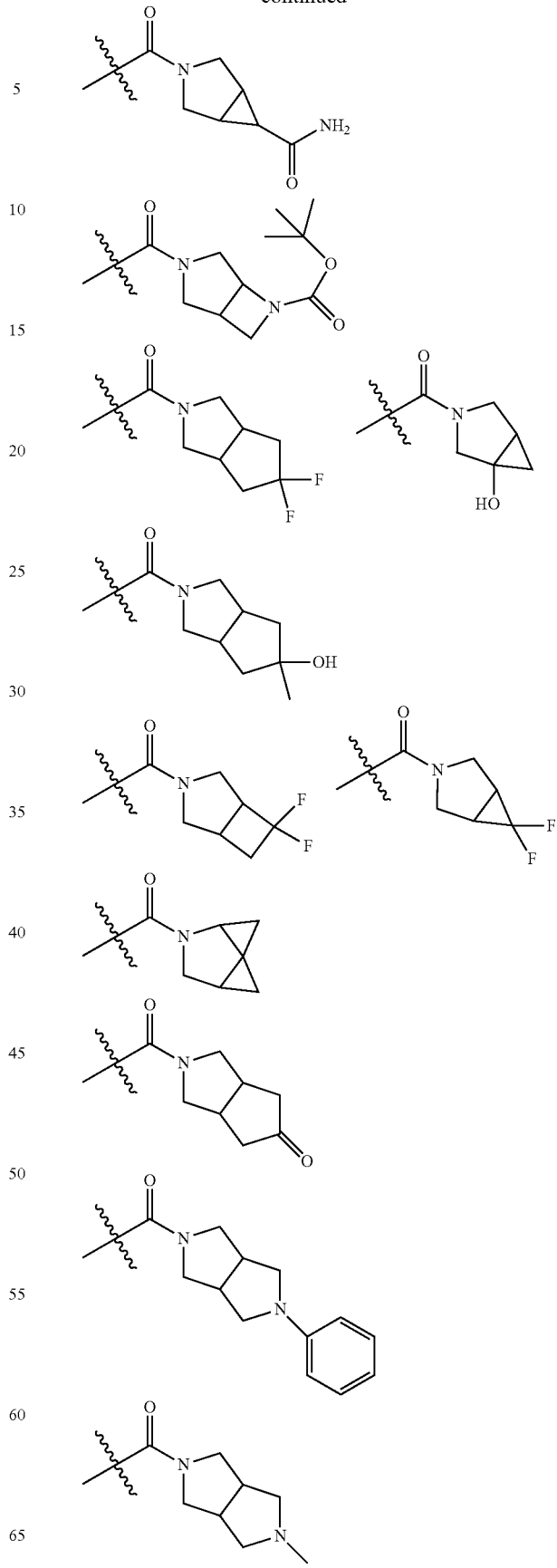

-continued
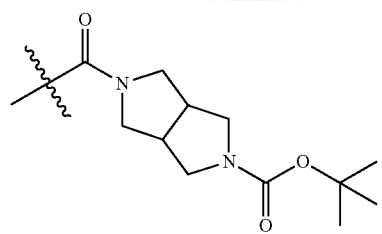
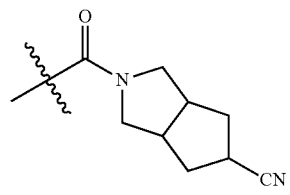
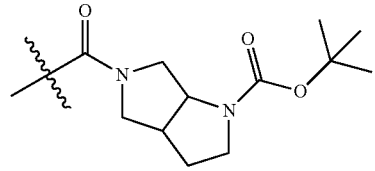
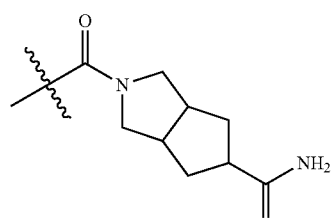
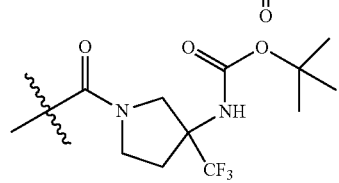
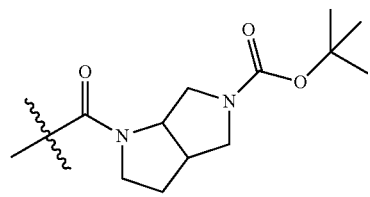
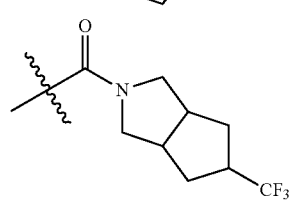
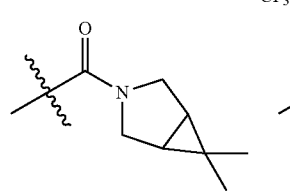
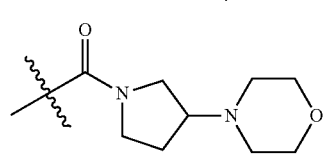
-continued
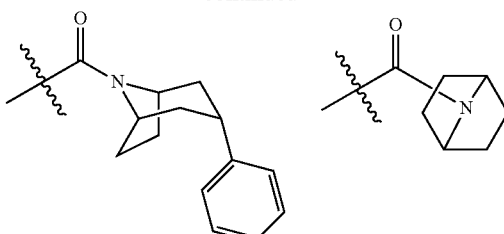
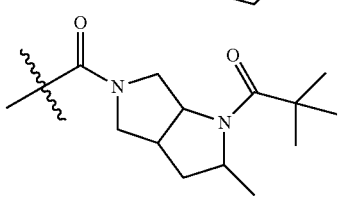
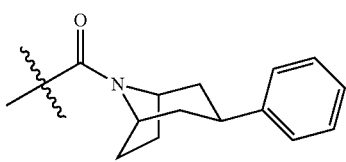
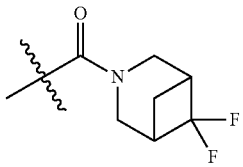
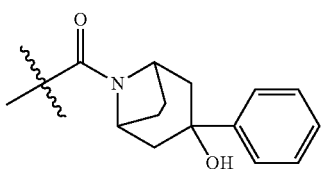
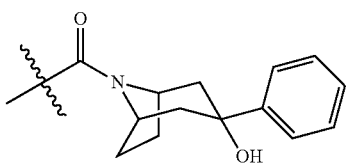
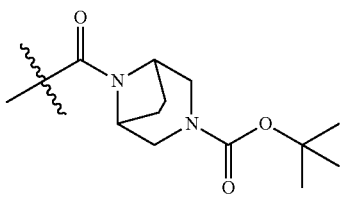
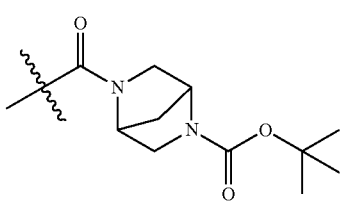
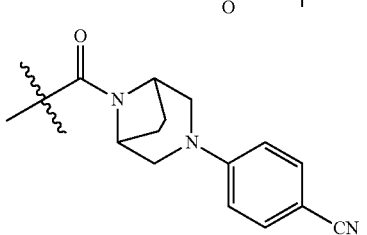

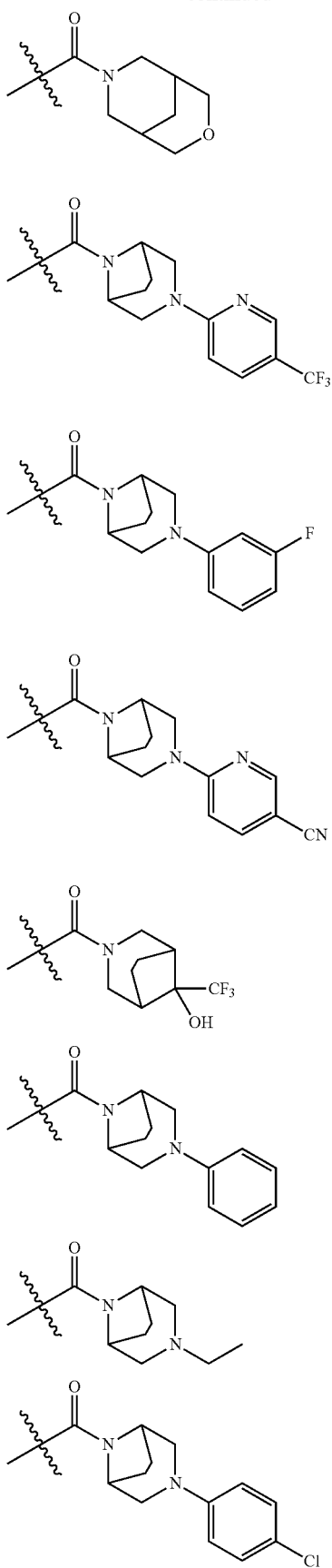
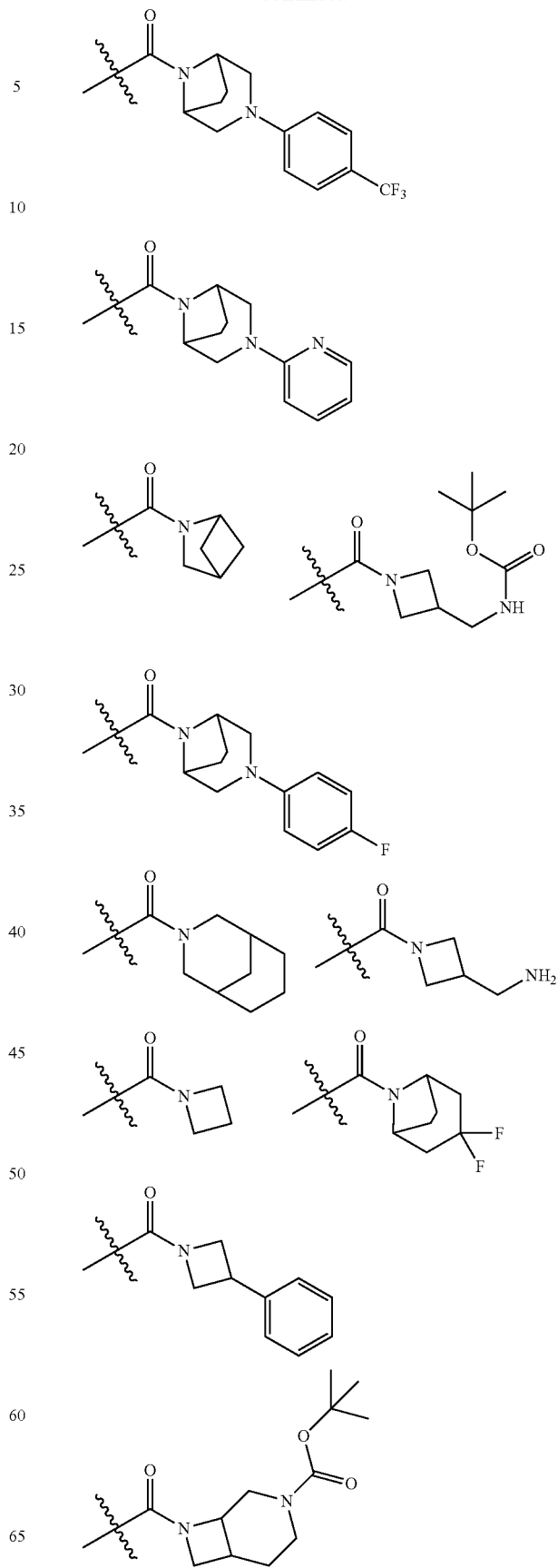

-continued
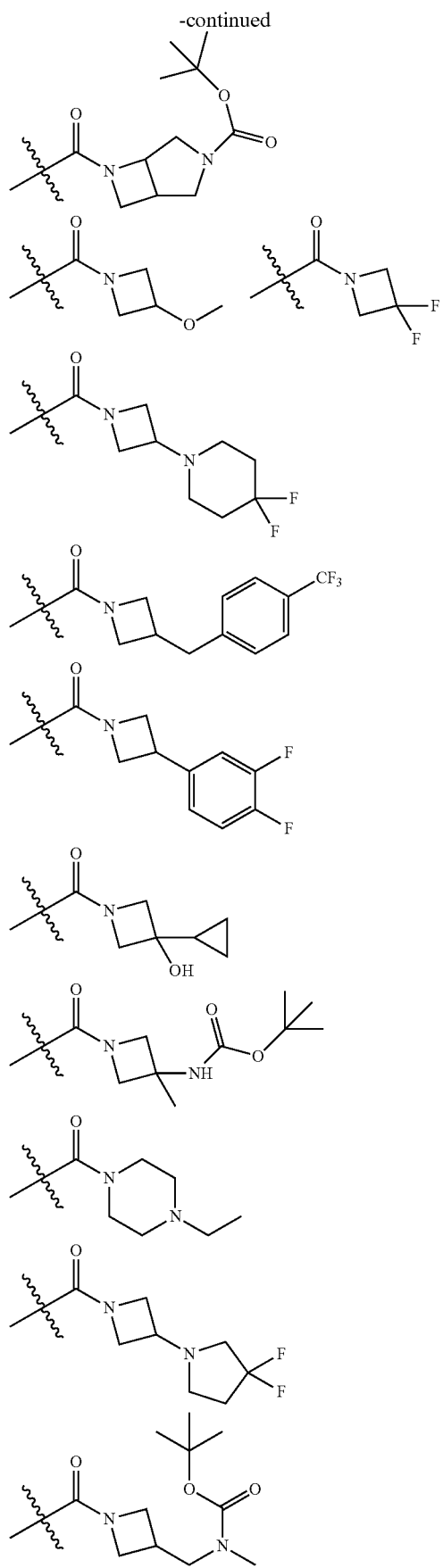
-continued
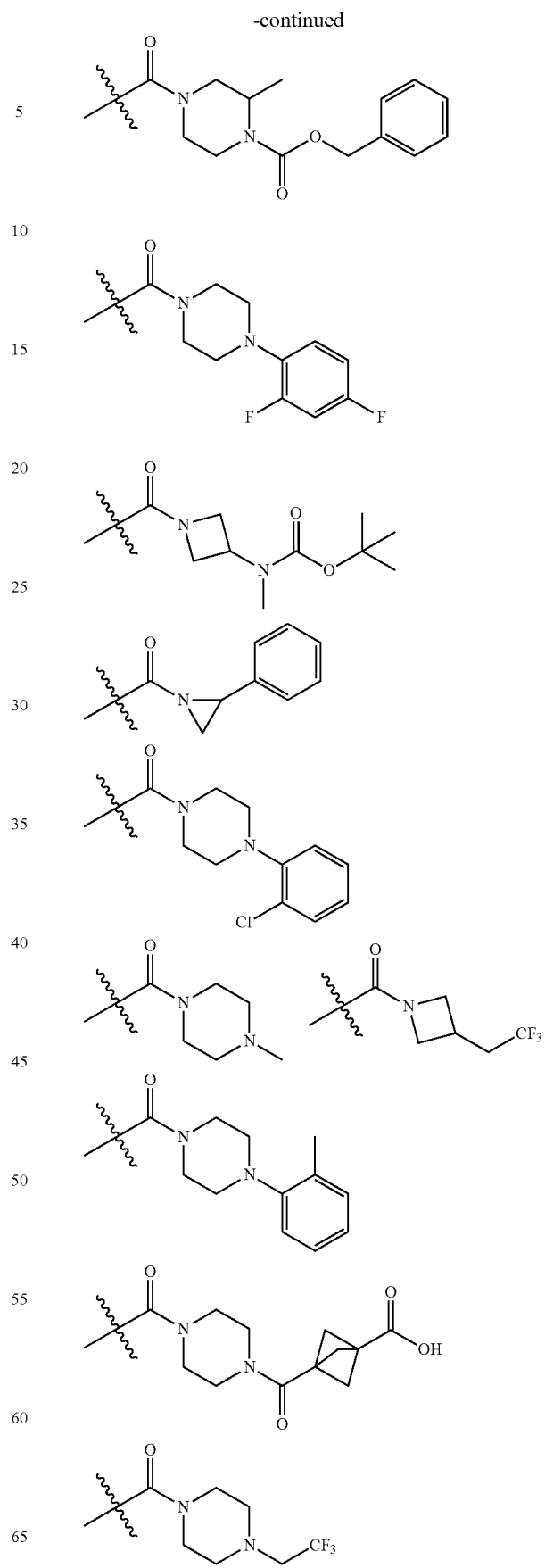

-continued
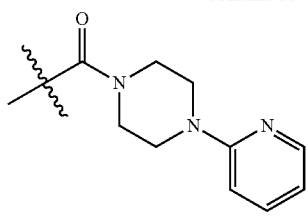
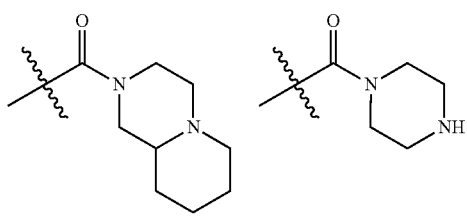
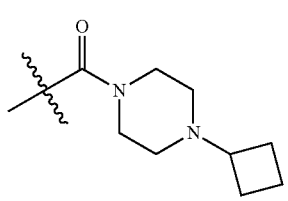
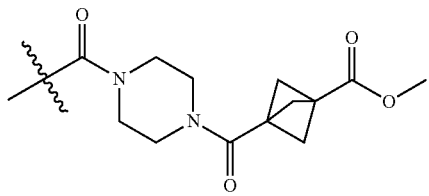
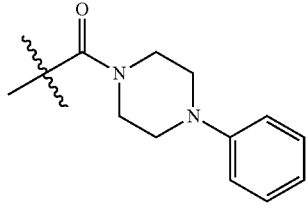
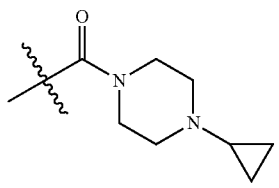
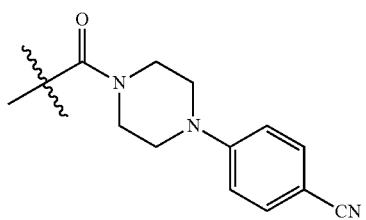
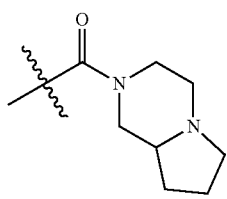
-continued
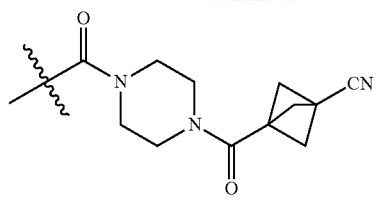
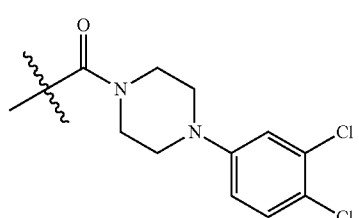
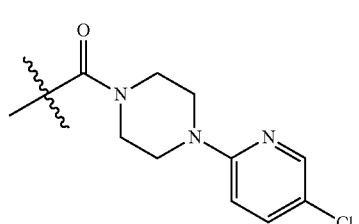
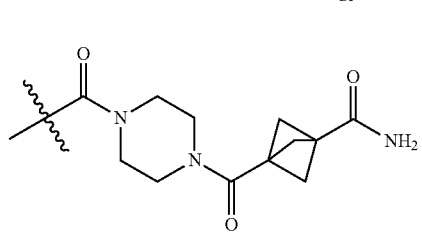
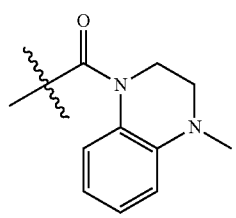
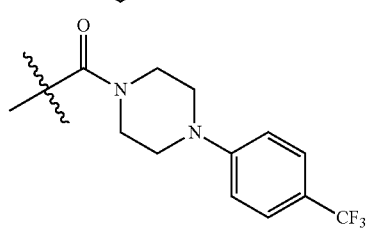
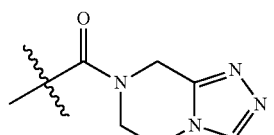
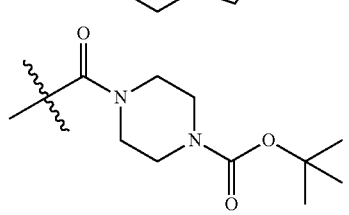

-continued
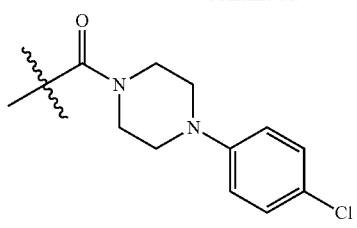
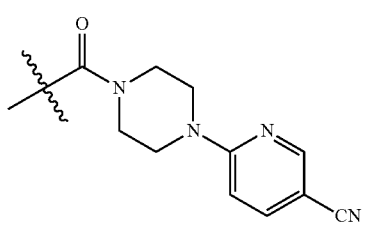
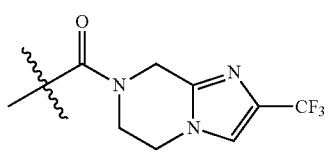
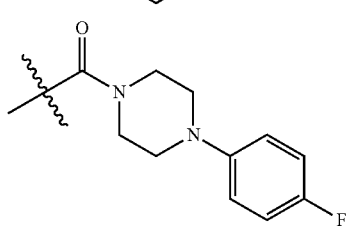
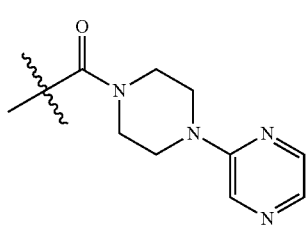
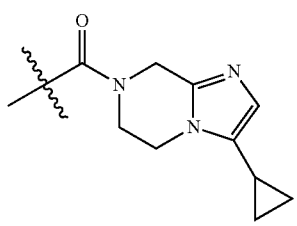
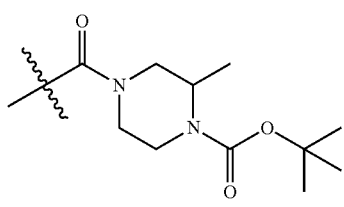
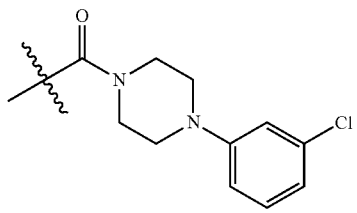
-continued
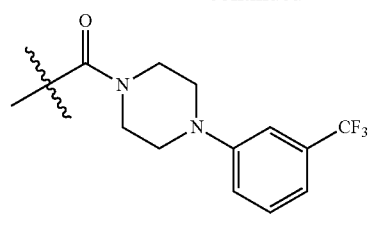
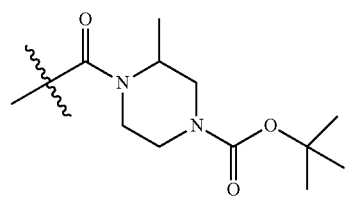
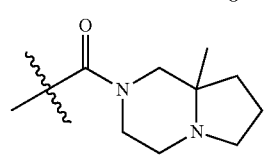
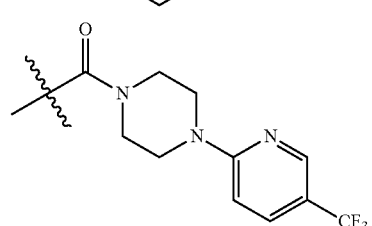
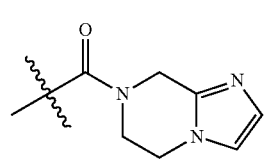
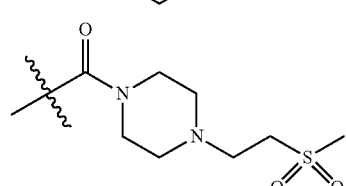
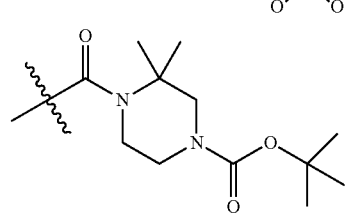
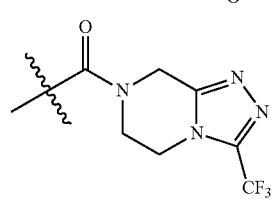
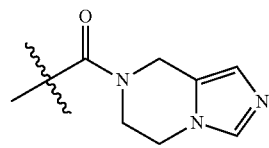

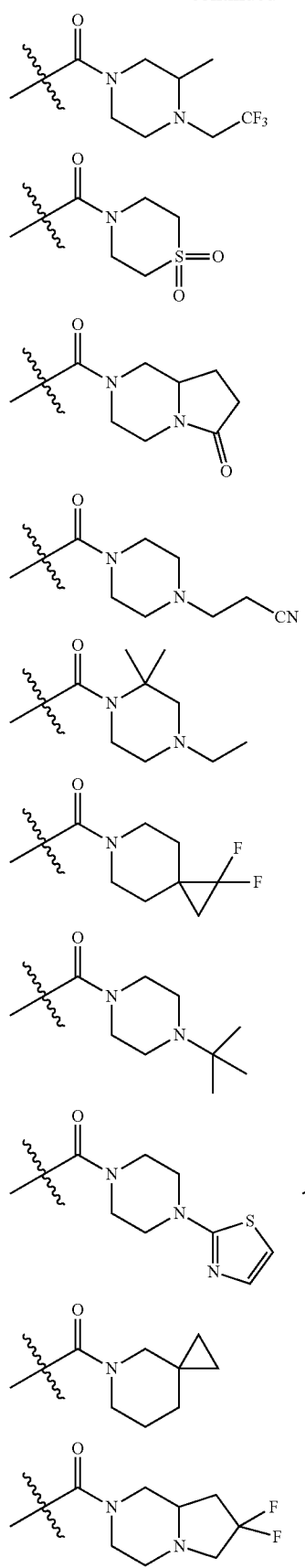
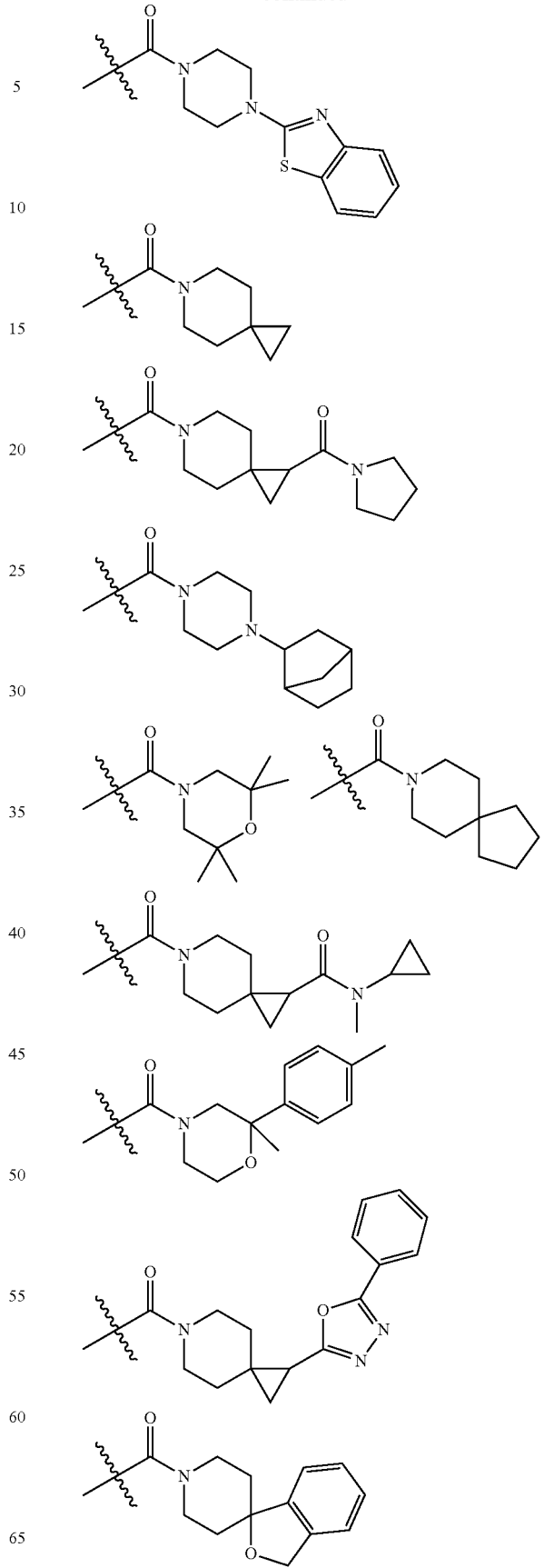

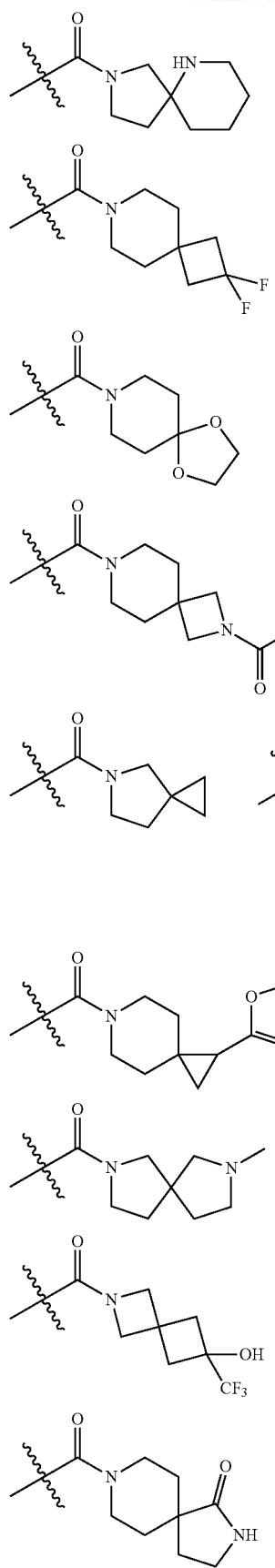
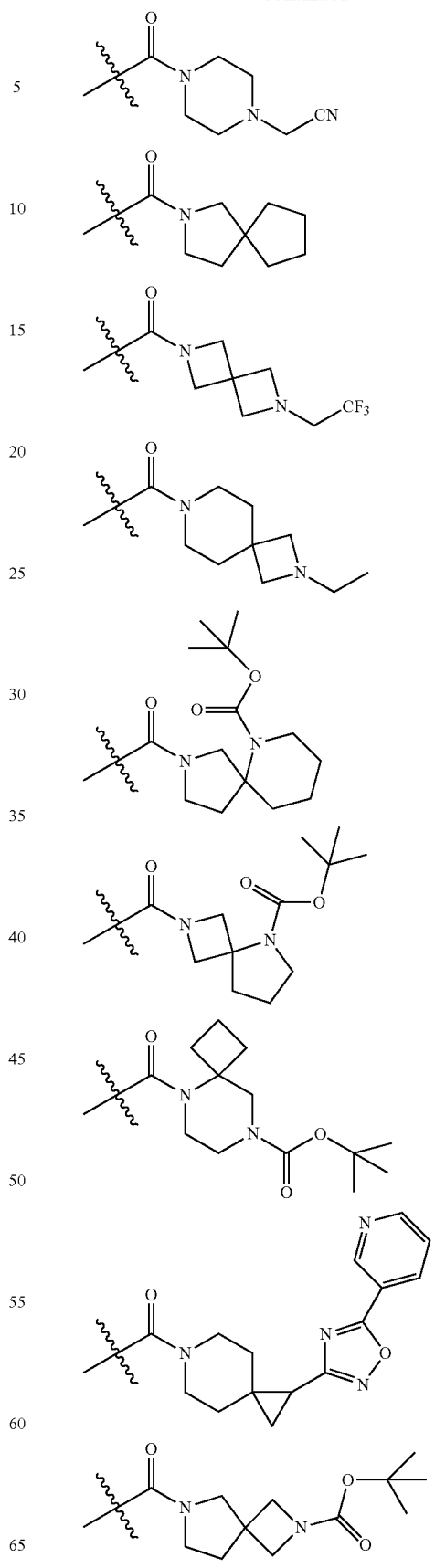

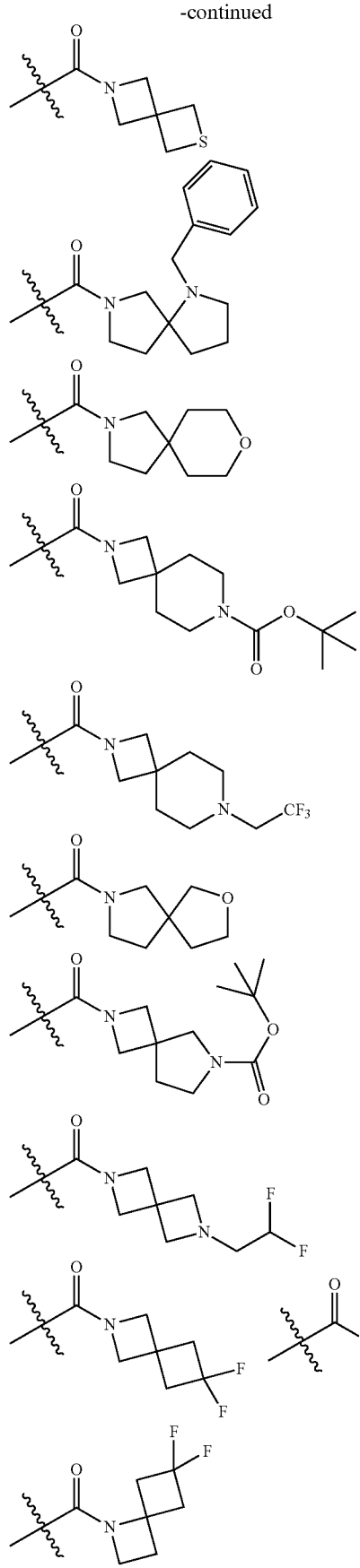
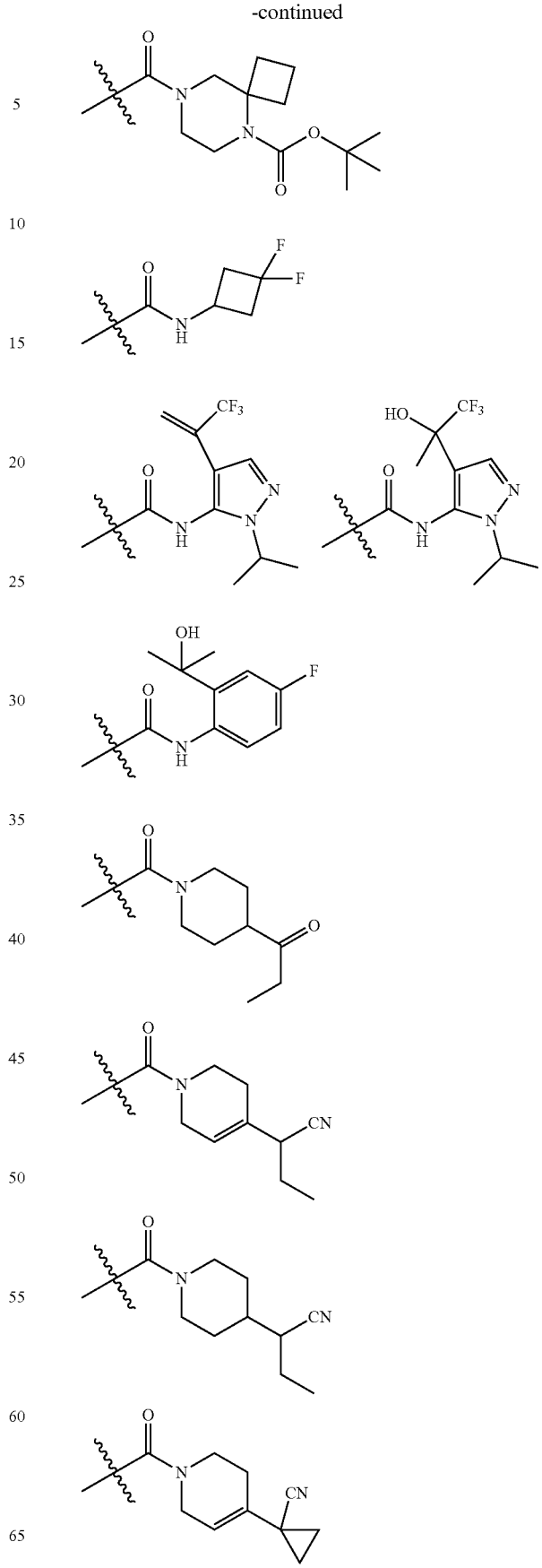

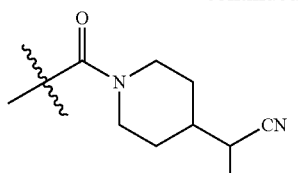
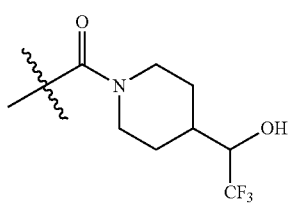
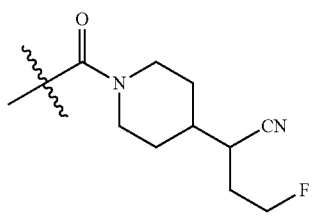
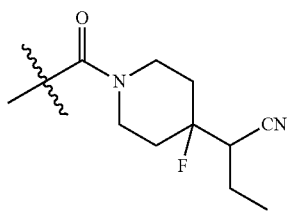
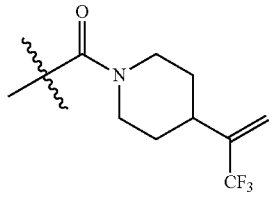
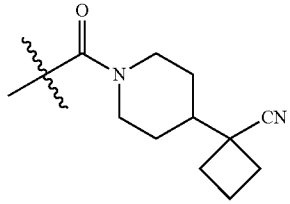
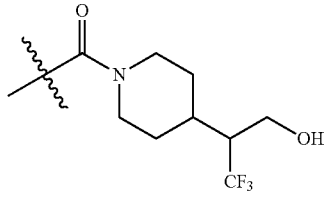
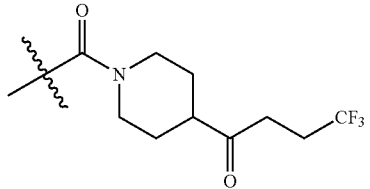
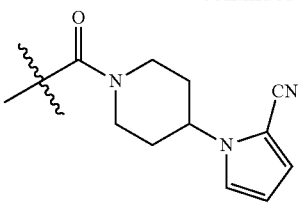
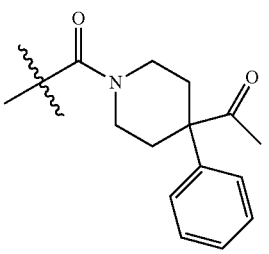
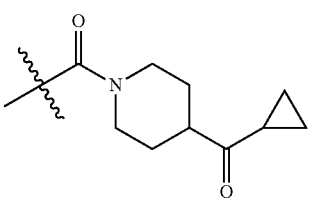
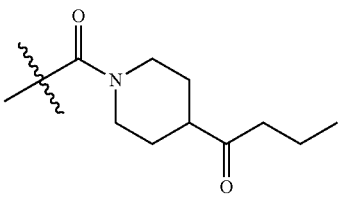
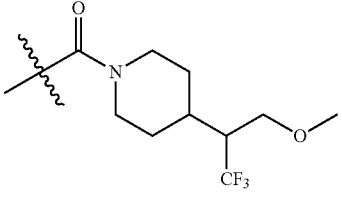
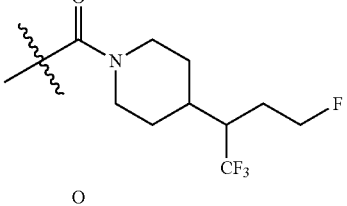
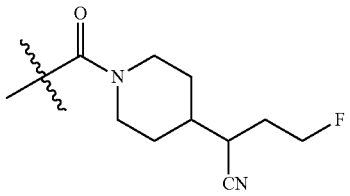
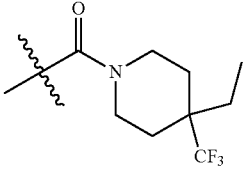

-continued
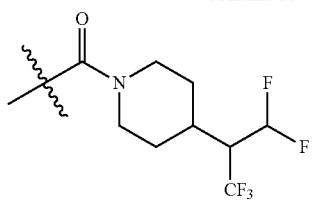
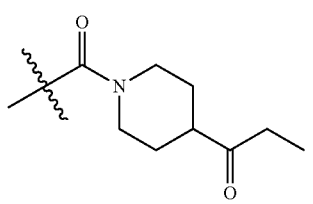
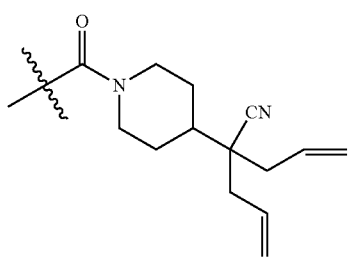
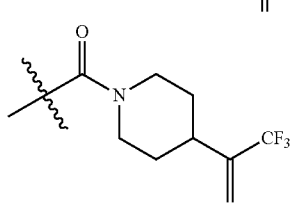
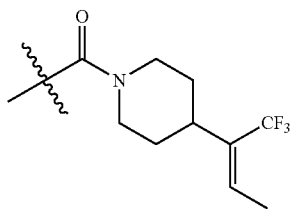
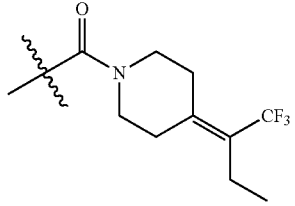
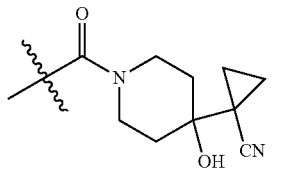
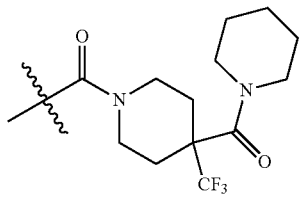
-continued
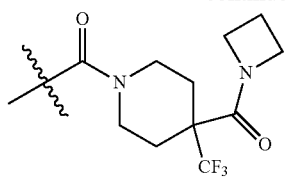
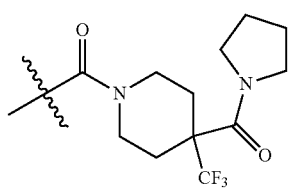
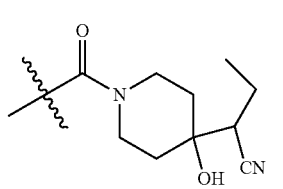
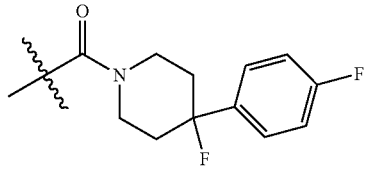
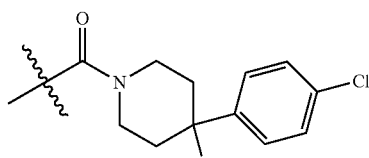
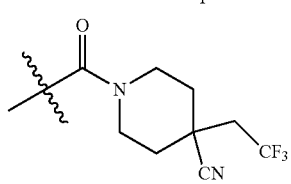
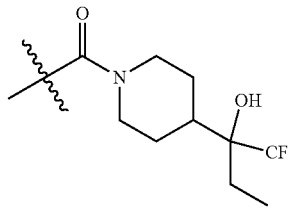
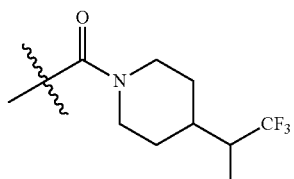
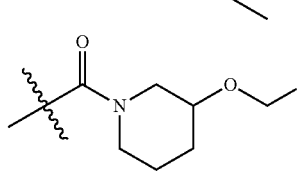

-continued
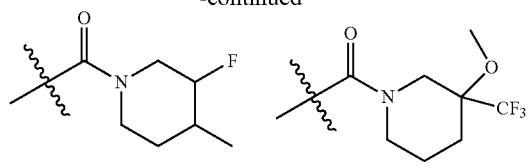
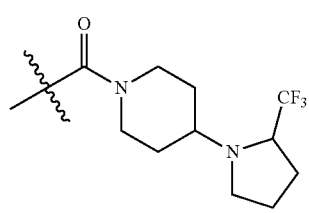
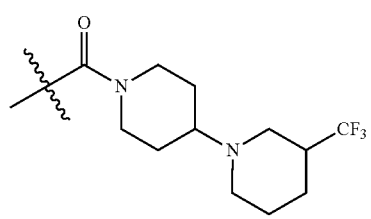
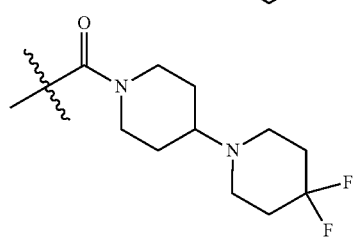
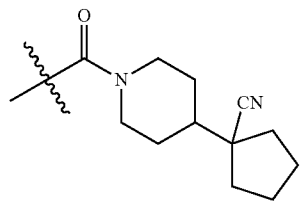
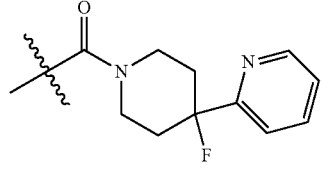
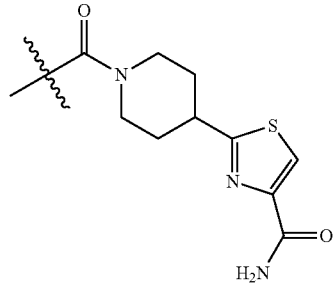
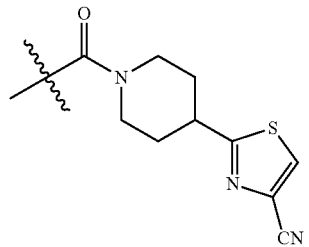
-continued
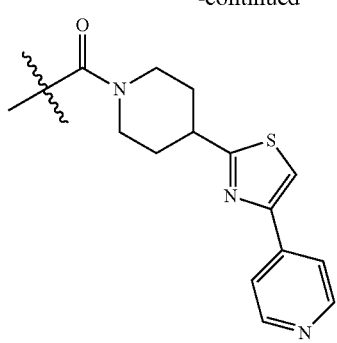
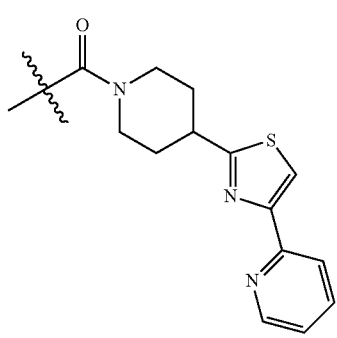
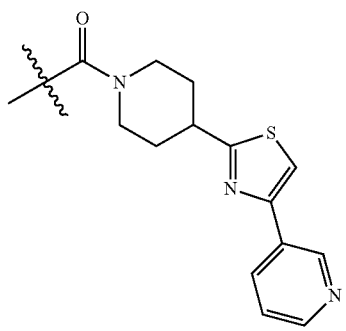
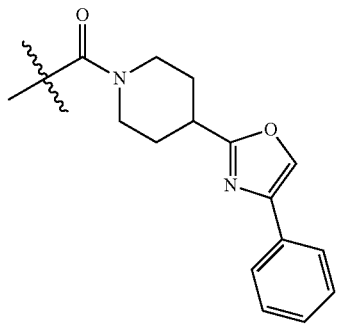
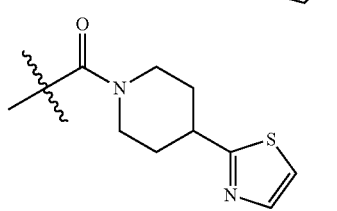

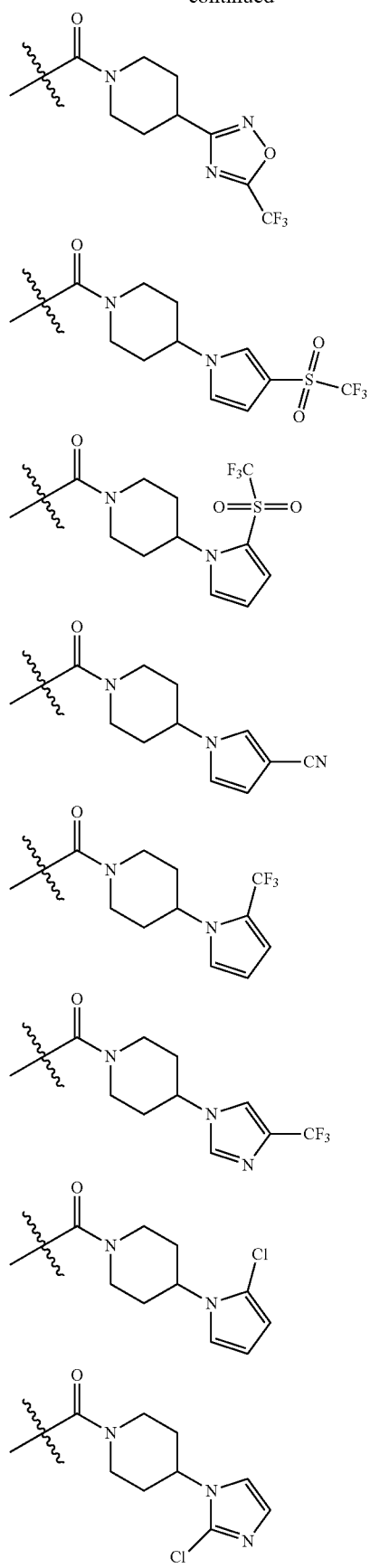
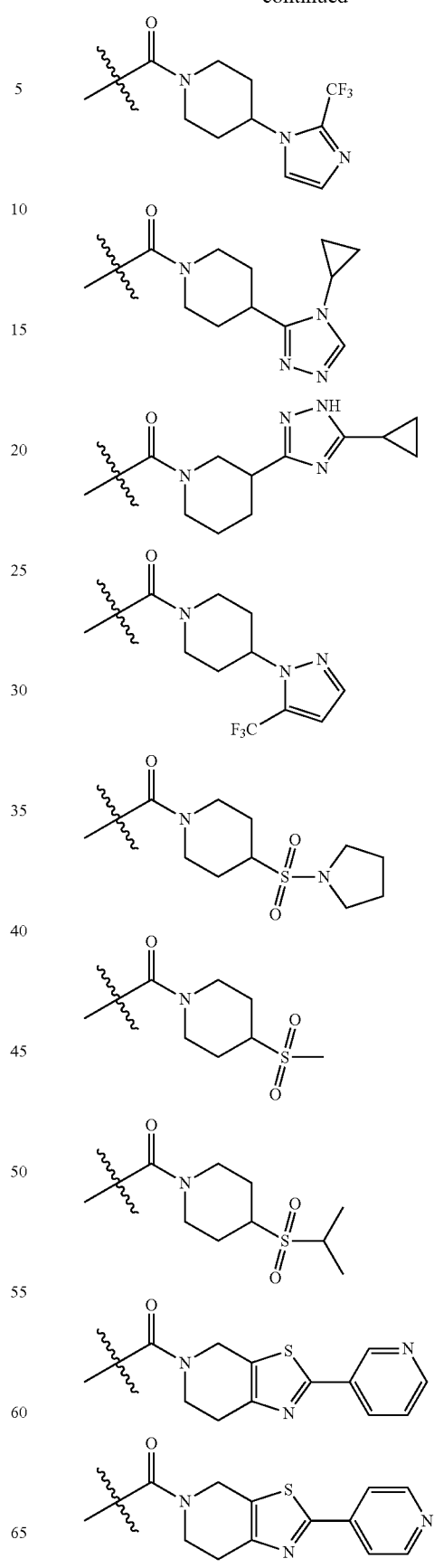

65
-continued
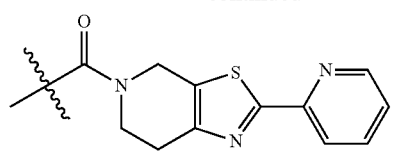
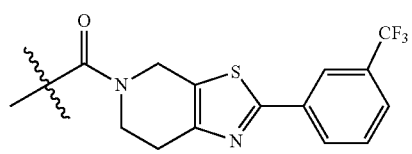
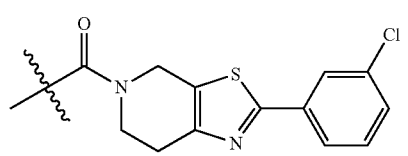
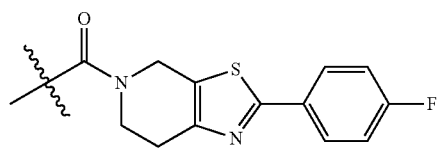
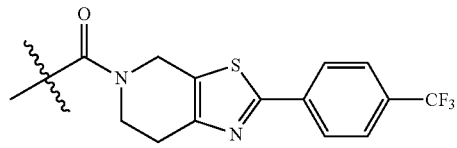
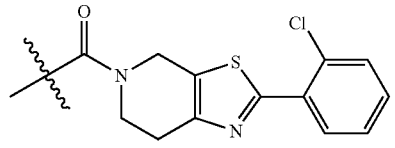
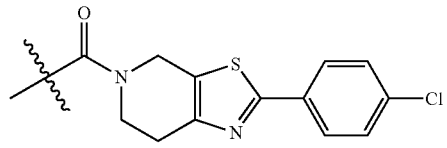
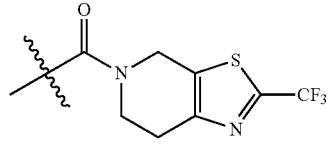
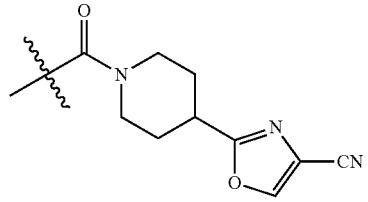
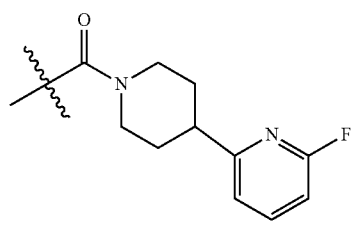
66
-continued
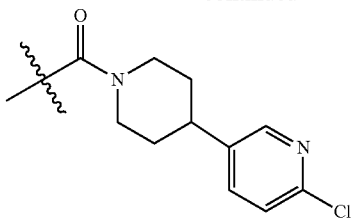
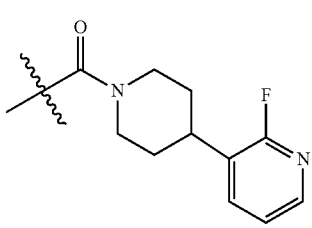
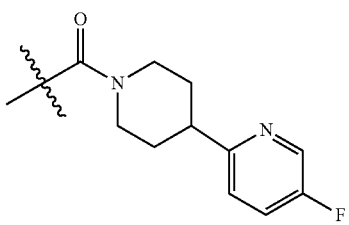
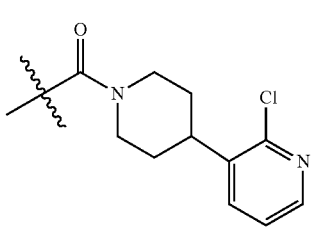
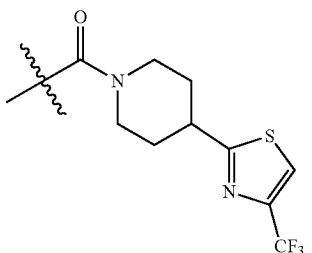
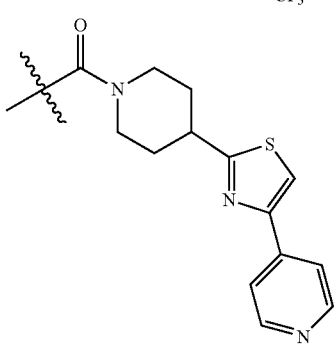

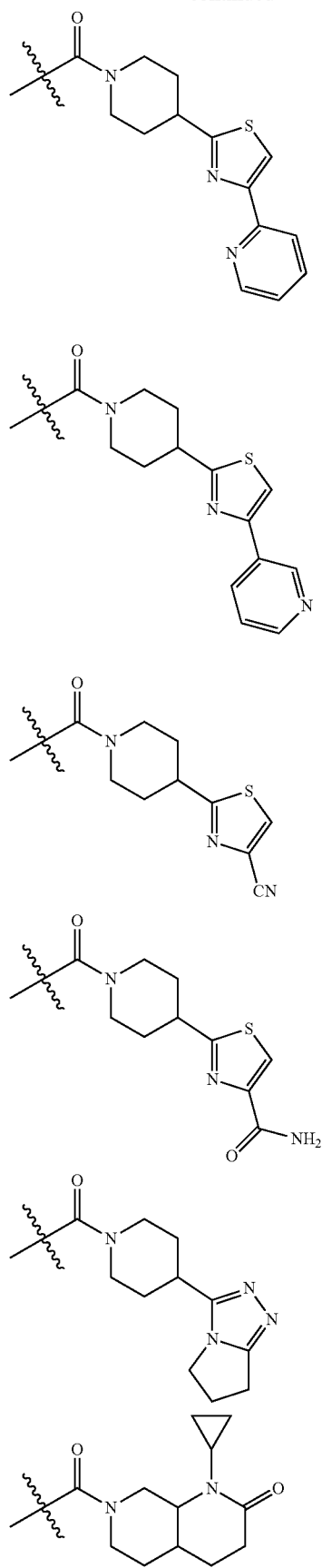
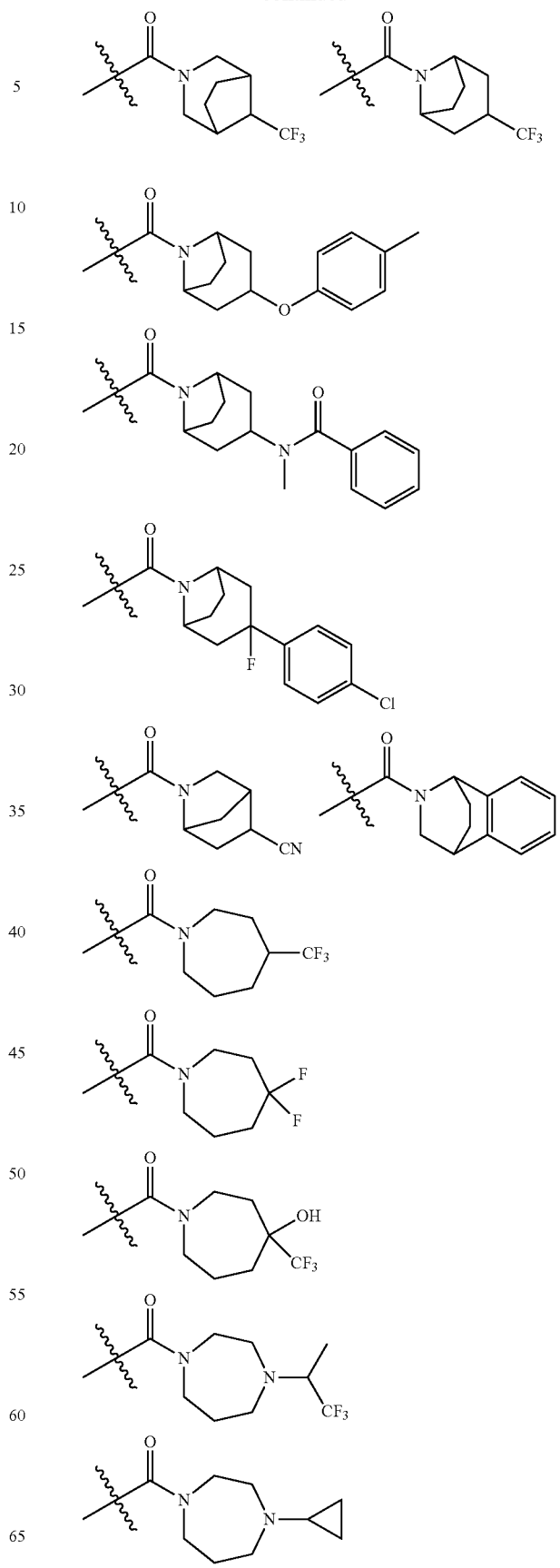

69
-continued
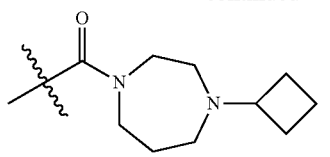
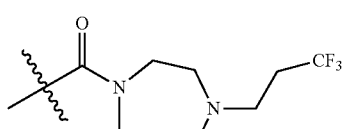
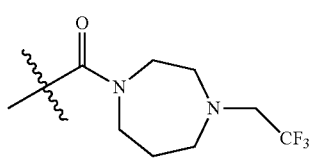
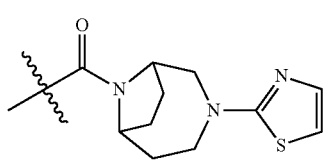
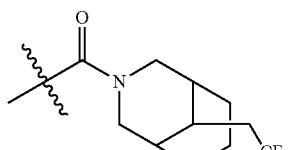
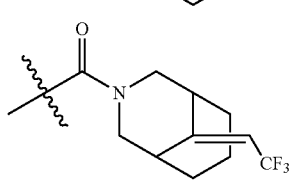
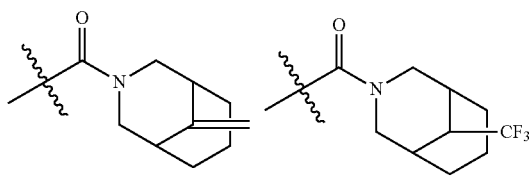
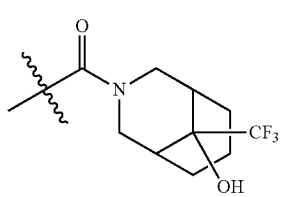
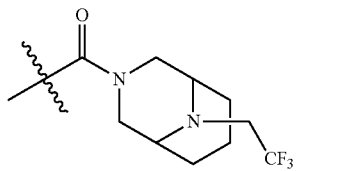
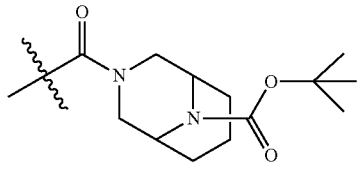
70
-continued
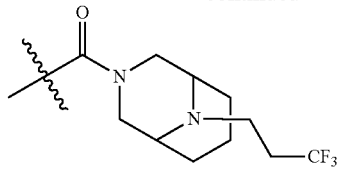
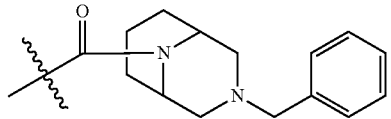
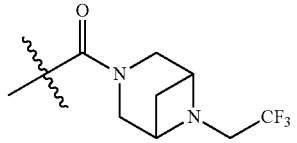
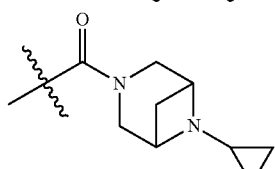
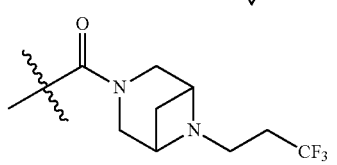
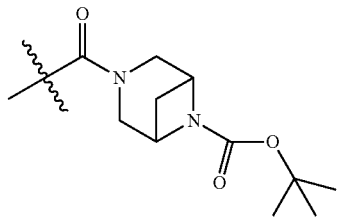
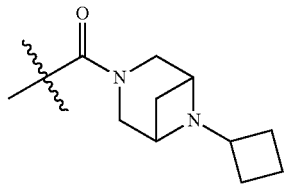
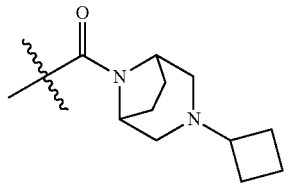
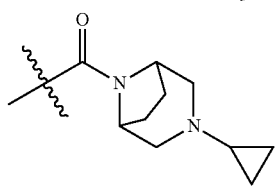
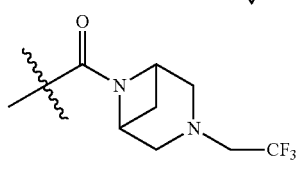

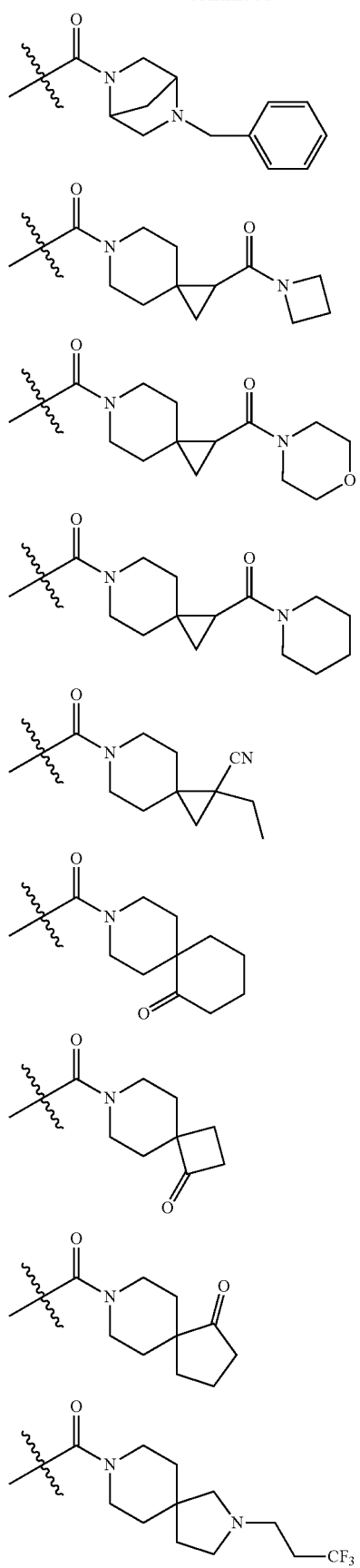
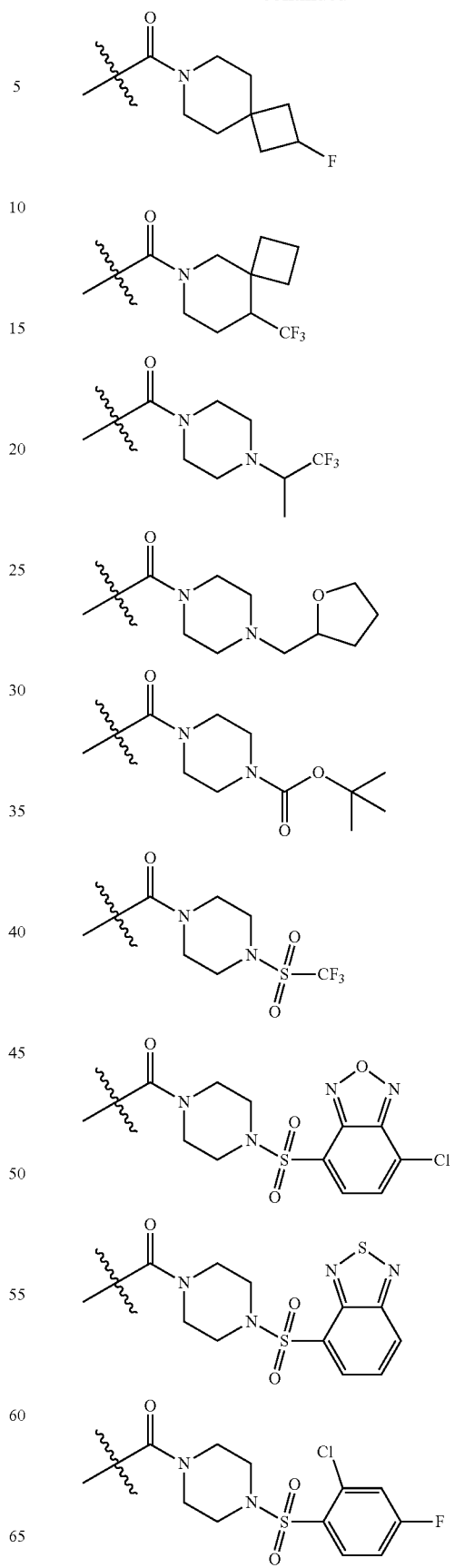

73
-continued
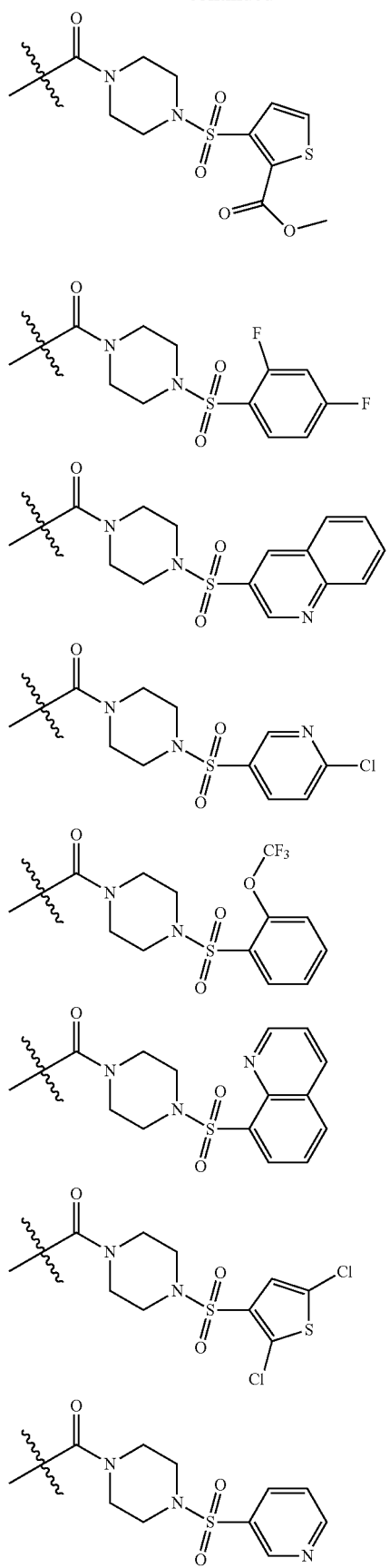
74
-continued
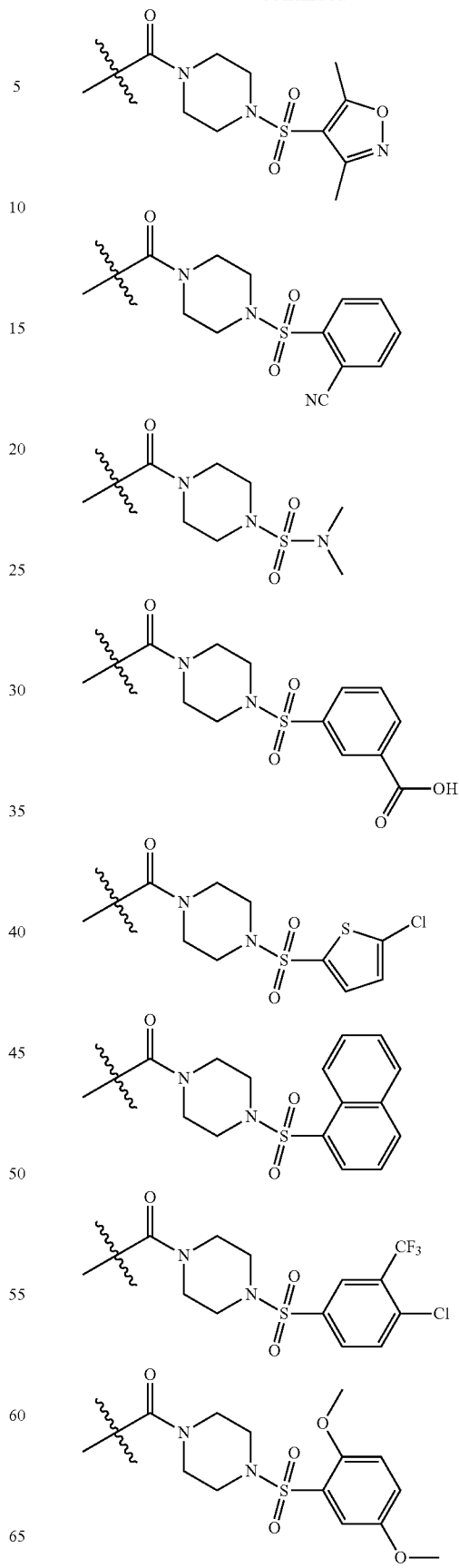

75
-continued
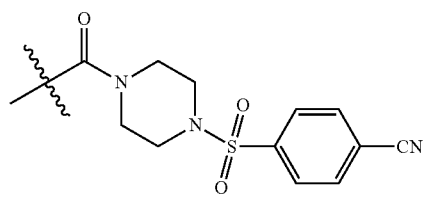
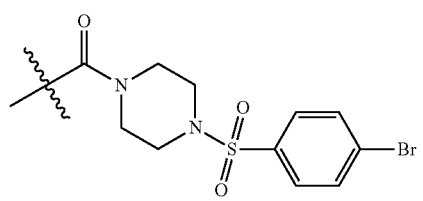
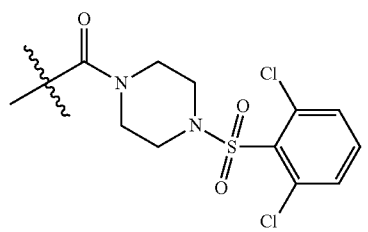
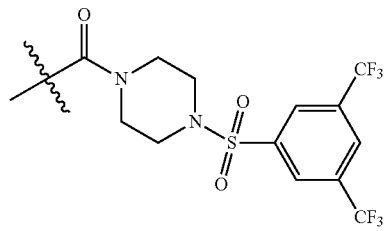
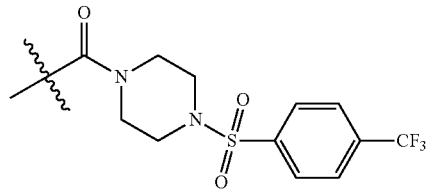
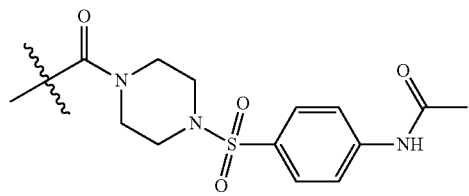
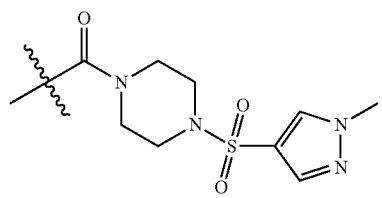
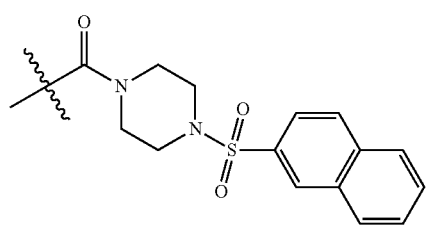
76
-continued
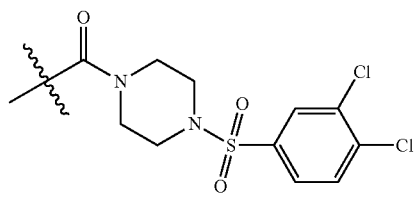
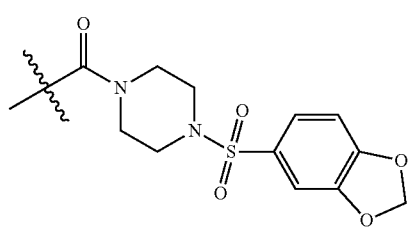
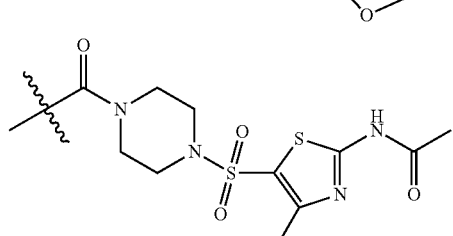
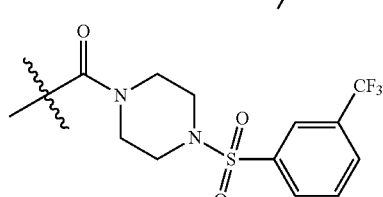
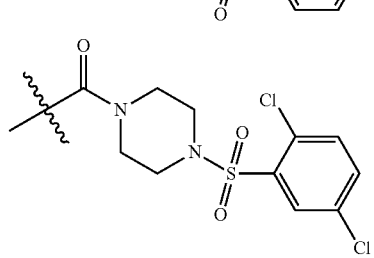
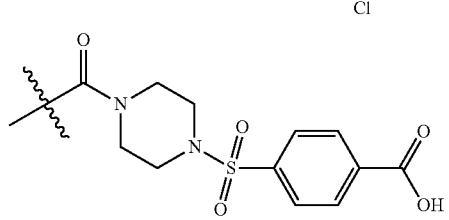
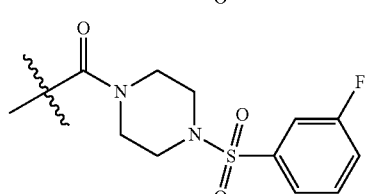
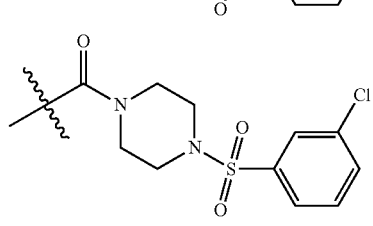

77
-continued
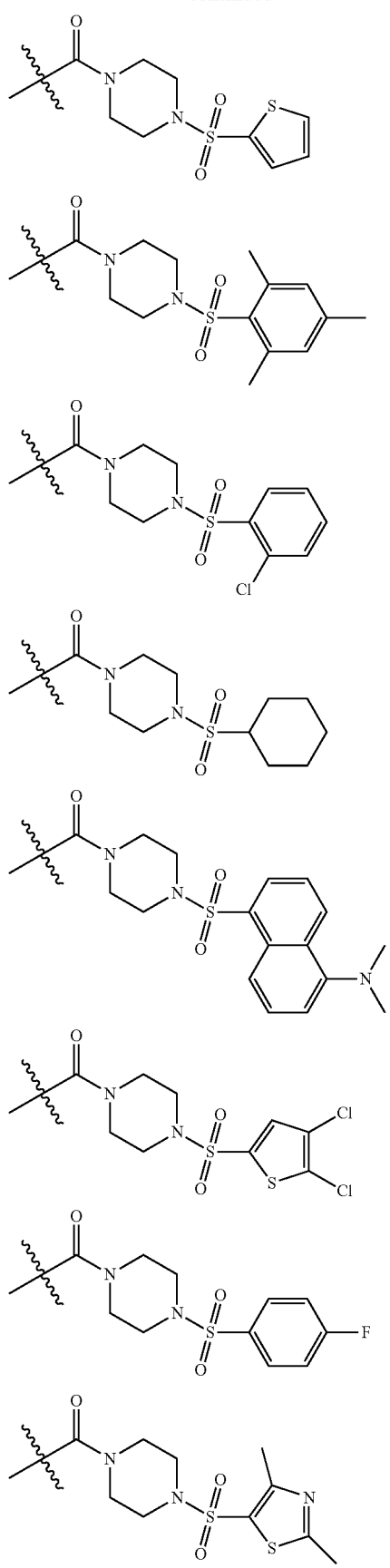
78
-continued
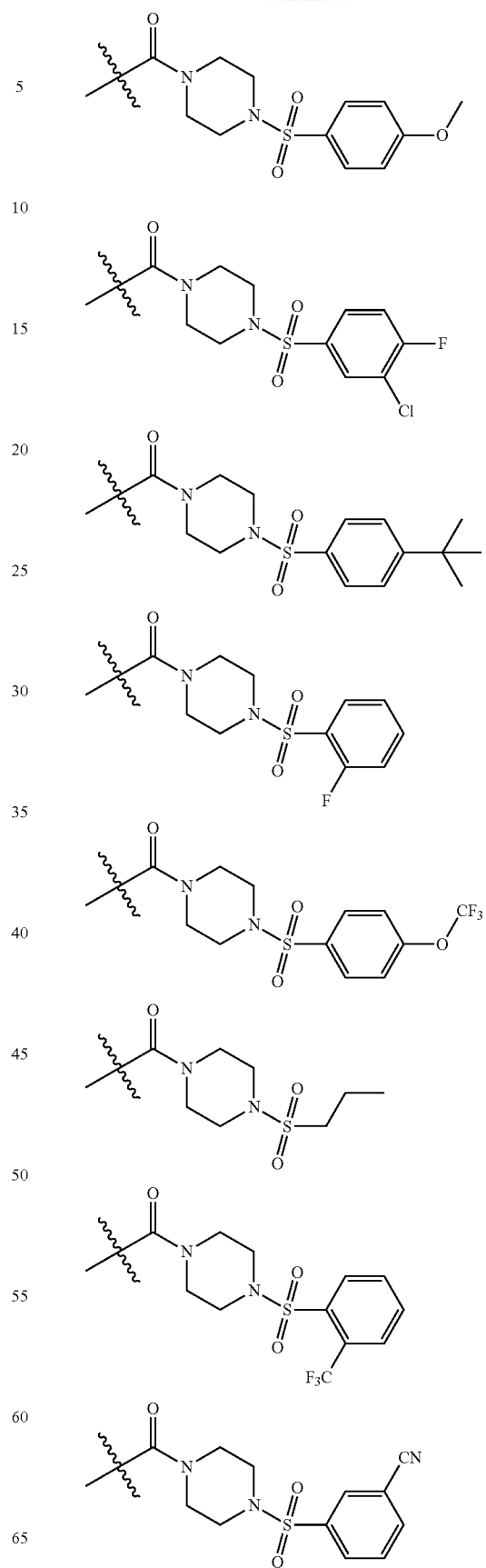

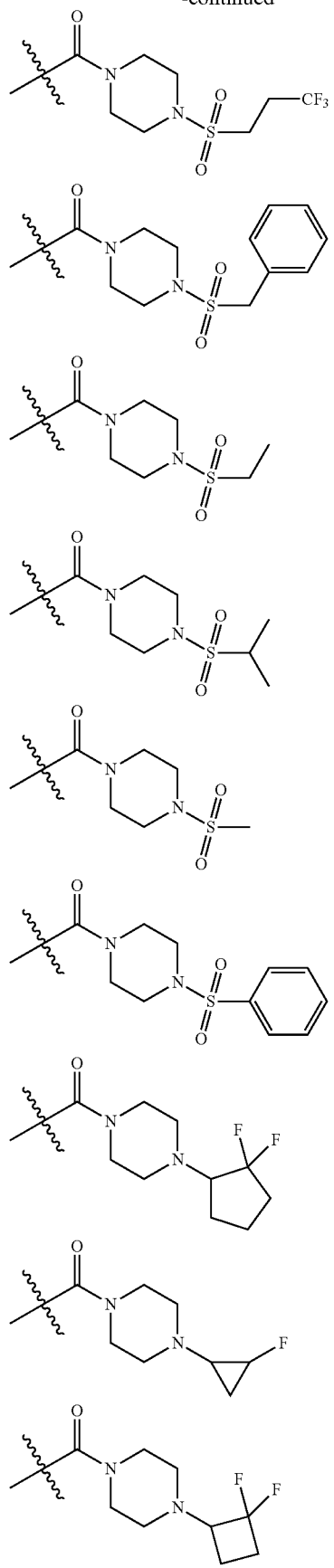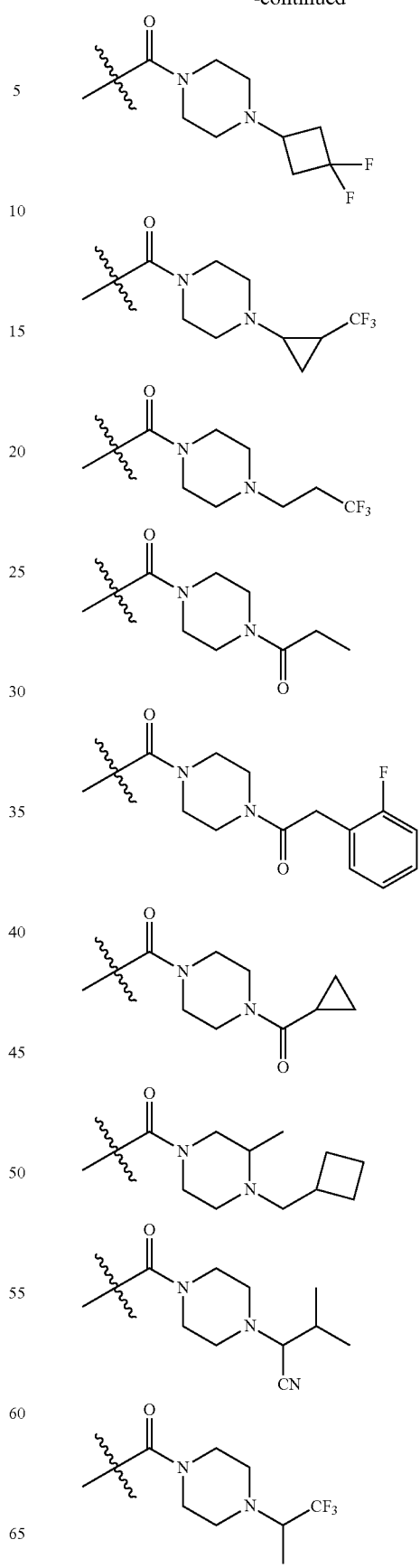

81
-continued
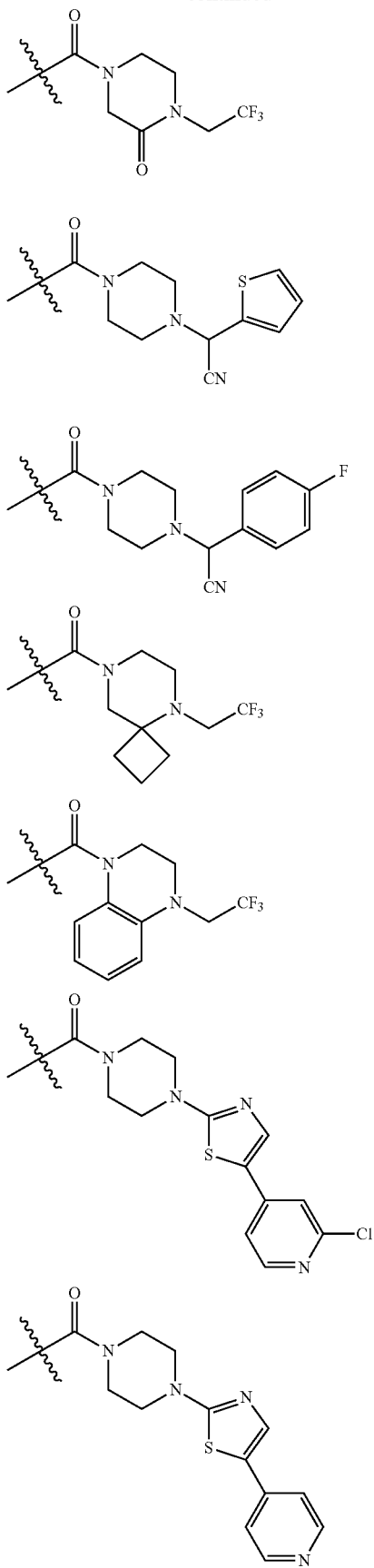
82
-continued
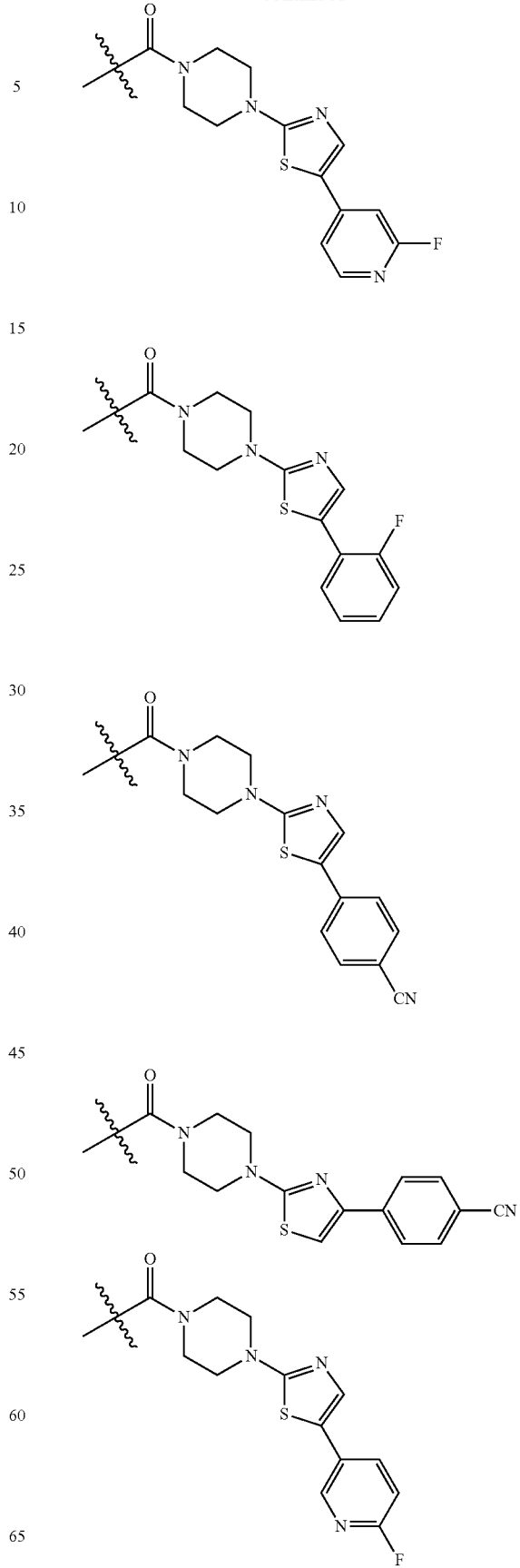

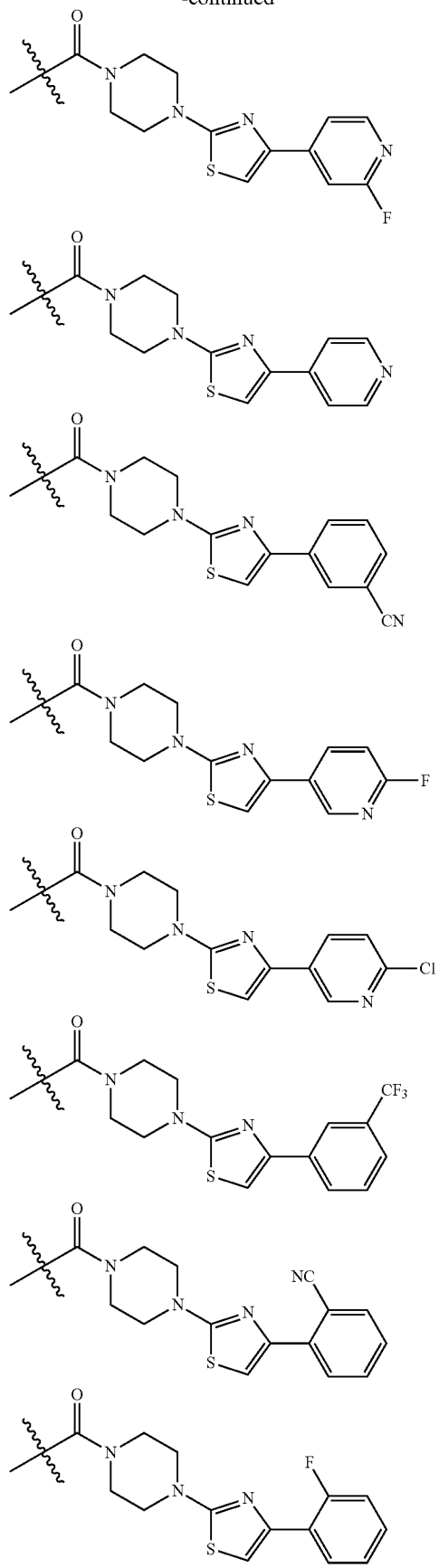
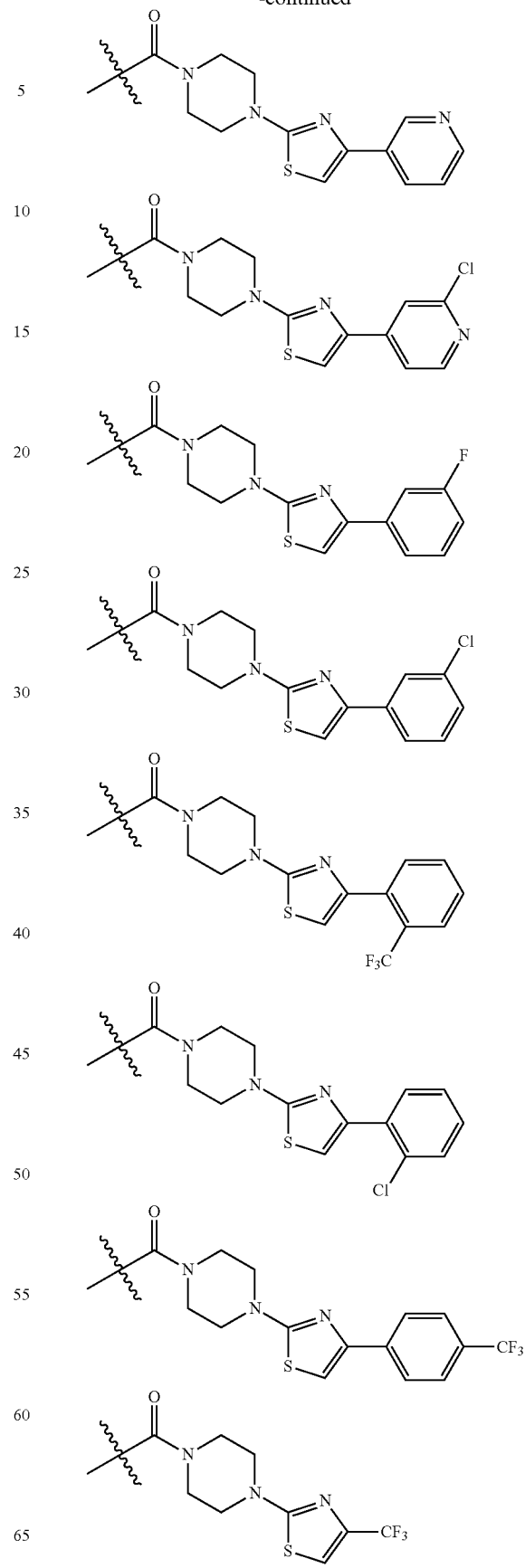

85
-continued
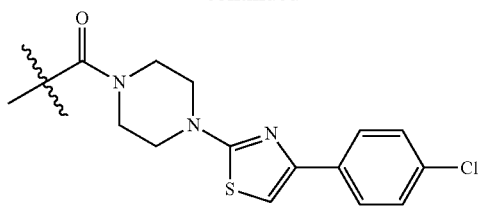
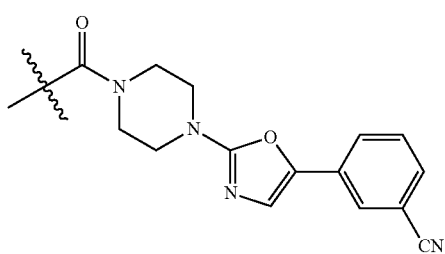
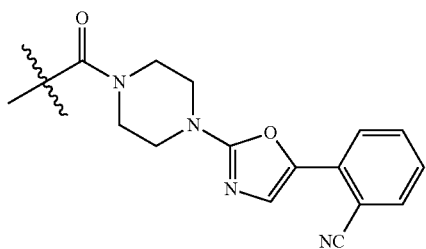
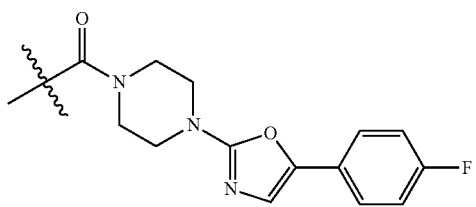
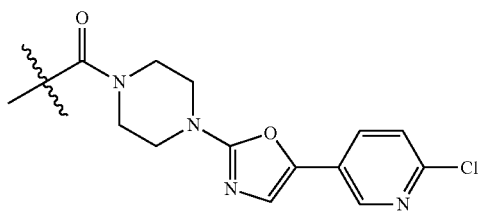
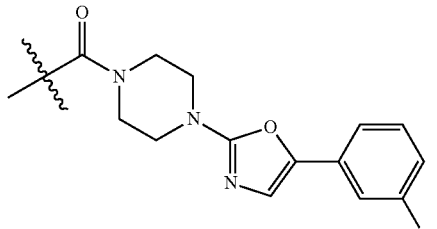
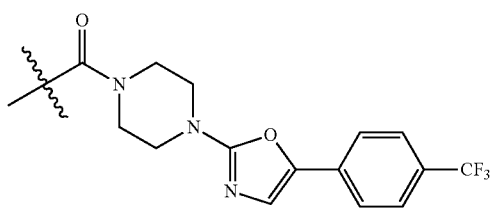
86
-continued
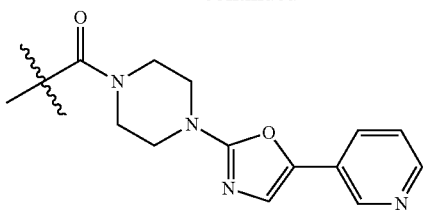
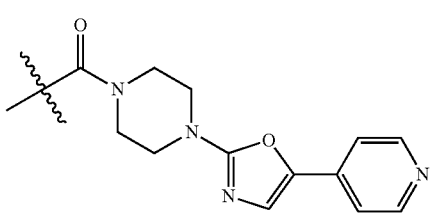
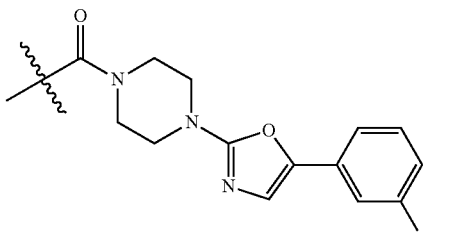
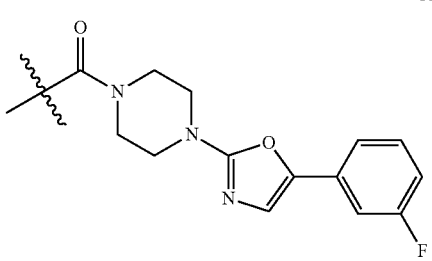
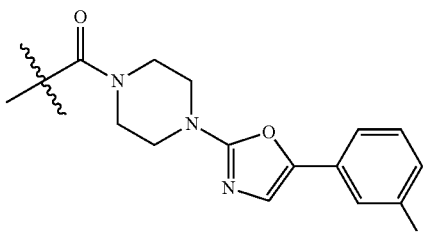
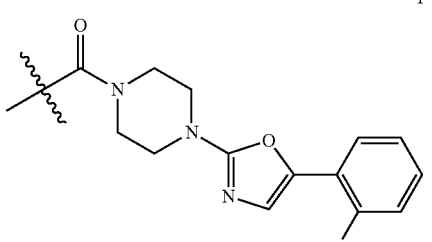
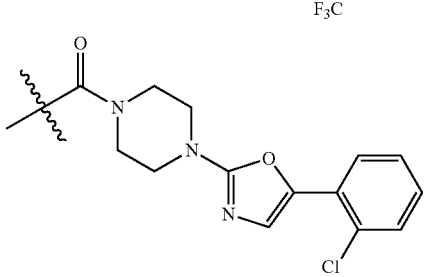

87
-continued
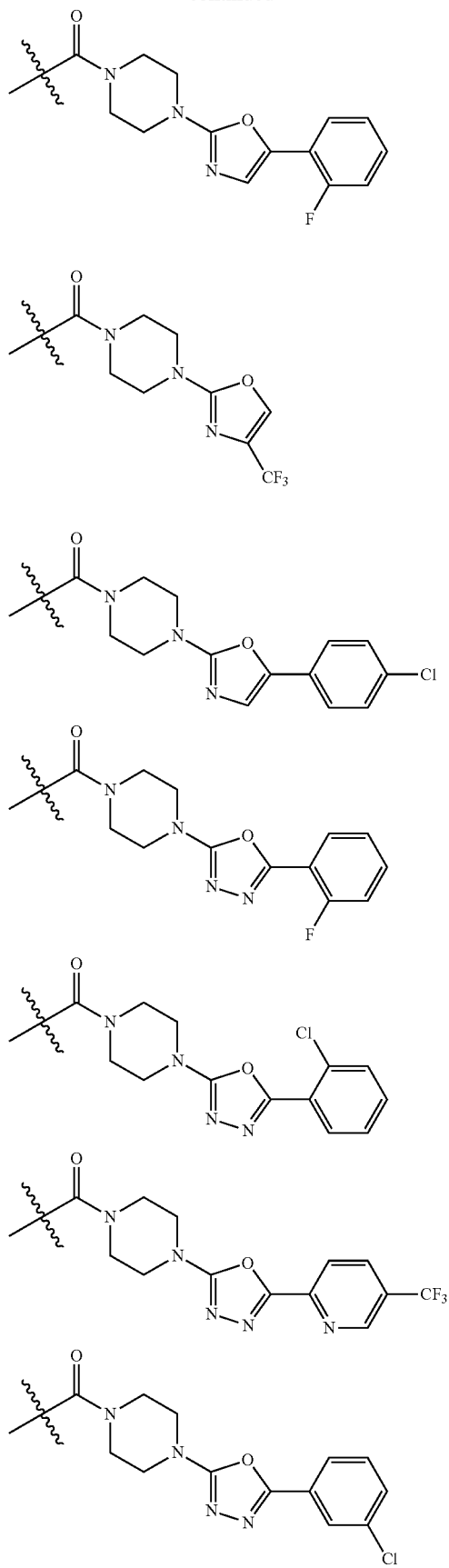
88
-continued
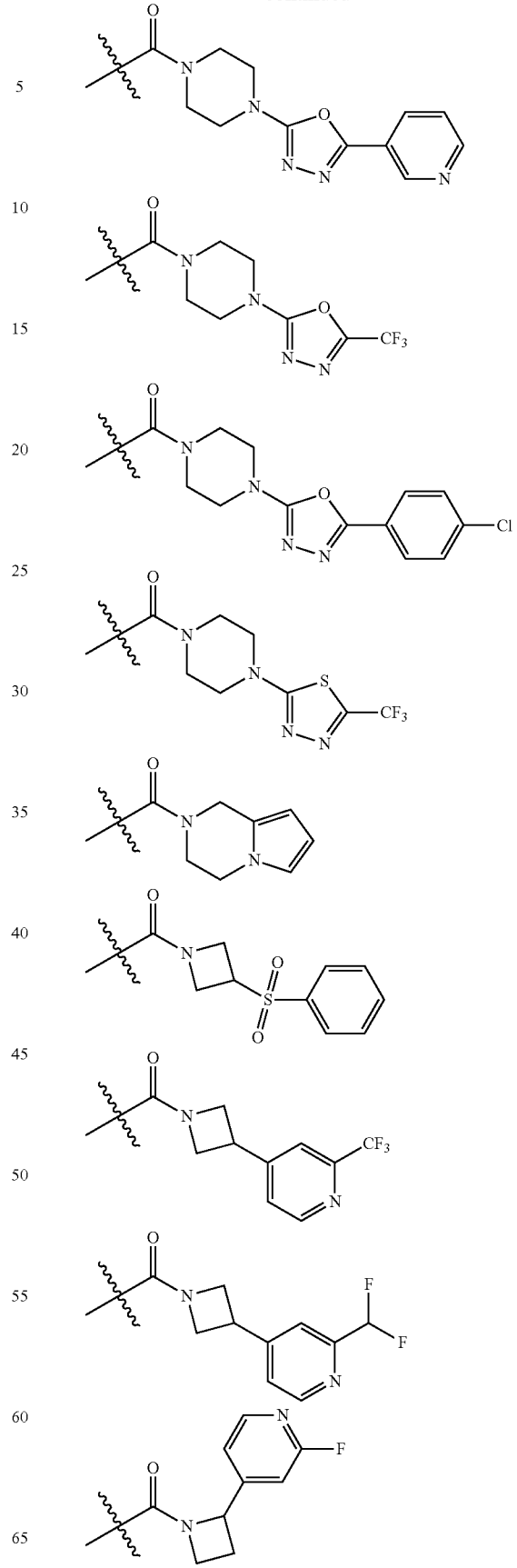

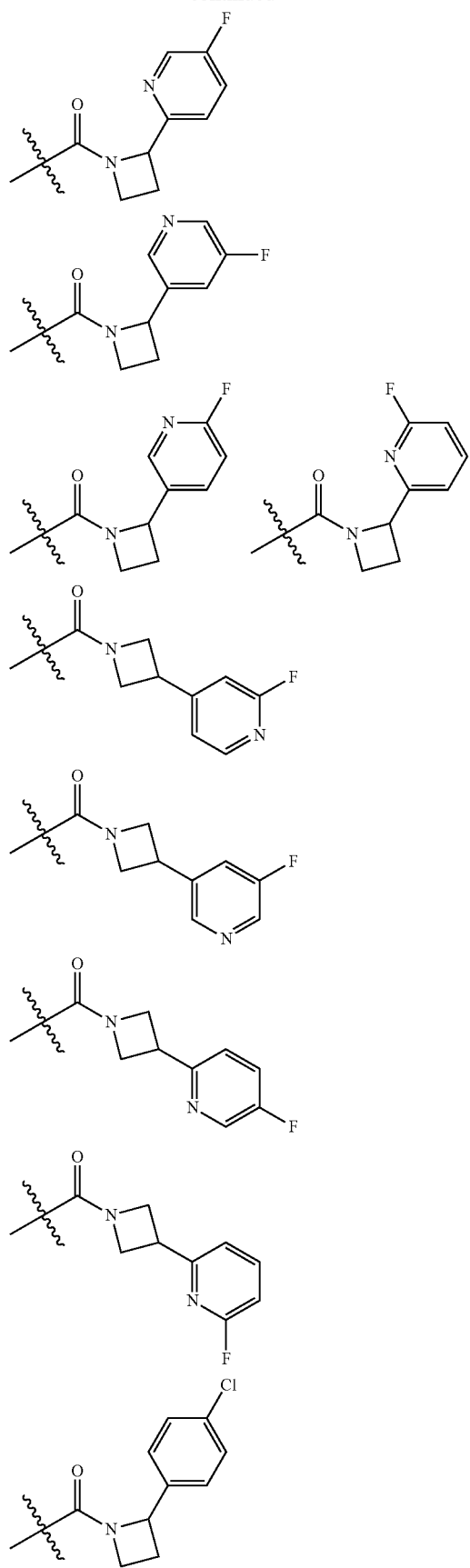
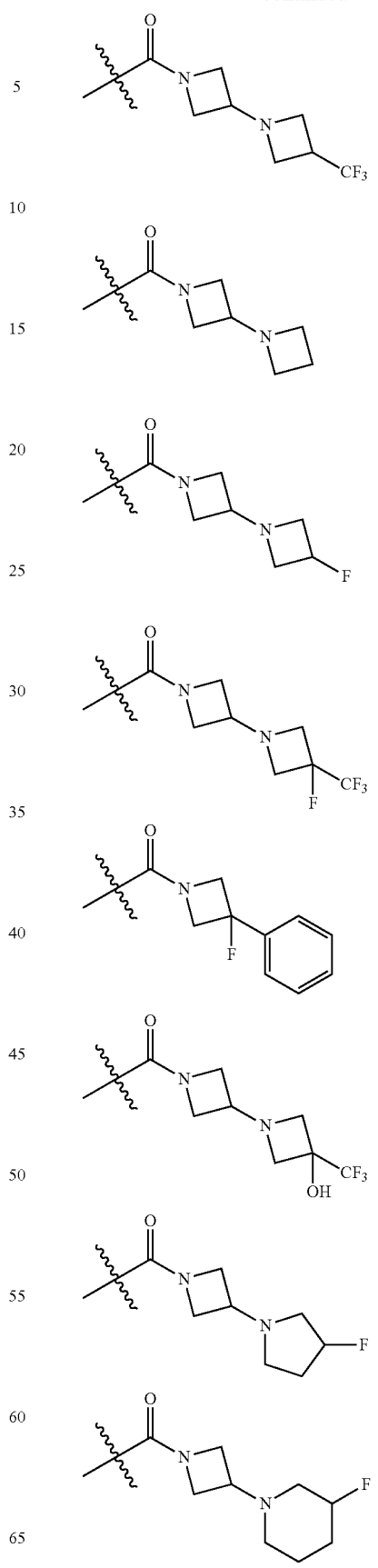

91
-continued
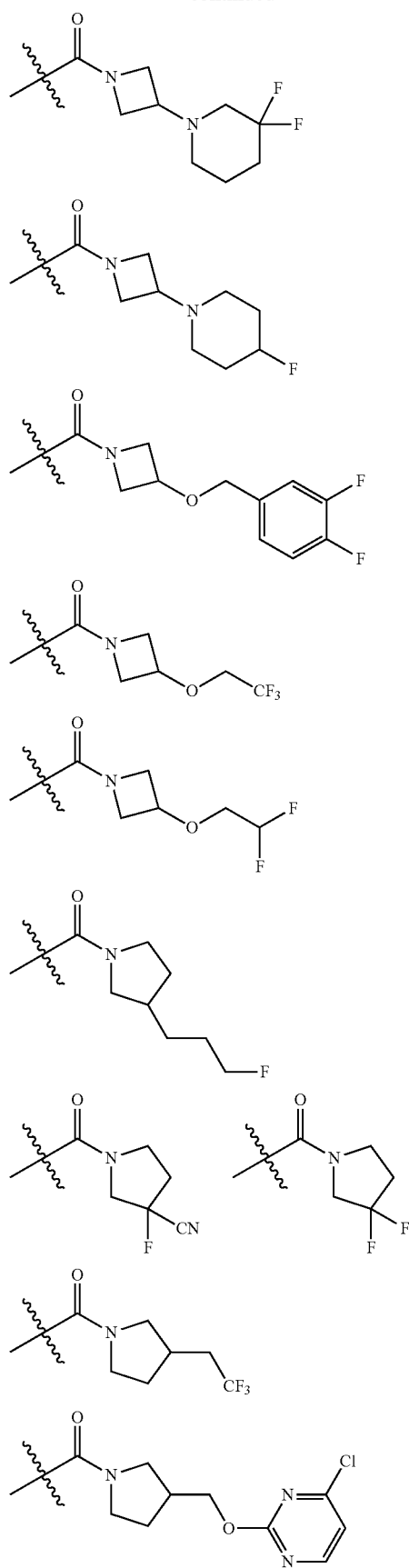
92
-continued
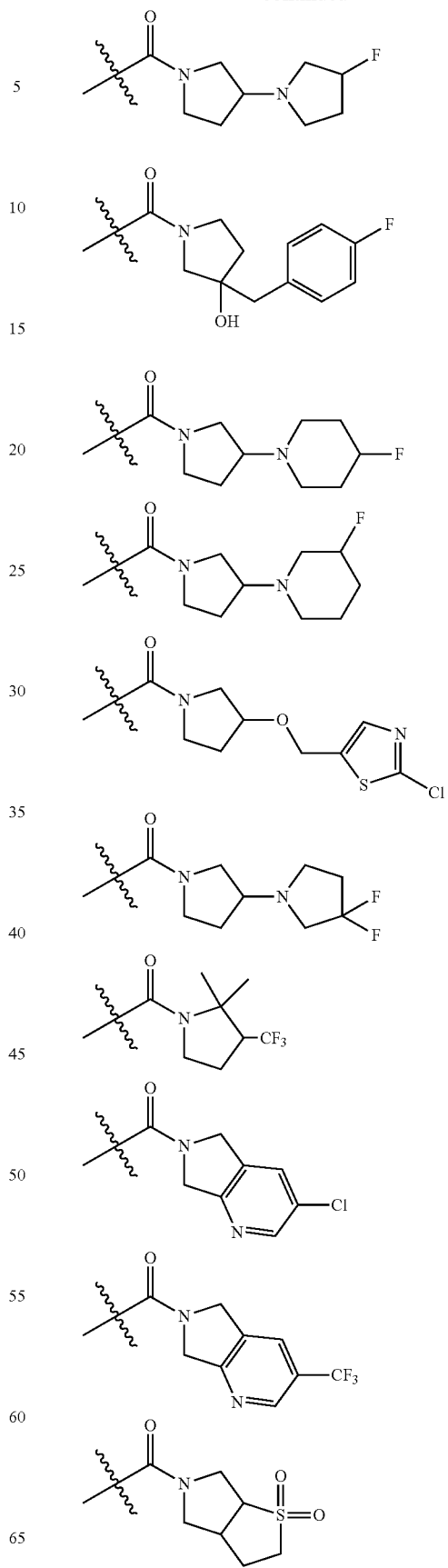

93
-continued
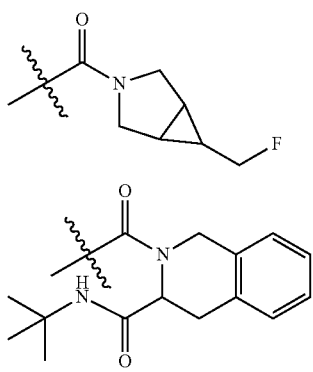
Exemplary compounds of formula I include, but are not limited to, the compounds listed in Table A.
94
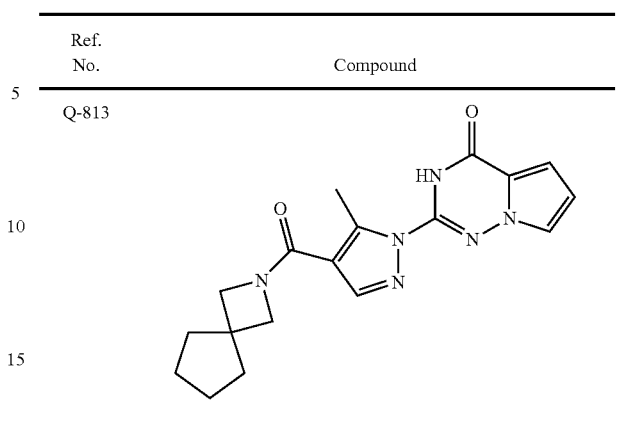

TABLE A-continued

| Ref. No. | Compound |
|---|---|
| Q-772 | (structure) |
| Q-768 | (structure) |
| Q-760 | (structure) |
| Q-739 | (structure) |
| Q-737 | (structure) |
| Q-691 | (structure) |
| Q-635 | (structure) |
| Q-586 | (structure) |
| Q-572 | (structure) |
| Q-520 | (structure) |

TABLE A-continued
| Ref. No. | Compound |
|---|---|
| Q-518 | 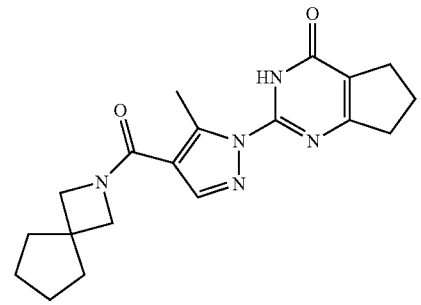 [SMILES: Cc1c(C(=O)N2CC3(CCCC3)C2)cnn1-c1nc2c(c(=O)[nH]1)CCC2] |
| Q-461 | |
Exemplary compounds of formula I also include, but are not limited to, the compounds listed in Table B.
TABLE B
| Ref. No. | Compound |
|---|---|
| Q-951 | 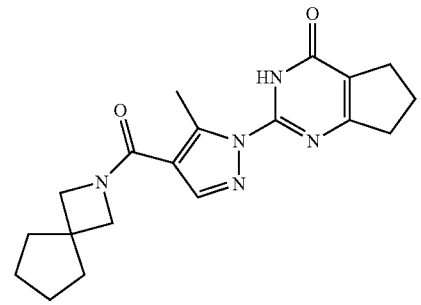 [SMILES: Cc1c(C(=O)N2CC3(CCCC3)C2)cnn1-c1nc2c(c(=O)[nH]1)CCC2] |
| Q-937 | |
TABLE B-continued
| Ref. No. | Compound |
|---|---|
| Q-931 | 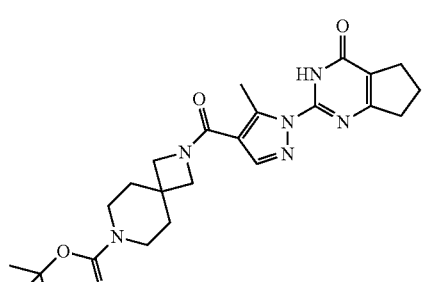 |
| Q-928 | |
| Q-924 | |
| Q-909 | |
| Q-908 | |

TABLE B-continued

| Ref. No. | Compound |
|---|---|
| Q-902 | |
| Q-891 | |
| Q-884 | |
| Q-876 | |
| Q-869 | |
| Q-850 | |
| Q-823 | |
| Q-819 | |
| Q-797 | |
| Q-757 | |

TABLE B-continued
| Ref. No. | Compound |
|---|---|
| Q-749 | 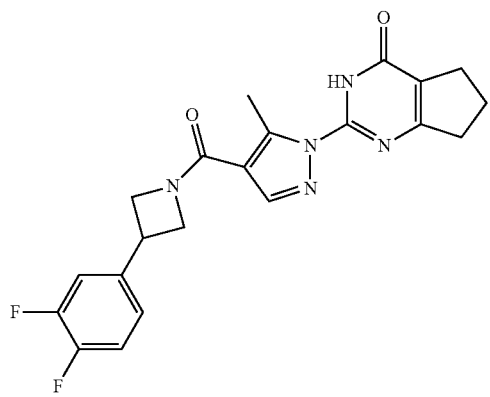 [SMILES: Cc1c(C(=O)N2CC(c3ccc(F)c(F)c3)C2)cnn1-c1nc2c(c(=O)[nH]1)CCC2] |
| Q-745 | 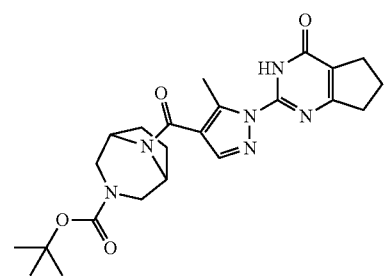 [SMILES: Cc1c(C(=O)N2C3CCC2CN(C(=O)OC(C)(C)C)C3)cnn1-c1nc2c(c(=O)[nH]1)CCC2] |
| Q-681 | 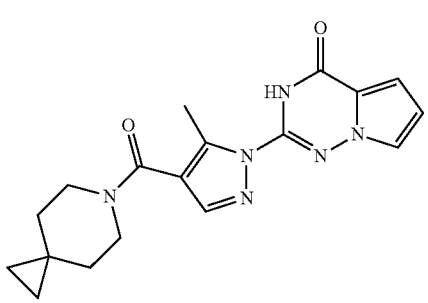 [SMILES: Cc1c(C(=O)N2CCC3(CC2)CC3)cnn1-c1nn2cccc2c(=O)[nH]1] |
| Q-615 | 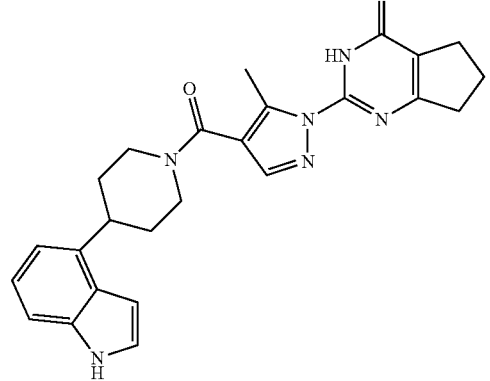 |
TABLE B-continued
| Ref. No. | Compound |
|---|---|
| Q-599 | 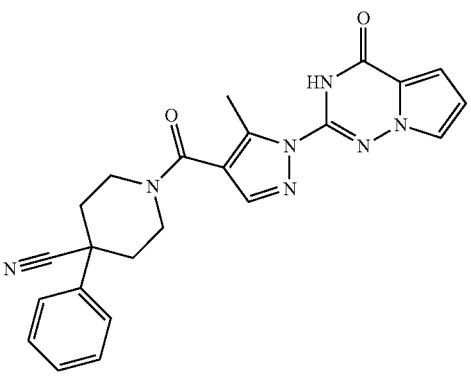 [SMILES: Cc1c(C(=O)N2CCC(C#N)(c3ccccc3)CC2)cnn1-c1nn2cccc2c(=O)[nH]1] |
| Q-598 | 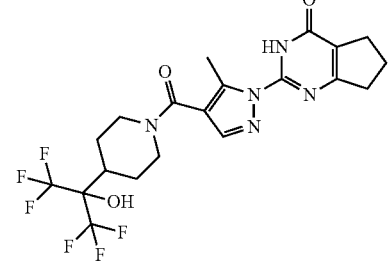 |
| Q-590 | 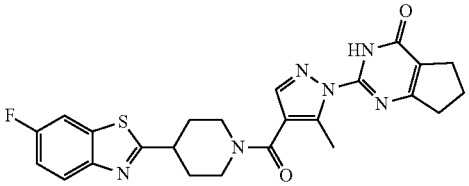 [SMILES: Cc1c(C(=O)N2CCC(c3nc4ccc(F)cc4s3)CC2)cnn1-c1nc2c(c(=O)[nH]1)CCC2] |
| Q-571 | 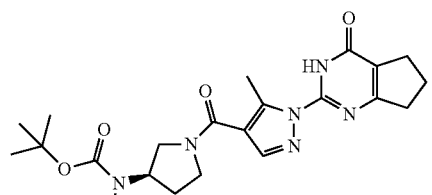 |
| Q-567 | 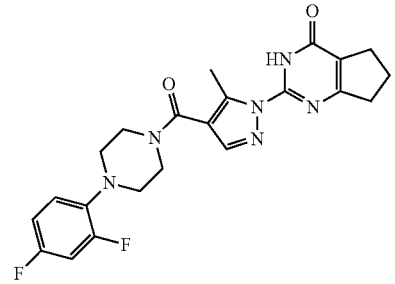 [SMILES: Cc1c(C(=O)N2CCN(c3ccc(F)cc3F)CC2)cnn1-c1nc2c(c(=O)[nH]1)CCC2] |

TABLE B-continued
| Ref. No. | Compound |
|---|---|
| Q-565 | 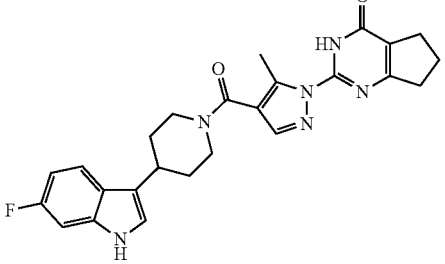 |
| Q-545 | 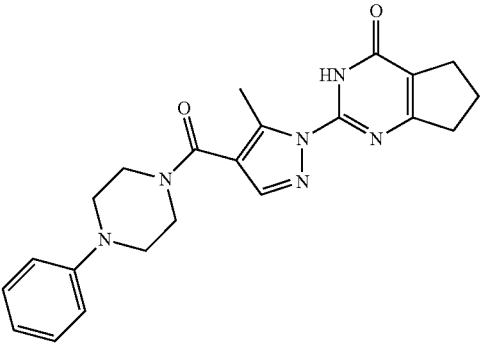 [SMILES: Cc1c(C(=O)N2CCN(c3ccccc3)CC2)cnn1-c1nc2c(c(=O)[nH]1)CCC2] |
| Q-521 | 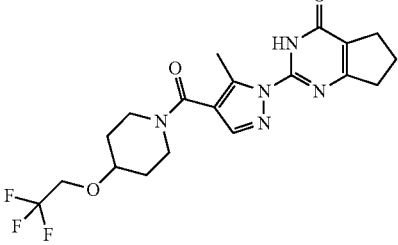 |
| Q-446 | 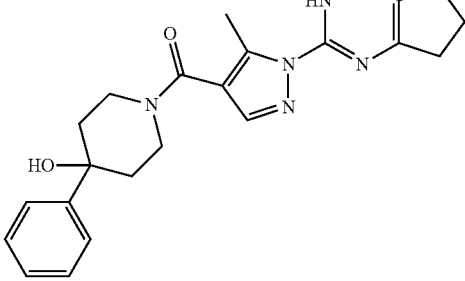 |
Provided herein are compounds as disclosed in Table C:
TABLE C
| Ref. No. | Compound |
|---|---|
| Q-280 | 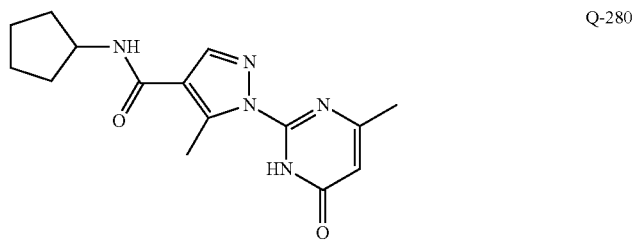 |
| Q-281 | 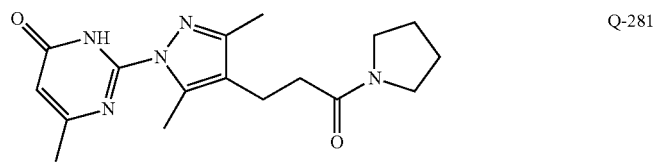 |
| Q-282 | 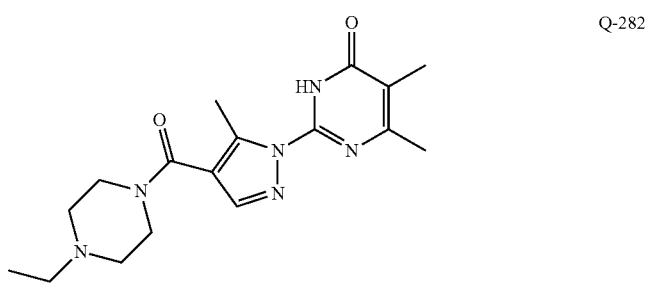 |

TABLE C-continued
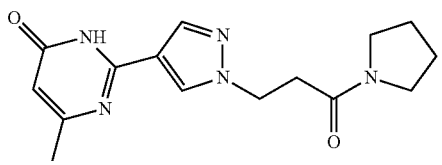 [SMILES: Cc1cc(=O)[nH]c(-c2cnn(CCC(=O)N3CCCC3)c2)n1] Q-283
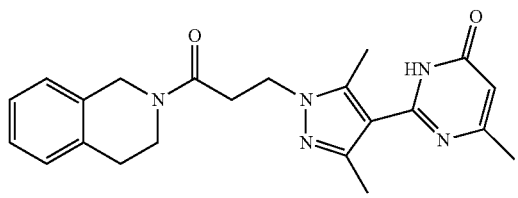 [SMILES: Cc1cc(=O)[nH]c(-c2c(C)nn(CCC(=O)N3CCc4ccccc4C3)c2C)n1] Q-284
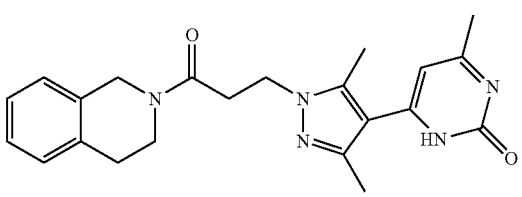 [SMILES: Cc1cc(-c2c(C)nn(CCC(=O)N3CCc4ccccc4C3)c2C)[nH]c(=O)n1] Q-285
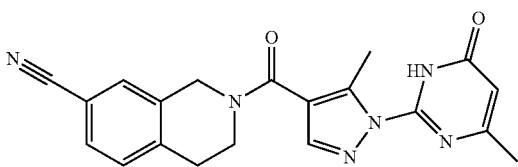 [SMILES: Cc1cc(=O)[nH]c(-n2ncc(C(=O)N3CCc4ccc(C#N)cc4C3)c2C)n1] Q-286
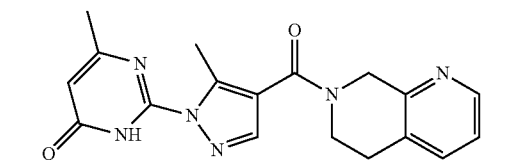 [SMILES: Cc1cc(=O)[nH]c(-n2ncc(C(=O)N3CCc4cccnc4C3)c2C)n1] Q-287
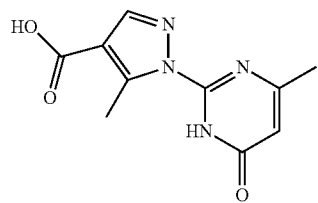 [SMILES: Cc1cc(=O)[nH]c(-n2ncc(C(=O)O)c2C)n1] Q-290
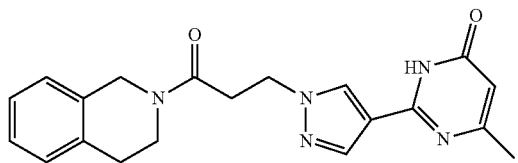 [SMILES: Cc1cc(=O)[nH]c(-c2cnn(CCC(=O)N3CCc4ccccc4C3)c2)n1] Q-291
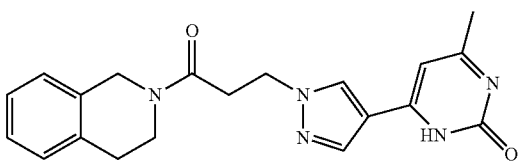 [SMILES: Cc1cc(-c2cnn(CCC(=O)N3CCc4ccccc4C3)c2)[nH]c(=O)n1] Q-292

TABLE C-continued
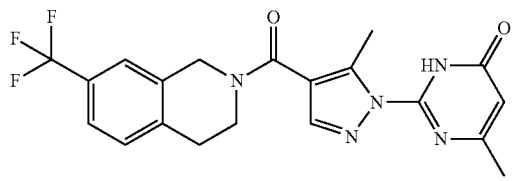 [SMILES: Cc1cc(=O)[nH]c(-n2ncc(C(=O)N3CCc4ccc(C(F)(F)F)cc4C3)c2C)n1]
Q-298
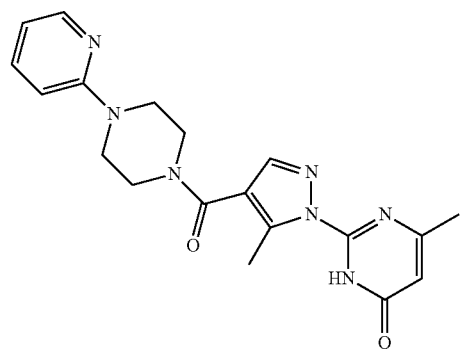 [SMILES: Cc1cc(=O)[nH]c(-n2ncc(C(=O)N3CCN(c4ccccn4)CC3)c2C)n1]
Q-299
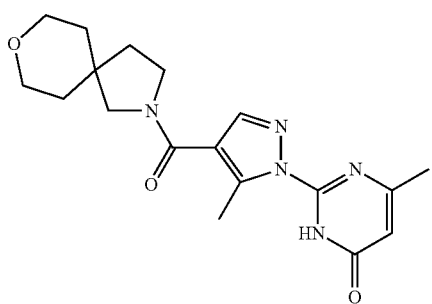 [SMILES: Cc1cc(=O)[nH]c(-n2ncc(C(=O)N3CCC4(CCOCC4)C3)c2C)n1]
Q-300
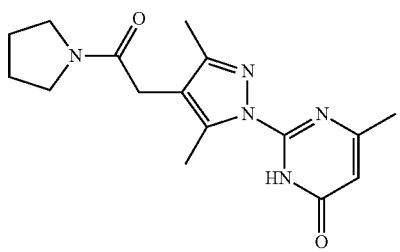 [SMILES: Cc1cc(=O)[nH]c(-n2nc(C)c(CC(=O)N3CCCC3)c2C)n1]
Q-301
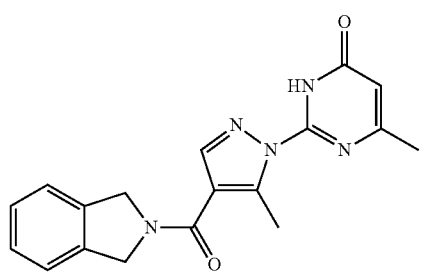 [SMILES: Cc1cc(=O)[nH]c(-n2ncc(C(=O)N3Cc4ccccc4C3)c2C)n1]
Q-302

TABLE C-continued
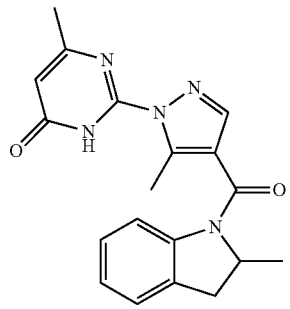 [SMILES: Cc1cc(=O)[nH]c(-n2ncc(C(=O)N3c4ccccc4CC3C)c2C)n1] Q-303
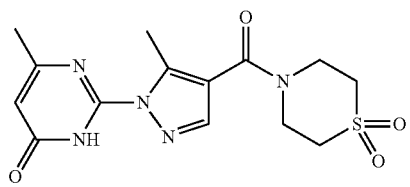 [SMILES: Cc1cc(=O)[nH]c(-n2ncc(C(=O)N3CCS(=O)(=O)CC3)c2C)n1] Q-304
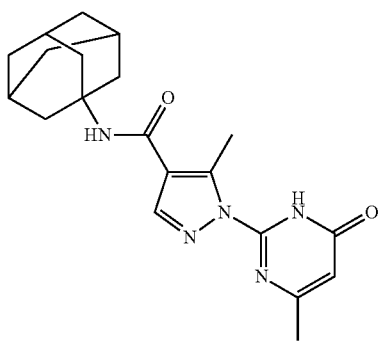 [SMILES: Cc1cc(=O)[nH]c(-n2ncc(C(=O)NC34CC5CC(CC(C5)C3)C4)c2C)n1] Q-305
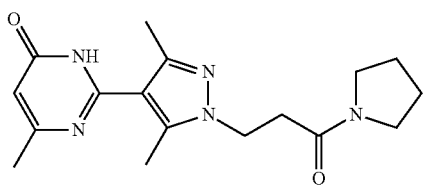 [SMILES: Cc1cc(=O)[nH]c(-c2c(C)nn(CCC(=O)N3CCCC3)c2C)n1] Q-306
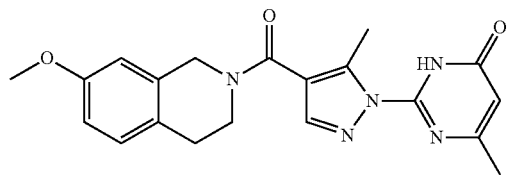 [SMILES: COc1ccc2c(c1)CN(C(=O)c1cnn(-c3nc(C)cc(=O)[nH]3)c1C)CC2] Q-307
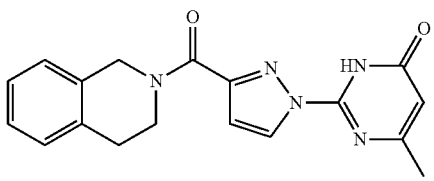 [SMILES: Cc1cc(=O)[nH]c(-n2ccc(C(=O)N3CCc4ccccc4C3)n2)n1] Q-308
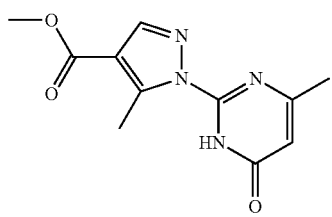 Q-310

TABLE C-continued

| | |
|---|---|
| (structure) | Q-311 |
| (structure) | Q-312 |
| (structure) | Q-313 |
| (structure) | Q-314 |
| (structure) | Q-316 |
| (structure) | Q-317 |
| (structure) | Q-318 |
| (structure) | Q-319 |

TABLE C-continued
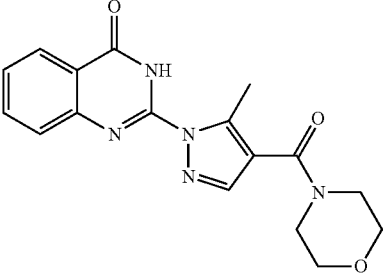 [SMILES: Cc1c(C(=O)N2CCOCC2)cnn1-c1nc2ccccc2c(=O)[nH]1] Q-320
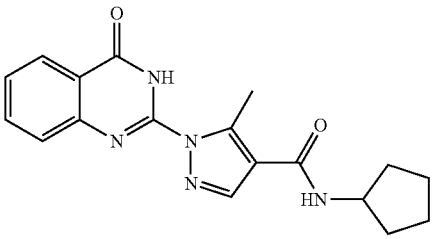 [SMILES: Cc1c(C(=O)NC2CCCC2)cnn1-c1nc2ccccc2c(=O)[nH]1] Q-321
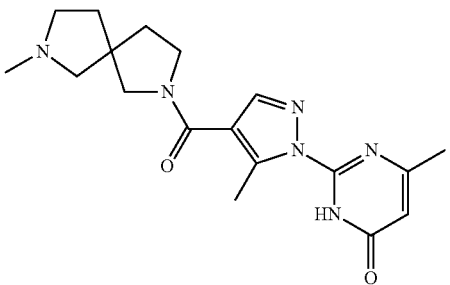 Q-322
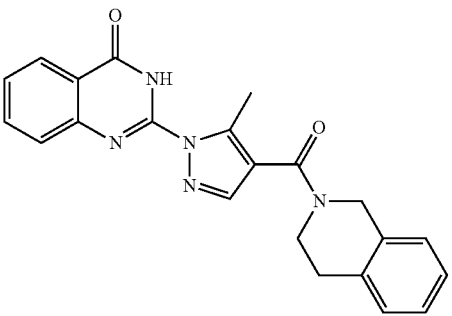 [SMILES: Cc1c(C(=O)N2CCc3ccccc3C2)cnn1-c1nc2ccccc2c(=O)[nH]1] Q-323
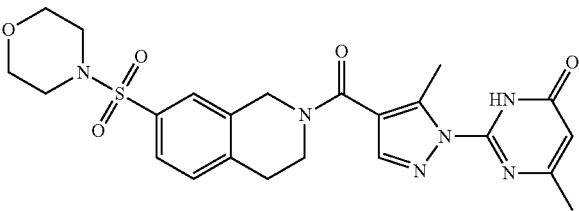 [SMILES: Cc1cc(=O)[nH]c(-n2ncc(C(=O)N3CCc4ccc(S(=O)(=O)N5CCOCC5)cc4C3)c2C)n1] Q-327
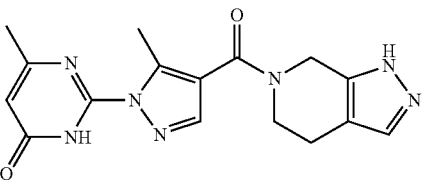 [SMILES: Cc1cc(=O)[nH]c(-n2ncc(C(=O)N3CCc4cn[nH]c4C3)c2C)n1] Q-328

TABLE C-continued
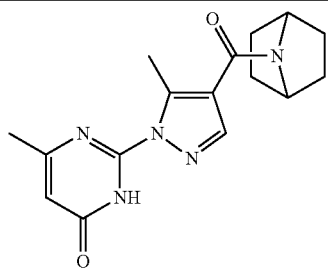 Q-329
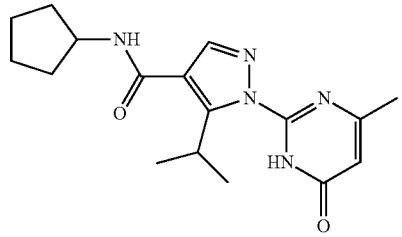 [SMILES: Cc1cc(=O)[nH]c(-n2ncc(C(=O)NC3CCCC3)c2C(C)C)n1] Q-330
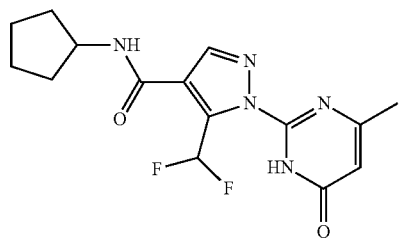 [SMILES: Cc1cc(=O)[nH]c(-n2ncc(C(=O)NC3CCCC3)c2C(F)F)n1] Q-331
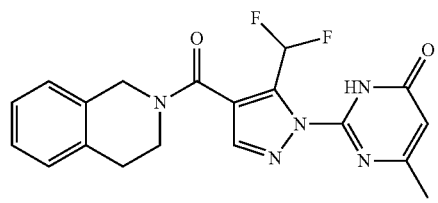 [SMILES: Cc1cc(=O)[nH]c(-n2ncc(C(=O)N3CCc4ccccc4C3)c2C(F)F)n1] Q-332
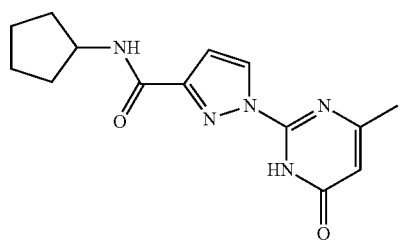 [SMILES: Cc1cc(=O)[nH]c(-n2ccc(C(=O)NC3CCCC3)n2)n1] Q-333
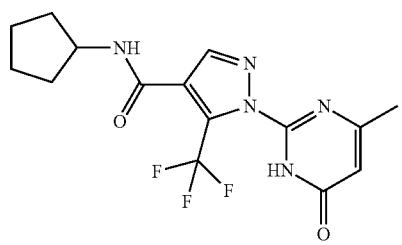 [SMILES: Cc1cc(=O)[nH]c(-n2ncc(C(=O)NC3CCCC3)c2C(F)(F)F)n1] Q-334
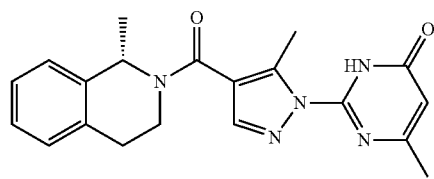 [SMILES: Cc1cc(=O)[nH]c(-n2ncc(C(=O)N3CCc4ccccc4[C@@H]3C)c2C)n1] Q-339

TABLE C-continued
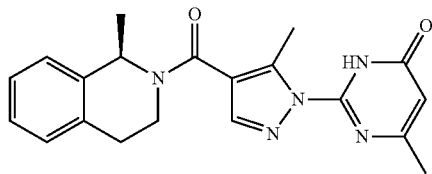 Q-340
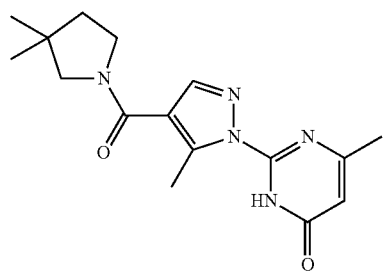 Q-341
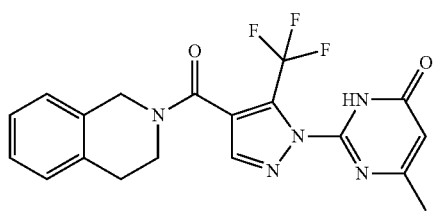 [SMILES: Cc1cc(=O)[nH]c(-n2ncc(C(=O)N3CCc4ccccc4C3)c2C(F)(F)F)n1] Q-342
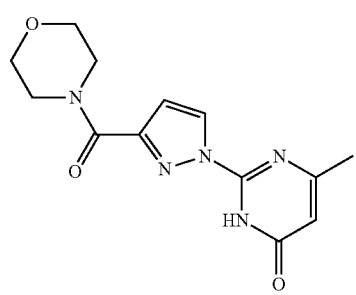 [SMILES: Cc1cc(=O)[nH]c(-n2ccc(C(=O)N3CCOCC3)n2)n1] Q-343
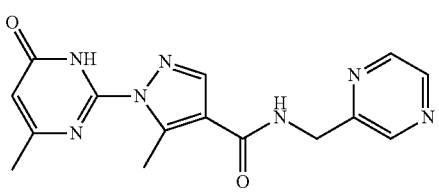 [SMILES: Cc1cc(=O)[nH]c(-n2ncc(C(=O)NCc3cnccn3)c2C)n1] Q-344
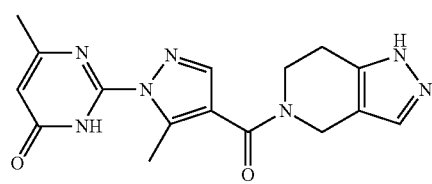 [SMILES: Cc1cc(=O)[nH]c(-n2ncc(C(=O)N3CCc4[nH]ncc4C3)c2C)n1] Q-345
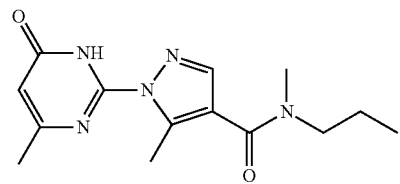 [SMILES: CCCN(C)C(=O)c1cnn(-c2nc(C)cc(=O)[nH]2)c1C] Q-346

TABLE C-continued
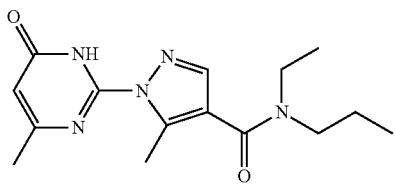 [SMILES: CCCN(CC)C(=O)c1cnn(-c2nc(C)cc(=O)[nH]2)c1C] Q-347
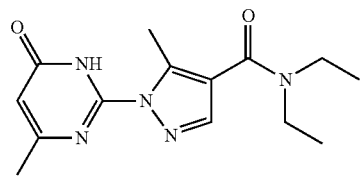 [SMILES: CCN(CC)C(=O)c1cnn(-c2nc(C)cc(=O)[nH]2)c1C] Q-348
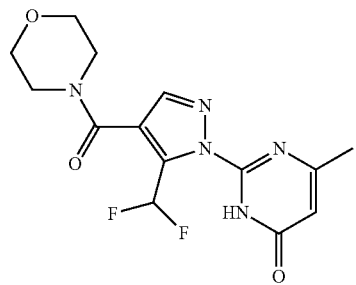 [SMILES: Cc1cc(=O)[nH]c(-n2ncc(C(=O)N3CCOCC3)c2C(F)F)n1] Q-349
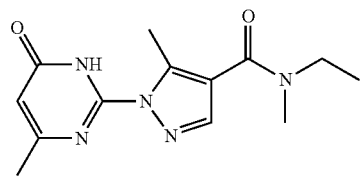 [SMILES: CCN(C)C(=O)c1cnn(-c2nc(C)cc(=O)[nH]2)c1C] Q-350
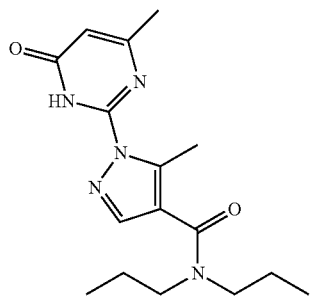 [SMILES: CCCN(CCC)C(=O)c1cnn(-c2nc(C)cc(=O)[nH]2)c1C] Q-351
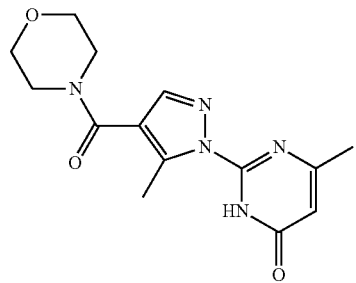 [SMILES: Cc1cc(=O)[nH]c(-n2ncc(C(=O)N3CCOCC3)c2C)n1] Q-352

TABLE C-continued
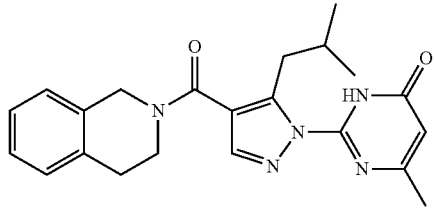 [SMILES: Cc1cc(=O)[nH]c(-n2ncc(C(=O)N3CCc4ccccc4C3)c2CC(C)C)n1] Q-353
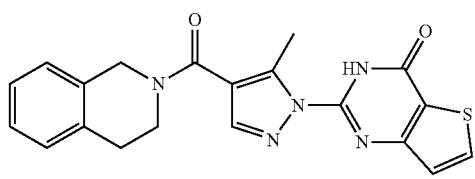 [SMILES: Cc1c(C(=O)N2CCc3ccccc3C2)cnn1-c1nc2ccsc2c(=O)[nH]1] Q-354
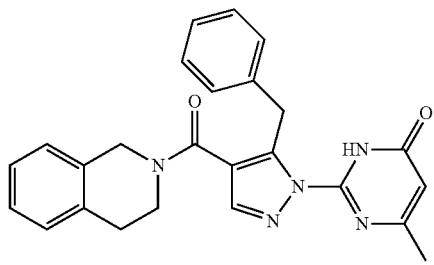 [SMILES: Cc1cc(=O)[nH]c(-n2ncc(C(=O)N3CCc4ccccc4C3)c2Cc2ccccc2)n1] Q-358
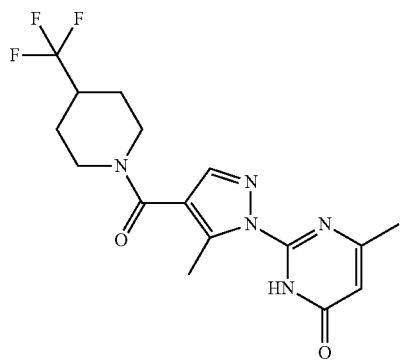 [SMILES: Cc1cc(=O)[nH]c(-n2ncc(C(=O)N3CCC(C(F)(F)F)CC3)c2C)n1] Q-359
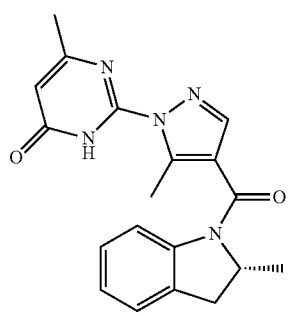 [SMILES: Cc1cc(=O)[nH]c(-n2ncc(C(=O)N3c4ccccc4C[C@H]3C)c2C)n1] Q-361
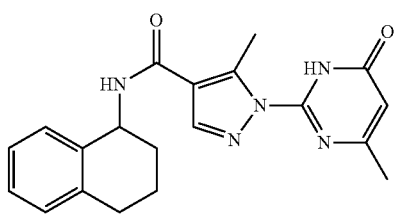 [SMILES: Cc1cc(=O)[nH]c(-n2ncc(C(=O)NC3CCCc4ccccc43)c2C)n1] Q-362

TABLE C-continued
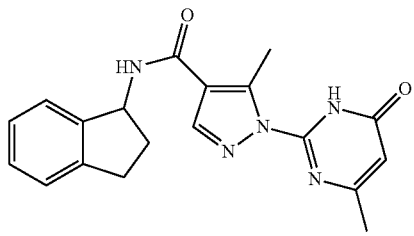 [SMILES: Cc1cc(=O)[nH]c(-n2ncc(C(=O)NC3CCc4ccccc43)c2C)n1] Q-363
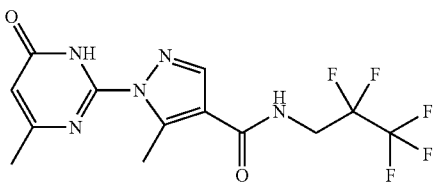 [SMILES: Cc1cc(=O)[nH]c(-n2ncc(C(=O)NCC(F)(F)C(F)(F)F)c2C)n1] Q-364
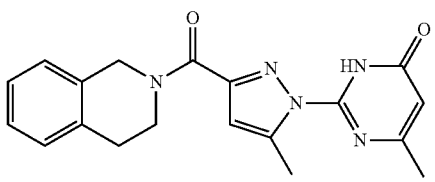 [SMILES: Cc1cc(=O)[nH]c(-n2nc(C(=O)N3CCc4ccccc4C3)cc2C)n1] Q-365
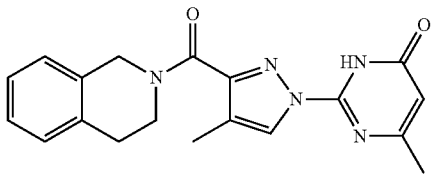 [SMILES: Cc1cc(=O)[nH]c(-n2cc(C)c(C(=O)N3CCc4ccccc4C3)n2)n1] Q-366
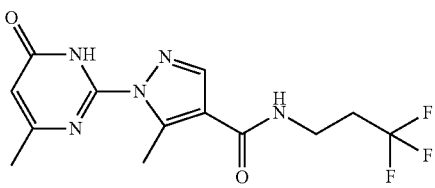 [SMILES: Cc1cc(=O)[nH]c(-n2ncc(C(=O)NCCC(F)(F)F)c2C)n1] Q-367
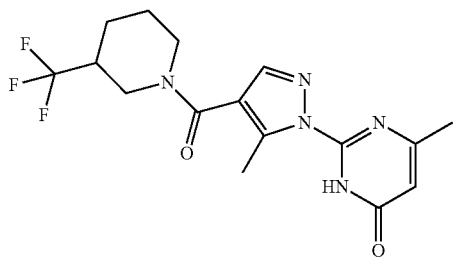 [SMILES: Cc1cc(=O)[nH]c(-n2ncc(C(=O)N3CCCC(C(F)(F)F)C3)c2C)n1] Q-368
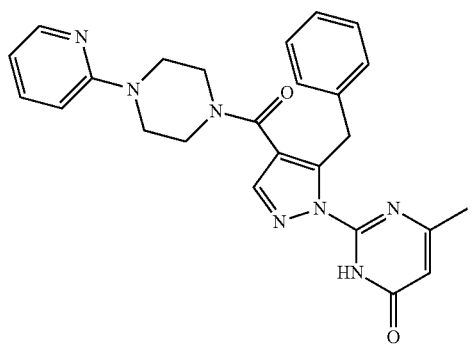 [SMILES: Cc1cc(=O)[nH]c(-n2ncc(C(=O)N3CCN(c4ccccn4)CC3)c2Cc2ccccc2)n1] Q-369

TABLE C-continued
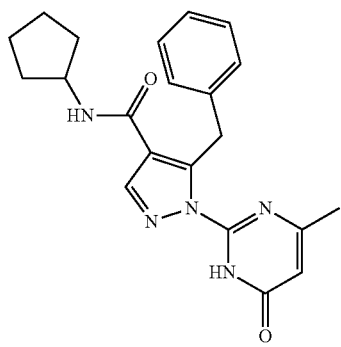 [SMILES: Cc1cc(=O)[nH]c(-n2ncc(C(=O)NC3CCCC3)c2Cc2ccccc2)n1] Q-370
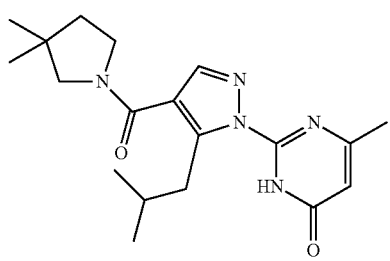 Q-371
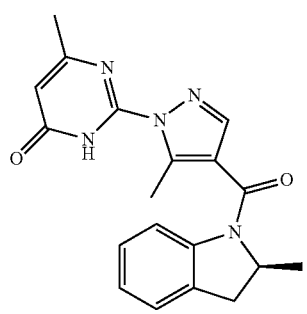 [SMILES: Cc1cc(=O)[nH]c(-n2ncc(C(=O)N3c4ccccc4C[C@@H]3C)c2C)n1] Q-372
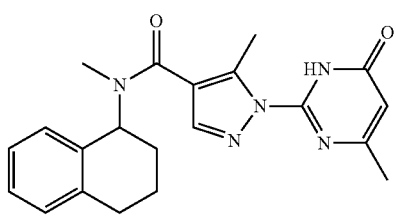 [SMILES: Cc1cc(=O)[nH]c(-n2ncc(C(=O)N(C)C3CCCc4ccccc43)c2C)n1] Q-373
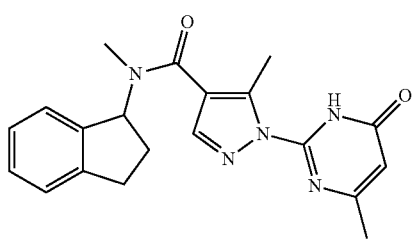 [SMILES: Cc1cc(=O)[nH]c(-n2ncc(C(=O)N(C)C3CCc4ccccc43)c2C)n1] Q-374
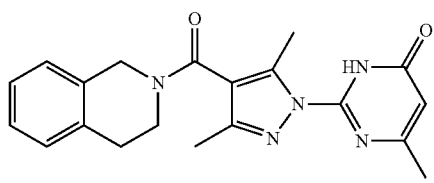 [SMILES: Cc1cc(=O)[nH]c(-n2nc(C)c(C(=O)N3CCc4ccccc4C3)c2C)n1] Q-375

TABLE C-continued
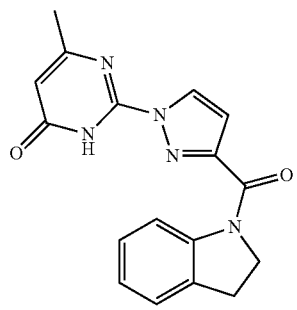 [SMILES: Cc1cc(=O)[nH]c(-n2ccc(C(=O)N3CCc4ccccc43)n2)n1]
Q-376
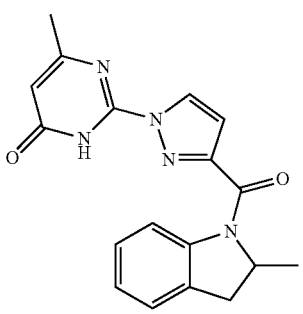 [SMILES: Cc1cc(=O)[nH]c(-n2ccc(C(=O)N3c4ccccc4CC3C)n2)n1]
Q-377
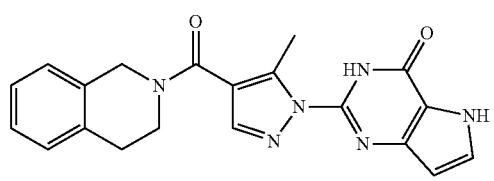 [SMILES: Cc1c(C(=O)N2CCc3ccccc3C2)cnn1-c1nc2cc[nH]c2c(=O)[nH]1]
Q-378
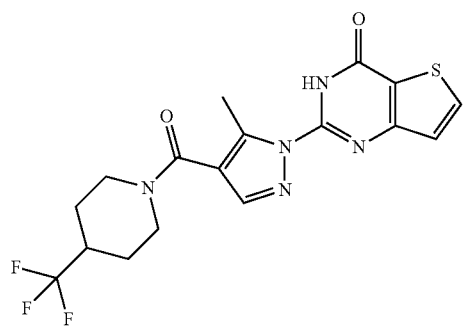
Q-379
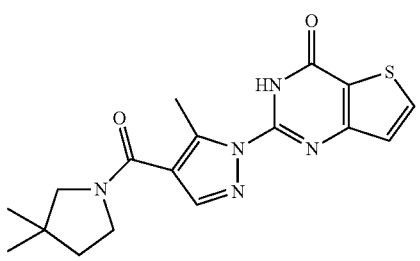 [SMILES: Cc1c(C(=O)N2CCC(C)(C)C2)cnn1-c1nc2ccsc2c(=O)[nH]1]
Q-380
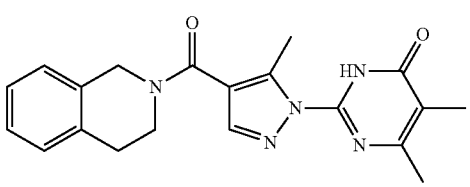 [SMILES: Cc1nc(-n2ncc(C(=O)N3CCc4ccccc4C3)c2C)[nH]c(=O)c1C]
Q-381

TABLE C-continued
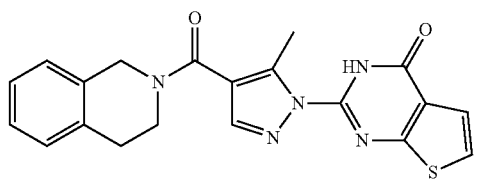 [SMILES: Cc1c(C(=O)N2CCc3ccccc3C2)cnn1-c1nc2sccc2c(=O)[nH]1] Q-382
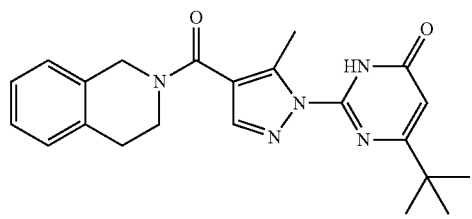 [SMILES: Cc1c(C(=O)N2CCc3ccccc3C2)cnn1-c1nc(C(C)(C)C)cc(=O)[nH]1] Q-383
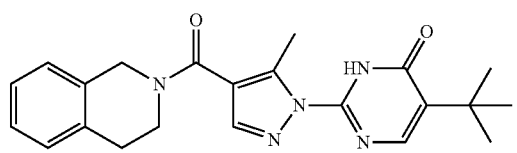 [SMILES: Cc1c(C(=O)N2CCc3ccccc3C2)cnn1-c1ncc(C(C)(C)C)c(=O)[nH]1] Q-384
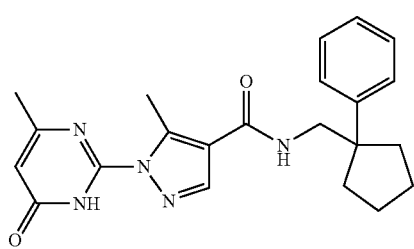 [SMILES: Cc1cc(=O)[nH]c(-n2ncc(C(=O)NCC3(c4ccccc4)CCCC3)c2C)n1] Q-385
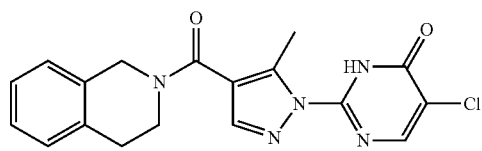 [SMILES: Cc1c(C(=O)N2CCc3ccccc3C2)cnn1-c1ncc(Cl)c(=O)[nH]1] Q-387
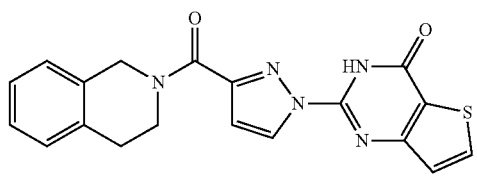 [SMILES: O=C(c1ccn(-c2nc3ccsc3c(=O)[nH]2)n1)N1CCc2ccccc2C1] Q-388
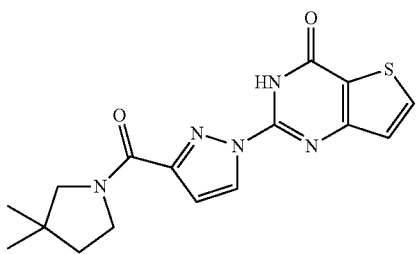 [SMILES: CC1(C)CCN(C(=O)c2ccn(-c3nc4ccsc4c(=O)[nH]3)n2)C1] Q-389

TABLE C-continued
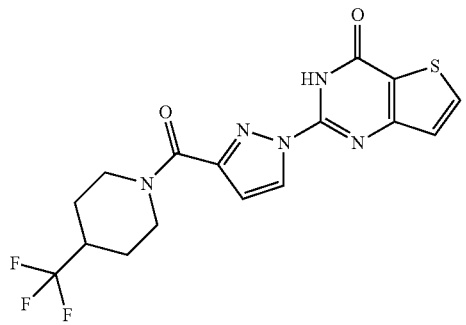 [SMILES: O=C(c1ccn(-c2nc3ccsc3c(=O)[nH]2)n1)N1CCC(C(F)(F)F)CC1] Q-390
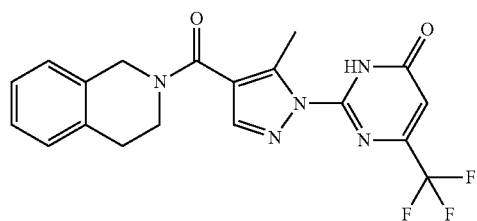 [SMILES: Cc1c(C(=O)N2CCc3ccccc3C2)cnn1-c1nc(C(F)(F)F)cc(=O)[nH]1] Q-393
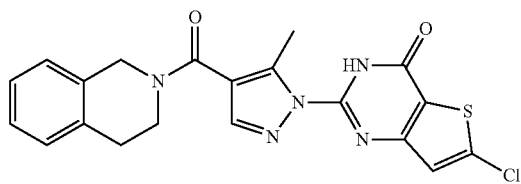 [SMILES: Cc1c(C(=O)N2CCc3ccccc3C2)cnn1-c1nc2cc(Cl)sc2c(=O)[nH]1] Q-394
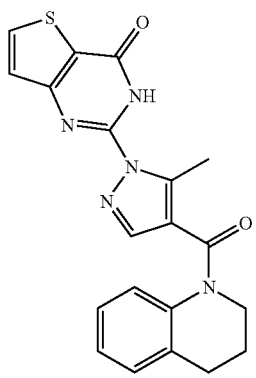 [SMILES: Cc1c(C(=O)N2CCCc3ccccc32)cnn1-c1nc2ccsc2c(=O)[nH]1] Q-395
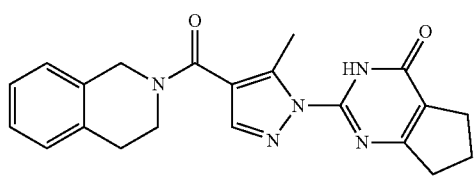 [SMILES: Cc1c(C(=O)N2CCc3ccccc3C2)cnn1-c1nc2c(c(=O)[nH]1)CCC2] Q-396
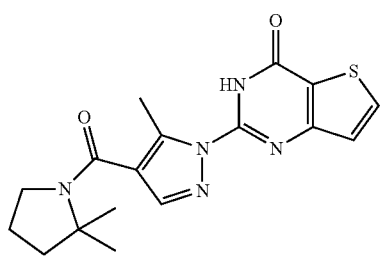 [SMILES: Cc1c(C(=O)N2CCCC2(C)C)cnn1-c1nc2ccsc2c(=O)[nH]1] Q-397

TABLE C-continued
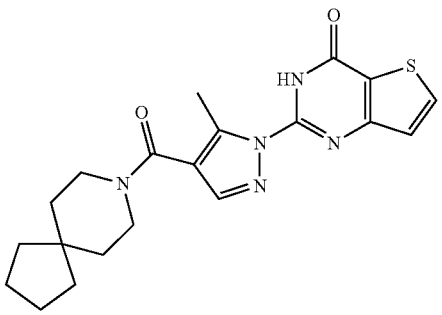 [SMILES: Cc1c(C(=O)N2CCC3(CCCC3)CC2)cnn1-c1nc2ccsc2c(=O)[nH]1] Q-398
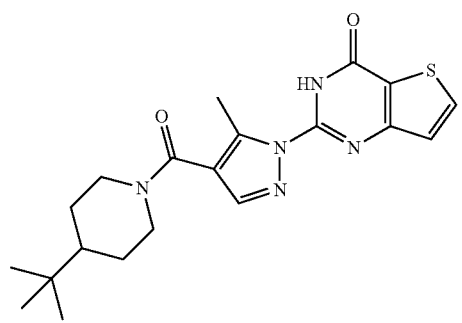 [SMILES: Cc1c(C(=O)N2CCC(C(C)(C)C)CC2)cnn1-c1nc2ccsc2c(=O)[nH]1] Q-399
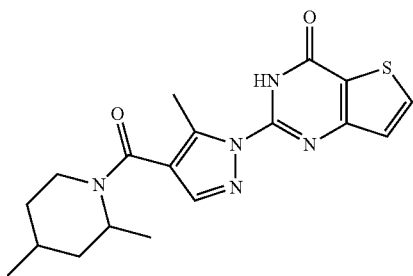 [SMILES: Cc1c(C(=O)N2CCC(C)CC2C)cnn1-c1nc2ccsc2c(=O)[nH]1] Q-400
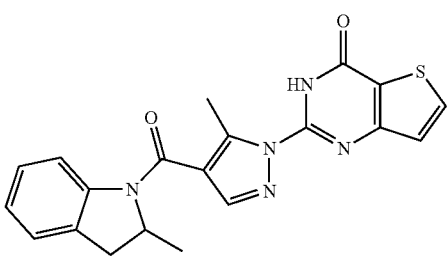 [SMILES: Cc1c(C(=O)N2c3ccccc3CC2C)cnn1-c1nc2ccsc2c(=O)[nH]1] Q-401
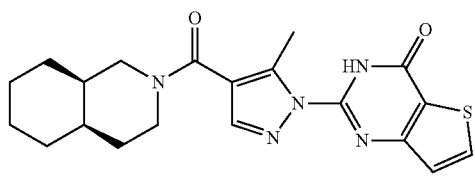 [SMILES: Cc1c(C(=O)N2CC[C@H]3CCCC[C@H]3C2)cnn1-c1nc2ccsc2c(=O)[nH]1] Q-402
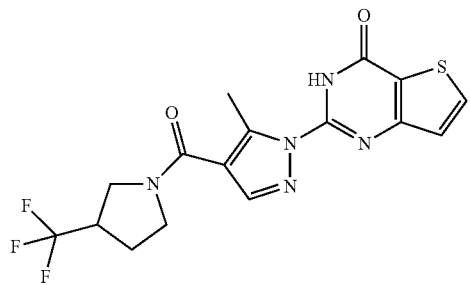 [SMILES: Cc1c(C(=O)N2CCC(C(F)(F)F)C2)cnn1-c1nc2ccsc2c(=O)[nH]1] Q-403

TABLE C-continued
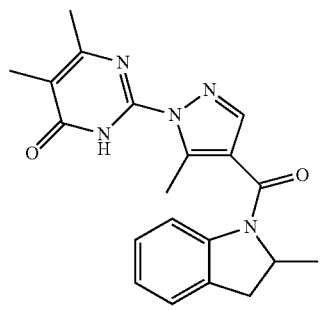
Q-404
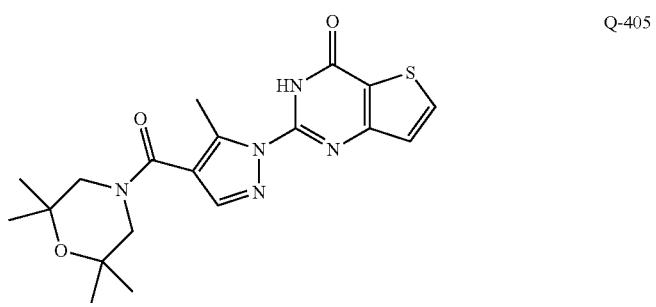
Q-405
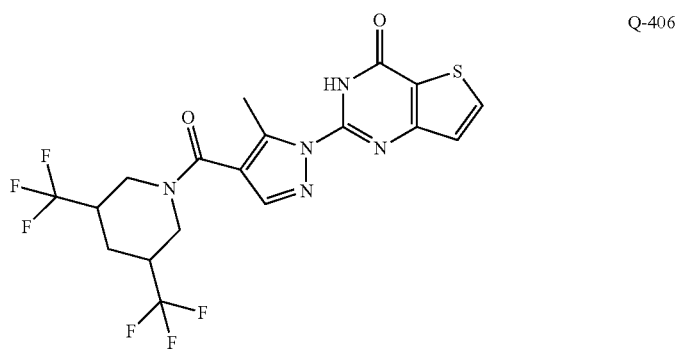
Q-406
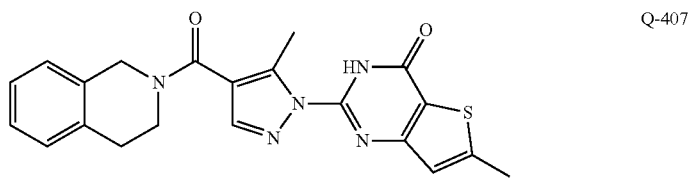
Q-407
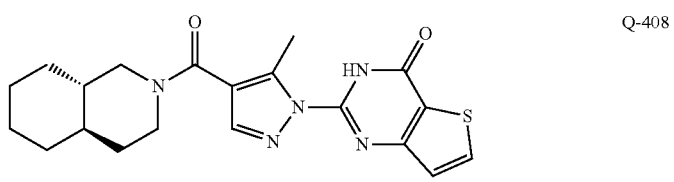
Q-408

TABLE C-continued
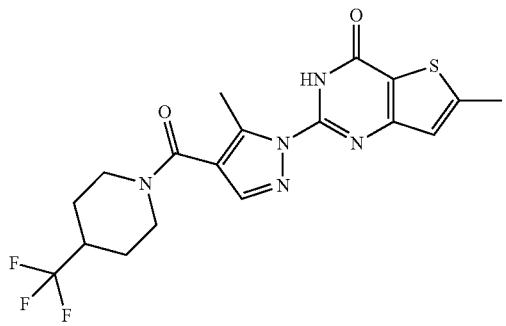 [SMILES: Cc1cc2nc(-n3ncc(C(=O)N4CCC(C(F)(F)F)CC4)c3C)[nH]c(=O)c2s1]
Q-409
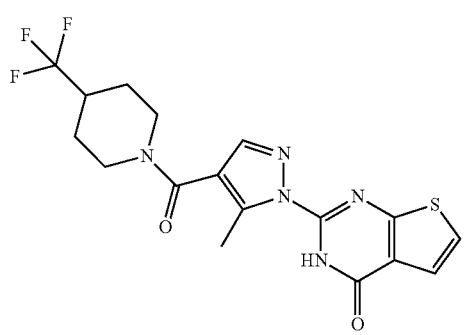 [SMILES: Cc1c(C(=O)N2CCC(C(F)(F)F)CC2)cnn1-c1nc2sccc2c(=O)[nH]1]
Q-410
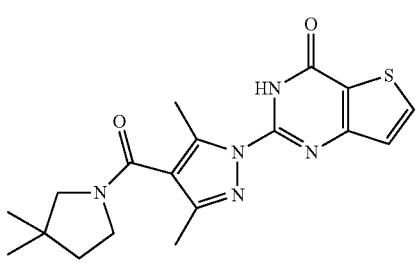 [SMILES: Cc1nn(-c2nc3ccsc3c(=O)[nH]2)c(C)c1C(=O)N1CCC(C)(C)C1]
Q-411
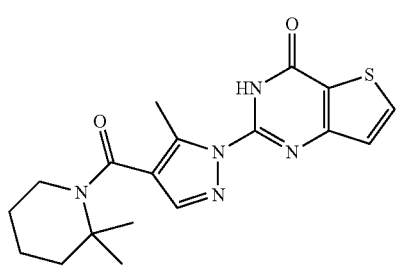 [SMILES: Cc1c(C(=O)N2CCCCC2(C)C)cnn1-c1nc2ccsc2c(=O)[nH]1]
Q-412
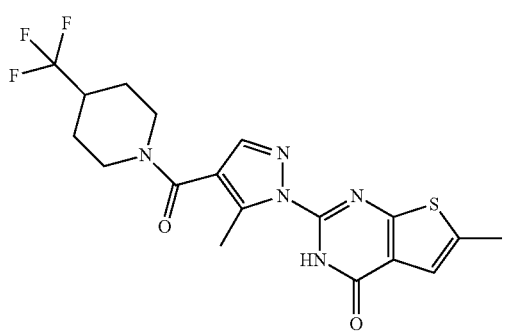 [SMILES: Cc1cc2c(=O)[nH]c(-n3ncc(C(=O)N4CCC(C(F)(F)F)CC4)c3C)nc2s1]
Q-413

TABLE C-continued
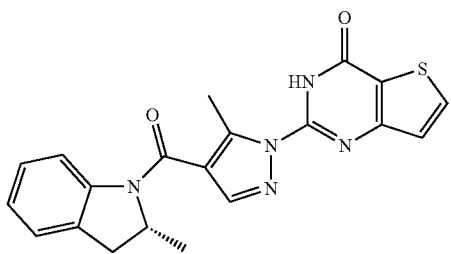 [SMILES: Cc1c(C(=O)N2c3ccccc3C[C@H]2C)cnn1-c1nc2ccsc2c(=O)[nH]1]
Q-414
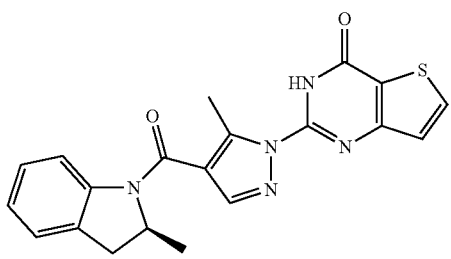 [SMILES: Cc1c(C(=O)N2c3ccccc3C[C@@H]2C)cnn1-c1nc2ccsc2c(=O)[nH]1]
Q-415
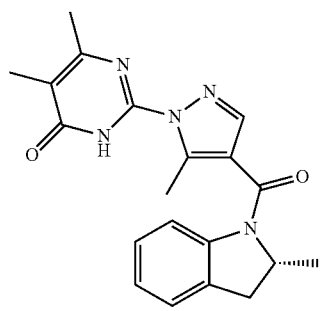
Q-416
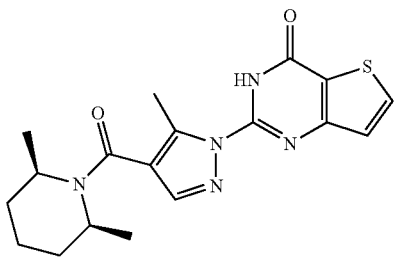 [SMILES: Cc1c(C(=O)N2[C@H](C)CCC[C@@H]2C)cnn1-c1nc2ccsc2c(=O)[nH]1]
Q-417
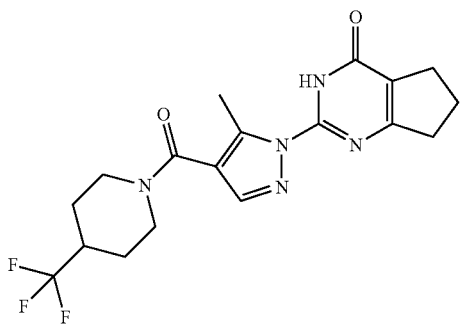 [SMILES: Cc1c(C(=O)N2CCC(C(F)(F)F)CC2)cnn1-c1nc2c(c(=O)[nH]1)CCC2]
Q-418

TABLE C-continued
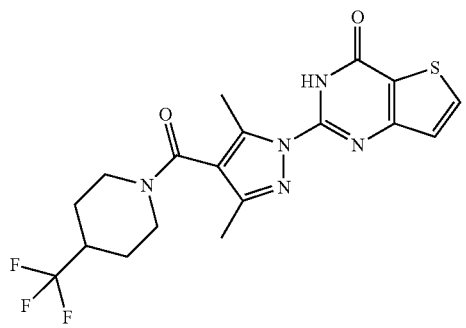 [SMILES: Cc1nn(-c2nc3ccsc3c(=O)[nH]2)c(C)c1C(=O)N1CCC(C(F)(F)F)CC1]
Q-419
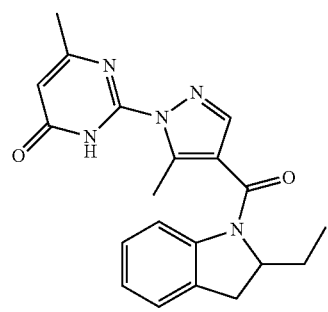 [SMILES: CCC1Cc2ccccc2N1C(=O)c1cnn(-c2nc(C)cc(=O)[nH]2)c1C]
Q-420
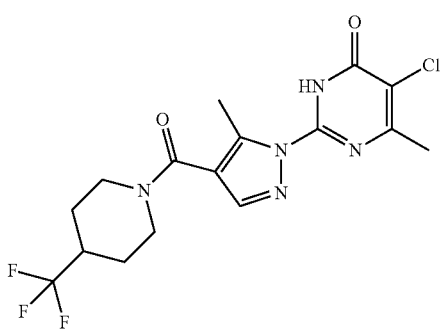 [SMILES: Cc1nc(-n2ncc(C(=O)N3CCC(C(F)(F)F)CC3)c2C)[nH]c(=O)c1Cl]
Q-421
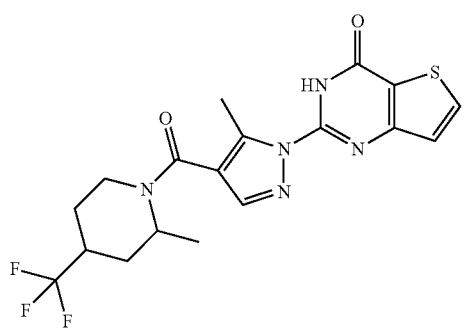 [SMILES: Cc1c(C(=O)N2CCC(C(F)(F)F)CC2C)cnn1-c1nc2ccsc2c(=O)[nH]1]
Q-422
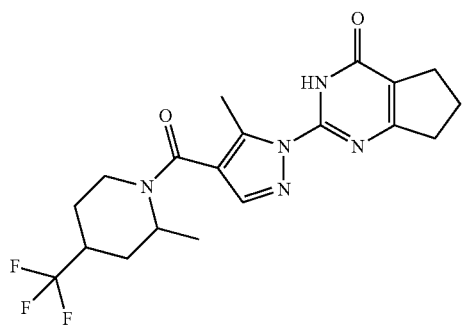 [SMILES: Cc1c(C(=O)N2CCC(C(F)(F)F)CC2C)cnn1-c1nc2c(c(=O)[nH]1)CCC2]
Q-423

TABLE C-continued
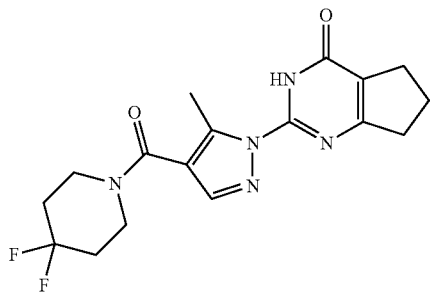 [SMILES: Cc1c(C(=O)N2CCC(F)(F)CC2)cnn1-c1nc2c(c(=O)[nH]1)CCC2]
Q-424
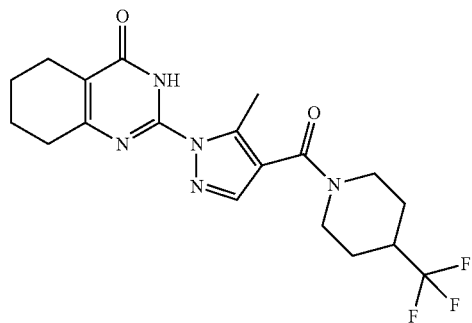 [SMILES: Cc1c(C(=O)N2CCC(C(F)(F)F)CC2)cnn1-c1nc2c(c(=O)[nH]1)CCCC2]
Q-425
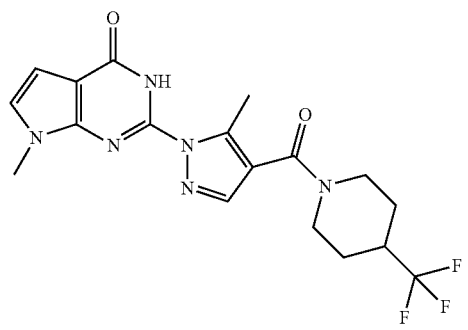 [SMILES: Cc1c(C(=O)N2CCC(C(F)(F)F)CC2)cnn1-c1nc2c(ccn2C)c(=O)[nH]1]
Q-426
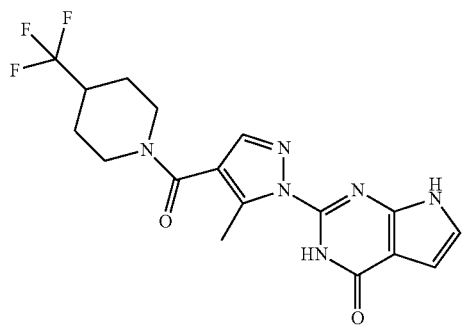 [SMILES: Cc1c(C(=O)N2CCC(C(F)(F)F)CC2)cnn1-c1nc2[nH]ccc2c(=O)[nH]1]
Q-427
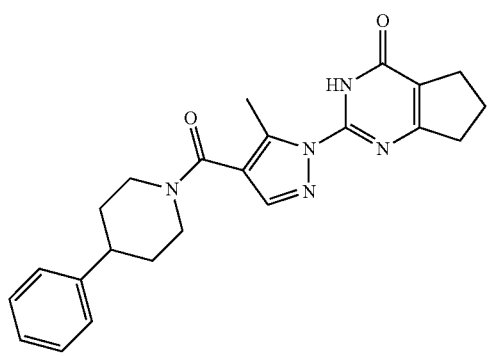 [SMILES: Cc1c(C(=O)N2CCC(c3ccccc3)CC2)cnn1-c1nc2c(c(=O)[nH]1)CCC2]
Q-428

TABLE C-continued
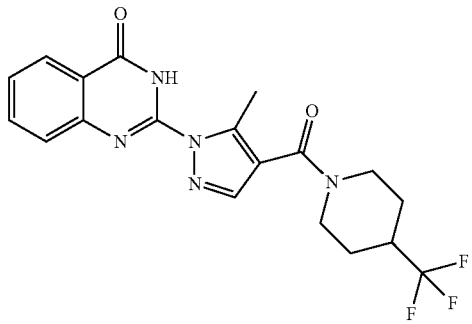 [SMILES: Cc1c(C(=O)N2CCC(C(F)(F)F)CC2)cnn1-c1nc2ccccc2c(=O)[nH]1] Q-429
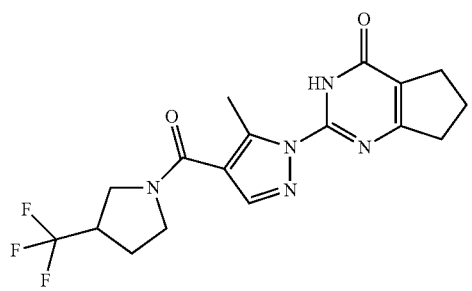 [SMILES: Cc1c(C(=O)N2CCC(C(F)(F)F)C2)cnn1-c1nc2c(c(=O)[nH]1)CCC2] Q-431
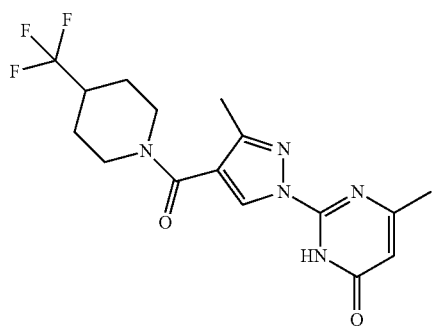 [SMILES: Cc1cc(=O)[nH]c(-n2cc(C(=O)N3CCC(C(F)(F)F)CC3)c(C)n2)n1] Q-432
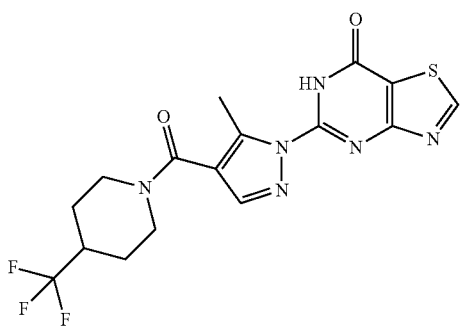 [SMILES: Cc1c(C(=O)N2CCC(C(F)(F)F)CC2)cnn1-c1nc2ncsc2c(=O)[nH]1] Q-433
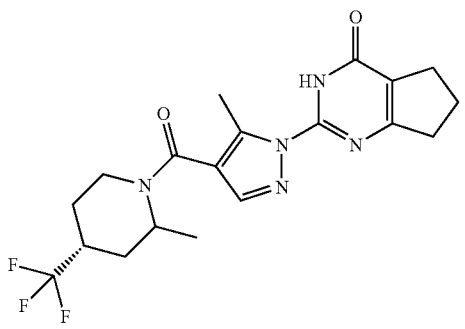 [SMILES: Cc1c(C(=O)N2CC[C@@H](C(F)(F)F)CC2C)cnn1-c1nc2c(c(=O)[nH]1)CCC2] Q-434

TABLE C-continued
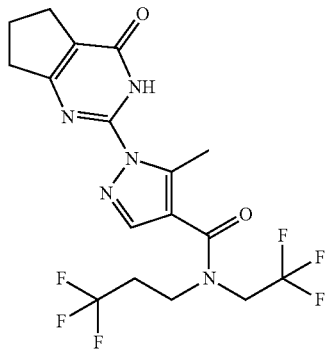 [SMILES: Cc1c(C(=O)N(CCC(F)(F)F)CC(F)(F)F)cnn1-c1nc2c(c(=O)[nH]1)CCC2] Q-435
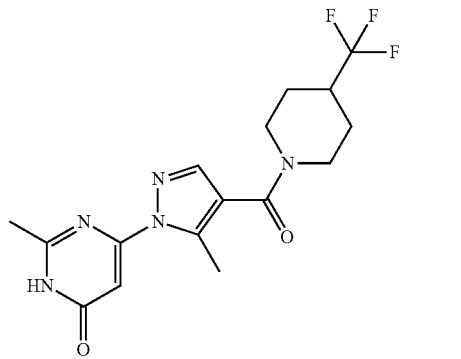 [SMILES: Cc1nc(-n2ncc(C(=O)N3CCC(C(F)(F)F)CC3)c2C)cc(=O)[nH]1] Q-436
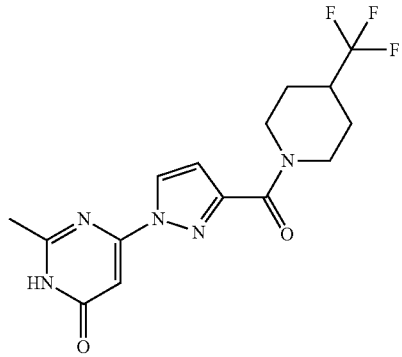 [SMILES: Cc1nc(-n2ccc(C(=O)N3CCC(C(F)(F)F)CC3)n2)cc(=O)[nH]1] Q-437
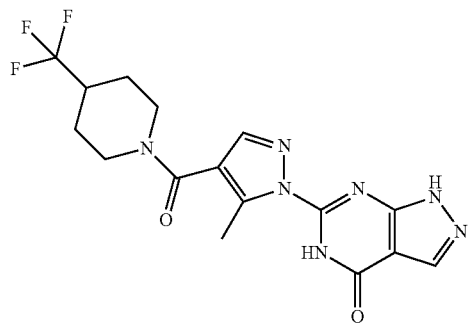 [SMILES: Cc1c(C(=O)N2CCC(C(F)(F)F)CC2)cnn1-c1nc2[nH]ncc2c(=O)[nH]1] Q-438

TABLE C-continued
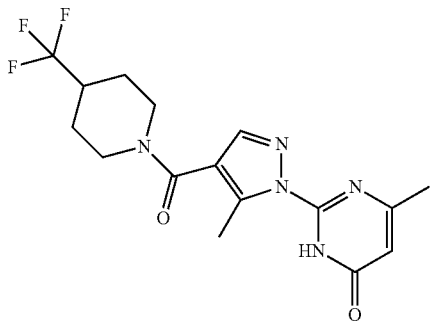 [SMILES: Cc1cc(=O)[nH]c(-n2ncc(C(=O)N3CCC(C(F)(F)F)CC3)c2C)n1]
Q-439
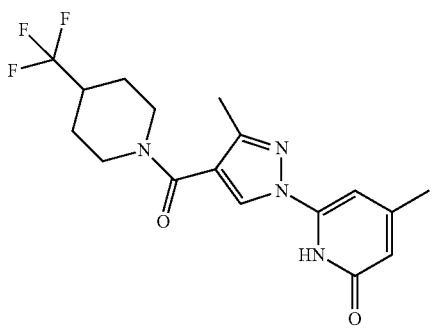 [SMILES: Cc1cc(-n2cc(C(=O)N3CCC(C(F)(F)F)CC3)c(C)n2)[nH]c(=O)c1]
Q-440
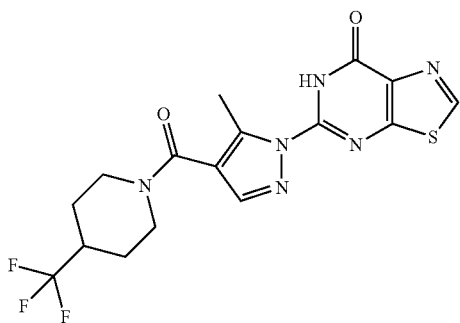 [SMILES: Cc1c(C(=O)N2CCC(C(F)(F)F)CC2)cnn1-c1nc2scnc2c(=O)[nH]1]
Q-441
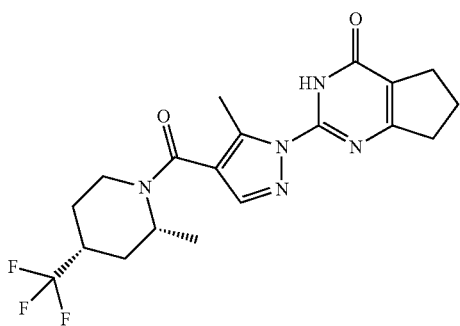
Q-442
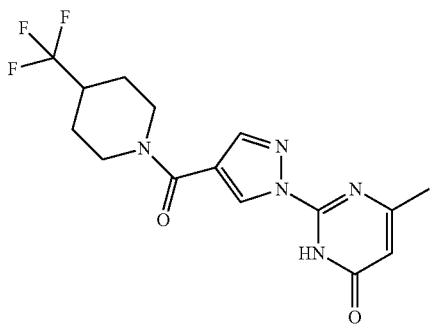 [SMILES: Cc1cc(=O)[nH]c(-n2cc(C(=O)N3CCC(C(F)(F)F)CC3)cn2)n1]
Q-443

TABLE C-continued
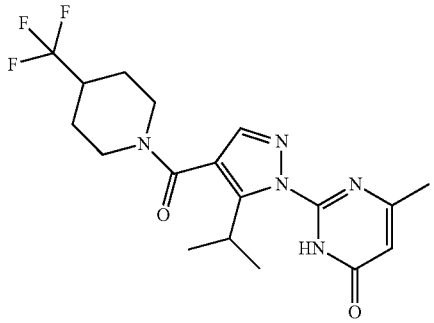 [SMILES: Cc1cc(=O)[nH]c(-n2ncc(C(=O)N3CCC(C(F)(F)F)CC3)c2C(C)C)n1]
Q-444
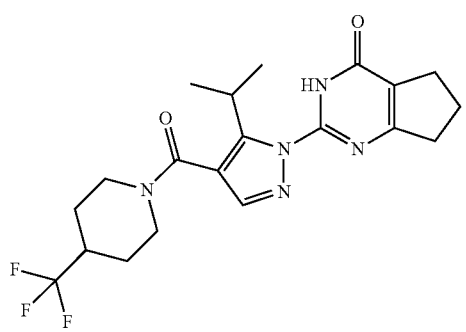 [SMILES: CC(C)c1c(C(=O)N2CCC(C(F)(F)F)CC2)cnn1-c1nc2c(c(=O)[nH]1)CCC2]
Q-445
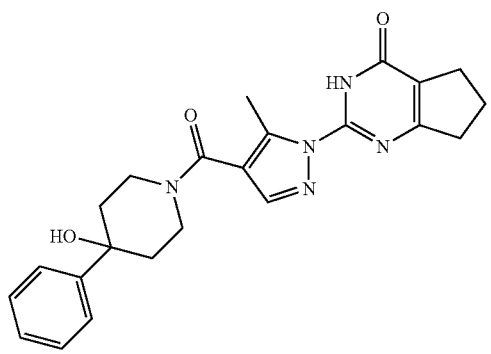 [SMILES: Cc1c(C(=O)N2CCC(O)(c3ccccc3)CC2)cnn1-c1nc2c(c(=O)[nH]1)CCC2]
Q-446
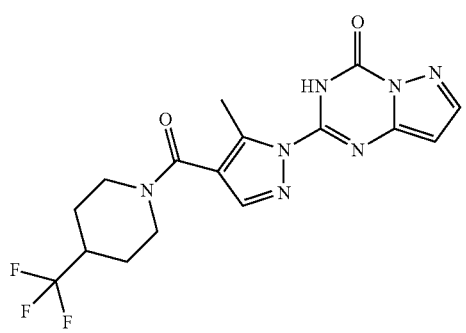 [SMILES: Cc1c(C(=O)N2CCC(C(F)(F)F)CC2)cnn1-c1nc2ccnn2c(=O)[nH]1]
Q-447

TABLE C-continued
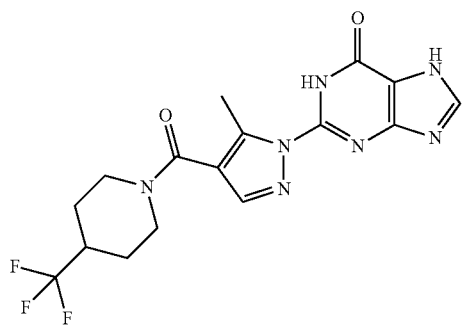 [SMILES: Cc1c(C(=O)N2CCC(C(F)(F)F)CC2)cnn1-c1nc2nc[nH]c2c(=O)[nH]1]
Q-448
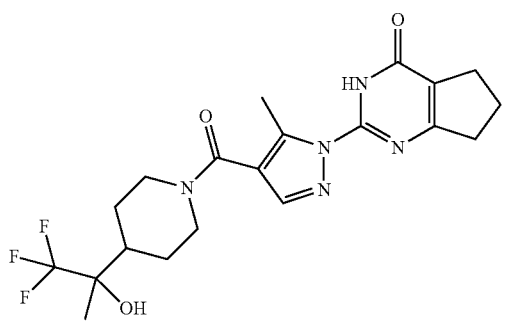 [SMILES: Cc1c(C(=O)N2CCC(C(C)(O)C(F)(F)F)CC2)cnn1-c1nc2c(c(=O)[nH]1)CCC2]
Q-449
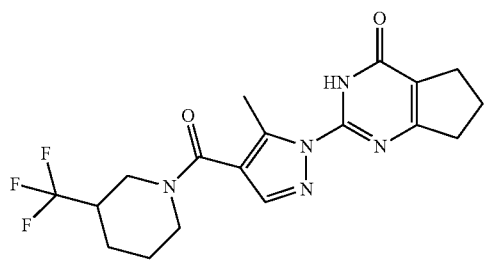 [SMILES: Cc1c(C(=O)N2CCCC(C(F)(F)F)C2)cnn1-c1nc2c(c(=O)[nH]1)CCC2]
Q-450
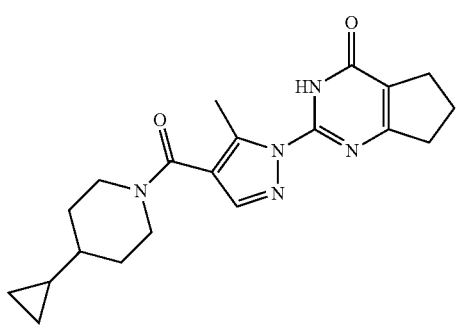 [SMILES: Cc1c(C(=O)N2CCC(C3CC3)CC2)cnn1-c1nc2c(c(=O)[nH]1)CCC2]
Q-451
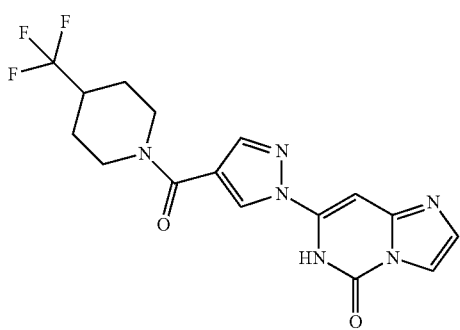 [SMILES: O=C(c1cnn(-c2cc3nccn3c(=O)[nH]2)c1)N1CCC(C(F)(F)F)CC1]
Q-452

TABLE C-continued
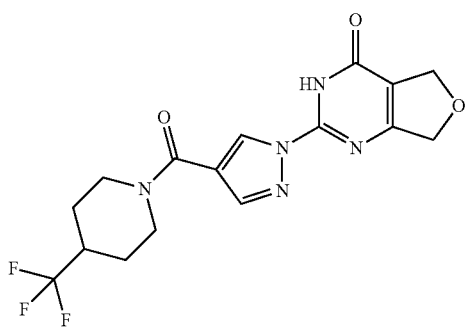 [SMILES: O=C(c1cnn(-c2nc3c(c(=O)[nH]2)COC3)c1)N1CCC(C(F)(F)F)CC1] Q-453
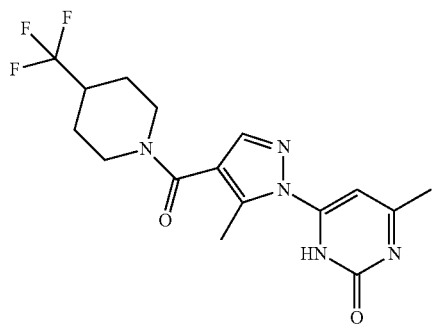 [SMILES: Cc1cc(-n2ncc(C(=O)N3CCC(C(F)(F)F)CC3)c2C)[nH]c(=O)n1] Q-454
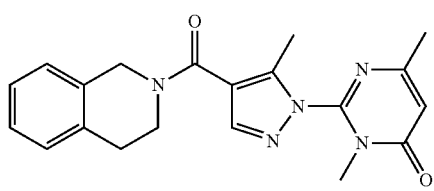 [SMILES: Cc1cc(=O)n(C)c(-n2ncc(C(=O)N3CCc4ccccc4C3)c2C)n1] Q-455
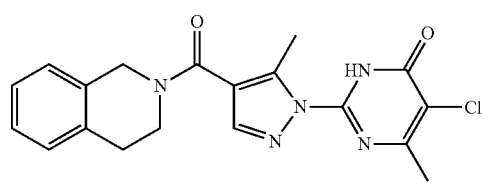 [SMILES: Cc1nc(-n2ncc(C(=O)N3CCc4ccccc4C3)c2C)[nH]c(=O)c1Cl] Q-456
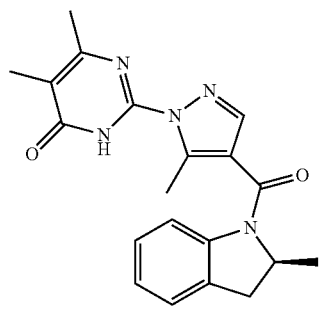 Q-457
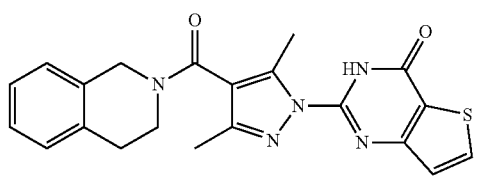 [SMILES: Cc1nn(-c2nc3ccsc3c(=O)[nH]2)c(C)c1C(=O)N1CCc2ccccc2C1] Q-458

TABLE C-continued
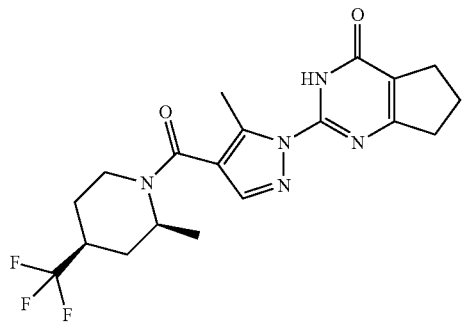 [SMILES: Cc1c(C(=O)N2CC[C@H](C(F)(F)F)C[C@@H]2C)cnn1-c1nc2c(c(=O)[nH]1)CCC2]
Q-459
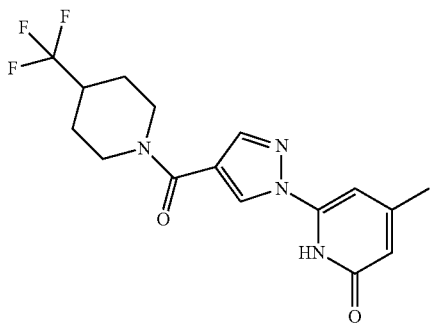 [SMILES: Cc1cc(-n2cc(C(=O)N3CCC(C(F)(F)F)CC3)cn2)[nH]c(=O)c1]
Q-460
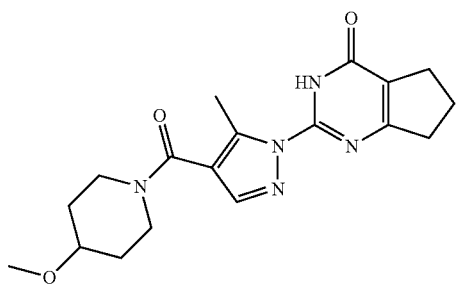 [SMILES: COC1CCN(C(=O)c2cnn(-c3nc4c(c(=O)[nH]3)CCC4)c2C)CC1]
Q-461
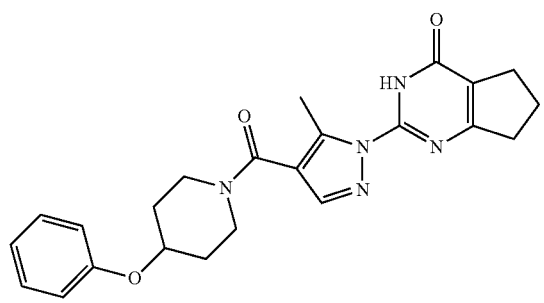 [SMILES: Cc1c(C(=O)N2CCC(Oc3ccccc3)CC2)cnn1-c1nc2c(c(=O)[nH]1)CCC2]
Q-462
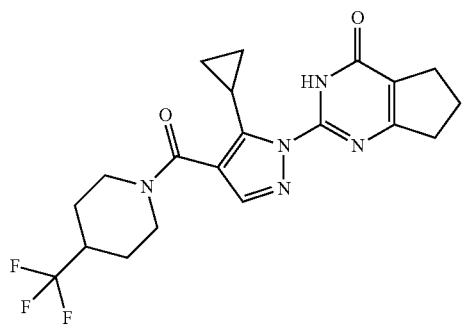 [SMILES: O=C(c1cnn(-c2nc3c(c(=O)[nH]2)CCC3)c1C1CC1)N1CCC(C(F)(F)F)CC1]
Q-463

TABLE C-continued
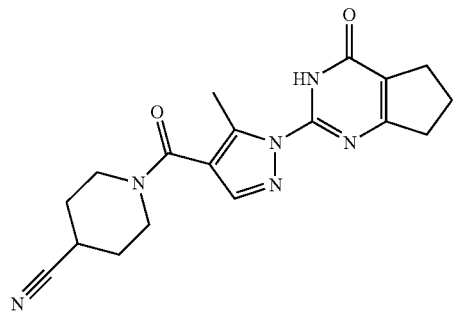 [SMILES: Cc1c(C(=O)N2CCC(C#N)CC2)cnn1-c1nc2c(c(=O)[nH]1)CCC2]
Q-464
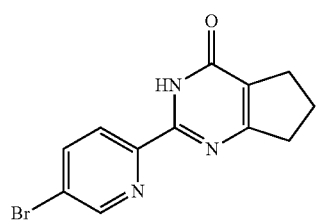 [SMILES: O=c1[nH]c(-c2ccc(Br)cn2)nc2c1CCC2]
Q-465
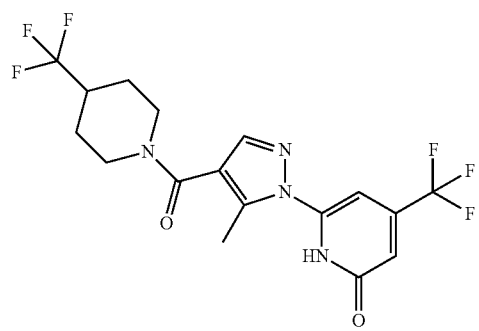 [SMILES: Cc1c(C(=O)N2CCC(C(F)(F)F)CC2)cnn1-c1cc(C(F)(F)F)cc(=O)[nH]1]
Q-466
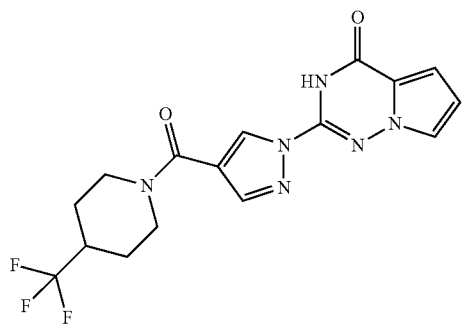 [SMILES: O=C(c1cnn(-c2nn3cccc3c(=O)[nH]2)c1)N1CCC(C(F)(F)F)CC1]
Q-467
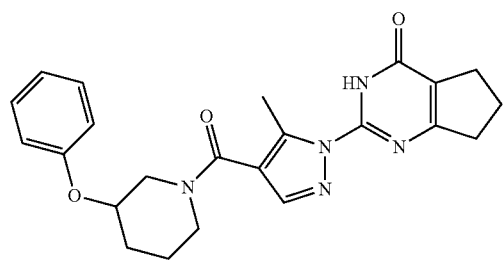 [SMILES: Cc1c(C(=O)N2CCCC(Oc3ccccc3)C2)cnn1-c1nc2c(c(=O)[nH]1)CCC2]
Q-468

TABLE C-continued
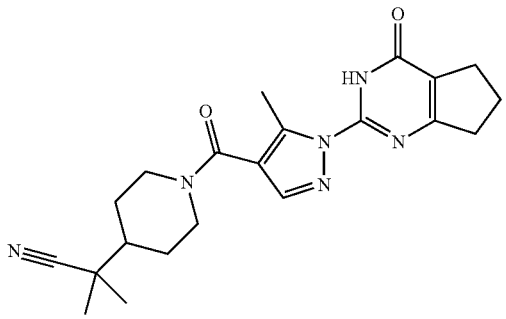 [SMILES: Cc1c(C(=O)N2CCC(C(C)(C)C#N)CC2)cnn1-c1nc2c(c(=O)[nH]1)CCC2]
Q-469
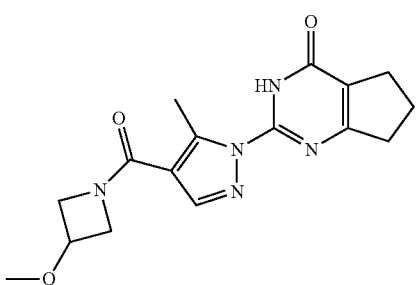 [SMILES: COC1CN(C(=O)c2cnn(-c3nc4c(c(=O)[nH]3)CCC4)c2C)C1]
Q-470
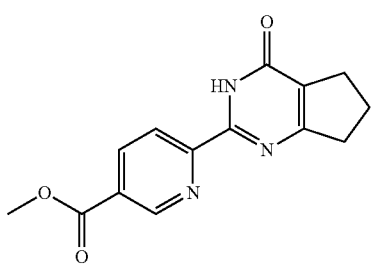 [SMILES: COC(=O)c1ccc(-c2nc3c(c(=O)[nH]2)CCC3)nc1]
Q-471
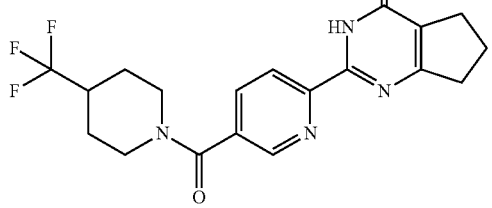
Q-472
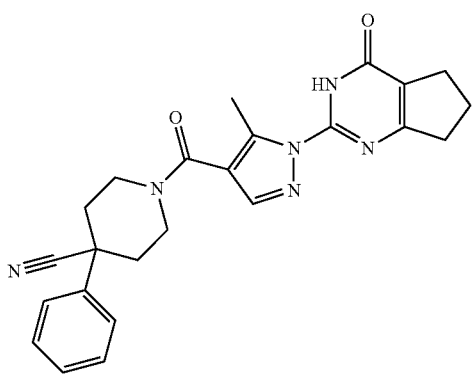 [SMILES: Cc1c(C(=O)N2CCC(C#N)(c3ccccc3)CC2)cnn1-c1nc2c(c(=O)[nH]1)CCC2]
Q-473

TABLE C-continued
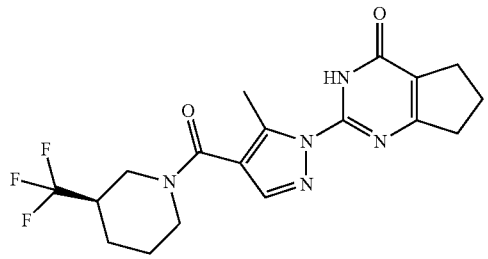 [SMILES: Cc1c(C(=O)N2CCC[C@@H](C(F)(F)F)C2)cnn1-c1nc2c(c(=O)[nH]1)CCC2]
Q-474
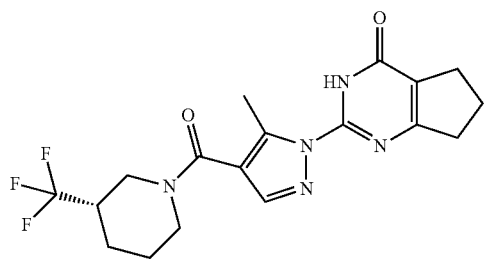 [SMILES: Cc1c(C(=O)N2CCC[C@H](C(F)(F)F)C2)cnn1-c1nc2c(c(=O)[nH]1)CCC2]
Q-475
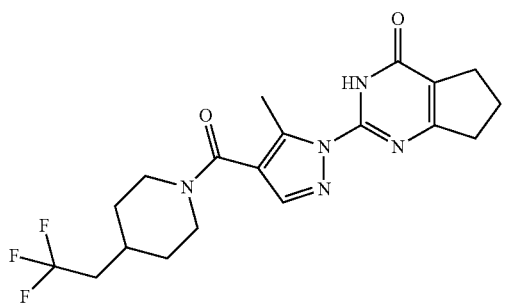 [SMILES: Cc1c(C(=O)N2CCC(CC(F)(F)F)CC2)cnn1-c1nc2c(c(=O)[nH]1)CCC2]
Q-476
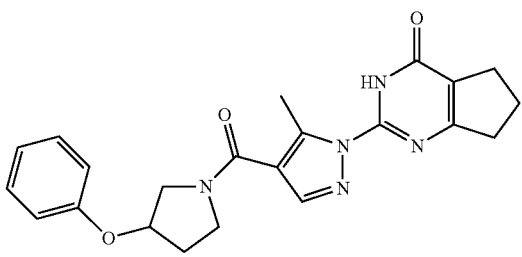 [SMILES: Cc1c(C(=O)N2CCC(Oc3ccccc3)C2)cnn1-c1nc2c(c(=O)[nH]1)CCC2]
Q-477
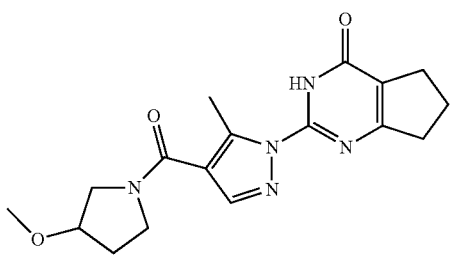 [SMILES: COC1CCN(C(=O)c2cnn(-c3nc4c(c(=O)[nH]3)CCC4)c2C)C1]
Q-478

TABLE C-continued
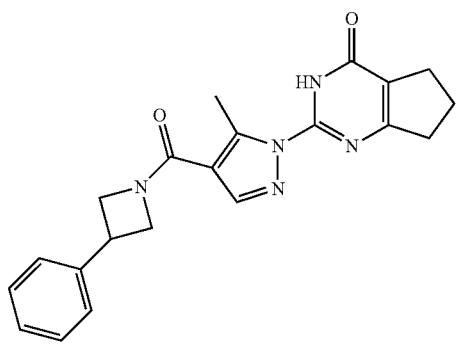 [SMILES: Cc1c(C(=O)N2CC(c3ccccc3)C2)cnn1-c1nc2c(c(=O)[nH]1)CCC2]
Q-479
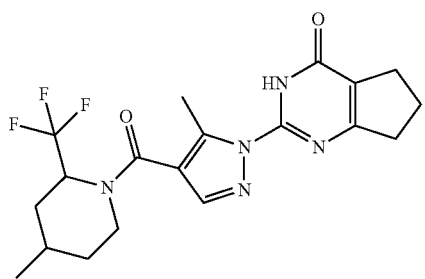 [SMILES: Cc1c(C(=O)N2CCC(C)CC2C(F)(F)F)cnn1-c1nc2c(c(=O)[nH]1)CCC2]
Q-480
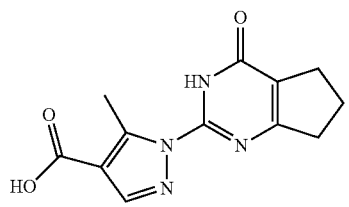 [SMILES: Cc1c(C(=O)O)cnn1-c1nc2c(c(=O)[nH]1)CCC2]
Q-481
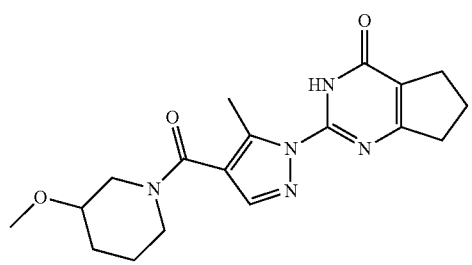 [SMILES: COC1CCCN(C(=O)c2cnn(-c3nc4c(c(=O)[nH]3)CCC4)c2C)C1]
Q-482
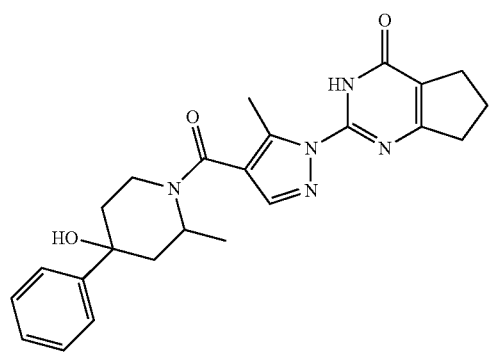 [SMILES: Cc1c(C(=O)N2CCC(O)(c3ccccc3)CC2C)cnn1-c1nc2c(c(=O)[nH]1)CCC2]
Q-483

TABLE C-continued
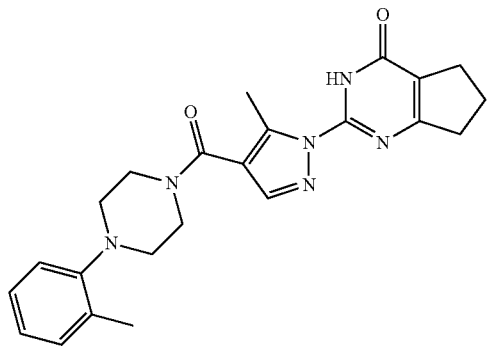 [SMILES: Cc1ccccc1N1CCN(C(=O)c2cnn(-c3nc4c(c(=O)[nH]3)CCC4)c2C)CC1]
Q-485
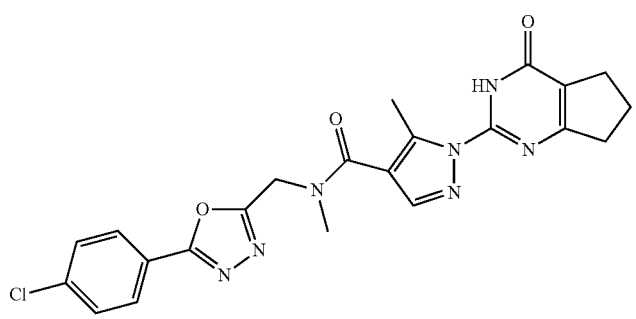 [SMILES: Cc1c(C(=O)N(C)Cc2nnc(-c3ccc(Cl)cc3)o2)cnn1-c1nc2c(c(=O)[nH]1)CCC2]
Q-486
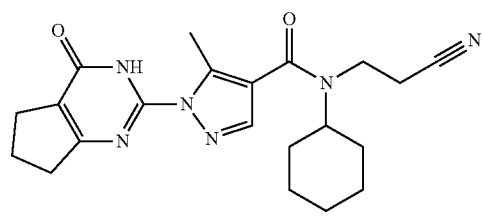 [SMILES: Cc1c(C(=O)N(CCC#N)C2CCCCC2)cnn1-c1nc2c(c(=O)[nH]1)CCC2]
Q-487
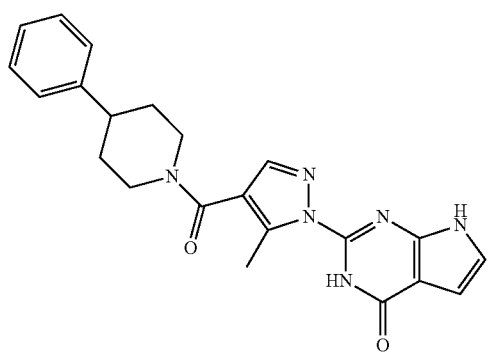 [SMILES: Cc1c(C(=O)N2CCC(c3ccccc3)CC2)cnn1-c1nc2[nH]ccc2c(=O)[nH]1]
Q-488

TABLE C-continued
Q-489
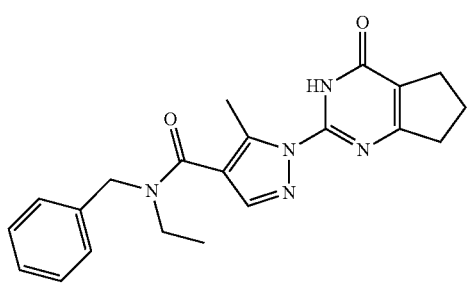 [SMILES: CCN(Cc1ccccc1)C(=O)c1cnn(-c2nc3c(c(=O)[nH]2)CCC3)c1C]
Q-490
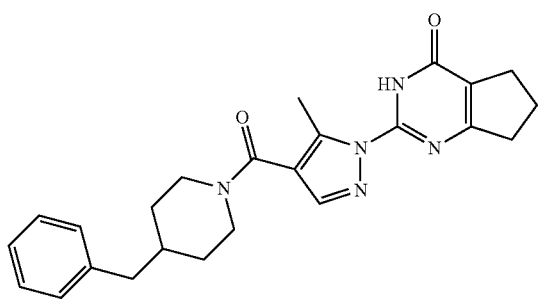 [SMILES: Cc1c(C(=O)N2CCC(Cc3ccccc3)CC2)cnn1-c1nc2c(c(=O)[nH]1)CCC2]
Q-491
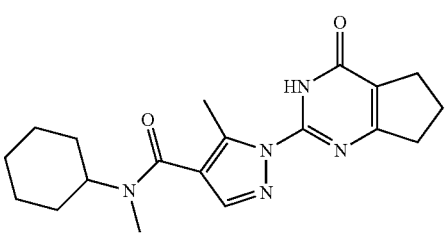 [SMILES: Cc1c(C(=O)N(C)C2CCCCC2)cnn1-c1nc2c(c(=O)[nH]1)CCC2]
Q-492
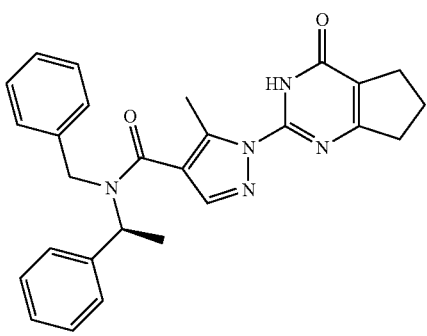 [SMILES: Cc1c(C(=O)N(Cc2ccccc2)[C@@H](C)c2ccccc2)cnn1-c1nc2c(c(=O)[nH]1)CCC2]
Q-493

TABLE C-continued
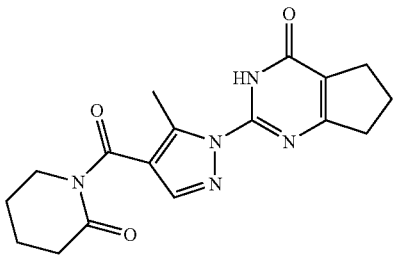 [SMILES: Cc1c(C(=O)N2CCCCC2=O)cnn1-c1nc2c(c(=O)[nH]1)CCC2]
Q-494
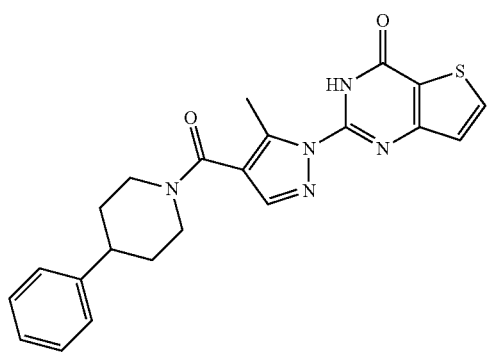 [SMILES: Cc1c(C(=O)N2CCC(c3ccccc3)CC2)cnn1-c1nc2ccsc2c(=O)[nH]1]
Q-495
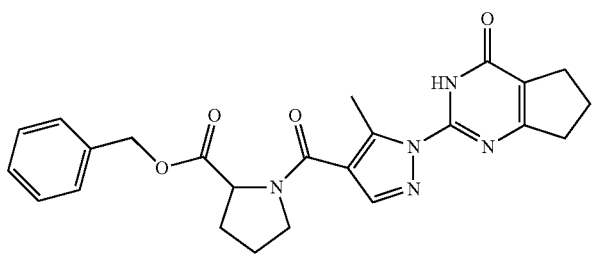 [SMILES: Cc1c(C(=O)N2CCCC2C(=O)OCc2ccccc2)cnn1-c1nc2c(c(=O)[nH]1)CCC2]
Q-496
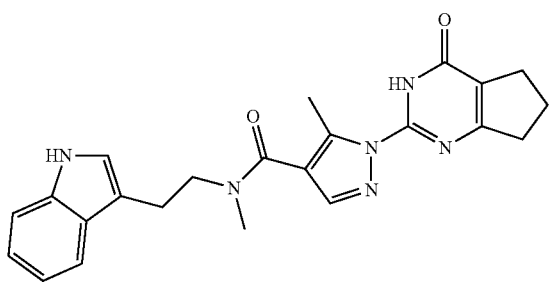 [SMILES: Cc1c(C(=O)N(C)CCc2c[nH]c3ccccc23)cnn1-c1nc2c(c(=O)[nH]1)CCC2]
Q-497
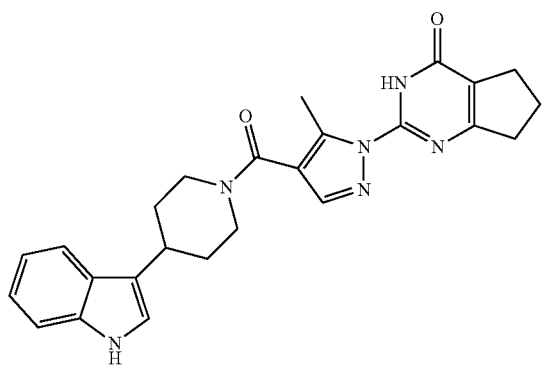 [SMILES: Cc1c(C(=O)N2CCC(c3c[nH]c4ccccc34)CC2)cnn1-c1nc2c(c(=O)[nH]1)CCC2]
Q-498

TABLE C-continued
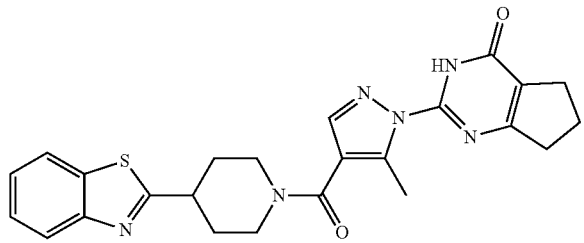 [SMILES: Cc1c(C(=O)N2CCC(c3nc4ccccc4s3)CC2)cnn1-c1nc2c(c(=O)[nH]1)CCC2]
Q-499
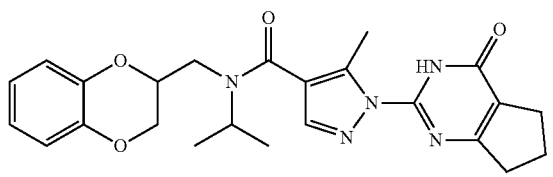 [SMILES: Cc1c(C(=O)N(CC2COc3ccccc3O2)C(C)C)cnn1-c1nc2c(c(=O)[nH]1)CCC2]
Q-500
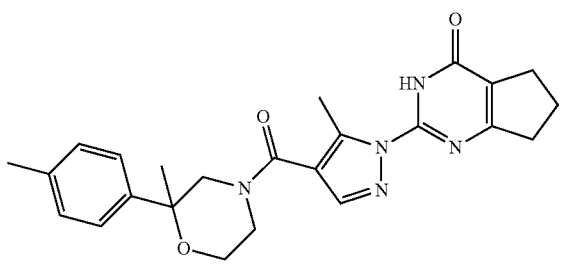 [SMILES: Cc1ccc(C2(C)CN(C(=O)c3cnn(-c4nc5c(c(=O)[nH]4)CCC5)c3C)CCO2)cc1]
Q-501
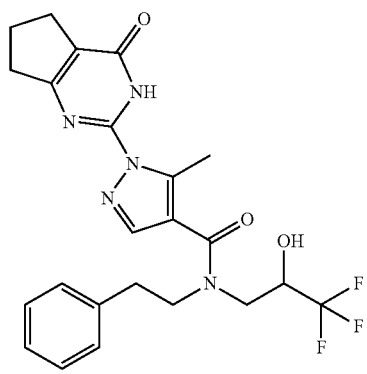 [SMILES: Cc1c(C(=O)N(CCc2ccccc2)CC(O)C(F)(F)F)cnn1-c1nc2c(c(=O)[nH]1)CCC2]
Q-502
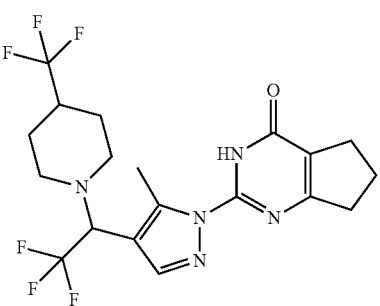 [SMILES: Cc1c(C(N2CCC(C(F)(F)F)CC2)C(F)(F)F)cnn1-c1nc2c(c(=O)[nH]1)CCC2]
Q-503

TABLE C-continued
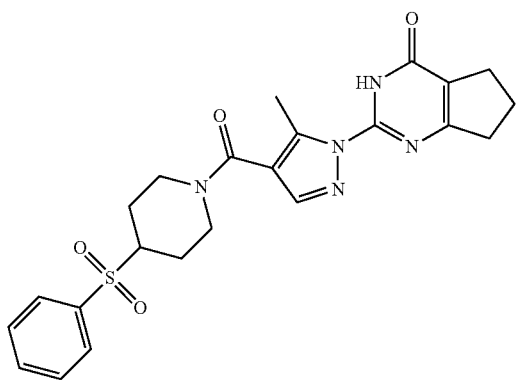 [SMILES: Cc1c(C(=O)N2CCC(S(=O)(=O)c3ccccc3)CC2)cnn1-c1nc2c(c(=O)[nH]1)CCC2]
Q-504
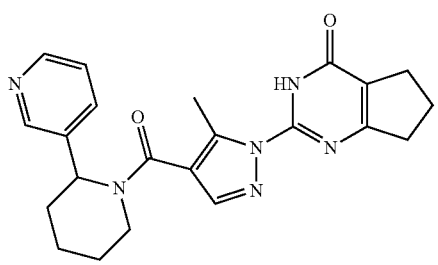 [SMILES: Cc1c(C(=O)N2CCCCC2c2cccnc2)cnn1-c1nc2c(c(=O)[nH]1)CCC2]
Q-505
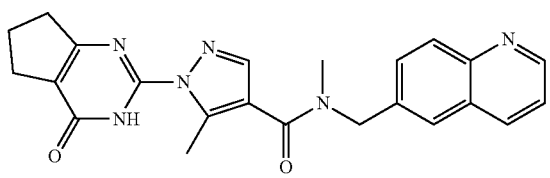 [SMILES: Cc1c(C(=O)N(C)Cc2ccc3ncccc3c2)cnn1-c1nc2c(c(=O)[nH]1)CCC2]
Q-506
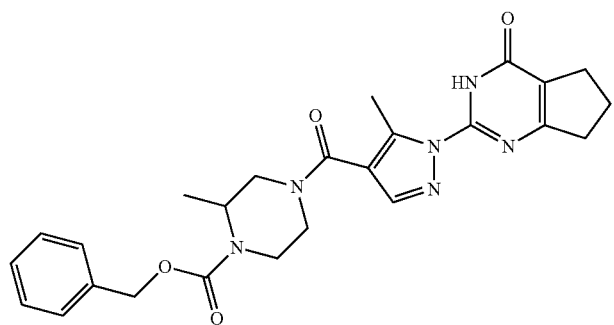 [SMILES: Cc1c(C(=O)N2CCN(C(=O)OCc3ccccc3)C(C)C2)cnn1-c1nc2c(c(=O)[nH]1)CCC2]
Q-507
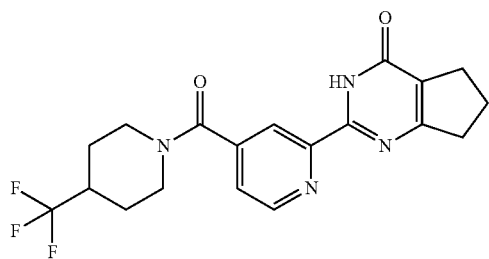 [SMILES: O=C(c1ccnc(-c2nc3c(c(=O)[nH]2)CCC3)c1)N1CCC(C(F)(F)F)CC1]
Q-508

TABLE C-continued
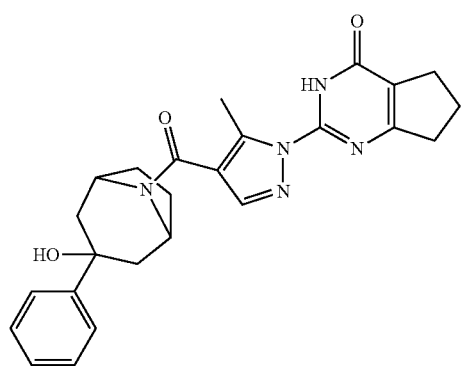 [SMILES: Cc1c(C(=O)N2C3CCC2CC(O)(c2ccccc2)C3)cnn1-c1nc2c(c(=O)[nH]1)CCC2]
Q-509
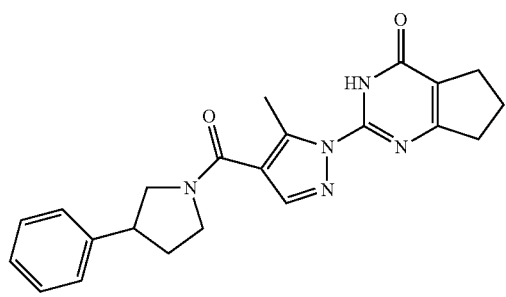 [SMILES: Cc1c(C(=O)N2CCC(c3ccccc3)C2)cnn1-c1nc2c(c(=O)[nH]1)CCC2]
Q-510
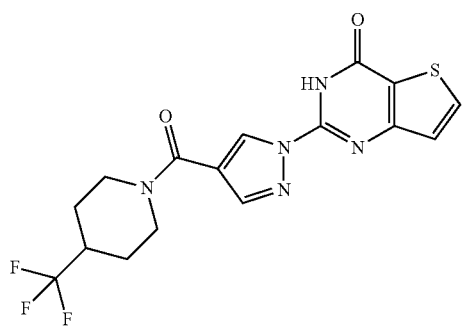 [SMILES: O=C(c1cnn(-c2nc3ccsc3c(=O)[nH]2)c1)N1CCC(C(F)(F)F)CC1]
Q-511
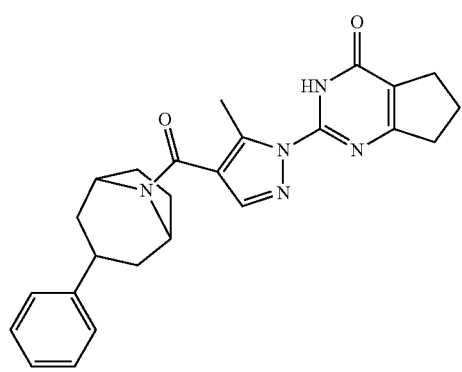 [SMILES: Cc1c(C(=O)N2C3CCC2CC(c2ccccc2)C3)cnn1-c1nc2c(c(=O)[nH]1)CCC2]
Q-513

TABLE C-continued
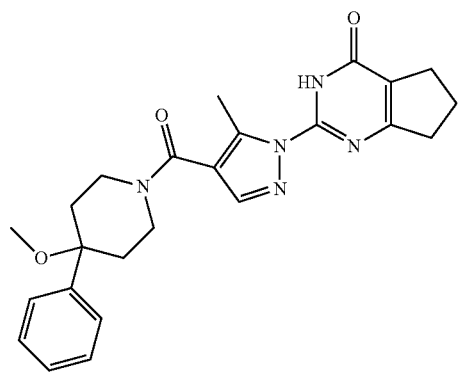 [SMILES: COC1(c2ccccc2)CCN(C(=O)c2cnn(-c3nc4c(c(=O)[nH]3)CCC4)c2C)CC1] Q-514
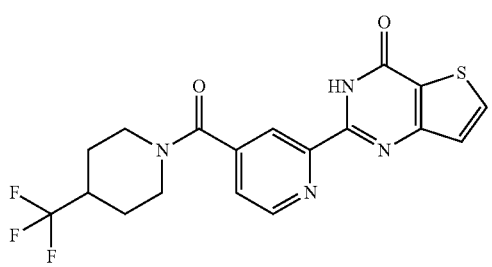 [SMILES: O=C(c1ccnc(-c2nc3ccsc3c(=O)[nH]2)c1)N1CCC(C(F)(F)F)CC1] Q-515
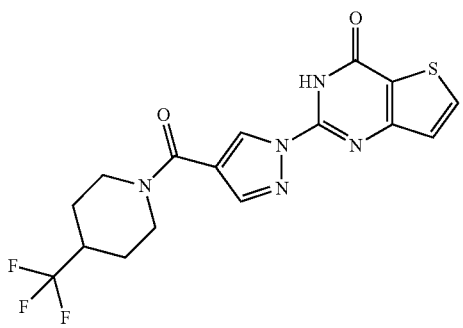 [SMILES: O=C(c1cnn(-c2nc3ccsc3c(=O)[nH]2)c1)N1CCC(C(F)(F)F)CC1] Q-517
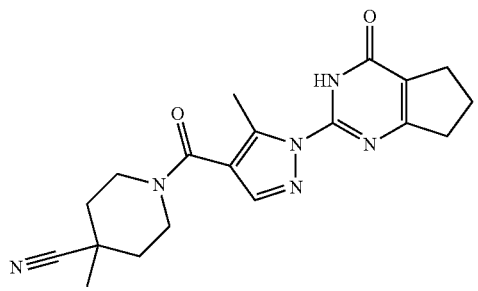 [SMILES: Cc1c(C(=O)N2CCC(C)(C#N)CC2)cnn1-c1nc2c(c(=O)[nH]1)CCC2] Q-518
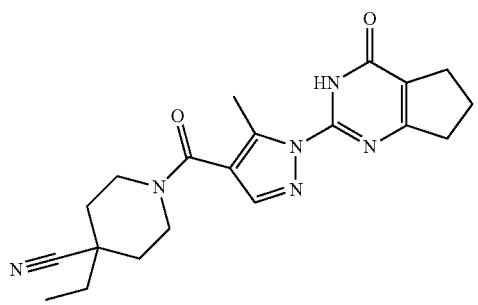 [SMILES: CCC1(C#N)CCN(C(=O)c2cnn(-c3nc4c(c(=O)[nH]3)CCC4)c2C)CC1] Q-519

TABLE C-continued
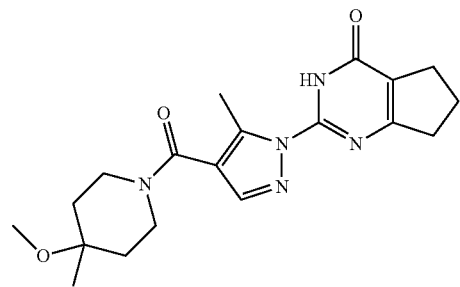 [SMILES: COC1(C)CCN(C(=O)c2cnn(-c3nc4c(c(=O)[nH]3)CCC4)c2C)CC1]
Q-520
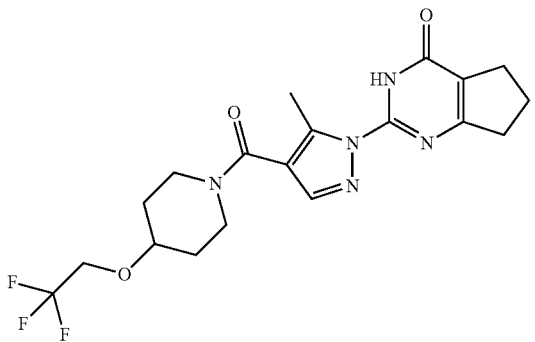 [SMILES: Cc1c(C(=O)N2CCC(OCC(F)(F)F)CC2)cnn1-c1nc2c(c(=O)[nH]1)CCC2]
Q-521
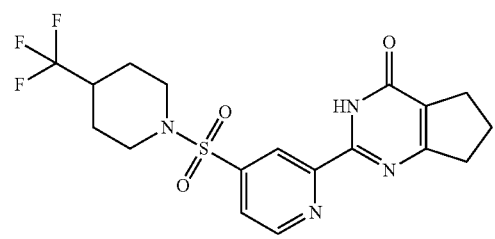 [SMILES: O=c1[nH]c(-c2cc(S(=O)(=O)N3CCC(C(F)(F)F)CC3)ccn2)nc2c1CCC2]
Q-522
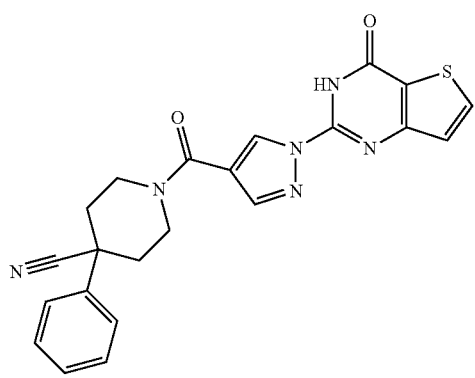 [SMILES: N#CC1(c2ccccc2)CCN(C(=O)c2cnn(-c3nc4ccsc4c(=O)[nH]3)c2)CC1]
Q-523
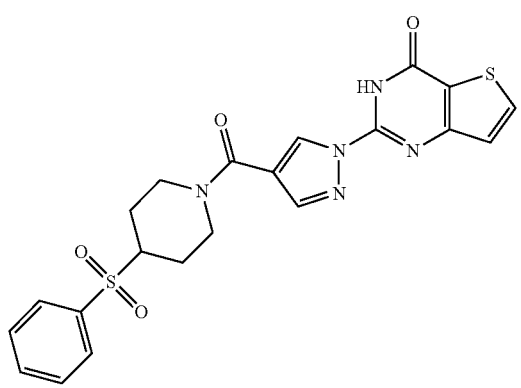 [SMILES: O=C(c1cnn(-c2nc3ccsc3c(=O)[nH]2)c1)N1CCC(S(=O)(=O)c2ccccc2)CC1]
Q-524

TABLE C-continued
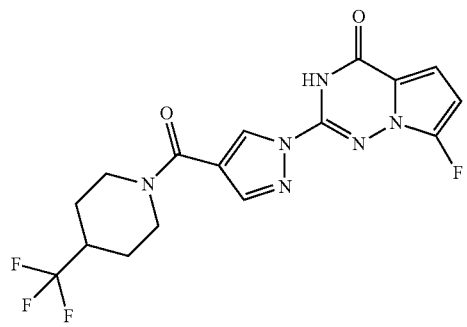 [SMILES: O=C(c1cnn(-c2nn3c(F)ccc3c(=O)[nH]2)c1)N1CCC(C(F)(F)F)CC1]
Q-525
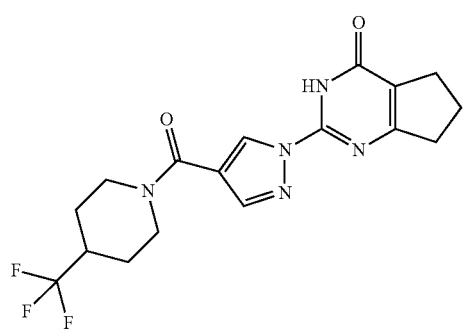 [SMILES: O=C(c1cnn(-c2nc3c(c(=O)[nH]2)CCC3)c1)N1CCC(C(F)(F)F)CC1]
Q-526
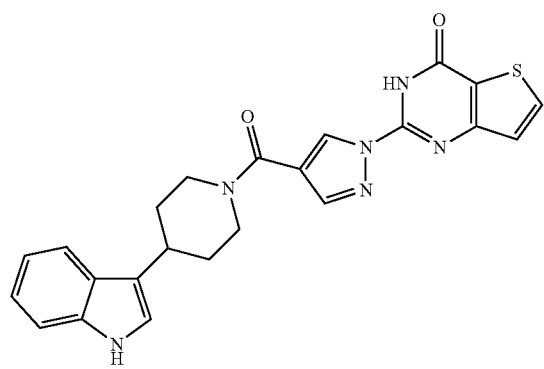 [SMILES: O=C(c1cnn(-c2nc3ccsc3c(=O)[nH]2)c1)N1CCC(c2c[nH]c3ccccc23)CC1]
Q-527
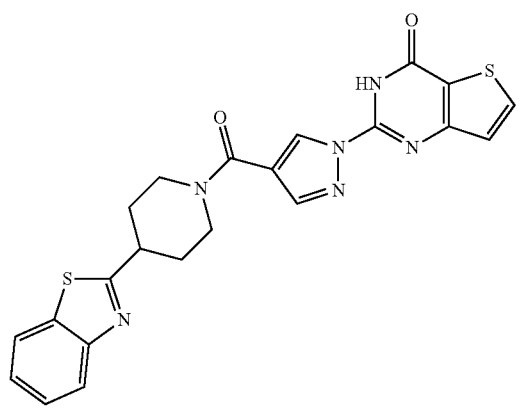 [SMILES: O=C(c1cnn(-c2nc3ccsc3c(=O)[nH]2)c1)N1CCC(c2nc3ccccc3s2)CC1]
Q-528
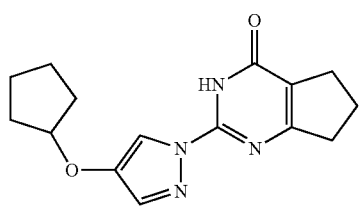 [SMILES: O=c1[nH]c(-n2cc(OC3CCCC3)cn2)nc2c1CCC2]
Q-529

TABLE C-continued
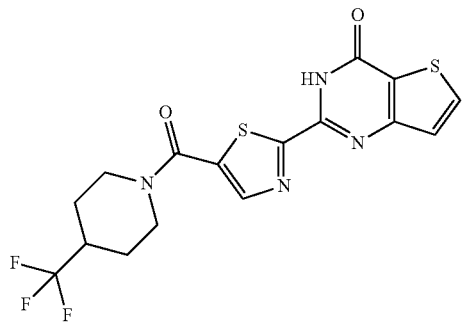 [SMILES: O=C(c1cnc(-c2nc3ccsc3c(=O)[nH]2)s1)N1CCC(C(F)(F)F)CC1]
Q-530
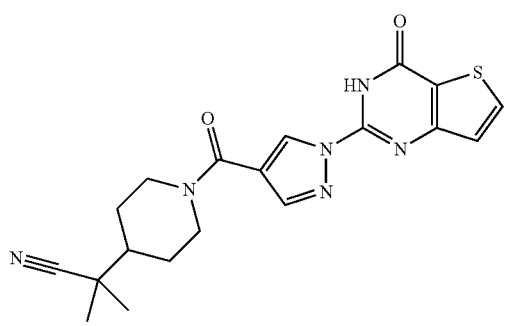 [SMILES: CC(C)(C#N)C1CCN(C(=O)c2cnn(-c3nc4ccsc4c(=O)[nH]3)c2)CC1]
Q-531
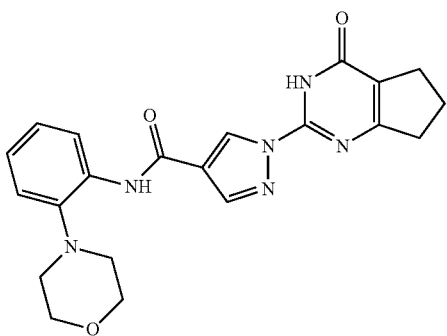 [SMILES: O=C(Nc1ccccc1N1CCOCC1)c1cnn(-c2nc3c(c(=O)[nH]2)CCC3)c1]
Q-532
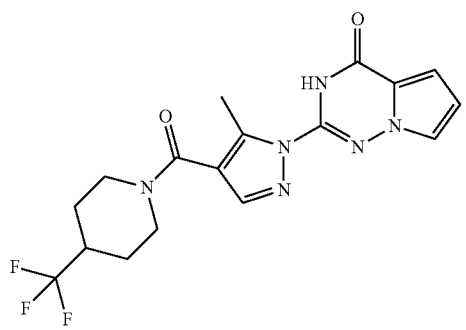 [SMILES: Cc1c(C(=O)N2CCC(C(F)(F)F)CC2)cnn1-c1nn2cccc2c(=O)[nH]1]
Q-533

TABLE C-continued
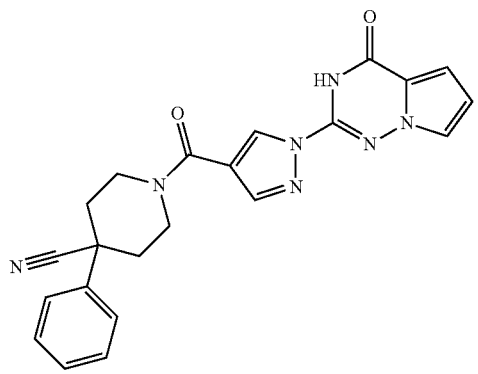 [SMILES: N#CC1(c2ccccc2)CCN(C(=O)c2cnn(-c3nn4cccc4c(=O)[nH]3)c2)CC1]
Q-534
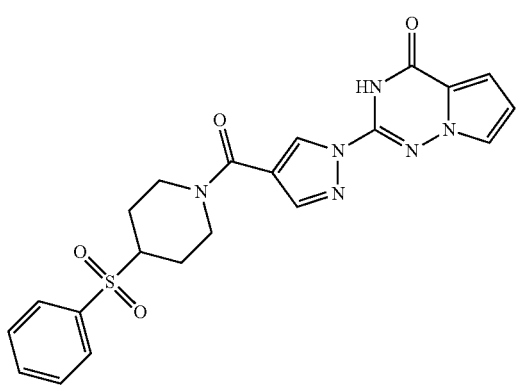 [SMILES: O=C(c1cnn(-c2nn3cccc3c(=O)[nH]2)c1)N1CCC(S(=O)(=O)c2ccccc2)CC1]
Q-535
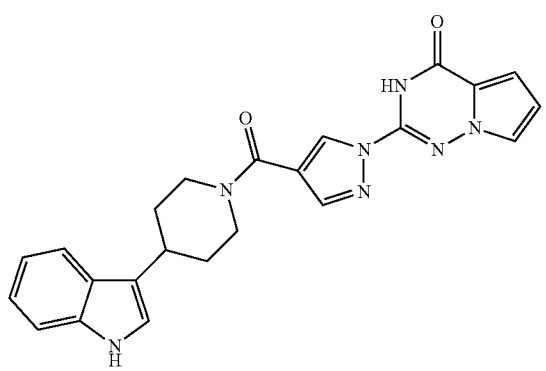 [SMILES: O=C(c1cnn(-c2nn3cccc3c(=O)[nH]2)c1)N1CCC(c2c[nH]c3ccccc23)CC1]
Q-536
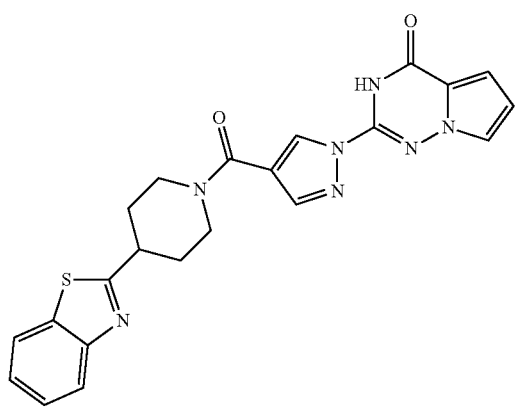 [SMILES: O=C(c1cnn(-c2nn3cccc3c(=O)[nH]2)c1)N1CCC(c2nc3ccccc3s2)CC1]
Q-537

TABLE C-continued
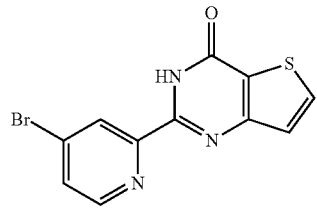 [SMILES: O=c1[nH]c(-c2cc(Br)ccn2)nc2ccsc12] Q-540
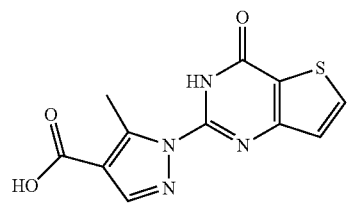 [SMILES: Cc1c(C(=O)O)cnn1-c1nc2ccsc2c(=O)[nH]1] Q-541
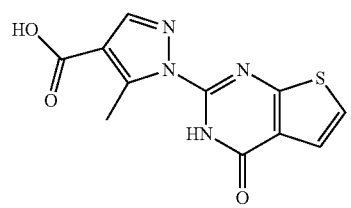 [SMILES: Cc1c(C(=O)O)cnn1-c1nc2sccc2c(=O)[nH]1] Q-542
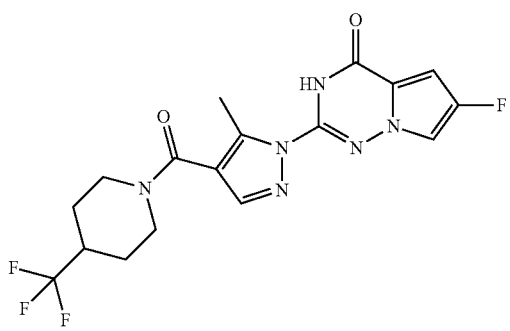 [SMILES: Cc1c(C(=O)N2CCC(C(F)(F)F)CC2)cnn1-c1nn2cc(F)cc2c(=O)[nH]1] Q-543
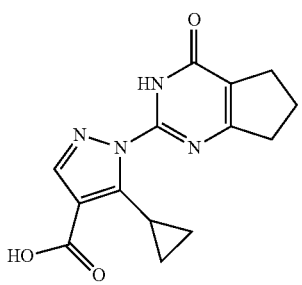 [SMILES: O=C(O)c1cnn(-c2nc3c(c(=O)[nH]2)CCC3)c1C1CC1] Q-544
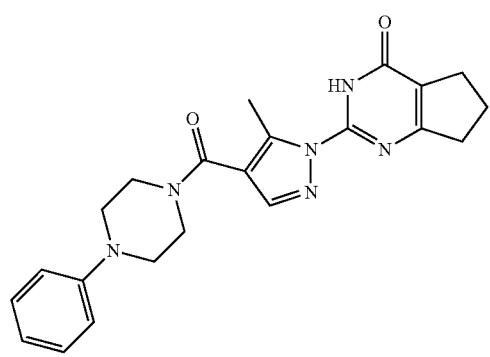 [SMILES: Cc1c(C(=O)N2CCN(c3ccccc3)CC2)cnn1-c1nc2c(c(=O)[nH]1)CCC2] Q-545

TABLE C-continued
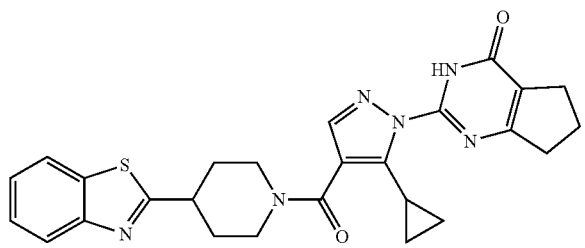 [SMILES: O=C(c1cnn(-c2nc3c(c(=O)[nH]2)CCC3)c1C1CC1)N1CCC(c2nc3ccccc3s2)CC1]
Q-546
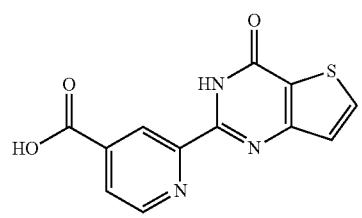 [SMILES: O=C(O)c1ccnc(-c2nc3ccsc3c(=O)[nH]2)c1]
Q-547
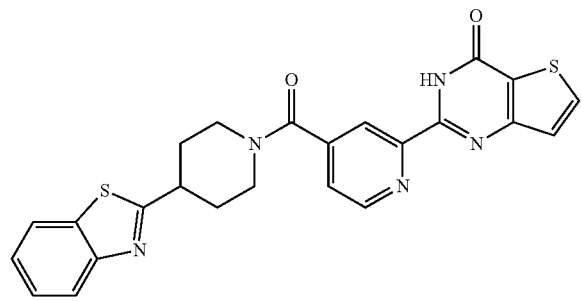 [SMILES: O=C(c1ccnc(-c2nc3ccsc3c(=O)[nH]2)c1)N1CCC(c2nc3ccccc3s2)CC1]
Q-548
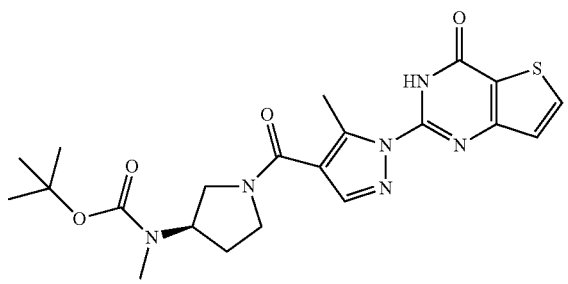 [SMILES: Cc1c(C(=O)N2CC[C@@H](N(C)C(=O)OC(C)(C)C)C2)cnn1-c1nc2ccsc2c(=O)[nH]1]
Q-549
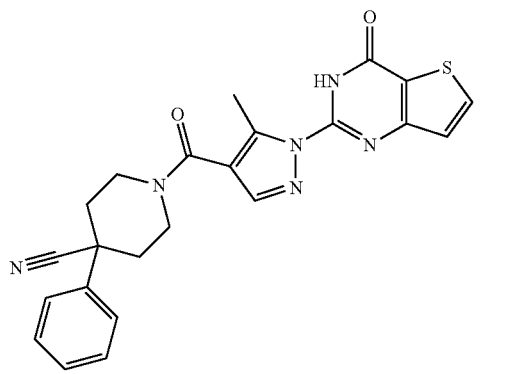 [SMILES: Cc1c(C(=O)N2CCC(C#N)(c3ccccc3)CC2)cnn1-c1nc2ccsc2c(=O)[nH]1]
Q-550

TABLE C-continued
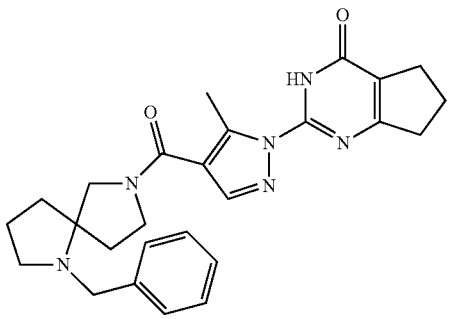 [SMILES: Cc1c(C(=O)N2CCC3(CCCN3Cc3ccccc3)C2)cnn1-c1nc2c(c(=O)[nH]1)CCC2]
Q-551
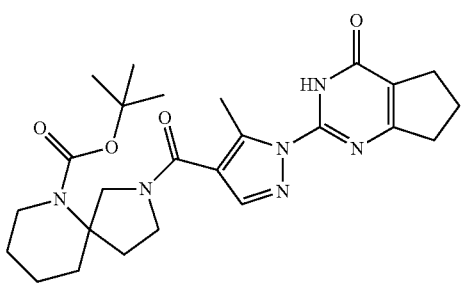 [SMILES: Cc1c(C(=O)N2CCC3(CCCCN3C(=O)OC(C)(C)C)C2)cnn1-c1nc2c(c(=O)[nH]1)CCC2]
Q-552
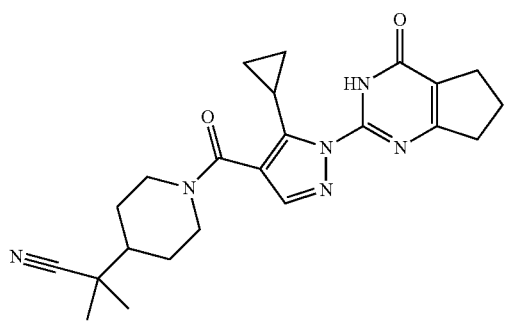 [SMILES: CC(C)(C#N)C1CCN(C(=O)c2cnn(-c3nc4c(c(=O)[nH]3)CCC4)c2C2CC2)CC1]
Q-553
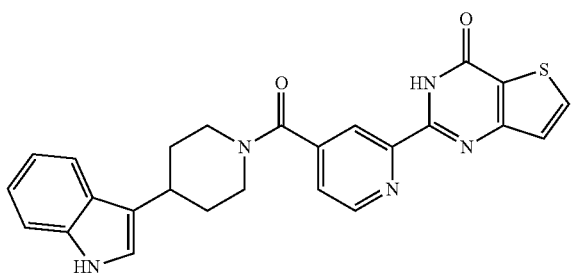 [SMILES: O=C(c1ccnc(-c2nc3ccsc3c(=O)[nH]2)c1)N1CCC(c2c[nH]c3ccccc23)CC1]
Q-555
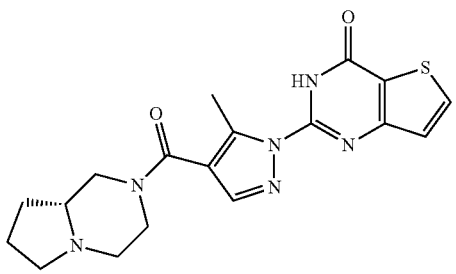 [SMILES: Cc1c(C(=O)N2CCN3CCC[C@@H]3C2)cnn1-c1nc2ccsc2c(=O)[nH]1]
Q-556

TABLE C-continued
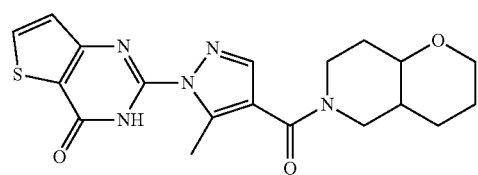 [SMILES: Cc1c(C(=O)N2CCC3OCCCC3C2)cnn1-c1nc2ccsc2c(=O)[nH]1]
Q-557
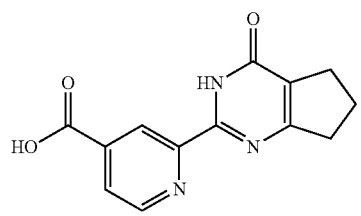 [SMILES: O=C(O)c1ccnc(-c2nc3c(c(=O)[nH]2)CCC3)c1]
Q-558
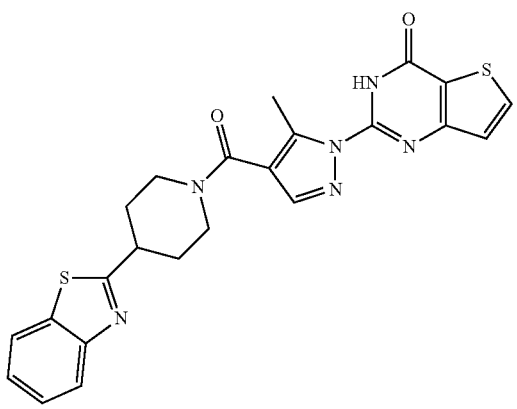 [SMILES: Cc1c(C(=O)N2CCC(c3nc4ccccc4s3)CC2)cnn1-c1nc2ccsc2c(=O)[nH]1]
Q-559
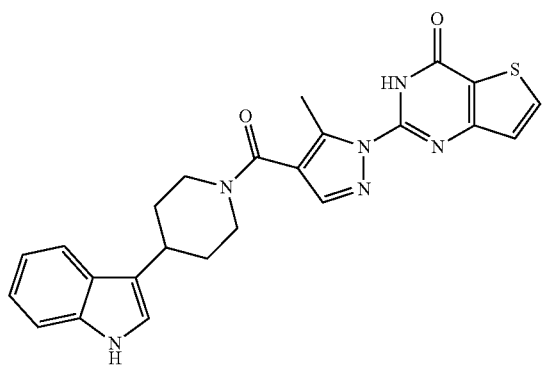 [SMILES: Cc1c(C(=O)N2CCC(c3c[nH]c4ccccc34)CC2)cnn1-c1nc2ccsc2c(=O)[nH]1]
Q-560
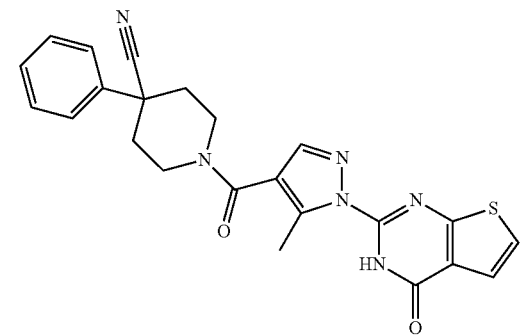 [SMILES: Cc1c(C(=O)N2CCC(C#N)(c3ccccc3)CC2)cnn1-c1nc2sccc2c(=O)[nH]1]
Q-561

TABLE C-continued
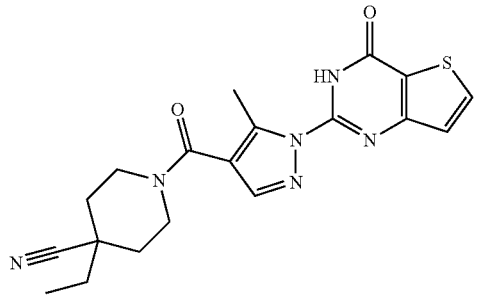 [SMILES: CCC1(C#N)CCN(C(=O)c2cnn(-c3nc4ccsc4c(=O)[nH]3)c2C)CC1]
Q-562
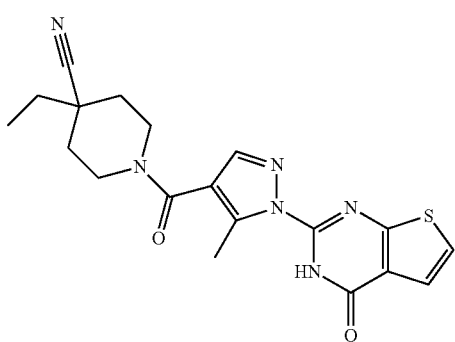 [SMILES: CCC1(C#N)CCN(C(=O)c2cnn(-c3nc4sccc4c(=O)[nH]3)c2C)CC1]
Q-563
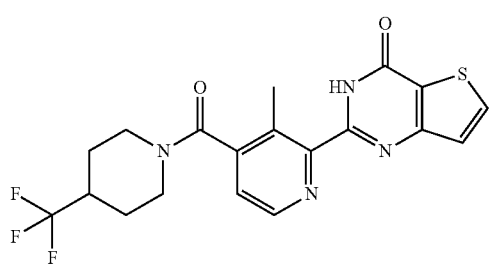 [SMILES: Cc1c(C(=O)N2CCC(C(F)(F)F)CC2)ccnc1-c1nc2ccsc2c(=O)[nH]1]
Q-564
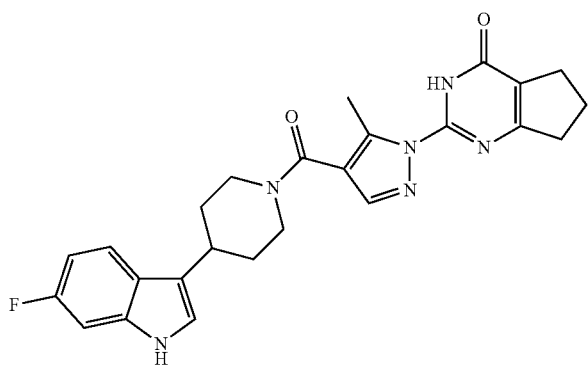 [SMILES: Cc1c(C(=O)N2CCC(c3c[nH]c4cc(F)ccc34)CC2)cnn1-c1nc2c(c(=O)[nH]1)CCC2]
Q-565
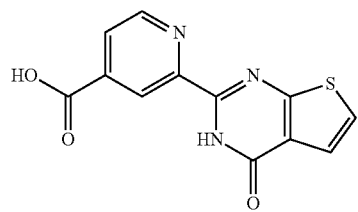 [SMILES: O=C(O)c1ccnc(-c2nc3sccc3c(=O)[nH]2)c1]
Q-566

TABLE C-continued
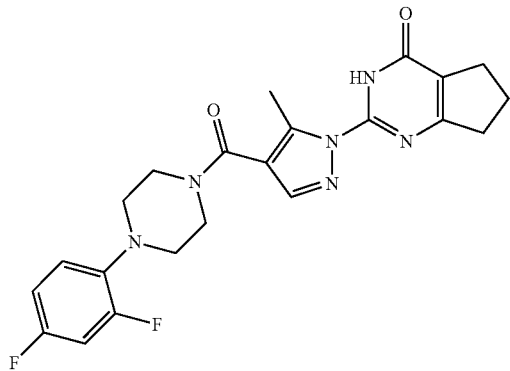 [SMILES: Cc1c(C(=O)N2CCN(c3ccc(F)cc3F)CC2)cnn1-c1nc2c(c(=O)[nH]1)CCC2]
Q-567
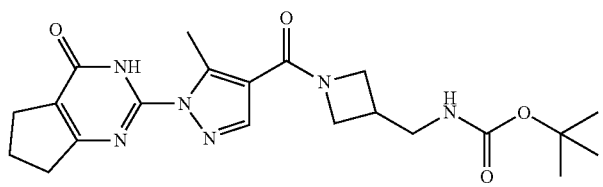 [SMILES: Cc1c(C(=O)N2CC(CNC(=O)OC(C)(C)C)C2)cnn1-c1nc2c(c(=O)[nH]1)CCC2]
Q-568
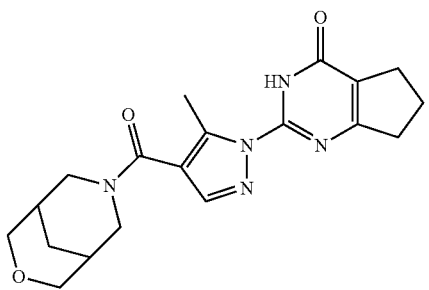 [SMILES: Cc1c(C(=O)N2CC3COCC(C3)C2)cnn1-c1nc2c(c(=O)[nH]1)CCC2]
Q-569
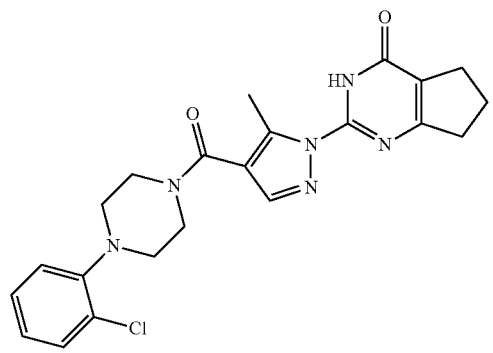 [SMILES: Cc1c(C(=O)N2CCN(c3ccccc3Cl)CC2)cnn1-c1nc2c(c(=O)[nH]1)CCC2]
Q-570
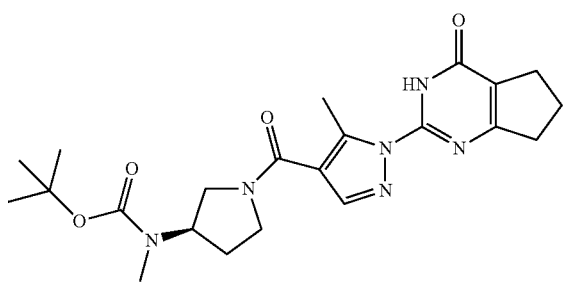 [SMILES: Cc1c(C(=O)N2CC[C@@H](N(C)C(=O)OC(C)(C)C)C2)cnn1-c1nc2c(c(=O)[nH]1)CCC2]
Q-571

TABLE C-continued
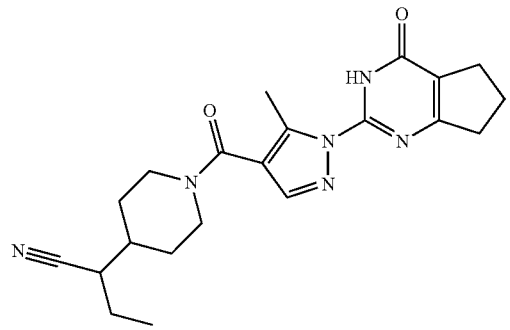 [SMILES: CCC(C#N)C1CCN(C(=O)c2cnn(-c3nc4c(c(=O)[nH]3)CCC4)c2C)CC1] Q-572
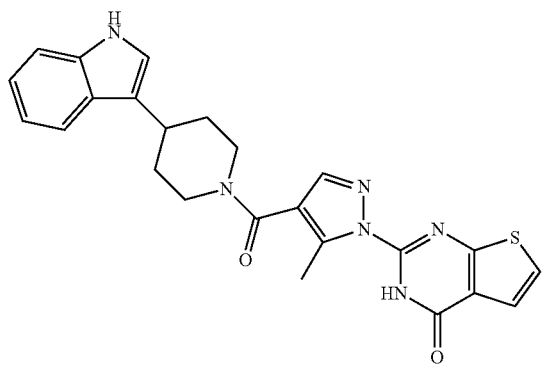 [SMILES: Cc1c(C(=O)N2CCC(c3c[nH]c4ccccc34)CC2)cnn1-c1nc2sccc2c(=O)[nH]1] Q-573
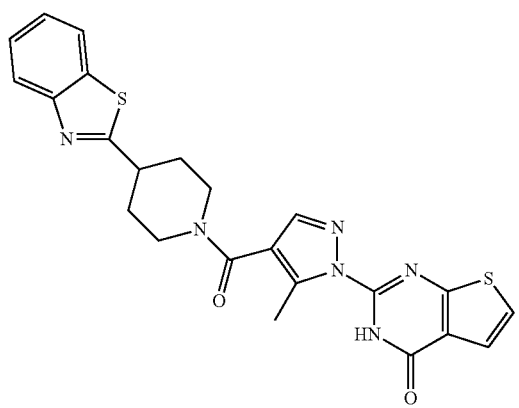 [SMILES: Cc1c(C(=O)N2CCC(c3nc4ccccc4s3)CC2)cnn1-c1nc2sccc2c(=O)[nH]1] Q-574
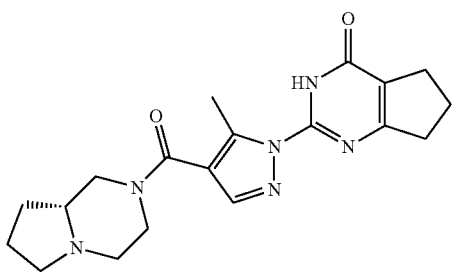 [SMILES: Cc1c(C(=O)N2CCN3CCC[C@@H]3C2)cnn1-c1nc2c(c(=O)[nH]1)CCC2] Q-575
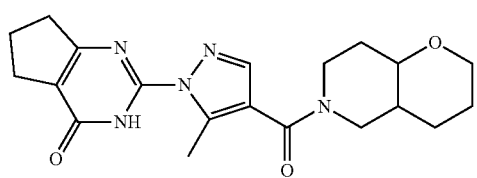 [SMILES: Cc1c(C(=O)N2CCC3OCCCC3C2)cnn1-c1nc2c(c(=O)[nH]1)CCC2] Q-576

TABLE C-continued
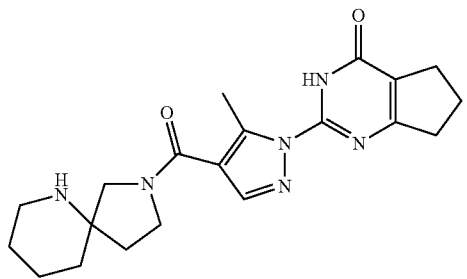 [SMILES: Cc1c(C(=O)N2CCC3(CCCCN3)C2)cnn1-c1nc2c(c(=O)[nH]1)CCC2]
Q-577
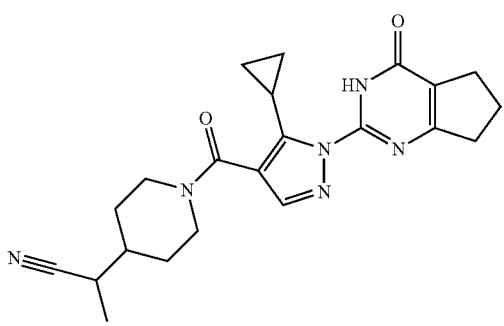 [SMILES: CC(C#N)C1CCN(C(=O)c2cnn(-c3nc4c(c(=O)[nH]3)CCC4)c2C2CC2)CC1]
Q-578
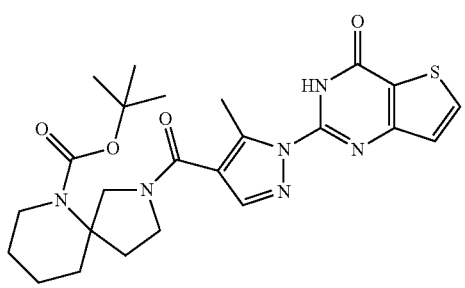 [SMILES: Cc1c(C(=O)N2CCC3(CCCCN3C(=O)OC(C)(C)C)C2)cnn1-c1nc2ccsc2c(=O)[nH]1]
Q-579
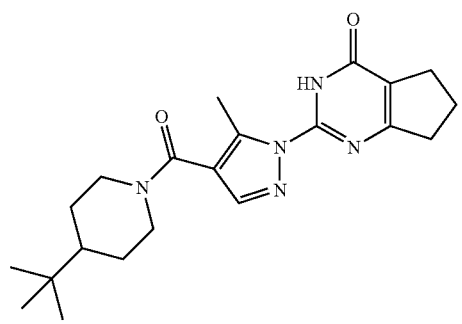 [SMILES: Cc1c(C(=O)N2CCC(C(C)(C)C)CC2)cnn1-c1nc2c(c(=O)[nH]1)CCC2]
Q-580
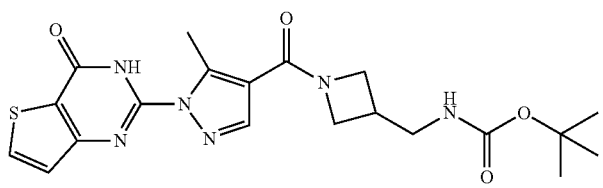 [SMILES: Cc1c(C(=O)N2CC(CNC(=O)OC(C)(C)C)C2)cnn1-c1nc2ccsc2c(=O)[nH]1]
Q-582

TABLE C-continued
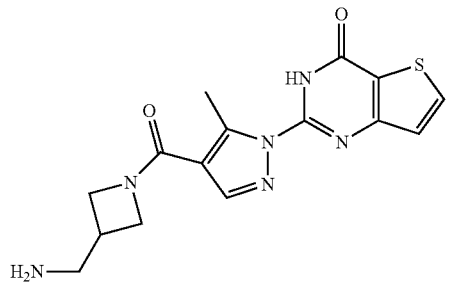 [SMILES: Cc1c(C(=O)N2CC(CN)C2)cnn1-c1nc2ccsc2c(=O)[nH]1]
Q-583
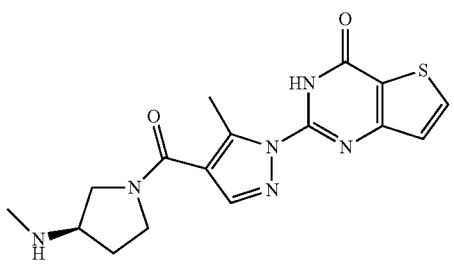 [SMILES: CN[C@@H]1CCN(C(=O)c2cnn(-c3nc4ccsc4c(=O)[nH]3)c2C)C1]
Q-584
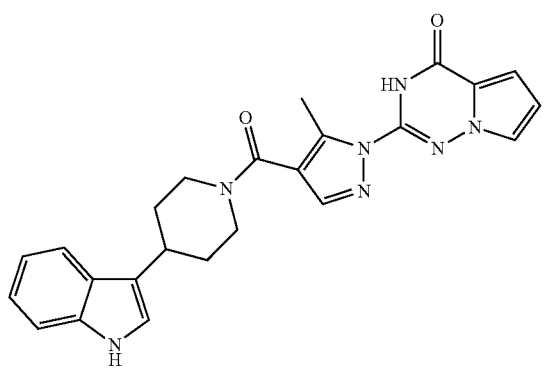 [SMILES: Cc1c(C(=O)N2CCC(c3c[nH]c4ccccc34)CC2)cnn1-c1nn2cccc2c(=O)[nH]1]
Q-585
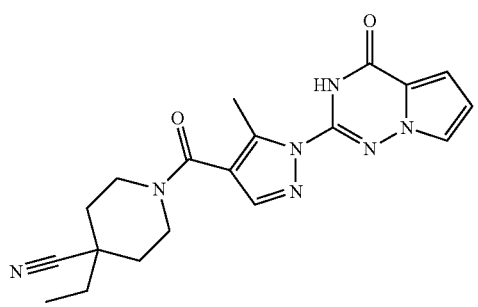 [SMILES: CCC1(C#N)CCN(C(=O)c2cnn(-c3nn4cccc4c(=O)[nH]3)c2C)CC1]
Q-586
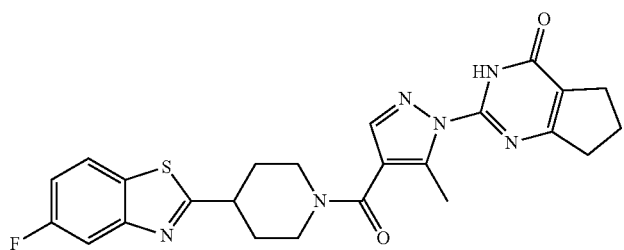 [SMILES: Cc1c(C(=O)N2CCC(c3nc4cc(F)ccc4s3)CC2)cnn1-c1nc2c(c(=O)[nH]1)CCC2]
Q-587

TABLE C-continued
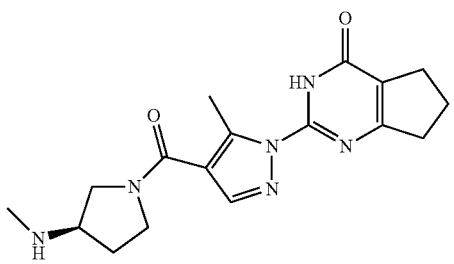 [SMILES: CN[C@@H]1CCN(C(=O)c2cnn(-c3nc4c(c(=O)[nH]3)CCC4)c2C)C1]
Q-588
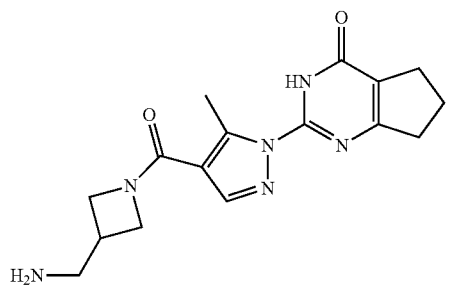 [SMILES: Cc1c(C(=O)N2CC(CN)C2)cnn1-c1nc2c(c(=O)[nH]1)CCC2]
Q-589
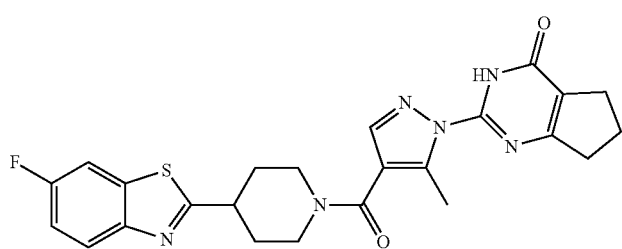
Q-590
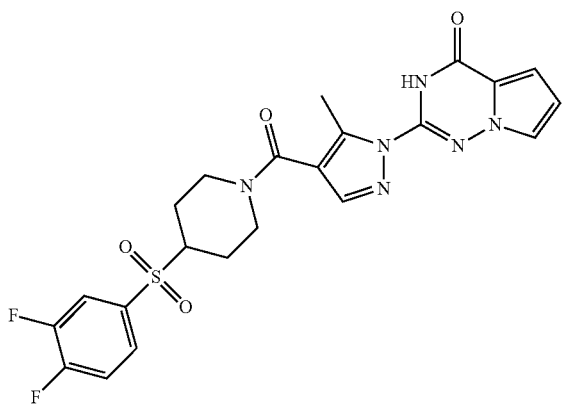 [SMILES: Cc1c(C(=O)N2CCC(S(=O)(=O)c3ccc(F)c(F)c3)CC2)cnn1-c1nn2cccc2c(=O)[nH]1]
Q-591
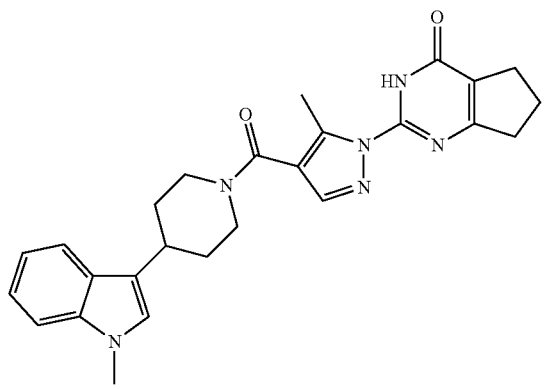 [SMILES: Cc1c(C(=O)N2CCC(c3cn(C)c4ccccc34)CC2)cnn1-c1nc2c(c(=O)[nH]1)CCC2]
Q-592

TABLE C-continued
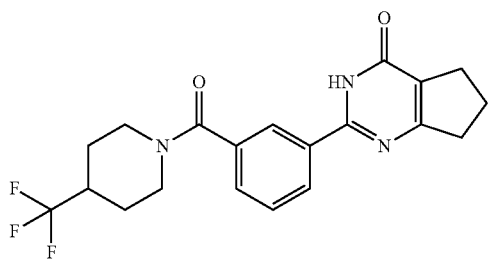 [SMILES: O=C(c1cccc(-c2nc3c(c(=O)[nH]2)CCC3)c1)N1CCC(C(F)(F)F)CC1] Q-593
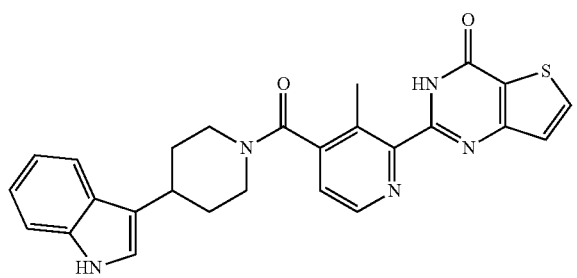 [SMILES: Cc1c(C(=O)N2CCC(c3c[nH]c4ccccc34)CC2)ccnc1-c1nc2ccsc2c(=O)[nH]1] Q-594
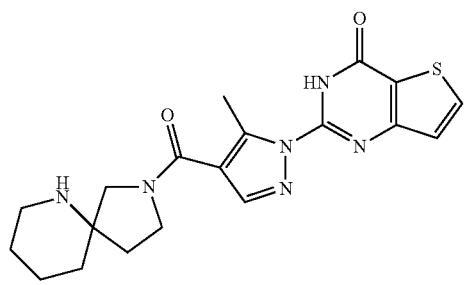 [SMILES: Cc1c(C(=O)N2CCC3(CCCCN3)C2)cnn1-c1nc2ccsc2c(=O)[nH]1] Q-595
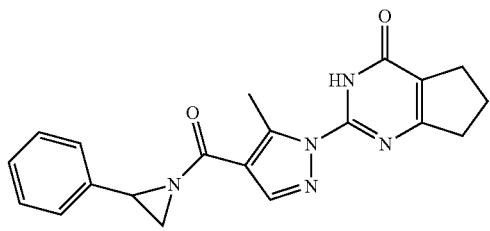 [SMILES: Cc1c(C(=O)N2CC2c2ccccc2)cnn1-c1nc2c(c(=O)[nH]1)CCC2] Q-596
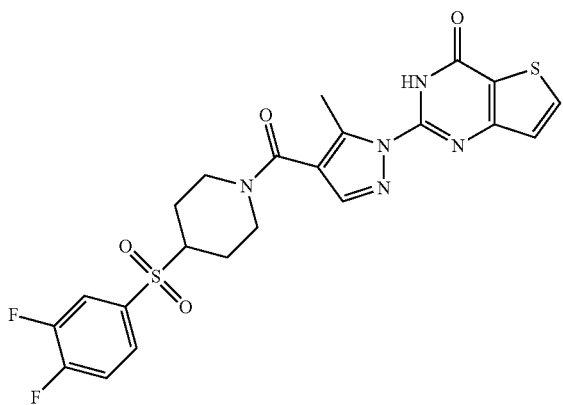 [SMILES: Cc1c(C(=O)N2CCC(S(=O)(=O)c3ccc(F)c(F)c3)CC2)cnn1-c1nc2ccsc2c(=O)[nH]1] Q-597

TABLE C-continued
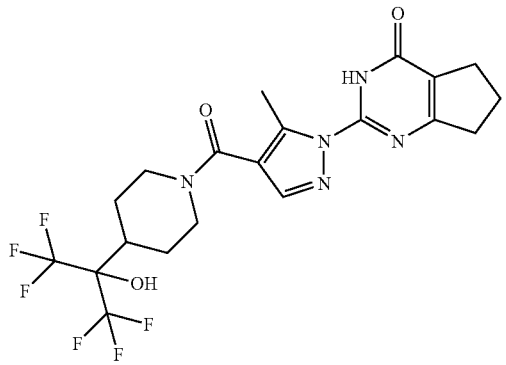 [SMILES: Cc1c(C(=O)N2CCC(C(O)(C(F)(F)F)C(F)(F)F)CC2)cnn1-c1nc2c(c(=O)[nH]1)CCC2]
Q-598
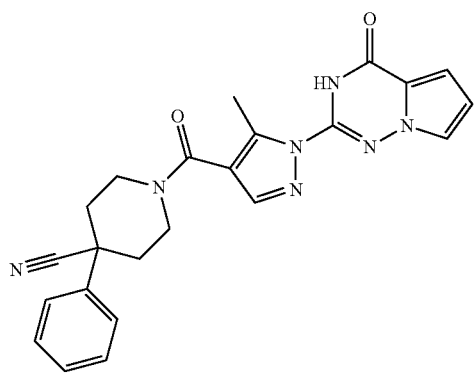 [SMILES: Cc1c(C(=O)N2CCC(C#N)(c3ccccc3)CC2)cnn1-c1nn2cccc2c(=O)[nH]1]
Q-599
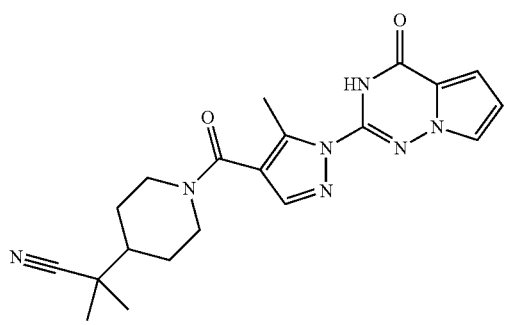 [SMILES: Cc1c(C(=O)N2CCC(C(C)(C)C#N)CC2)cnn1-c1nn2cccc2c(=O)[nH]1]
Q-600
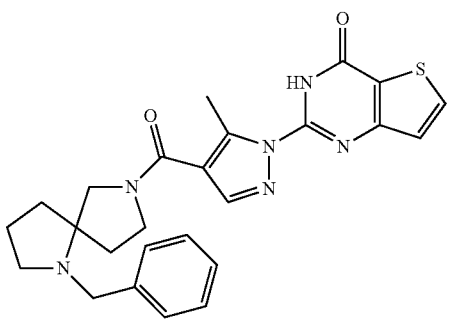 [SMILES: Cc1c(C(=O)N2CCC3(CCCN3Cc3ccccc3)C2)cnn1-c1nc2ccsc2c(=O)[nH]1]
Q-601

TABLE C-continued
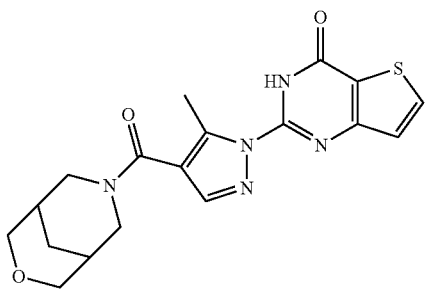 [SMILES: Cc1c(C(=O)N2CC3COCC(C3)C2)cnn1-c1nc2ccsc2c(=O)[nH]1]
Q-602
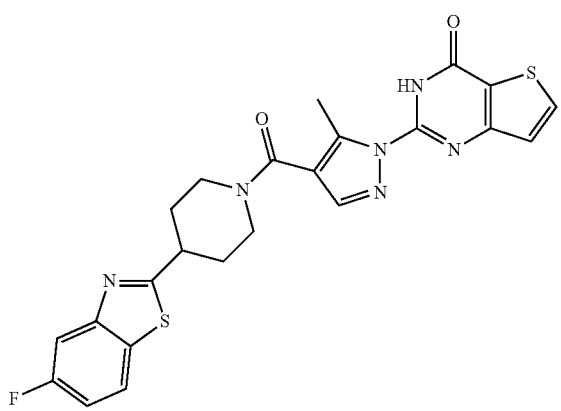 [SMILES: Cc1c(C(=O)N2CCC(c3nc4cc(F)ccc4s3)CC2)cnn1-c1nc2ccsc2c(=O)[nH]1]
Q-603
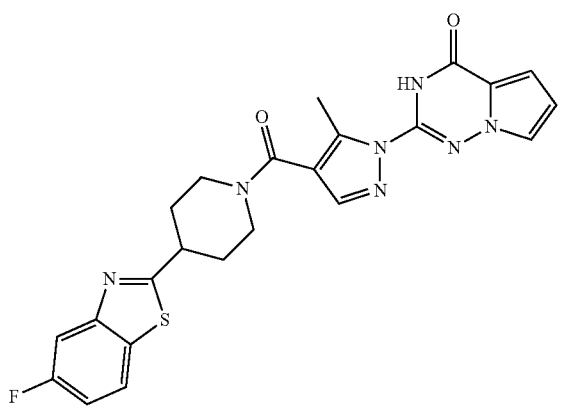 [SMILES: Cc1c(C(=O)N2CCC(c3nc4cc(F)ccc4s3)CC2)cnn1-c1nn2cccc2c(=O)[nH]1]
Q-604
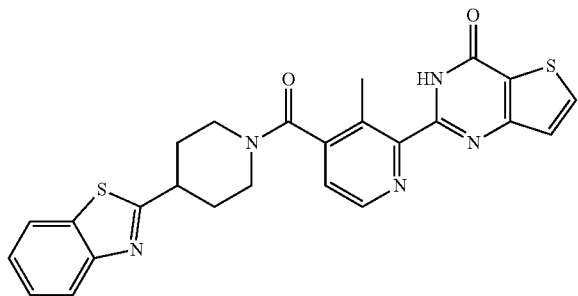 [SMILES: Cc1c(C(=O)N2CCC(c3nc4ccccc4s3)CC2)ccnc1-c1nc2ccsc2c(=O)[nH]1]
Q-605

TABLE C-continued
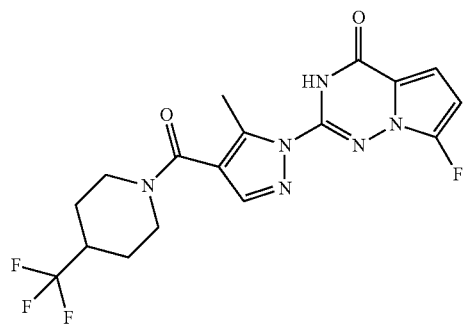 [SMILES: Cc1c(C(=O)N2CCC(C(F)(F)F)CC2)cnn1-c1nn2c(F)ccc2c(=O)[nH]1]
Q-606
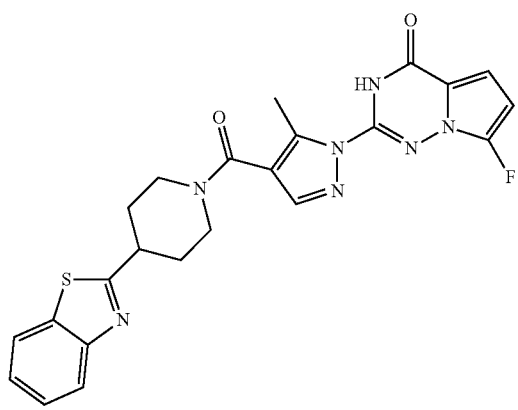 [SMILES: Cc1c(C(=O)N2CCC(c3nc4ccccc4s3)CC2)cnn1-c1nn2c(F)ccc2c(=O)[nH]1]
Q-607
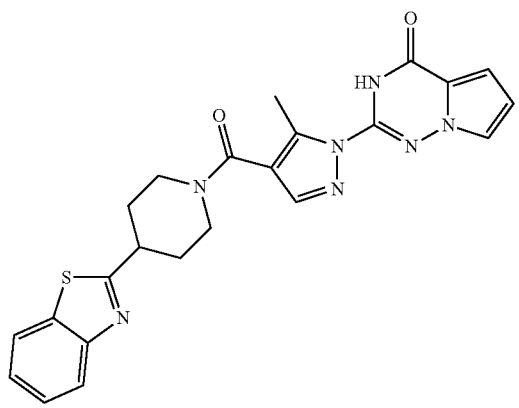
Q-608
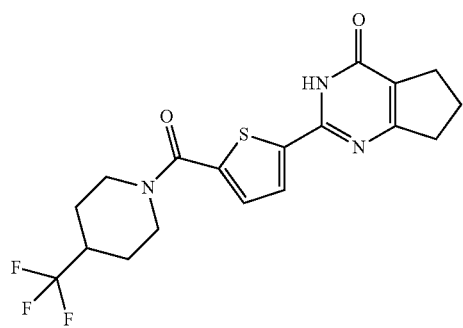 [SMILES: O=C(c1ccc(-c2nc3c(c(=O)[nH]2)CCC3)s1)N1CCC(C(F)(F)F)CC1]
Q-609

TABLE C-continued
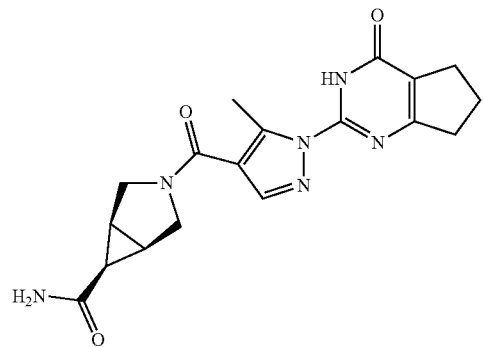 [SMILES: Cc1c(C(=O)N2C[C@@H]3[C@H](C2)[C@@H]3C(N)=O)cnn1-c1nc2c(c(=O)[nH]1)CCC2]
Q-610
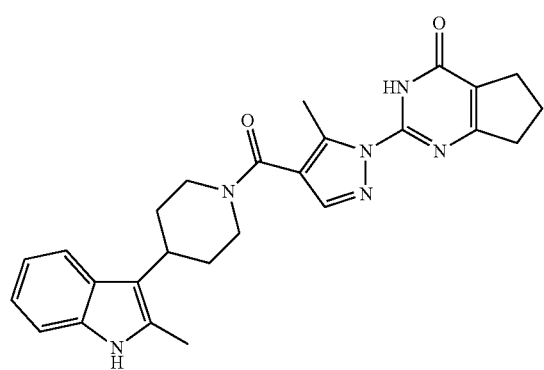 [SMILES: Cc1[nH]c2ccccc2c1C1CCN(C(=O)c2cnn(-c3nc4c(c(=O)[nH]3)CCC4)c2C)CC1]
Q-611
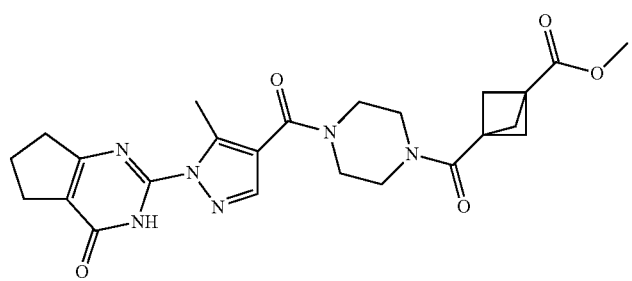 [SMILES: COC(=O)C12CC(C(=O)N3CCN(C(=O)c4cnn(-c5nc6c(c(=O)[nH]5)CCC6)c4C)CC3)(C1)C2]
Q-612
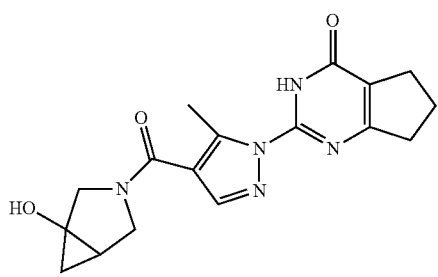 [SMILES: Cc1c(C(=O)N2CC3CC3(O)C2)cnn1-c1nc2c(c(=O)[nH]1)CCC2]
Q-614

TABLE C-continued
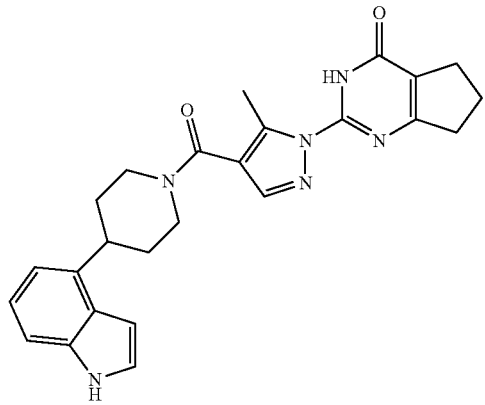 [SMILES: Cc1c(C(=O)N2CCC(c3cccc4[nH]ccc34)CC2)cnn1-c1nc2c(c(=O)[nH]1)CCC2]
Q-615
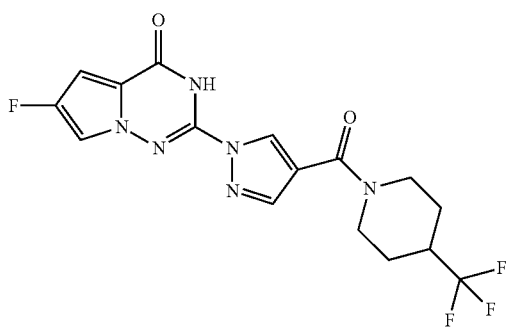 [SMILES: O=C(c1cnn(-c2nn3cc(F)cc3c(=O)[nH]2)c1)N1CCC(C(F)(F)F)CC1]
Q-616
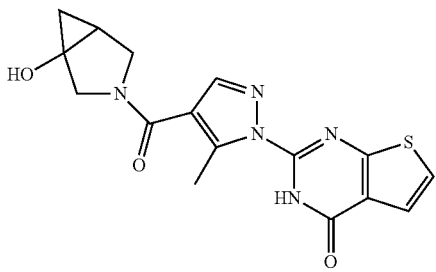 [SMILES: Cc1c(C(=O)N2CC3CC3(O)C2)cnn1-c1nc2sccc2c(=O)[nH]1]
Q-617
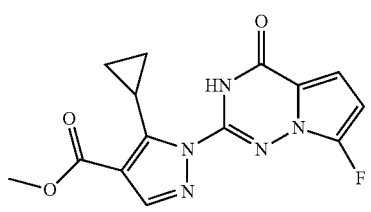 [SMILES: COC(=O)c1cnn(-c2nn3c(F)ccc3c(=O)[nH]2)c1C1CC1]
Q-618
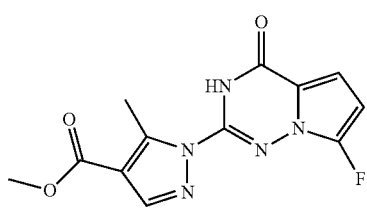 [SMILES: COC(=O)c1cnn(-c2nn3c(F)ccc3c(=O)[nH]2)c1C]
Q-619

TABLE C-continued
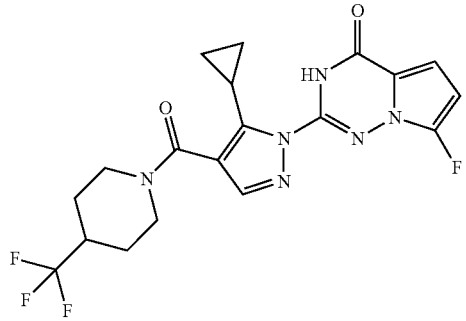 [SMILES: O=C(c1cnn(-c2nn3c(F)ccc3c(=O)[nH]2)c1C1CC1)N1CCC(C(F)(F)F)CC1]
Q-620
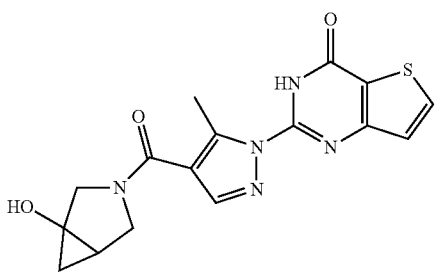 [SMILES: Cc1c(C(=O)N2CC3CC3(O)C2)cnn1-c1nc2ccsc2c(=O)[nH]1]
Q-621
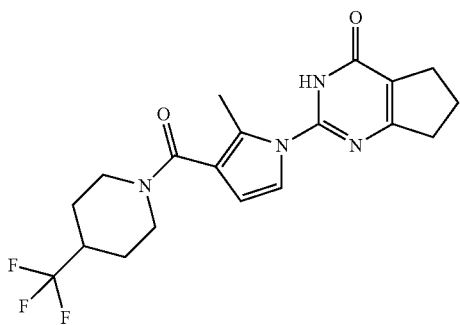 [SMILES: Cc1c(C(=O)N2CCC(C(F)(F)F)CC2)ccn1-c1nc2c(c(=O)[nH]1)CCC2]
Q-622
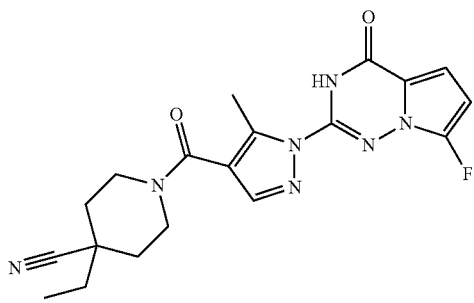 [SMILES: CCC1(C#N)CCN(C(=O)c2cnn(-c3nn4c(F)ccc4c(=O)[nH]3)c2C)CC1]
Q-623
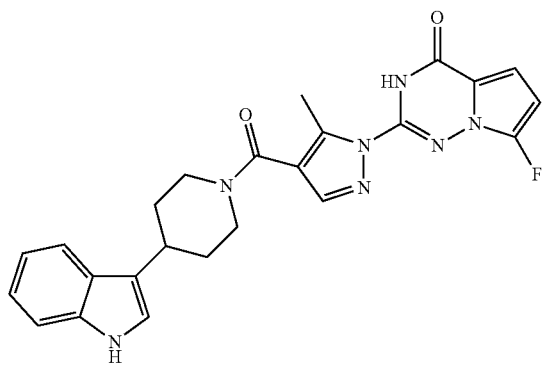 [SMILES: Cc1c(C(=O)N2CCC(c3c[nH]c4ccccc34)CC2)cnn1-c1nn2c(F)ccc2c(=O)[nH]1]
Q-624

TABLE C-continued
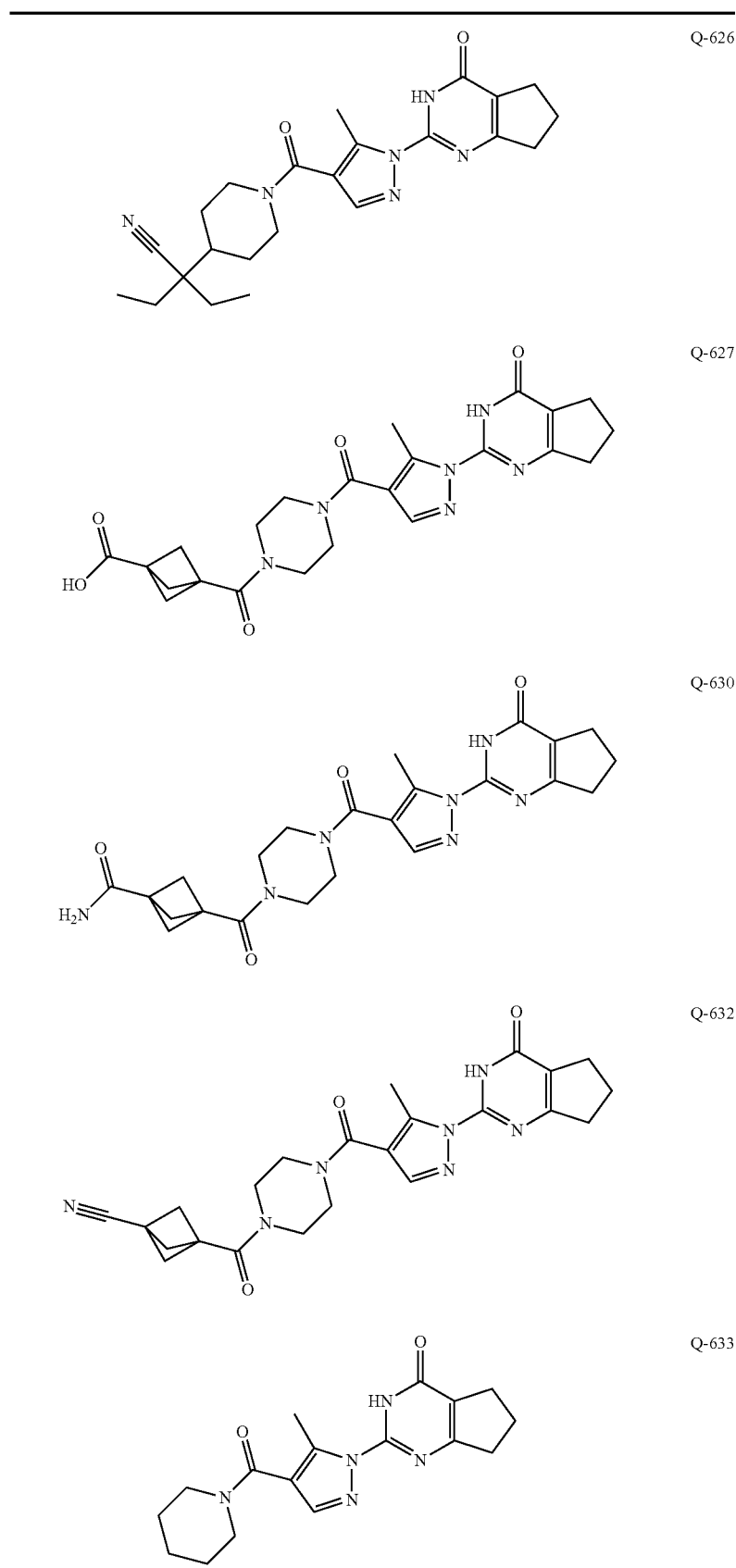
Q-626
Q-627
Q-630
Q-632
Q-633

TABLE C-continued
Q-634
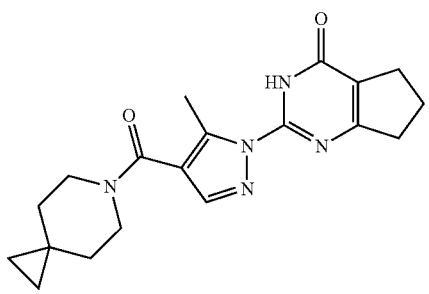 [SMILES: Cc1c(C(=O)N2CCC3(CC2)CC3)cnn1-c1nc2c(c(=O)[nH]1)CCC2]
Q-635
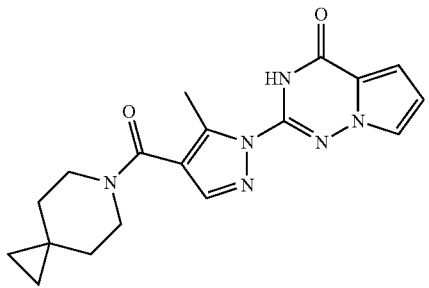 [SMILES: Cc1c(C(=O)N2CCC3(CC2)CC3)cnn1-c1nn2cccc2c(=O)[nH]1]
Q-681
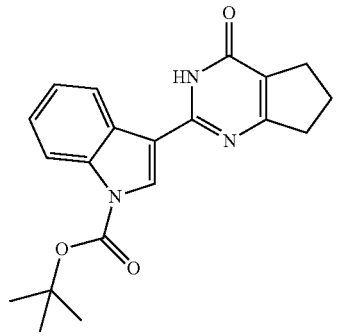 [SMILES: CC(C)(C)OC(=O)n1cc(-c2nc3c(c(=O)[nH]2)CCC3)c2ccccc21]
Q-687
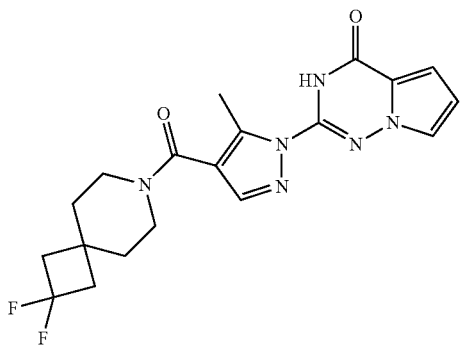 [SMILES: Cc1c(C(=O)N2CCC3(CC2)CC(F)(F)C3)cnn1-c1nn2cccc2c(=O)[nH]1]
Q-690

TABLE C-continued
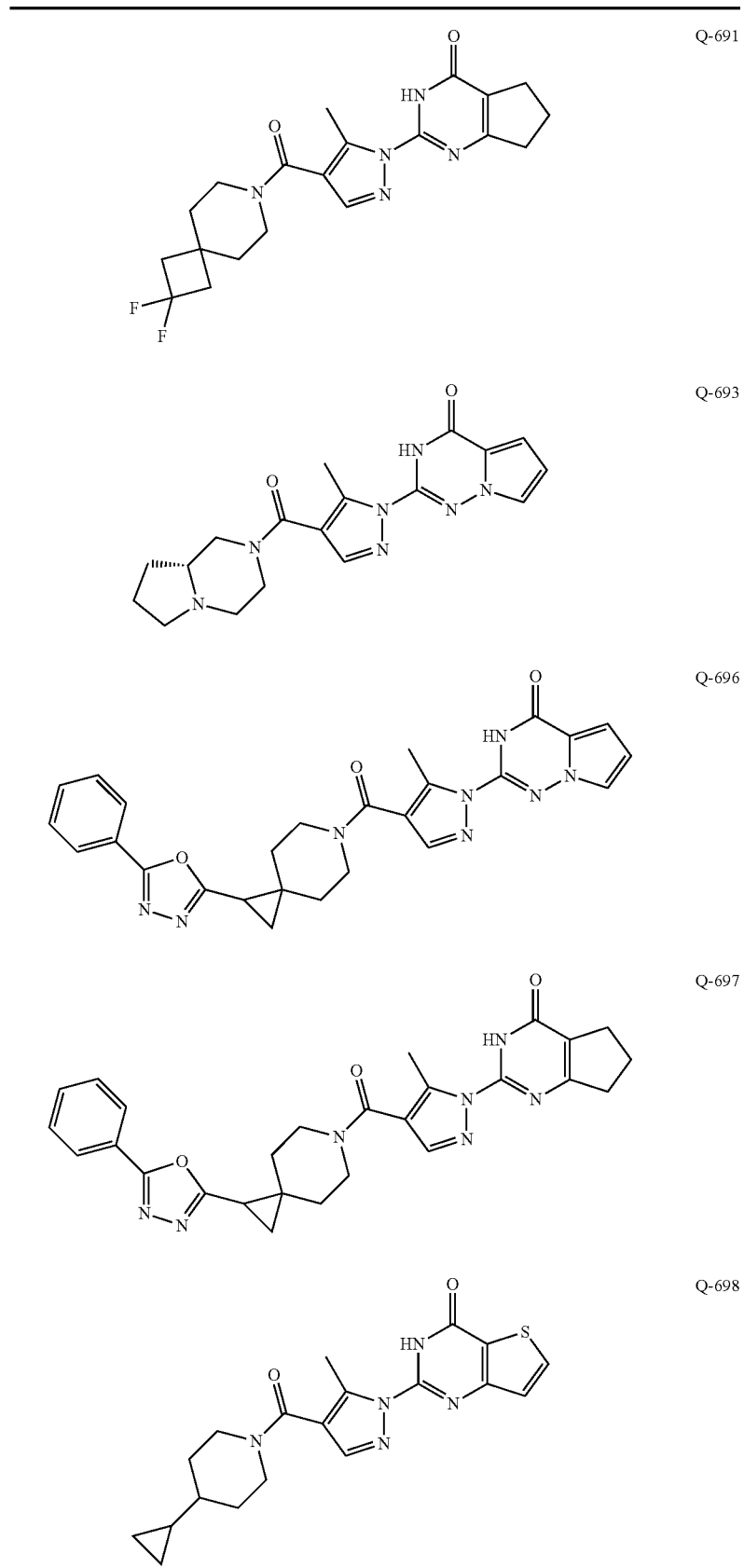
Q-691
Q-693
Q-696
Q-697
Q-698

TABLE C-continued
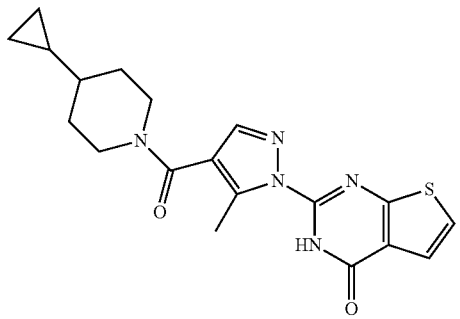 [SMILES: Cc1c(C(=O)N2CCC(C3CC3)CC2)cnn1-c1nc2sccc2c(=O)[nH]1]
Q-700
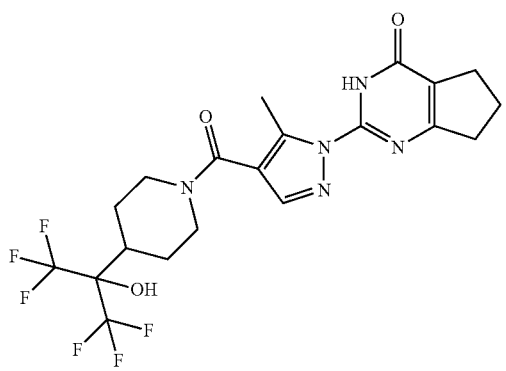 [SMILES: Cc1c(C(=O)N2CCC(C(O)(C(F)(F)F)C(F)(F)F)CC2)cnn1-c1nc2c(c(=O)[nH]1)CCC2]
Q-701
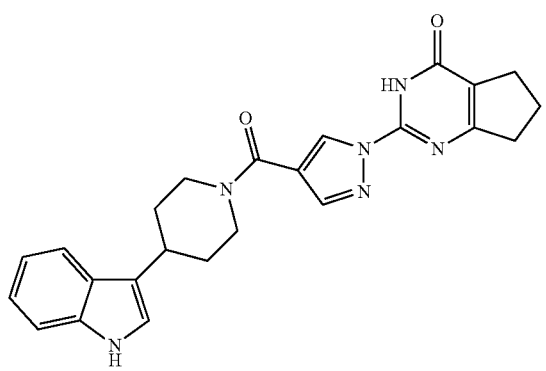 [SMILES: O=C(c1cnn(-c2nc3c(c(=O)[nH]2)CCC3)c1)N1CCC(c2c[nH]c3ccccc23)CC1]
Q-702
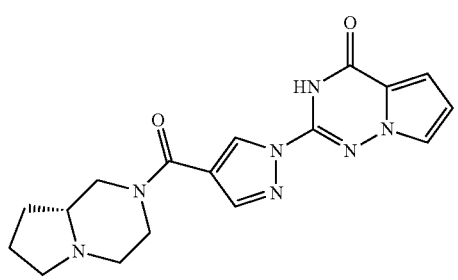 [SMILES: O=C(c1cnn(-c2nn3cccc3c(=O)[nH]2)c1)N1CCN2CCC[C@@H]2C1]
Q-703
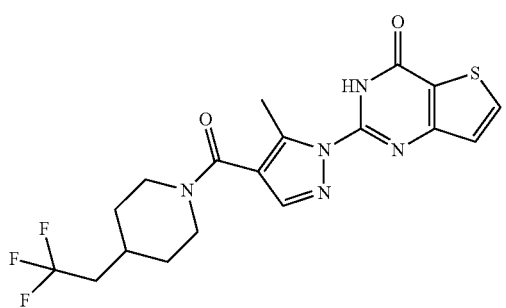 [SMILES: Cc1c(C(=O)N2CCC(CC(F)(F)F)CC2)cnn1-c1nc2ccsc2c(=O)[nH]1]
Q-704

TABLE C-continued
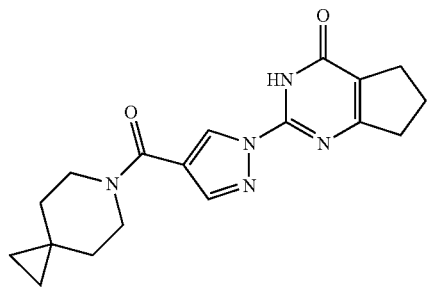 [SMILES: O=C(c1cnn(-c2nc3c(c(=O)[nH]2)CCC3)c1)N1CCC2(CC1)CC2] Q-705
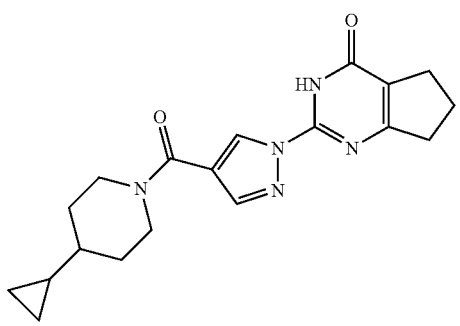 [SMILES: O=C(c1cnn(-c2nc3c(c(=O)[nH]2)CCC3)c1)N1CCC(C2CC2)CC1] Q-706
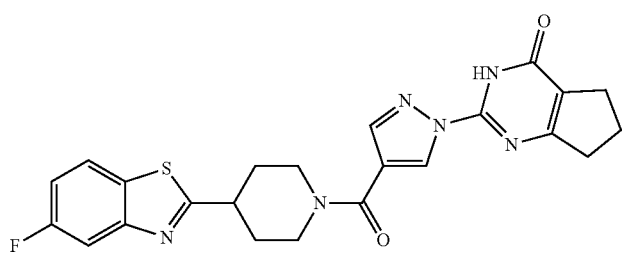 [SMILES: O=C(c1cnn(-c2nc3c(c(=O)[nH]2)CCC3)c1)N1CCC(c2nc3cc(F)ccc3s2)CC1] Q-707
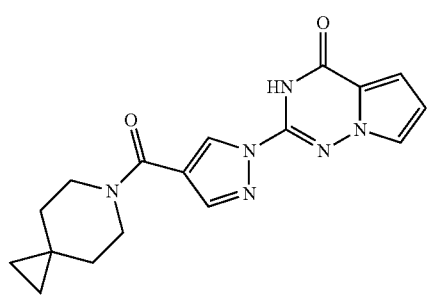 [SMILES: O=C(c1cnn(-c2nn3cccc3c(=O)[nH]2)c1)N1CCC2(CC1)CC2] Q-708
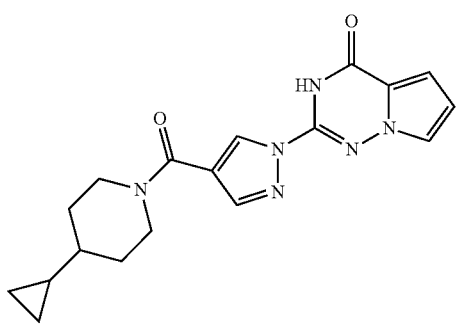 [SMILES: O=C(c1cnn(-c2nn3cccc3c(=O)[nH]2)c1)N1CCC(C2CC2)CC1] Q-709

TABLE C-continued
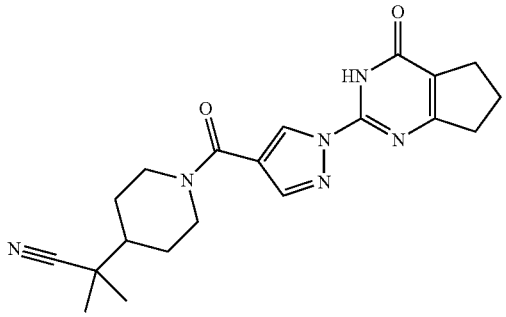 [SMILES: CC(C)(C#N)C1CCN(C(=O)c2cnn(-c3nc4c(c(=O)[nH]3)CCC4)c2)CC1]
Q-710
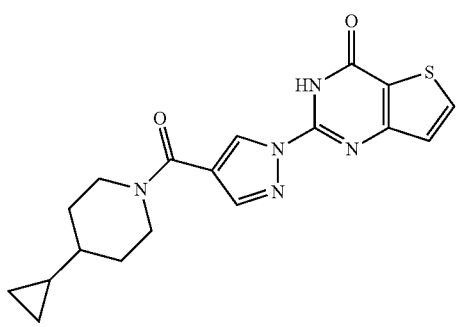 [SMILES: O=C(c1cnn(-c2nc3ccsc3c(=O)[nH]2)c1)N1CCC(C2CC2)CC1]
Q-711
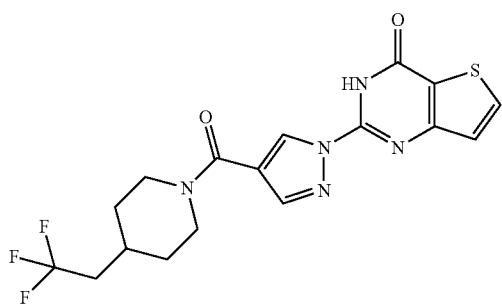 [SMILES: O=C(c1cnn(-c2nc3ccsc3c(=O)[nH]2)c1)N1CCC(CC(F)(F)F)CC1]
Q-712
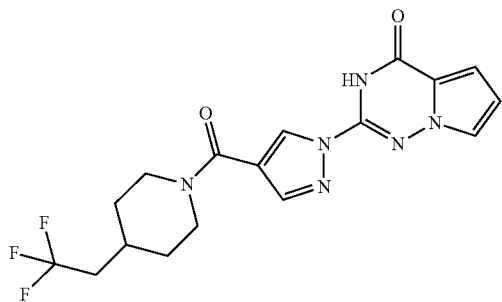 [SMILES: O=C(c1cnn(-c2nn3cccc3c(=O)[nH]2)c1)N1CCC(CC(F)(F)F)CC1]
Q-713
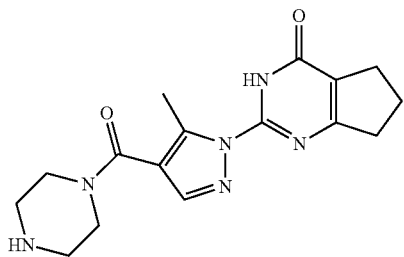 [SMILES: Cc1c(C(=O)N2CCNCC2)cnn1-c1nc2c(c(=O)[nH]1)CCC2]
Q-714

TABLE C-continued
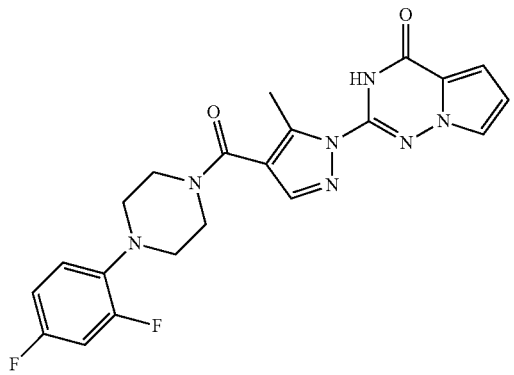 [SMILES: Cc1c(C(=O)N2CCN(c3ccc(F)cc3F)CC2)cnn1-c1nn2cccc2c(=O)[nH]1]
Q-715
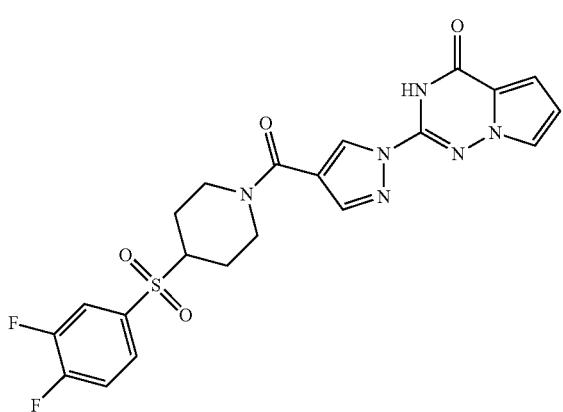 [SMILES: O=C(c1cnn(-c2nn3cccc3c(=O)[nH]2)c1)N1CCC(S(=O)(=O)c2ccc(F)c(F)c2)CC1]
Q-716
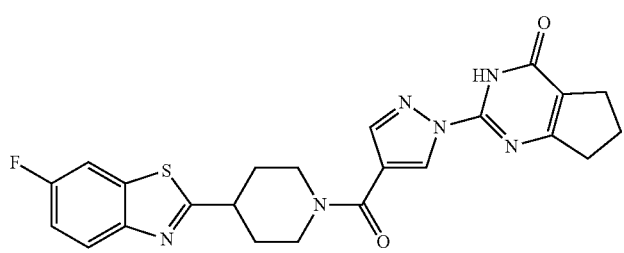 [SMILES: O=C(c1cnn(-c2nc3c(c(=O)[nH]2)CCC3)c1)N1CCC(c2nc3ccc(F)cc3s2)CC1]
Q-718
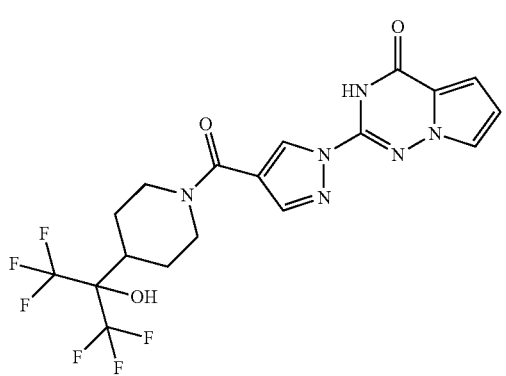 [SMILES: O=C(c1cnn(-c2nn3cccc3c(=O)[nH]2)c1)N1CCC(C(O)(C(F)(F)F)C(F)(F)F)CC1]
Q-719

TABLE C-continued
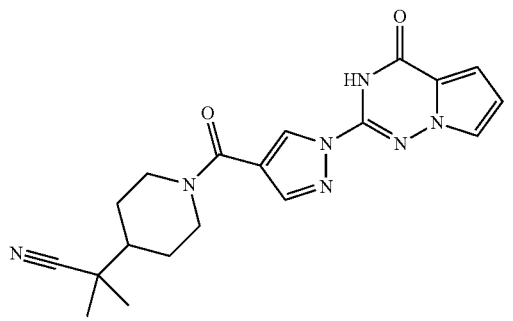 [SMILES: CC(C)(C#N)C1CCN(C(=O)c2cnn(-c3nn4cccc4c(=O)[nH]3)c2)CC1] Q-720
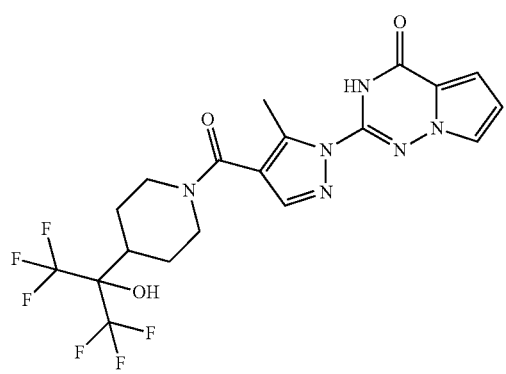 [SMILES: Cc1c(C(=O)N2CCC(C(O)(C(F)(F)F)C(F)(F)F)CC2)cnn1-c1nn2cccc2c(=O)[nH]1] Q-721
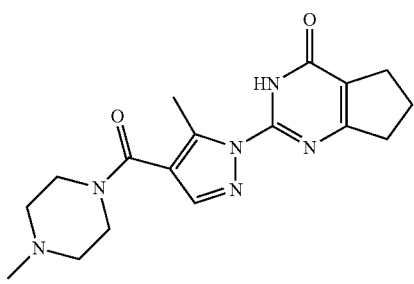 [SMILES: Cc1c(C(=O)N2CCN(C)CC2)cnn1-c1nc2c(c(=O)[nH]1)CCC2] Q-722
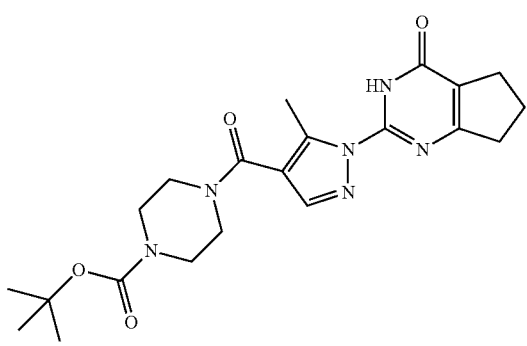 [SMILES: Cc1c(C(=O)N2CCN(C(=O)OC(C)(C)C)CC2)cnn1-c1nc2c(c(=O)[nH]1)CCC2] Q-723
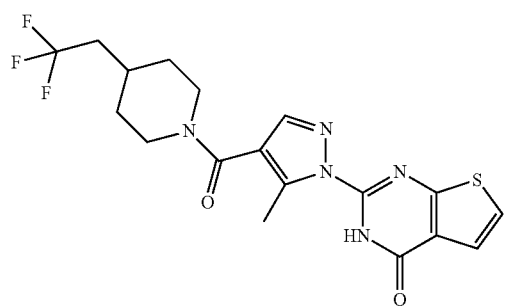 [SMILES: Cc1c(C(=O)N2CCC(CC(F)(F)F)CC2)cnn1-c1nc2sccc2c(=O)[nH]1] Q-724

TABLE C-continued
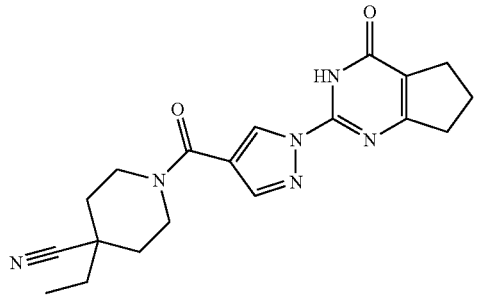 [SMILES: CCC1(C#N)CCN(C(=O)c2cnn(-c3nc4c(c(=O)[nH]3)CCC4)c2)CC1]
Q-725
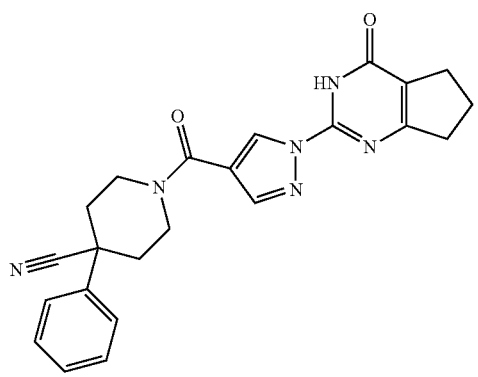 [SMILES: N#CC1(c2ccccc2)CCN(C(=O)c2cnn(-c3nc4c(c(=O)[nH]3)CCC4)c2)CC1]
Q-726
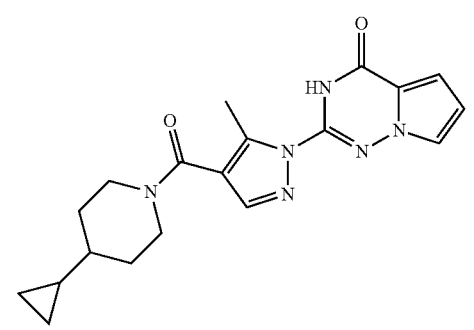 [SMILES: Cc1c(C(=O)N2CCC(C3CC3)CC2)cnn1-c1nn2cccc2c(=O)[nH]1]
Q-727
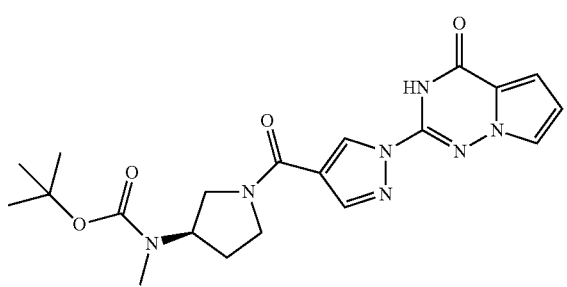 [SMILES: CN(C(=O)OC(C)(C)C)[C@@H]1CCN(C(=O)c2cnn(-c3nn4cccc4c(=O)[nH]3)c2)C1]
Q-730

TABLE C-continued
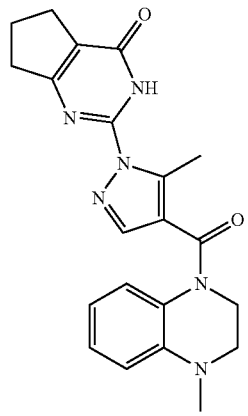 [SMILES: Cc1c(C(=O)N2CCN(C)c3ccccc32)cnn1-c1nc2c(c(=O)[nH]1)CCC2]
Q-731
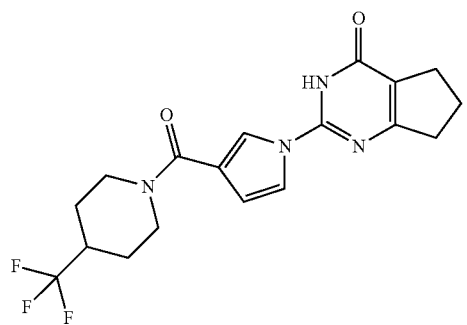 [SMILES: O=C(c1ccn(-c2nc3c(c(=O)[nH]2)CCC3)c1)N1CCC(C(F)(F)F)CC1]
Q-732
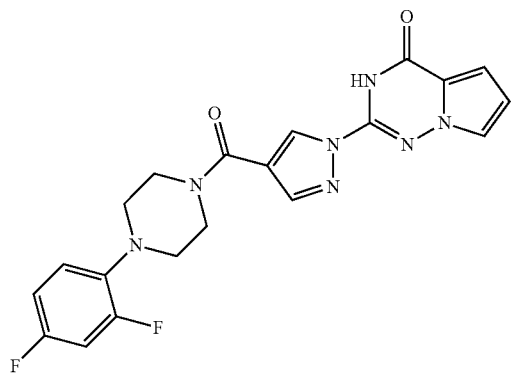
Q-734
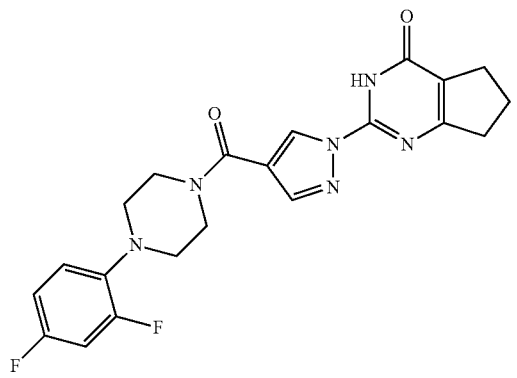 [SMILES: O=C(c1cnn(-c2nc3c(c(=O)[nH]2)CCC3)c1)N1CCN(c2ccc(F)cc2F)CC1]
Q-735

TABLE C-continued
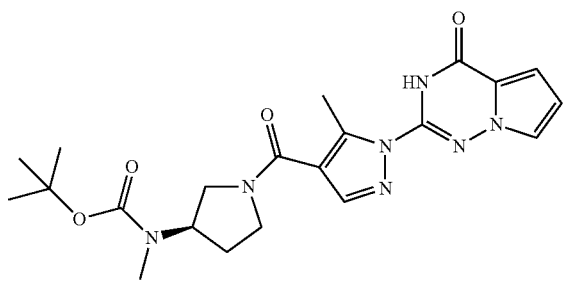 [SMILES: Cc1c(C(=O)N2CC[C@@H](N(C)C(=O)OC(C)(C)C)C2)cnn1-c1nn2cccc2c(=O)[nH]1]
Q-736
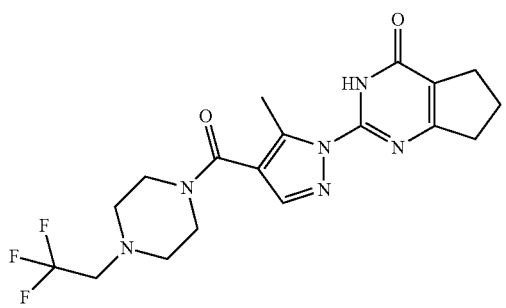
Q-737
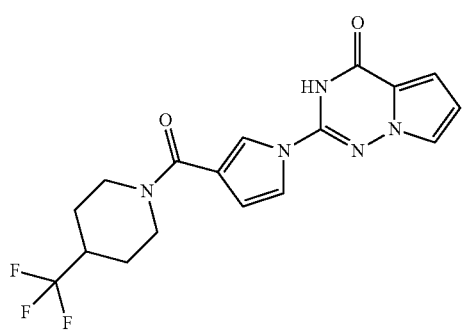 [SMILES: O=C(c1ccn(-c2nn3cccc3c(=O)[nH]2)c1)N1CCC(C(F)(F)F)CC1]
Q-738
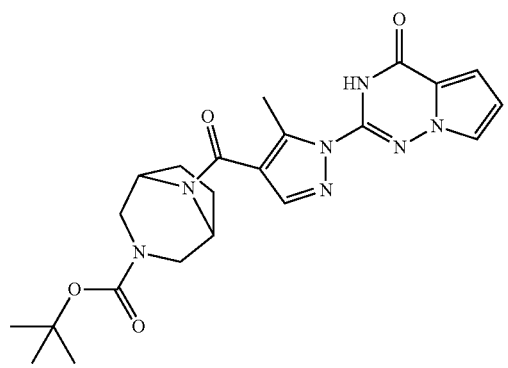 [SMILES: Cc1c(C(=O)N2C3CCC2CN(C(=O)OC(C)(C)C)C3)cnn1-c1nn2cccc2c(=O)[nH]1]
Q-739
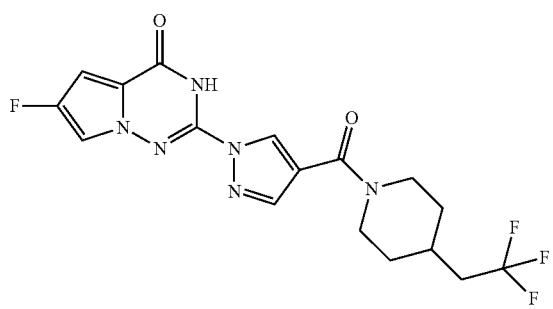 [SMILES: O=C(c1cnn(-c2nn3cc(F)cc3c(=O)[nH]2)c1)N1CCC(CC(F)(F)F)CC1]
Q-741

TABLE C-continued
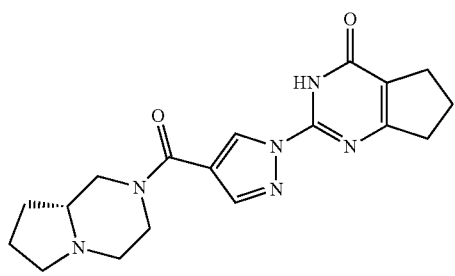 [SMILES: O=C(c1cnn(-c2nc3c(c(=O)[nH]2)CCC3)c1)N1CCN2CCC[C@@H]2C1] Q-743
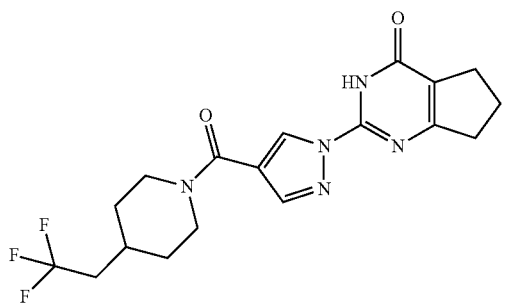 [SMILES: O=C(c1cnn(-c2nc3c(c(=O)[nH]2)CCC3)c1)N1CCC(CC(F)(F)F)CC1] Q-744
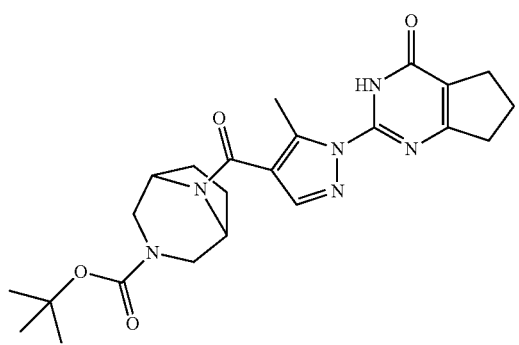 [SMILES: Cc1c(C(=O)N2C3CCC2CN(C(=O)OC(C)(C)C)C3)cnn1-c1nc2c(c(=O)[nH]1)CCC2] Q-745
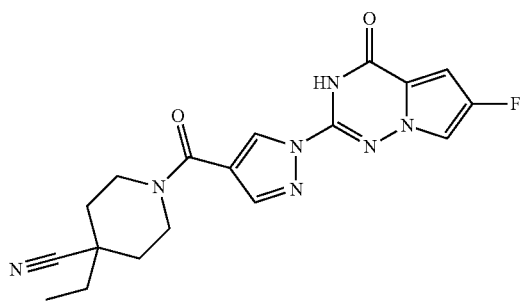 [SMILES: CCC1(C#N)CCN(C(=O)c2cnn(-c3nn4cc(F)cc4c(=O)[nH]3)c2)CC1] Q-746
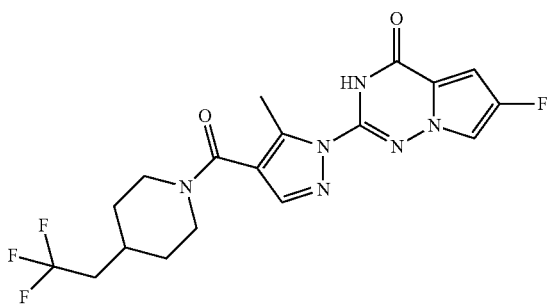 [SMILES: Cc1c(C(=O)N2CCC(CC(F)(F)F)CC2)cnn1-c1nn2cc(F)cc2c(=O)[nH]1] Q-747

TABLE C-continued
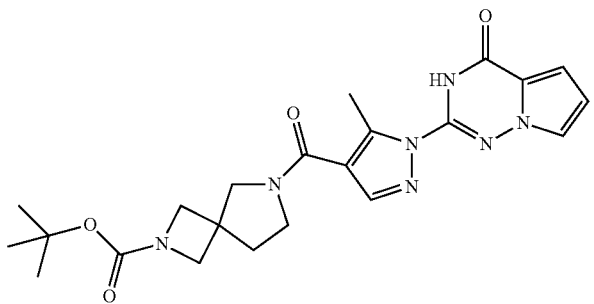 [SMILES: Cc1c(C(=O)N2CCC3(CN(C(=O)OC(C)(C)C)C3)C2)cnn1-c1nn2cccc2c(=O)[nH]1] Q-748
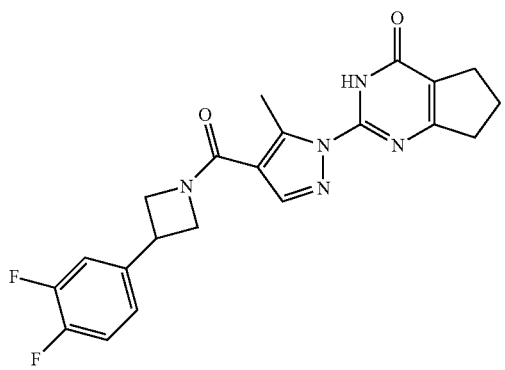 [SMILES: Cc1c(C(=O)N2CC(c3ccc(F)c(F)c3)C2)cnn1-c1nc2c(c(=O)[nH]1)CCC2] Q-749
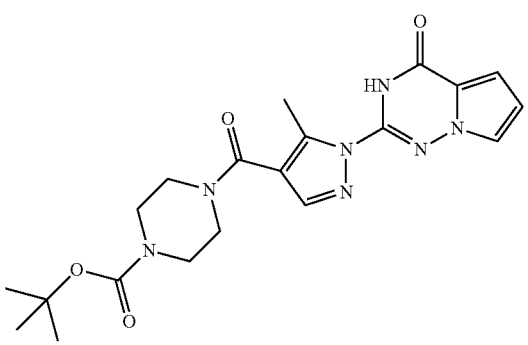 [SMILES: Cc1c(C(=O)N2CCN(C(=O)OC(C)(C)C)CC2)cnn1-c1nn2cccc2c(=O)[nH]1] Q-750
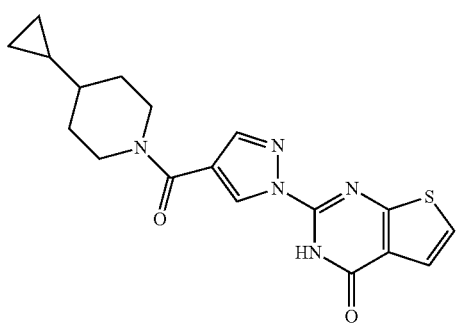 [SMILES: O=C(c1cnn(-c2nc3sccc3c(=O)[nH]2)c1)N1CCC(C2CC2)CC1] Q-751
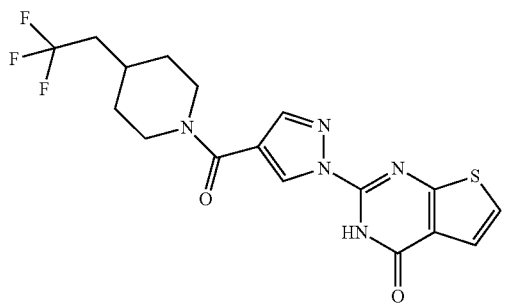 [SMILES: O=C(c1cnn(-c2nc3sccc3c(=O)[nH]2)c1)N1CCC(CC(F)(F)F)CC1] Q-752

TABLE C-continued
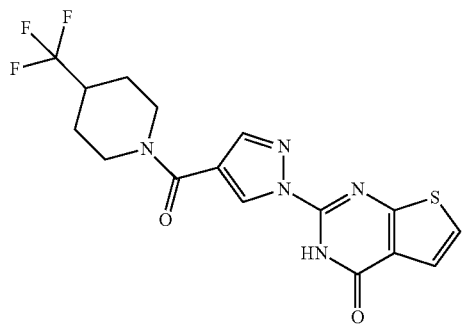 [SMILES: O=C(c1cnn(-c2nc3sccc3c(=O)[nH]2)c1)N1CCC(C(F)(F)F)CC1]
Q-753
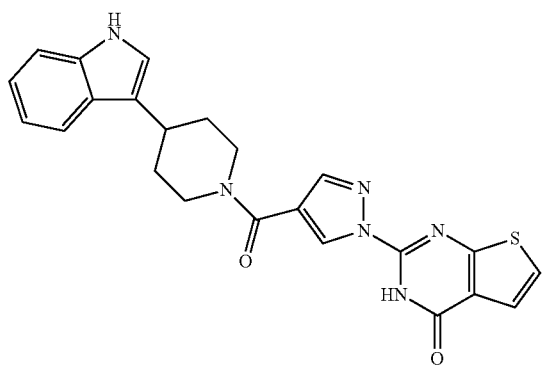 [SMILES: O=C(c1cnn(-c2nc3sccc3c(=O)[nH]2)c1)N1CCC(c2c[nH]c3ccccc23)CC1]
Q-754
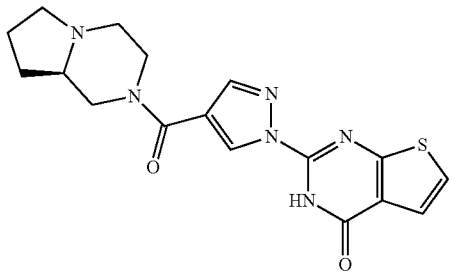 [SMILES: O=C(c1cnn(-c2nc3sccc3c(=O)[nH]2)c1)N1CCN2CCC[C@@H]2C1]
Q-755
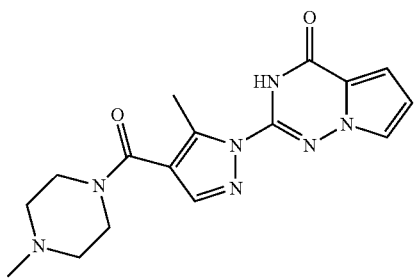 [SMILES: Cc1c(C(=O)N2CCN(C)CC2)cnn1-c1nn2cccc2c(=O)[nH]1]
Q-756
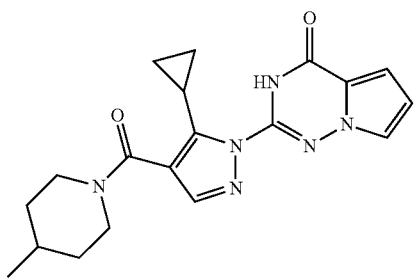 [SMILES: CC1CCN(C(=O)c2cnn(-c3nn4cccc4c(=O)[nH]3)c2C2CC2)CC1]
Q-757

TABLE C-continued
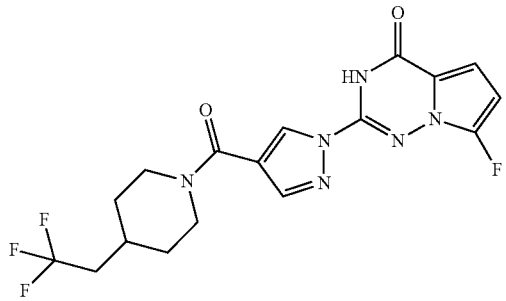 [SMILES: O=C(c1cnn(-c2nn3c(F)ccc3c(=O)[nH]2)c1)N1CCC(CC(F)(F)F)CC1] Q-758
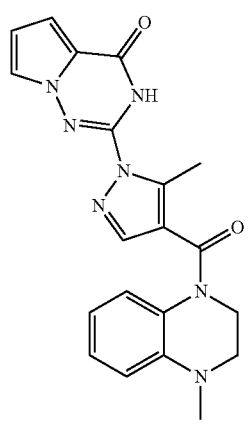 [SMILES: Cc1c(C(=O)N2CCN(C)c3ccccc32)cnn1-c1nn2cccc2c(=O)[nH]1] Q-759
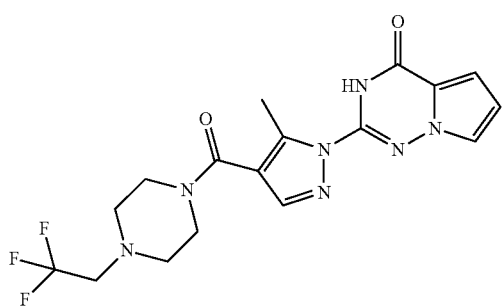 [SMILES: Cc1c(C(=O)N2CCN(CC(F)(F)F)CC2)cnn1-c1nn2cccc2c(=O)[nH]1] Q-760
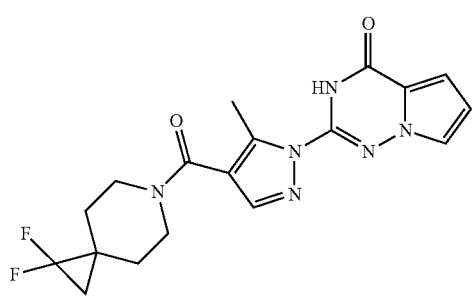 [SMILES: Cc1c(C(=O)N2CCC3(CC2)CC3(F)F)cnn1-c1nn2cccc2c(=O)[nH]1] Q-761

TABLE C-continued
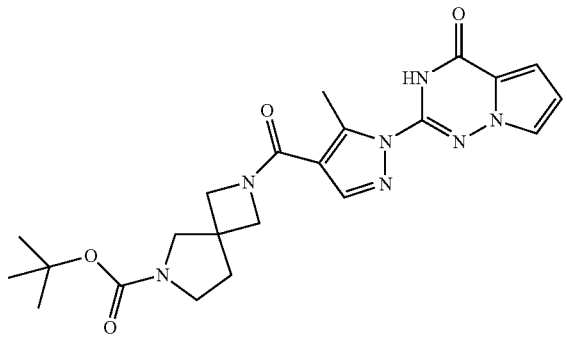 [SMILES: Cc1c(C(=O)N2CC3(CCN(C(=O)OC(C)(C)C)C3)C2)cnn1-c1nn2cccc2c(=O)[nH]1]
Q-762
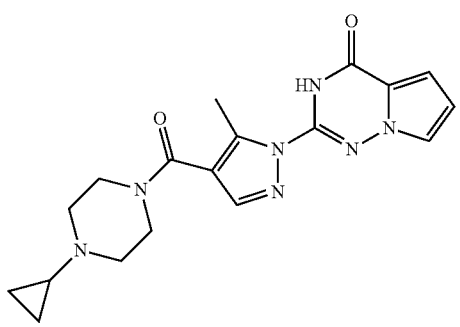 [SMILES: Cc1c(C(=O)N2CCN(C3CC3)CC2)cnn1-c1nn2cccc2c(=O)[nH]1]
Q-764
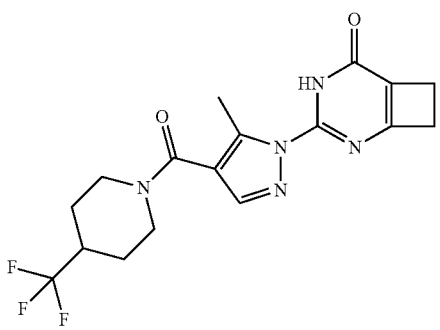 [SMILES: Cc1c(C(=O)N2CCC(C(F)(F)F)CC2)cnn1-c1nc2c(c(=O)[nH]1)CC2]
Q-765
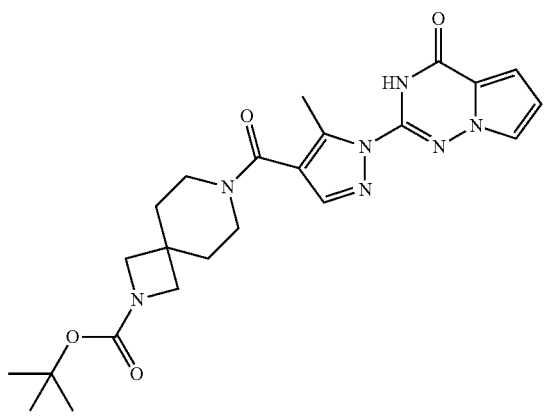 [SMILES: Cc1c(C(=O)N2CCC3(CC2)CN(C(=O)OC(C)(C)C)C3)cnn1-c1nn2cccc2c(=O)[nH]1]
Q-768

TABLE C-continued
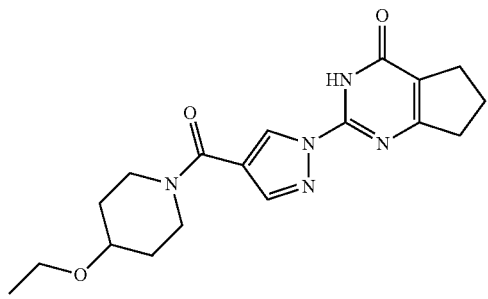 [SMILES: CCOC1CCN(C(=O)c2cnn(-c3nc4c(c(=O)[nH]3)CCC4)c2)CC1] Q-770
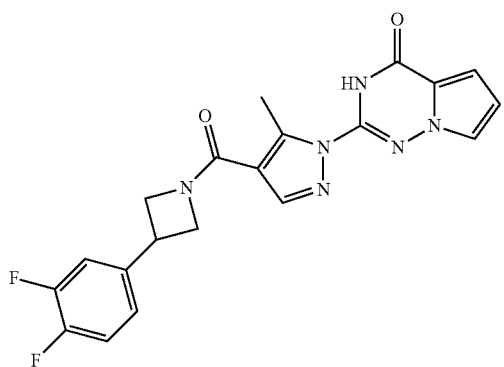 [SMILES: Cc1c(C(=O)N2CC(c3ccc(F)c(F)c3)C2)cnn1-c1nn2cccc2c(=O)[nH]1] Q-771
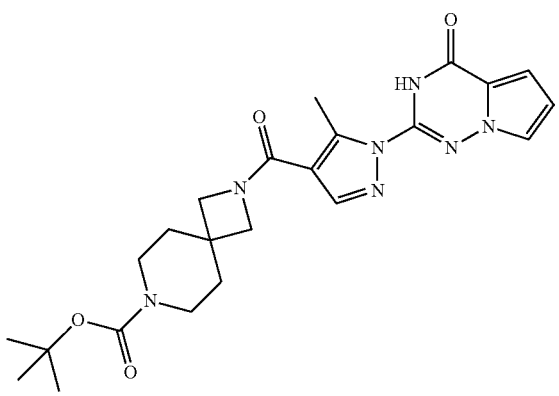 [SMILES: Cc1c(C(=O)N2CC3(CCN(C(=O)OC(C)(C)C)CC3)C2)cnn1-c1nn2cccc2c(=O)[nH]1] Q-772
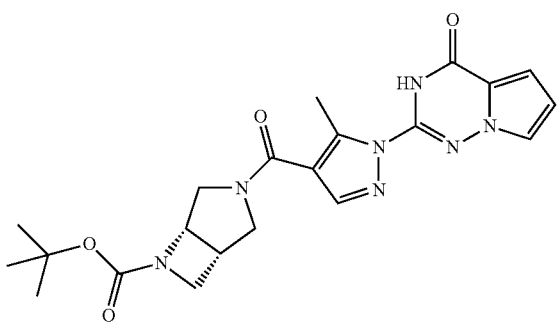 [SMILES: Cc1c(C(=O)N2C[C@@H]3CN(C(=O)OC(C)(C)C)[C@@H]3C2)cnn1-c1nn2cccc2c(=O)[nH]1] Q-773
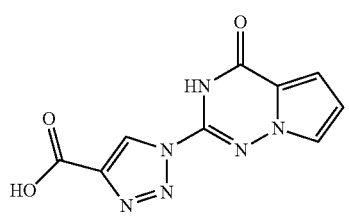 [SMILES: O=C(O)c1cn(-c2nn3cccc3c(=O)[nH]2)nn1] Q-774

TABLE C-continued
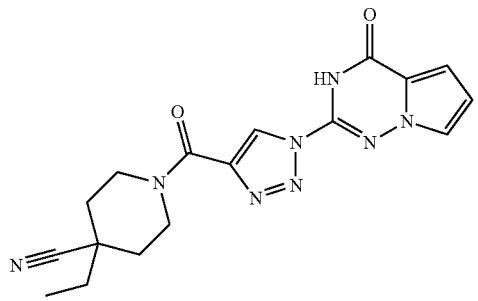 [SMILES: CCC1(C#N)CCN(C(=O)c2cn(-c3nn4cccc4c(=O)[nH]3)nn2)CC1] Q-775
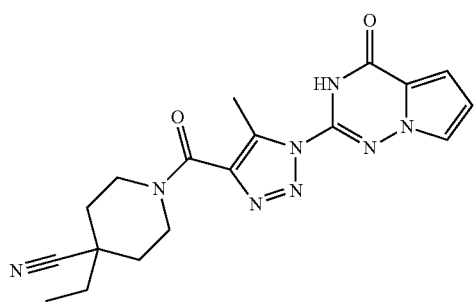 [SMILES: CCC1(C#N)CCN(C(=O)c2nnn(-c3nn4cccc4c(=O)[nH]3)c2C)CC1] Q-777
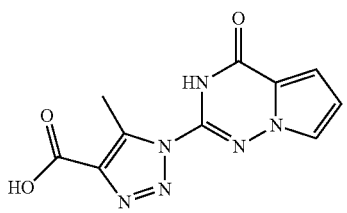 [SMILES: Cc1c(C(=O)O)nnn1-c1nn2cccc2c(=O)[nH]1] Q-779
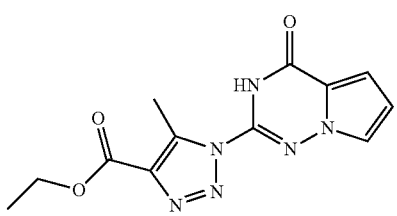 [SMILES: CCOC(=O)c1nnn(-c2nn3cccc3c(=O)[nH]2)c1C] Q-780
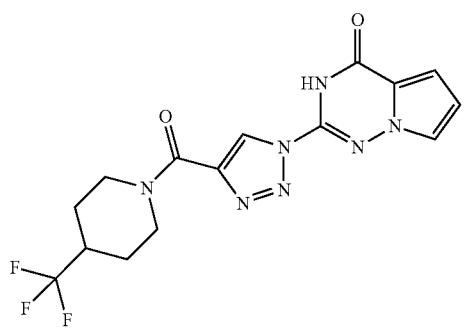 [SMILES: O=C(c1cn(-c2nn3cccc3c(=O)[nH]2)nn1)N1CCC(C(F)(F)F)CC1] Q-781

TABLE C-continued
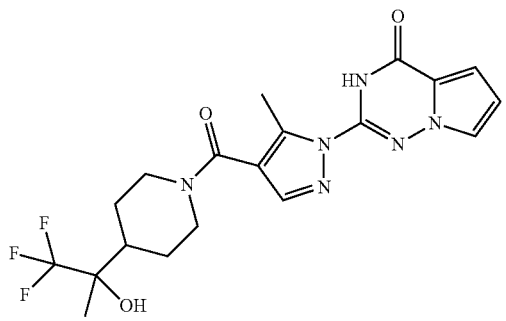 [SMILES: Cc1c(C(=O)N2CCC(C(C)(O)C(F)(F)F)CC2)cnn1-c1nn2cccc2c(=O)[nH]1]
Q-782
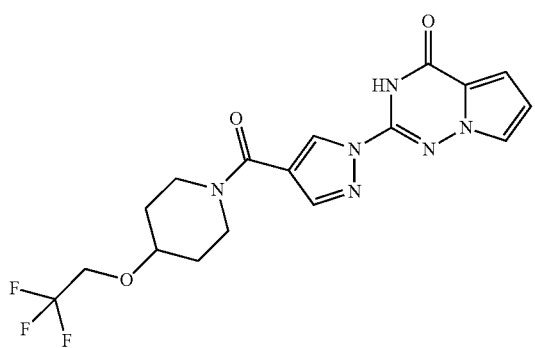 [SMILES: O=C(c1cnn(-c2nn3cccc3c(=O)[nH]2)c1)N1CCC(OCC(F)(F)F)CC1]
Q-783
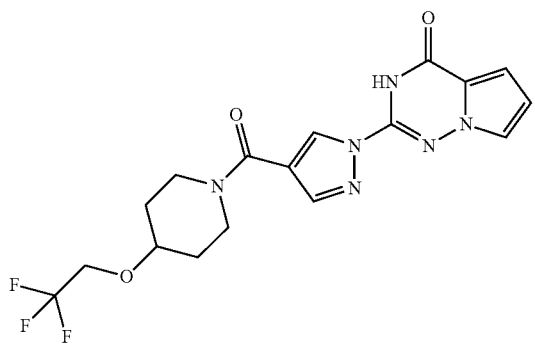 [SMILES: O=C(c1cnn(-c2nn3cccc3c(=O)[nH]2)c1)N1CCC(OCC(F)(F)F)CC1]
Q-784
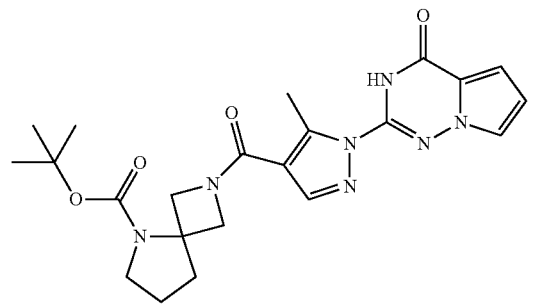 [SMILES: Cc1c(C(=O)N2CC3(CCCN3C(=O)OC(C)(C)C)C2)cnn1-c1nn2cccc2c(=O)[nH]1]
Q-785
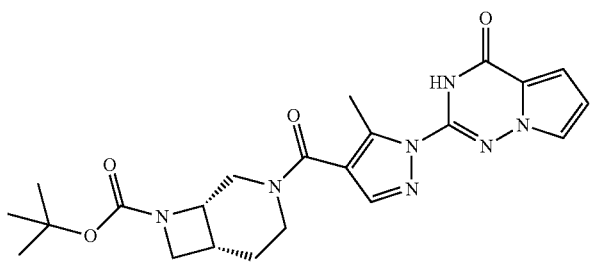 [SMILES: Cc1c(C(=O)N2CC[C@@H]3CN(C(=O)OC(C)(C)C)[C@@H]3C2)cnn1-c1nn2cccc2c(=O)[nH]1]
Q-788

TABLE C-continued
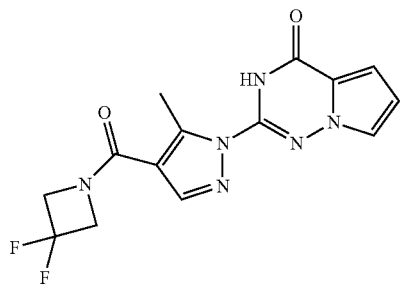 [SMILES: Cc1c(C(=O)N2CC(F)(F)C2)cnn1-c1nn2cccc2c(=O)[nH]1]
Q-789
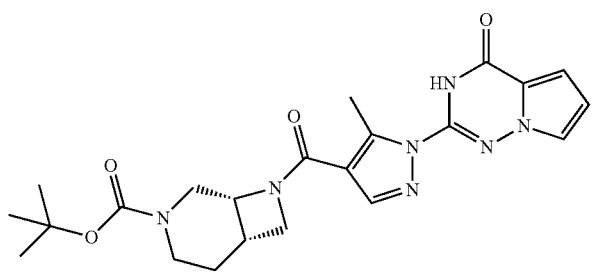 [SMILES: Cc1c(C(=O)N2C[C@@H]3CCN(C(=O)OC(C)(C)C)C[C@@H]32)cnn1-c1nn2cccc2c(=O)[nH]1]
Q-790
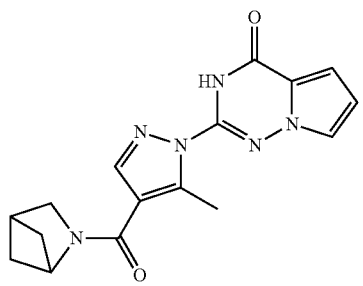 [SMILES: Cc1c(C(=O)N2CC3CC2C3)cnn1-c1nn2cccc2c(=O)[nH]1]
Q-791
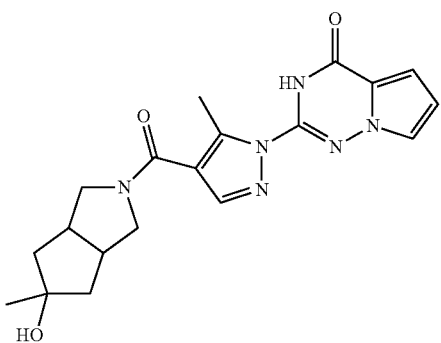 [SMILES: Cc1c(C(=O)N2CC3CC(C)(O)CC3C2)cnn1-c1nn2cccc2c(=O)[nH]1]
Q-792
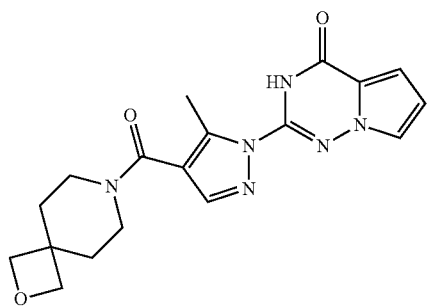 [SMILES: Cc1c(C(=O)N2CCC3(CC2)COC3)cnn1-c1nn2cccc2c(=O)[nH]1]
Q-793

TABLE C-continued
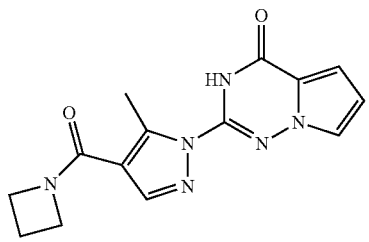 [SMILES: Cc1c(C(=O)N2CCC2)cnn1-c1nn2cccc2c(=O)[nH]1] Q-794
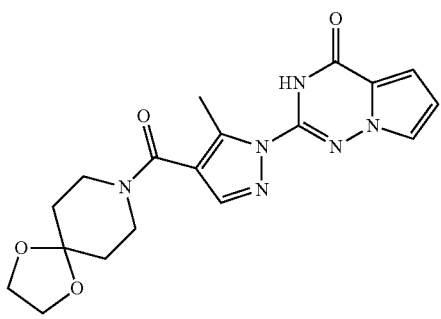 [SMILES: Cc1c(C(=O)N2CCC3(CC2)OCCO3)cnn1-c1nn2cccc2c(=O)[nH]1] Q-795
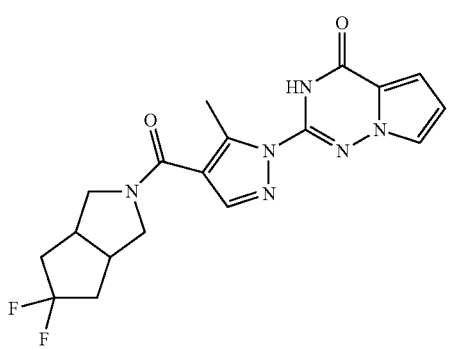 [SMILES: Cc1c(C(=O)N2CC3CC(F)(F)CC3C2)cnn1-c1nn2cccc2c(=O)[nH]1] Q-796
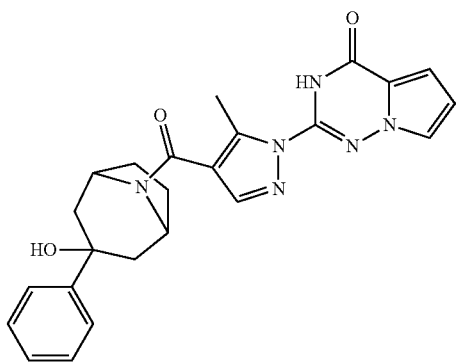 [SMILES: Cc1c(C(=O)N2C3CCC2CC(O)(c2ccccc2)C3)cnn1-c1nn2cccc2c(=O)[nH]1] Q-797
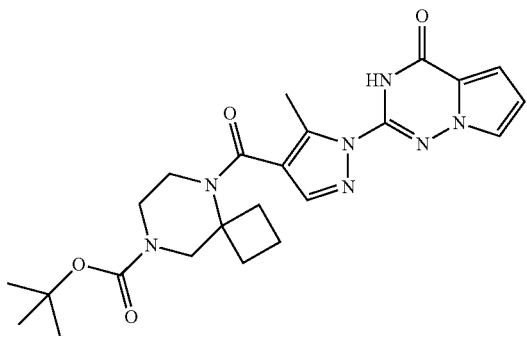 [SMILES: Cc1c(C(=O)N2CCN(C(=O)OC(C)(C)C)CC23CCC3)cnn1-c1nn2cccc2c(=O)[nH]1] Q-798

TABLE C-continued
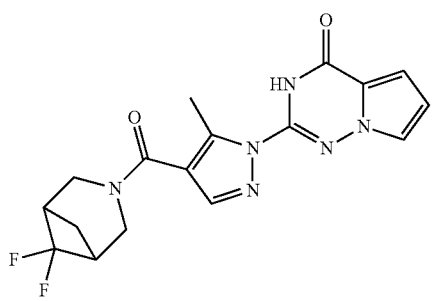 [SMILES: Cc1c(C(=O)N2CC3CC(C2)C3(F)F)cnn1-c1nn2cccc2c(=O)[nH]1]
Q-799
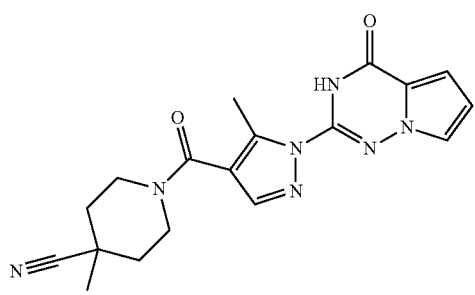 [SMILES: Cc1c(C(=O)N2CCC(C)(C#N)CC2)cnn1-c1nn2cccc2c(=O)[nH]1]
Q-800
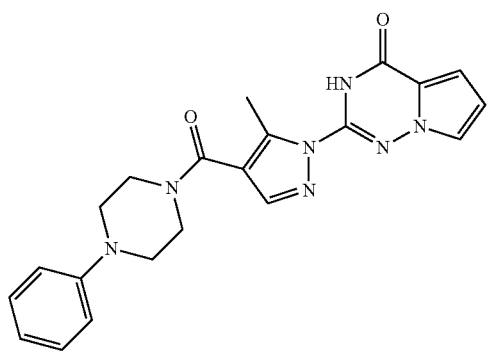 [SMILES: Cc1c(C(=O)N2CCN(c3ccccc3)CC2)cnn1-c1nn2cccc2c(=O)[nH]1]
Q-802
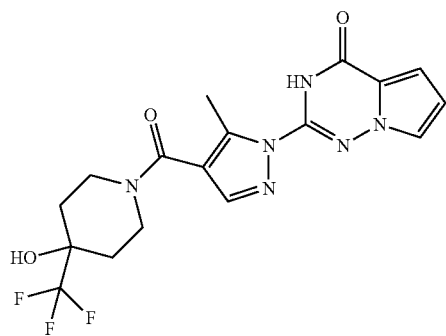 [SMILES: Cc1c(C(=O)N2CCC(O)(C(F)(F)F)CC2)cnn1-c1nn2cccc2c(=O)[nH]1]
Q-803
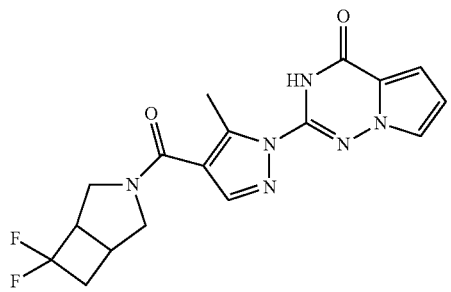 [SMILES: Cc1c(C(=O)N2CC3CC(F)(F)C3C2)cnn1-c1nn2cccc2c(=O)[nH]1]
Q-804

TABLE C-continued
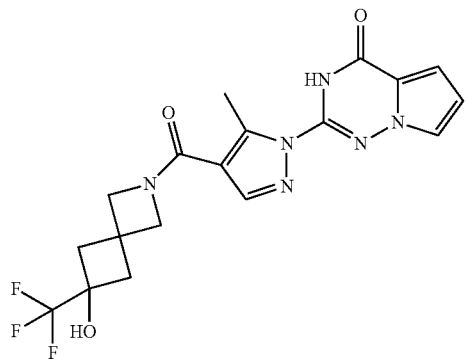 [SMILES: Cc1c(C(=O)N2CC3(C2)CC(O)(C(F)(F)F)C3)cnn1-c1nn2cccc2c(=O)[nH]1] Q-805
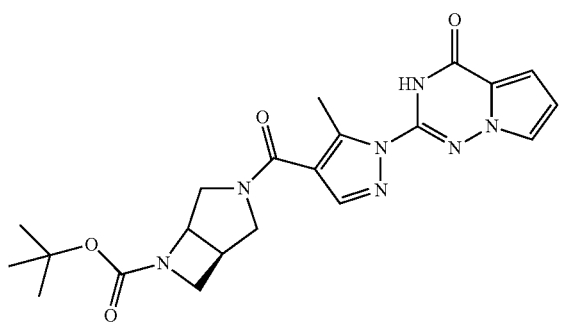 Q-806
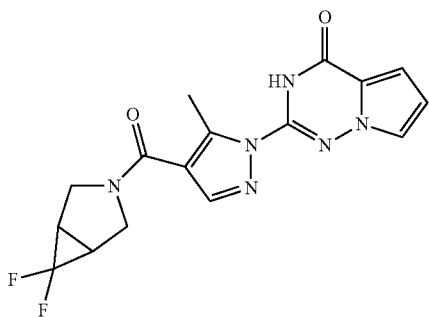 [SMILES: Cc1c(C(=O)N2CC3C(C2)C3(F)F)cnn1-c1nn2cccc2c(=O)[nH]1] Q-807
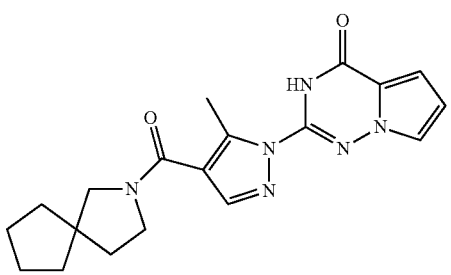 [SMILES: Cc1c(C(=O)N2CCC3(CCCC3)C2)cnn1-c1nn2cccc2c(=O)[nH]1] Q-808

TABLE C-continued
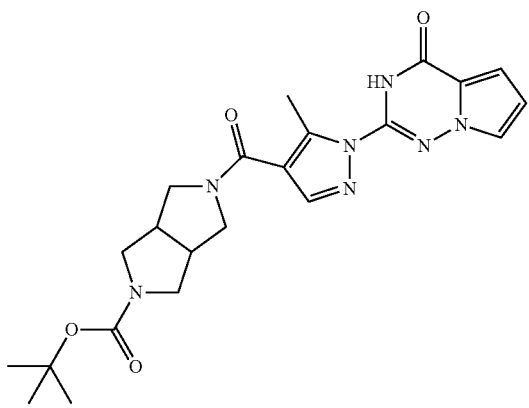 [SMILES: Cc1c(C(=O)N2CC3CN(C(=O)OC(C)(C)C)CC3C2)cnn1-c1nn2cccc2c(=O)[nH]1]
Q-809
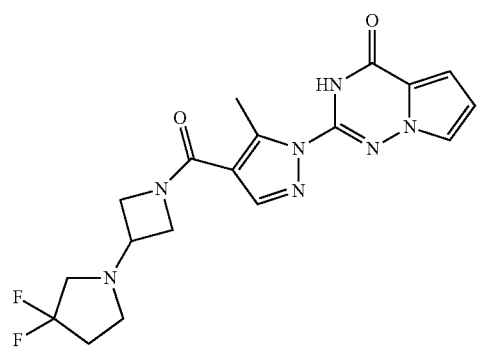 [SMILES: Cc1c(C(=O)N2CC(N3CCC(F)(F)C3)C2)cnn1-c1nn2cccc2c(=O)[nH]1]
Q-812
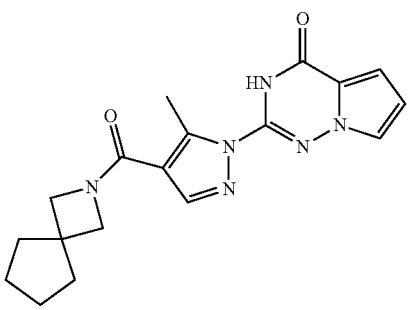 [SMILES: Cc1c(C(=O)N2CC3(CCCC3)C2)cnn1-c1nn2cccc2c(=O)[nH]1]
Q-813
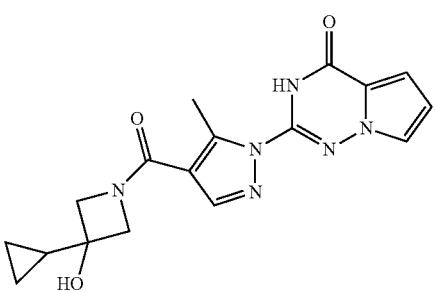 [SMILES: Cc1c(C(=O)N2CC(O)(C3CC3)C2)cnn1-c1nn2cccc2c(=O)[nH]1]
Q-814

TABLE C-continued
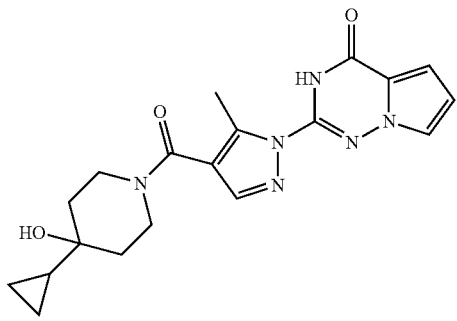 [SMILES: Cc1c(C(=O)N2CCC(O)(C3CC3)CC2)cnn1-c1nn2cccc2c(=O)[nH]1]
Q-815
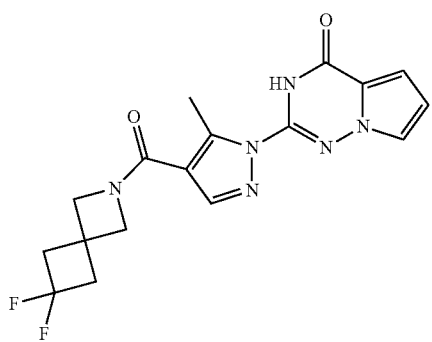 [SMILES: Cc1c(C(=O)N2CC3(C2)CC(F)(F)C3)cnn1-c1nn2cccc2c(=O)[nH]1]
Q-816
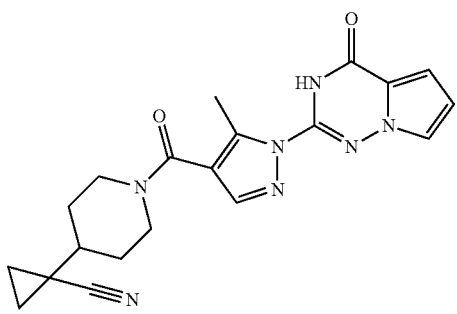 [SMILES: Cc1c(C(=O)N2CCC(C3(C#N)CC3)CC2)cnn1-c1nn2cccc2c(=O)[nH]1]
Q-817
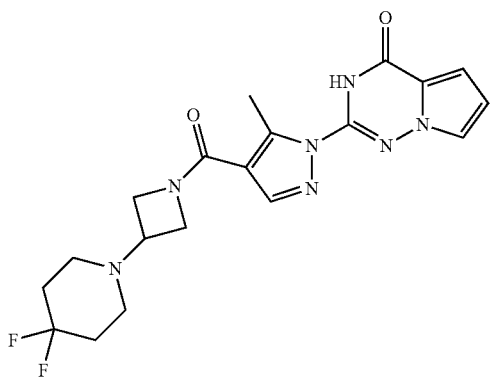 [SMILES: Cc1c(C(=O)N2CC(N3CCC(F)(F)CC3)C2)cnn1-c1nn2cccc2c(=O)[nH]1]
Q-818
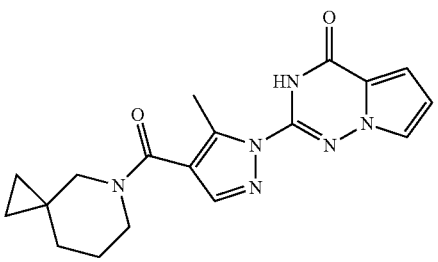 [SMILES: Cc1c(C(=O)N2CCCC3(CC3)C2)cnn1-c1nn2cccc2c(=O)[nH]1]
Q-819

TABLE C-continued
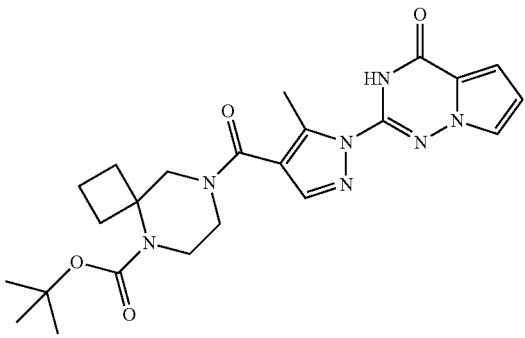 [SMILES: Cc1c(C(=O)N2CCN(C(=O)OC(C)(C)C)C3(CCC3)C2)cnn1-c1nn2cccc2c(=O)[nH]1]
Q-820
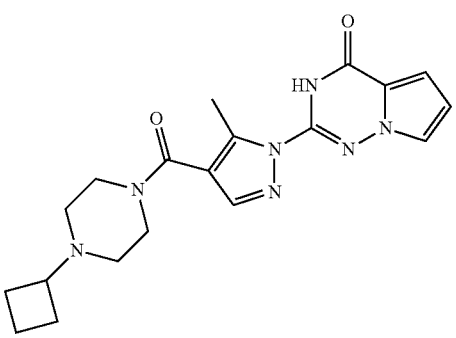 [SMILES: Cc1c(C(=O)N2CCN(C3CCC3)CC2)cnn1-c1nn2cccc2c(=O)[nH]1]
Q-821
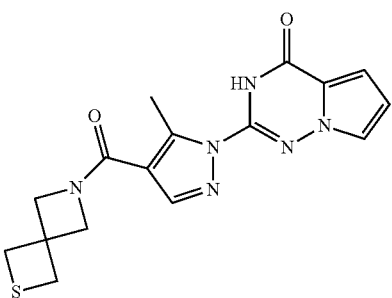 [SMILES: Cc1c(C(=O)N2CC3(CSC3)C2)cnn1-c1nn2cccc2c(=O)[nH]1]
Q-822
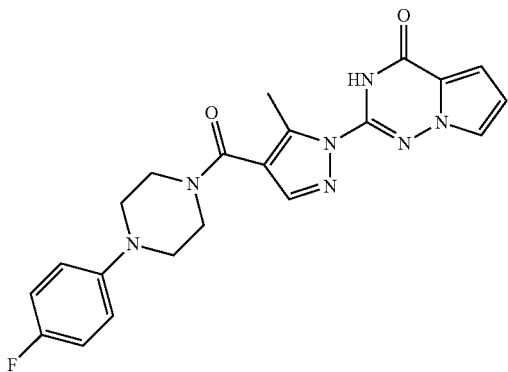 [SMILES: Cc1c(C(=O)N2CCN(c3ccc(F)cc3)CC2)cnn1-c1nn2cccc2c(=O)[nH]1]
Q-823

TABLE C-continued
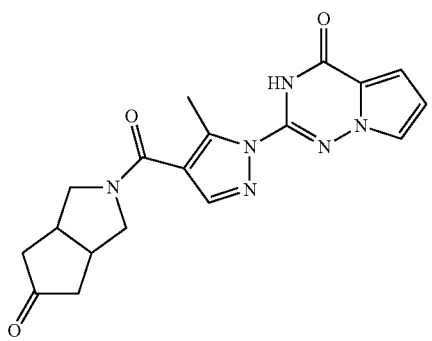 [SMILES: Cc1c(C(=O)N2CC3CC(=O)CC3C2)cnn1-c1nn2cccc2c(=O)[nH]1]
Q-824
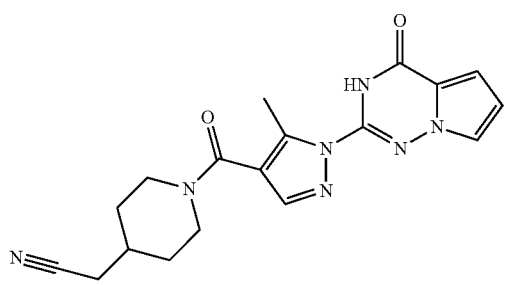 [SMILES: Cc1c(C(=O)N2CCC(CC#N)CC2)cnn1-c1nn2cccc2c(=O)[nH]1]
Q-825
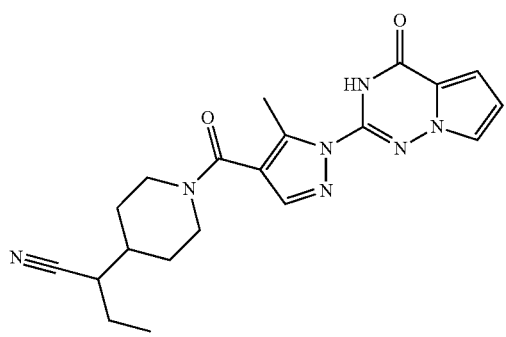 [SMILES: CCC(C#N)C1CCN(C(=O)c2cnn(-c3nn4cccc4c(=O)[nH]3)c2C)CC1]
Q-826
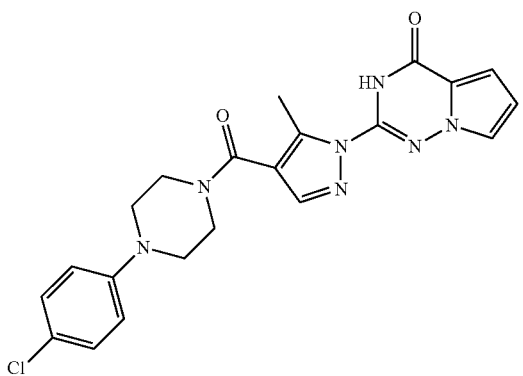 [SMILES: Cc1c(C(=O)N2CCN(c3ccc(Cl)cc3)CC2)cnn1-c1nn2cccc2c(=O)[nH]1]
Q-827

TABLE C-continued
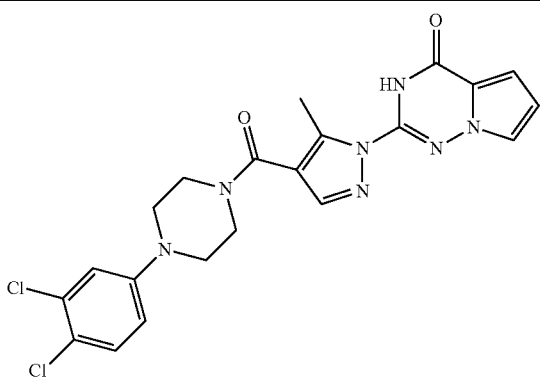
Q-828
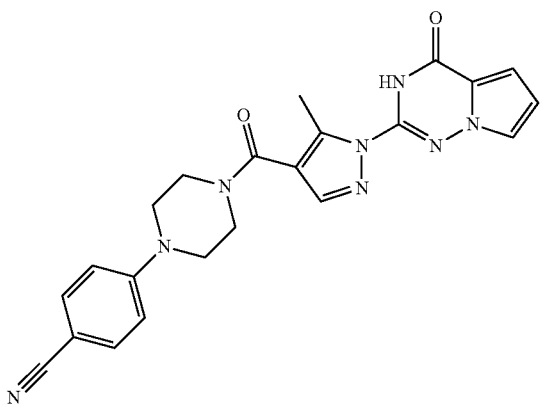 [SMILES: Cc1c(C(=O)N2CCN(c3ccc(C#N)cc3)CC2)cnn1-c1nn2cccc2c(=O)[nH]1]
Q-829
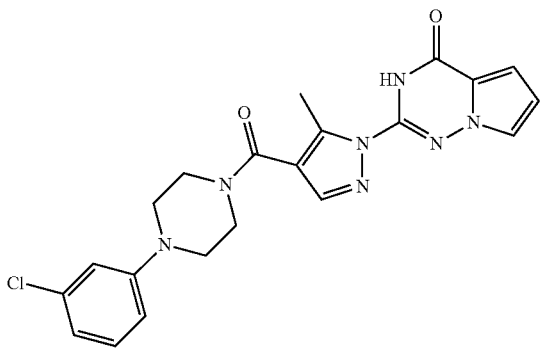 [SMILES: Cc1c(C(=O)N2CCN(c3cccc(Cl)c3)CC2)cnn1-c1nn2cccc2c(=O)[nH]1]
Q-830
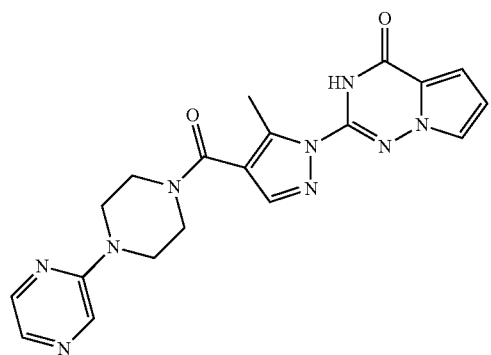 [SMILES: Cc1c(C(=O)N2CCN(c3cnccn3)CC2)cnn1-c1nn2cccc2c(=O)[nH]1]
Q-831

TABLE C-continued
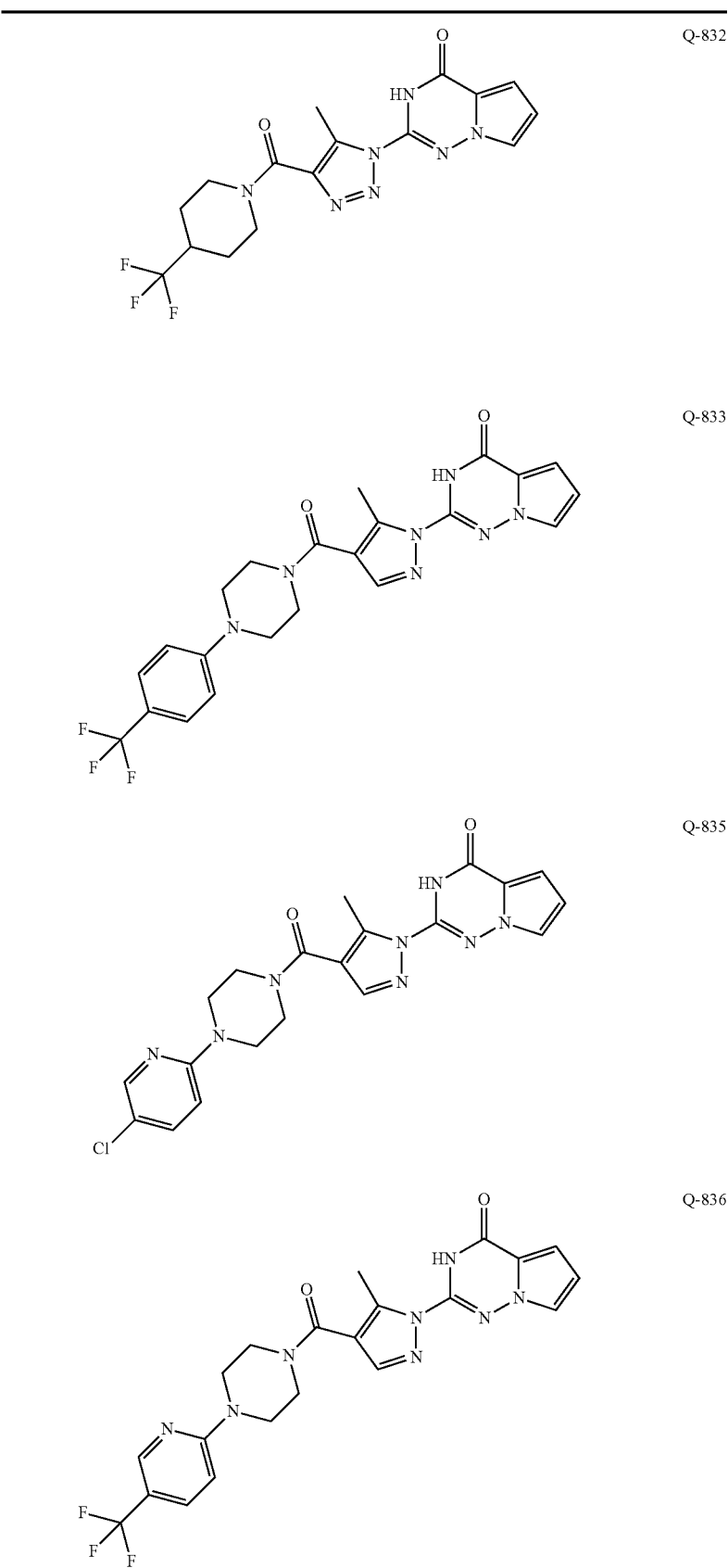
Q-832
Q-833
Q-835
Q-836

TABLE C-continued
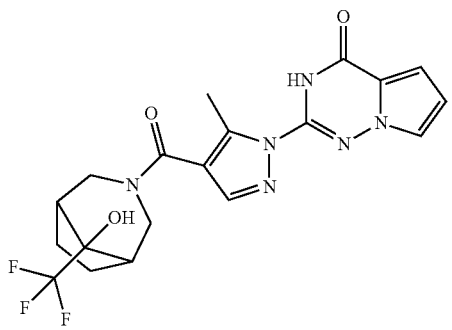 [SMILES: Cc1c(C(=O)N2CC3CCC(C2)C3(O)C(F)(F)F)cnn1-c1nn2cccc2c(=O)[nH]1]
Q-837
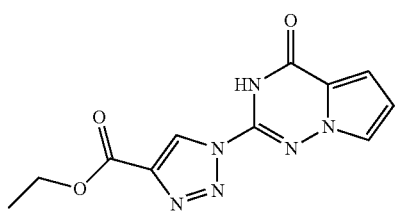 [SMILES: CCOC(=O)c1cn(-c2nn3cccc3c(=O)[nH]2)nn1]
Q-839
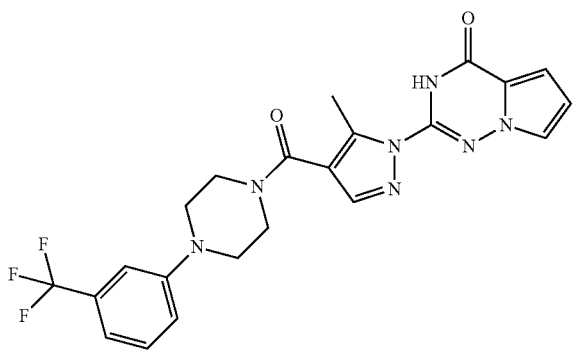 [SMILES: Cc1c(C(=O)N2CCN(c3cccc(C(F)(F)F)c3)CC2)cnn1-c1nn2cccc2c(=O)[nH]1]
Q-840
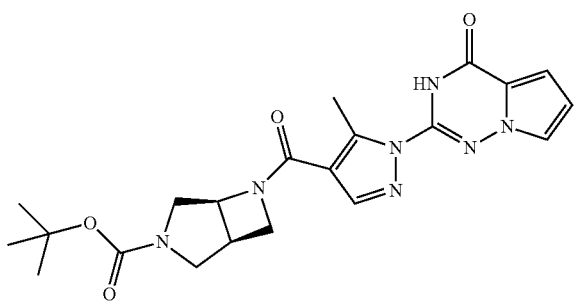 [SMILES: Cc1c(C(=O)N2C[C@H]3CN(C(=O)OC(C)(C)C)C[C@H]32)cnn1-c1nn2cccc2c(=O)[nH]1]
Q-842
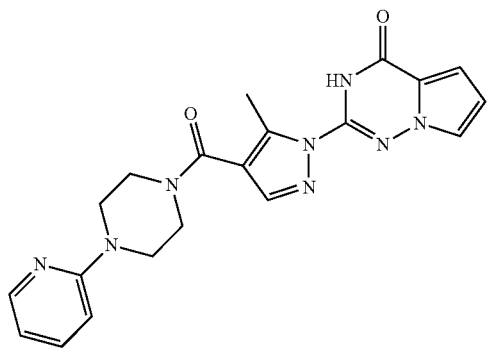
Q-843

TABLE C-continued
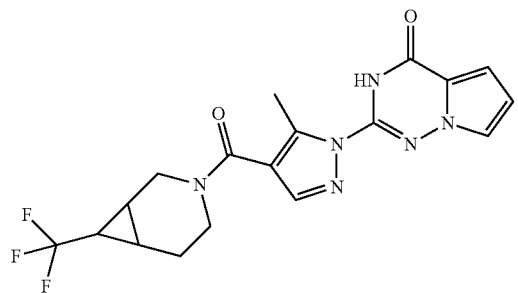 [SMILES: Cc1c(C(=O)N2CCC3C(C2)C3C(F)(F)F)cnn1-c1nn2cccc2c(=O)[nH]1]
Q-844
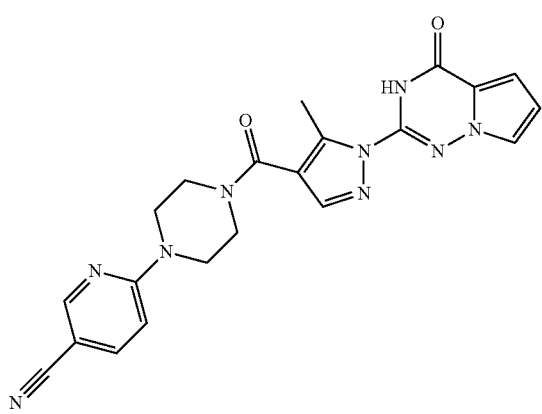 [SMILES: Cc1c(C(=O)N2CCN(c3ccc(C#N)cn3)CC2)cnn1-c1nn2cccc2c(=O)[nH]1]
Q-845
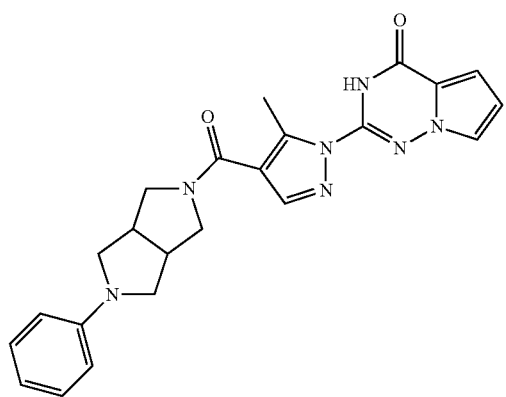 [SMILES: Cc1c(C(=O)N2CC3CN(c4ccccc4)CC3C2)cnn1-c1nn2cccc2c(=O)[nH]1]
Q-846
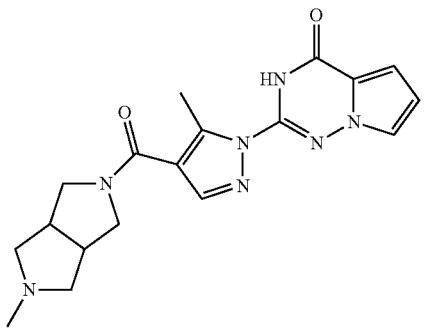 [SMILES: Cc1c(C(=O)N2CC3CN(C)CC3C2)cnn1-c1nn2cccc2c(=O)[nH]1]
Q-847

TABLE C-continued
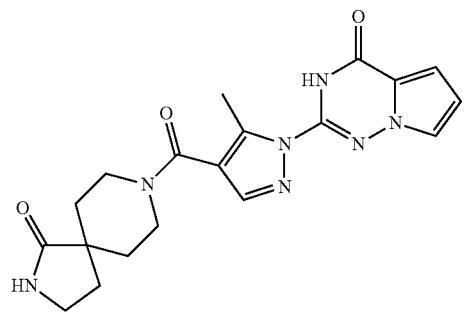 [SMILES: Cc1c(C(=O)N2CCC3(CCNC3=O)CC2)cnn1-c1nn2cccc2c(=O)[nH]1] Q-848
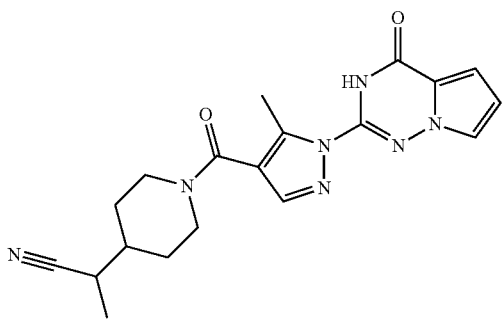 [SMILES: Cc1c(C(=O)N2CCC(C(C)C#N)CC2)cnn1-c1nn2cccc2c(=O)[nH]1] Q-849
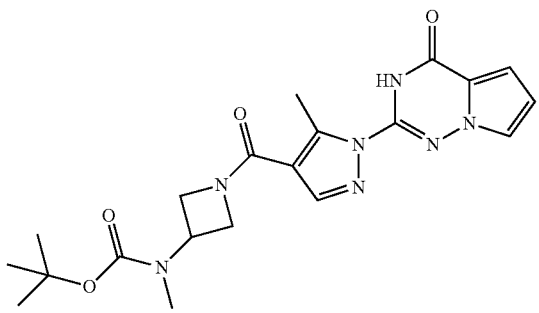 [SMILES: Cc1c(C(=O)N2CC(N(C)C(=O)OC(C)(C)C)C2)cnn1-c1nn2cccc2c(=O)[nH]1] Q-850
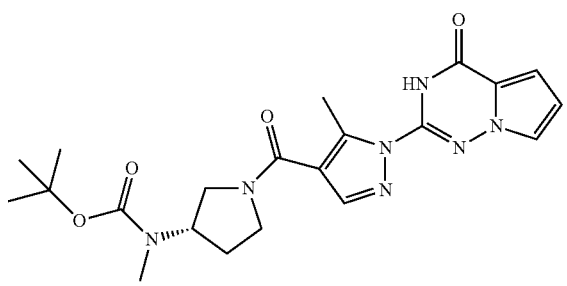 [SMILES: Cc1c(C(=O)N2CC[C@H](N(C)C(=O)OC(C)(C)C)C2)cnn1-c1nn2cccc2c(=O)[nH]1] Q-851
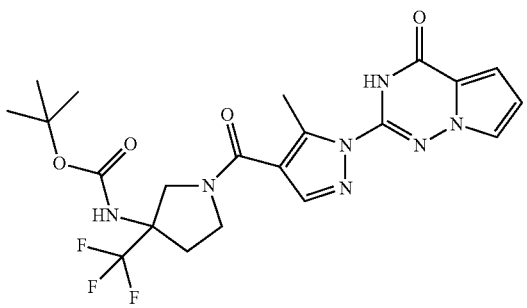 [SMILES: Cc1c(C(=O)N2CCC(NC(=O)OC(C)(C)C)(C(F)(F)F)C2)cnn1-c1nn2cccc2c(=O)[nH]1] Q-852

TABLE C-continued
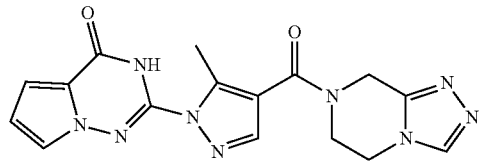 [SMILES: Cc1c(C(=O)N2CCn3cnnc3C2)cnn1-c1nn2cccc2c(=O)[nH]1] Q-853
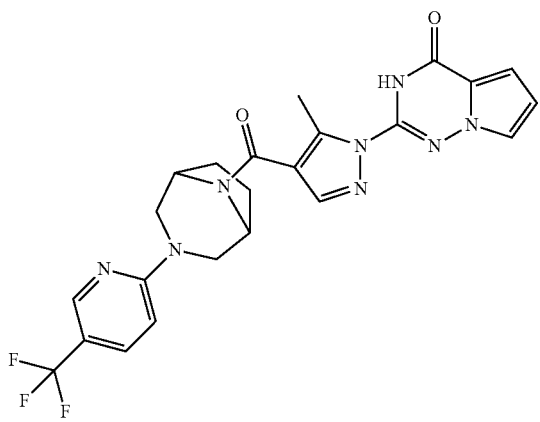 [SMILES: Cc1c(C(=O)N2C3CCC2CN(c2ccc(C(F)(F)F)cn2)C3)cnn1-c1nn2cccc2c(=O)[nH]1] Q-854
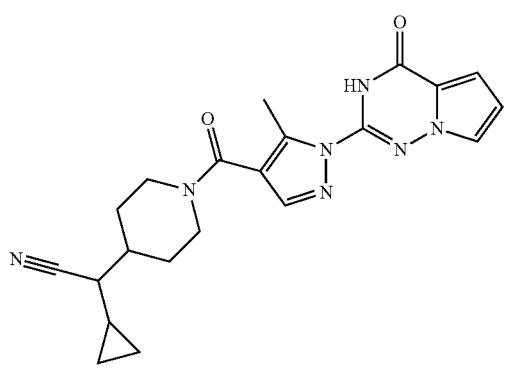 [SMILES: Cc1c(C(=O)N2CCC(C(C#N)C3CC3)CC2)cnn1-c1nn2cccc2c(=O)[nH]1] Q-855
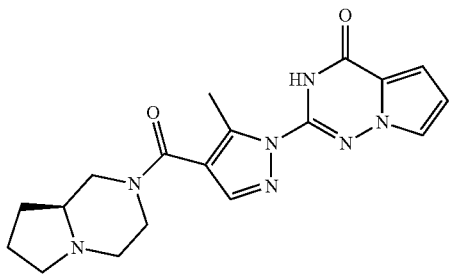 [SMILES: Cc1c(C(=O)N2CCN3CCC[C@H]3C2)cnn1-c1nn2cccc2c(=O)[nH]1] Q-856
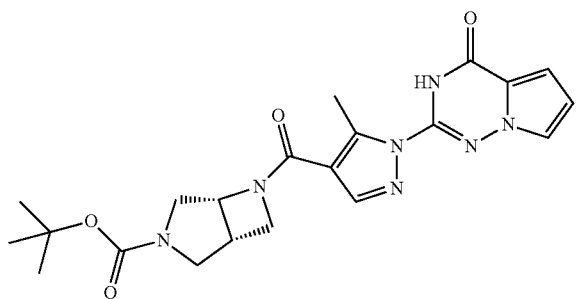 [SMILES: Cc1c(C(=O)N2C[C@@H]3CN(C(=O)OC(C)(C)C)C[C@@H]32)cnn1-c1nn2cccc2c(=O)[nH]1] Q-857

TABLE C-continued
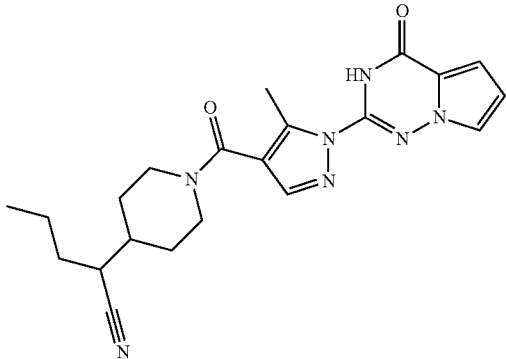 [SMILES: CCCC(C#N)C1CCN(C(=O)c2cnn(-c3nn4cccc4c(=O)[nH]3)c2C)CC1]
Q-858
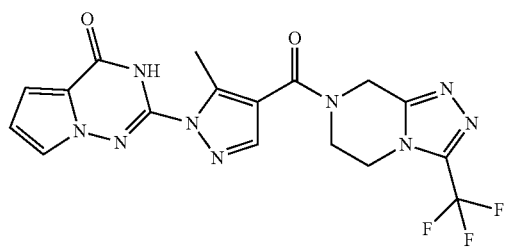 [SMILES: Cc1c(C(=O)N2CCn3c(nnc3C(F)(F)F)C2)cnn1-c1nn2cccc2c(=O)[nH]1]
Q-859
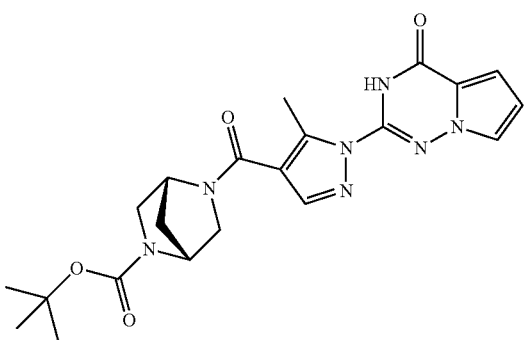 [SMILES: Cc1c(C(=O)N2C[C@H]3C[C@@H]2CN3C(=O)OC(C)(C)C)cnn1-c1nn2cccc2c(=O)[nH]1]
Q-860
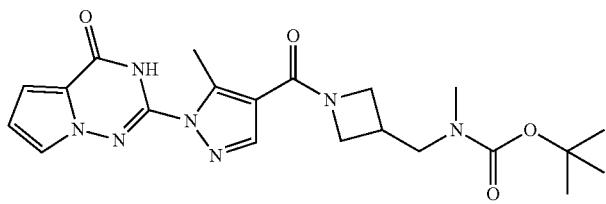 [SMILES: Cc1c(C(=O)N2CC(CN(C)C(=O)OC(C)(C)C)C2)cnn1-c1nn2cccc2c(=O)[nH]1]
Q-861
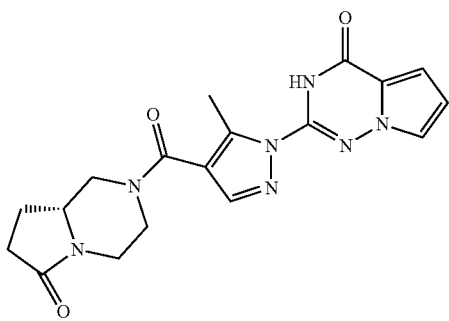 [SMILES: Cc1c(C(=O)N2CCN3C(=O)CC[C@@H]3C2)cnn1-c1nn2cccc2c(=O)[nH]1]
Q-862

TABLE C-continued
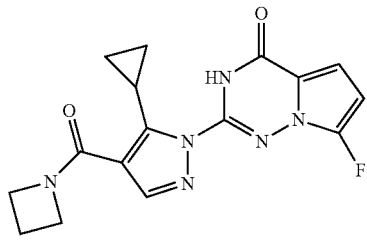 [SMILES: O=C(c1cnn(-c2nn3c(F)ccc3c(=O)[nH]2)c1C1CC1)N1CCC1]
Q-863
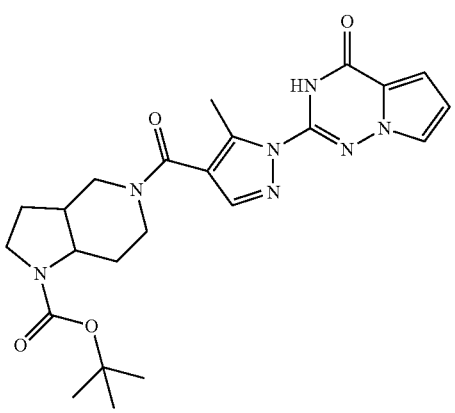 [SMILES: Cc1c(C(=O)N2CCC3C(CCN3C(=O)OC(C)(C)C)C2)cnn1-c1nn2cccc2c(=O)[nH]1]
Q-865
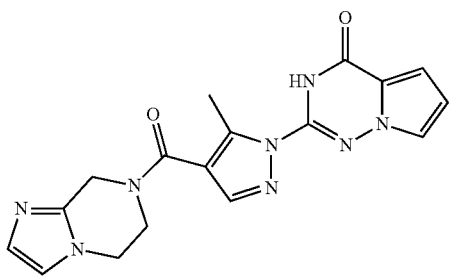 [SMILES: Cc1c(C(=O)N2CCn3ccnc3C2)cnn1-c1nn2cccc2c(=O)[nH]1]
Q-866
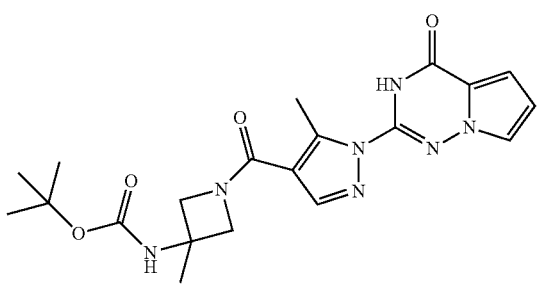 [SMILES: Cc1c(C(=O)N2CC(C)(NC(=O)OC(C)(C)C)C2)cnn1-c1nn2cccc2c(=O)[nH]1]
Q-867
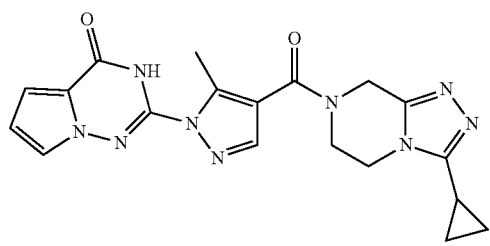 [SMILES: Cc1c(C(=O)N2CCn3c(nnc3C3CC3)C2)cnn1-c1nn2cccc2c(=O)[nH]1]
Q-868

TABLE C-continued
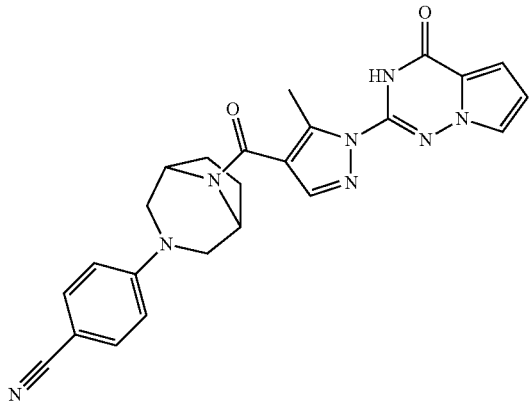 [SMILES: Cc1c(C(=O)N2C3CCC2CN(c2ccc(C#N)cc2)C3)cnn1-c1nn2cccc2c(=O)[nH]1]
Q-869
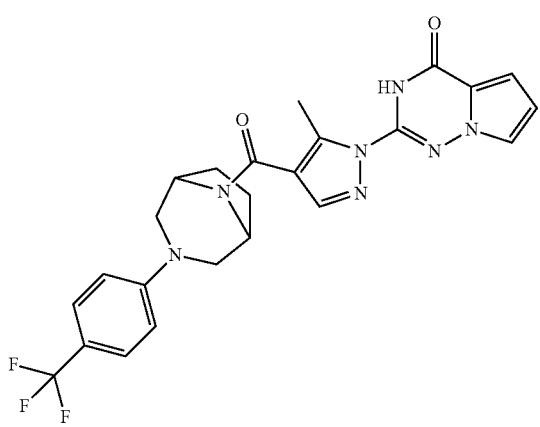 [SMILES: Cc1c(C(=O)N2C3CCC2CN(c2ccc(C(F)(F)F)cc2)C3)cnn1-c1nn2cccc2c(=O)[nH]1]
Q-870
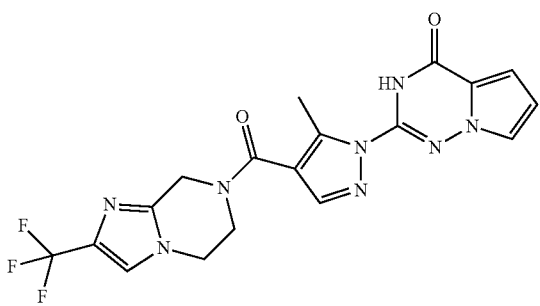 [SMILES: Cc1c(C(=O)N2CCn3cc(C(F)(F)F)nc3C2)cnn1-c1nn2cccc2c(=O)[nH]1]
Q-871
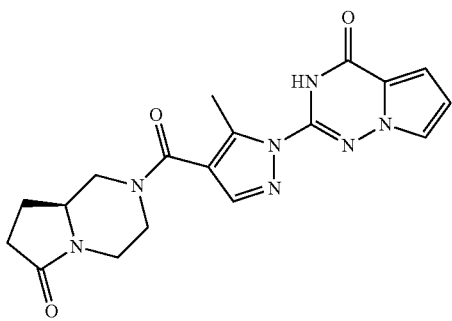 [SMILES: Cc1c(C(=O)N2CCN3C(=O)CC[C@H]3C2)cnn1-c1nn2cccc2c(=O)[nH]1]
Q-872

TABLE C-continued
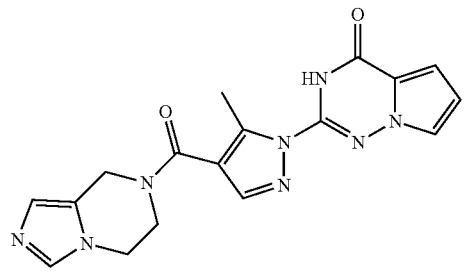 [SMILES: Cc1c(C(=O)N2CCn3cncc3C2)cnn1-c1nn2cccc2c(=O)[nH]1]
Q-873
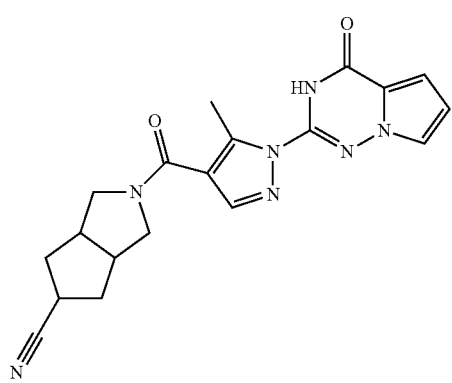 [SMILES: Cc1c(C(=O)N2CC3CC(C#N)CC3C2)cnn1-c1nn2cccc2c(=O)[nH]1]
Q-874
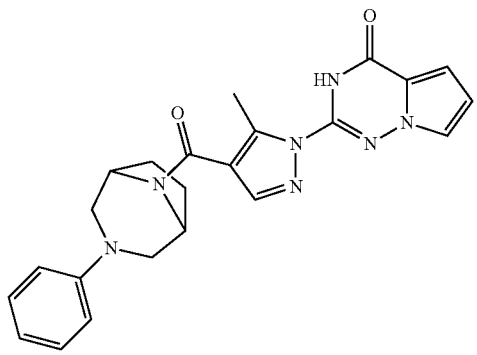 [SMILES: Cc1c(C(=O)N2C3CCC2CN(c2ccccc2)C3)cnn1-c1nn2cccc2c(=O)[nH]1]
Q-875
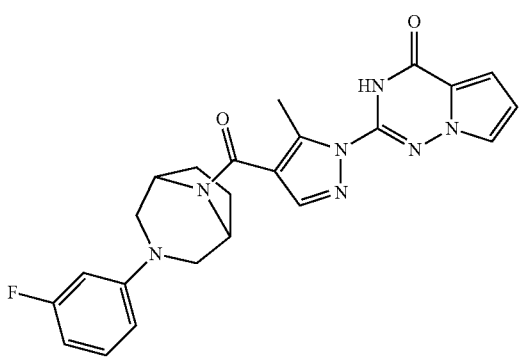 [SMILES: Cc1c(C(=O)N2C3CCC2CN(c2cccc(F)c2)C3)cnn1-c1nn2cccc2c(=O)[nH]1]
Q-876

TABLE C-continued
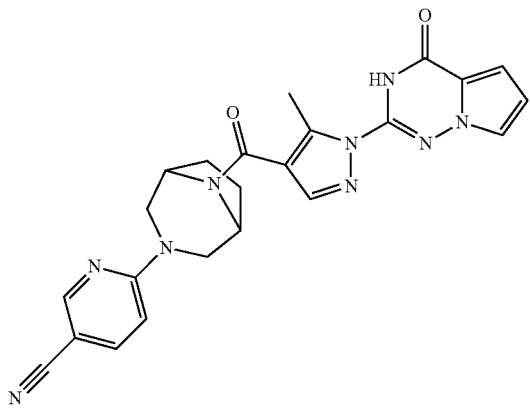 [SMILES: Cc1c(C(=O)N2C3CCC2CN(c2ccc(C#N)cn2)C3)cnn1-c1nn2cccc2c(=O)[nH]1]
Q-877
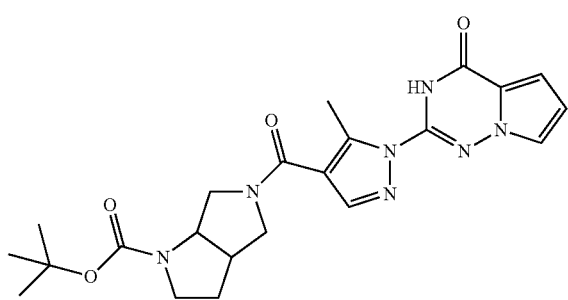 [SMILES: Cc1c(C(=O)N2CC3CCN(C(=O)OC(C)(C)C)C3C2)cnn1-c1nn2cccc2c(=O)[nH]1]
Q-878
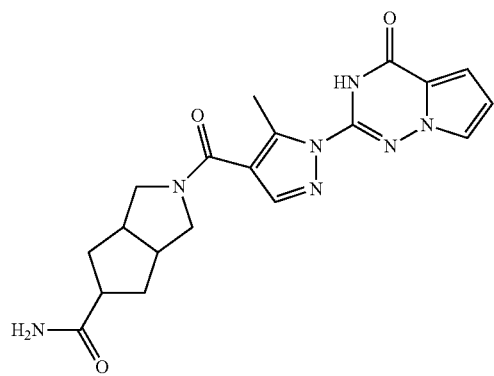 [SMILES: Cc1c(C(=O)N2CC3CC(C(N)=O)CC3C2)cnn1-c1nn2cccc2c(=O)[nH]1]
Q-879
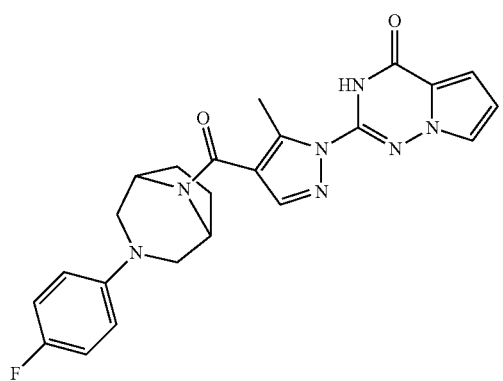 [SMILES: Cc1c(C(=O)N2C3CCC2CN(c2ccc(F)cc2)C3)cnn1-c1nn2cccc2c(=O)[nH]1]
Q-880

TABLE C-continued
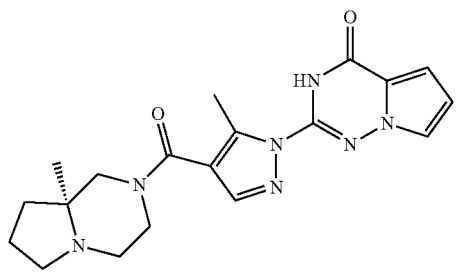 [SMILES: Cc1c(C(=O)N2CCN3CCC[C@@]3(C)C2)cnn1-c1nn2cccc2c(=O)[nH]1] Q-881
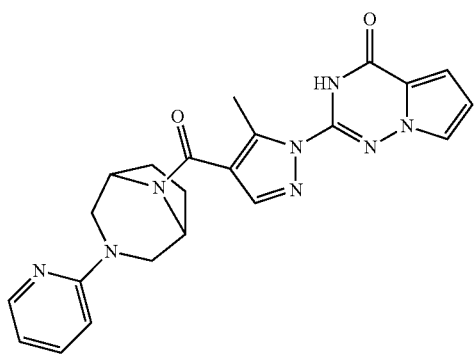 Q-882
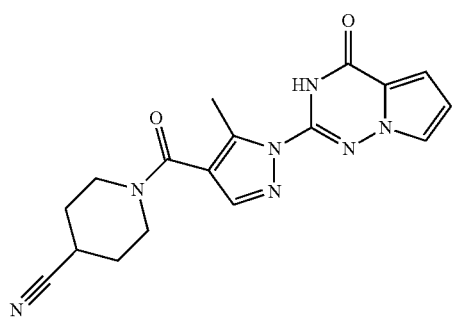 [SMILES: Cc1c(C(=O)N2CCC(C#N)CC2)cnn1-c1nn2cccc2c(=O)[nH]1] Q-883
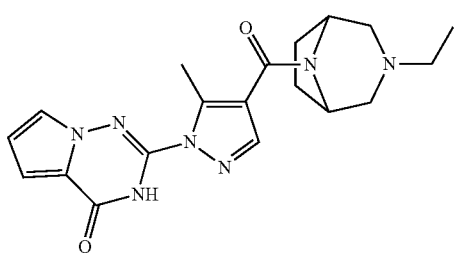 [SMILES: CCN1CC2CCC(C1)N2C(=O)c1cnn(-c2nn3cccc3c(=O)[nH]2)c1C] Q-884
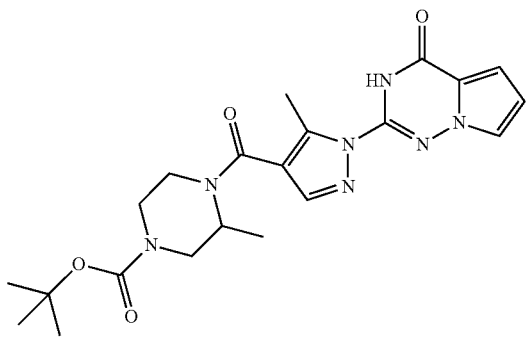 Q-885

TABLE C-continued
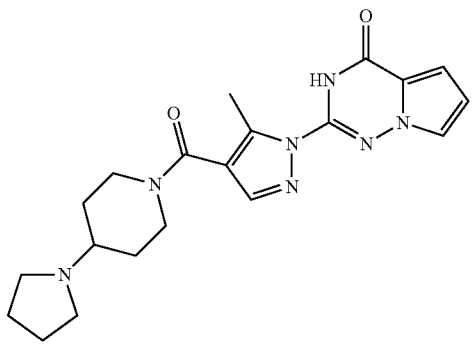 [SMILES: Cc1c(C(=O)N2CCC(N3CCCC3)CC2)cnn1-c1nn2cccc2c(=O)[nH]1] Q-886
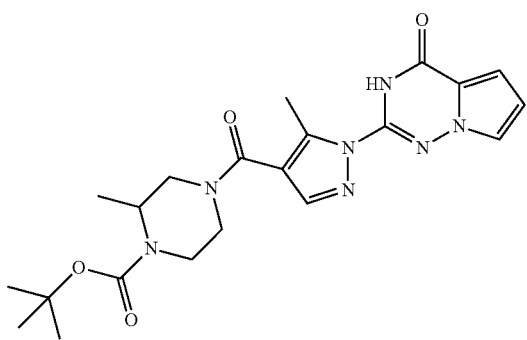 [SMILES: Cc1c(C(=O)N2CCN(C(=O)OC(C)(C)C)C(C)C2)cnn1-c1nn2cccc2c(=O)[nH]1] Q-887
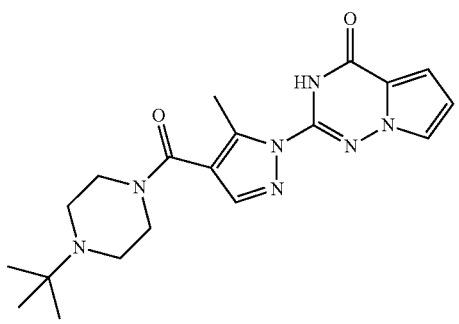 [SMILES: Cc1c(C(=O)N2CCN(C(C)(C)C)CC2)cnn1-c1nn2cccc2c(=O)[nH]1] Q-888
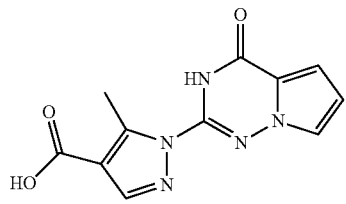 [SMILES: Cc1c(C(=O)O)cnn1-c1nn2cccc2c(=O)[nH]1] Q-890
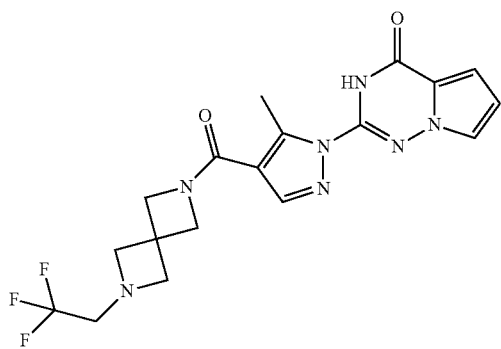 [SMILES: Cc1c(C(=O)N2CC3(CN(CC(F)(F)F)C3)C2)cnn1-c1nn2cccc2c(=O)[nH]1] Q-891

TABLE C-continued
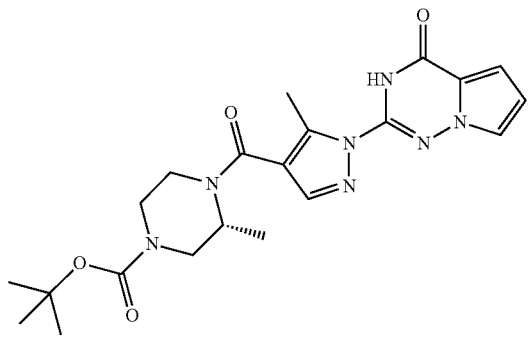 [SMILES: Cc1c(C(=O)N2CCN(C(=O)OC(C)(C)C)C[C@H]2C)cnn1-c1nn2cccc2c(=O)[nH]1]
Q-892
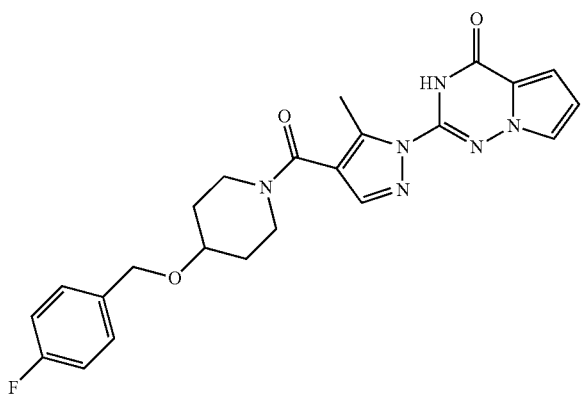 [SMILES: Cc1c(C(=O)N2CCC(OCc3ccc(F)cc3)CC2)cnn1-c1nn2cccc2c(=O)[nH]1]
Q-893
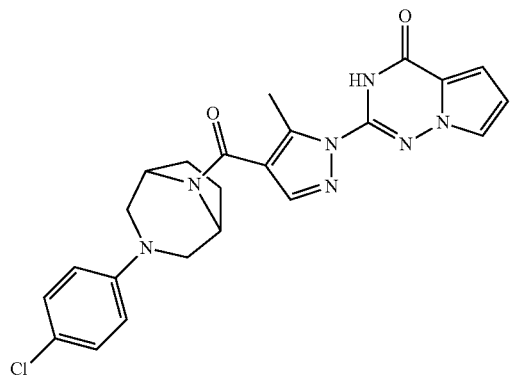 [SMILES: Cc1c(C(=O)N2C3CCC2CN(c2ccc(Cl)cc2)C3)cnn1-c1nn2cccc2c(=O)[nH]1]
Q-894
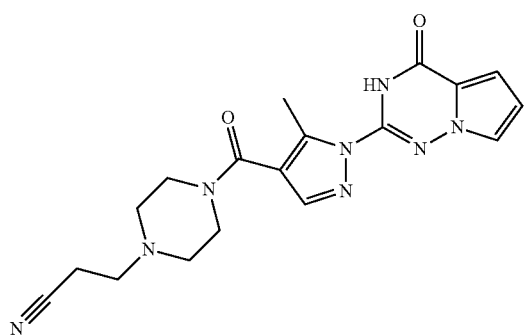 [SMILES: Cc1c(C(=O)N2CCN(CCC#N)CC2)cnn1-c1nn2cccc2c(=O)[nH]1]
Q-895

TABLE C-continued
Q-896
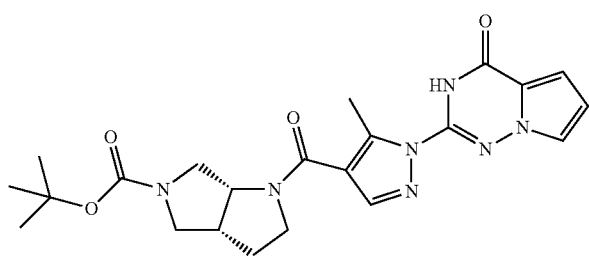 [SMILES: Cc1c(C(=O)N2CC[C@@H]3CN(C(=O)OC(C)(C)C)C[C@@H]32)cnn1-c1nn2cccc2c(=O)[nH]1]
Q-897
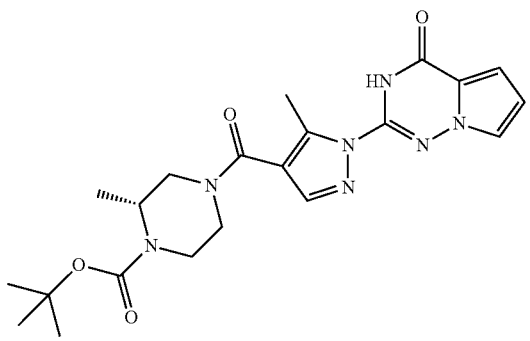 [SMILES: Cc1c(C(=O)N2CCN(C(=O)OC(C)(C)C)[C@H](C)C2)cnn1-c1nn2cccc2c(=O)[nH]1]
Q-899
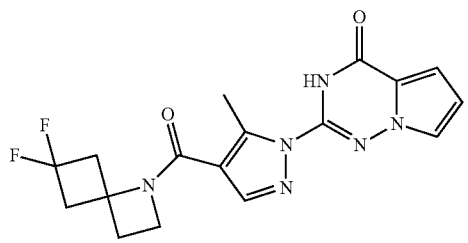 [SMILES: Cc1c(C(=O)N2CCC23CC(F)(F)C3)cnn1-c1nn2cccc2c(=O)[nH]1]
Q-900
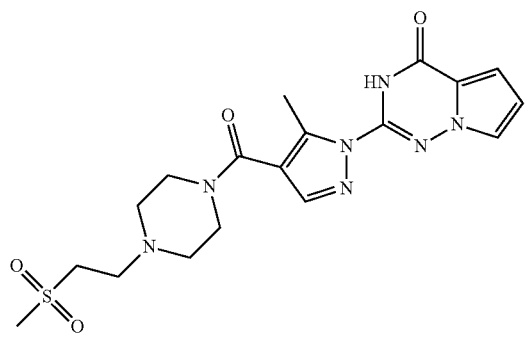 [SMILES: Cc1c(C(=O)N2CCN(CCS(C)(=O)=O)CC2)cnn1-c1nn2cccc2c(=O)[nH]1]
Q-901

TABLE C-continued
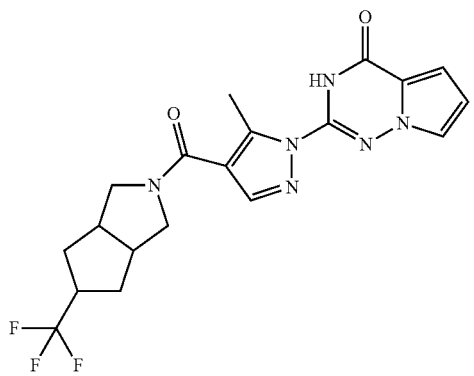 [SMILES: Cc1c(C(=O)N2CC3CC(C(F)(F)F)CC3C2)cnn1-c1nn2cccc2c(=O)[nH]1] Q-902
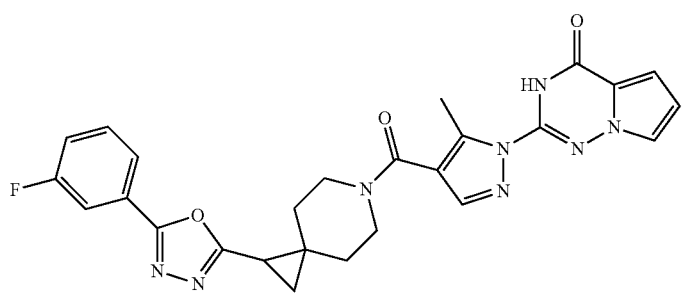 [SMILES: Cc1c(C(=O)N2CCC3(CC2)CC3c2nnc(-c3cccc(F)c3)o2)cnn1-c1nn2cccc2c(=O)[nH]1] Q-905
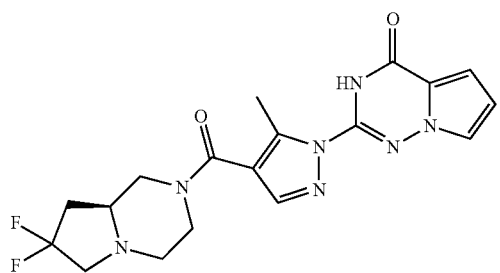 [SMILES: Cc1c(C(=O)N2CCN3CC(F)(F)C[C@H]3C2)cnn1-c1nn2cccc2c(=O)[nH]1] Q-906
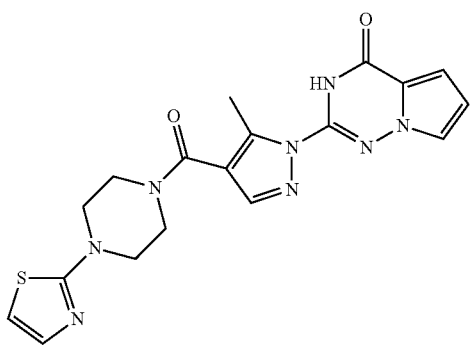 [SMILES: Cc1c(C(=O)N2CCN(c3nccs3)CC2)cnn1-c1nn2cccc2c(=O)[nH]1] Q-907
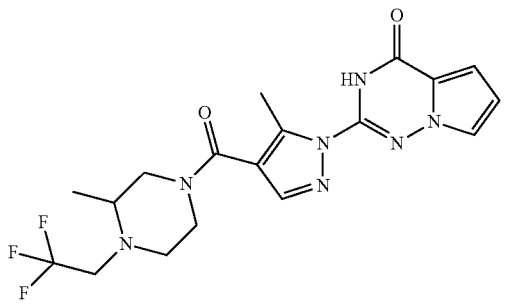 [SMILES: Cc1c(C(=O)N2CCN(CC(F)(F)F)C(C)C2)cnn1-c1nn2cccc2c(=O)[nH]1] Q-908

TABLE C-continued
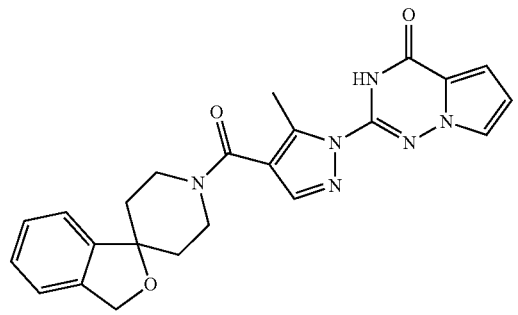 [SMILES: Cc1c(C(=O)N2CCC3(CC2)OCc2ccccc23)cnn1-c1nn2cccc2c(=O)[nH]1]
Q-909
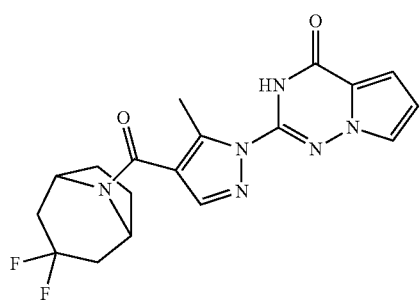 [SMILES: Cc1c(C(=O)N2C3CCC2CC(F)(F)C3)cnn1-c1nn2cccc2c(=O)[nH]1]
Q-910
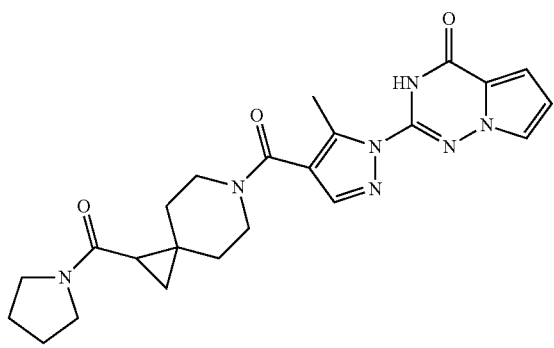 [SMILES: Cc1c(C(=O)N2CCC3(CC2)CC3C(=O)N2CCCC2)cnn1-c1nn2cccc2c(=O)[nH]1]
Q-911
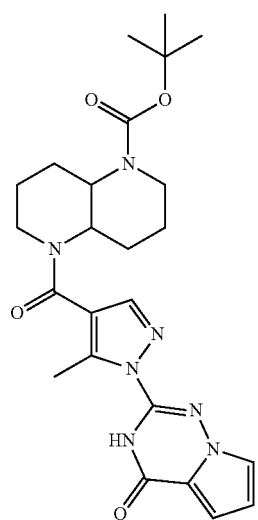 [SMILES: Cc1c(C(=O)N2CCCC3C2CCCN3C(=O)OC(C)(C)C)cnn1-c1nn2cccc2c(=O)[nH]1]
Q-912

TABLE C-continued
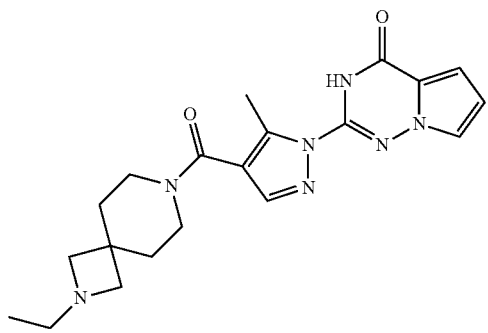 [SMILES: CCN1CC2(CCN(C(=O)c3cnn(-c4nn5cccc5c(=O)[nH]4)c3C)CC2)C1]
Q-913
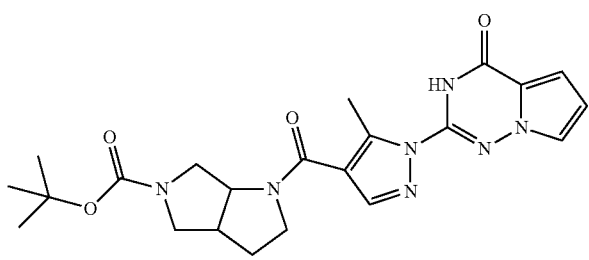 [SMILES: Cc1c(C(=O)N2CCC3CN(C(=O)OC(C)(C)C)CC32)cnn1-c1nn2cccc2c(=O)[nH]1]
Q-914
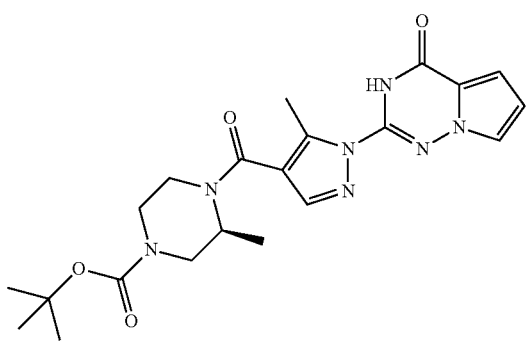 [SMILES: Cc1c(C(=O)N2CCN(C(=O)OC(C)(C)C)C[C@@H]2C)cnn1-c1nn2cccc2c(=O)[nH]1]
Q-915
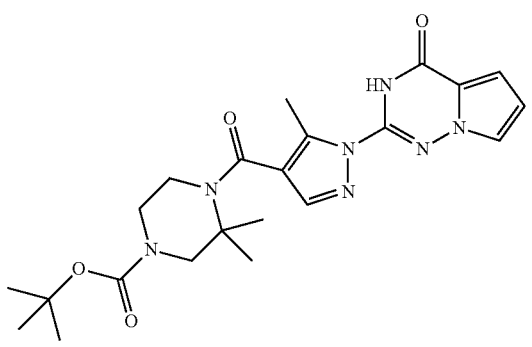 [SMILES: Cc1c(C(=O)N2CCN(C(=O)OC(C)(C)C)CC2(C)C)cnn1-c1nn2cccc2c(=O)[nH]1]
Q-916
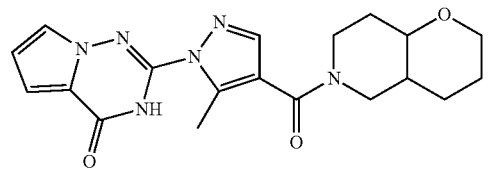 [SMILES: Cc1c(C(=O)N2CCC3OCCCC3C2)cnn1-c1nn2cccc2c(=O)[nH]1]
Q-917

TABLE C-continued
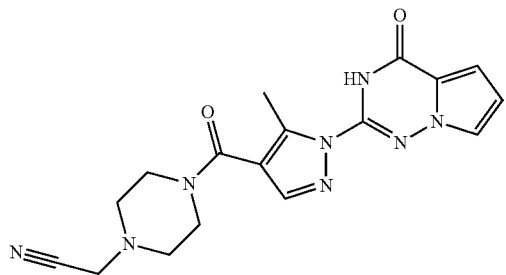 [SMILES: Cc1c(C(=O)N2CCN(CC#N)CC2)cnn1-c1nn2cccc2c(=O)[nH]1]
Q-918
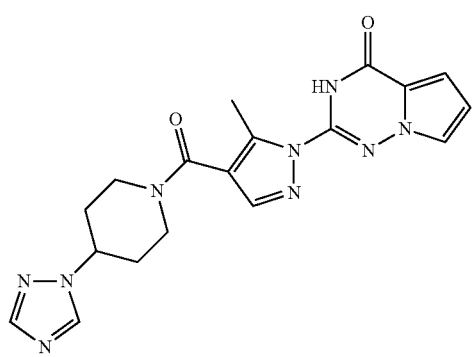 [SMILES: Cc1c(C(=O)N2CCC(n3cncn3)CC2)cnn1-c1nn2cccc2c(=O)[nH]1]
Q-919
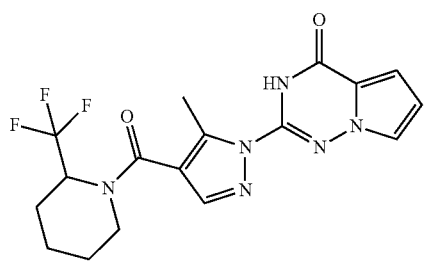 [SMILES: Cc1c(C(=O)N2CCCCC2C(F)(F)F)cnn1-c1nn2cccc2c(=O)[nH]1]
Q-920
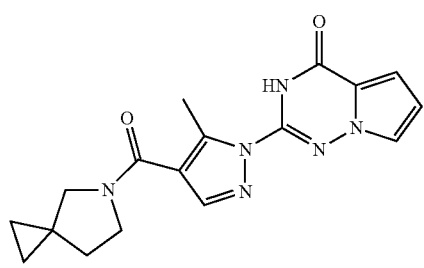 [SMILES: Cc1c(C(=O)N2CCC3(CC3)C2)cnn1-c1nn2cccc2c(=O)[nH]1]
Q-921
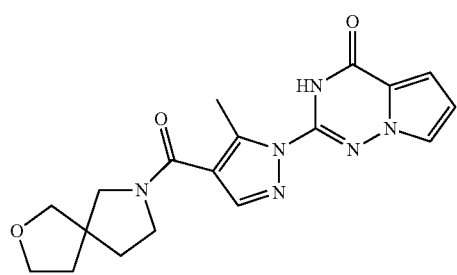 [SMILES: Cc1c(C(=O)N2CCC3(CCOC3)C2)cnn1-c1nn2cccc2c(=O)[nH]1]
Q-922

TABLE C-continued
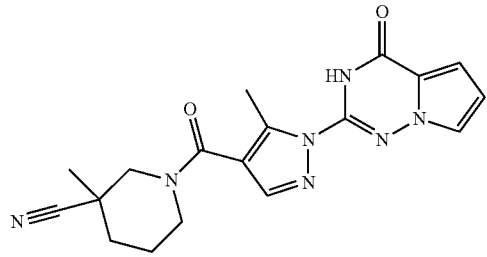 [SMILES: Cc1c(C(=O)N2CCCC(C)(C#N)C2)cnn1-c1nn2cccc2c(=O)[nH]1]
Q-923
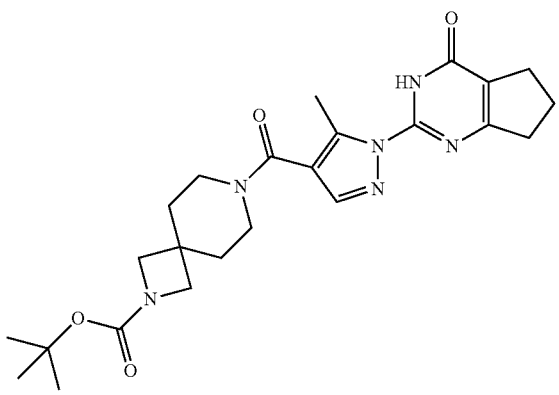 [SMILES: Cc1c(C(=O)N2CCC3(CC2)CN(C(=O)OC(C)(C)C)C3)cnn1-c1nc2c(c(=O)[nH]1)CCC2]
Q-924
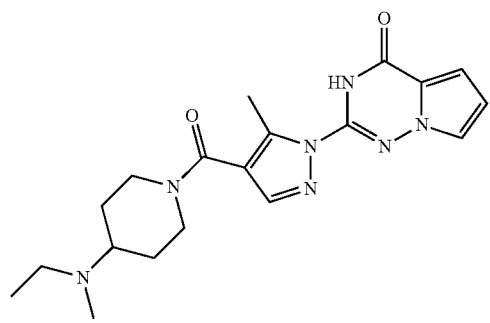 [SMILES: CCN(C)C1CCN(C(=O)c2cnn(-c3nn4cccc4c(=O)[nH]3)c2C)CC1]
Q-925
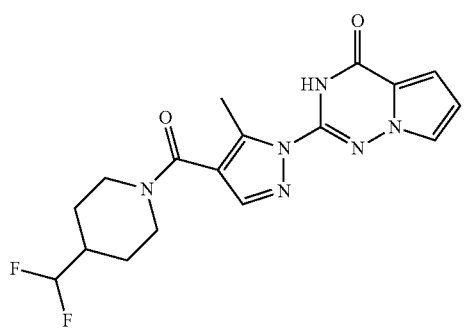 [SMILES: Cc1c(C(=O)N2CCC(C(F)F)CC2)cnn1-c1nn2cccc2c(=O)[nH]1]
Q-926
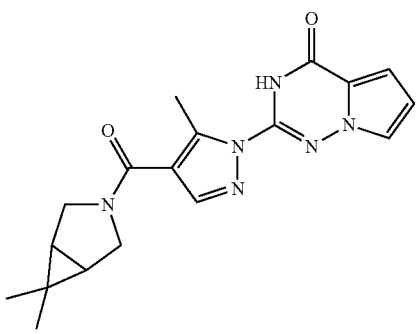 [SMILES: Cc1c(C(=O)N2CC3C(C2)C3(C)C)cnn1-c1nn2cccc2c(=O)[nH]1]
Q-927

TABLE C-continued
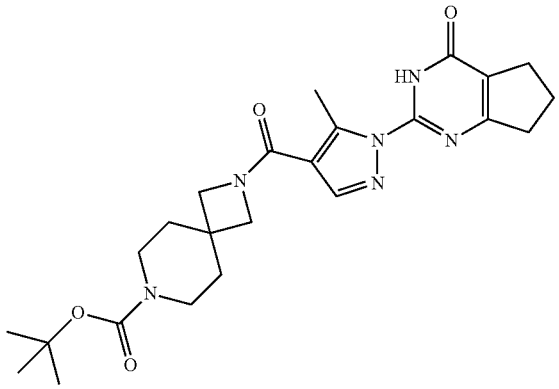 [SMILES: Cc1c(C(=O)N2CC3(CCN(C(=O)OC(C)(C)C)CC3)C2)cnn1-c1nc2c(c(=O)[nH]1)CCC2] Q-928
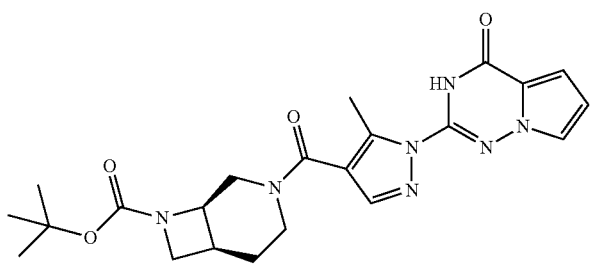 [SMILES: Cc1c(C(=O)N2CC[C@H]3CN(C(=O)OC(C)(C)C)[C@H]3C2)cnn1-c1nn2cccc2c(=O)[nH]1] Q-929
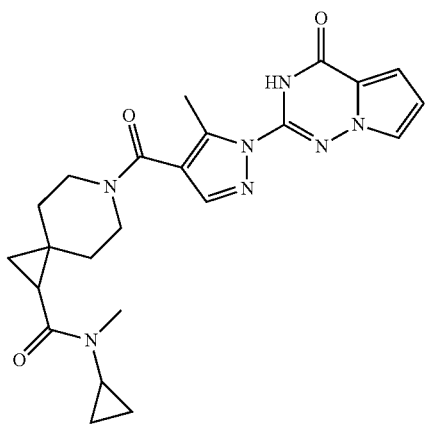 [SMILES: Cc1c(C(=O)N2CCC3(CC2)CC3C(=O)N(C)C2CC2)cnn1-c1nn2cccc2c(=O)[nH]1] Q-930
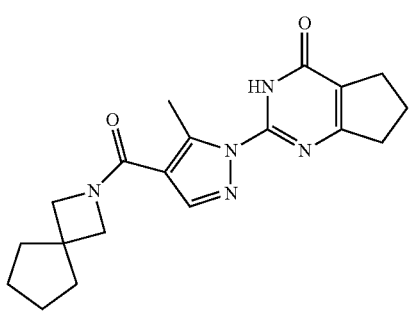 [SMILES: Cc1c(C(=O)N2CC3(CCCC3)C2)cnn1-c1nc2c(c(=O)[nH]1)CCC2] Q-931

TABLE C-continued
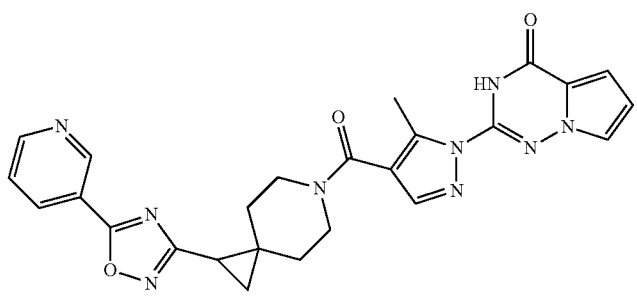 [SMILES: Cc1c(C(=O)N2CCC3(CC2)CC3c2noc(-c3cccnc3)n2)cnn1-c1nn2cccc2c(=O)[nH]1]
Q-932
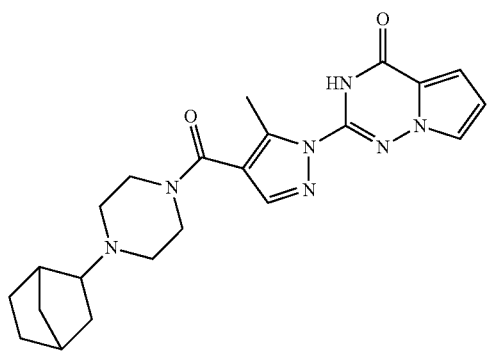 [SMILES: Cc1c(C(=O)N2CCN(C3CC4CCC3C4)CC2)cnn1-c1nn2cccc2c(=O)[nH]1]
Q-933
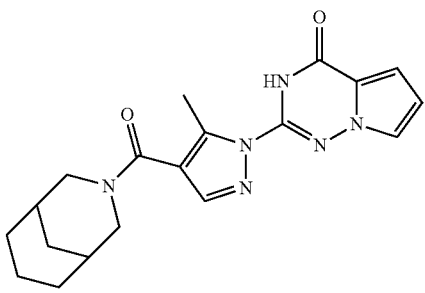 [SMILES: Cc1c(C(=O)N2CC3CCCC(C3)C2)cnn1-c1nn2cccc2c(=O)[nH]1]
Q-934
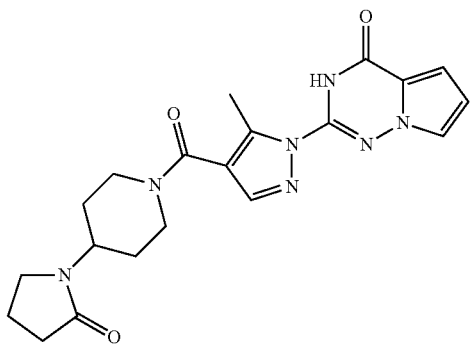 [SMILES: Cc1c(C(=O)N2CCC(N3CCCC3=O)CC2)cnn1-c1nn2cccc2c(=O)[nH]1]
Q-935

TABLE C-continued
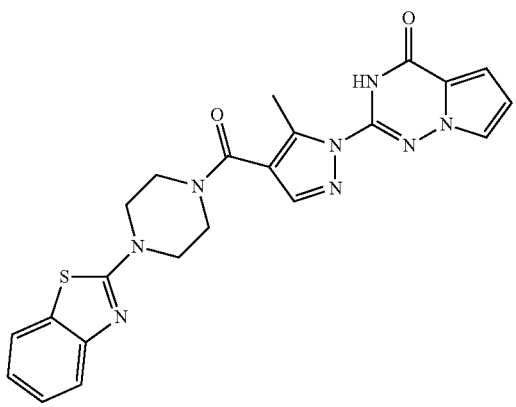 [SMILES: Cc1c(C(=O)N2CCN(c3nc4ccccc4s3)CC2)cnn1-c1nn2cccc2c(=O)[nH]1]
Q-936
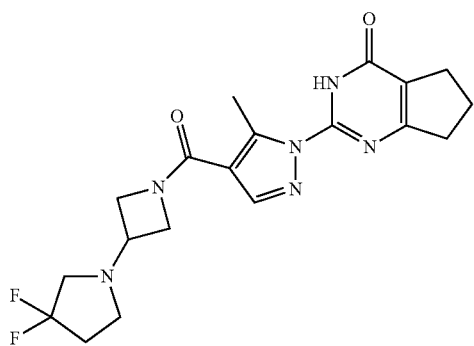 [SMILES: Cc1c(C(=O)N2CC(N3CCC(F)(F)C3)C2)cnn1-c1nc2c(c(=O)[nH]1)CCC2]
Q-937
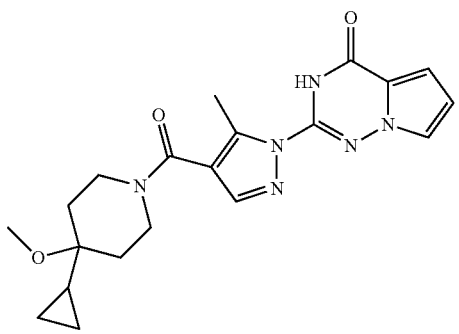 [SMILES: COC1(C2CC2)CCN(C(=O)c2cnn(-c3nn4cccc4c(=O)[nH]3)c2C)CC1]
Q-938
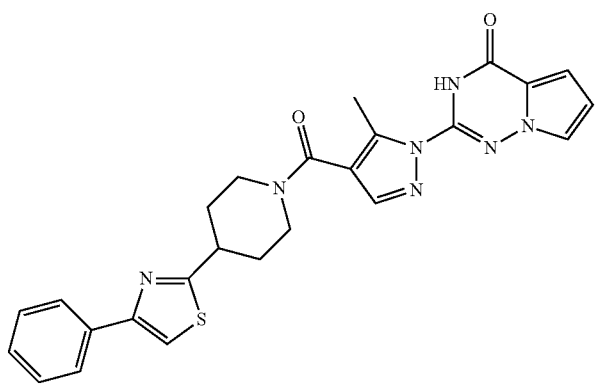 [SMILES: Cc1c(C(=O)N2CCC(c3nc(-c4ccccc4)cs3)CC2)cnn1-c1nn2cccc2c(=O)[nH]1]
Q-939

TABLE C-continued
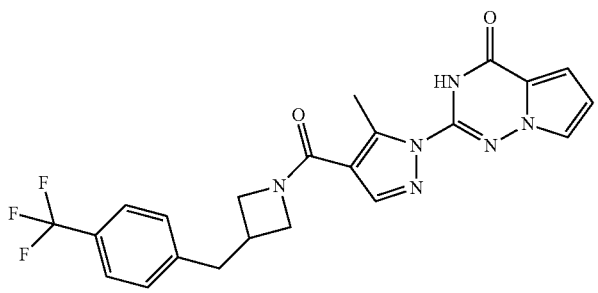 [SMILES: Cc1c(C(=O)N2CC(Cc3ccc(C(F)(F)F)cc3)C2)cnn1-c1nn2cccc2c(=O)[nH]1]
Q-940
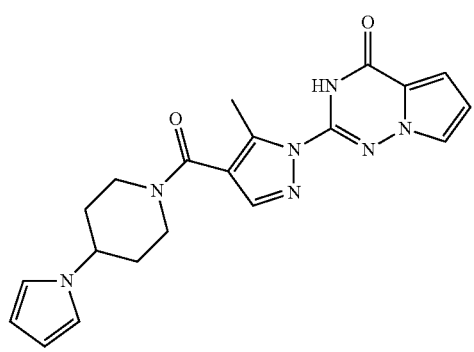 [SMILES: Cc1c(C(=O)N2CCC(n3cccc3)CC2)cnn1-c1nn2cccc2c(=O)[nH]1]
Q-941
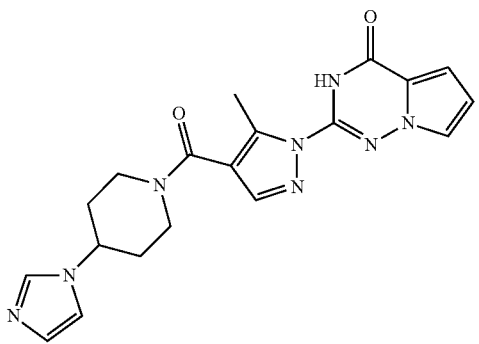 [SMILES: Cc1c(C(=O)N2CCC(n3ccnc3)CC2)cnn1-c1nn2cccc2c(=O)[nH]1]
Q-942
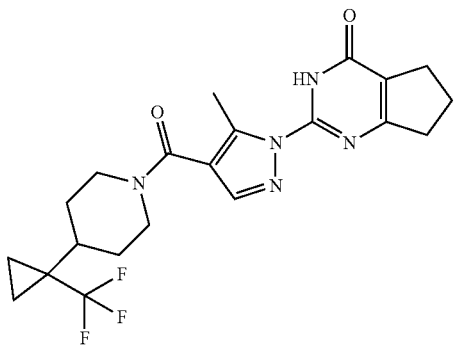 [SMILES: Cc1c(C(=O)N2CCC(C3(C(F)(F)F)CC3)CC2)cnn1-c1nc2c(c(=O)[nH]1)CCC2]
Q-943

TABLE C-continued
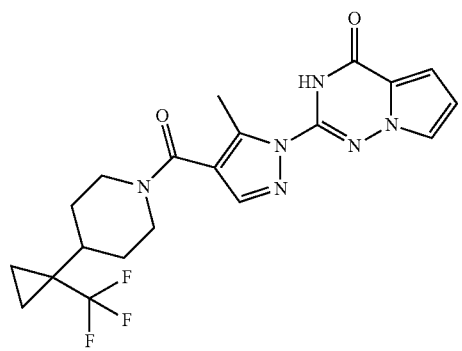 [SMILES: Cc1c(C(=O)N2CCC(C3(C(F)(F)F)CC3)CC2)cnn1-c1nn2cccc2c(=O)[nH]1]
Q-944
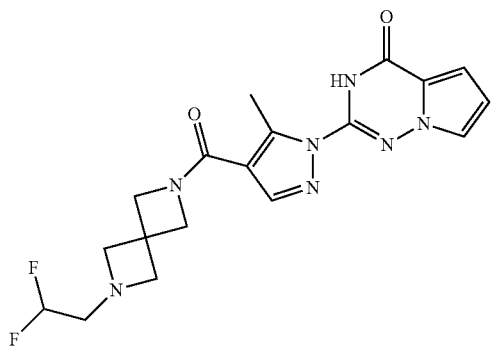 [SMILES: Cc1c(C(=O)N2CC3(CN(CC(F)F)C3)C2)cnn1-c1nn2cccc2c(=O)[nH]1]
Q-945
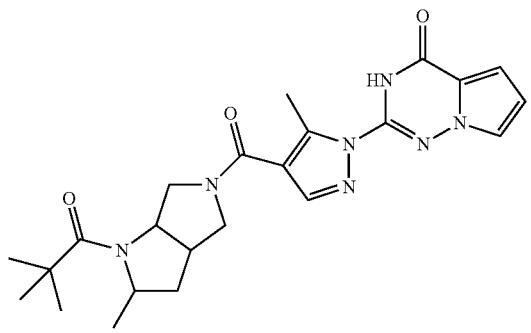 [SMILES: Cc1c(C(=O)N2CC3CC(C)N(C(=O)C(C)(C)C)C3C2)cnn1-c1nn2cccc2c(=O)[nH]1]
Q-946
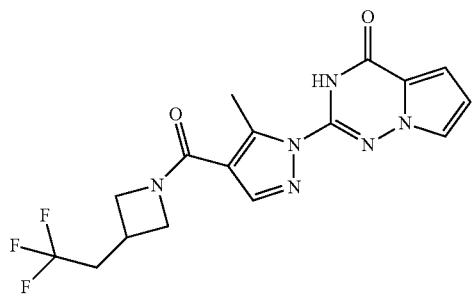 [SMILES: Cc1c(C(=O)N2CC(CC(F)(F)F)C2)cnn1-c1nn2cccc2c(=O)[nH]1]
Q-947
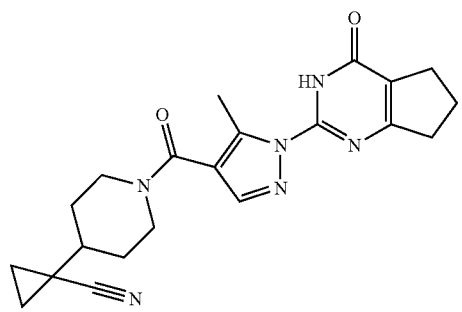 [SMILES: Cc1c(C(=O)N2CCC(C3(C#N)CC3)CC2)cnn1-c1nc2c(c(=O)[nH]1)CCC2]
Q-948

TABLE C-continued
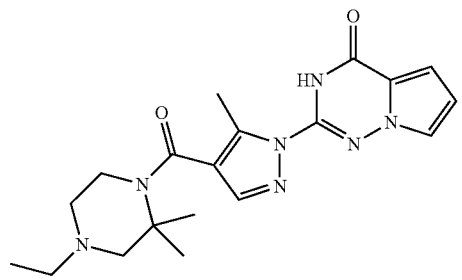 [SMILES: CCN1CCN(C(=O)c2cnn(-c3nn4cccc4c(=O)[nH]3)c2C)C(C)(C)C1]
Q-949
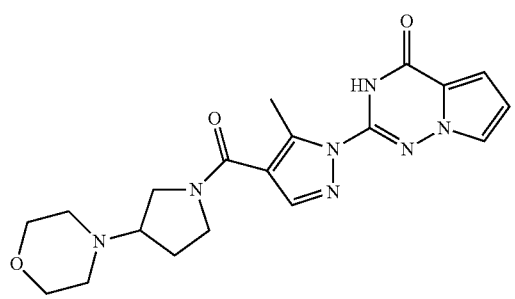 [SMILES: Cc1c(C(=O)N2CCC(N3CCOCC3)C2)cnn1-c1nn2cccc2c(=O)[nH]1]
Q-950
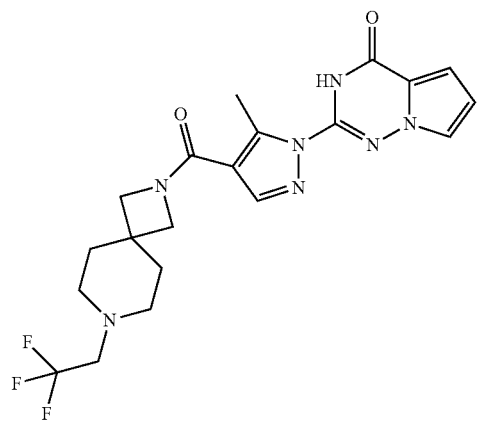 [SMILES: Cc1c(C(=O)N2CC3(CCN(CC(F)(F)F)CC3)C2)cnn1-c1nn2cccc2c(=O)[nH]1]
Q-951
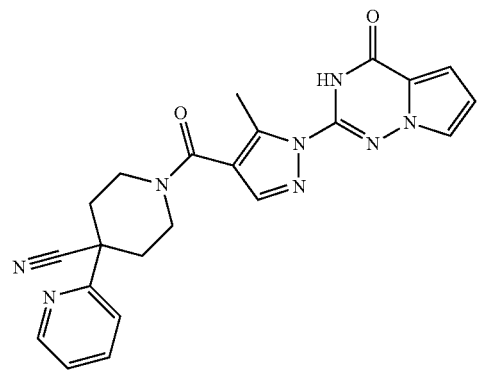 [SMILES: Cc1c(C(=O)N2CCC(C#N)(c3ccccn3)CC2)cnn1-c1nn2cccc2c(=O)[nH]1]
Q-952

TABLE C-continued
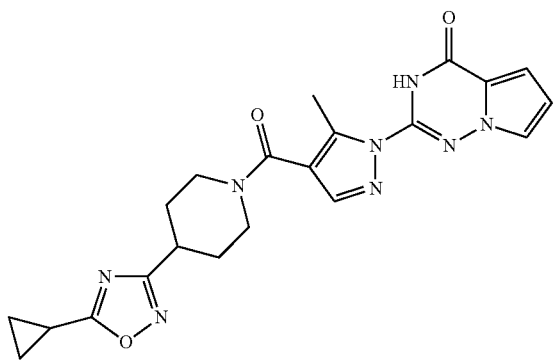 [SMILES: Cc1c(C(=O)N2CCC(c3noc(C4CC4)n3)CC2)cnn1-c1nn2cccc2c(=O)[nH]1]
Q-953
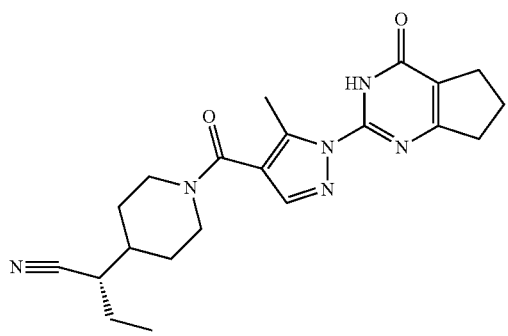 [SMILES: CC[C@H](C#N)C1CCN(C(=O)c2cnn(-c3nc4c(c(=O)[nH]3)CCC4)c2C)CC1]
Q-572a
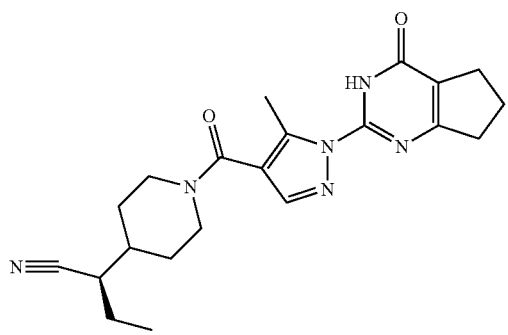 [SMILES: CC[C@@H](C#N)C1CCN(C(=O)c2cnn(-c3nc4c(c(=O)[nH]3)CCC4)c2C)CC1]
Q-572b
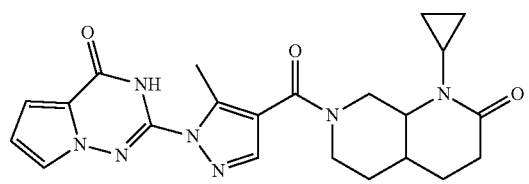 [SMILES: Cc1c(C(=O)N2CCC3CCC(=O)N(C4CC4)C3C2)cnn1-c1nn2cccc2c(=O)[nH]1]
Q-954
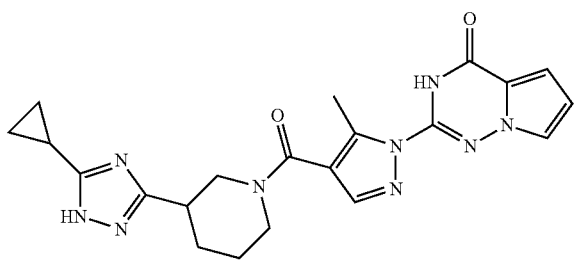 [SMILES: Cc1c(C(=O)N2CCCC(c3n[nH]c(C4CC4)n3)C2)cnn1-c1nn2cccc2c(=O)[nH]1]
Q-955

TABLE C-continued
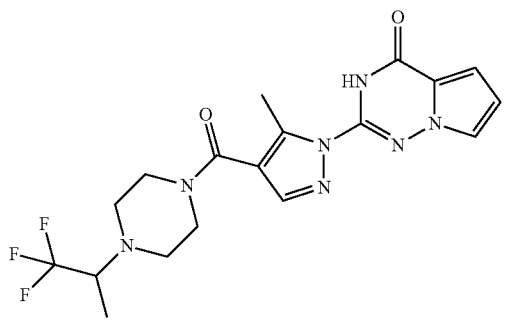
Q-956
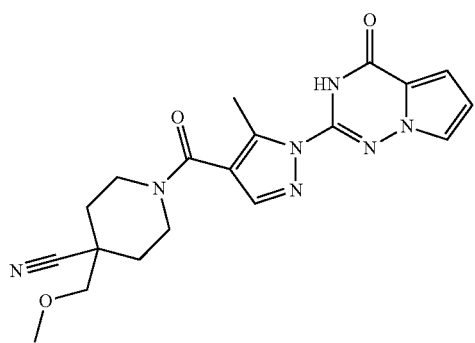 [SMILES: COCC1(C#N)CCN(C(=O)c2cnn(-c3nn4cccc4c(=O)[nH]3)c2C)CC1]
Q-957
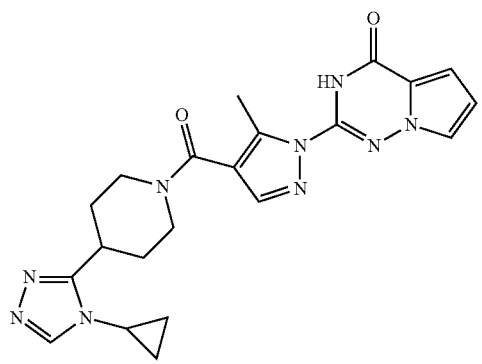 [SMILES: Cc1c(C(=O)N2CCC(c3nncn3C3CC3)CC2)cnn1-c1nn2cccc2c(=O)[nH]1]
Q-958
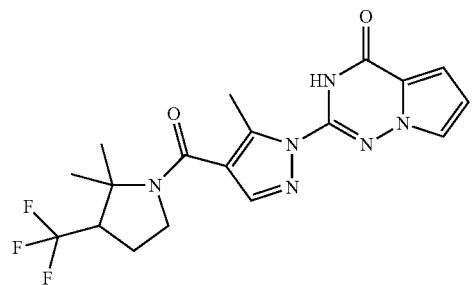 [SMILES: Cc1c(C(=O)N2CCC(C(F)(F)F)C2(C)C)cnn1-c1nn2cccc2c(=O)[nH]1]
Q-959
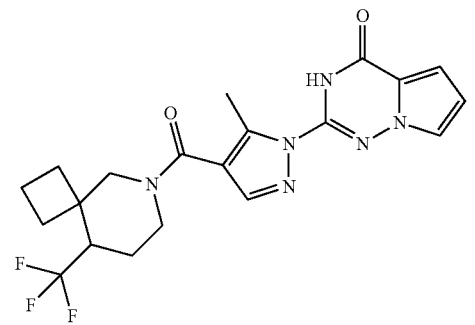 [SMILES: Cc1c(C(=O)N2CCC(C(F)(F)F)C3(CCC3)C2)cnn1-c1nn2cccc2c(=O)[nH]1]
Q-960

TABLE C-continued
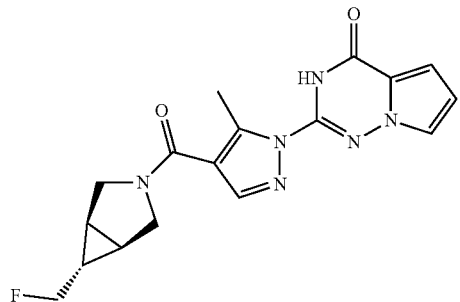 [SMILES: Cc1c(C(=O)N2C[C@@H]3[C@@H](CF)[C@@H]3C2)cnn1-c1nn2cccc2c(=O)[nH]1]
Q-961
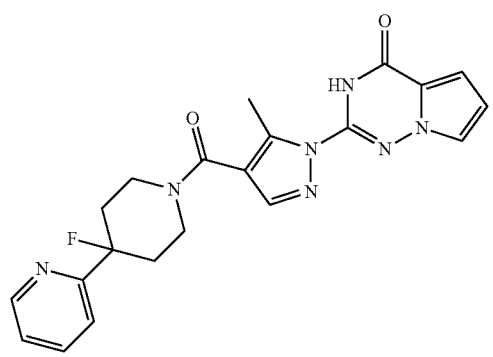 [SMILES: Cc1c(C(=O)N2CCC(F)(c3ccccn3)CC2)cnn1-c1nn2cccc2c(=O)[nH]1]
Q-962
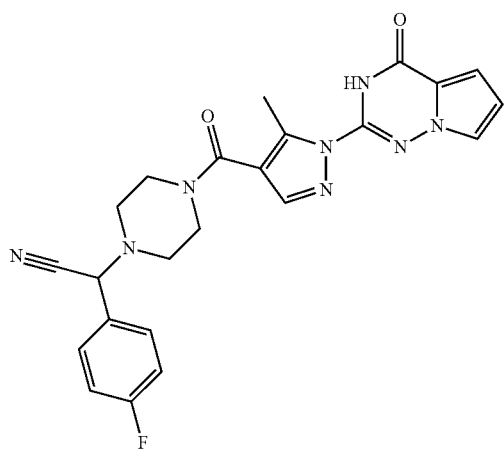 [SMILES: Cc1c(C(=O)N2CCN(C(C#N)c3ccc(F)cc3)CC2)cnn1-c1nn2cccc2c(=O)[nH]1]
Q-963
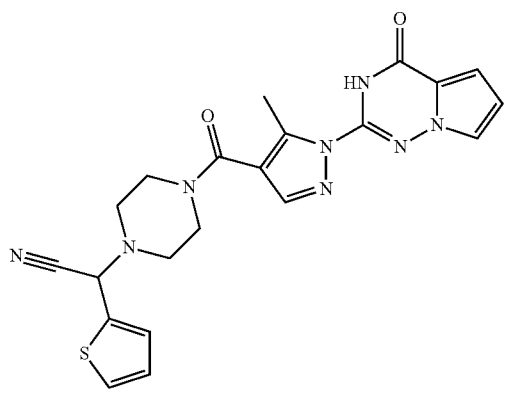 [SMILES: Cc1c(C(=O)N2CCN(C(C#N)c3cccs3)CC2)cnn1-c1nn2cccc2c(=O)[nH]1]
Q-964

TABLE C-continued
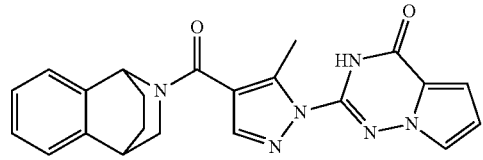 [SMILES: Cc1c(C(=O)N2CC3CCC2c2ccccc23)cnn1-c1nn2cccc2c(=O)[nH]1]
Q-965
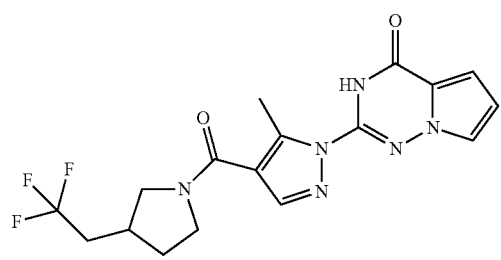 [SMILES: Cc1c(C(=O)N2CCC(CC(F)(F)F)C2)cnn1-c1nn2cccc2c(=O)[nH]1]
Q-966
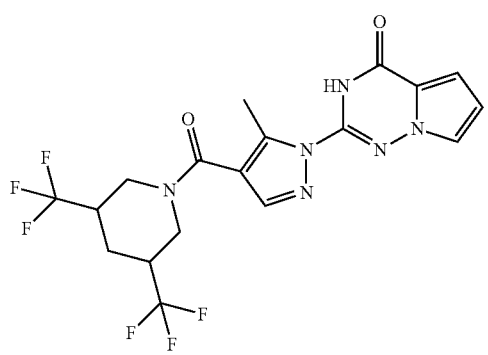 [SMILES: Cc1c(C(=O)N2CC(C(F)(F)F)CC(C(F)(F)F)C2)cnn1-c1nn2cccc2c(=O)[nH]1]
Q-967
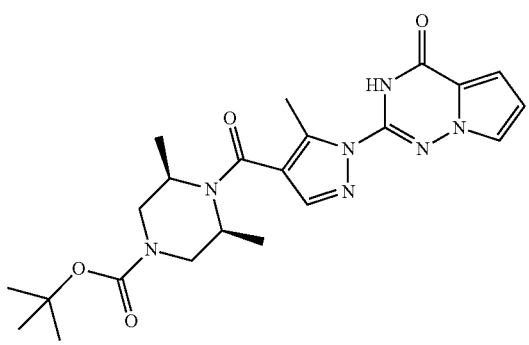 [SMILES: Cc1c(C(=O)N2[C@H](C)CN(C(=O)OC(C)(C)C)C[C@@H]2C)cnn1-c1nn2cccc2c(=O)[nH]1]
Q-968
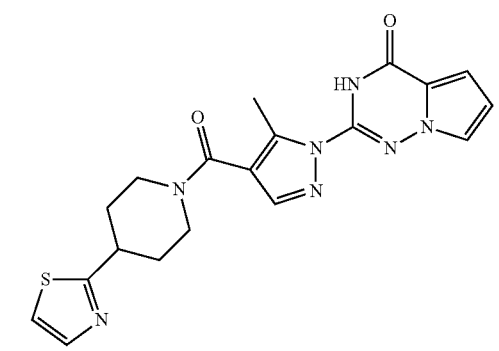 [SMILES: Cc1c(C(=O)N2CCC(c3nccs3)CC2)cnn1-c1nn2cccc2c(=O)[nH]1]
Q-969

TABLE C-continued
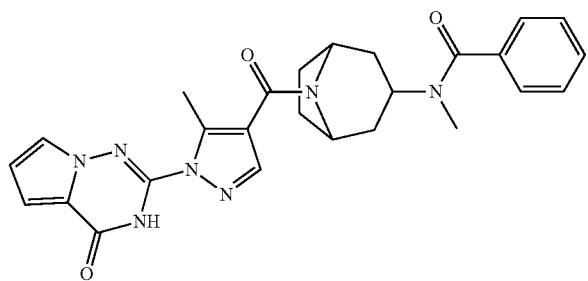 [SMILES: Cc1c(C(=O)N2C3CCC2CC(N(C)C(=O)c2ccccc2)C3)cnn1-c1nn2cccc2c(=O)[nH]1]
Q-970
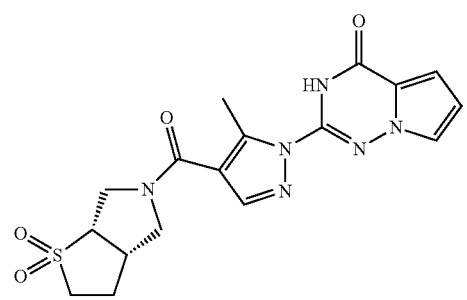 [SMILES: Cc1c(C(=O)N2C[C@@H]3CCS(=O)(=O)[C@@H]3C2)cnn1-c1nn2cccc2c(=O)[nH]1]
Q-971
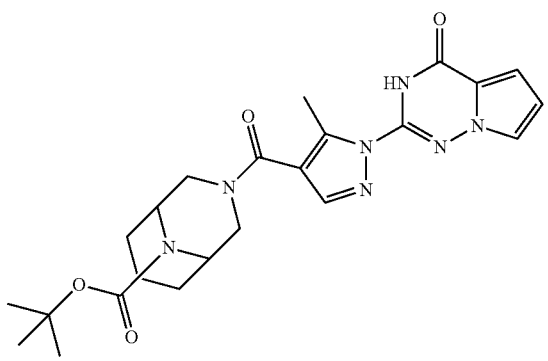 [SMILES: Cc1c(C(=O)N2CC3CCCC(C2)N3C(=O)OC(C)(C)C)cnn1-c1nn2cccc2c(=O)[nH]1]
Q-972
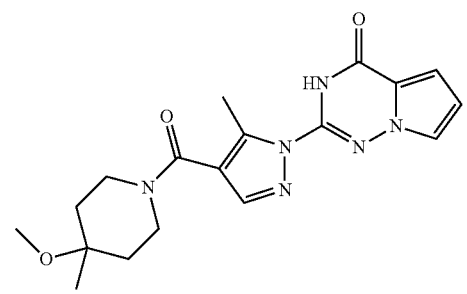 [SMILES: COC1(C)CCN(C(=O)c2cnn(-c3nn4cccc4c(=O)[nH]3)c2C)CC1]
Q-973
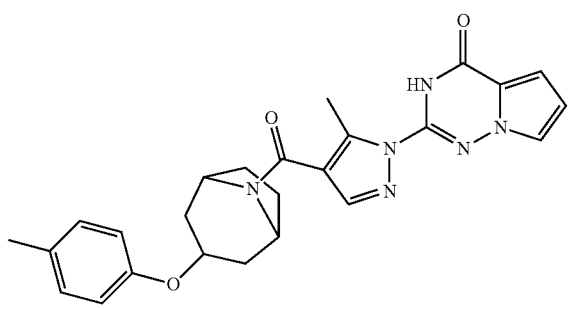 [SMILES: Cc1ccc(OC2CC3CCC(C2)N3C(=O)c2cnn(-c3nn4cccc4c(=O)[nH]3)c2C)cc1]
Q-974

TABLE C-continued
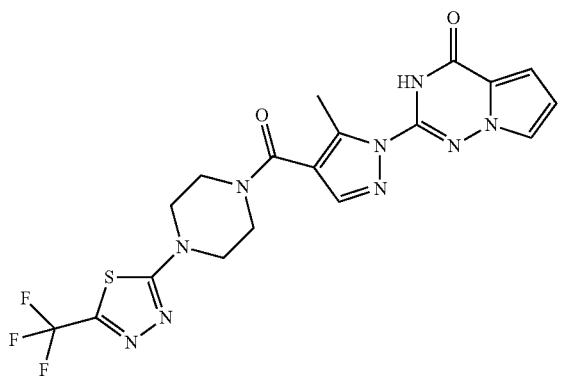 [SMILES: Cc1c(C(=O)N2CCN(c3nnc(C(F)(F)F)s3)CC2)cnn1-c1nn2cccc2c(=O)[nH]1]
Q-975
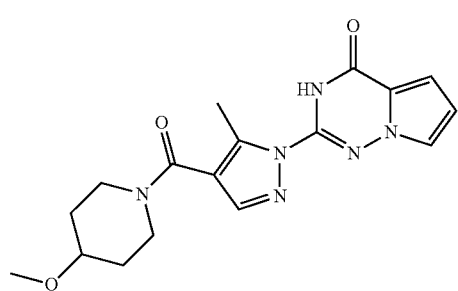 [SMILES: COC1CCN(C(=O)c2cnn(-c3nn4cccc4c(=O)[nH]3)c2C)CC1]
Q-976
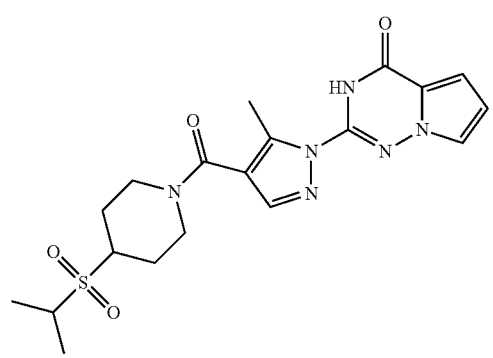 [SMILES: Cc1c(C(=O)N2CCC(S(=O)(=O)C(C)C)CC2)cnn1-c1nn2cccc2c(=O)[nH]1]
Q-977
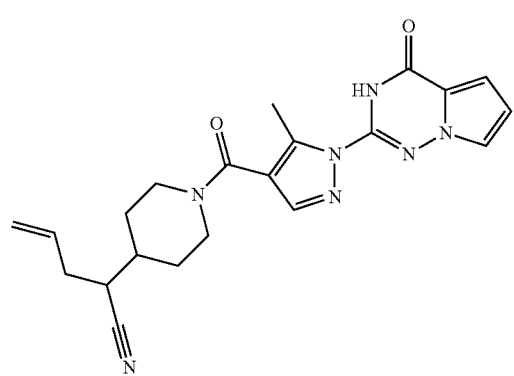 [SMILES: C=CCC(C#N)C1CCN(C(=O)c2cnn(-c3nn4cccc4c(=O)[nH]3)c2C)CC1]
Q-978

TABLE C-continued
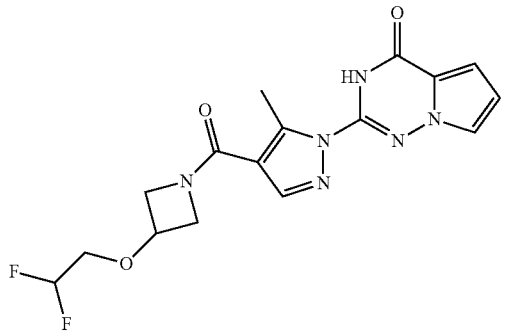 [SMILES: Cc1c(C(=O)N2CC(OCC(F)F)C2)cnn1-c1nn2cccc2c(=O)[nH]1]
Q-979
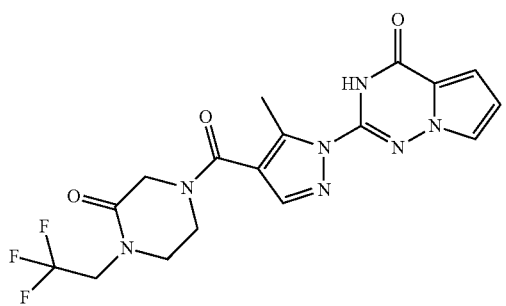 [SMILES: Cc1c(C(=O)N2CCN(CC(F)(F)F)C(=O)C2)cnn1-c1nn2cccc2c(=O)[nH]1]
Q-980
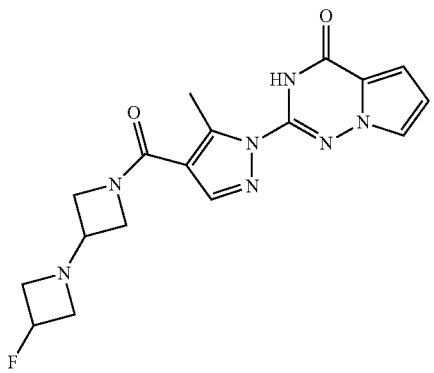 [SMILES: Cc1c(C(=O)N2CC(N3CC(F)C3)C2)cnn1-c1nn2cccc2c(=O)[nH]1]
Q-981
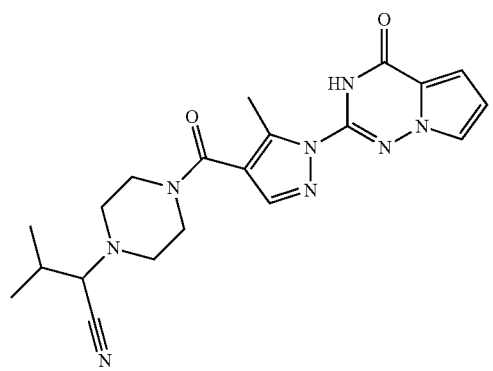 [SMILES: Cc1c(C(=O)N2CCN(C(C#N)C(C)C)CC2)cnn1-c1nn2cccc2c(=O)[nH]1]
Q-982

TABLE C-continued
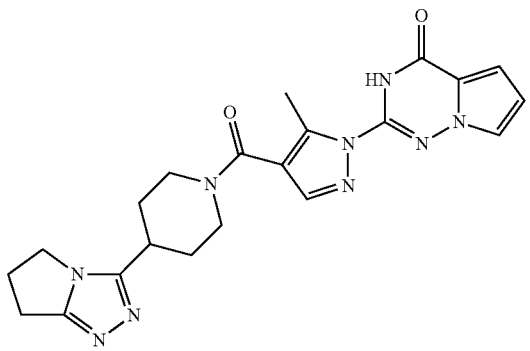 [SMILES: Cc1c(C(=O)N2CCC(c3nnc4n3CCC4)CC2)cnn1-c1nn2cccc2c(=O)[nH]1]
Q-983
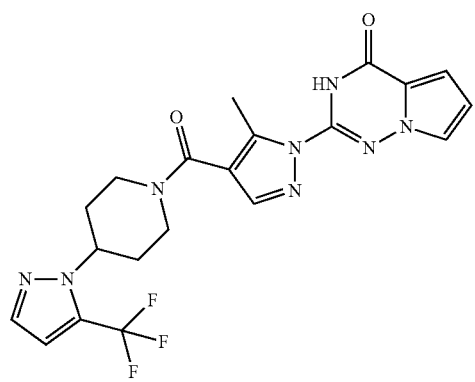 [SMILES: Cc1c(C(=O)N2CCC(n3nccc3C(F)(F)F)CC2)cnn1-c1nn2cccc2c(=O)[nH]1]
Q-984
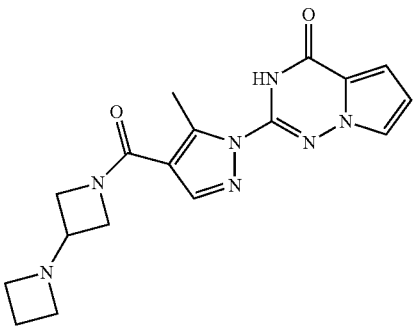 [SMILES: Cc1c(C(=O)N2CC(N3CCC3)C2)cnn1-c1nn2cccc2c(=O)[nH]1]
Q-985
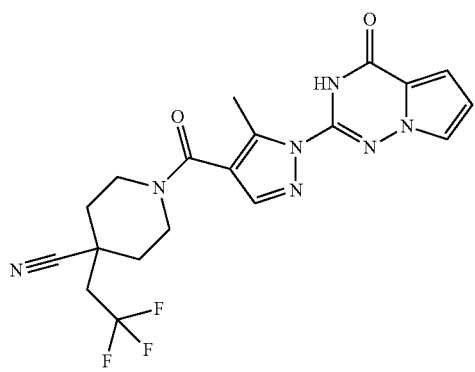 [SMILES: Cc1c(C(=O)N2CCC(C#N)(CC(F)(F)F)CC2)cnn1-c1nn2cccc2c(=O)[nH]1]
Q-986

TABLE C-continued
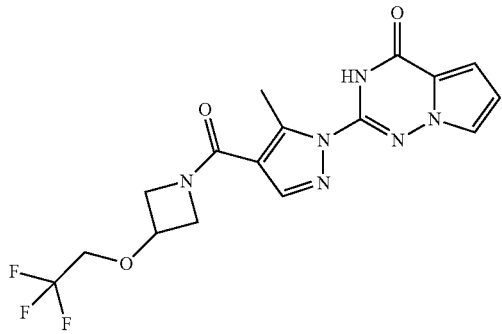 [SMILES: Cc1c(C(=O)N2CC(OCC(F)(F)F)C2)cnn1-c1nn2cccc2c(=O)[nH]1]
Q-987
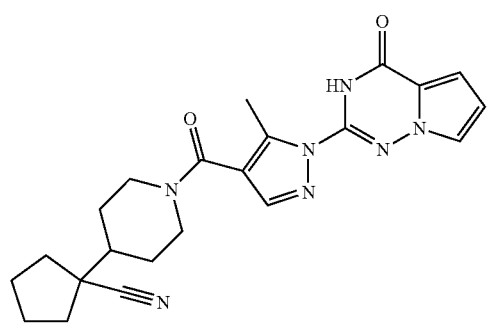 [SMILES: Cc1c(C(=O)N2CCC(C3(C#N)CCCC3)CC2)cnn1-c1nn2cccc2c(=O)[nH]1]
Q-988
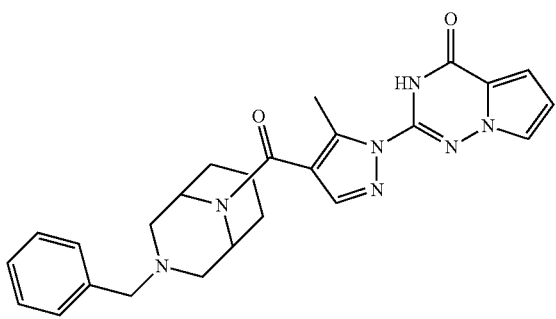 [SMILES: Cc1c(C(=O)N2C3CCCC2CN(Cc2ccccc2)C3)cnn1-c1nn2cccc2c(=O)[nH]1]
Q-989
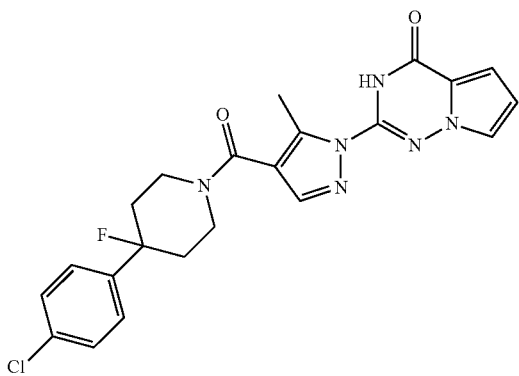 [SMILES: Cc1c(C(=O)N2CCC(F)(c3ccc(Cl)cc3)CC2)cnn1-c1nn2cccc2c(=O)[nH]1]
Q-990

TABLE C-continued
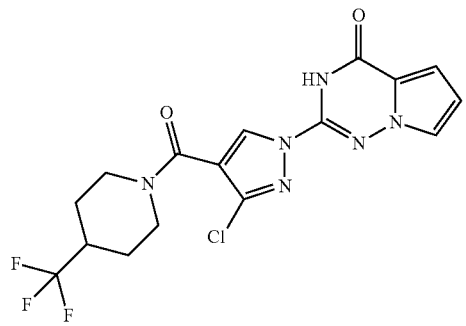 [SMILES: O=C(c1cn(-c2nn3cccc3c(=O)[nH]2)nc1Cl)N1CCC(C(F)(F)F)CC1] Q-991
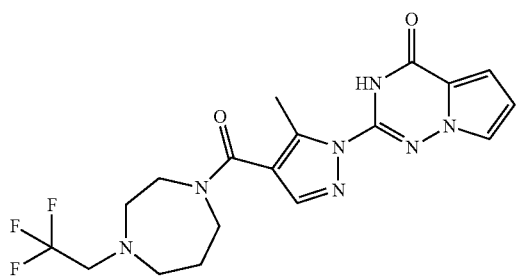 [SMILES: Cc1c(C(=O)N2CCCN(CC(F)(F)F)CC2)cnn1-c1nn2cccc2c(=O)[nH]1] Q-992
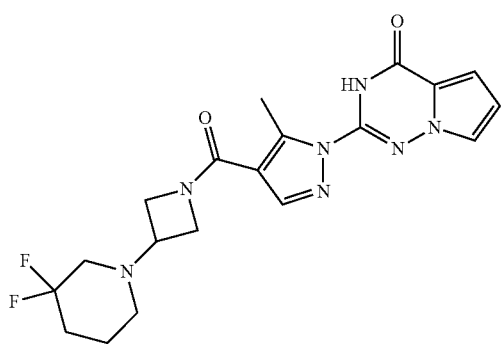 [SMILES: Cc1c(C(=O)N2CC(N3CCCC(F)(F)C3)C2)cnn1-c1nn2cccc2c(=O)[nH]1] Q-993
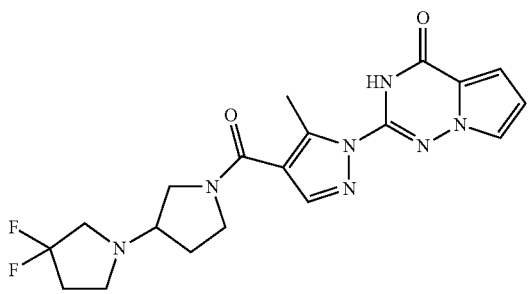 [SMILES: Cc1c(C(=O)N2CCC(N3CCC(F)(F)C3)C2)cnn1-c1nn2cccc2c(=O)[nH]1] Q-994
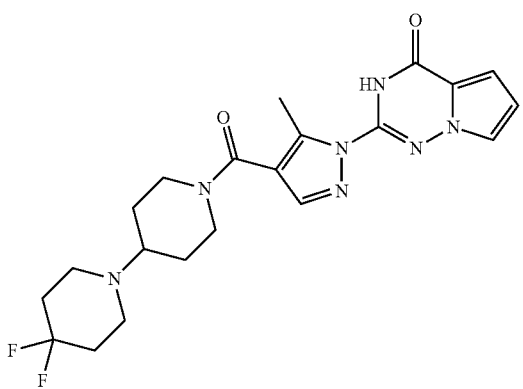 [SMILES: Cc1c(C(=O)N2CCC(N3CCC(F)(F)CC3)CC2)cnn1-c1nn2cccc2c(=O)[nH]1] Q-995

TABLE C-continued
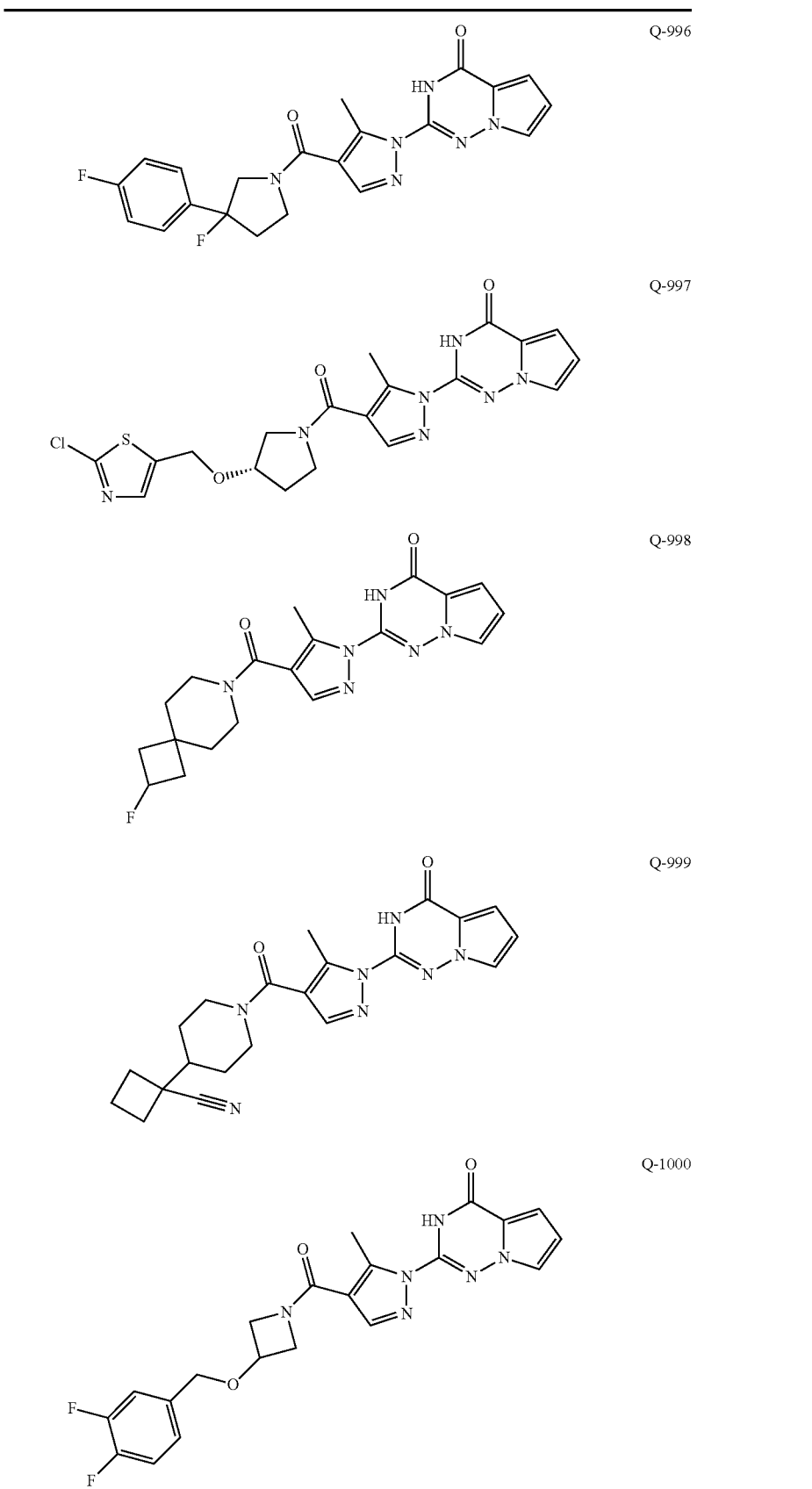

TABLE C-continued
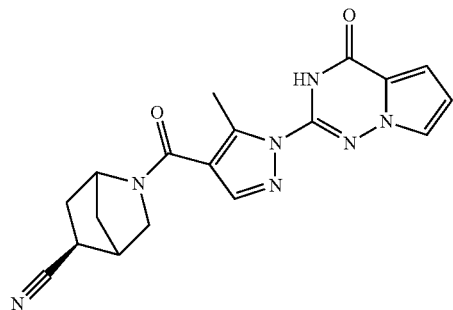 [SMILES: Cc1c(C(=O)N2CC3CC2C[C@@H]3C#N)cnn1-c1nn2cccc2c(=O)[nH]1]
Q-1001
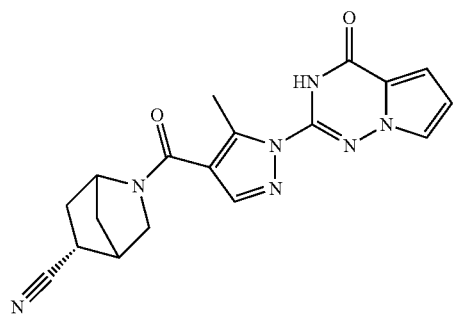 [SMILES: Cc1c(C(=O)N2CC3CC2C[C@H]3C#N)cnn1-c1nn2cccc2c(=O)[nH]1]
Q-1002
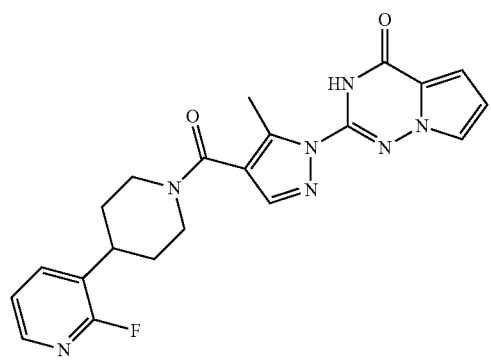 [SMILES: Cc1c(C(=O)N2CCC(c3cccnc3F)CC2)cnn1-c1nn2cccc2c(=O)[nH]1]
Q-1003
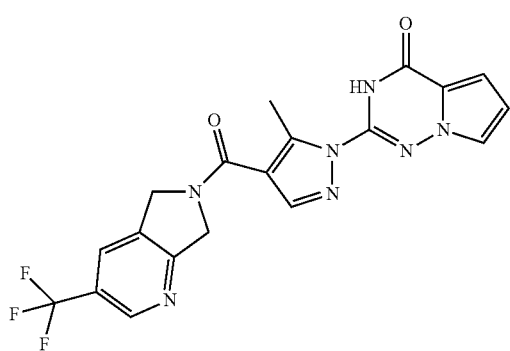 [SMILES: Cc1c(C(=O)N2Cc3cc(C(F)(F)F)cnc3C2)cnn1-c1nn2cccc2c(=O)[nH]1]
Q-1004
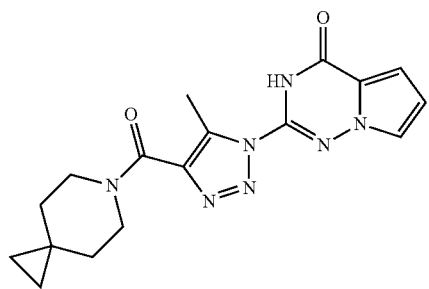 [SMILES: Cc1c(C(=O)N2CCC3(CC2)CC3)nnn1-c1nn2cccc2c(=O)[nH]1]
Q-1005

TABLE C-continued
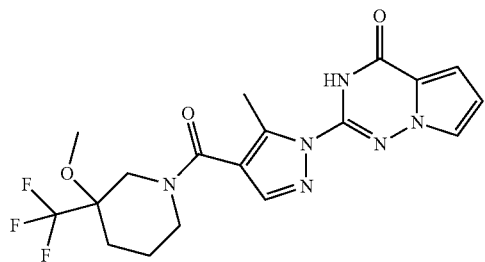 [SMILES: COC1(C(F)(F)F)CCCN(C(=O)c2cnn(-c3nn4cccc4c(=O)[nH]3)c2C)C1]
Q-1006
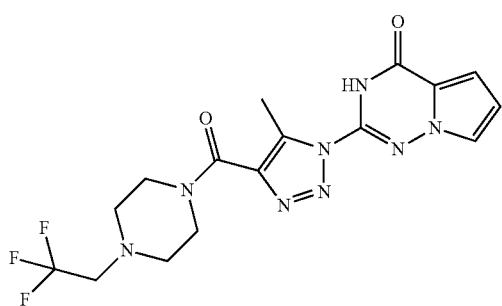 [SMILES: Cc1c(C(=O)N2CCN(CC(F)(F)F)CC2)nnn1-c1nn2cccc2c(=O)[nH]1]
Q-1007
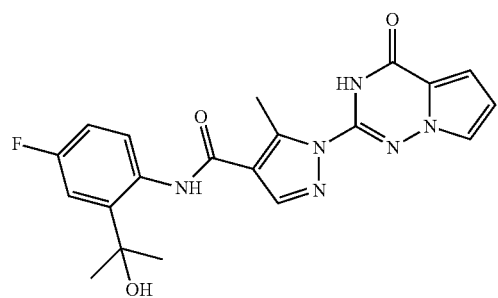 [SMILES: Cc1c(C(=O)Nc2ccc(F)cc2C(C)(C)O)cnn1-c1nn2cccc2c(=O)[nH]1]
Q-1008
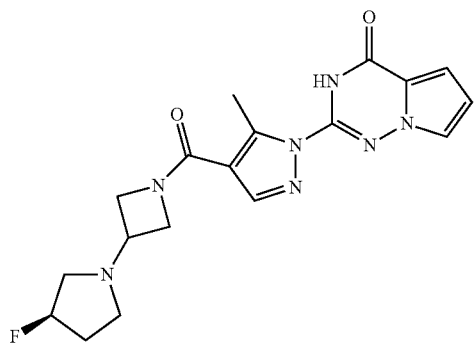 [SMILES: Cc1c(C(=O)N2CC(N3CC[C@@H](F)C3)C2)cnn1-c1nn2cccc2c(=O)[nH]1]
Q-1009
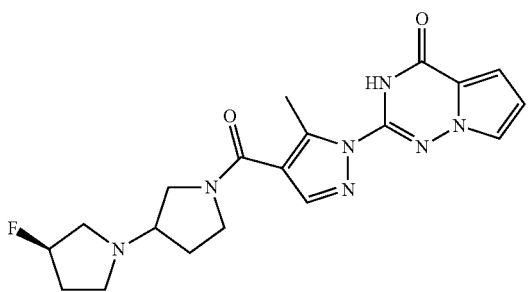 [SMILES: Cc1c(C(=O)N2CCC(N3CC[C@@H](F)C3)C2)cnn1-c1nn2cccc2c(=O)[nH]1]
Q-1010

TABLE C-continued
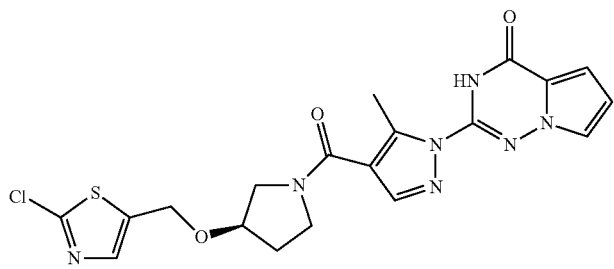 [SMILES: Cc1c(C(=O)N2CC[C@@H](OCc3cnc(Cl)s3)C2)cnn1-c1nn2cccc2c(=O)[nH]1]
Q-1011
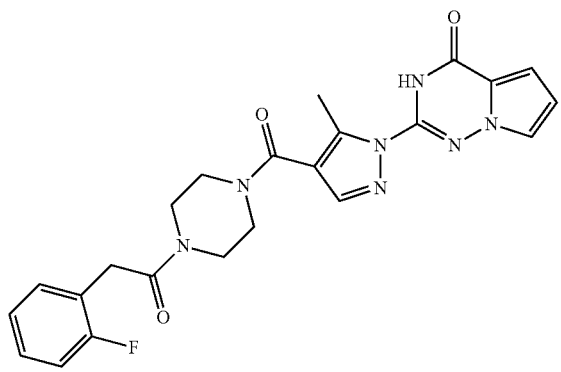 [SMILES: Cc1c(C(=O)N2CCN(C(=O)Cc3ccccc3F)CC2)cnn1-c1nn2cccc2c(=O)[nH]1]
Q-1012
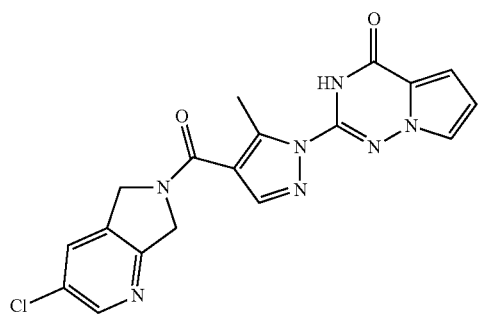 [SMILES: Cc1c(C(=O)N2Cc3cc(Cl)cnc3C2)cnn1-c1nn2cccc2c(=O)[nH]1]
Q-1013
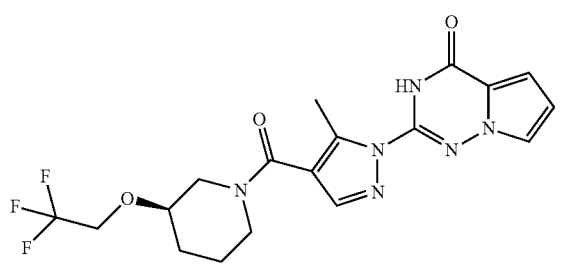 [SMILES: Cc1c(C(=O)N2CCC[C@@H](OCC(F)(F)F)C2)cnn1-c1nn2cccc2c(=O)[nH]1]
Q-1014
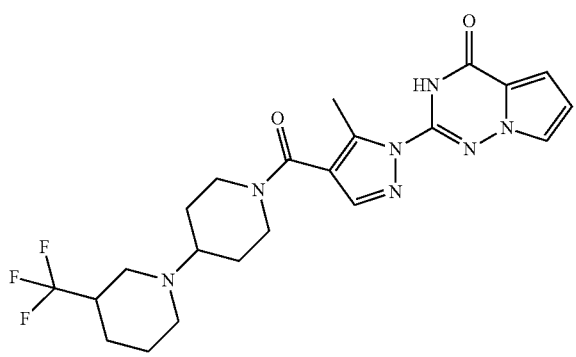 [SMILES: Cc1c(C(=O)N2CCC(N3CCCC(C(F)(F)F)C3)CC2)cnn1-c1nn2cccc2c(=O)[nH]1]
Q-1015

TABLE C-continued
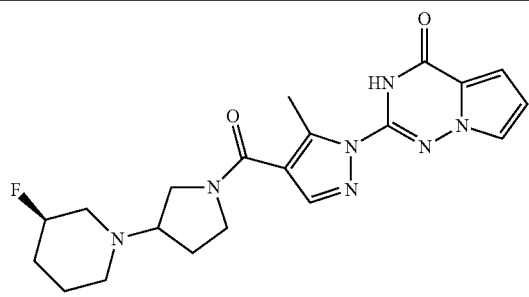
Q-1016
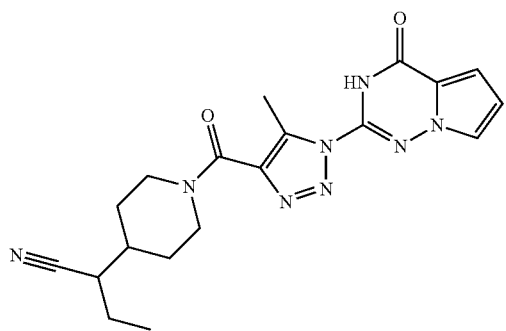 [SMILES: CCC(C#N)C1CCN(C(=O)c2nnn(-c3nn4cccc4c(=O)[nH]3)c2C)CC1]
Q-1017
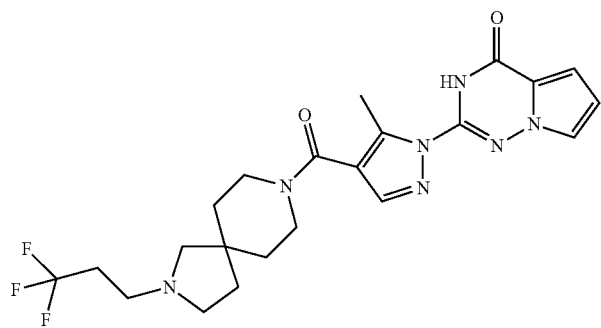 [SMILES: Cc1c(C(=O)N2CCC3(CCN(CCC(F)(F)F)C3)CC2)cnn1-c1nn2cccc2c(=O)[nH]1]
Q-1018
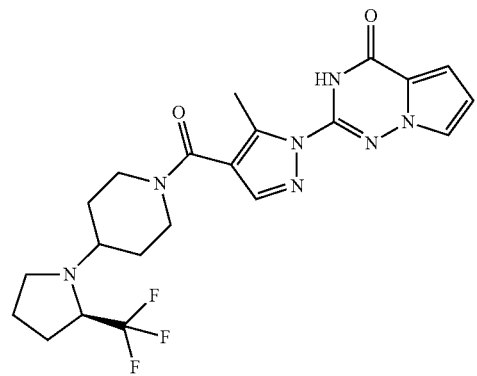 [SMILES: Cc1c(C(=O)N2CCC(N3CCC[C@@H]3C(F)(F)F)CC2)cnn1-c1nn2cccc2c(=O)[nH]1]
Q-1019
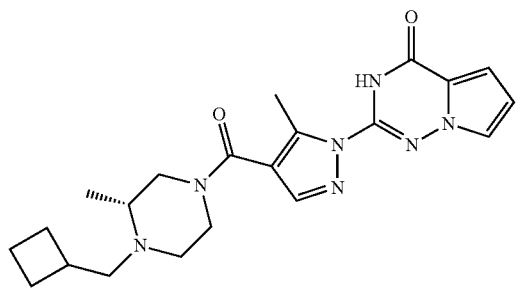 [SMILES: Cc1c(C(=O)N2CCN(CC3CCC3)[C@H](C)C2)cnn1-c1nn2cccc2c(=O)[nH]1]
Q-1020

TABLE C-continued
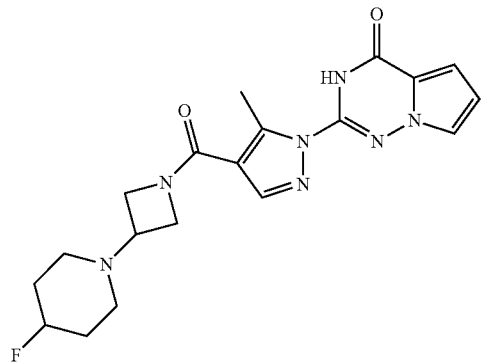 [SMILES: Cc1c(C(=O)N2CC(N3CCC(F)CC3)C2)cnn1-c1nn2cccc2c(=O)[nH]1] Q-1021
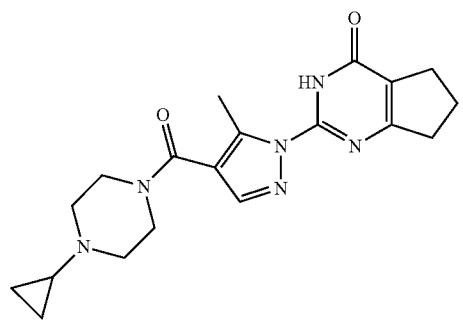 [SMILES: Cc1c(C(=O)N2CCN(C3CC3)CC2)cnn1-c1nc2c(c(=O)[nH]1)CCC2] Q-1022
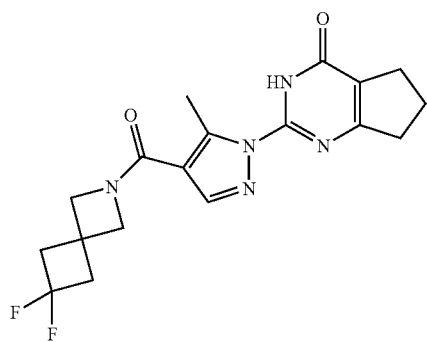 [SMILES: Cc1c(C(=O)N2CC3(C2)CC(F)(F)C3)cnn1-c1nc2c(c(=O)[nH]1)CCC2] Q-1023
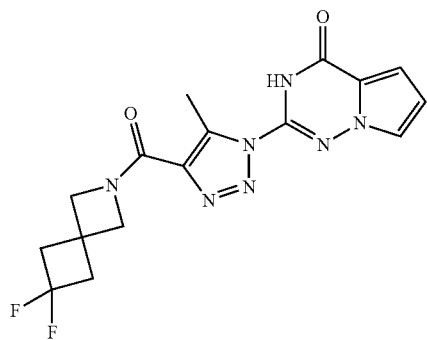 [SMILES: Cc1c(C(=O)N2CC3(C2)CC(F)(F)C3)nnn1-c1nn2cccc2c(=O)[nH]1] Q-1024

TABLE C-continued
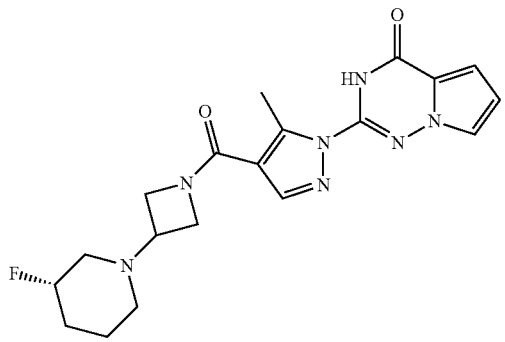 [SMILES: Cc1c(C(=O)N2CC(N3CCC[C@H](F)C3)C2)cnn1-c1nn2cccc2c(=O)[nH]1] Q-1025
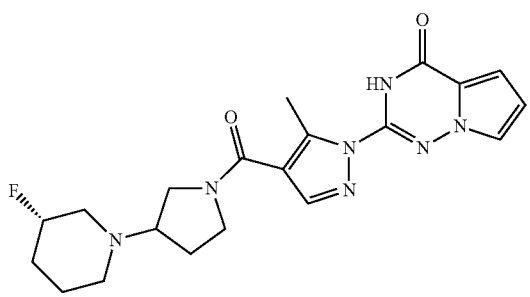 [SMILES: Cc1c(C(=O)N2CCC(N3CCC[C@H](F)C3)C2)cnn1-c1nn2cccc2c(=O)[nH]1] Q-1026
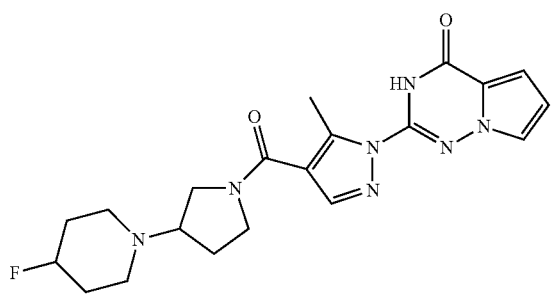 [SMILES: Cc1c(C(=O)N2CCC(N3CCC(F)CC3)C2)cnn1-c1nn2cccc2c(=O)[nH]1] Q-1027
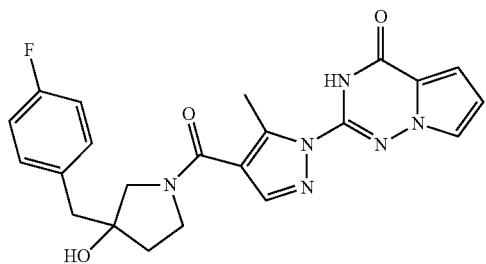 [SMILES: Cc1c(C(=O)N2CCC(O)(Cc3ccc(F)cc3)C2)cnn1-c1nn2cccc2c(=O)[nH]1] Q-1028
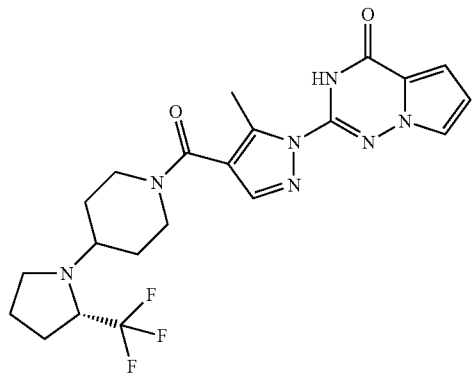 [SMILES: Cc1c(C(=O)N2CCC(N3CCC[C@H]3C(F)(F)F)CC2)cnn1-c1nn2cccc2c(=O)[nH]1] Q-1029

TABLE C-continued
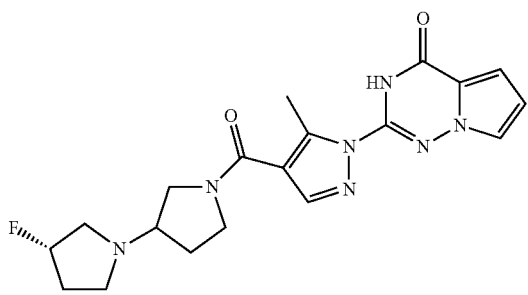 [SMILES: Cc1c(C(=O)N2CCC(N3CC[C@H](F)C3)C2)cnn1-c1nn2cccc2c(=O)[nH]1]
Q-1030
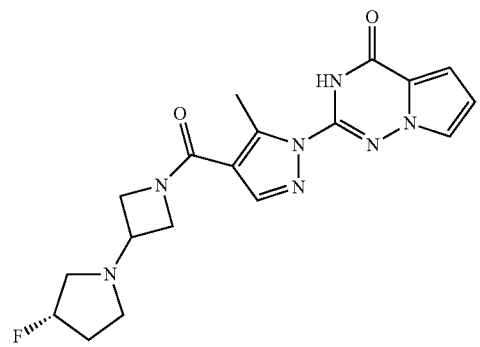 [SMILES: Cc1c(C(=O)N2CC(N3CC[C@H](F)C3)C2)cnn1-c1nn2cccc2c(=O)[nH]1]
Q-1031
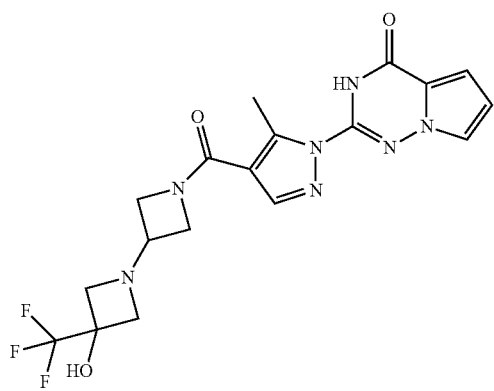 [SMILES: Cc1c(C(=O)N2CC(N3CC(O)(C(F)(F)F)C3)C2)cnn1-c1nn2cccc2c(=O)[nH]1]
Q-1032
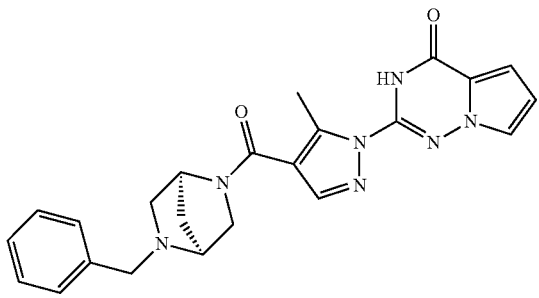 [SMILES: Cc1c(C(=O)N2C[C@@H]3C[C@H]2CN3Cc2ccccc2)cnn1-c1nn2cccc2c(=O)[nH]1]
Q-1033
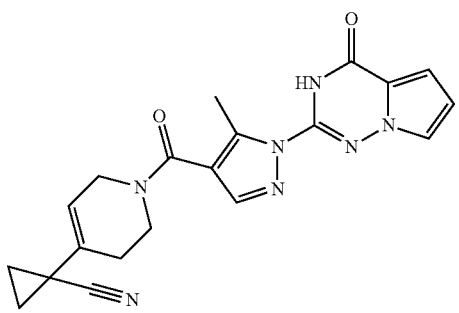 [SMILES: Cc1c(C(=O)N2CC=C(C3(C#N)CC3)CC2)cnn1-c1nn2cccc2c(=O)[nH]1]
Q-1034

TABLE C-continued
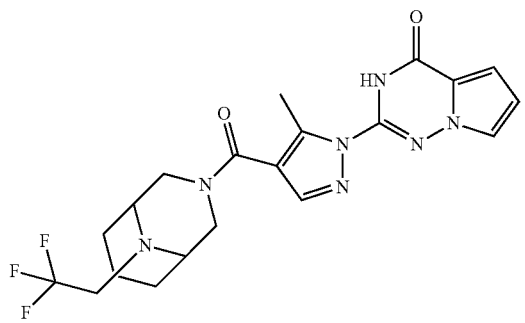 [SMILES: Cc1c(C(=O)N2CC3CCCC(C2)N3CC(F)(F)F)cnn1-c1nn2cccc2c(=O)[nH]1] Q-1035
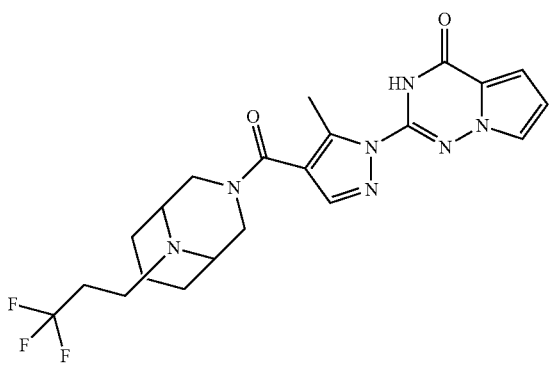 [SMILES: Cc1c(C(=O)N2CC3CCCC(C2)N3CCC(F)(F)F)cnn1-c1nn2cccc2c(=O)[nH]1] Q-1036
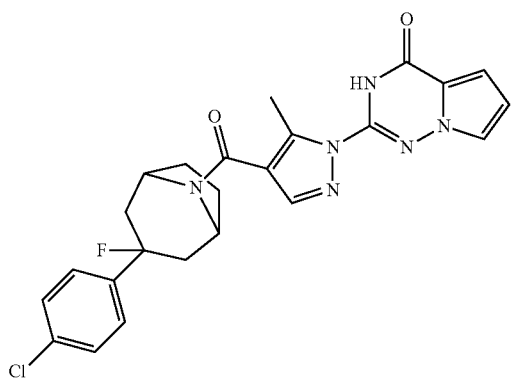 [SMILES: Cc1c(C(=O)N2C3CCC2CC(F)(c2ccc(Cl)cc2)C3)cnn1-c1nn2cccc2c(=O)[nH]1] Q-1037
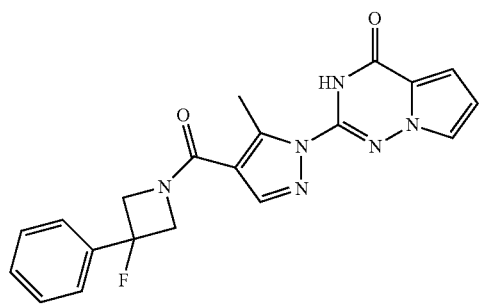 [SMILES: Cc1c(C(=O)N2CC(F)(c3ccccc3)C2)cnn1-c1nn2cccc2c(=O)[nH]1] Q-1038

TABLE C-continued
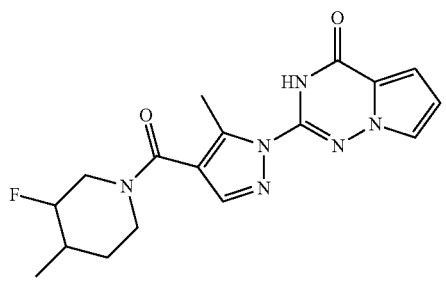 [SMILES: Cc1c(C(=O)N2CCC(C)C(F)C2)cnn1-c1nn2cccc2c(=O)[nH]1]
Q-1039
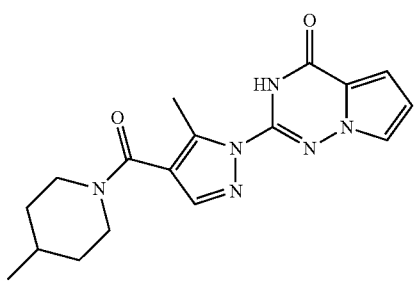
Q-1040
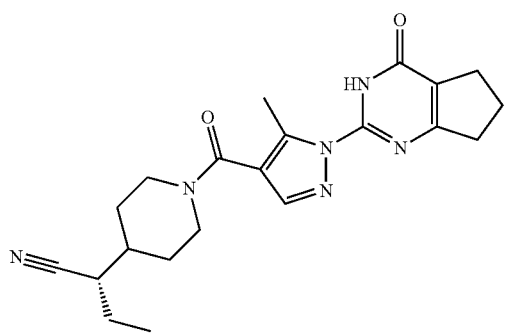 [SMILES: CC[C@H](C#N)C1CCN(C(=O)c2cnn(-c3nc4c(c(=O)[nH]3)CCC4)c2C)CC1]
Q-1041
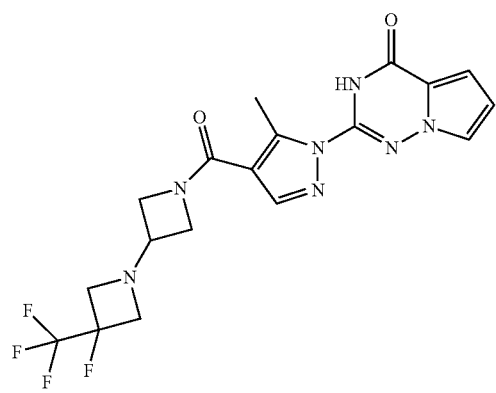 [SMILES: Cc1c(C(=O)N2CC(N3CC(F)(C(F)(F)F)C3)C2)cnn1-c1nn2cccc2c(=O)[nH]1]
Q-1042
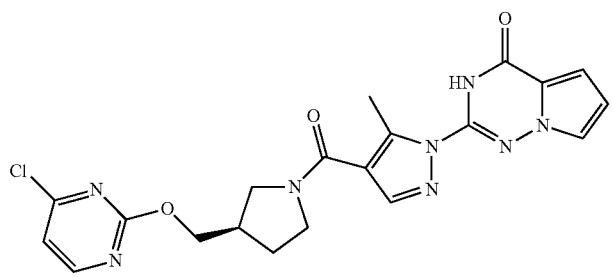 [SMILES: Cc1c(C(=O)N2CC[C@@H](COc3nccc(Cl)n3)C2)cnn1-c1nn2cccc2c(=O)[nH]1]
Q-1043

TABLE C-continued
Q-1044
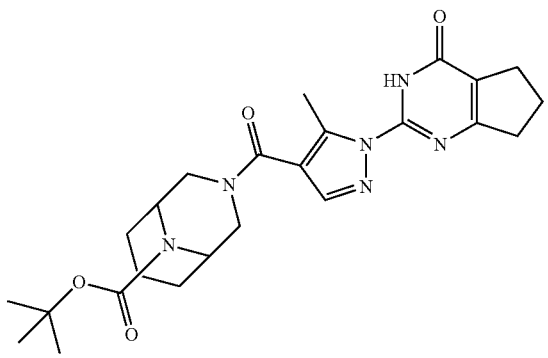 [SMILES: Cc1c(C(=O)N2CC3CCCC(C2)N3C(=O)OC(C)(C)C)cnn1-c1nc2c(c(=O)[nH]1)CCC2]
Q-1045
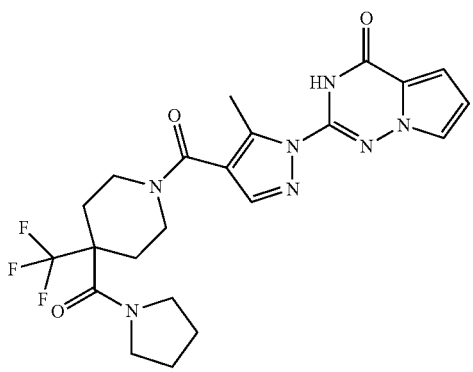 [SMILES: Cc1c(C(=O)N2CCC(C(=O)N3CCCC3)(C(F)(F)F)CC2)cnn1-c1nn2cccc2c(=O)[nH]1]
Q-1046
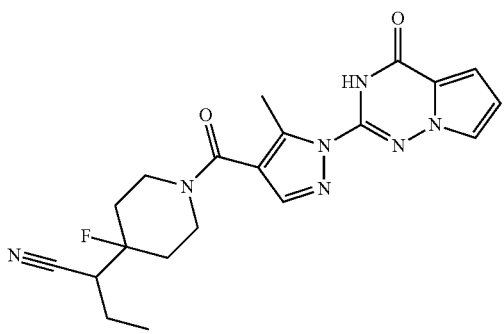 [SMILES: CCC(C#N)C1(F)CCN(C(=O)c2cnn(-c3nn4cccc4c(=O)[nH]3)c2C)CC1]
Q-1047
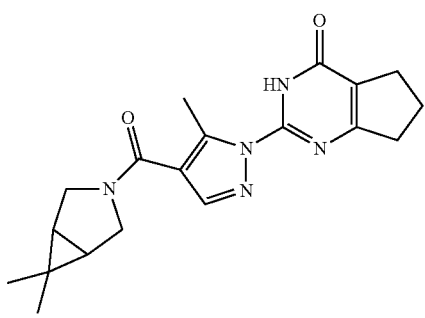 [SMILES: Cc1c(C(=O)N2CC3C(C2)C3(C)C)cnn1-c1nc2c(c(=O)[nH]1)CCC2]
Q-1048

TABLE C-continued
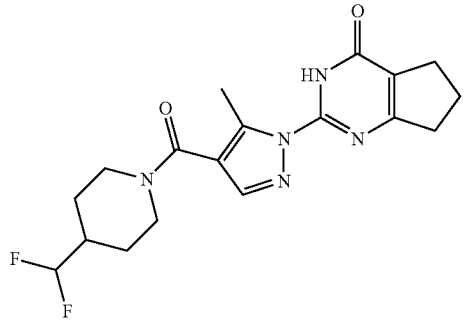 [SMILES: Cc1c(C(=O)N2CCC(C(F)F)CC2)cnn1-c1nc2c(c(=O)[nH]1)CCC2]
Q-1049
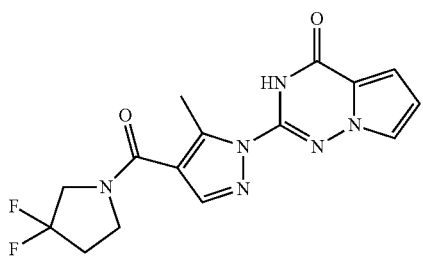 [SMILES: Cc1c(C(=O)N2CCC(F)(F)C2)cnn1-c1nn2cccc2c(=O)[nH]1]
Q-1050
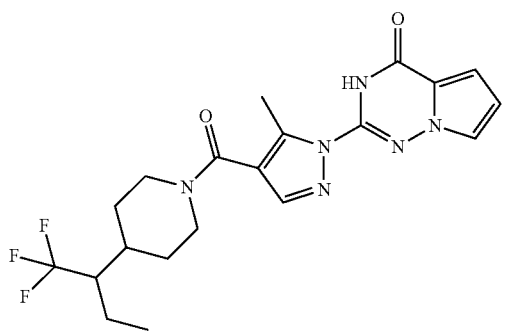 [SMILES: CCC(C1CCN(C(=O)c2cnn(-c3nn4cccc4c(=O)[nH]3)c2C)CC1)C(F)(F)F]
Q-1051
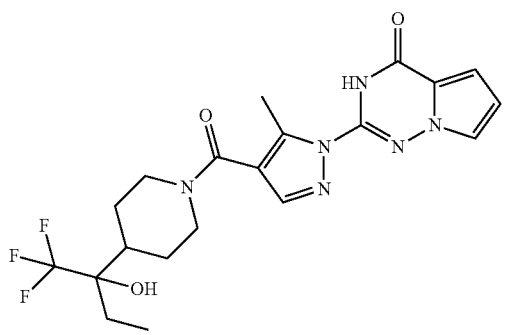 [SMILES: CCC(O)(C1CCN(C(=O)c2cnn(-c3nn4cccc4c(=O)[nH]3)c2C)CC1)C(F)(F)F]
Q-1052
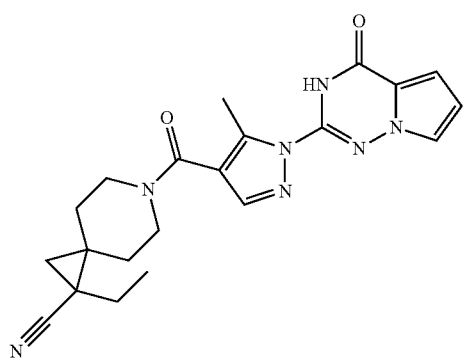 [SMILES: CCC1(C#N)CC12CCN(C(=O)c1cnn(-c3nn4cccc4c(=O)[nH]3)c1C)CC2]
Q-1053

TABLE C-continued
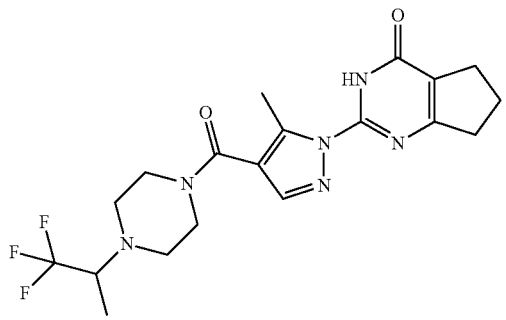 [SMILES: Cc1c(C(=O)N2CCN(C(C)C(F)(F)F)CC2)cnn1-c1nc2c(c(=O)[nH]1)CCC2]
Q-1054
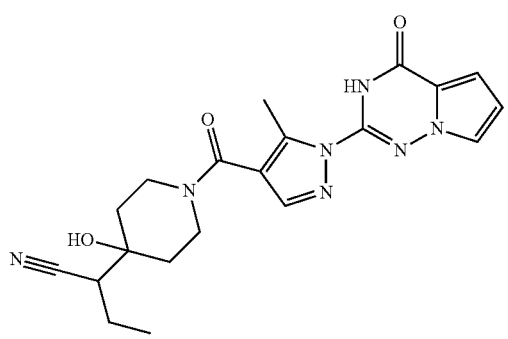 [SMILES: CCC(C#N)C1(O)CCN(C(=O)c2cnn(-c3nn4cccc4c(=O)[nH]3)c2C)CC1]
Q-1055
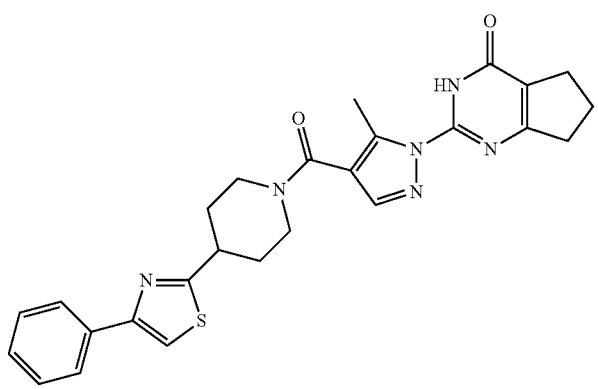 [SMILES: Cc1c(C(=O)N2CCC(c3nc(-c4ccccc4)cs3)CC2)cnn1-c1nc2c(c(=O)[nH]1)CCC2]
Q-1056
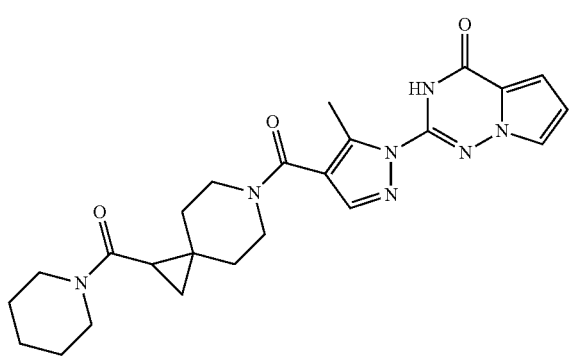 [SMILES: Cc1c(C(=O)N2CCC3(CC2)CC3C(=O)N2CCCCC2)cnn1-c1nn2cccc2c(=O)[nH]1]
Q-1057

TABLE C-continued
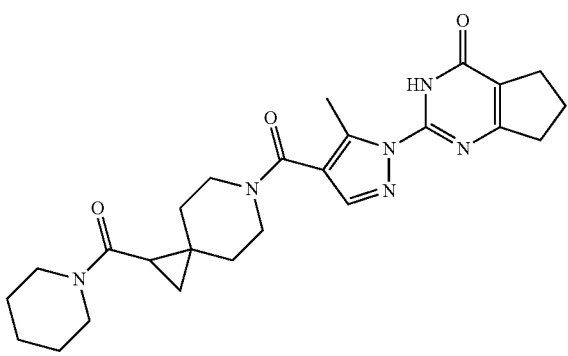 [SMILES: Cc1c(C(=O)N2CCC3(CC2)CC3C(=O)N2CCCCC2)cnn1-c1nc2c(c(=O)[nH]1)CCC2]
Q-1058
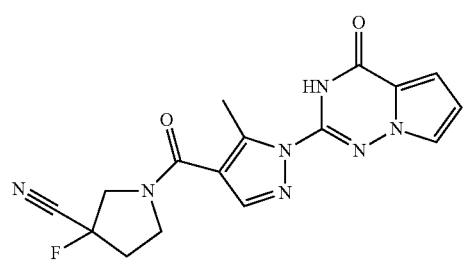 [SMILES: Cc1c(C(=O)N2CCC(F)(C#N)C2)cnn1-c1nn2cccc2c(=O)[nH]1]
Q-1059
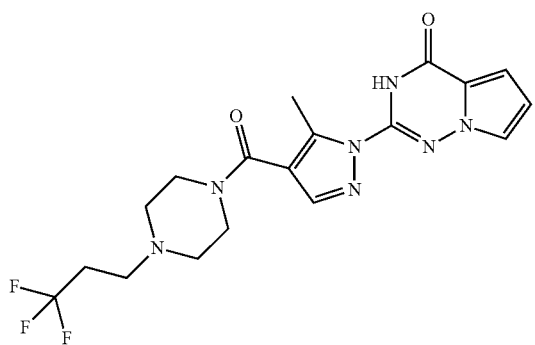 [SMILES: Cc1c(C(=O)N2CCN(CCC(F)(F)F)CC2)cnn1-c1nn2cccc2c(=O)[nH]1]
Q-1060
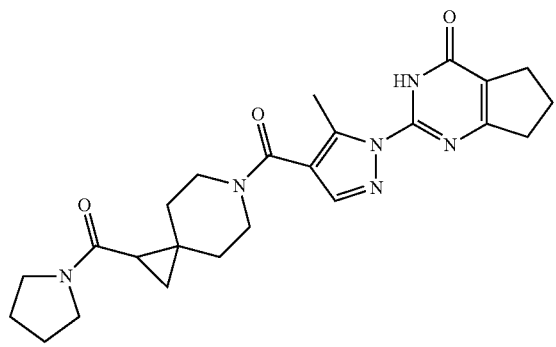 [SMILES: Cc1c(C(=O)N2CCC3(CC2)CC3C(=O)N2CCCC2)cnn1-c1nc2c(c(=O)[nH]1)CCC2]
Q-1061

TABLE C-continued
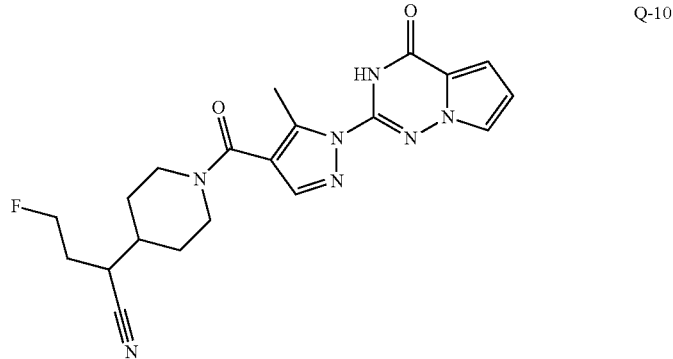
Q-1062
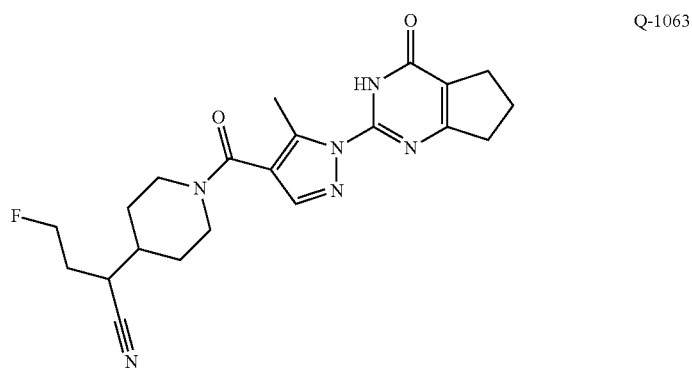
Q-1063
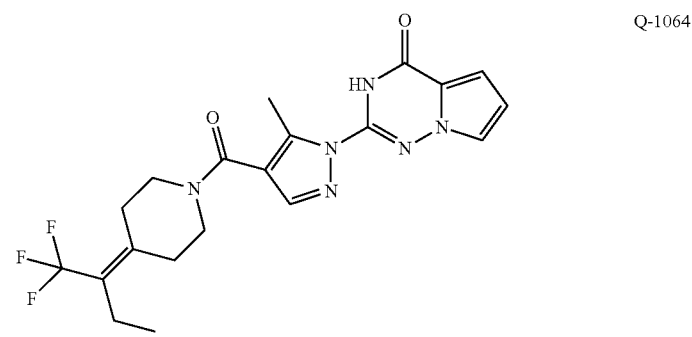
Q-1064
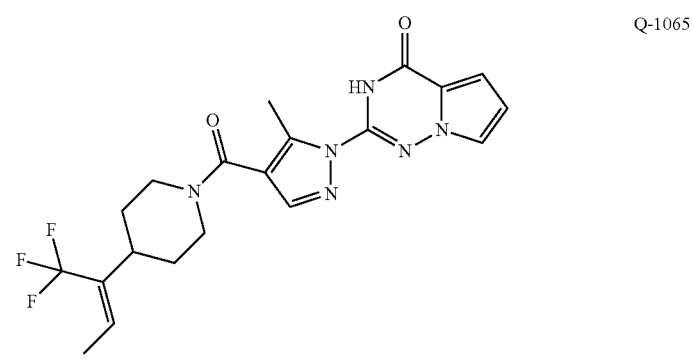
Q-1065

TABLE C-continued
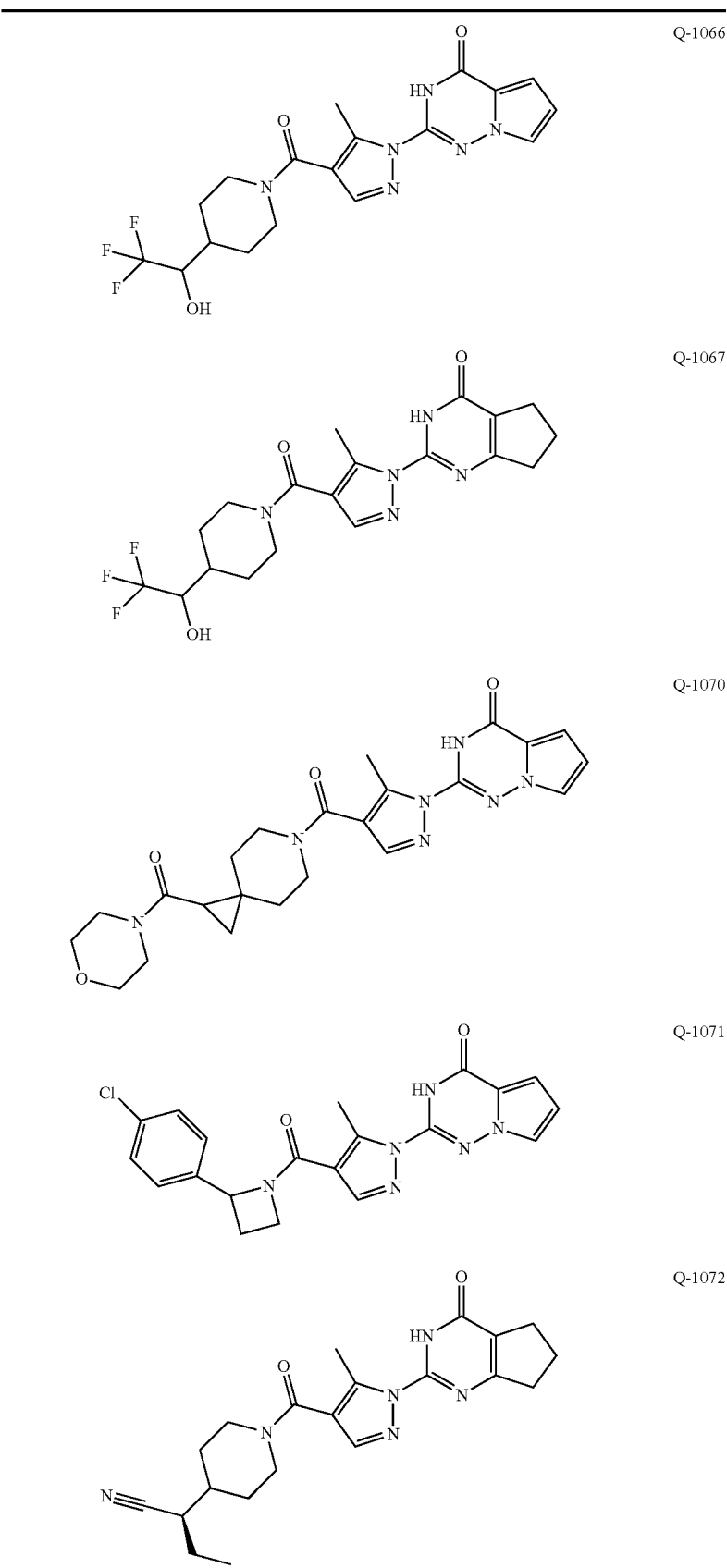
Q-1066
Q-1067
Q-1070
Q-1071
Q-1072

TABLE C-continued
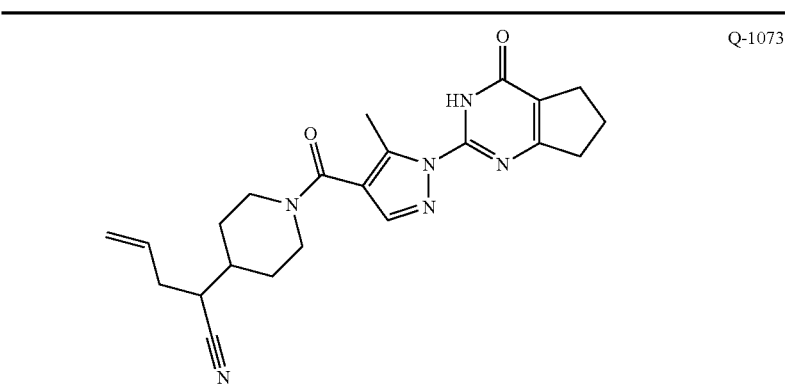
Q-1073
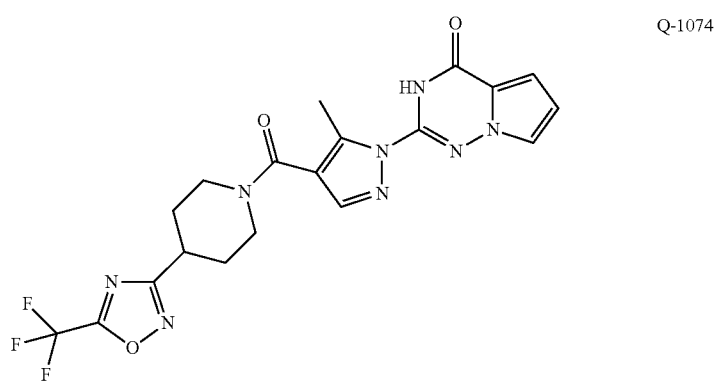
Q-1074
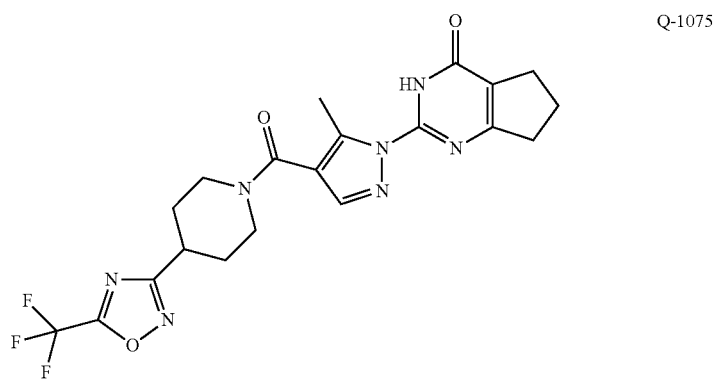
Q-1075
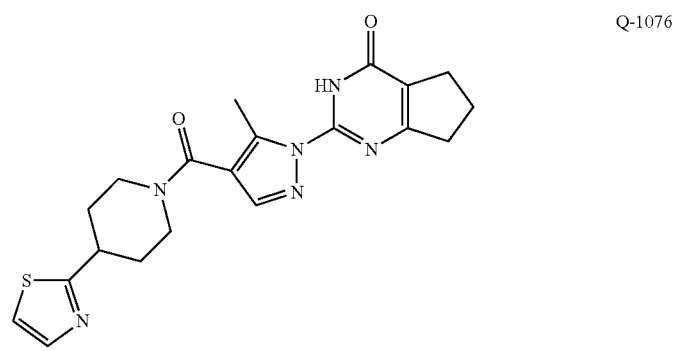
Q-1076

TABLE C-continued
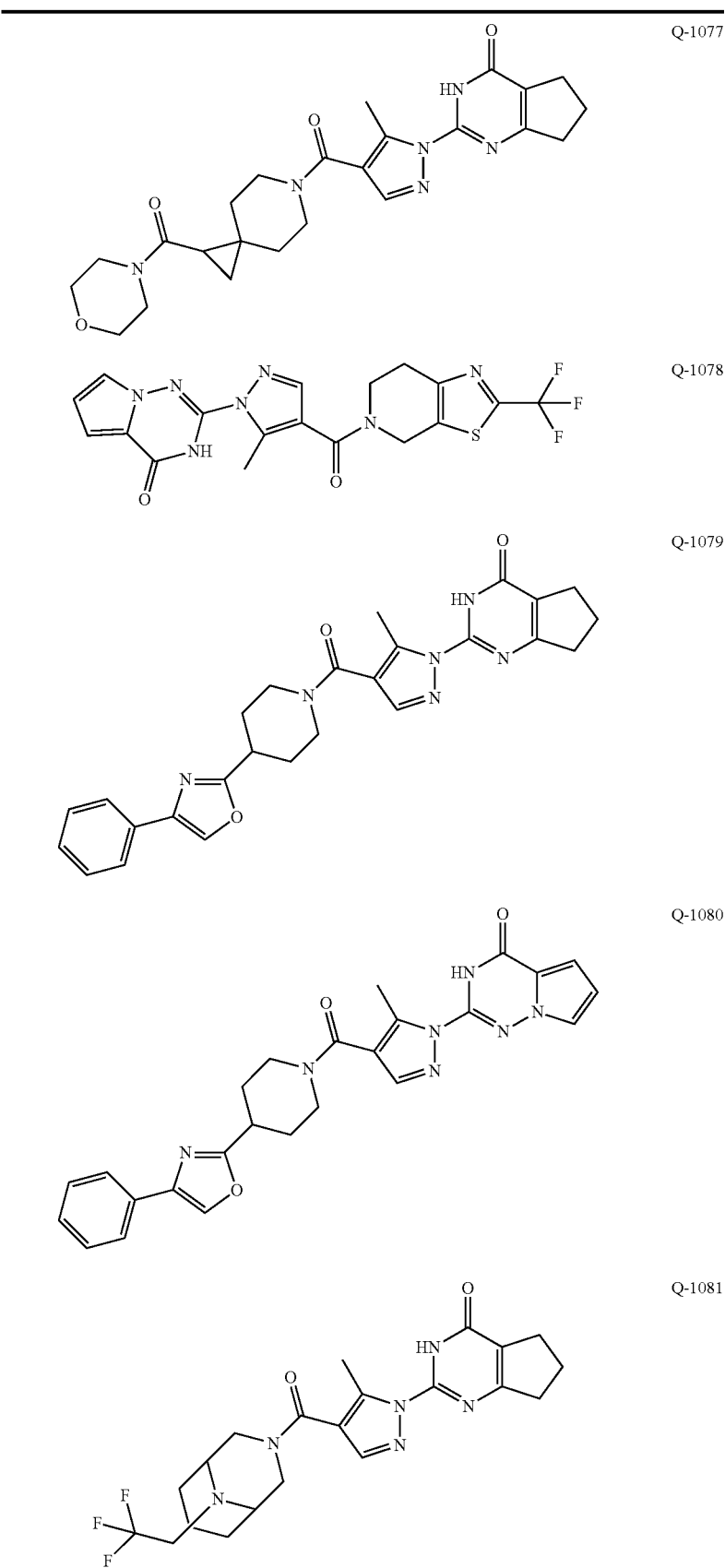
Q-1077
Q-1078
Q-1079
Q-1080
Q-1081

TABLE C-continued
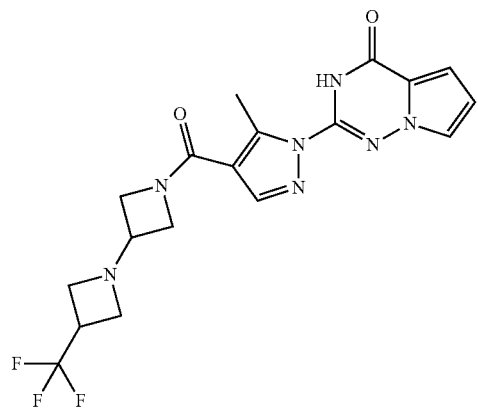 [SMILES: Cc1c(C(=O)N2CC(N3CC(C(F)(F)F)C3)C2)cnn1-c1nn2cccc2c(=O)[nH]1]
Q-1082
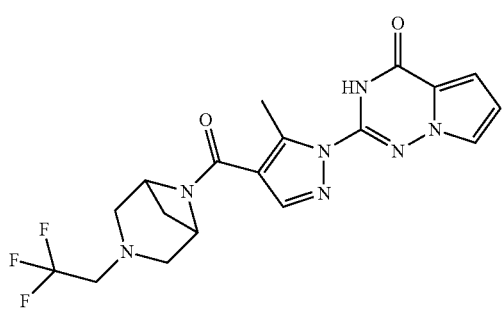 [SMILES: Cc1c(C(=O)N2C3CC2CN(CC(F)(F)F)C3)cnn1-c1nn2cccc2c(=O)[nH]1]
Q-1083
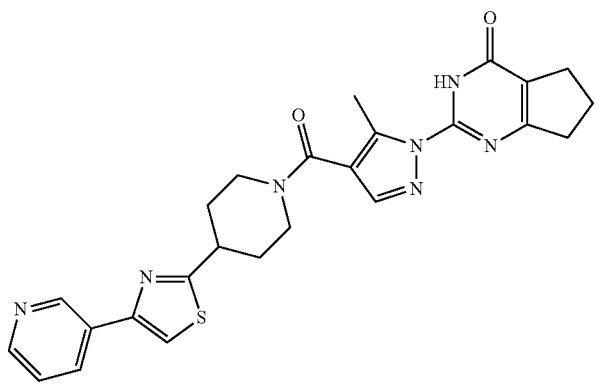
Q-1084
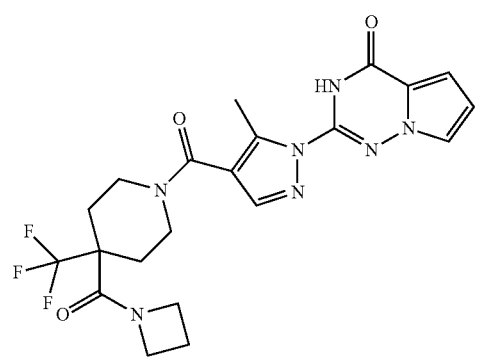 [SMILES: Cc1c(C(=O)N2CCC(C(=O)N3CCC3)(C(F)(F)F)CC2)cnn1-c1nn2cccc2c(=O)[nH]1]
Q-1085

TABLE C-continued
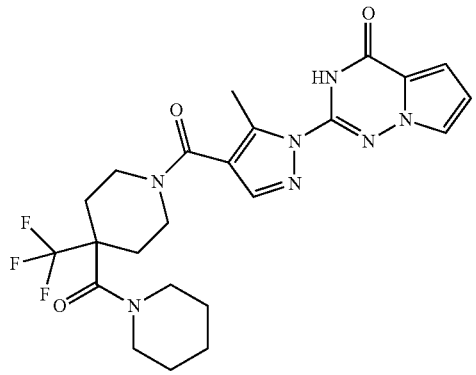 [SMILES: Cc1c(C(=O)N2CCC(C(=O)N3CCCCC3)(C(F)(F)F)CC2)cnn1-c1nn2cccc2c(=O)[nH]1]
Q-1086
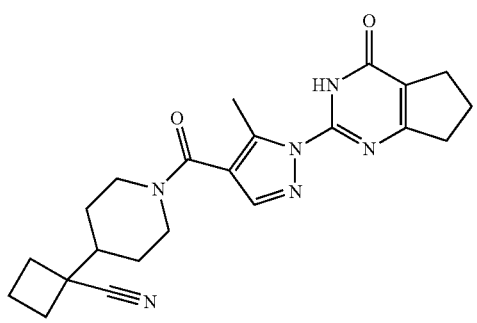 [SMILES: Cc1c(C(=O)N2CCC(C3(C#N)CCC3)CC2)cnn1-c1nc2c(c(=O)[nH]1)CCC2]
Q-1087
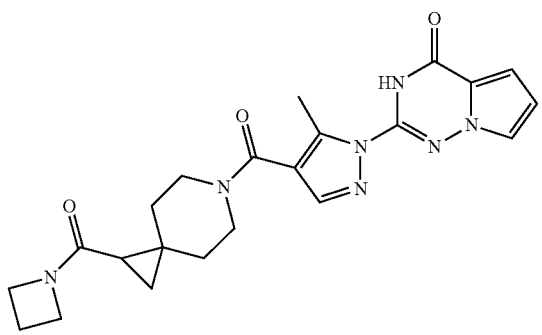 [SMILES: Cc1c(C(=O)N2CCC3(CC2)CC3C(=O)N2CCC2)cnn1-c1nn2cccc2c(=O)[nH]1]
Q-1088
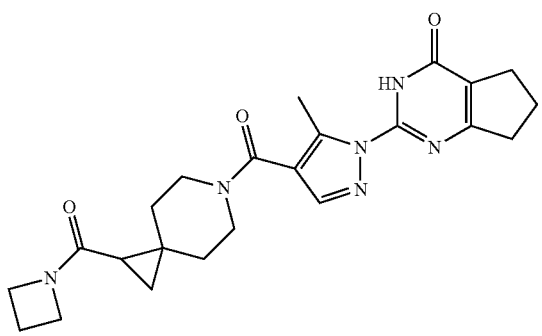 [SMILES: Cc1c(C(=O)N2CCC3(CC2)CC3C(=O)N2CCC2)cnn1-c1nc2c(c(=O)[nH]1)CCC2]
Q-1089

TABLE C-continued
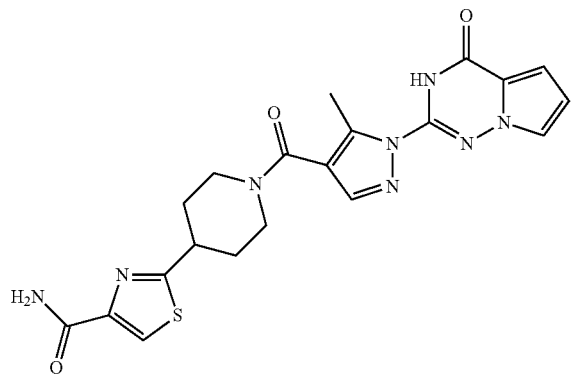 [SMILES: Cc1c(C(=O)N2CCC(c3nc(C(N)=O)cs3)CC2)cnn1-c1nn2cccc2c(=O)[nH]1]
Q-1090
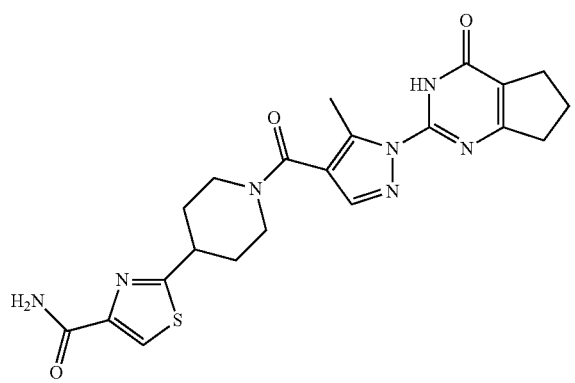 [SMILES: Cc1c(C(=O)N2CCC(c3nc(C(N)=O)cs3)CC2)cnn1-c1nc2c(c(=O)[nH]1)CCC2]
Q-1091
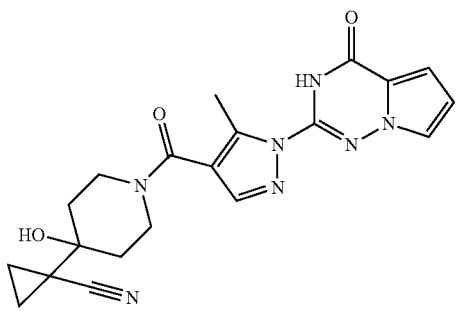 [SMILES: Cc1c(C(=O)N2CCC(O)(C3(C#N)CC3)CC2)cnn1-c1nn2cccc2c(=O)[nH]1]
Q-1092
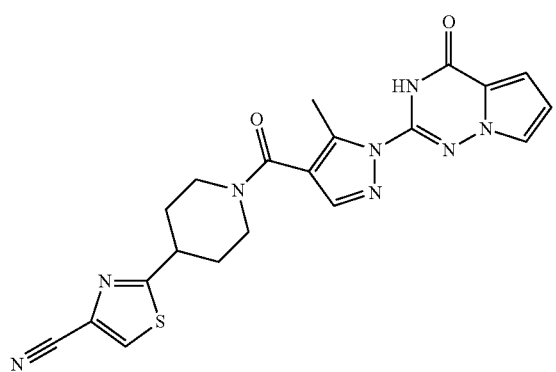 [SMILES: Cc1c(C(=O)N2CCC(c3nc(C#N)cs3)CC2)cnn1-c1nn2cccc2c(=O)[nH]1]
Q-1093

TABLE C-continued
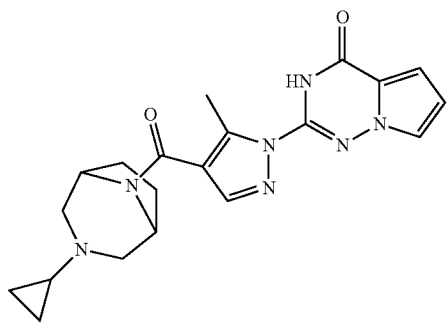 [SMILES: Cc1c(C(=O)N2C3CCC2CN(C2CC2)C3)cnn1-c1nn2cccc2c(=O)[nH]1]
Q-1094
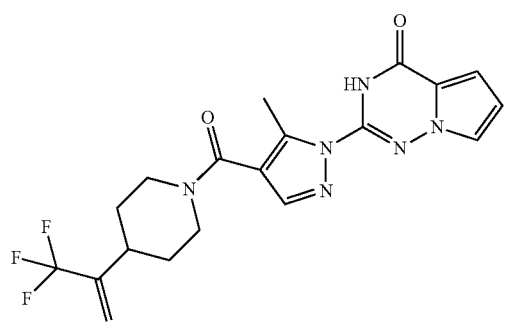 [SMILES: C=C(C1CCN(C(=O)c2cnn(-c3nn4cccc4c(=O)[nH]3)c2C)CC1)C(F)(F)F]
Q-1095
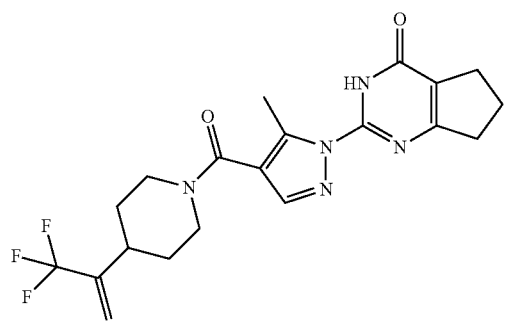 [SMILES: C=C(C1CCN(C(=O)c2cnn(-c3nc4c(c(=O)[nH]3)CCC4)c2C)CC1)C(F)(F)F]
Q-1096
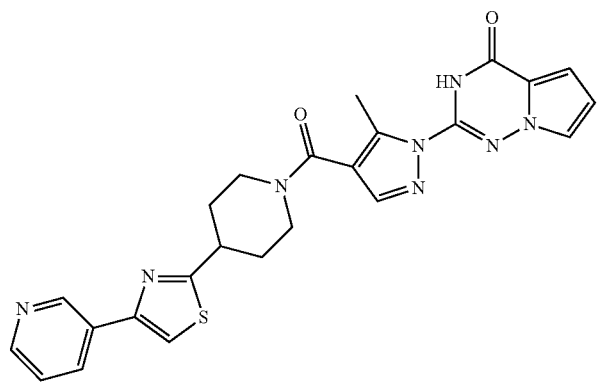 [SMILES: Cc1c(C(=O)N2CCC(c3nc(-c4cccnc4)cs3)CC2)cnn1-c1nn2cccc2c(=O)[nH]1]
Q-1097
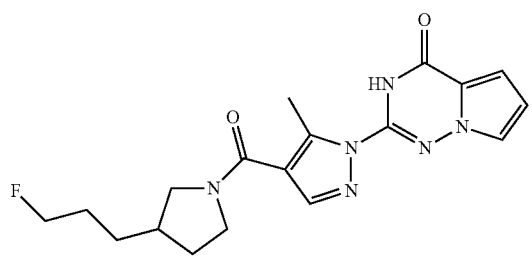 [SMILES: Cc1c(C(=O)N2CCC(CCCF)C2)cnn1-c1nn2cccc2c(=O)[nH]1]
Q-1098

TABLE C-continued
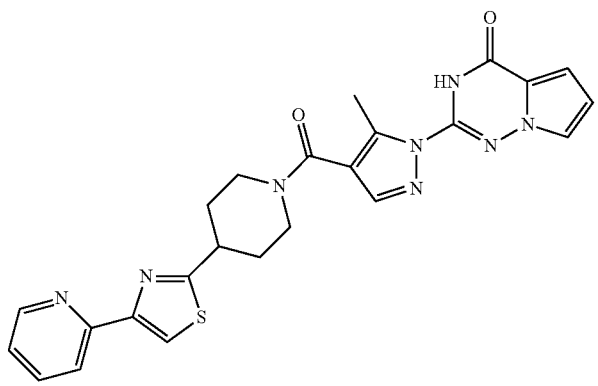
Q-1099
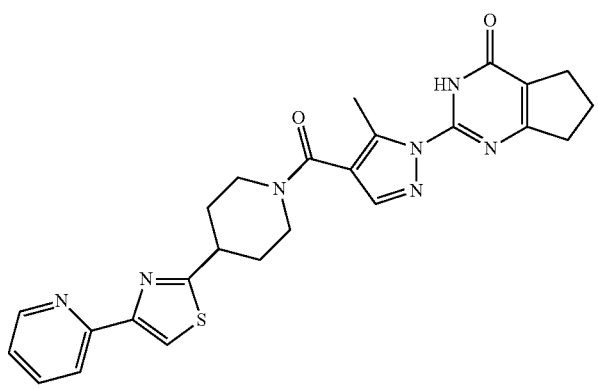 [SMILES: Cc1c(C(=O)N2CCC(c3nc(-c4ccccn4)cs3)CC2)cnn1-c1nc2c(c(=O)[nH]1)CCC2]
Q-1100
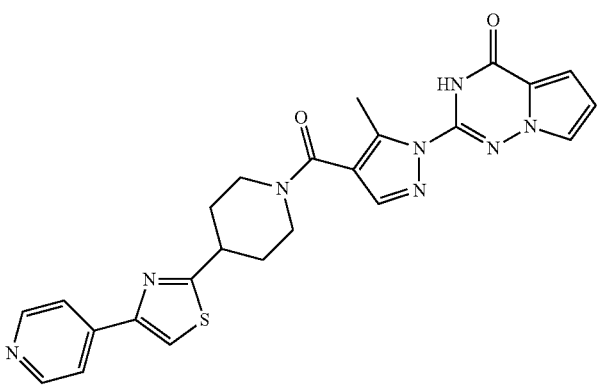
Q-1101
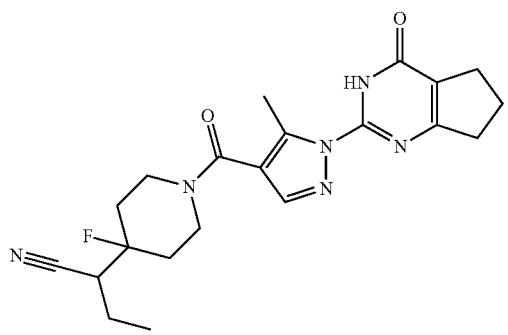 [SMILES: CCC(C#N)C1(F)CCN(C(=O)c2cnn(-c3nc4c(c(=O)[nH]3)CCC4)c2C)CC1]
Q-1102

TABLE C-continued
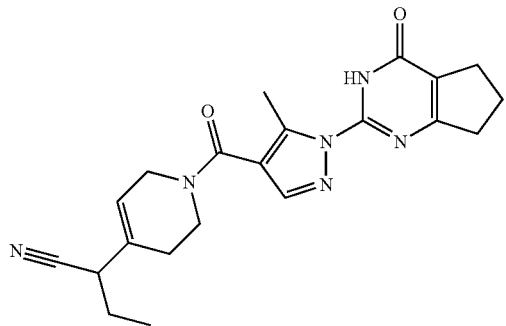 [SMILES: CCC(C#N)C1=CCN(C(=O)c2cnn(-c3nc4c(c(=O)[nH]3)CCC4)c2C)CC1]
Q-1103
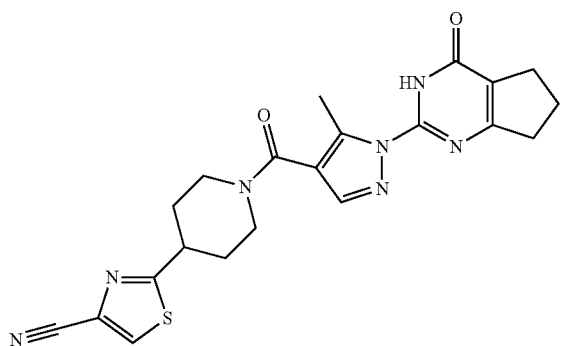 [SMILES: Cc1c(C(=O)N2CCC(c3nc(C#N)cs3)CC2)cnn1-c1nc2c(c(=O)[nH]1)CCC2]
Q-1104
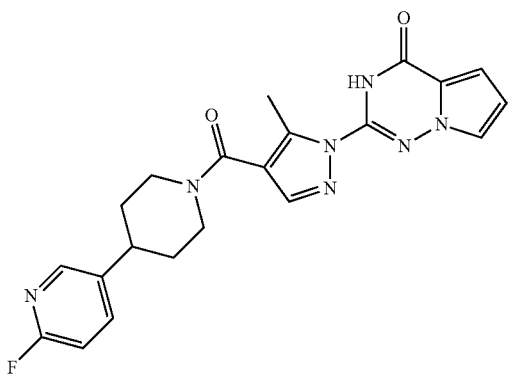 [SMILES: Cc1c(C(=O)N2CCC(c3ccc(F)nc3)CC2)cnn1-c1nn2cccc2c(=O)[nH]1]
Q-1105
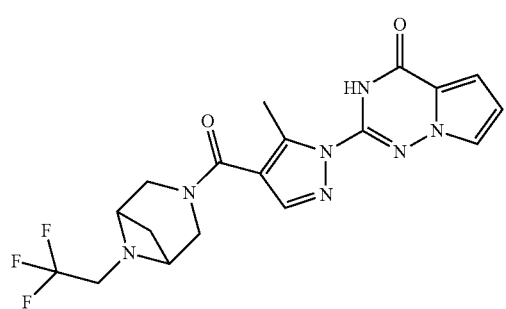 [SMILES: Cc1c(C(=O)N2CC3CC(C2)N3CC(F)(F)F)cnn1-c1nn2cccc2c(=O)[nH]1]
Q-1106

TABLE C-continued
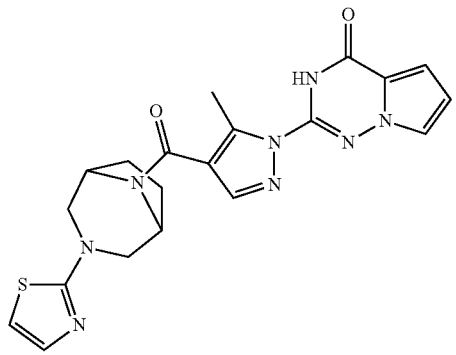 [SMILES: Cc1c(C(=O)N2C3CCC2CN(c2nccs2)C3)cnn1-c1nn2cccc2c(=O)[nH]1]
Q-1107
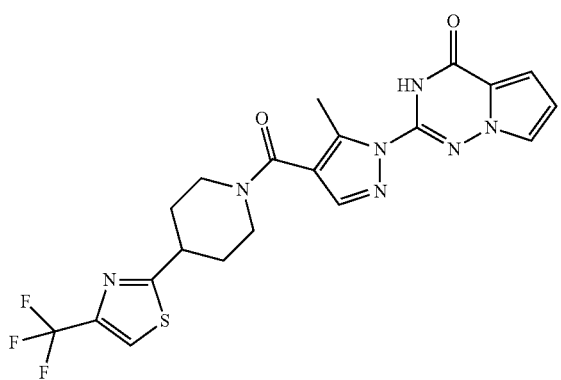 [SMILES: Cc1c(C(=O)N2CCC(c3nc(C(F)(F)F)cs3)CC2)cnn1-c1nn2cccc2c(=O)[nH]1]
Q-1108
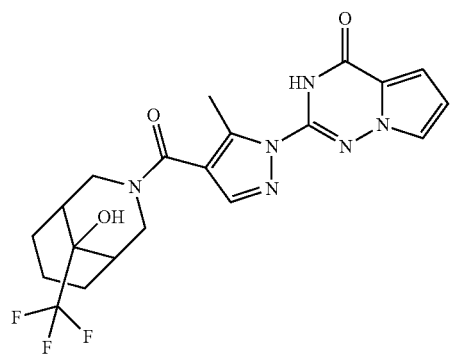 [SMILES: Cc1c(C(=O)N2CC3CCCC(C2)C3(O)C(F)(F)F)cnn1-c1nn2cccc2c(=O)[nH]1]
Q-1109
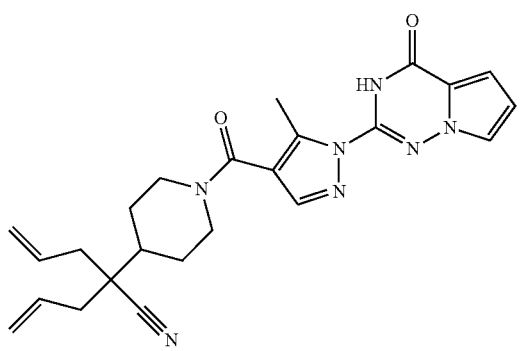 [SMILES: C=CCC(C#N)(CC=C)C1CCN(C(=O)c2cnn(-c3nn4cccc4c(=O)[nH]3)c2C)CC1]
Q-1110

TABLE C-continued
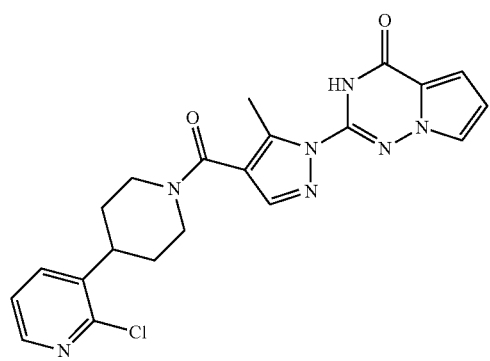
Q-1111
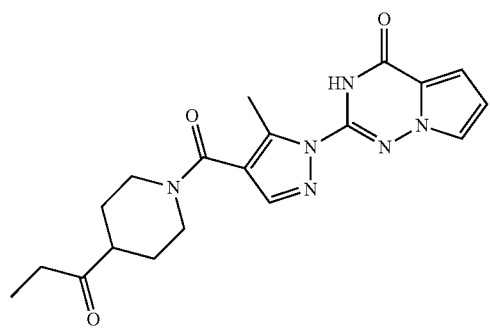 [SMILES: CCC(=O)C1CCN(C(=O)c2cnn(-c3nn4cccc4c(=O)[nH]3)c2C)CC1]
Q-1112
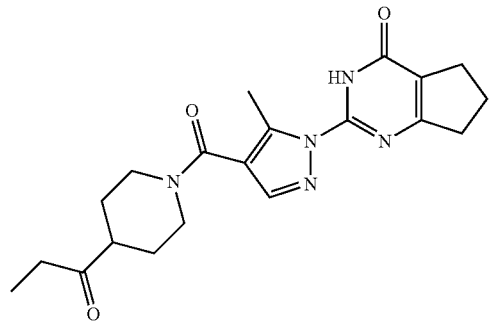 [SMILES: CCC(=O)C1CCN(C(=O)c2cnn(-c3nc4c(c(=O)[nH]3)CCC4)c2C)CC1]
Q-1113
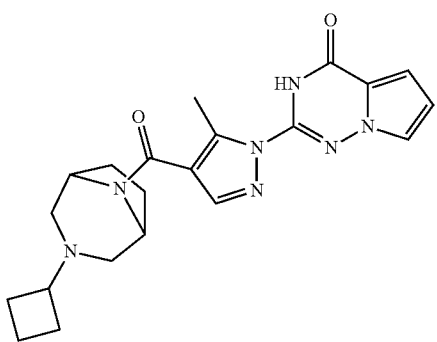 [SMILES: Cc1c(C(=O)N2C3CCC2CN(C2CCC2)C3)cnn1-c1nn2cccc2c(=O)[nH]1]
Q-1114

TABLE C-continued
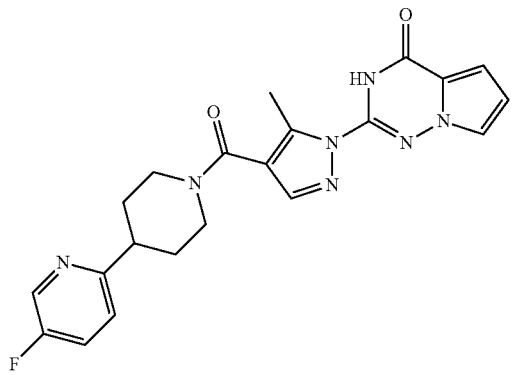
Q-1115
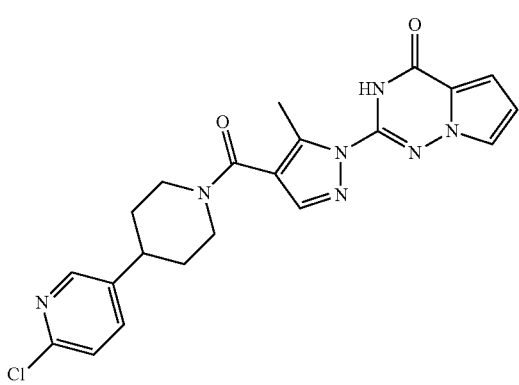 [SMILES: Cc1c(C(=O)N2CCC(c3ccc(Cl)nc3)CC2)cnn1-c1nn2cccc2c(=O)[nH]1]
Q-1116
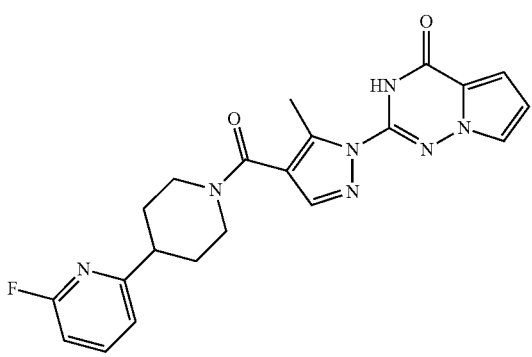 [SMILES: Cc1c(C(=O)N2CCC(c3cccc(F)n3)CC2)cnn1-c1nn2cccc2c(=O)[nH]1]
Q-1117
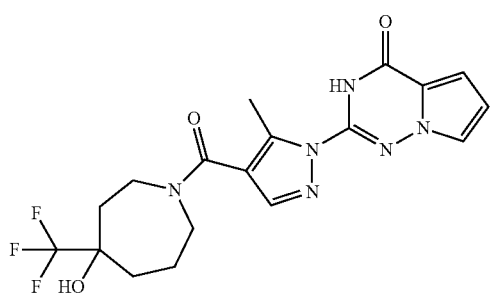 [SMILES: Cc1c(C(=O)N2CCCC(O)(C(F)(F)F)CC2)cnn1-c1nn2cccc2c(=O)[nH]1]
Q-1118

TABLE C-continued
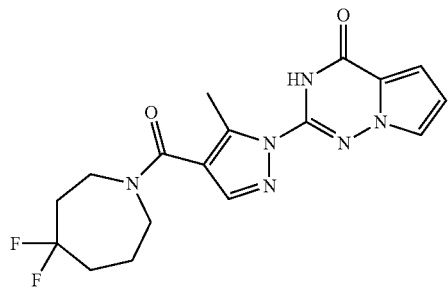 [SMILES: Cc1c(C(=O)N2CCCC(F)(F)CC2)cnn1-c1nn2cccc2c(=O)[nH]1]
Q-1119
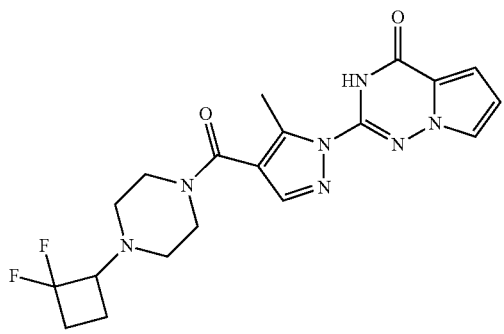 [SMILES: Cc1c(C(=O)N2CCN(C3CCC3(F)F)CC2)cnn1-c1nn2cccc2c(=O)[nH]1]
Q-1120
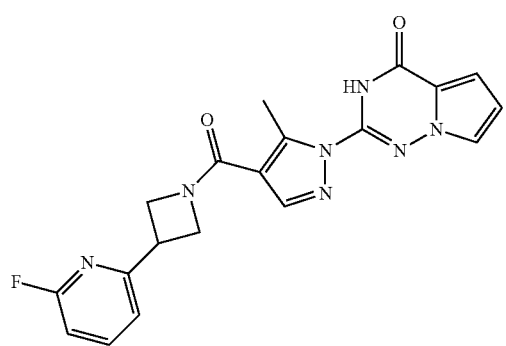 [SMILES: Cc1c(C(=O)N2CC(c3cccc(F)n3)C2)cnn1-c1nn2cccc2c(=O)[nH]1]
Q-1121
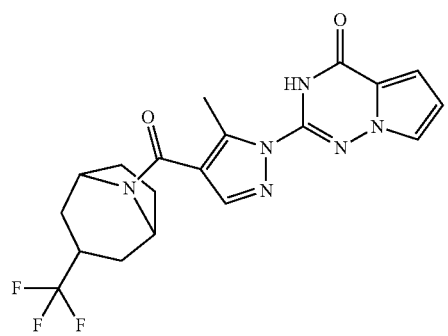 [SMILES: Cc1c(C(=O)N2C3CCC2CC(C(F)(F)F)C3)cnn1-c1nn2cccc2c(=O)[nH]1]
Q-1122
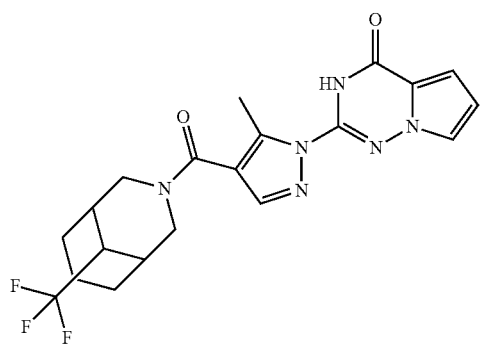 [SMILES: Cc1c(C(=O)N2CC3CCCC(C2)C3C(F)(F)F)cnn1-c1nn2cccc2c(=O)[nH]1]
Q-1123

TABLE C-continued
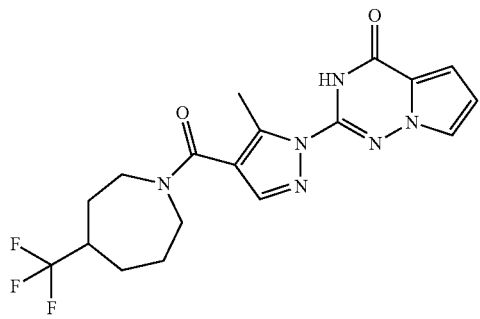 [SMILES: Cc1c(C(=O)N2CCCC(C(F)(F)F)CC2)cnn1-c1nn2cccc2c(=O)[nH]1] Q-1124
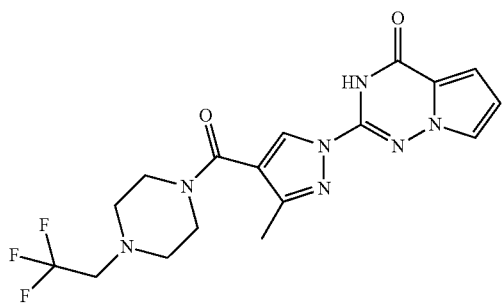 [SMILES: Cc1nn(-c2nn3cccc3c(=O)[nH]2)cc1C(=O)N1CCN(CC(F)(F)F)CC1] Q-1125
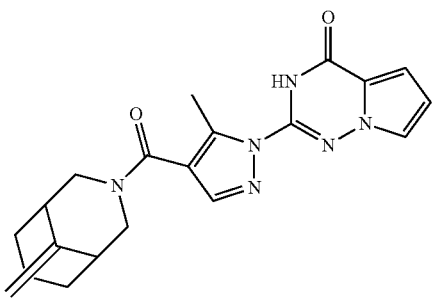 [SMILES: C=C1C2CCCC1CN(C(=O)c1cnn(-c3nn4cccc4c(=O)[nH]3)c1C)C2] Q-1126
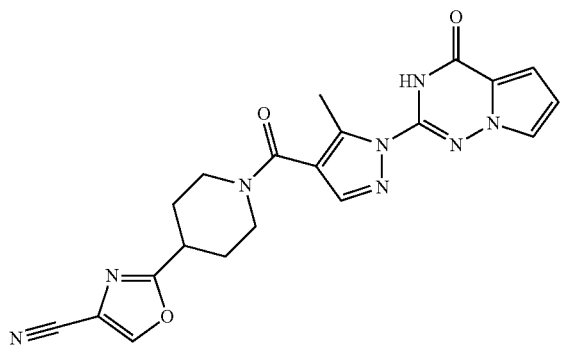 [SMILES: Cc1c(C(=O)N2CCC(c3nc(C#N)co3)CC2)cnn1-c1nn2cccc2c(=O)[nH]1] Q-1127

TABLE C-continued
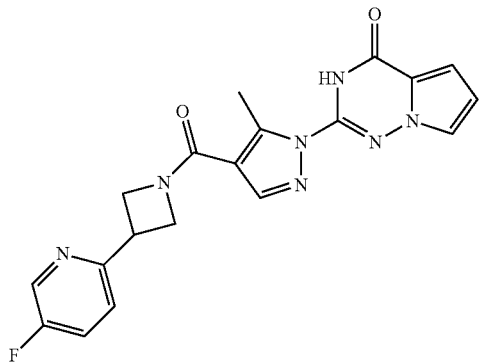 [SMILES: Cc1c(C(=O)N2CC(c3ccc(F)cn3)C2)cnn1-c1nn2cccc2c(=O)[nH]1]
Q-1128
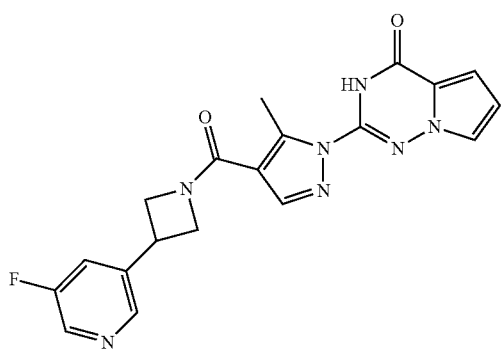 [SMILES: Cc1c(C(=O)N2CC(c3cncc(F)c3)C2)cnn1-c1nn2cccc2c(=O)[nH]1]
Q-1129
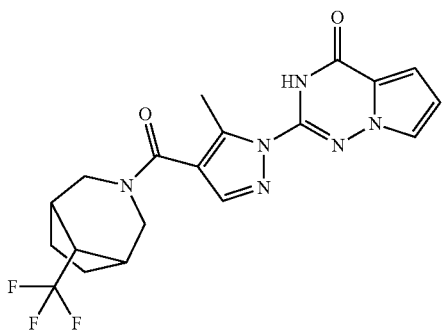 [SMILES: Cc1c(C(=O)N2CC3CCC(C2)C3C(F)(F)F)cnn1-c1nn2cccc2c(=O)[nH]1]
Q-1130
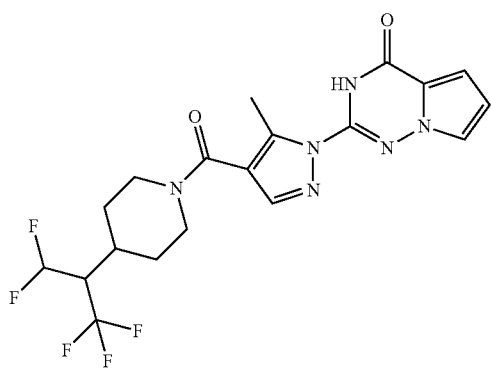 [SMILES: Cc1c(C(=O)N2CCC(C(C(F)F)C(F)(F)F)CC2)cnn1-c1nn2cccc2c(=O)[nH]1]
Q-1131

TABLE C-continued
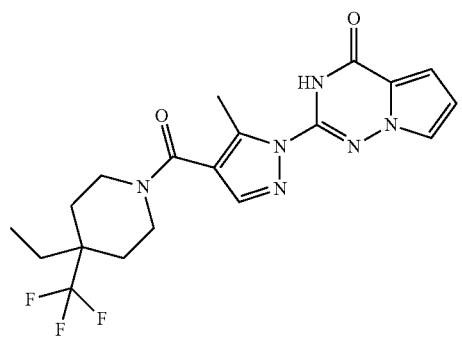 [SMILES: CCC1(C(F)(F)F)CCN(C(=O)c2cnn(-c3nn4cccc4c(=O)[nH]3)c2C)CC1]
Q-1132
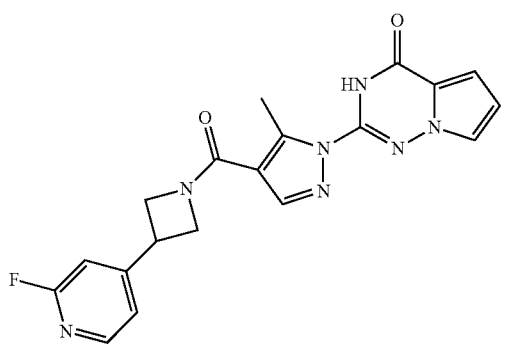 [SMILES: Cc1c(C(=O)N2CC(c3ccnc(F)c3)C2)cnn1-c1nn2cccc2c(=O)[nH]1]
Q-1133
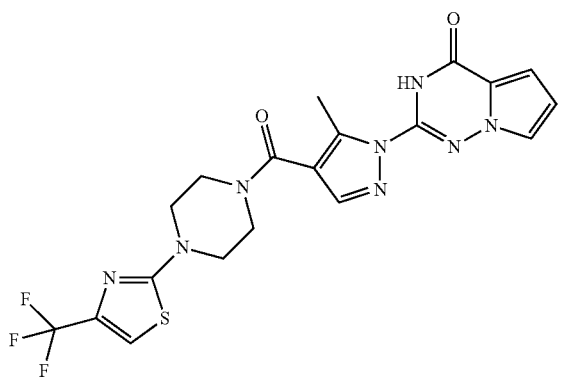 [SMILES: Cc1c(C(=O)N2CCN(c3nc(C(F)(F)F)cs3)CC2)cnn1-c1nn2cccc2c(=O)[nH]1]
Q-1134
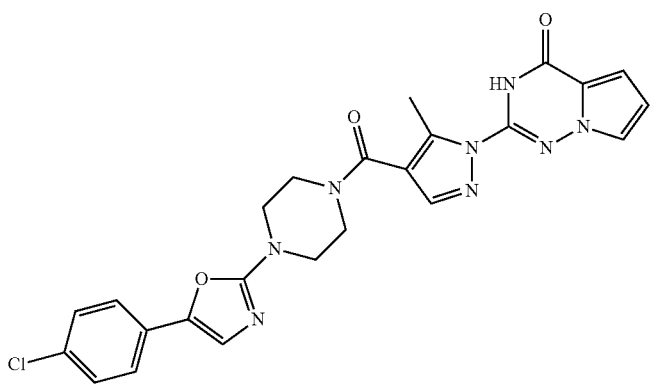 [SMILES: Cc1c(C(=O)N2CCN(c3ncc(-c4ccc(Cl)cc4)o3)CC2)cnn1-c1nn2cccc2c(=O)[nH]1]
Q-1135

TABLE C-continued
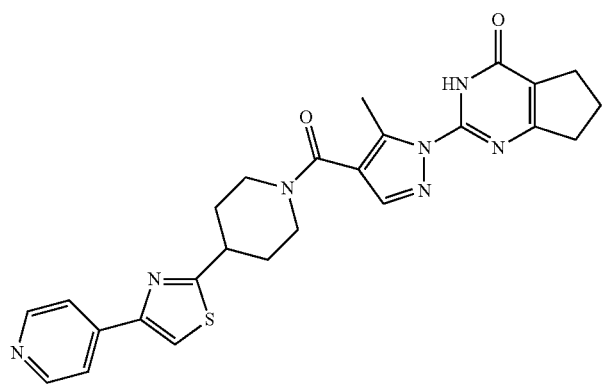 [SMILES: Cc1c(C(=O)N2CCC(c3nc(-c4ccncc4)cs3)CC2)cnn1-c1nc2c(c(=O)[nH]1)CCC2]
Q-1136
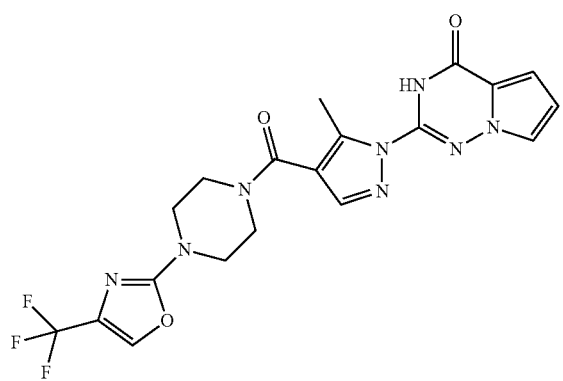 [SMILES: Cc1c(C(=O)N2CCN(c3nc(C(F)(F)F)co3)CC2)cnn1-c1nn2cccc2c(=O)[nH]1]
Q-1137
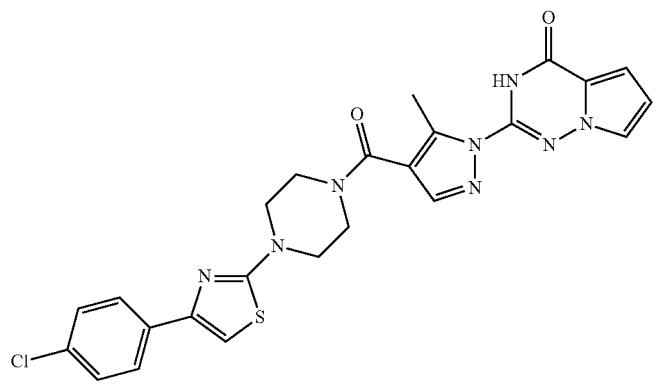
Q-1138
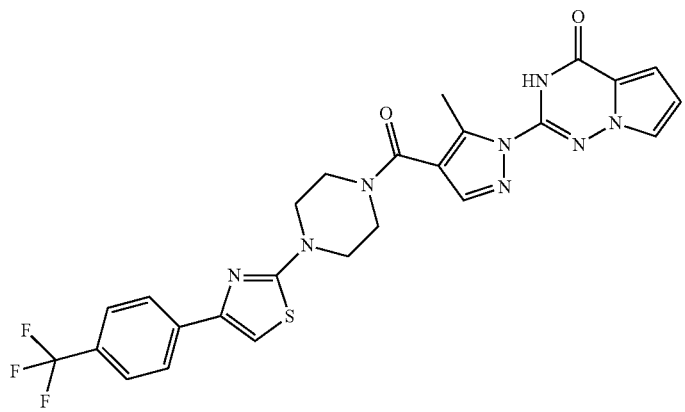 [SMILES: Cc1c(C(=O)N2CCN(c3nc(-c4ccc(C(F)(F)F)cc4)cs3)CC2)cnn1-c1nn2cccc2c(=O)[nH]1]
Q-1139

TABLE C-continued
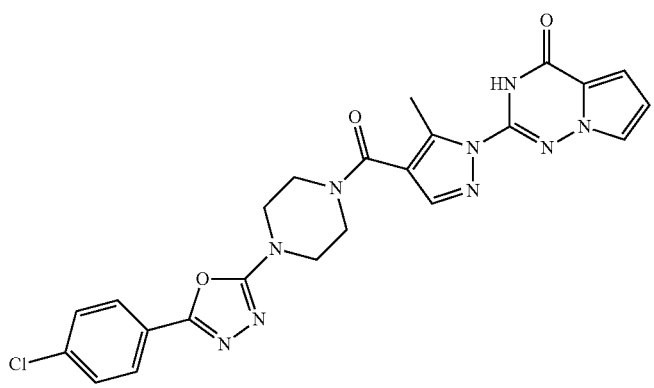 [SMILES: Cc1c(C(=O)N2CCN(c3nnc(-c4ccc(Cl)cc4)o3)CC2)cnn1-c1nn2cccc2c(=O)[nH]1]
Q-1140
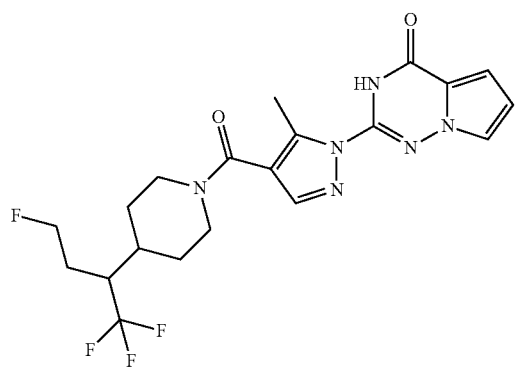 [SMILES: Cc1c(C(=O)N2CCC(C(CCF)C(F)(F)F)CC2)cnn1-c1nn2cccc2c(=O)[nH]1]
Q-1141
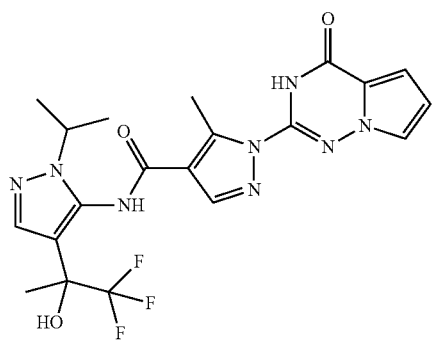 [SMILES: Cc1c(C(=O)Nc2c(C(C)(O)C(F)(F)F)cnn2C(C)C)cnn1-c1nn2cccc2c(=O)[nH]1]
Q-1142
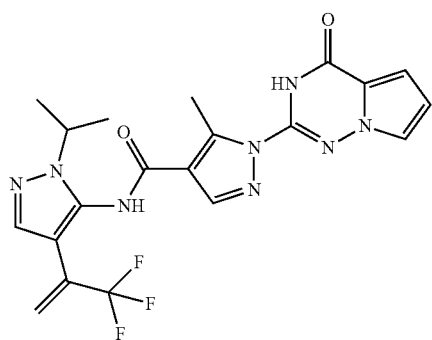 [SMILES: C=C(c1cnn(C(C)C)c1NC(=O)c1cnn(-c2nn3cccc3c(=O)[nH]2)c1C)C(F)(F)F]
Q-1143

TABLE C-continued
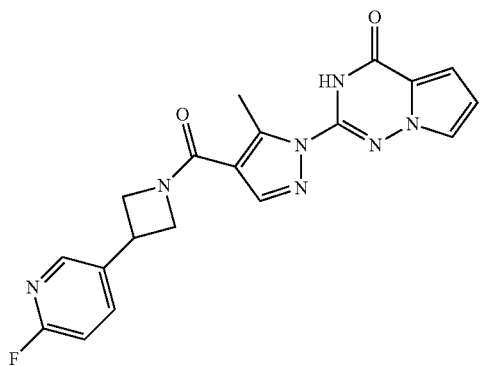 [SMILES: Cc1c(C(=O)N2CC(c3ccc(F)nc3)C2)cnn1-c1nn2cccc2c(=O)[nH]1]
Q-1144
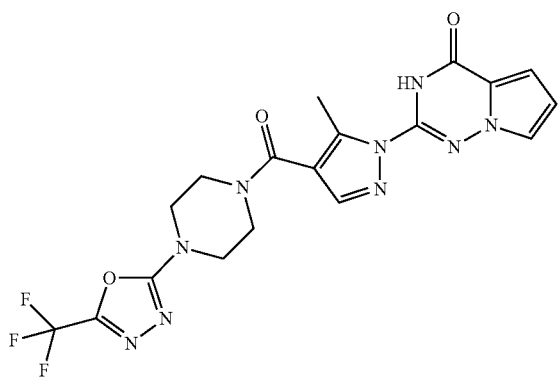
Q-1145
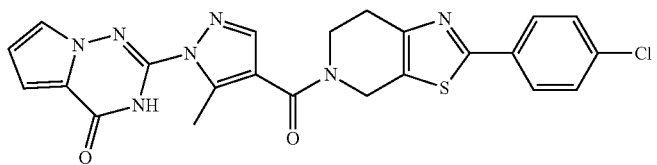 [SMILES: Cc1c(C(=O)N2CCc3nc(-c4ccc(Cl)cc4)sc3C2)cnn1-c1nn2cccc2c(=O)[nH]1]
Q-1146
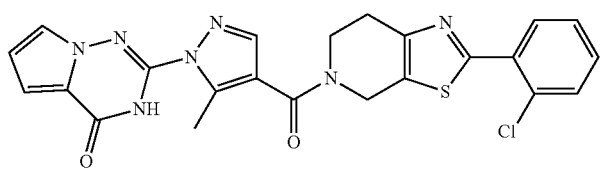
Q-1147
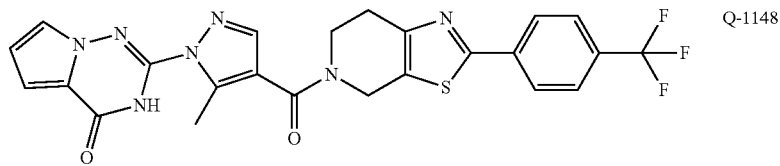
Q-1148

TABLE C-continued
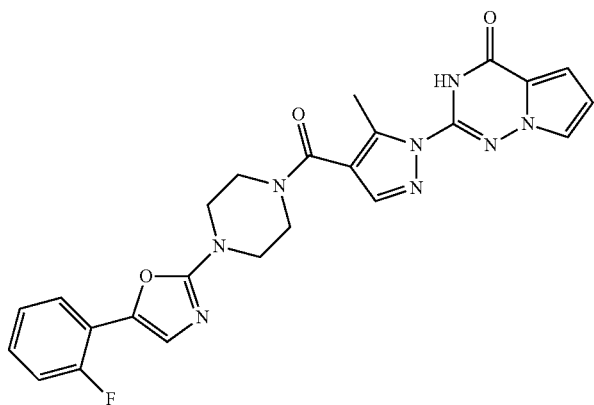 [SMILES: Cc1c(C(=O)N2CCN(c3ncc(-c4ccccc4F)o3)CC2)cnn1-c1nn2cccc2c(=O)[nH]1]
Q-1149
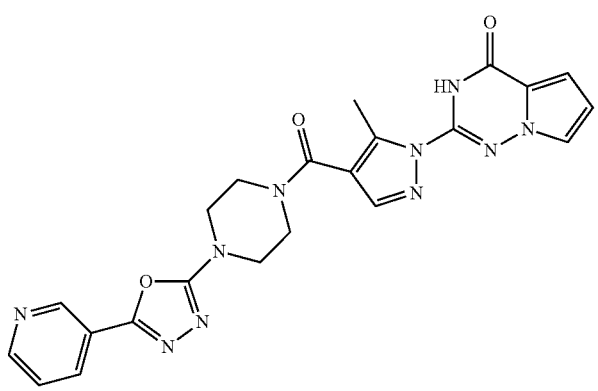 [SMILES: Cc1c(C(=O)N2CCN(c3nnc(-c4cccnc4)o3)CC2)cnn1-c1nn2cccc2c(=O)[nH]1]
Q-1150
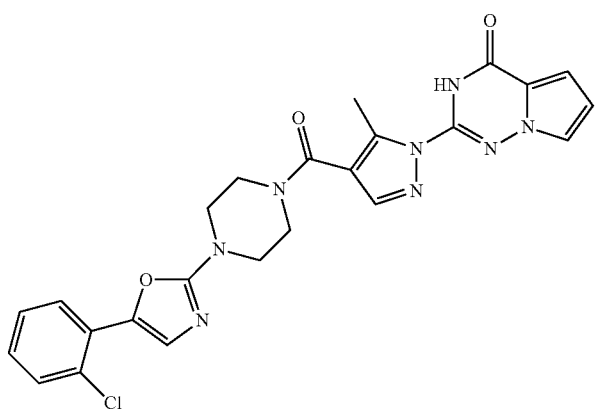
Q-1151
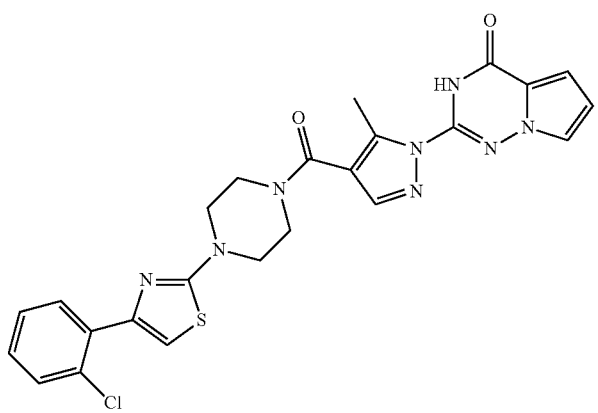 [SMILES: Cc1c(C(=O)N2CCN(c3nc(-c4ccccc4Cl)cs3)CC2)cnn1-c1nn2cccc2c(=O)[nH]1]
Q-1152

TABLE C-continued
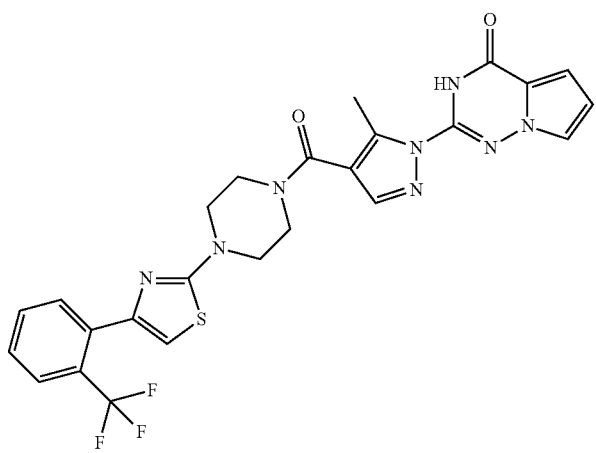 [SMILES: Cc1c(C(=O)N2CCN(c3nc(-c4ccccc4C(F)(F)F)cs3)CC2)cnn1-c1nn2cccc2c(=O)[nH]1]
Q-1153
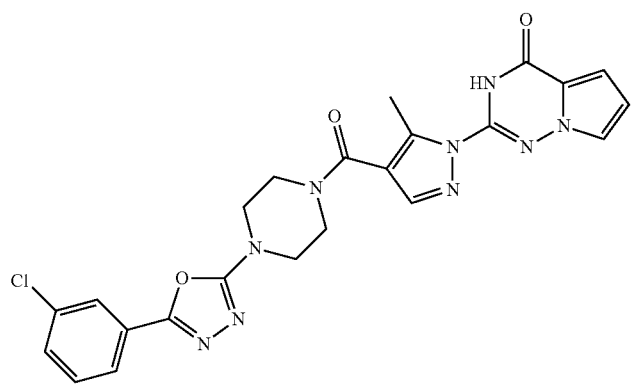 [SMILES: Cc1c(C(=O)N2CCN(c3nnc(-c4cccc(Cl)c4)o3)CC2)cnn1-c1nn2cccc2c(=O)[nH]1]
Q-1154
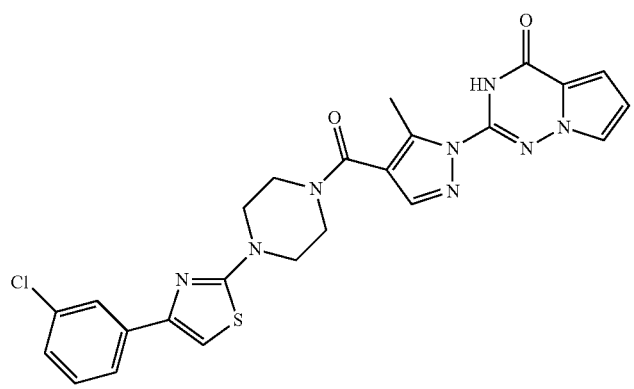 [SMILES: Cc1c(C(=O)N2CCN(c3nc(-c4cccc(Cl)c4)cs3)CC2)cnn1-c1nn2cccc2c(=O)[nH]1]
Q-1155
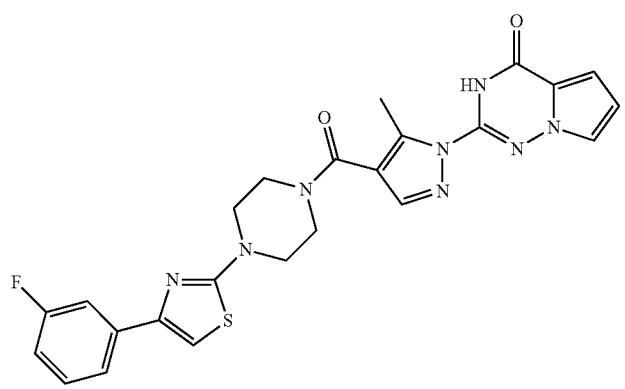
Q-1156

TABLE C-continued
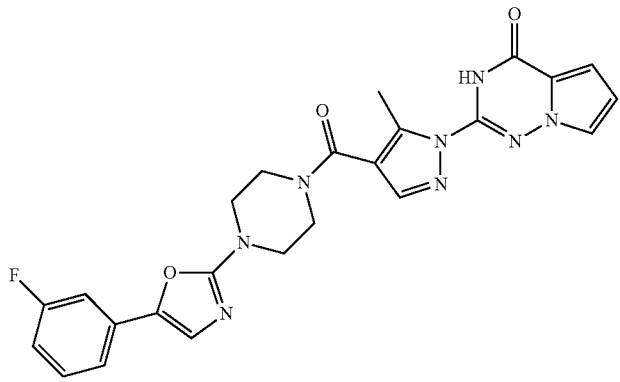 [SMILES: Cc1c(C(=O)N2CCN(c3ncc(-c4cccc(F)c4)o3)CC2)cnn1-c1nn2cccc2c(=O)[nH]1]
Q-1157
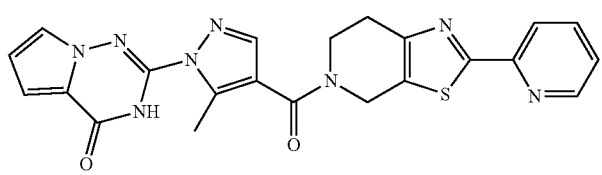 [SMILES: Cc1c(C(=O)N2CCc3nc(-c4ccccn4)sc3C2)cnn1-c1nn2cccc2c(=O)[nH]1]
Q-1158
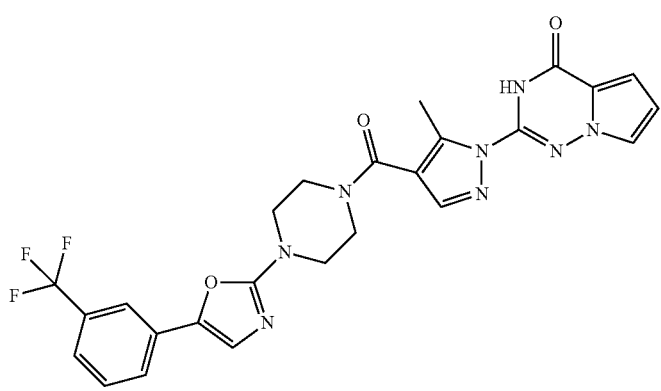 [SMILES: Cc1c(C(=O)N2CCN(c3ncc(-c4cccc(C(F)(F)F)c4)o3)CC2)cnn1-c1nn2cccc2c(=O)[nH]1]
Q-1159
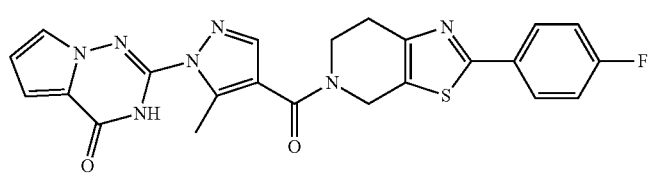 [SMILES: Cc1c(C(=O)N2CCc3nc(-c4ccc(F)cc4)sc3C2)cnn1-c1nn2cccc2c(=O)[nH]1]
Q-1160
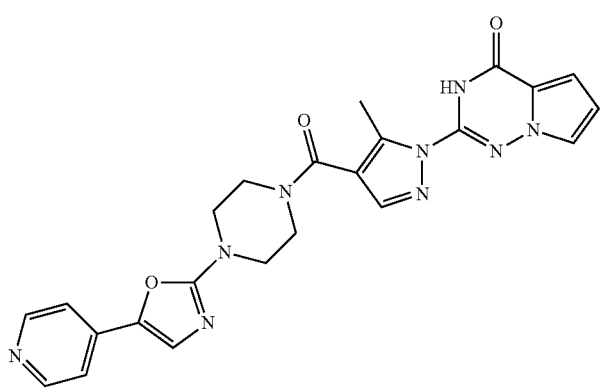 [SMILES: Cc1c(C(=O)N2CCN(c3ncc(-c4ccncc4)o3)CC2)cnn1-c1nn2cccc2c(=O)[nH]1]
Q-1161

TABLE C-continued
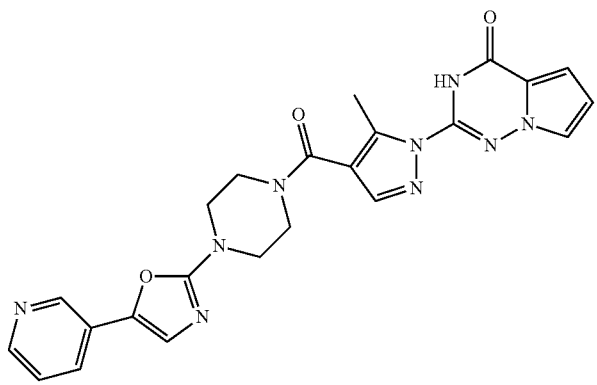 [SMILES: Cc1c(C(=O)N2CCN(c3ncc(-c4cccnc4)o3)CC2)cnn1-c1nn2cccc2c(=O)[nH]1]
Q-1162
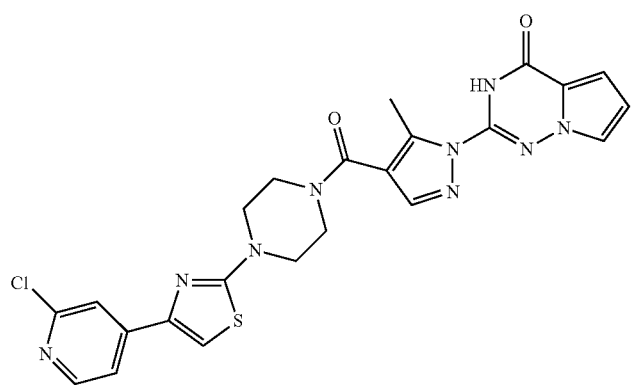 [SMILES: Cc1c(C(=O)N2CCN(c3nc(-c4ccnc(Cl)c4)cs3)CC2)cnn1-c1nn2cccc2c(=O)[nH]1]
Q-1163
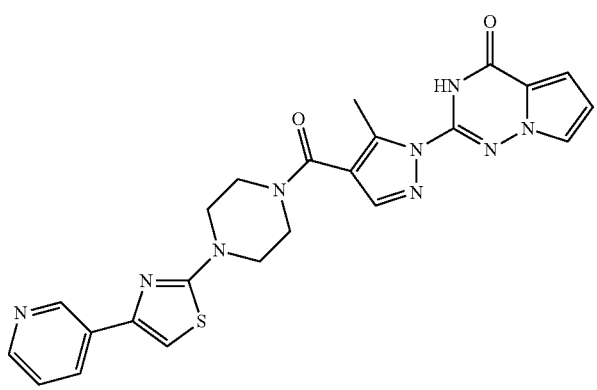
Q-1164
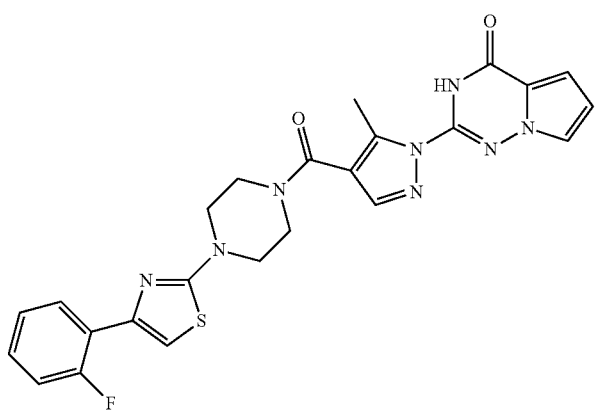
Q-1165

TABLE C-continued
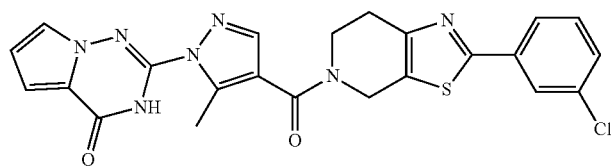 [SMILES: Cc1c(C(=O)N2CCc3nc(-c4cccc(Cl)c4)sc3C2)cnn1-c1nn2cccc2c(=O)[nH]1]
Q-1166
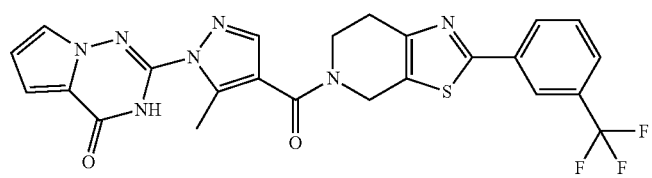 [SMILES: Cc1c(C(=O)N2CCc3nc(-c4cccc(C(F)(F)F)c4)sc3C2)cnn1-c1nn2cccc2c(=O)[nH]1]
Q-1167
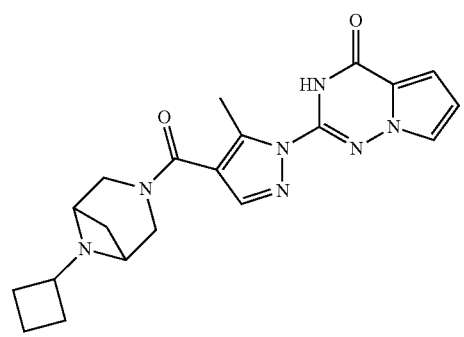 [SMILES: Cc1c(C(=O)N2CC3CC(C2)N3C2CCC2)cnn1-c1nn2cccc2c(=O)[nH]1]
Q-1168
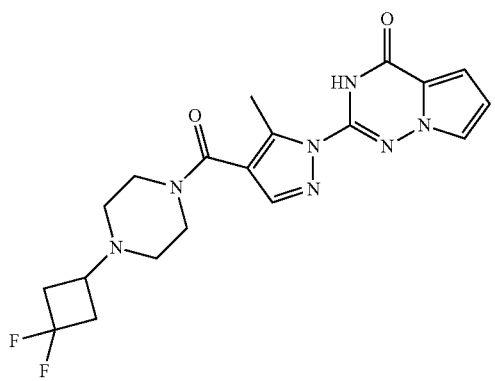 [SMILES: Cc1c(C(=O)N2CCN(C3CC(F)(F)C3)CC2)cnn1-c1nn2cccc2c(=O)[nH]1]
Q-1169
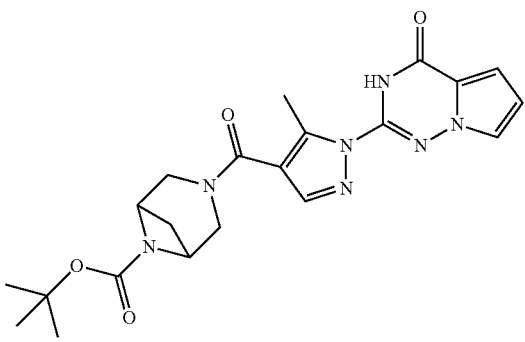 [SMILES: Cc1c(C(=O)N2CC3CC(C2)N3C(=O)OC(C)(C)C)cnn1-c1nn2cccc2c(=O)[nH]1]
Q-1170

TABLE C-continued
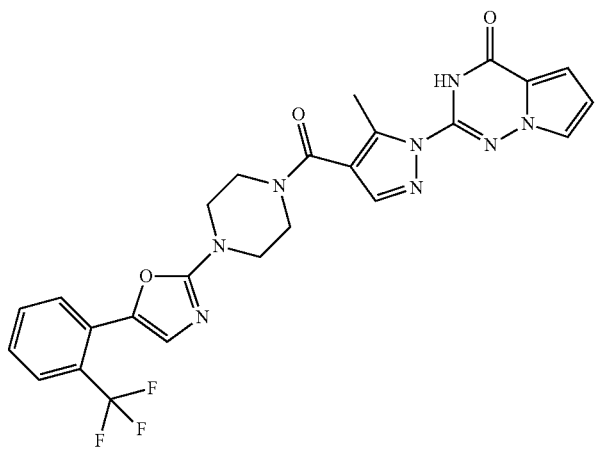 [SMILES: Cc1c(C(=O)N2CCN(c3ncc(-c4ccccc4C(F)(F)F)o3)CC2)cnn1-c1nn2cccc2c(=O)[nH]1]
Q-1171
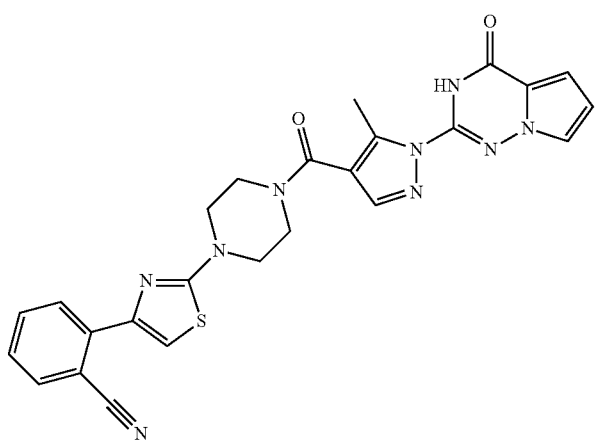 [SMILES: Cc1c(C(=O)N2CCN(c3nc(-c4ccccc4C#N)cs3)CC2)cnn1-c1nn2cccc2c(=O)[nH]1]
Q-1172
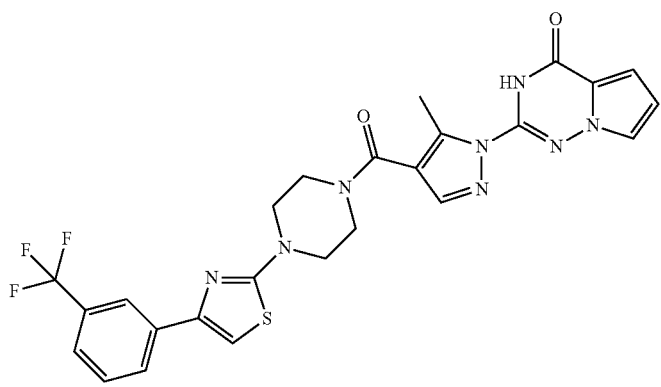
Q-1173
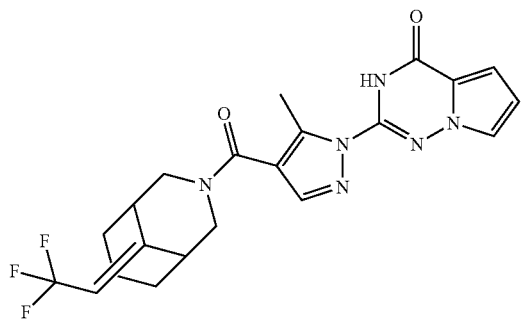 [SMILES: Cc1c(C(=O)N2CC3CCCC(C2)C3=CC(F)(F)F)cnn1-c1nn2cccc2c(=O)[nH]1]
Q-1174

TABLE C-continued
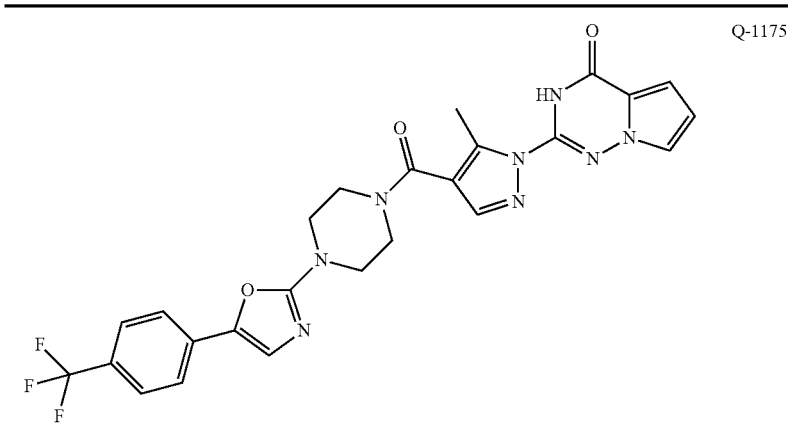
Q-1175
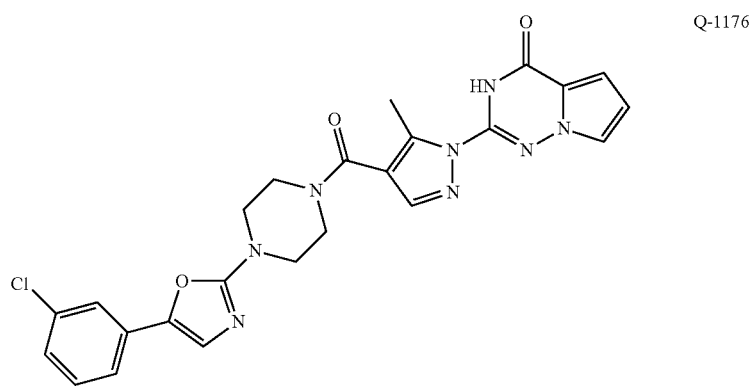
Q-1176
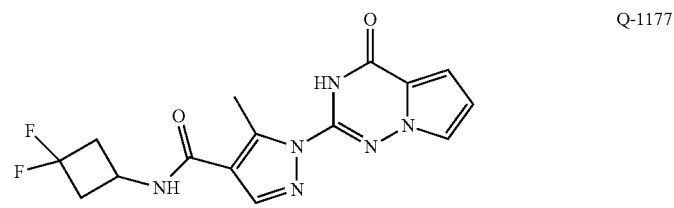
Q-1177
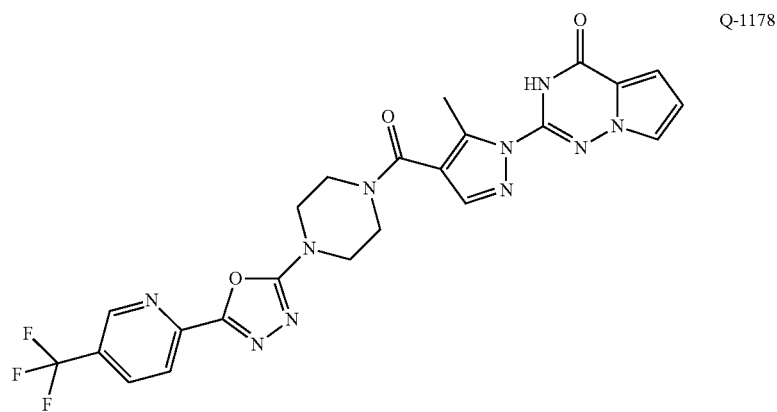
Q-1178

TABLE C-continued
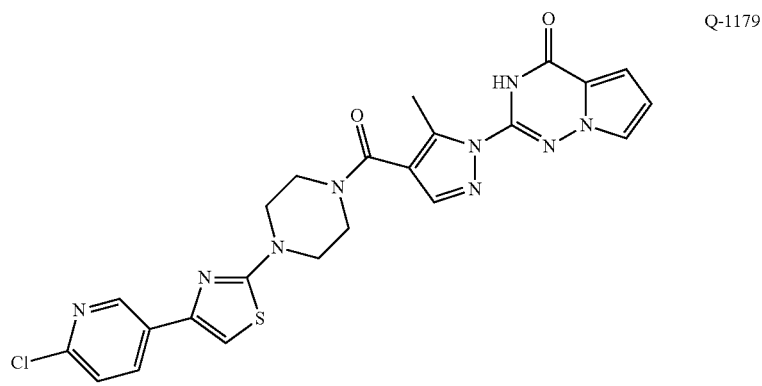
Q-1179
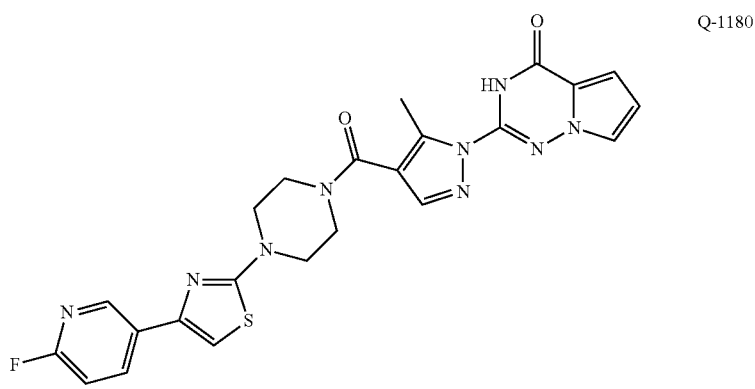
Q-1180
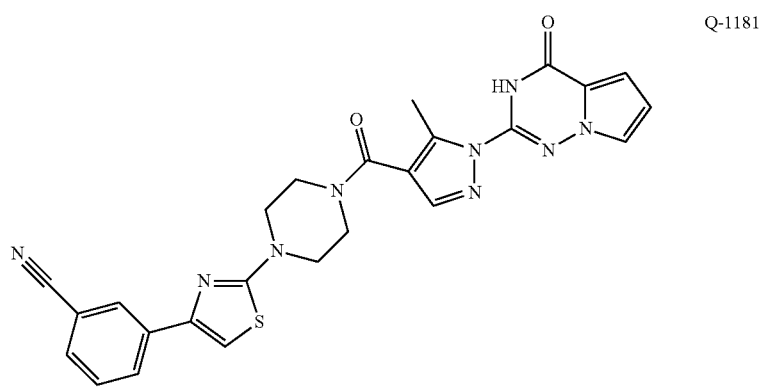
Q-1181
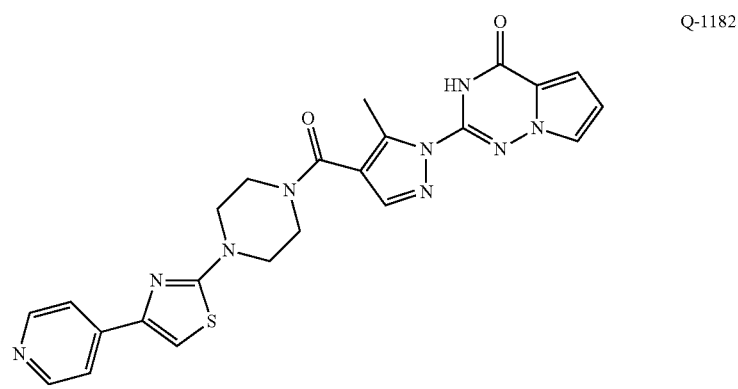
Q-1182

TABLE C-continued
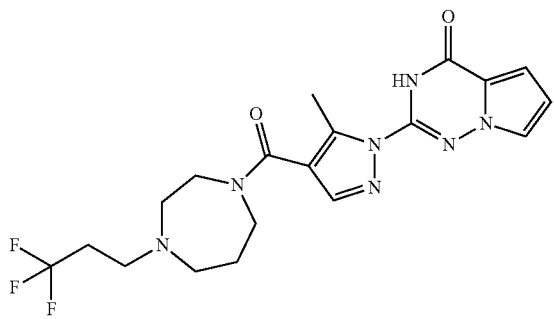 [SMILES: Cc1c(C(=O)N2CCCN(CCC(F)(F)F)CC2)cnn1-c1nn2cccc2c(=O)[nH]1]
Q-1183
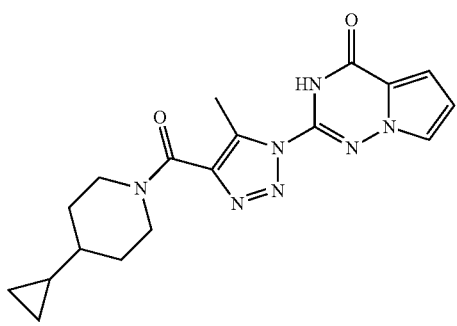
Q-1184
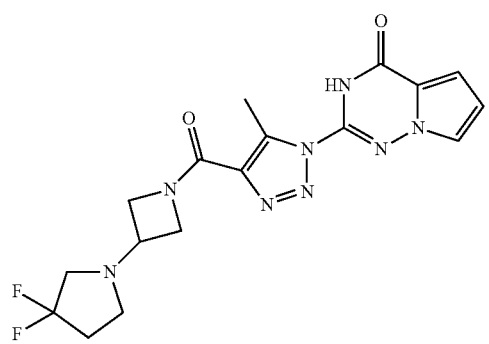 [SMILES: Cc1c(C(=O)N2CC(N3CCC(F)(F)C3)C2)nnn1-c1nn2cccc2c(=O)[nH]1]
Q-1185
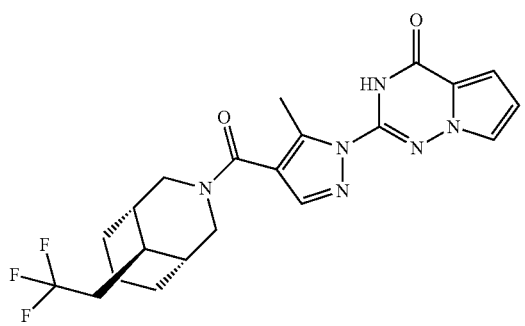 [SMILES: Cc1c(C(=O)N2C[C@H]3CCC[C@@H](C2)[C@H]3CC(F)(F)F)cnn1-c1nn2cccc2c(=O)[nH]1]
Q-1186
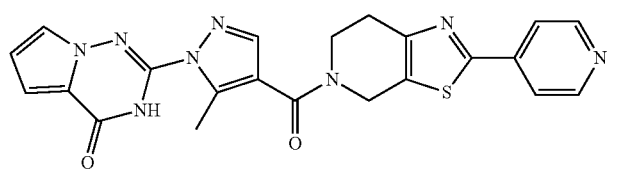 [SMILES: Cc1c(C(=O)N2CCc3nc(-c4ccncc4)sc3C2)cnn1-c1nn2cccc2c(=O)[nH]1]
Q-1187

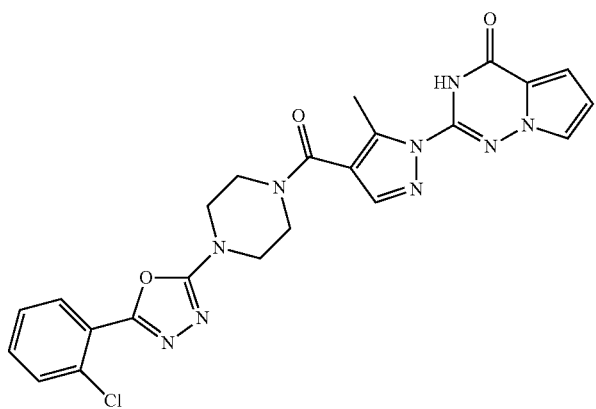 [SMILES: Cc1c(C(=O)N2CCN(c3nnc(-c4ccccc4Cl)o3)CC2)cnn1-c1nn2cccc2c(=O)[nH]1]
Q-1188
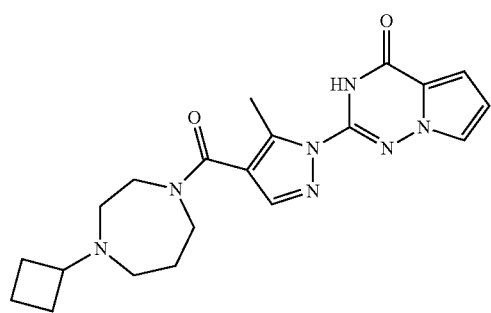 [SMILES: Cc1c(C(=O)N2CCCN(C3CCC3)CC2)cnn1-c1nn2cccc2c(=O)[nH]1]
Q-1189
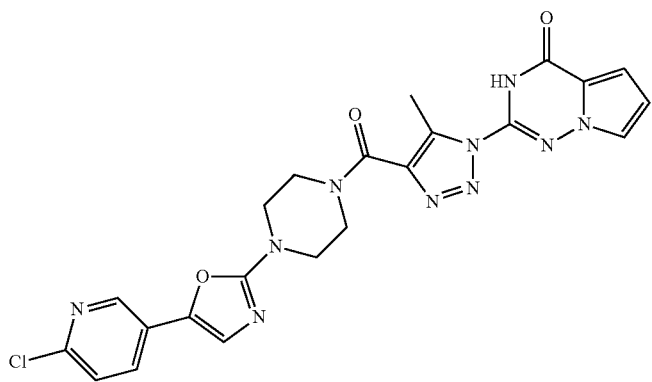 [SMILES: Cc1c(C(=O)N2CCN(c3ncc(-c4ccc(Cl)nc4)o3)CC2)nnn1-c1nn2cccc2c(=O)[nH]1]
Q-1190
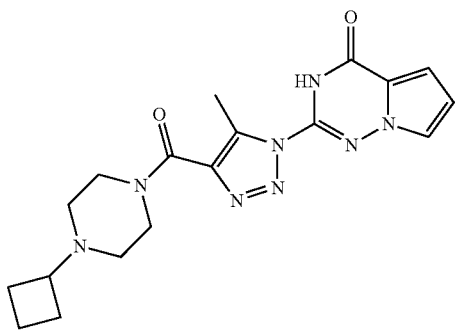 [SMILES: Cc1c(C(=O)N2CCN(C3CCC3)CC2)nnn1-c1nn2cccc2c(=O)[nH]1]
Q-1191

TABLE C-continued
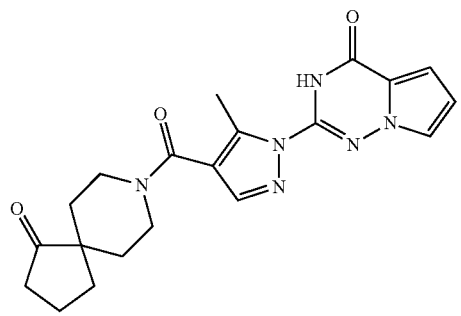 [SMILES: Cc1c(C(=O)N2CCC3(CCCC3=O)CC2)cnn1-c1nn2cccc2c(=O)[nH]1]
Q-1192
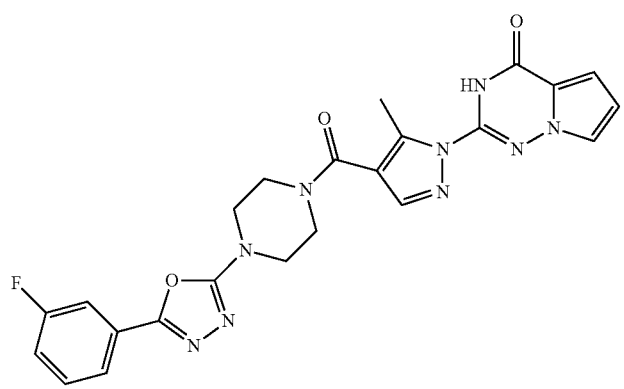 [SMILES: Cc1c(C(=O)N2CCN(c3nnc(-c4cccc(F)c4)o3)CC2)cnn1-c1nn2cccc2c(=O)[nH]1]
Q-1193
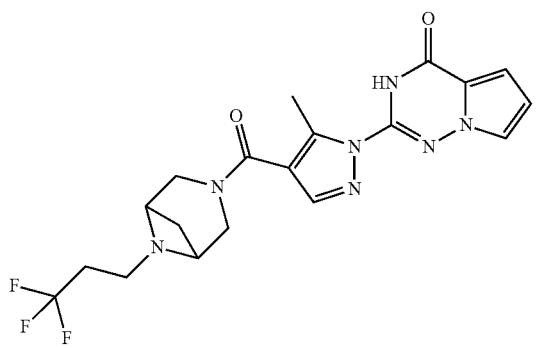 [SMILES: Cc1c(C(=O)N2CC3CC(C2)N3CCC(F)(F)F)cnn1-c1nn2cccc2c(=O)[nH]1]
Q-1194
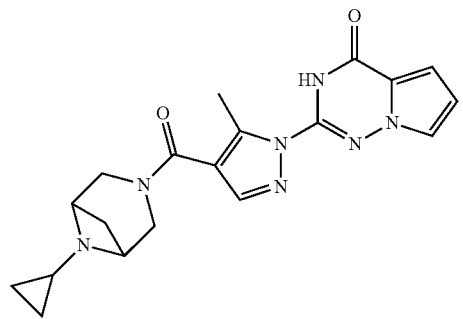 [SMILES: Cc1c(C(=O)N2CC3CC(C2)N3C2CC2)cnn1-c1nn2cccc2c(=O)[nH]1]
Q-1195

TABLE C-continued
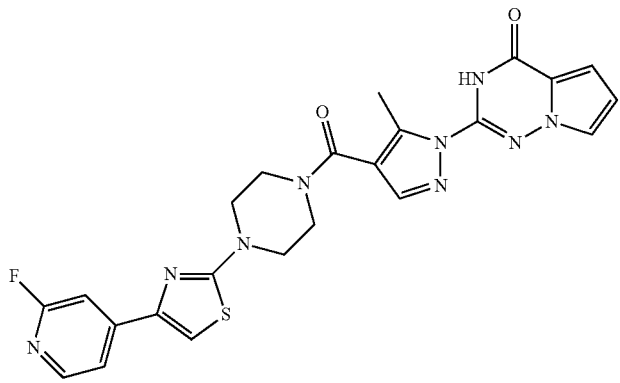 [SMILES: Cc1c(C(=O)N2CCN(c3nc(-c4ccnc(F)c4)cs3)CC2)cnn1-c1nn2cccc2c(=O)[nH]1]
Q-1196
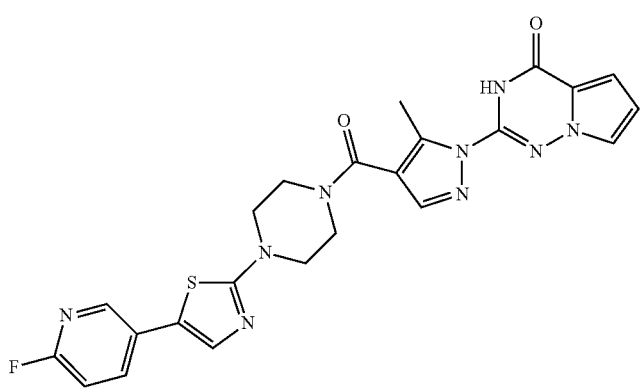 [SMILES: Cc1c(C(=O)N2CCN(c3ncc(-c4ccc(F)nc4)s3)CC2)cnn1-c1nn2cccc2c(=O)[nH]1]
Q-1197
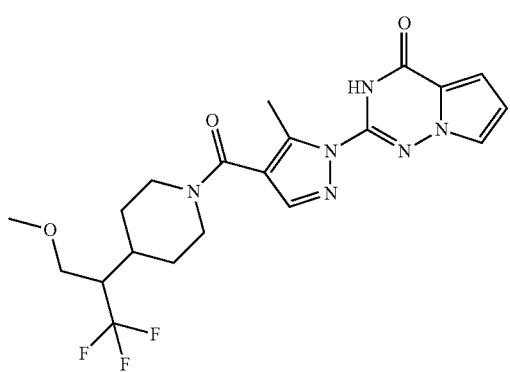 [SMILES: COCC(C1CCN(C(=O)c2cnn(-c3nn4cccc4c(=O)[nH]3)c2C)CC1)C(F)(F)F]
Q-1198
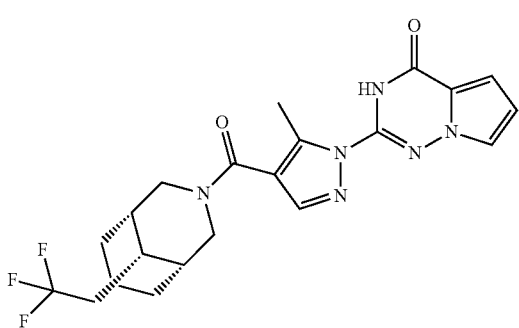 [SMILES: Cc1c(C(=O)N2C[C@H]3CCC[C@@H](C2)[C@@H]3CC(F)(F)F)cnn1-c1nn2cccc2c(=O)[nH]1]
Q-1199

TABLE C-continued
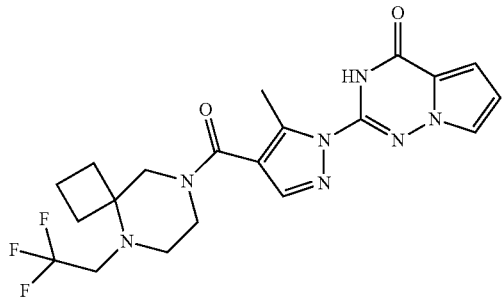 [SMILES: Cc1c(C(=O)N2CCN(CC(F)(F)F)C3(CCC3)C2)cnn1-c1nn2cccc2c(=O)[nH]1] Q-1200
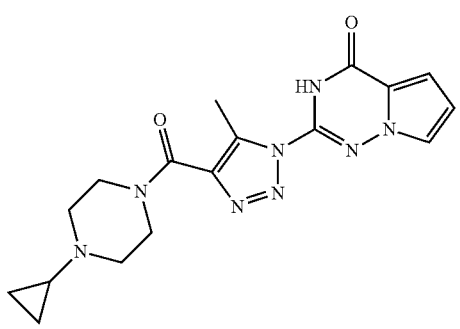 [SMILES: Cc1c(C(=O)N2CCN(C3CC3)CC2)nnn1-c1nn2cccc2c(=O)[nH]1] Q-1201
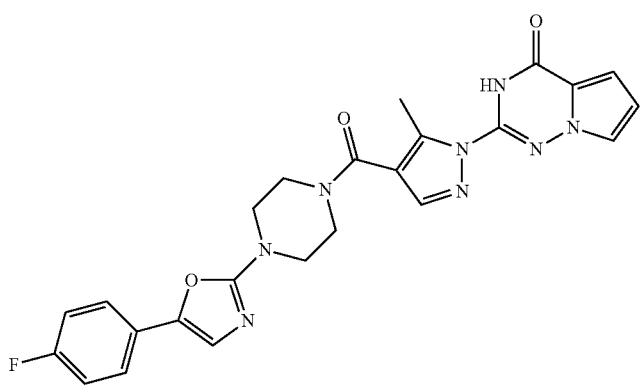 [SMILES: Cc1c(C(=O)N2CCN(c3ncc(-c4ccc(F)cc4)o3)CC2)cnn1-c1nn2cccc2c(=O)[nH]1] Q-1202
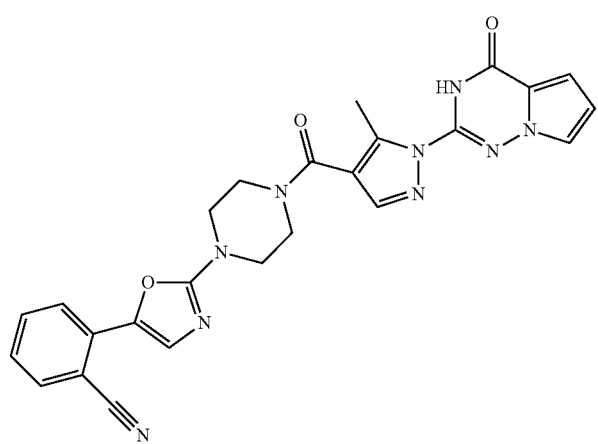 [SMILES: Cc1c(C(=O)N2CCN(c3ncc(-c4ccccc4C#N)o3)CC2)cnn1-c1nn2cccc2c(=O)[nH]1] Q-1203

TABLE C-continued
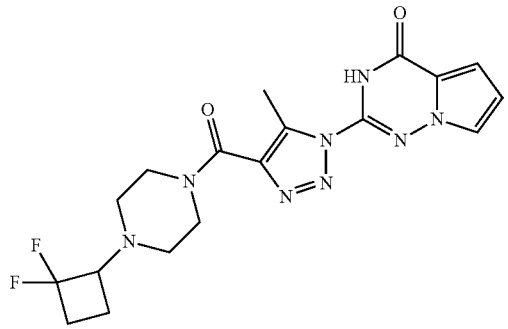 [SMILES: Cc1c(C(=O)N2CCN(C3CCC3(F)F)CC2)nnn1-c1nn2cccc2c(=O)[nH]1]
Q-1204
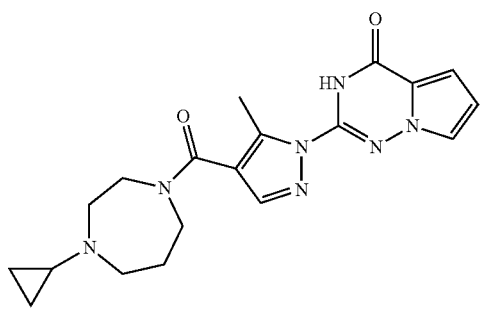 [SMILES: Cc1c(C(=O)N2CCCN(C3CC3)CC2)cnn1-c1nn2cccc2c(=O)[nH]1]
Q-1205
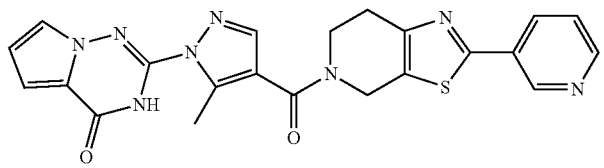 [SMILES: Cc1c(C(=O)N2CCc3nc(-c4cccnc4)sc3C2)cnn1-c1nn2cccc2c(=O)[nH]1]
Q-1206
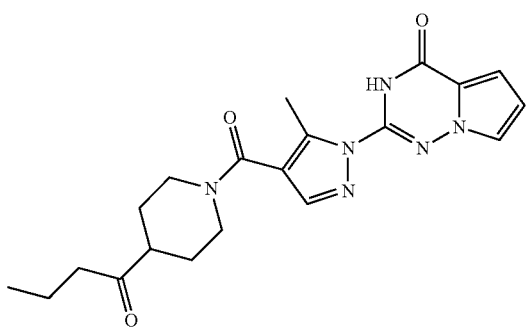 [SMILES: CCCC(=O)C1CCN(C(=O)c2cnn(-c3nn4cccc4c(=O)[nH]3)c2C)CC1]
Q-1207
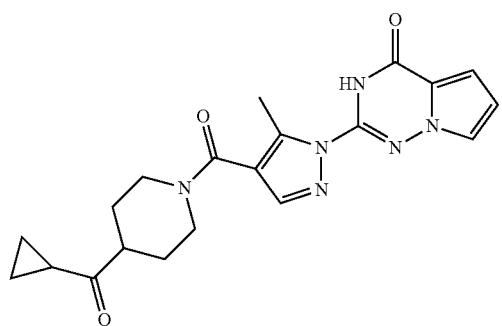 [SMILES: Cc1c(C(=O)N2CCC(C(=O)C3CC3)CC2)cnn1-c1nn2cccc2c(=O)[nH]1]
Q-1208

TABLE C-continued
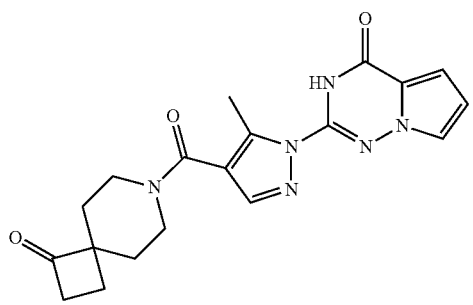 [SMILES: Cc1c(C(=O)N2CCC3(CCC3=O)CC2)cnn1-c1nn2cccc2c(=O)[nH]1]
Q-1209
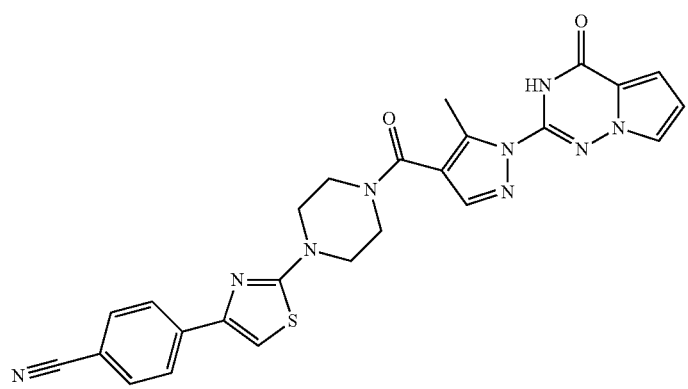 [SMILES: Cc1c(C(=O)N2CCN(c3nc(-c4ccc(C#N)cc4)cs3)CC2)cnn1-c1nn2cccc2c(=O)[nH]1]
Q-1210
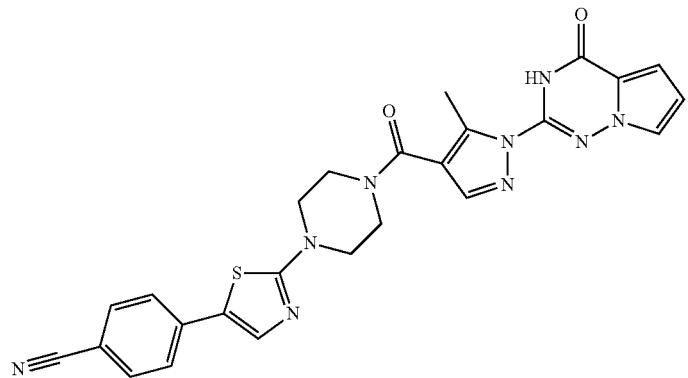 [SMILES: Cc1c(C(=O)N2CCN(c3ncc(-c4ccc(C#N)cc4)s3)CC2)cnn1-c1nn2cccc2c(=O)[nH]1]
Q-1211
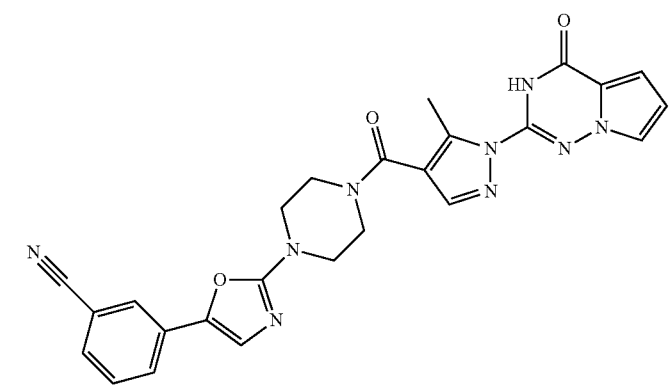 [SMILES: Cc1c(C(=O)N2CCN(c3ncc(-c4cccc(C#N)c4)o3)CC2)cnn1-c1nn2cccc2c(=O)[nH]1]
Q-1212

TABLE C-continued
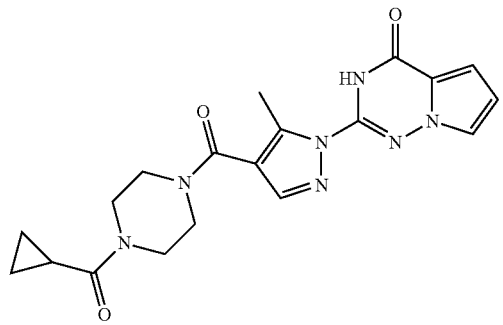 [SMILES: Cc1c(C(=O)N2CCN(C(=O)C3CC3)CC2)cnn1-c1nn2cccc2c(=O)[nH]1]
Q-1213
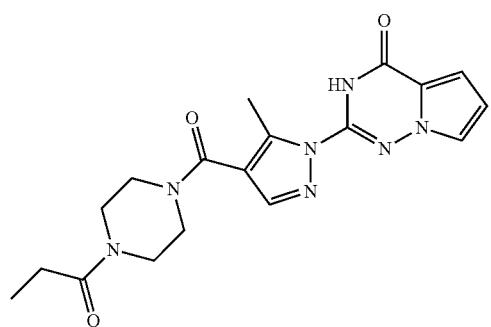 [SMILES: CCC(=O)N1CCN(C(=O)c2cnn(-c3nn4cccc4c(=O)[nH]3)c2C)CC1]
Q-1214
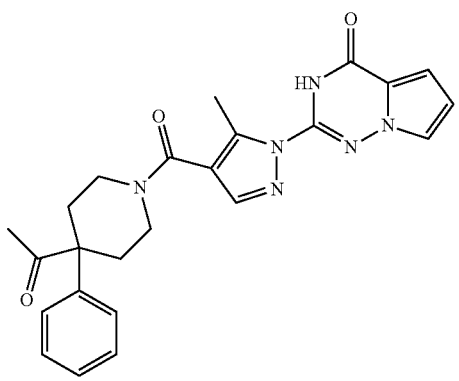 [SMILES: CC(=O)C1(c2ccccc2)CCN(C(=O)c2cnn(-c3nn4cccc4c(=O)[nH]3)c2C)CC1]
Q-1215
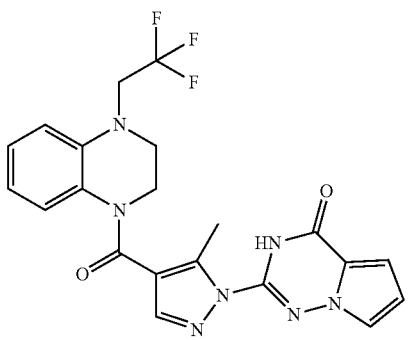 [SMILES: Cc1c(C(=O)N2CCN(CC(F)(F)F)c3ccccc32)cnn1-c1nn2cccc2c(=O)[nH]1]
Q-1216
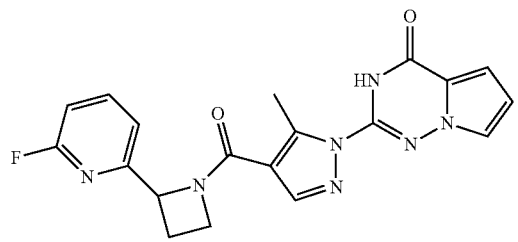 [SMILES: Cc1c(C(=O)N2CCC2c2cccc(F)n2)cnn1-c1nn2cccc2c(=O)[nH]1]
Q-1217

TABLE C-continued
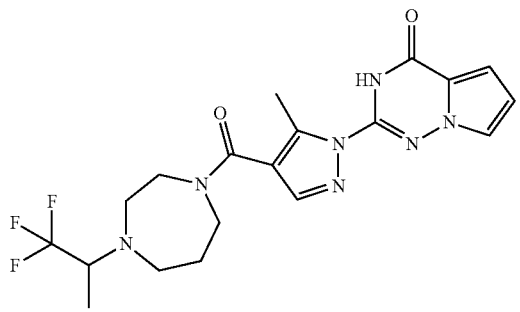 [SMILES: Cc1c(C(=O)N2CCCN(C(C)C(F)(F)F)CC2)cnn1-c1nn2cccc2c(=O)[nH]1]
Q-1218
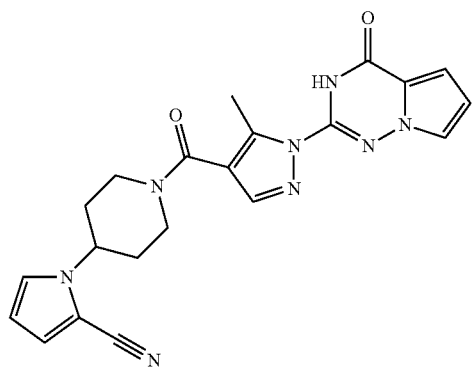 [SMILES: Cc1c(C(=O)N2CCC(n3cccc3C#N)CC2)cnn1-c1nn2cccc2c(=O)[nH]1]
Q-1219
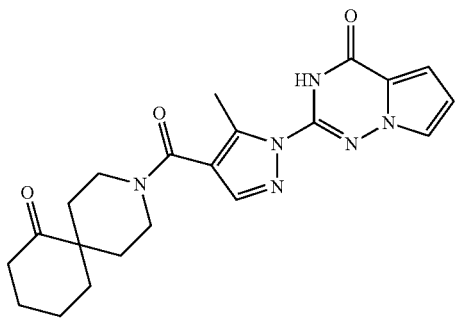 [SMILES: Cc1c(C(=O)N2CCC3(CCCCC3=O)CC2)cnn1-c1nn2cccc2c(=O)[nH]1]
Q-1220
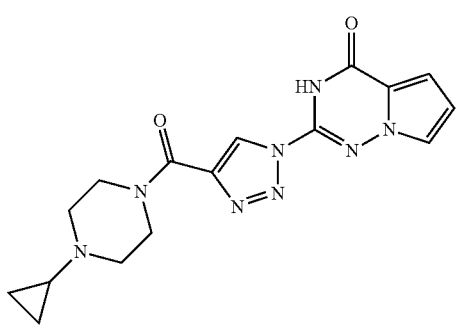
Q-1221
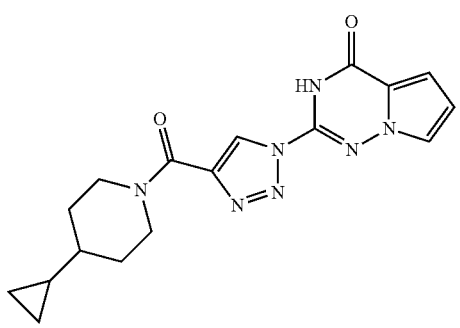 [SMILES: O=C(c1cn(-c2nn3cccc3c(=O)[nH]2)nn1)N1CCC(C2CC2)CC1]
Q-1222

TABLE C-continued
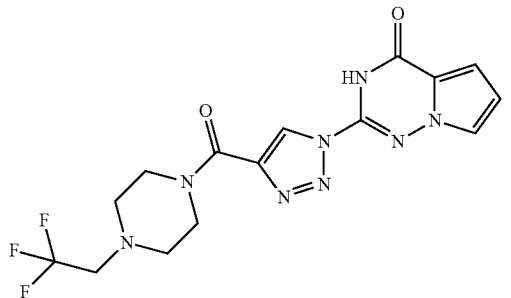 [SMILES: O=C(c1cn(-c2nn3cccc3c(=O)[nH]2)nn1)N1CCN(CC(F)(F)F)CC1] Q-1223
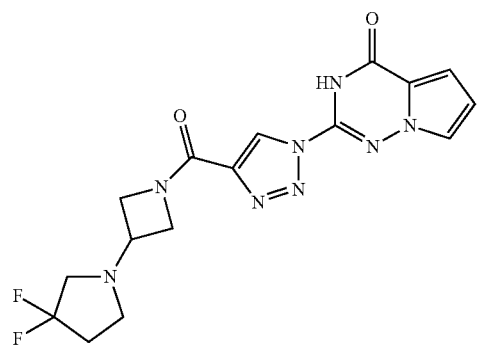 [SMILES: O=C(c1cn(-c2nn3cccc3c(=O)[nH]2)nn1)N1CC(N2CCC(F)(F)C2)C1] Q-1224
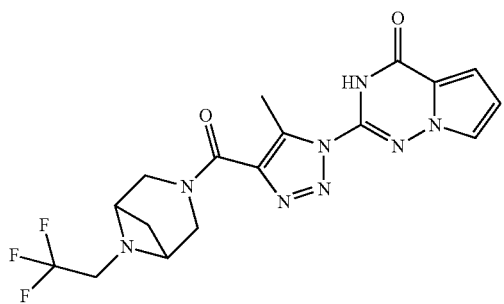 [SMILES: Cc1c(C(=O)N2CC3CC(C2)N3CC(F)(F)F)nnn1-c1nn2cccc2c(=O)[nH]1] Q-1225
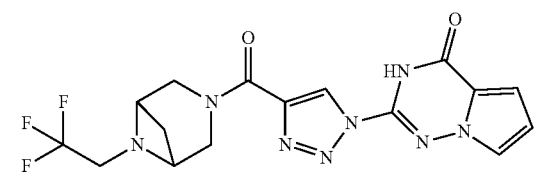 [SMILES: O=C(c1cn(-c2nn3cccc3c(=O)[nH]2)nn1)N1CC2CC(C1)N2CC(F)(F)F] Q-1226
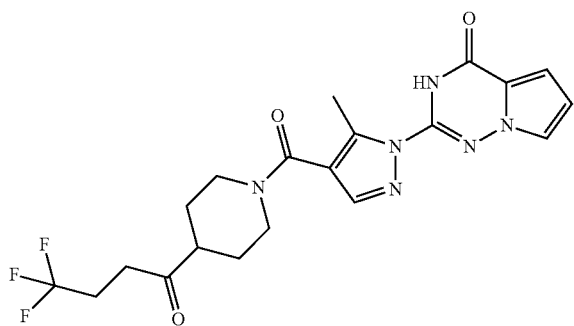 [SMILES: Cc1c(C(=O)N2CCC(C(=O)CCC(F)(F)F)CC2)cnn1-c1nn2cccc2c(=O)[nH]1] Q-1227

TABLE C-continued
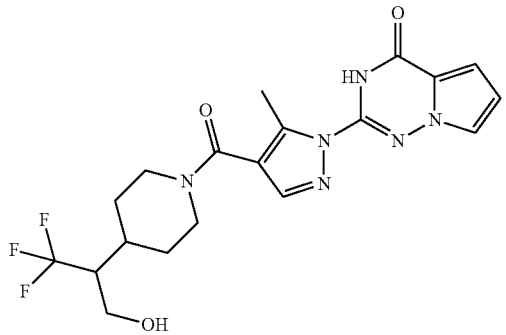 [SMILES: Cc1c(C(=O)N2CCC(C(CO)C(F)(F)F)CC2)cnn1-c1nn2cccc2c(=O)[nH]1]
Q-1228
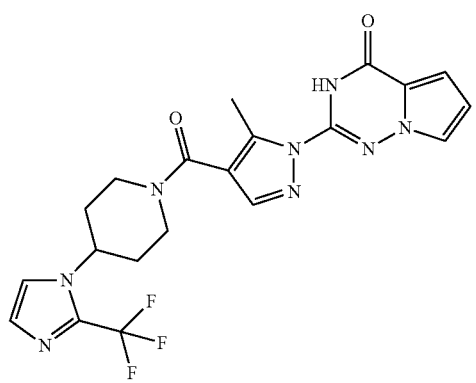 [SMILES: Cc1c(C(=O)N2CCC(n3ccnc3C(F)(F)F)CC2)cnn1-c1nn2cccc2c(=O)[nH]1]
Q-1229
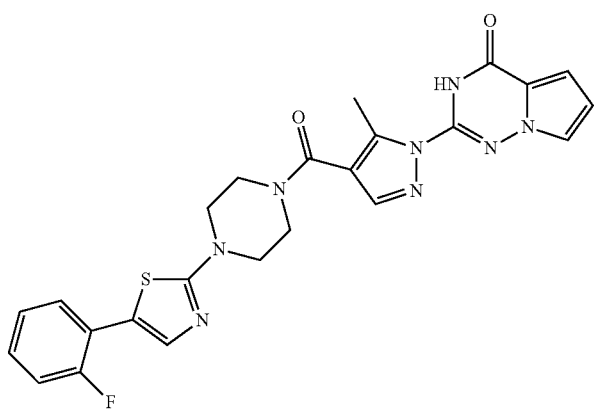
Q-1230
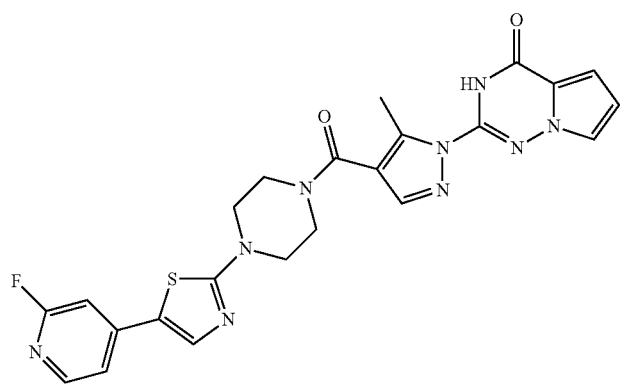
Q-1231

TABLE C-continued
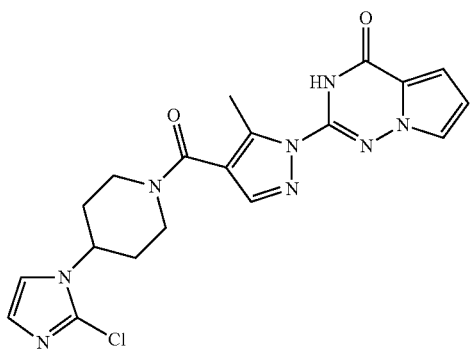 [SMILES: Cc1c(C(=O)N2CCC(n3ccnc3Cl)CC2)cnn1-c1nn2cccc2c(=O)[nH]1]
Q-1232
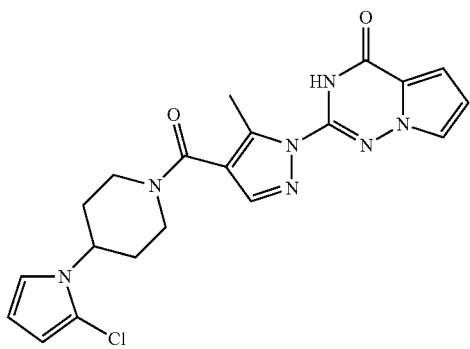 [SMILES: Cc1c(C(=O)N2CCC(n3cccc3Cl)CC2)cnn1-c1nn2cccc2c(=O)[nH]1]
Q-1233
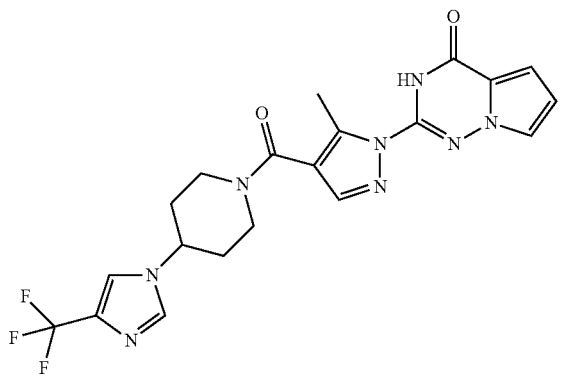 [SMILES: Cc1c(C(=O)N2CCC(n3cnc(C(F)(F)F)c3)CC2)cnn1-c1nn2cccc2c(=O)[nH]1]
Q-1234
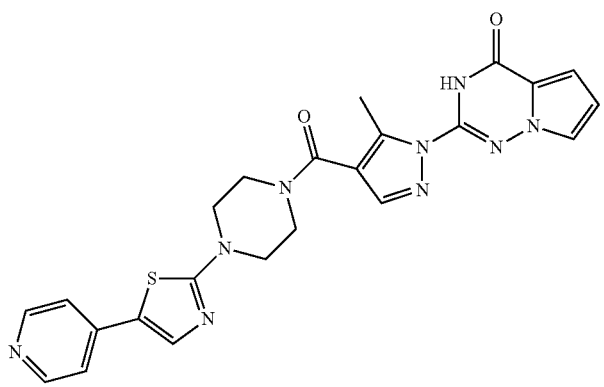
Q-1235

TABLE C-continued
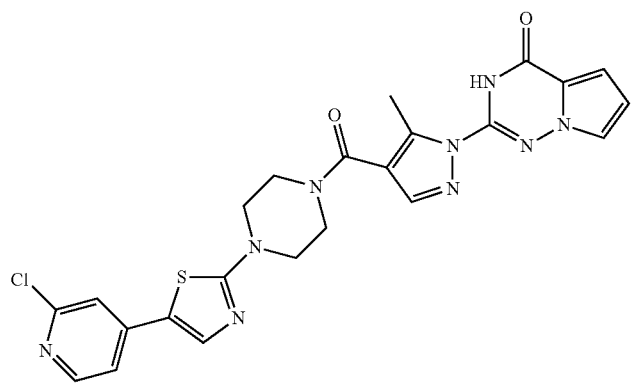
Q-1236
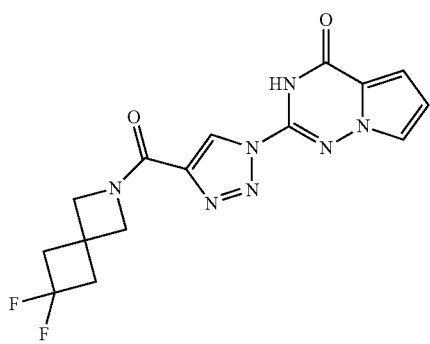 [SMILES: O=C(c1cn(-c2nn3cccc3c(=O)[nH]2)nn1)N1CC2(C1)CC(F)(F)C2]
Q-1237
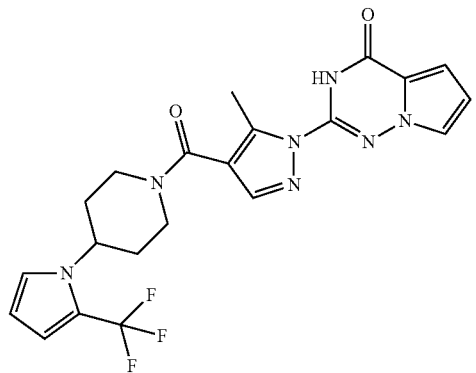
Q-1238
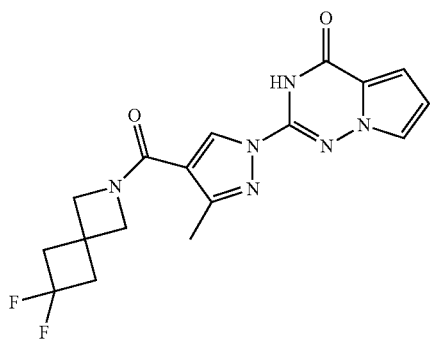 [SMILES: Cc1nn(-c2nn3cccc3c(=O)[nH]2)cc1C(=O)N1CC2(C1)CC(F)(F)C2]
Q-1239

TABLE C-continued
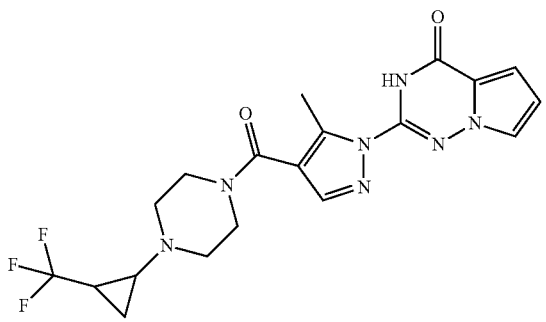 [SMILES: Cc1c(C(=O)N2CCN(C3CC3C(F)(F)F)CC2)cnn1-c1nn2cccc2c(=O)[nH]1]
Q-1240
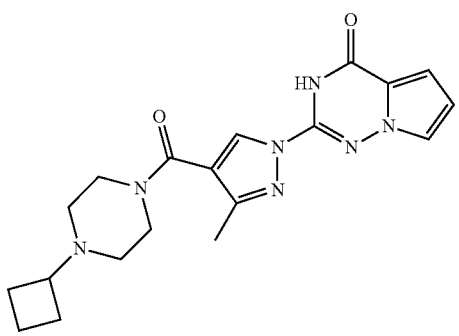 [SMILES: Cc1nn(-c2nn3cccc3c(=O)[nH]2)cc1C(=O)N1CCN(C2CCC2)CC1]
Q-1241
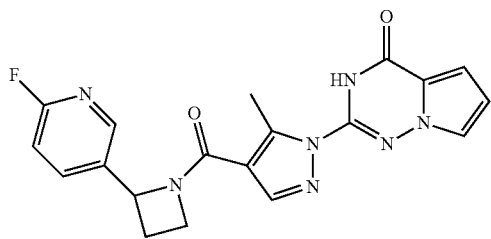 [SMILES: Cc1c(C(=O)N2CCC2c2ccc(F)nc2)cnn1-c1nn2cccc2c(=O)[nH]1]
Q-1242
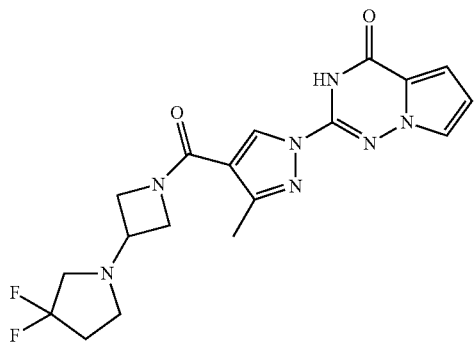 [SMILES: Cc1nn(-c2nn3cccc3c(=O)[nH]2)cc1C(=O)N1CC(N2CCC(F)(F)C2)C1]
Q-1243
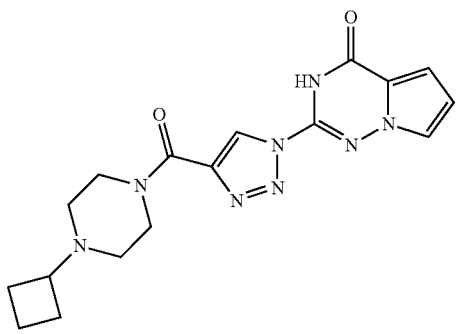 [SMILES: O=C(c1cn(-c2nn3cccc3c(=O)[nH]2)nn1)N1CCN(C2CCC2)CC1]
Q-1244

TABLE C-continued
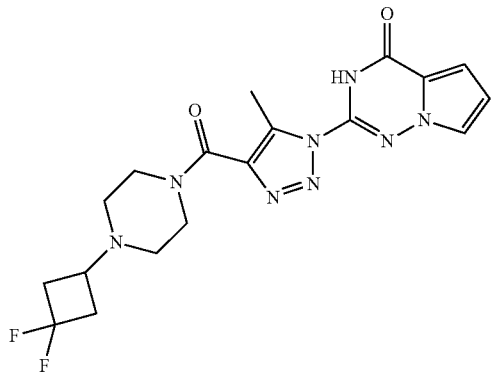 [SMILES: Cc1c(C(=O)N2CCN(C3CC(F)(F)C3)CC2)nnn1-c1nn2cccc2c(=O)[nH]1]
Q-1245
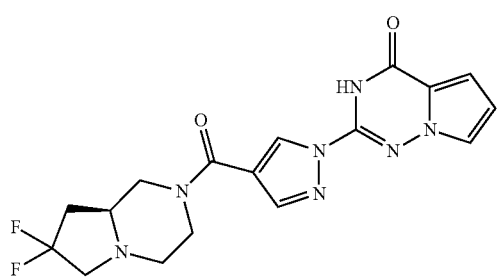 [SMILES: O=C(c1cnn(-c2nn3cccc3c(=O)[nH]2)c1)N1CCN2CC(F)(F)C[C@H]2C1]
Q-1246
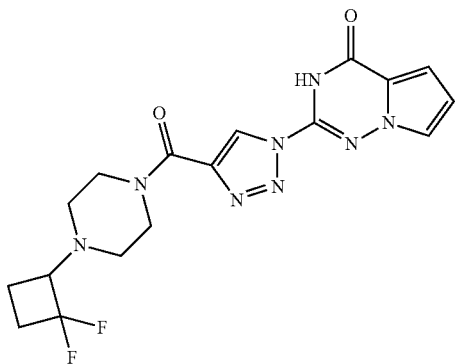 [SMILES: O=C(c1cn(-c2nn3cccc3c(=O)[nH]2)nn1)N1CCN(C2CCC2(F)F)CC1]
Q-1247
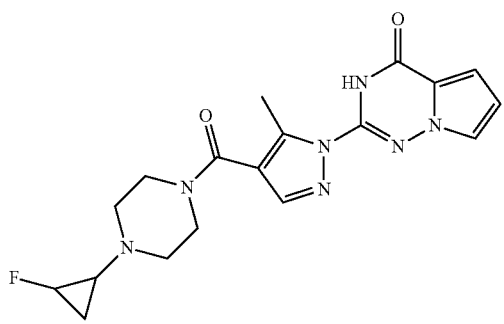 [SMILES: Cc1c(C(=O)N2CCN(C3CC3F)CC2)cnn1-c1nn2cccc2c(=O)[nH]1]
Q-1249

TABLE C-continued
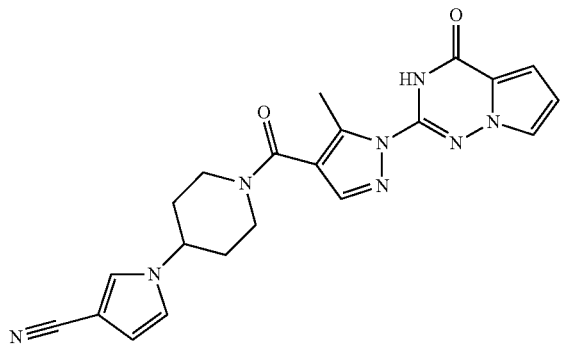 [SMILES: Cc1c(C(=O)N2CCC(n3ccc(C#N)c3)CC2)cnn1-c1nn2cccc2c(=O)[nH]1]
Q-1250
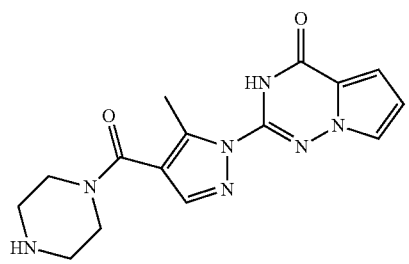 [SMILES: Cc1c(C(=O)N2CCNCC2)cnn1-c1nn2cccc2c(=O)[nH]1]
Q-1251
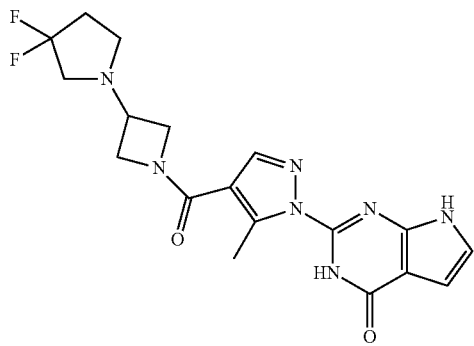 [SMILES: Cc1c(C(=O)N2CC(N3CCC(F)(F)C3)C2)cnn1-c1nc2[nH]ccc2c(=O)[nH]1]
Q-1254
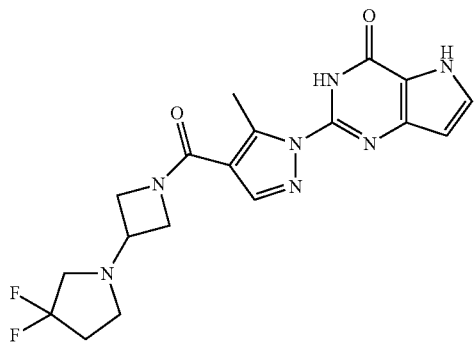 [SMILES: Cc1c(C(=O)N2CC(N3CCC(F)(F)C3)C2)cnn1-c1nc2cc[nH]c2c(=O)[nH]1]
Q-1255
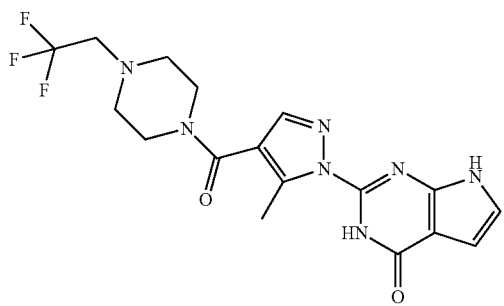 [SMILES: Cc1c(C(=O)N2CCN(CC(F)(F)F)CC2)cnn1-c1nc2[nH]ccc2c(=O)[nH]1]
Q-1256

TABLE C-continued
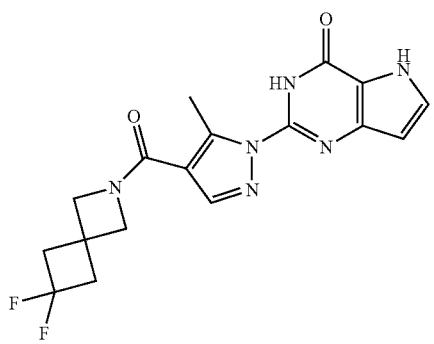 [SMILES: Cc1c(C(=O)N2CC3(C2)CC(F)(F)C3)cnn1-c1nc2cc[nH]c2c(=O)[nH]1] Q-1259
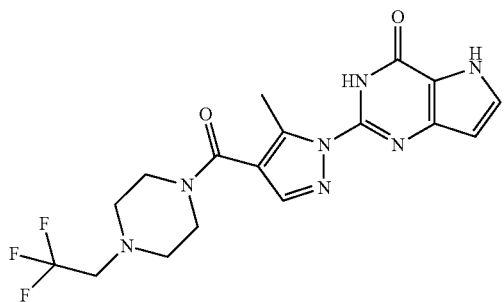 [SMILES: Cc1c(C(=O)N2CCN(CC(F)(F)F)CC2)cnn1-c1nc2cc[nH]c2c(=O)[nH]1] Q-1260
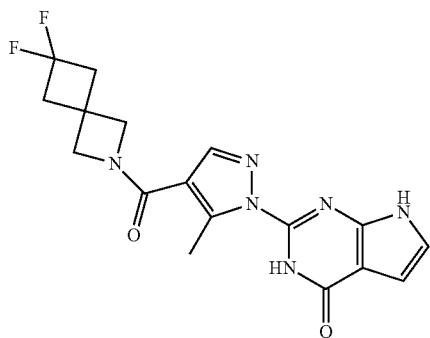 [SMILES: Cc1c(C(=O)N2CC3(C2)CC(F)(F)C3)cnn1-c1nc2[nH]ccc2c(=O)[nH]1] Q-1263
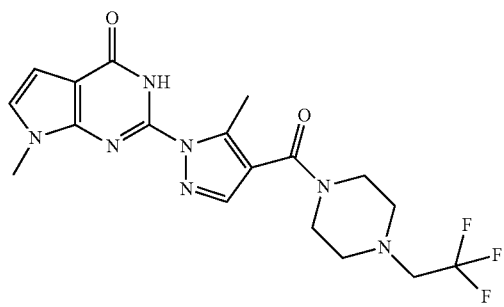 [SMILES: Cc1c(C(=O)N2CCN(CC(F)(F)F)CC2)cnn1-c1nc2c(ccn2C)c(=O)[nH]1] Q-1266
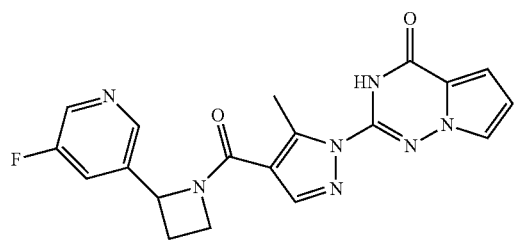 [SMILES: Cc1c(C(=O)N2CCC2c2cncc(F)c2)cnn1-c1nn2cccc2c(=O)[nH]1] Q-1269

TABLE C-continued
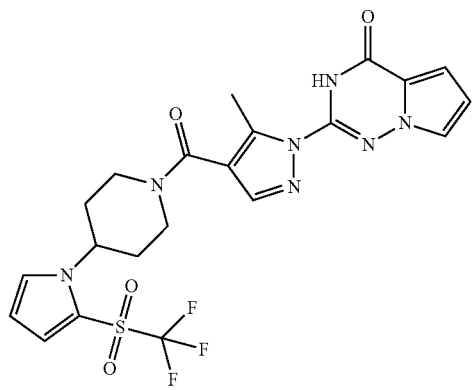 [SMILES: Cc1c(C(=O)N2CCC(n3cccc3S(=O)(=O)C(F)(F)F)CC2)cnn1-c1nn2cccc2c(=O)[nH]1]
Q-1288
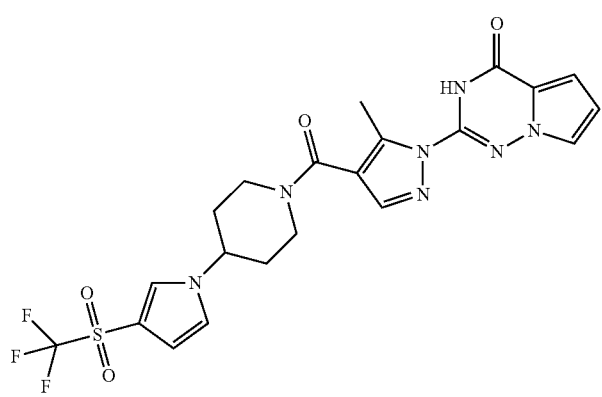 [SMILES: Cc1c(C(=O)N2CCC(n3ccc(S(=O)(=O)C(F)(F)F)c3)CC2)cnn1-c1nn2cccc2c(=O)[nH]1]
Q-1289
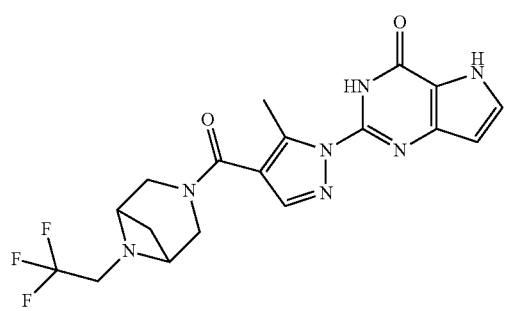 [SMILES: Cc1c(C(=O)N2CC3CC(C2)N3CC(F)(F)F)cnn1-c1nc2cc[nH]c2c(=O)[nH]1]
Q-1291
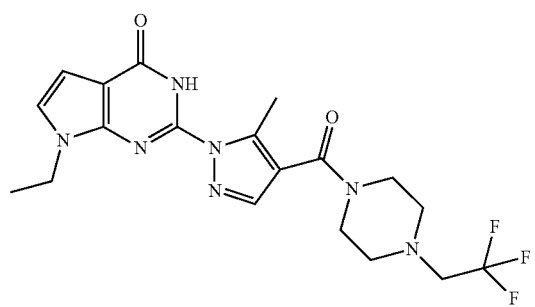 [SMILES: CCn1ccc2c(=O)[nH]c(-n3ncc(C(=O)N4CCN(CC(F)(F)F)CC4)c3C)nc21]
Q-1292

TABLE C-continued
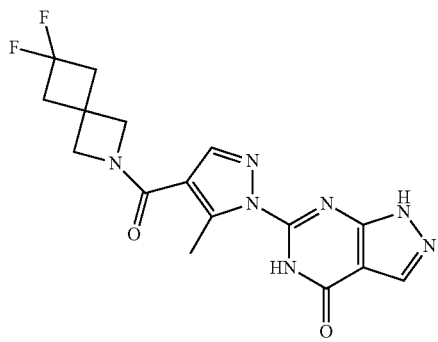 [SMILES: Cc1c(C(=O)N2CC3(C2)CC(F)(F)C3)cnn1-c1nc2[nH]ncc2c(=O)[nH]1]
Q-1295
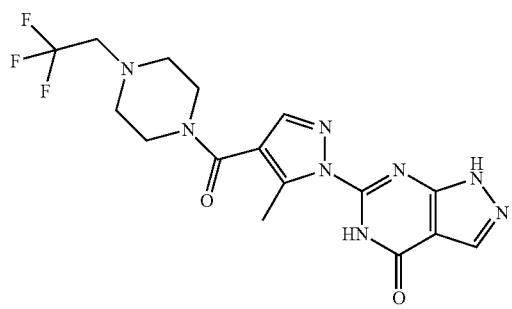 [SMILES: Cc1c(C(=O)N2CCN(CC(F)(F)F)CC2)cnn1-c1nc2[nH]ncc2c(=O)[nH]1]
Q-1296
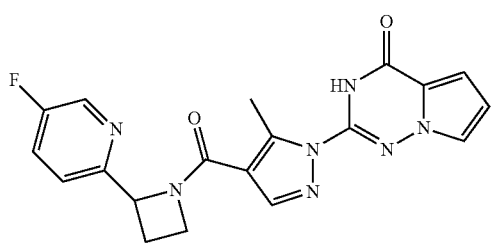 [SMILES: Cc1c(C(=O)N2CCC2c2ccc(F)cn2)cnn1-c1nn2cccc2c(=O)[nH]1]
Q-1301
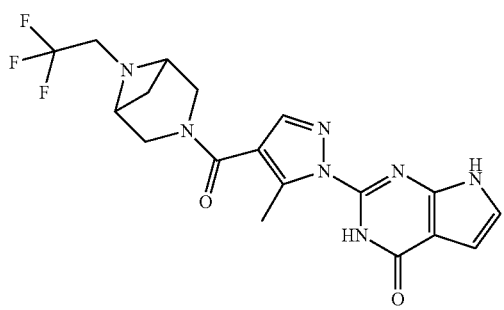 [SMILES: Cc1c(C(=O)N2CC3CC(C2)N3CC(F)(F)F)cnn1-c1nc2[nH]ccc2c(=O)[nH]1]
Q-1305
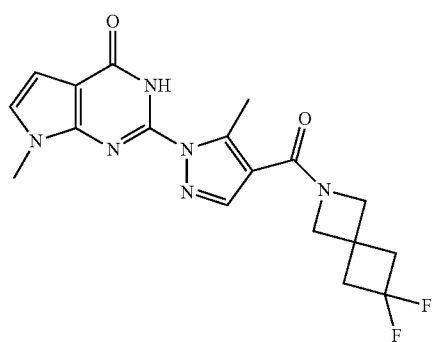 [SMILES: Cc1c(C(=O)N2CC3(C2)CC(F)(F)C3)cnn1-c1nc2c(ccn2C)c(=O)[nH]1]
Q-1306

TABLE C-continued
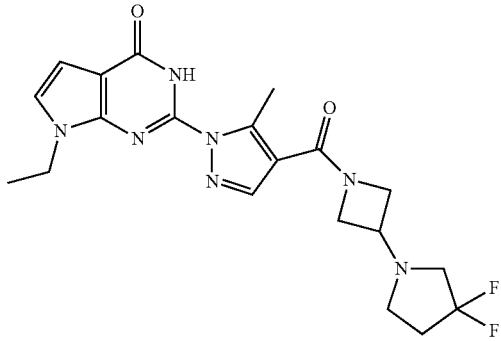 [SMILES: CCn1ccc2c(=O)[nH]c(-n3ncc(C(=O)N4CC(N5CCC(F)(F)C5)C4)c3C)nc21]
Q-1311
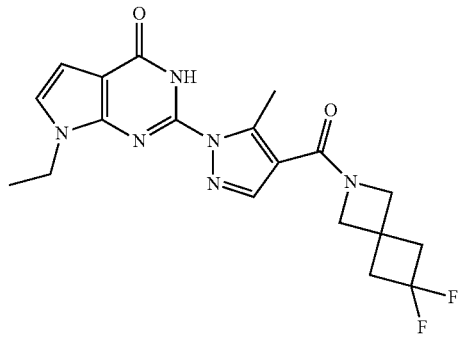 [SMILES: CCn1ccc2c(=O)[nH]c(-n3ncc(C(=O)N4CC5(C4)CC(F)(F)C5)c3C)nc21]
Q-1313
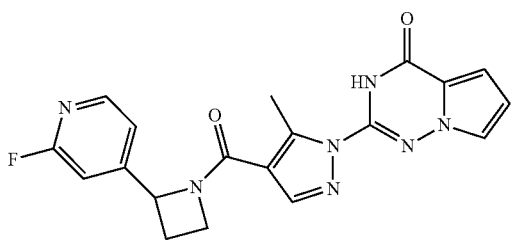 [SMILES: Cc1c(C(=O)N2CCC2c2ccnc(F)c2)cnn1-c1nn2cccc2c(=O)[nH]1]
Q-1320
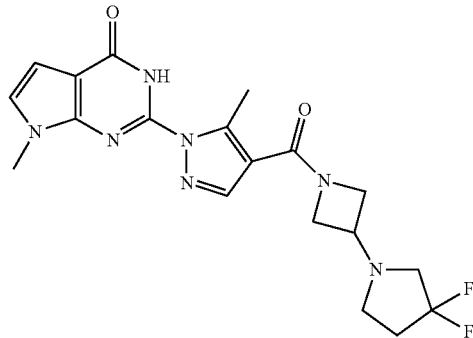 [SMILES: Cc1c(C(=O)N2CC(N3CCC(F)(F)C3)C2)cnn1-c1nc2c(ccn2C)c(=O)[nH]1]
Q-1322
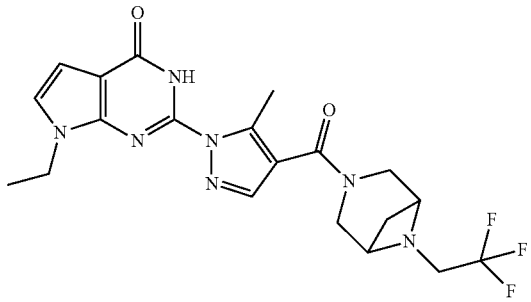 [SMILES: CCn1ccc2c(=O)[nH]c(-n3ncc(C(=O)N4CC5CC(C4)N5CC(F)(F)F)c3C)nc21]
Q-1341

TABLE C-continued
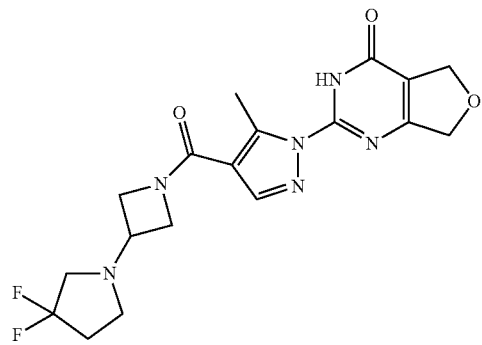 [SMILES: Cc1c(C(=O)N2CC(N3CCC(F)(F)C3)C2)cnn1-c1nc2c(c(=O)[nH]1)COC2]
Q-1343
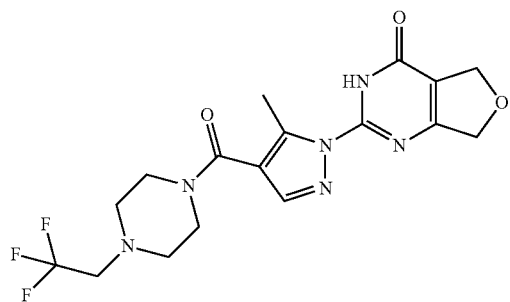 [SMILES: Cc1c(C(=O)N2CCN(CC(F)(F)F)CC2)cnn1-c1nc2c(c(=O)[nH]1)COC2]
Q-1344
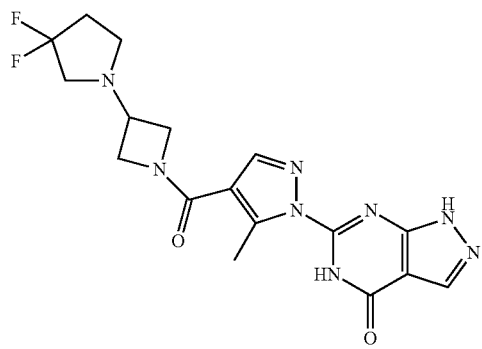 [SMILES: Cc1c(C(=O)N2CC(N3CCC(F)(F)C3)C2)cnn1-c1nc2[nH]ncc2c(=O)[nH]1]
Q-1345
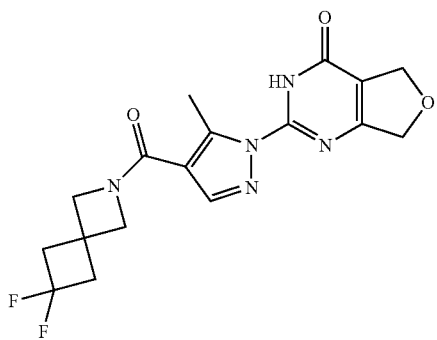 [SMILES: Cc1c(C(=O)N2CC3(C2)CC(F)(F)C3)cnn1-c1nc2c(c(=O)[nH]1)COC2]
Q-1346

475
476
TABLE C-continued
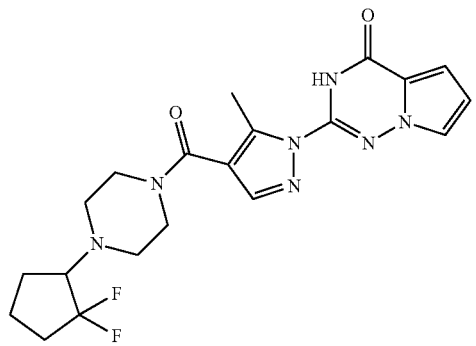 [SMILES: Cc1c(C(=O)N2CCN(C3CCCC3(F)F)CC2)cnn1-c1nn2cccc2c(=O)[nH]1]
Q-1362
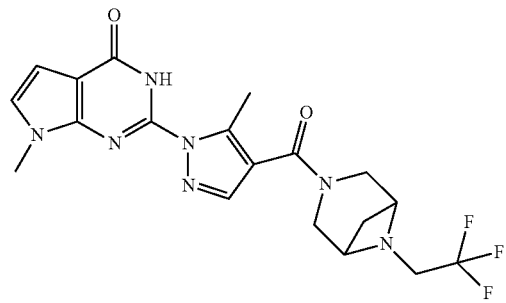 [SMILES: Cc1c(C(=O)N2CC3CC(C2)N3CC(F)(F)F)cnn1-c1nc2c(ccn2C)c(=O)[nH]1]
Q-1365
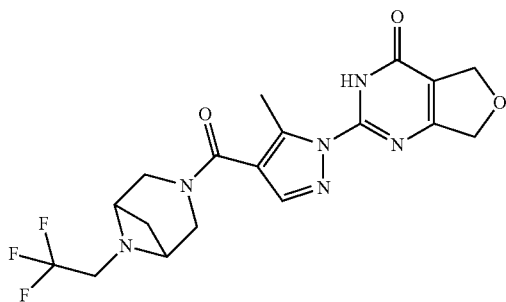 [SMILES: Cc1c(C(=O)N2CC3CC(C2)N3CC(F)(F)F)cnn1-c1nc2c(c(=O)[nH]1)COC2]
Q-1483
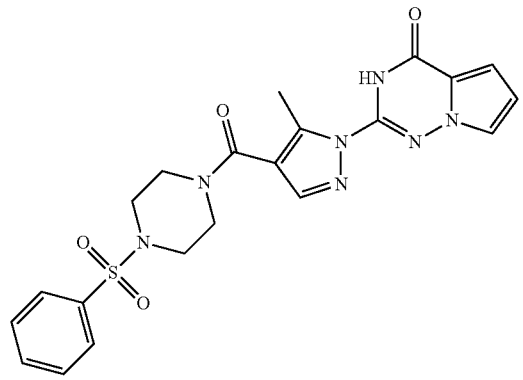 [SMILES: Cc1c(C(=O)N2CCN(S(=O)(=O)c3ccccc3)CC2)cnn1-c1nn2cccc2c(=O)[nH]1]
Q-1535
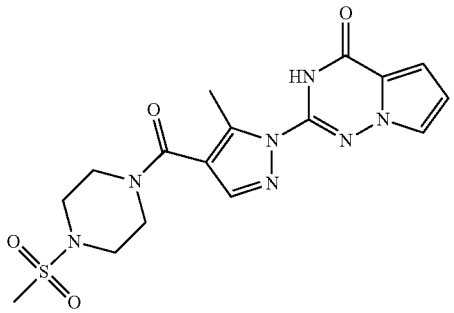 [SMILES: Cc1c(C(=O)N2CCN(S(C)(=O)=O)CC2)cnn1-c1nn2cccc2c(=O)[nH]1]
Q-1539

TABLE C-continued
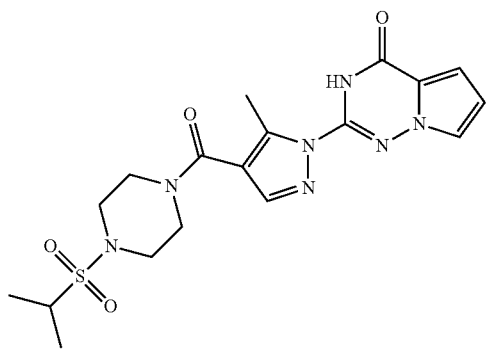
Q-1558
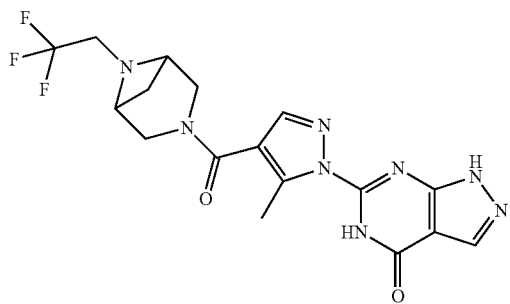 [SMILES: Cc1c(C(=O)N2CC3CC(C2)N3CC(F)(F)F)cnn1-c1nc2[nH]ncc2c(=O)[nH]1]
Q-1560
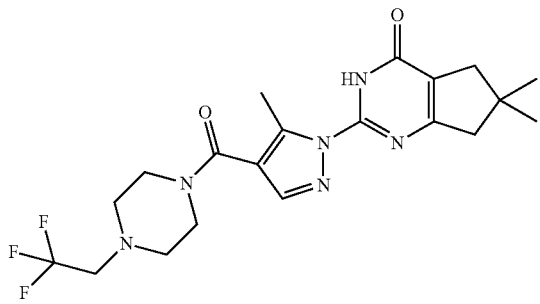 [SMILES: Cc1c(C(=O)N2CCN(CC(F)(F)F)CC2)cnn1-c1nc2c(c(=O)[nH]1)CC(C)(C)C2]
Q-1563
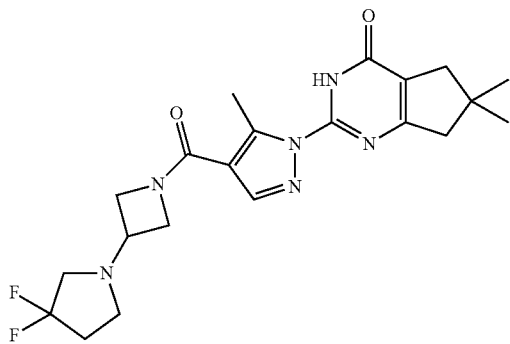 [SMILES: Cc1c(C(=O)N2CC(N3CCC(F)(F)C3)C2)cnn1-c1nc2c(c(=O)[nH]1)CC(C)(C)C2]
Q-1564

TABLE C-continued
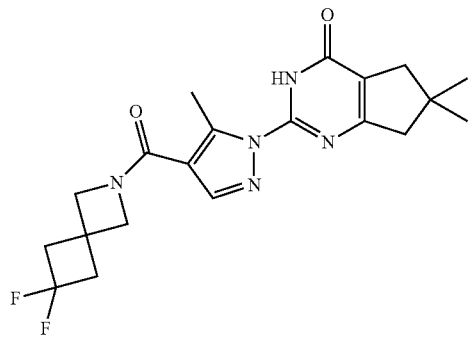 [SMILES: Cc1c(C(=O)N2CC3(C2)CC(F)(F)C3)cnn1-c1nc2c(c(=O)[nH]1)CC(C)(C)C2]
Q-1565
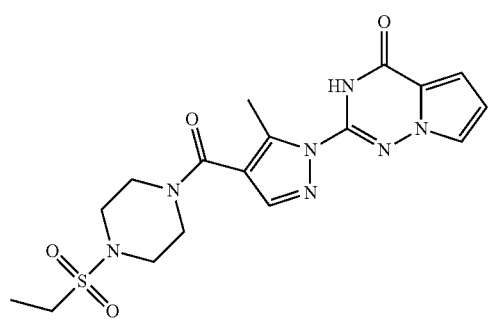 [SMILES: CCS(=O)(=O)N1CCN(C(=O)c2cnn(-c3nn4cccc4c(=O)[nH]3)c2C)CC1]
Q-1581
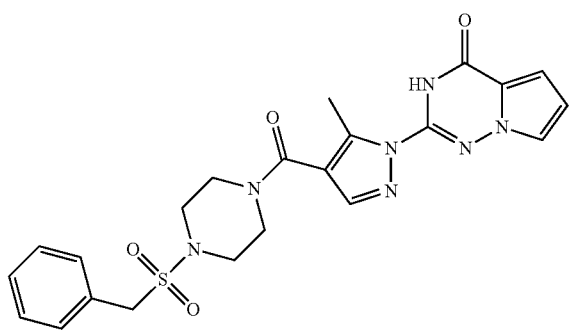 [SMILES: Cc1c(C(=O)N2CCN(S(=O)(=O)Cc3ccccc3)CC2)cnn1-c1nn2cccc2c(=O)[nH]1]
Q-1591
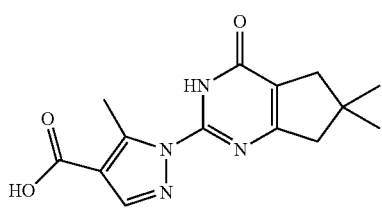 [SMILES: Cc1c(C(=O)O)cnn1-c1nc2c(c(=O)[nH]1)CC(C)(C)C2]
Q-1597
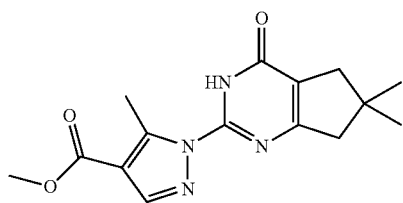
Q-1641

TABLE C-continued
Q-1728
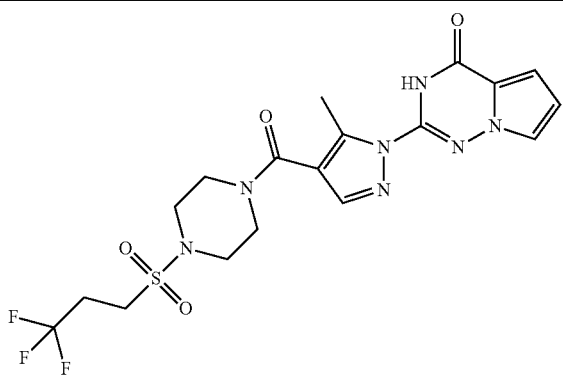
Q-1794
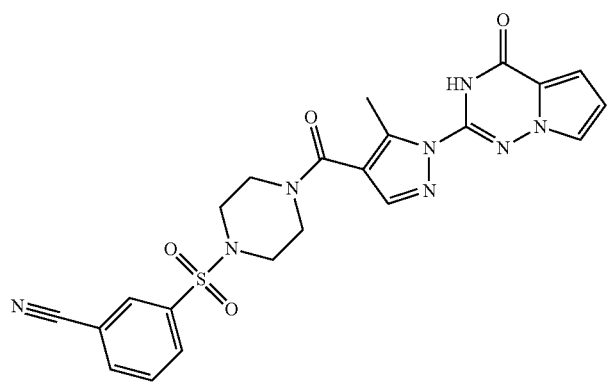 [SMILES: Cc1c(C(=O)N2CCN(S(=O)(=O)c3cccc(C#N)c3)CC2)cnn1-c1nn2cccc2c(=O)[nH]1]
Q-1796
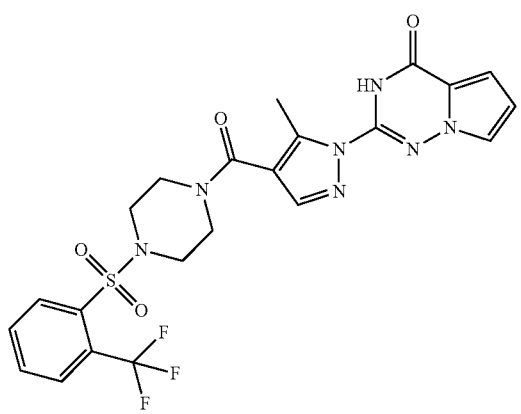 [SMILES: Cc1c(C(=O)N2CCN(S(=O)(=O)c3ccccc3C(F)(F)F)CC2)cnn1-c1nn2cccc2c(=O)[nH]1]
Q-1797
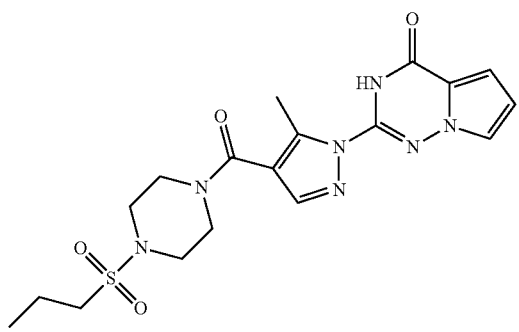 [SMILES: CCCS(=O)(=O)N1CCN(C(=O)c2cnn(-c3nn4cccc4c(=O)[nH]3)c2C)CC1]

TABLE C-continued
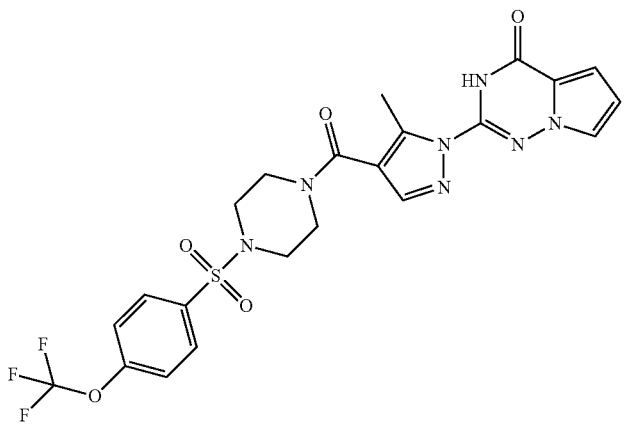 [SMILES: Cc1c(C(=O)N2CCN(S(=O)(=O)c3ccc(OC(F)(F)F)cc3)CC2)cnn1-c1nn2cccc2c(=O)[nH]1]
Q-1798
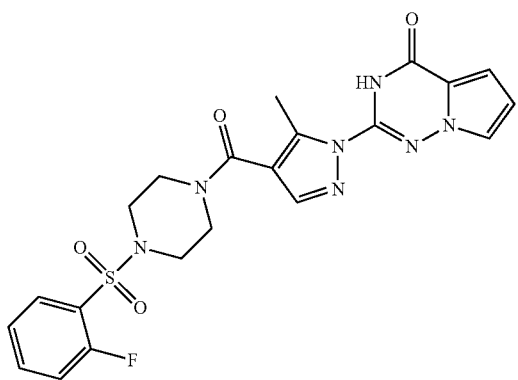 [SMILES: Cc1c(C(=O)N2CCN(S(=O)(=O)c3ccccc3F)CC2)cnn1-c1nn2cccc2c(=O)[nH]1]
Q-1799
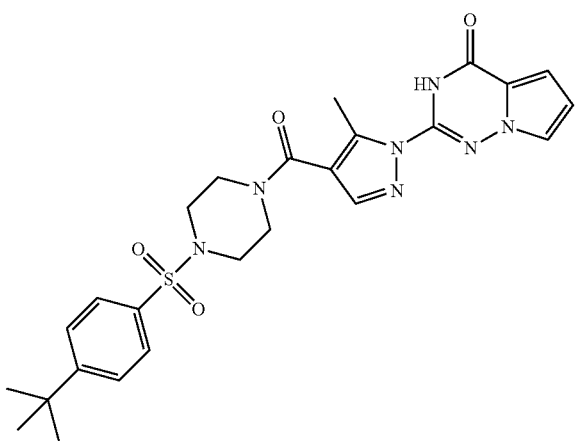 [SMILES: Cc1c(C(=O)N2CCN(S(=O)(=O)c3ccc(C(C)(C)C)cc3)CC2)cnn1-c1nn2cccc2c(=O)[nH]1]
Q-1800
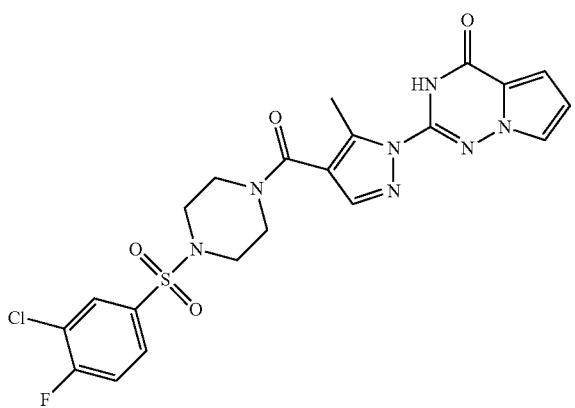 [SMILES: Cc1c(C(=O)N2CCN(S(=O)(=O)c3ccc(F)c(Cl)c3)CC2)cnn1-c1nn2cccc2c(=O)[nH]1]
Q-1801

TABLE C-continued
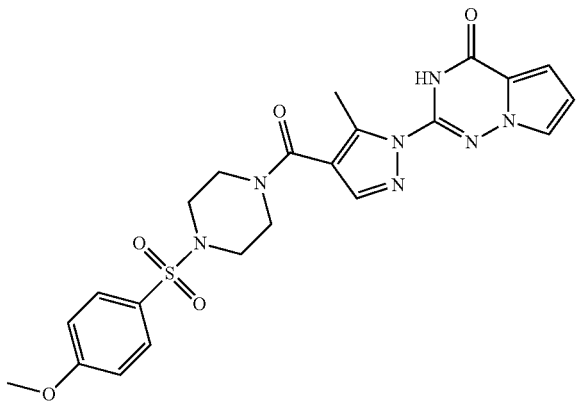 [SMILES: COc1ccc(S(=O)(=O)N2CCN(C(=O)c3cnn(-c4nn5cccc5c(=O)[nH]4)c3C)CC2)cc1]
Q-1804
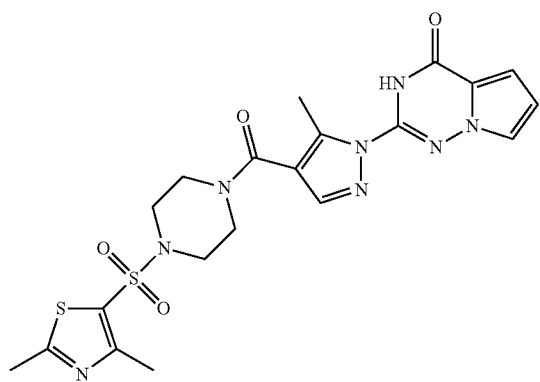 [SMILES: Cc1nc(C)c(S(=O)(=O)N2CCN(C(=O)c3cnn(-c4nn5cccc5c(=O)[nH]4)c3C)CC2)s1]
Q-1805
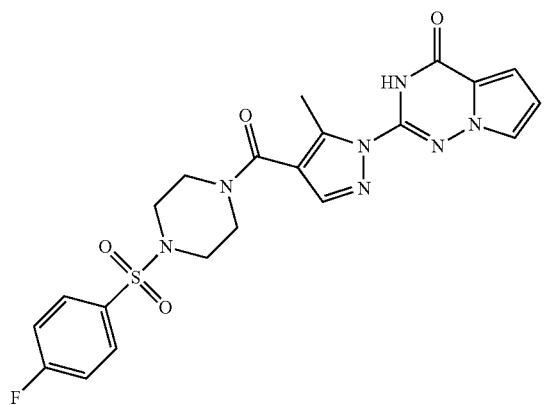 [SMILES: Cc1c(C(=O)N2CCN(S(=O)(=O)c3ccc(F)cc3)CC2)cnn1-c1nn2cccc2c(=O)[nH]1]
Q-1807
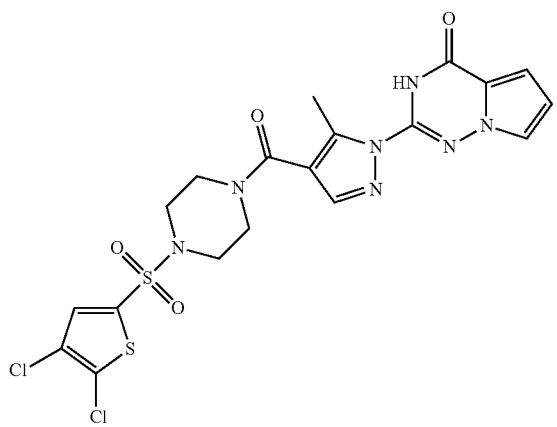 [SMILES: Cc1c(C(=O)N2CCN(S(=O)(=O)c3cc(Cl)c(Cl)s3)CC2)cnn1-c1nn2cccc2c(=O)[nH]1]
Q-1814

TABLE C-continued
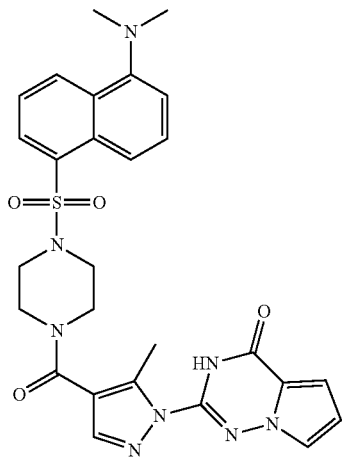 [SMILES: Cc1c(C(=O)N2CCN(S(=O)(=O)c3cccc4c(N(C)C)cccc34)CC2)cnn1-c1nn2cccc2c(=O)[nH]1]
Q-1815
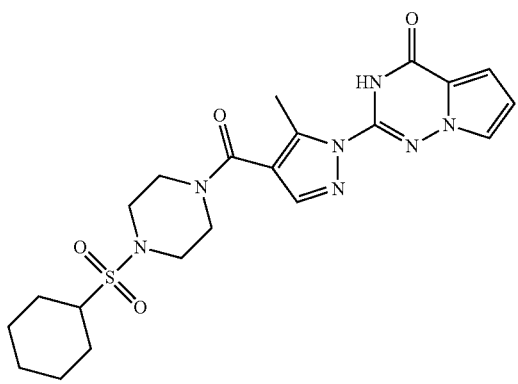 [SMILES: Cc1c(C(=O)N2CCN(S(=O)(=O)C3CCCCC3)CC2)cnn1-c1nn2cccc2c(=O)[nH]1]
Q-1818
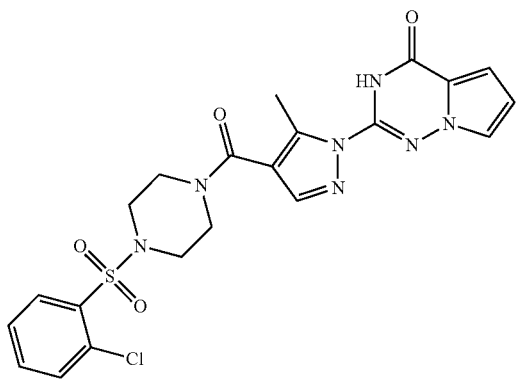
Q-1819
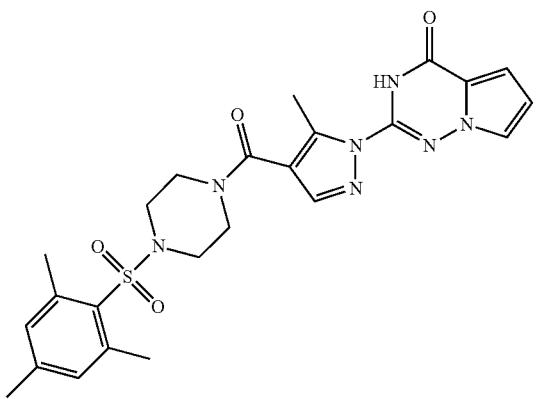 [SMILES: Cc1cc(C)c(S(=O)(=O)N2CCN(C(=O)c3cnn(-c4nn5cccc5c(=O)[nH]4)c3C)CC2)c(C)c1]
Q-1820

TABLE C-continued
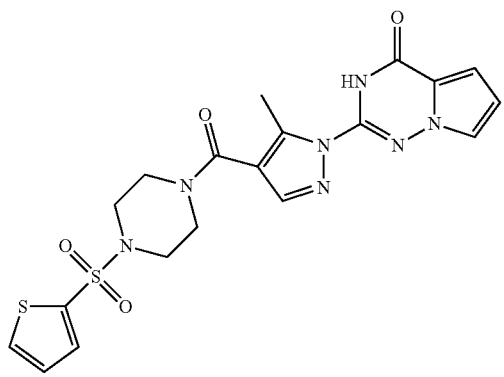 [SMILES: Cc1c(C(=O)N2CCN(S(=O)(=O)c3cccs3)CC2)cnn1-c1nn2cccc2c(=O)[nH]1]
Q-1821
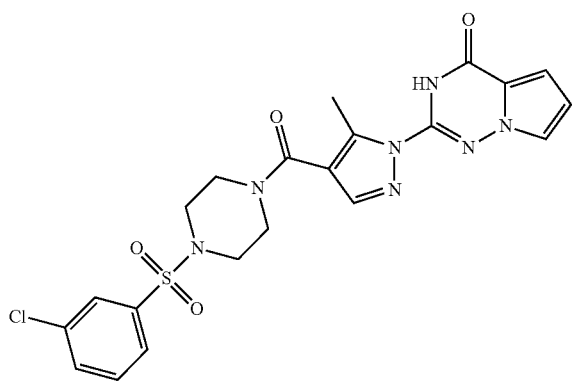 [SMILES: Cc1c(C(=O)N2CCN(S(=O)(=O)c3cccc(Cl)c3)CC2)cnn1-c1nn2cccc2c(=O)[nH]1]
Q-1822
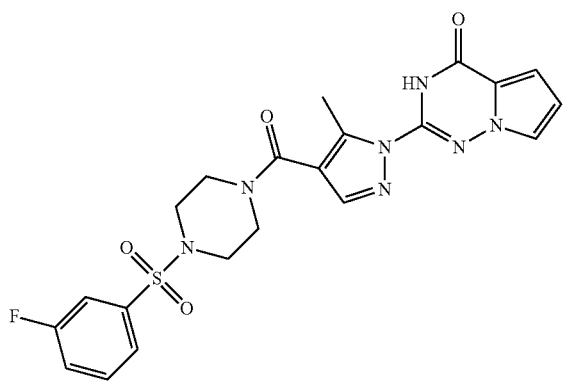 [SMILES: Cc1c(C(=O)N2CCN(S(=O)(=O)c3cccc(F)c3)CC2)cnn1-c1nn2cccc2c(=O)[nH]1]
Q-1823
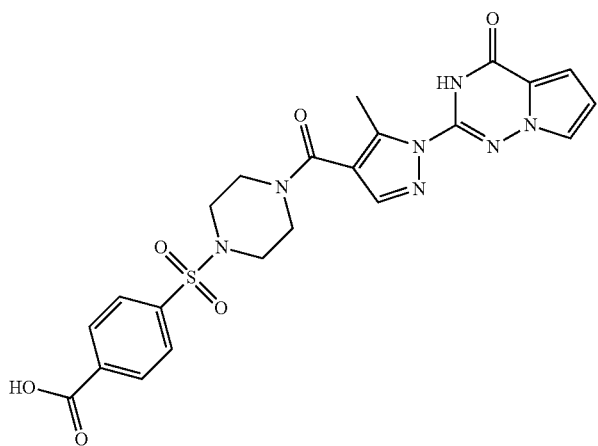 [SMILES: Cc1c(C(=O)N2CCN(S(=O)(=O)c3ccc(C(=O)O)cc3)CC2)cnn1-c1nn2cccc2c(=O)[nH]1]
Q-1824

TABLE C-continued
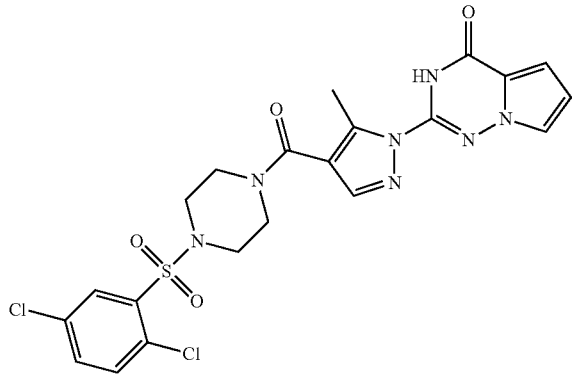 [SMILES: Cc1c(C(=O)N2CCN(S(=O)(=O)c3cc(Cl)ccc3Cl)CC2)cnn1-c1nn2cccc2c(=O)[nH]1]
Q-1825
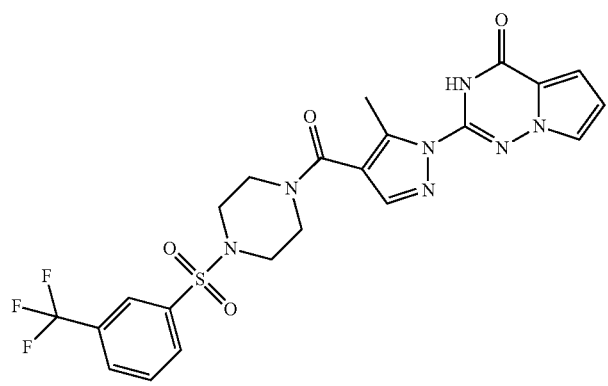 [SMILES: Cc1c(C(=O)N2CCN(S(=O)(=O)c3cccc(C(F)(F)F)c3)CC2)cnn1-c1nn2cccc2c(=O)[nH]1]
Q-1826
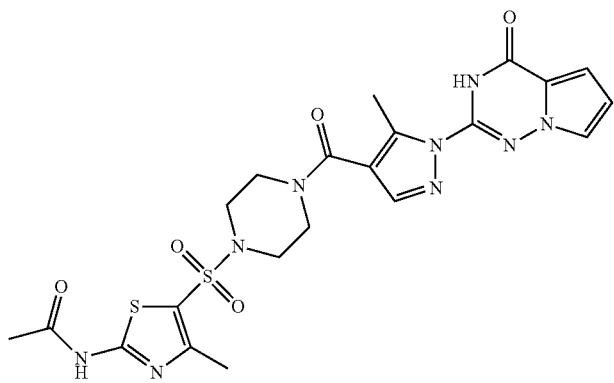 [SMILES: CC(=O)Nc1nc(C)c(S(=O)(=O)N2CCN(C(=O)c3cnn(-c4nn5cccc5c(=O)[nH]4)c3C)CC2)s1]
Q-1827
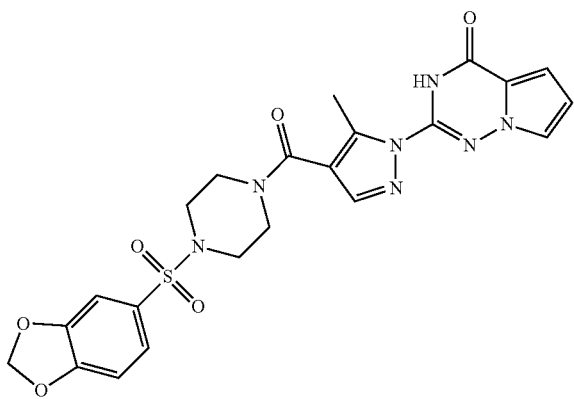 [SMILES: Cc1c(C(=O)N2CCN(S(=O)(=O)c3ccc4c(c3)OCO4)CC2)cnn1-c1nn2cccc2c(=O)[nH]1]
Q-1829

TABLE C-continued
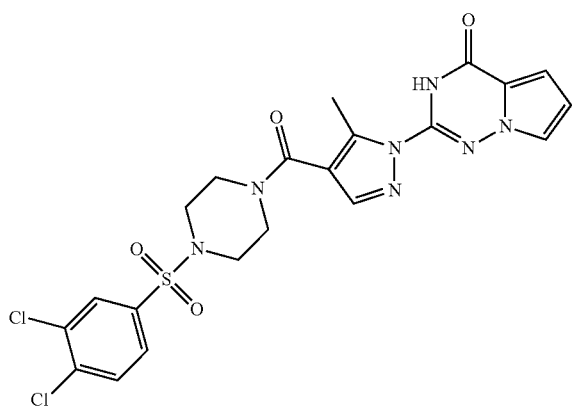 [SMILES: Cc1c(C(=O)N2CCN(S(=O)(=O)c3ccc(Cl)c(Cl)c3)CC2)cnn1-c1nn2cccc2c(=O)[nH]1]
Q-1830
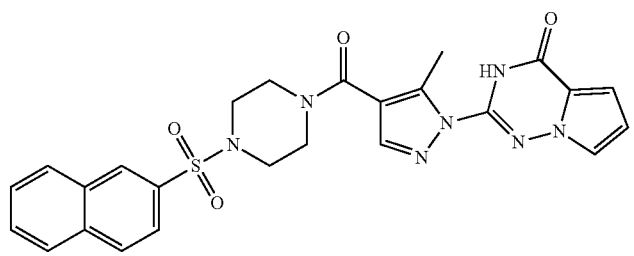 [SMILES: Cc1c(C(=O)N2CCN(S(=O)(=O)c3ccc4ccccc4c3)CC2)cnn1-c1nn2cccc2c(=O)[nH]1]
Q-1831
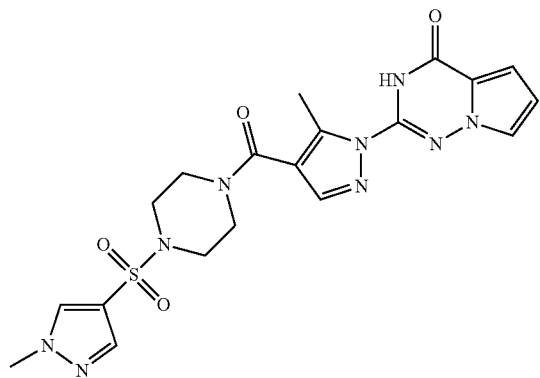 [SMILES: Cc1c(C(=O)N2CCN(S(=O)(=O)c3cnn(C)c3)CC2)cnn1-c1nn2cccc2c(=O)[nH]1]
Q-1832
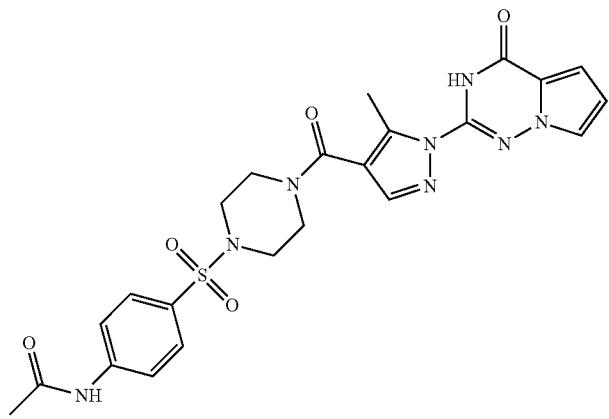 [SMILES: CC(=O)Nc1ccc(S(=O)(=O)N2CCN(C(=O)c3cnn(-c4nn5cccc5c(=O)[nH]4)c3C)CC2)cc1]
Q-1833

TABLE C-continued
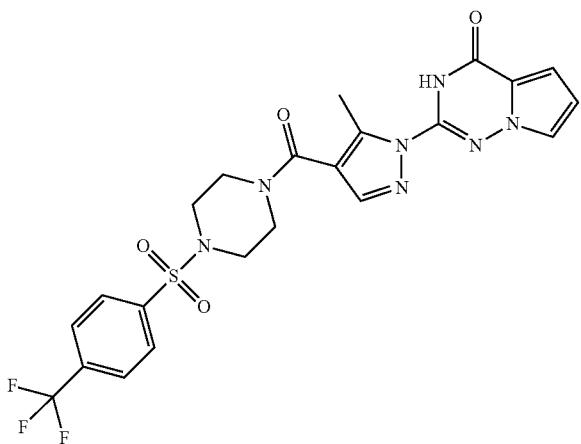 [SMILES: Cc1c(C(=O)N2CCN(S(=O)(=O)c3ccc(C(F)(F)F)cc3)CC2)cnn1-c1nn2cccc2c(=O)[nH]1]
Q-1834
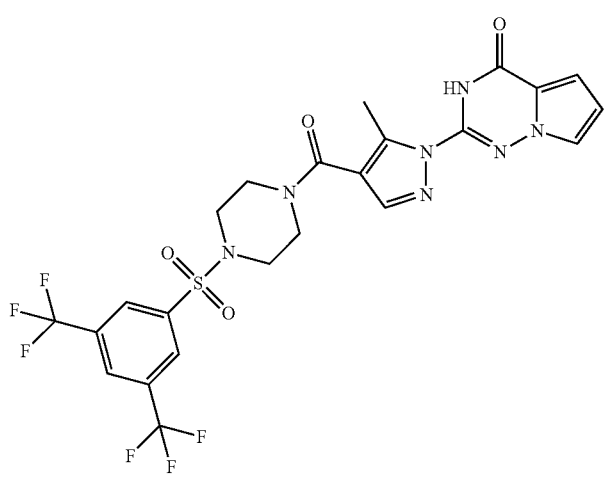 [SMILES: Cc1c(C(=O)N2CCN(S(=O)(=O)c3cc(C(F)(F)F)cc(C(F)(F)F)c3)CC2)cnn1-c1nn2cccc2c(=O)[nH]1]
Q-1835
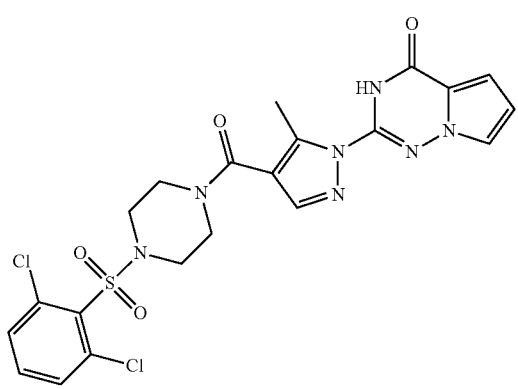 [SMILES: Cc1c(C(=O)N2CCN(S(=O)(=O)c3c(Cl)cccc3Cl)CC2)cnn1-c1nn2cccc2c(=O)[nH]1]
Q-1836

TABLE C-continued
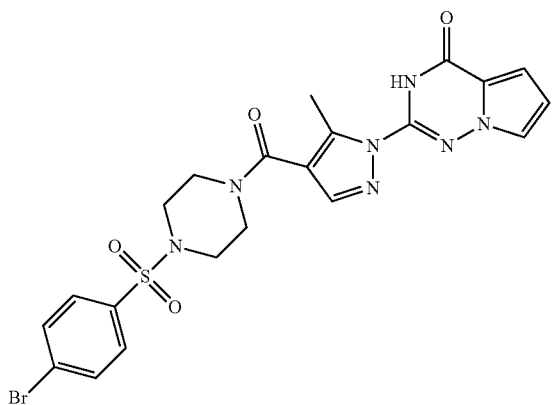 [SMILES: Cc1c(C(=O)N2CCN(S(=O)(=O)c3ccc(Br)cc3)CC2)cnn1-c1nn2cccc2c(=O)[nH]1]
Q-1837
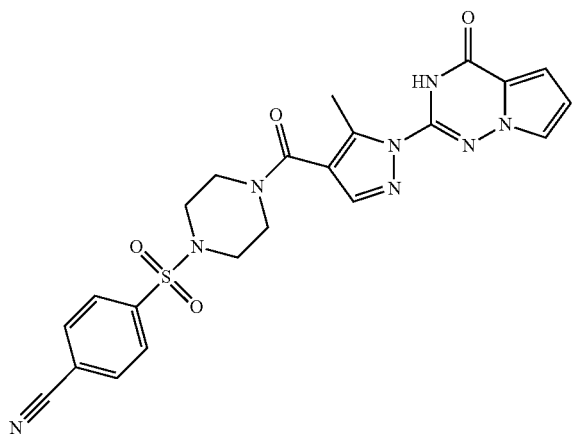 [SMILES: Cc1c(C(=O)N2CCN(S(=O)(=O)c3ccc(C#N)cc3)CC2)cnn1-c1nn2cccc2c(=O)[nH]1]
Q-1838
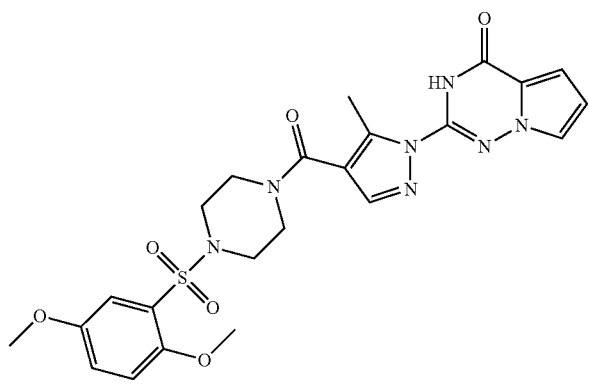 [SMILES: COc1ccc(OC)c(S(=O)(=O)N2CCN(C(=O)c3cnn(-c4nn5cccc5c(=O)[nH]4)c3C)CC2)c1]
Q-1839
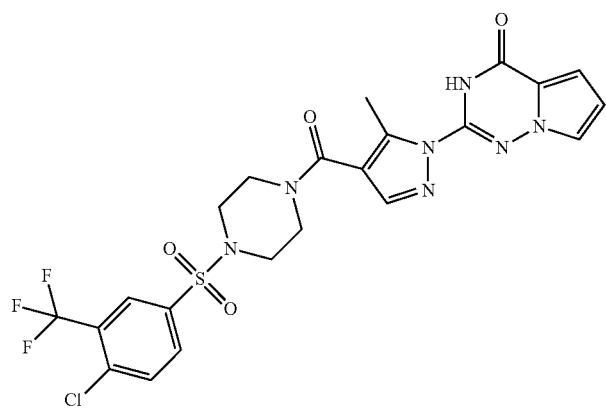 [SMILES: Cc1c(C(=O)N2CCN(S(=O)(=O)c3ccc(Cl)c(C(F)(F)F)c3)CC2)cnn1-c1nn2cccc2c(=O)[nH]1]
Q-1840

TABLE C-continued
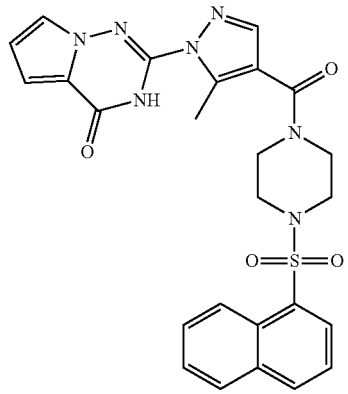 [SMILES: Cc1c(C(=O)N2CCN(S(=O)(=O)c3cccc4ccccc34)CC2)cnn1-c1nn2cccc2c(=O)[nH]1]
Q-1841
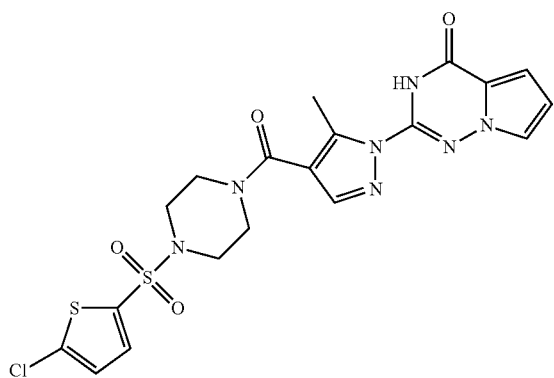 [SMILES: Cc1c(C(=O)N2CCN(S(=O)(=O)c3ccc(Cl)s3)CC2)cnn1-c1nn2cccc2c(=O)[nH]1]
Q-1842
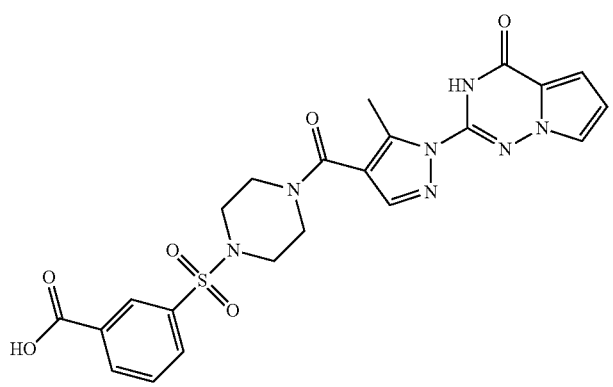 [SMILES: Cc1c(C(=O)N2CCN(S(=O)(=O)c3cccc(C(=O)O)c3)CC2)cnn1-c1nn2cccc2c(=O)[nH]1]
Q-1845
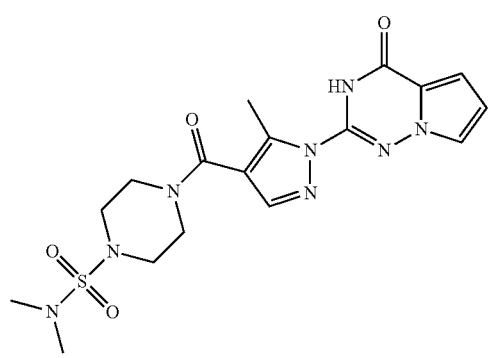 [SMILES: Cc1c(C(=O)N2CCN(S(=O)(=O)N(C)C)CC2)cnn1-c1nn2cccc2c(=O)[nH]1]
Q-1846

TABLE C-continued
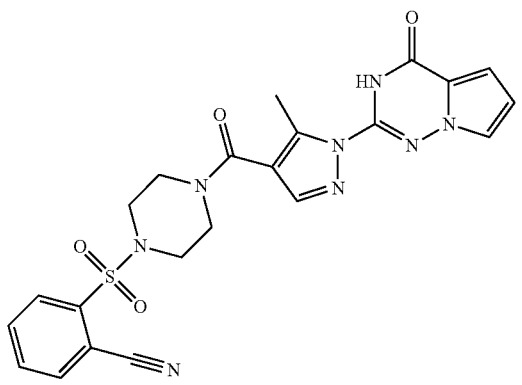 [SMILES: Cc1c(C(=O)N2CCN(S(=O)(=O)c3ccccc3C#N)CC2)cnn1-c1nn2cccc2c(=O)[nH]1]
Q-1847
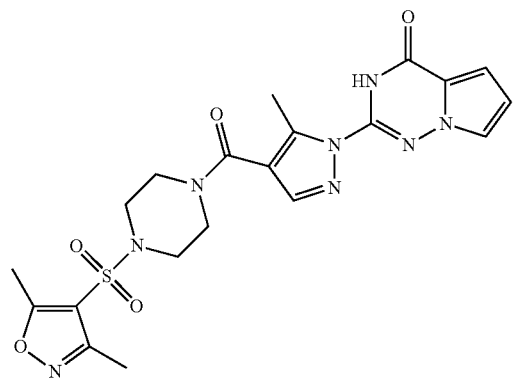 [SMILES: Cc1noc(C)c1S(=O)(=O)N1CCN(C(=O)c2cnn(-c3nn4cccc4c(=O)[nH]3)c2C)CC1]
Q-1848
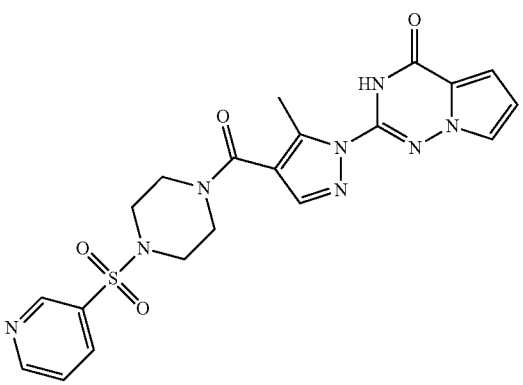 [SMILES: Cc1c(C(=O)N2CCN(S(=O)(=O)c3cccnc3)CC2)cnn1-c1nn2cccc2c(=O)[nH]1]
Q-1857
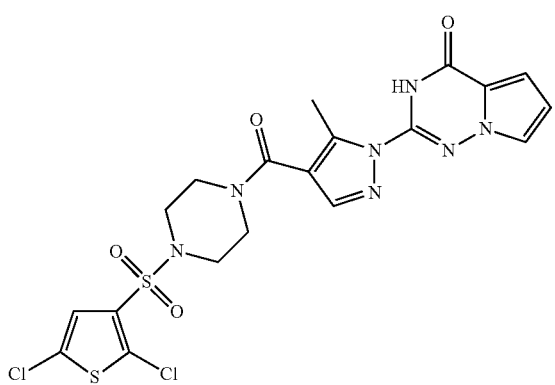 [SMILES: Cc1c(C(=O)N2CCN(S(=O)(=O)c3cc(Cl)sc3Cl)CC2)cnn1-c1nn2cccc2c(=O)[nH]1]
Q-1858

TABLE C-continued
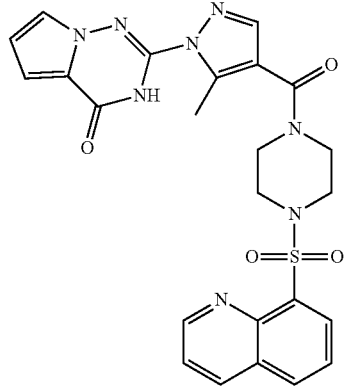 [SMILES: Cc1c(C(=O)N2CCN(S(=O)(=O)c3cccc4cccnc34)CC2)cnn1-c1nn2cccc2c(=O)[nH]1]
Q-1859
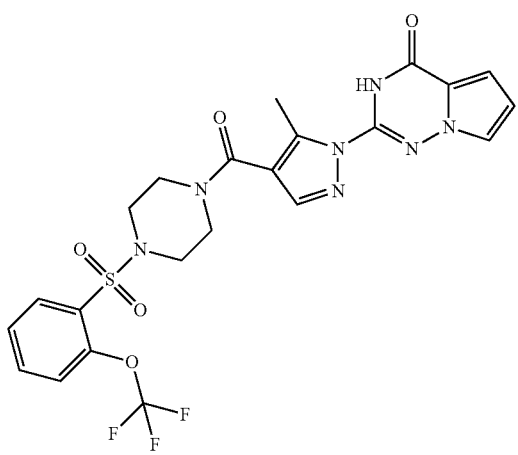 [SMILES: Cc1c(C(=O)N2CCN(S(=O)(=O)c3ccccc3OC(F)(F)F)CC2)cnn1-c1nn2cccc2c(=O)[nH]1]
Q-1861
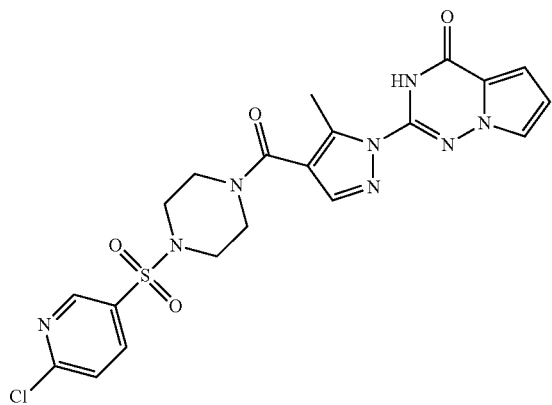 [SMILES: Cc1c(C(=O)N2CCN(S(=O)(=O)c3ccc(Cl)nc3)CC2)cnn1-c1nn2cccc2c(=O)[nH]1]
Q-1862
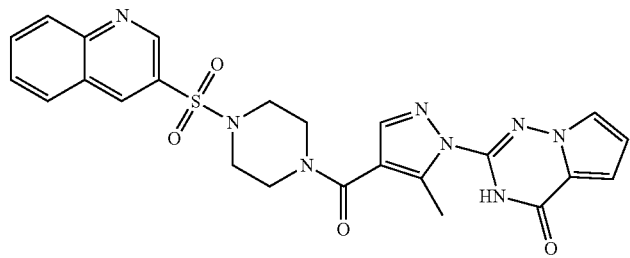 [SMILES: Cc1c(C(=O)N2CCN(S(=O)(=O)c3cnc4ccccc4c3)CC2)cnn1-c1nn2cccc2c(=O)[nH]1]
Q-1864

TABLE C-continued
Q-1866
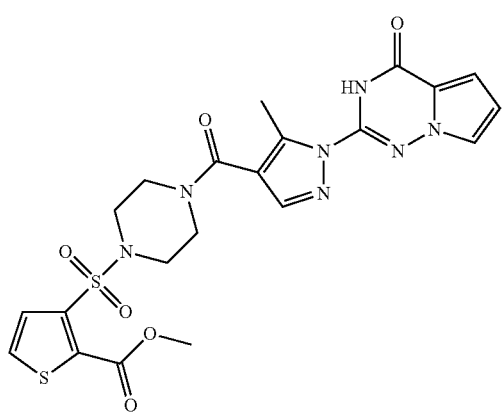
Q-1875
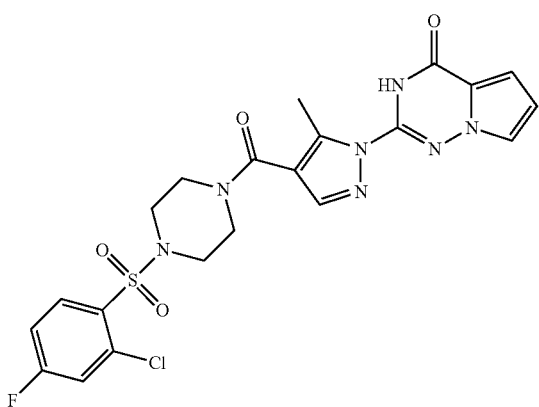 [SMILES: Cc1c(C(=O)N2CCN(S(=O)(=O)c3ccc(F)cc3F)CC2)cnn1-c1nn2cccc2c(=O)[nH]1]
Q-1876
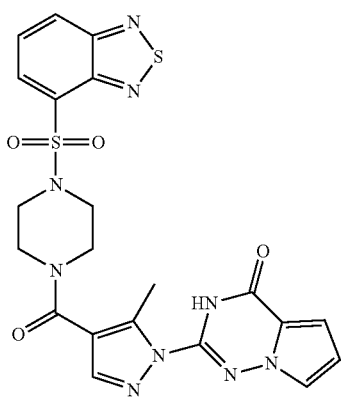 [SMILES: Cc1c(C(=O)N2CCN(S(=O)(=O)c3cccc4nsnc34)CC2)cnn1-c1nn2cccc2c(=O)[nH]1]
Q-1882

TABLE C-continued
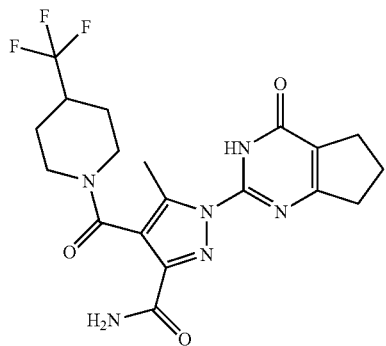 [SMILES: Cc1c(C(=O)N2CCC(C(F)(F)F)CC2)c(C(N)=O)nn1-c1nc2c(c(=O)[nH]1)CCC2]
Q-1884
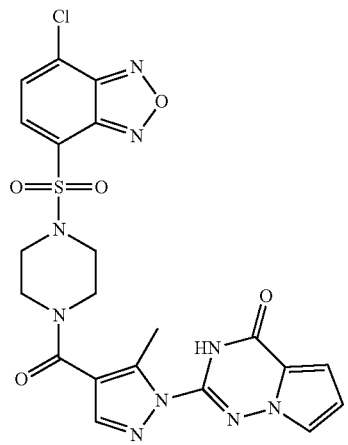 [SMILES: Cc1c(C(=O)N2CCN(S(=O)(=O)c3ccc(Cl)c4nonc34)CC2)cnn1-c1nn2cccc2c(=O)[nH]1]
Q-1885
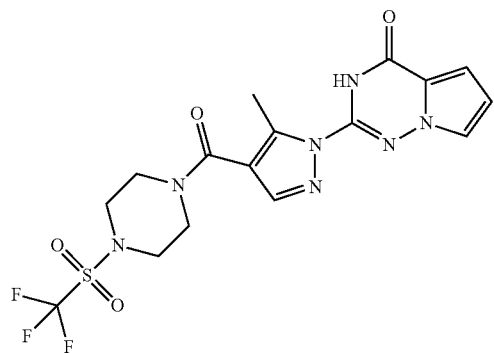 [SMILES: Cc1c(C(=O)N2CCN(S(=O)(=O)C(F)(F)F)CC2)cnn1-c1nn2cccc2c(=O)[nH]1]
Q-1886
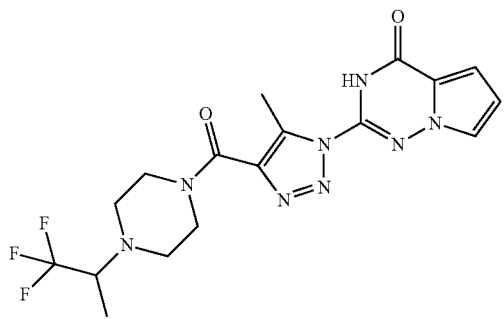 [SMILES: Cc1c(C(=O)N2CCN(C(C)C(F)(F)F)CC2)nnn1-c1nn2cccc2c(=O)[nH]1]
Q-1889

TABLE C-continued
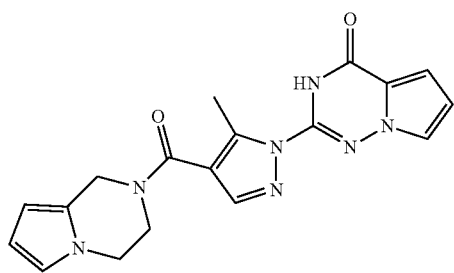 [SMILES: Cc1c(C(=O)N2CCn3cccc3C2)cnn1-c1nn2cccc2c(=O)[nH]1]
Q-1925
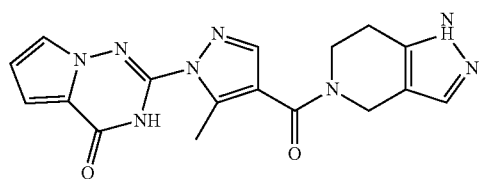 [SMILES: Cc1c(C(=O)N2CCc3[nH]ncc3C2)cnn1-c1nn2cccc2c(=O)[nH]1]
Q-1932
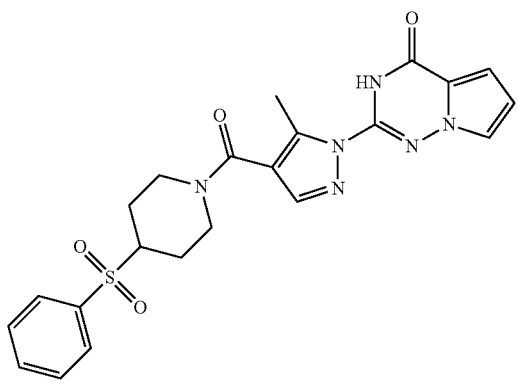 [SMILES: Cc1c(C(=O)N2CCC(S(=O)(=O)c3ccccc3)CC2)cnn1-c1nn2cccc2c(=O)[nH]1]
Q-1984
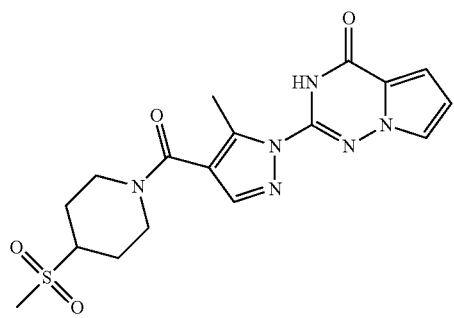 [SMILES: Cc1c(C(=O)N2CCC(S(C)(=O)=O)CC2)cnn1-c1nn2cccc2c(=O)[nH]1]
Q-1985
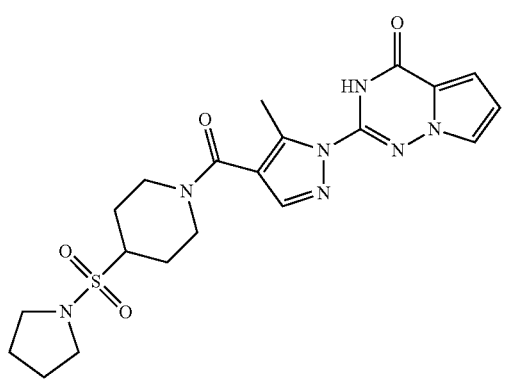 [SMILES: Cc1c(C(=O)N2CCC(S(=O)(=O)N3CCCC3)CC2)cnn1-c1nn2cccc2c(=O)[nH]1]
Q-2007

TABLE C-continued
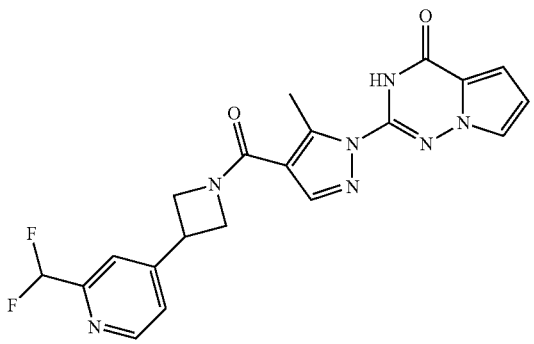 [SMILES: Cc1c(C(=O)N2CC(c3ccnc(C(F)F)c3)C2)cnn1-c1nn2cccc2c(=O)[nH]1]
Q-2008
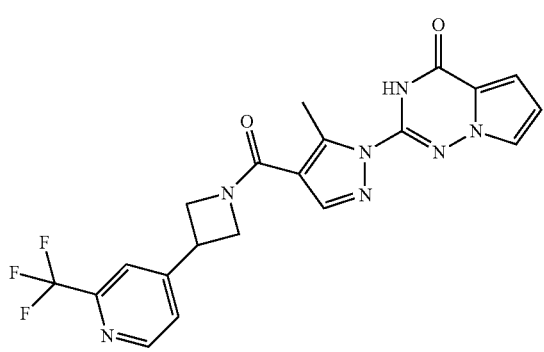 [SMILES: Cc1c(C(=O)N2CC(c3ccnc(C(F)(F)F)c3)C2)cnn1-c1nn2cccc2c(=O)[nH]1]
Q-2009
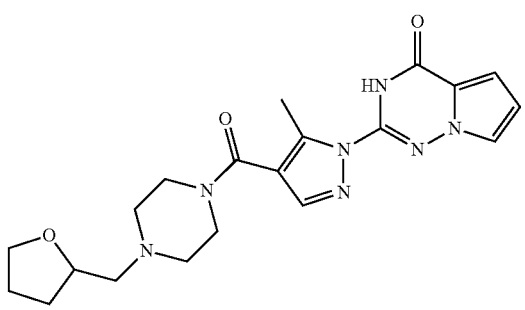 [SMILES: Cc1c(C(=O)N2CCN(CC3CCCO3)CC2)cnn1-c1nn2cccc2c(=O)[nH]1]
Q-2016
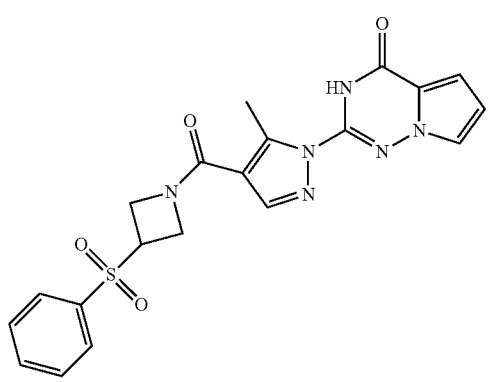 [SMILES: Cc1c(C(=O)N2CC(S(=O)(=O)c3ccccc3)C2)cnn1-c1nn2cccc2c(=O)[nH]1]
Q-2017
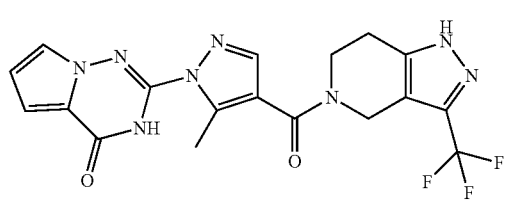 [SMILES: Cc1c(C(=O)N2CCc3[nH]nc(C(F)(F)F)c3C2)cnn1-c1nn2cccc2c(=O)[nH]1]
Q-2031

TABLE C-continued
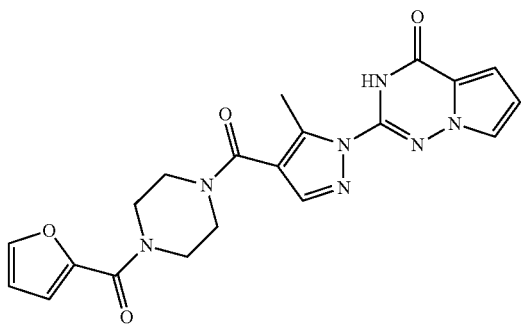 [SMILES: Cc1c(C(=O)N2CCN(C(=O)c3ccco3)CC2)cnn1-c1nn2cccc2c(=O)[nH]1]
Q-2032
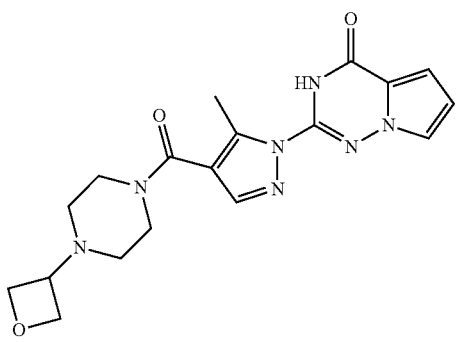 [SMILES: Cc1c(C(=O)N2CCN(C3COC3)CC2)cnn1-c1nn2cccc2c(=O)[nH]1]
Q-2041
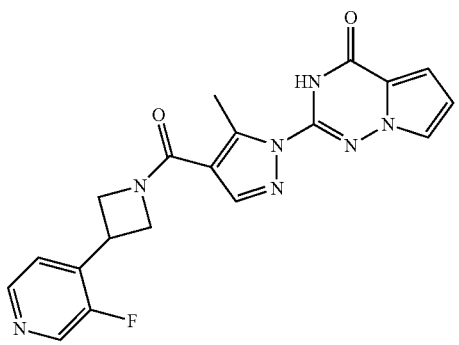 [SMILES: Cc1c(C(=O)N2CC(c3ccncc3F)C2)cnn1-c1nn2cccc2c(=O)[nH]1]
Q-2043
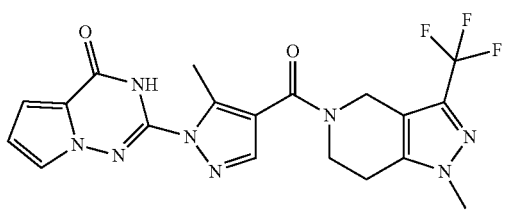 [SMILES: Cc1c(C(=O)N2CCc3c(c(C(F)(F)F)nn3C)C2)cnn1-c1nn2cccc2c(=O)[nH]1]
Q-2048
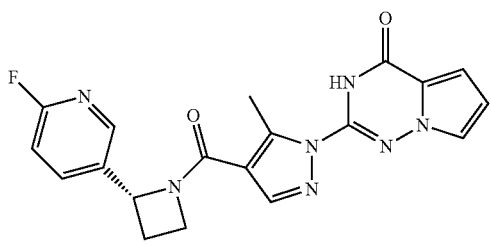 [SMILES: Cc1c(C(=O)N2CC[C@@H]2c2ccc(F)nc2)cnn1-c1nn2cccc2c(=O)[nH]1]
Q-2054

TABLE C-continued

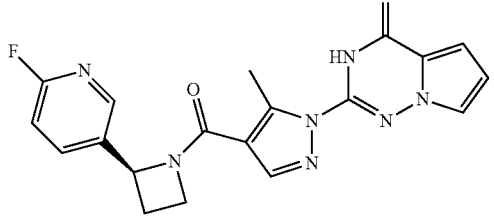

Q-2055

In one aspect, the disclosure provides a compound of formula II or II', or a pharmaceutically acceptable salt thereof:

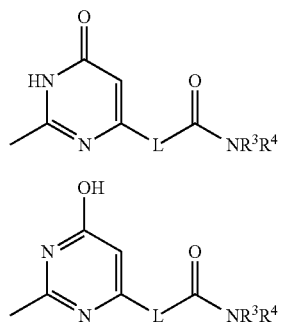

(II)

(II')

wherein L is heteroaryl or aryl; and $R^3$ is selected from the group consisting of H, $C_{1-5}$alkyl, $C_{3-10}$cycloalkyl, $C_{1-5}$haloalkyl, aryl, heteroaryl, and $C_{1-5}$alkylene-G;

$R^4$ is selected from the group consisting of $C_{1-5}$alkyl, $C_{3-10}$cycloalkyl, $C_{1-5}$haloalkyl, aryl, heteroaryl, and $C_{1-5}$alkylene-G; or $R^3$ and $R^4$, taken together with the nitrogen atom to which they are attached form a 3-, 4-, 5-, 6-, or 7-membered monocyclic ring or a 6-, 7-, 8-, 9-, 10-, 11-, 12-, 13-, or 14-membered spiro, fused, or bridged bicyclic ring, and each G is independently selected from the group consisting of CN, aryl, heteroaryl, cycloalkyl, and heterocycloalkyl.

In one aspect, the disclosure provides a compound of formula III or III', or a pharmaceutically acceptable salt thereof:

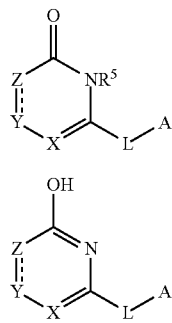

(III)

(III')

wherein:

═══ is an optional double bond;

Z is $CR^1$ or $NR^1$, or if the double bond is present, then Z is $CR^1$ or N;

Y is $CR^2$ or $NR^2$, or if the double bond is present, then Y is $CR^2$ or N;

X is CH or N;

$R^1$ and $R^2$ are independently selected from the group consisting of H, $C_{1-5}$alkyl, $C_{3-5}$cycloalkyl, $C_{1-5}$haloalkyl, and halo; or $R^1$ and $R^2$, taken together with the atoms to which they are attached form a 5- to 6-membered ring;

$R^5$ is selected from the group consisting of H and $C_{1-5}$alkyl;

L is heteroaryl-$C_{0-5}$alkylene-, aryl-$C_{0-5}$alkylene-, —S—$C_{1-5}$alkylene-aryl, —S—$C_{1-5}$alkylene-heteroaryl, —$C_{1-5}$alkylene-S-aryl, or —$C_{1-5}$alkylene-S-heteroaryl;

A is selected from the group consisting of

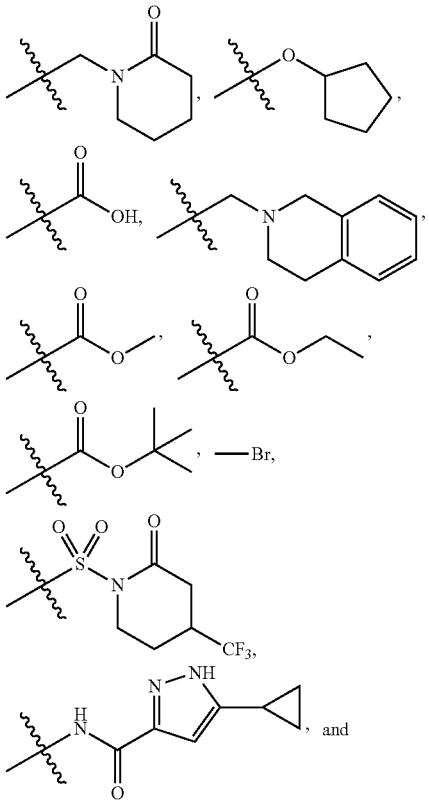

-continued

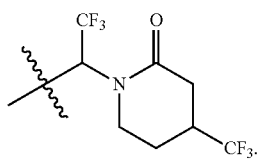

In some embodiments, the compound of formula III or III' does not include a compound having a structure:

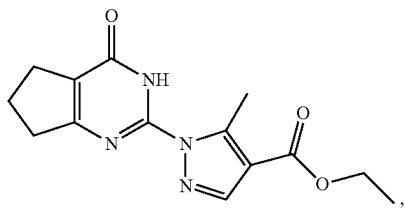

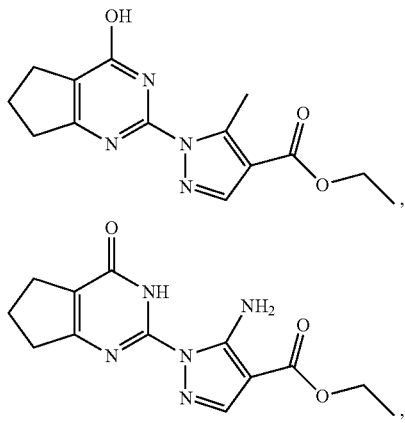

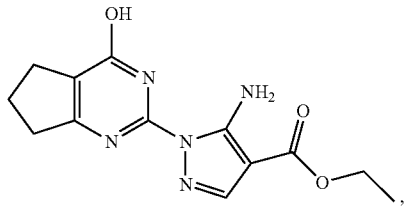

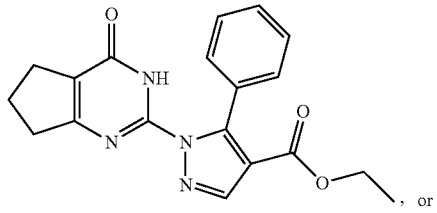, or

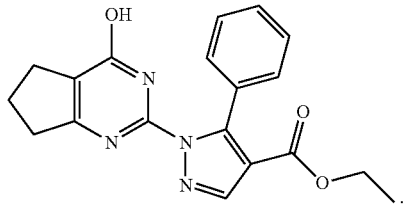.

In one aspect, the disclosure provides a compound of formula IV or IV', or a pharmaceutically acceptable salt thereof:

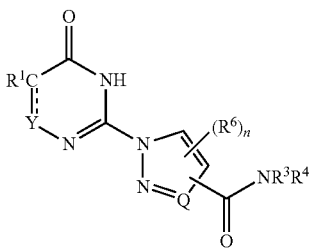

(IV)

(IV')

wherein:
═══ is an optional double bond;
Y is $NR^2$, or if the double bond is present, then Y is $CR^2$;
$R^1$ and $R^2$, taken together with the atoms to which they are attached form a 5-membered ring;
n is 0 or 1;
each $R^6$ is selected from the group consisting of $C_{1-5}$alkyl, $C_{3-5}$cycloalkyl, $C_{1-5}$haloalkyl, halo, and benzyl;
Q is CH, $CR^6$, or N;
$R^3$ and $R^4$, taken together with nitrogen atom to which they are attached form a 3-, 4-, 5-, 6-, or 7-membered monocyclic ring or 6-, 7-, 8-, 9-, 10-, 11-, 12-, 13-, or 14-membered spiro, fused, or bridged bicyclic ring.

In some embodiments,

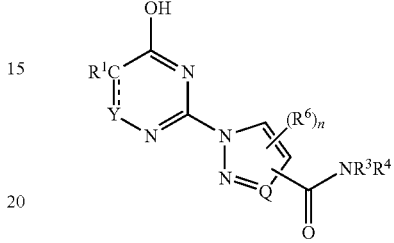

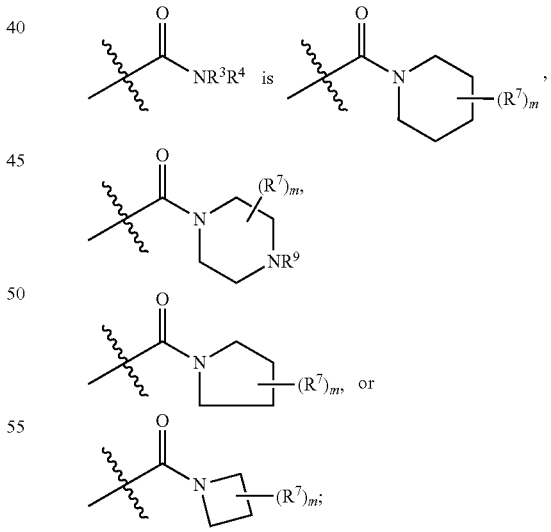

m is 0, 1, 2, or 3;
$R^7$ and $R^9$ are each independently selected from the group consisting of halo, $C_{1-5}$alkyl, $C_{3-5}$cycloalkyl, heterocycloalkyl, $C_{1-5}$haloalkyl, $C_{1-5}$haloalkylene-OH, $C_{1-5}$alkylene-CN, $C_{1-5}$alkoxy, $C_{1-5}$haloalkoxy, aryloxy, heteroaryloxy, CN, OH, —$NHR^8$, —$NR^8CO_2R^{8a}$, —$SO_2R^8$, —$CO_2R^8$, —$CONHR^8$, aryl, and heteroaryl, or two R⁷ groups, together with the carbon atom(s) to which they are attached, form a 3-, 4-, 5-, 6-, 7-, or 8-membered cycloalkyl, a 3-, 4-, 5-, 6-, 7-, or 8-membered heterocycloalkyl, aryl, or a 5- or 6-membered heteroaryl ring; and R⁸ and R⁸ᵃ are each independently selected from the group consisting of H, $C_{1-5}$alkyl, $C_{1-5}$haloalkyl, —$C_{0-5}$alkylene-$C_{3-6}$cycloalkyl, —$C_{0-5}$alkylene-heterocycloalkyl, —$C_{0-5}$alkylene-aryl, and —$C_{0-5}$alkylene-heteroaryl; or one R⁷ group and R⁹, together with the atoms to which they are attached, form a 5- or 6-membered heterocycloalkyl or heteroaryl ring.

In some embodiments,

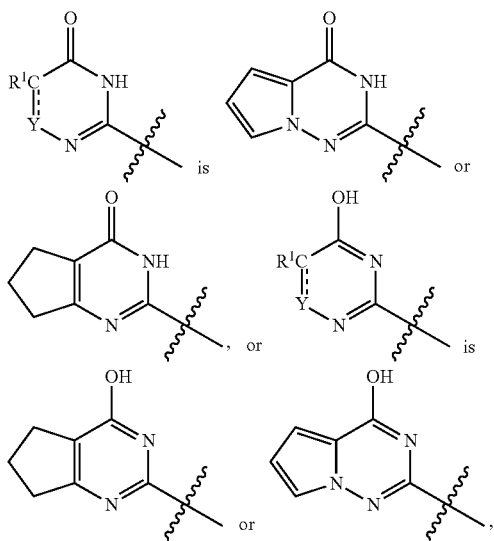

and is optionally substituted with one to four substituents selected from the group consisting of F, Cl, and $C_{1-3}$alkyl.

In some embodiments,

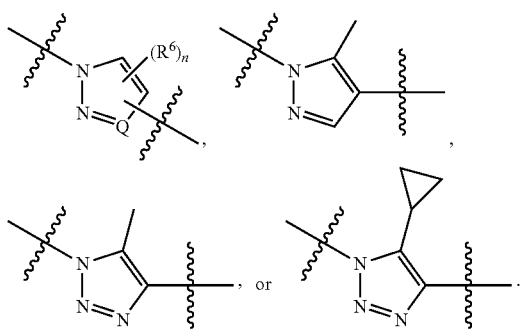

In some embodiments, two R⁷ groups are present on adjacent carbon atoms, and in some cases, the two R⁷ groups and the carbons to which they are attached form a 3-, 4-, 5-, 6-, or 7-membered heterocycloalkyl group or cycloalkyl group. In some embodiments, two R⁷ groups are present on the same carbon atom, and in some cases, the two R⁷ groups and the carbon to which they are attached form a 3-, 4-, 5-, 6-, or 7-membered heterocycloalkyl or cycloalkyl group. In some embodiments, the 6- to 14-membered spiro, fused, or bridged polycyclic (e.g., bicyclic) ring is substituted with one or two substituents independently selected from the group consisting of halo, $C_{1-5}$alkyl, $C_{1-5}$haloalkyl, $C_{1-5}$alkoxy, aryloxy, heteroaryloxy, CN, OH, —$SO_2R^{10}$, —$CO_2R^{10}$, $CONHR^{10}$, $C_{3-5}$cycloalkyl, aryl, and heteroaryl; and $R^{10}$ is selected from the group consisting of H, $C_{1-5}$alkyl, —$C_{0-5}$alkylene-aryl, and —$C_{0-5}$alkylene-heteroaryl. In some embodiments, the 3-, 4-, 5-, 6-, or 7-membered heterocycloalkyl or cycloalkyl group is substituted with one or two substituents selected from the group consisting of fluoro, hydroxy, cyano, methyl, ethyl, trifluoromethyl, trifluoroethyl, cyanopropyl, methoxy, trifluoromethoxy, trifluoroethoxy, hexafluorohydroxypropyl, cyclopropyl, 1-cyano-cyclopropyl, 1-trifluoromethylcyclopropyl, 3,3-difluoropyrrolidine, C(O)-t-butoxy, phenyl, fluorophenyl, difluorophenyl, cyanophenyl, indolyl, difluoropyrrolindinyl, benzothiazolyl, and N(methyl)C(O)t-butoxy.

Suitable 6- to 14-membered spiro, fused, or bridged bicyclic rings include, but are not limited to, 10-azabicyclodecane, 9-azabicyclononane, 8-azabicyclooctane (e.g., 8-azabicyclo[3.2.1]octane), azabicycloheptane (e.g., 7-azabicycloheptane), 3-azabicyclohexane (e.g., 3-azabicyclo[3.1.0]hexane), diazabicyclononane (e.g., 1,4-diazabicyclo[4.3.0]nonane), diazabicyclooctane, diazabicycloheptane, diazaspirononane, azaspirononane, diazaspirooctane, azaspirooctane, spiroksobenzofuran-piperidine, diazaspiroheptane, azaspiroheptane, octahydrocyclopenta[b]pyrrole, or octahydrocyclopenta[c]pyrrole. In some embodiments, the 6- to 14-membered spiro, fused, or bicyclic ring is substituted with one or two substituents independently selected from the group consisting of halo, $C_{1-5}$alkyl, $C_{1-5}$haloalkyl, $C_{1-5}$alkoxy, aryloxy, heteroaryloxy, CN, OH, —$SO_2R^{10}$, —$CO_2R^{10}$, —$CONHR^{10}$, $C_{3-5}$cycloalkyl, aryl, and heteroaryl; and $R^{10}$ is selected from the group consisting of H, $C_{1-5}$alkyl, —$C_{0-5}$alkylene-aryl, and —$C_{0-5}$alkylene-heteroaryl.

In one aspect, the disclosure provides a compound of formula V or V', or a pharmaceutically acceptable salt thereof:

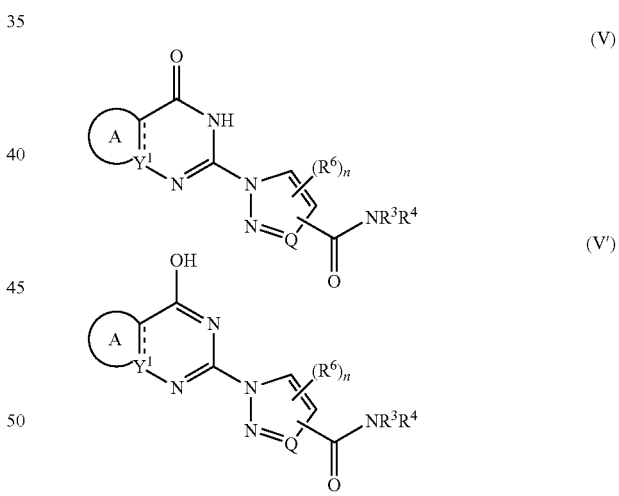

wherein:
╌╌╌ is an optional double bond;
Y¹ is N, or if the double bond is present, then Y¹ is C;

is a 5-membered ring;
n is 0 or 1;
each R⁶ is selected from the group consisting of $C_{1-5}$alkyl, $C_{3-5}$cycloalkyl, $C_{1-5}$haloalkyl, halo, and benzyl;
Q is CH, CR⁶, or N;

$R^3$ and $R^4$, taken together with nitrogen atom to which they are attached form a 3-, 4-, 5-, 6-, or 7-membered monocyclic ring or 6-, 7-, 8-, 9-, 10-, 11-, 12-, 13-, or 14-membered spiro, fused, and/or bridged polycyclic ring.

In some embodiments,

is a pyrrole ring, a cyclopentene ring, a thiophene ring, a dihydrofuran ring, a pyrazole ring, a thiazole ring, or an imidazole ring. In some embodiments,

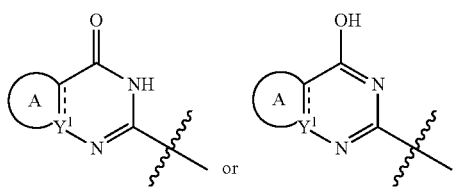

or is selected from the group consisting of:

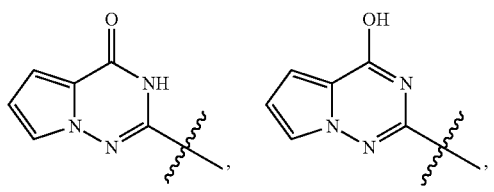

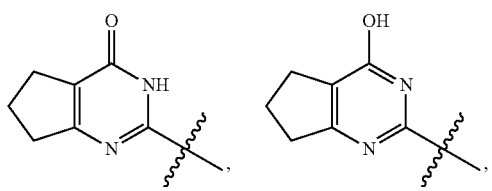

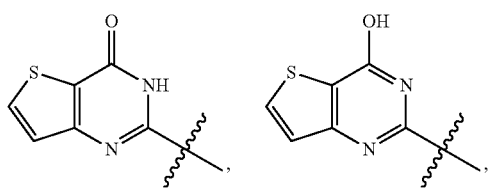

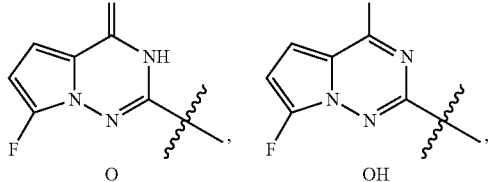

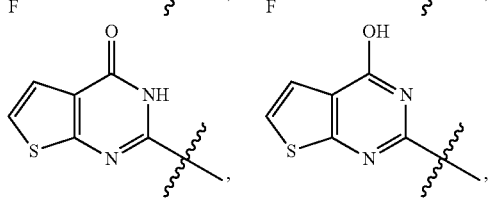

-continued

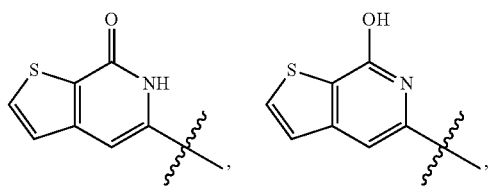

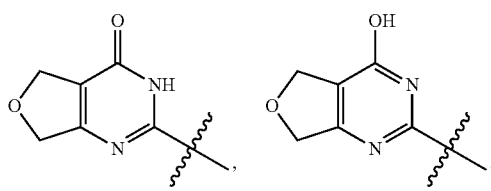

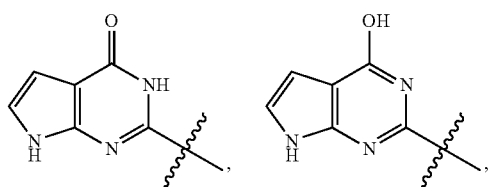

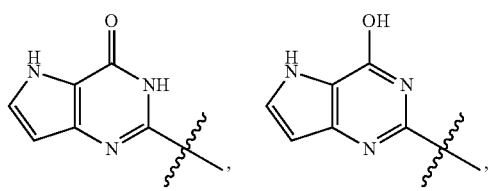

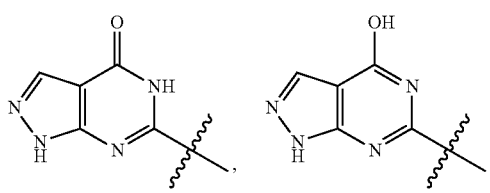

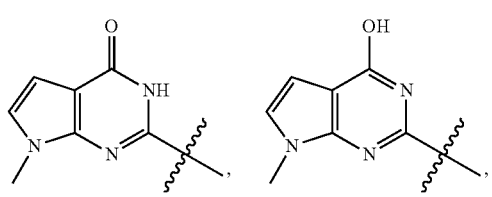

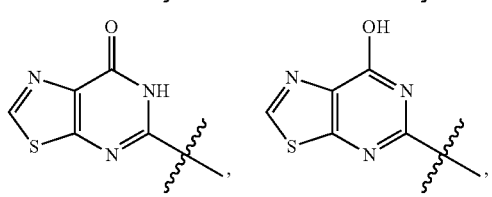

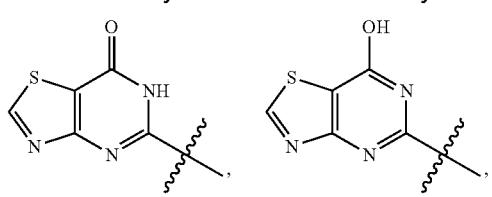

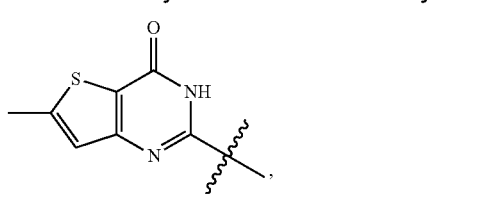

523
-continued
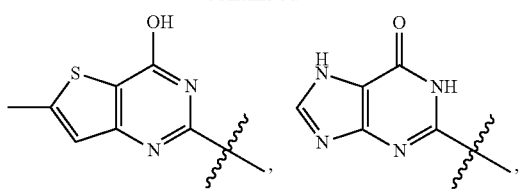
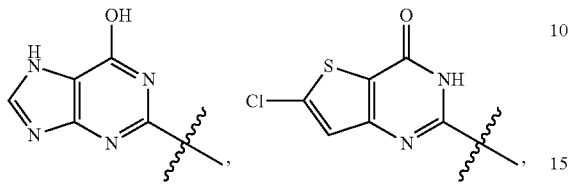
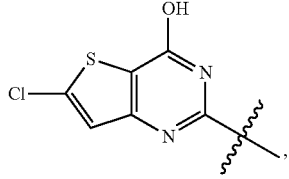
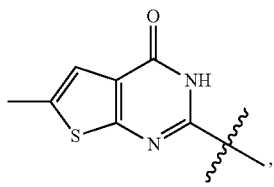
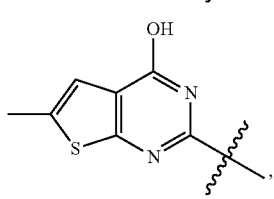
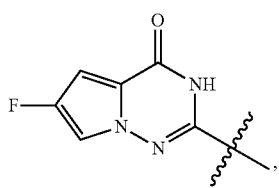
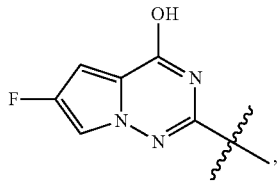
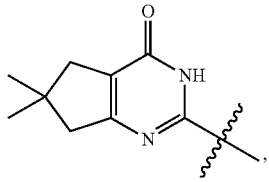
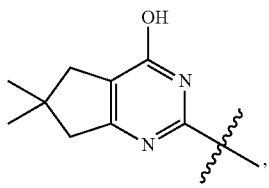
524
-continued
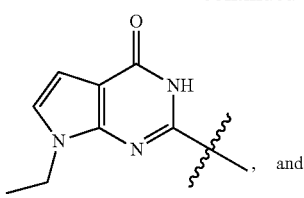, and
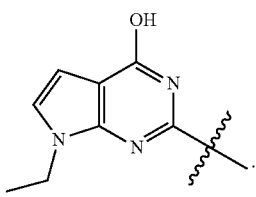.
In some embodiments,
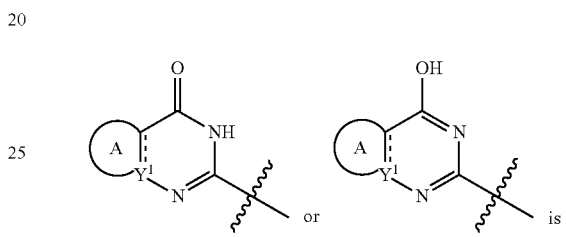 or is
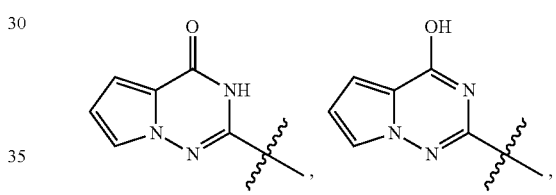,
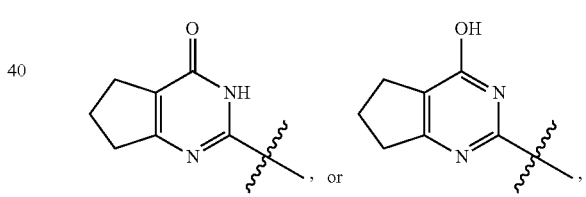, or
and is optionally substituted with one to four substituents selected from the group consisting of F, Cl, and $C_{1-3}$alkyl. In some embodiments,
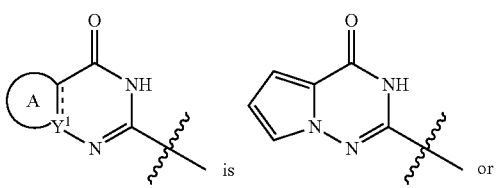 is or
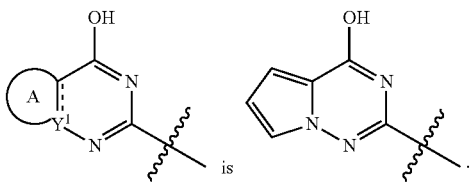 is .

In some embodiments,

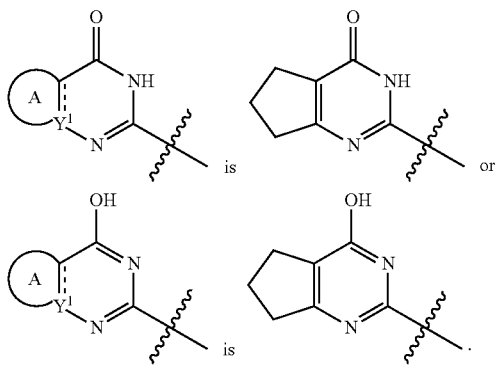

In some embodiments,

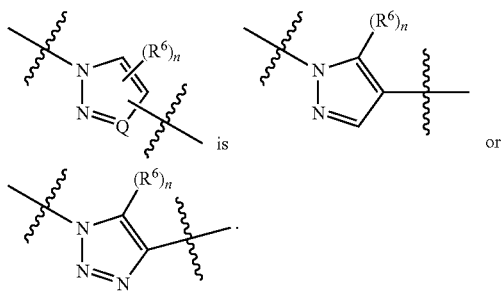

In some embodiments,

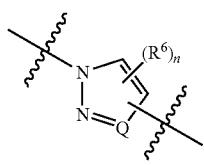

is selected from the group consisting of

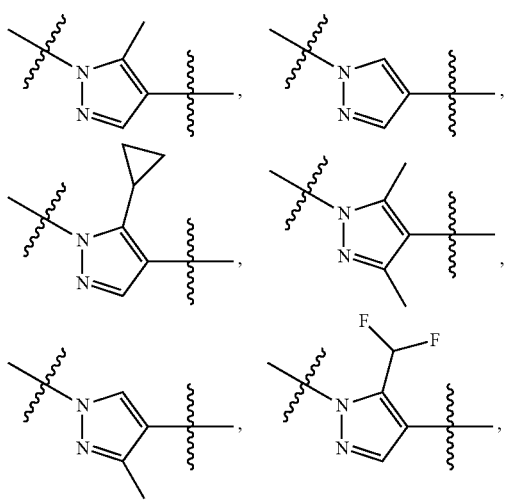

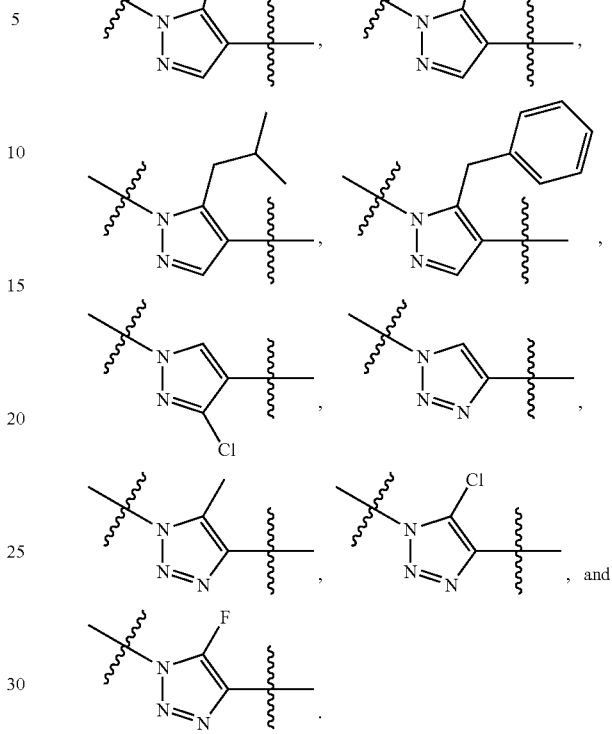

In some embodiments,

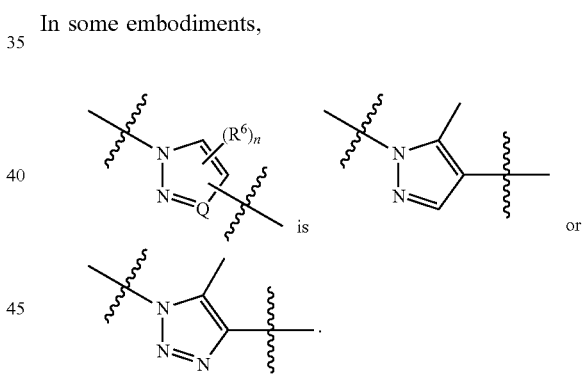

In some embodiments, $R^3$ and $R^4$, taken together with nitrogen atom to which they are attached form a 3-, 4-, 5-, 6-, or 7-membered ring. Suitable 3-, 4-, 5-, 6-, or 7-membered rings include, but are not limited to, piperidinyl, pyrrolidinyl, azetidinyl, piperazinyl, morpholinyl, thiomorpholinyl, aziridinyl, oxaziridinyl, imidazolidinyl, pyrazolidinyl, oxazolidinyl, isoxazolidinyl, thiazolidinyl, isothiazolidinyl, azepanyl, diazepanyl, or diazabicycloheptane.

In some embodiments,

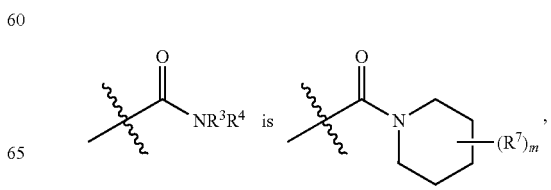

-continued

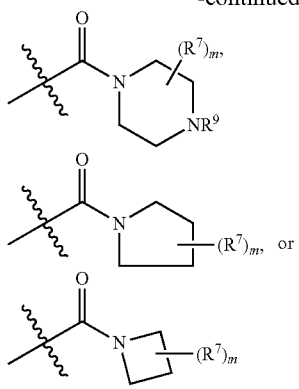

m is 0, 1, 2, or 3;

R$^7$ and R$^9$ are each independently selected from the group consisting of halo, C$_{1-5}$alkyl, C$_{3-5}$ cycloalkyl, heterocycloalkyl, C$_{1-5}$haloalkyl, C$_{1-5}$haloalkylene-OH, C$_{1-5}$alkylene-CN, C$_{1-5}$alkoxy, C$_{1-5}$haloalkoxy, aryloxy, heteroaryloxy, CN, OH, —NHR$^8$, —NR$^8$CO$_2$R$^{8a}$, —SO$_2$R$^8$, —CO$_2$R$^8$, —CONHR$^8$, aryl, and heteroaryl, or two R$^7$ groups, together with the carbon atom(s) to which they are attached, form a 3-, 4-, 5-, 6-, 7-, or 8-membered cycloalkyl, a 3-, 4-, 5-, 6-, 7-, or 8-membered heterocycloalkyl, aryl, or a 5- or 6-membered heteroaryl ring; and R$^8$ and R$^{8a}$ are each independently selected from the group consisting of H, C$_{1-5}$alkyl, —C$_{0-5}$alkylene-aryl, and —C$_{0-5}$alkylene-heteroaryl; or one R$^7$ group and R$^9$, together with the atoms to which they are attached, form a 5- or 6-membered heterocyclic or heteroaryl ring.

In some embodiments,

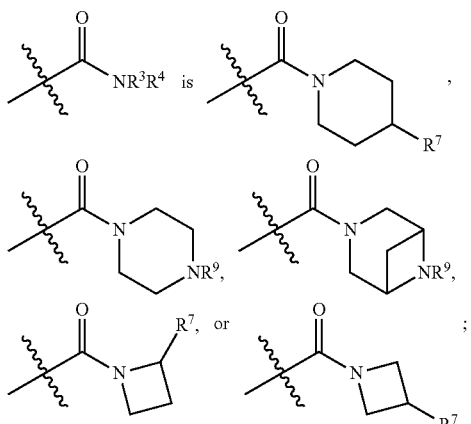

R$^7$ and R$^9$ are each independently selected from the group consisting of halo, C$_{1-5}$alkyl, C$_{3-5}$ cycloalkyl, heterocycloalkyl, C$_{1-5}$haloalkyl, C$_{1-5}$haloalkylene-OH, C$_{1-5}$alkylene-CN, C$_{1-5}$alkoxy, C$_{1-5}$haloalkoxy, aryloxy, heteroaryloxy, CN, OH, —NHR$^8$, —NR$^8$CO$_2$R$^{8a}$, —SO$_2$R$^8$, —CO$_2$R$^8$, —CONHR$^8$, aryl, and heteroaryl; and R$^8$ and R$^{8a}$ are each independently selected from the group consisting of H, C$_{1-5}$alkyl, —C$_{0-5}$alkylene-aryl, and —C$_{0-5}$alkylene-heteroaryl.

In some embodiments, R$^7$ or R$^9$ is selected from the group consisting of C$_{3-5}$cycloalkyl, heterocycloalkyl, aryloxy, heteroaryloxy, aryl, and heteroaryl. In some embodiments, R$^7$ is oxazolyl or pyridinyl, each of which is optionally substituted with CN or F. In some embodiments, R$^7$ is selected from the group consisting of

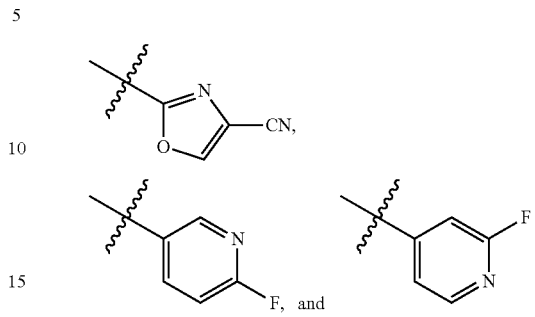

In some embodiments, R$^9$ is C$_{3-5}$cycloalkyl. In some embodiments, R$^9$ is cyclopropyl or cyclobutyl, each of which is optionally substituted with 1, 2, 3, or 4 F atoms. In some embodiments, R$^9$ is selected from the group consisting of

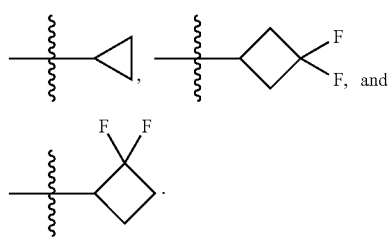

In some embodiments, the compound is selected from

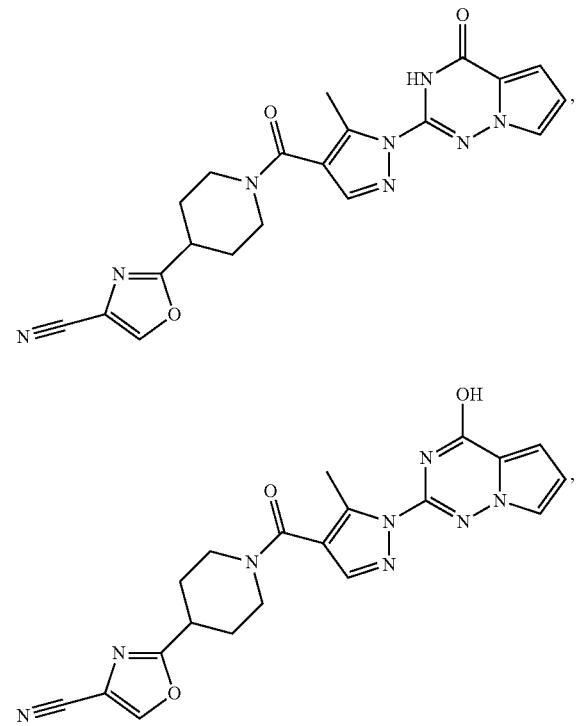

529
-continued
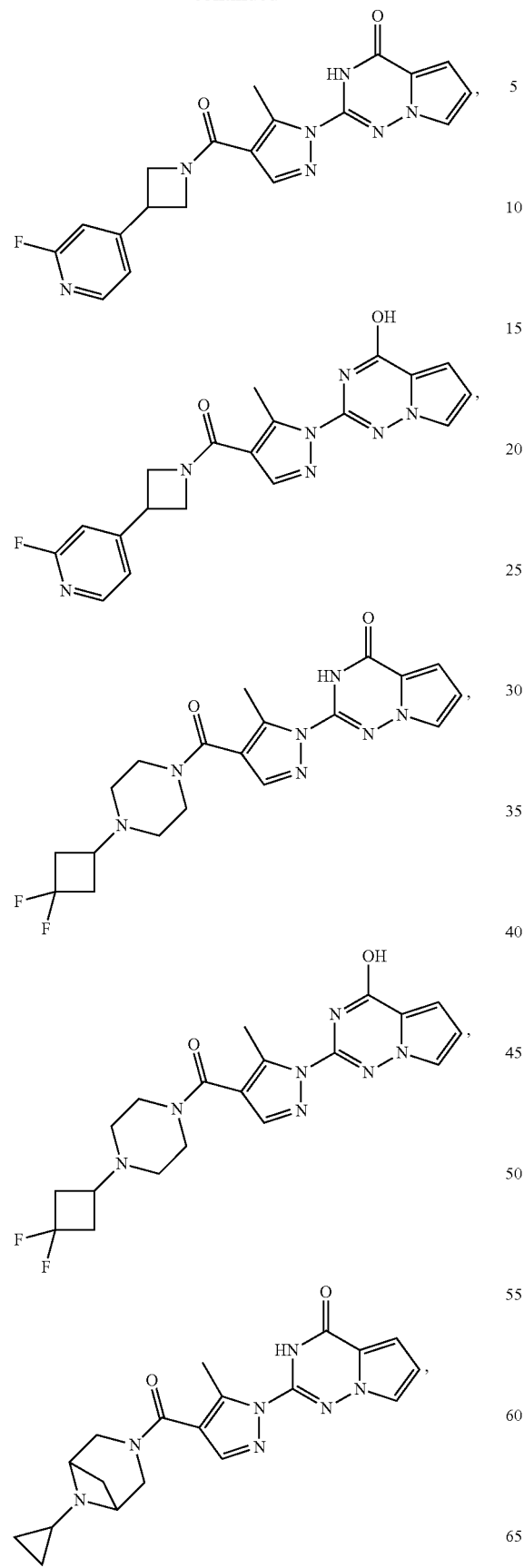
530
-continued
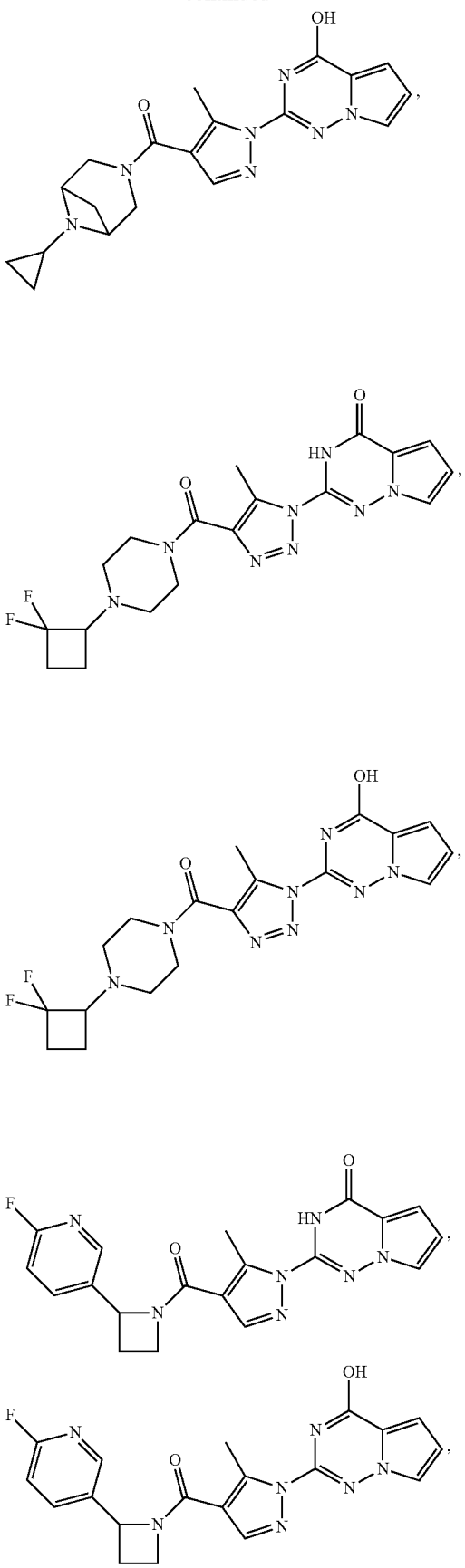

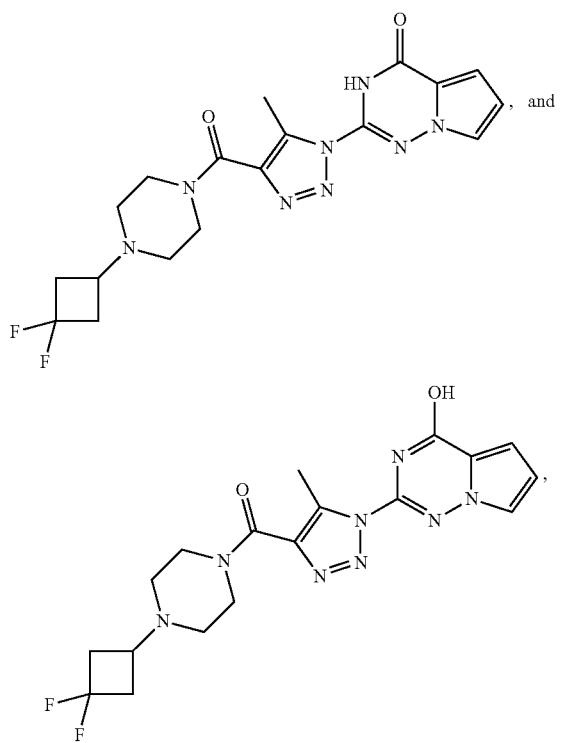
, and
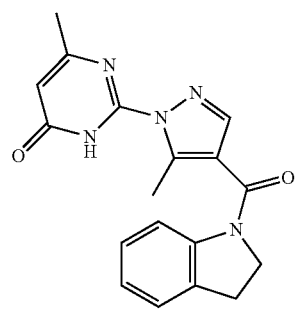 [SMILES: Cc1cc(=O)[nH]c(-n2ncc(C(=O)N3CCc4ccccc43)c2C)n1]
or a pharmaceutically acceptable salt thereof.
Further disclosed are compounds listed in Table D, below, for use in inhibiting SPR.
TABLE D
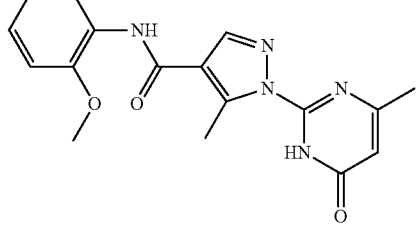
Q-001
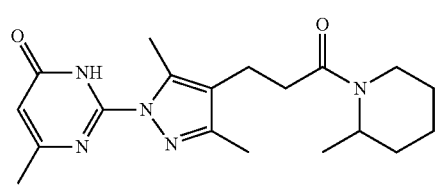 [SMILES: Cc1cc(=O)[nH]c(-n2nc(C)c(CCC(=O)N3CCCCC3C)c2C)n1]
Q-002
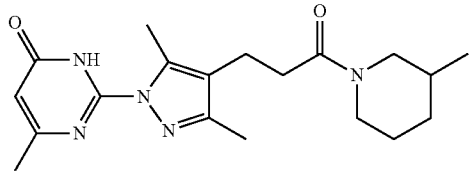 [SMILES: Cc1cc(=O)[nH]c(-n2nc(C)c(CCC(=O)N3CCCC(C)C3)c2C)n1]
Q-003
TABLE D-continued
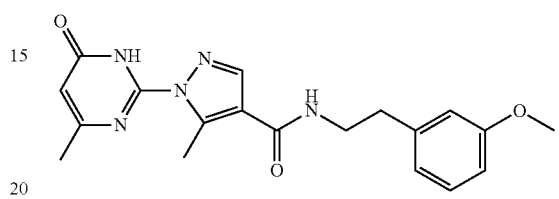
Q-004
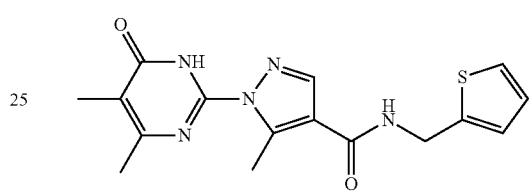
Q-005
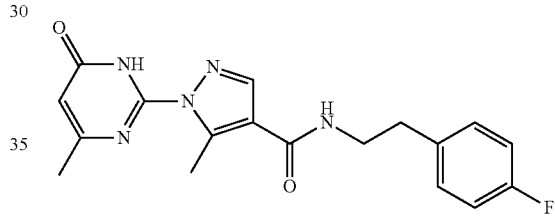
Q-006
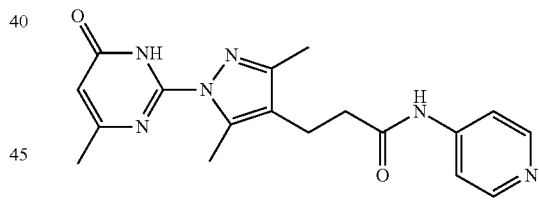
Q-007
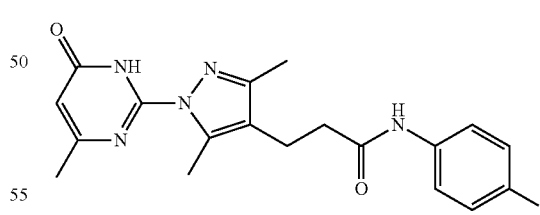
Q-008
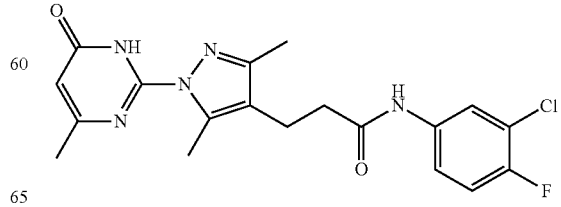
Q-009
Q-010

TABLE D-continued
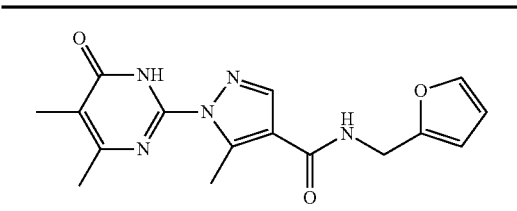 Q-011
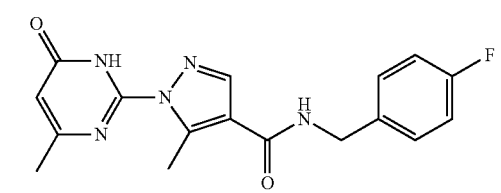 [SMILES: Cc1cc(=O)[nH]c(-n2ncc(C(=O)NCc3ccc(F)cc3)c2C)n1] Q-012
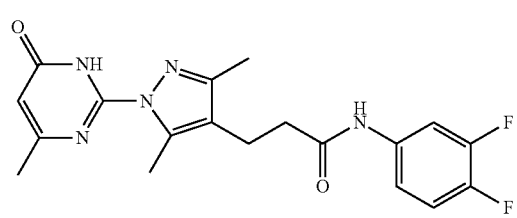 [SMILES: Cc1cc(=O)[nH]c(-n2nc(C)c(CCC(=O)Nc3ccc(F)c(F)c3)c2C)n1] Q-013
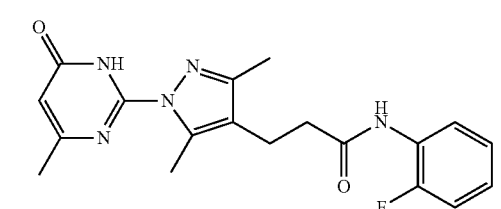 Q-014
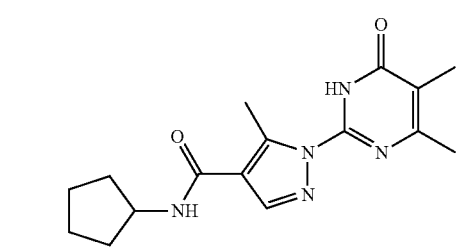 [SMILES: Cc1nc(-n2ncc(C(=O)NC3CCCC3)c2C)[nH]c(=O)c1C] Q-015
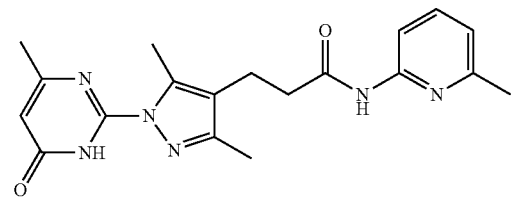 [SMILES: Cc1cccc(NC(=O)CCc2c(C)nn(-c3nc(C)cc(=O)[nH]3)c2C)n1] Q-016
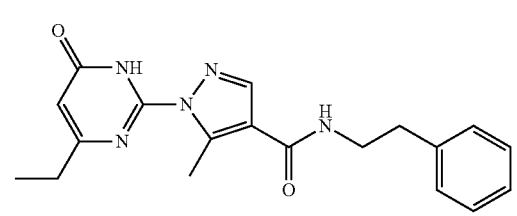 [SMILES: CCc1cc(=O)[nH]c(-n2ncc(C(=O)NCCc3ccccc3)c2C)n1] Q-017
TABLE D-continued
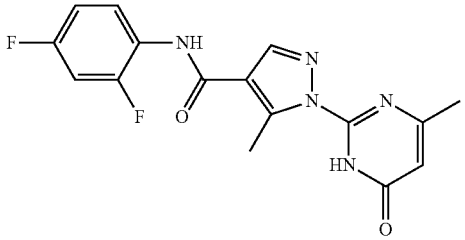 [SMILES: Cc1cc(=O)[nH]c(-n2ncc(C(=O)Nc3ccc(F)cc3F)c2C)n1] Q-018
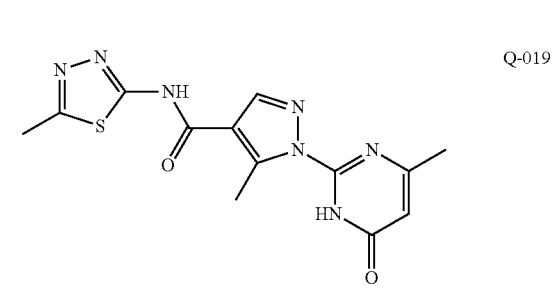 Q-019
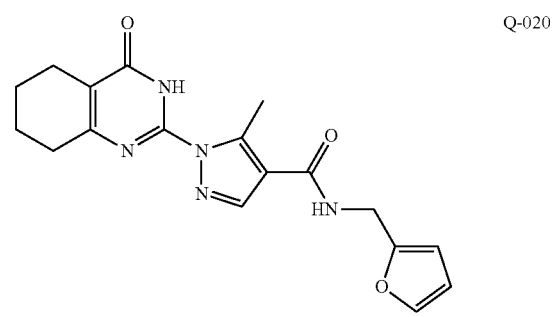 Q-020
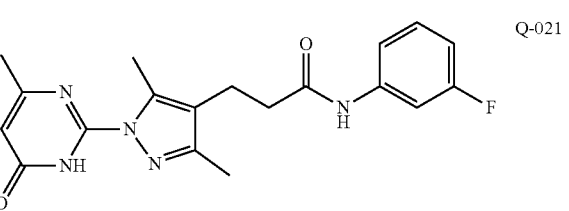 Q-021
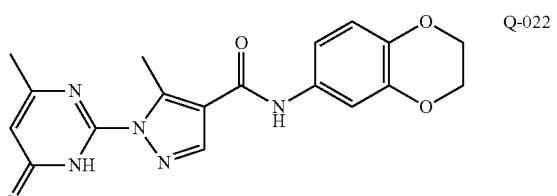 Q-022
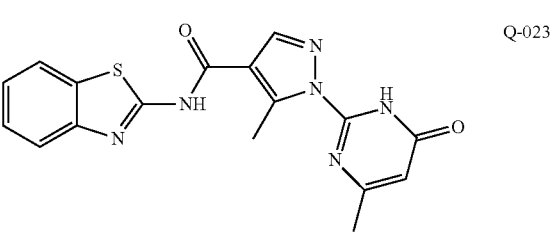 Q-023

TABLE D-continued

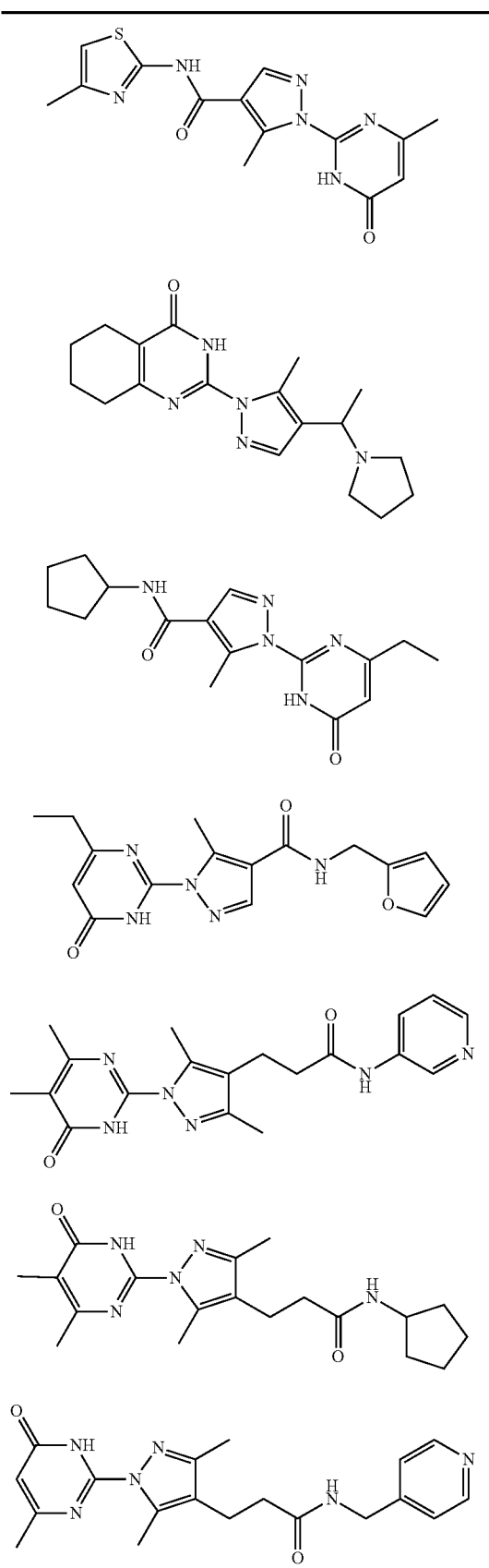

Q-024
Q-025
Q-026
Q-027
Q-028
Q-029
Q-030

TABLE D-continued

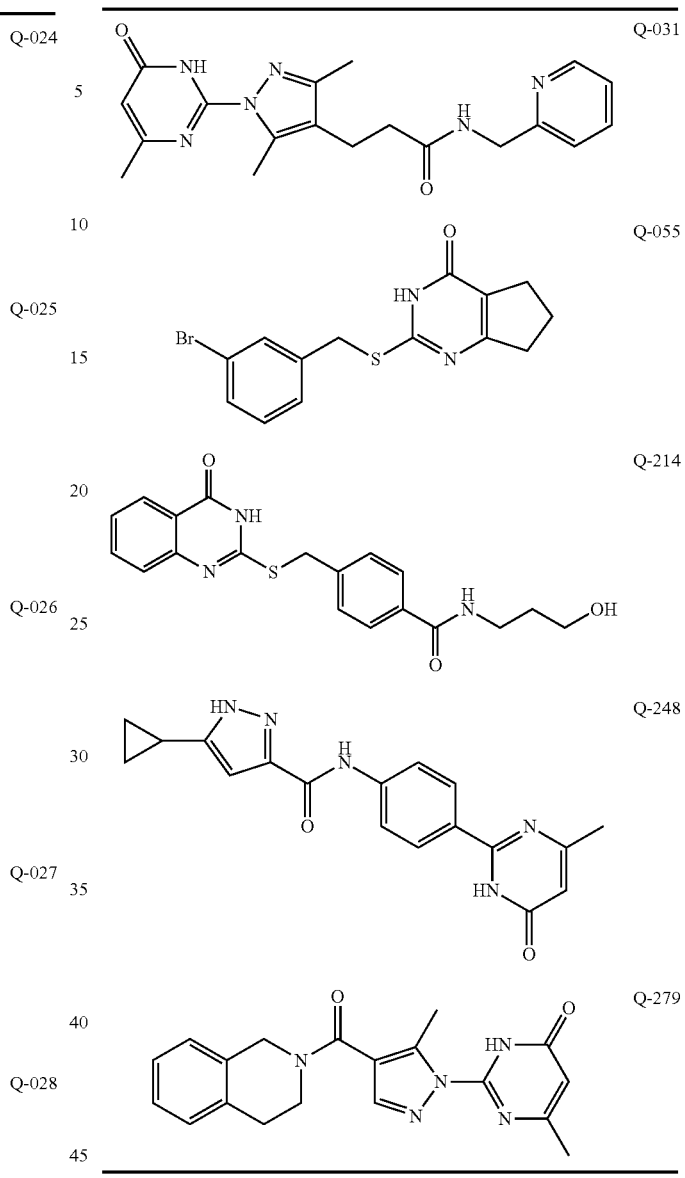

Q-031
Q-055
Q-214
Q-248
Q-279

Methods of Using SPR Inhibitors

The uses of the compounds and compositions disclosed herein include use as an SPR inhibitor, an analgesic, a treatment for acute or chronic pain, an anti-inflammatory, and/or as an immune cell regulator. The disclosed methods include inhibiting sepiapterin reductase (SPR) by a method comprising contacting SPR with a compound or composition disclosed herein in an amount effective to inhibit SPR. In some aspects, the contacting is in vitro. In other aspects, the contacting is in vivo. In various aspects, contacting comprises administering the compound or the composition to a subject in need thereof. In various aspects, the subject is a mammal. In a preferred aspect, the mammalian subject is human.

It is contemplated that the SPR inhibitor compounds, compositions, and methods are useful in the treatment of diseases and disorders associated with the BH4 synthesis pathway, such as, but not limited to, pain, inflammation, and immunological disorders. In addition, it is contemplated that the SPR inhibitor compounds, compositions, and methods are useful in the treatment of diseases and disorders associated with increased levels of BH4, such as, but not limited to, pain, inflammation, and immunological disorders, compared with normal subjects not known to suffer from pain, inflammation, and/or immunological disorders. In other aspects, the subject suffers from pain (e.g., acute or chronic pain), inflammation, and/or an immunological disorder.

The disclosed methods include methods of treating a subject suffering from pain, such as acute pain or chronic pain, comprising administering to the subject a therapeutically effective amount of a compound or composition as disclosed herein. The disclosed methods also include methods of treating a subject suffering from inflammation, such as chronic inflammation, comprising administering to the subject a therapeutically effective amount of a compound or composition as disclosed herein. The disclosed methods further include methods of treating a subject suffering from an immunological disorder, comprising administering to the subject a therapeutically effective amount of a compound or composition as disclosed herein.

Pain includes, but is not limited to, AIDS/HIV-related pain, ankylosing spondylitis, arachnoiditis, back pain, breakthrough pain, burning mouth syndrome, bursitis, cancer pain, carpal tunnel syndrome pain, cauda equina syndrome, central pain syndrome, Charcot-Marie-Tooth disease, chronic functional abdominal pain, chronic pancreatitis pain, complex regional pain syndrome, corneal neuropathic pain, degenerative disc disease, Dercum's disease, dermatomyositis, diabetic peripheral neuropathy, Ehlers-Danlos syndrome, endometriosis, erythromelalgia, failed back surgery syndrome, fibromyalgia, intercostal neuralgia, interstitial cystitis, irritable bowel syndrome, juvenile dermatositis, leg pain, loin pain-haematuria syndrome, meralgia paresthetica, migraine, multiple sclerosis pain, musculoskeletal pain, myofascial pain, myositis, neuropathic pain, occipital neuralgia, osteoarthritis pain, Paget's disease, pelvic pain, peripheral neuropathy, phantom limb pain, pinched nerve, polymyalgia rhuematica, polymyositis, post-herniorraphy pain syndrome, post-mastectomy pain syndrome, post-stroke pain, post-thorocotomy pain syndrome, post-traumatic neuropathy, postherpetic neuralgia, post-polio syndrome, primary lateral sclerosis, psoriatic arthritis, pudendal neuralgia, Raynaud's disease, restless leg syndrome, rheumatoid arthritis, sacroiliac joint dysfunction, sarcoidosis, sciatica, postherpetic neuralgia, sickle cell pain, Sjogren's syndrome, spasmodic torticollis, sphincter of Oddi dysfunction, spinal cord injury, spinal stenosis, syringomyelia, Tarlov cysts, thoracic outlet syndrome (TOS), temporomandibular joint disorder, transverse myelitis, trigeminal neuralgia, ulcerative Colitis, vascular pain, vulvodynia, and whiplash pain.

Immunological disorders include, but are not limited to, acid-induced lung injury, acne (PAPA), acute respiratory distress syndrome, ageing, headache, AIDS, alcoholic hepatitis, alcoholic liver disease, nonalcoholic steatohepatitis (NASH), allergen induced asthma, allergic bronchpulmonay aspergillosis, Alzheimer's disease, amyotropic lateral sclerosis (ALS), angina pectoris, anhidrotic ecodermal dysplasia-ID, ankylosiing spondylitis, antiphospholipid syndrome, aphthous stomatitis, appendicitis, arthritis, asthma, atopic dermatitis, autoimmune diseases, bee sting-induced inflammation, Behcet's disease, Bell's palsey, Blau syndrome, bronchiolitis, burns, cancer, cardiac hypertrophy, catabolic disorders, cataracts, cerebral aneurysm, Cystic Fibrosis, chemical irritant-induced inflammation, chronic heart failure, chronic lung disease of prematurity, chronic obstructive pulmonary disease, colitis, complex regional pain syndrome, congenital muscular dystrophies, connective tissue diseases, crohn's disease, cryopyrin-associated periodic syndromes, cyrptococcosis, cystic fibrosis, deficiency of the interleukin-1-receptor antagonist (DIRA), dermatitis, dermatomyositis, DIPG (Diffuse Intrinsic Pontine Glioma), endometriosis, endotoxemia, eosiniphilic esophagitis, familial amyloidotic polyneuropathy, familial cold urticarial, familial mediterranean fever, fetal growth, FSHD, glaucoma, glomerular disease, glomerular nephritis, gut diseases, peritoneal endometriosis, head injury, hearing loss, heart disease, Henoch-Scholein purpura, hepatitis, hereditary periodic fever syndrome, Herpes zoster and simplex, HIV-1, Huntington's disease, hyaline membrane disease, hypercholesterolemia, hyperimmunoglobulinemia D with recurrent fever (HIDS), hypoplastic and tother anemias, incontinentia pigmenti, infectious mononucleosis, inflammatory bowel disease, inflammatory lung disease, inflammatory neuropathy, inflammatory pain, insect bite-induced inflammation, irritant-induced inflammation, ischemia/reperfusion, Kawasaki Disease, kidney disease, kidney injury caused by parasitic infections[m1], leptospiriosis, leukemia, limb girdle muscular dystrophy 2A, limb girdle muscular dystrophy 2B, lung injury, lupus, lupus nephritis, lymphoma, meningitis, mesothelioma, Muckle-Wells syndrome (urticaria deafness amyloidosis), multiple sclerosis, muscle wasting, muscular dystrophy, myasthenia gravis, mycarditis, mycosis fungoides, myelodysplastic syndrome, myositis, nasal sinusitis, necrotizing enterocolitis, neonatal onset multisystem inflammatory disease (NOMID), nephrotic eyndrome, neuritis, neuropathological diseases, non-allergen induced asthma, obesity, ocular allergy, organ transplant, osterarthritis, otitis media, paget's disease, pancreatitis, Parkinson's disease, pericarditis, periodic fever, periodonitis, pertussis, pharyngitis and adenitis (PFAPA syndrome), plant irritant-induced inflammation, Pneumosystis infection, poison ivy/urushiol oil-induced inflammation, polyarteritis nodosa, polycystic kidney disease, polymyositis, pontine glioma, psoriasis, psychosocial stress diseases, pulmonary disease, pulmonary fibrosis, pulmonary hypertension, pyoderma gangrenosum, pyogenic sterile arthritis, renal disease, retardation, retinal disease, rheumatic disease, sarcoidosis, sebborrhea, sepsis, sickle cell, silica-induced diseases, Sjogren's syndrome, skin diseases, sleep apnea, solid tumors including brain tumors, spinal cord injury, statin induced myopathy, stroke, subarachnoid hemorrhage, sunburn, thrombocytopenia, tissue transplant, TNF receptor associated periodic syndrome (TRAPS), toxoplasmosis, traumatic brain injury, tuberculosis, type 1 diabetes, type 2 diabetes, ulcerative colitis, uveitis, and wound repair.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases SPR activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or it may be divided into multiple doses.

An SPR inhibitor is contemplated to be useful in the treatment of any condition wherein the lowering of BH4 levels will provide benefits. The SPR inhibitor is useful alone, or in combination with other compounds, which may act to promote the reduction of BH4 levels. The present section provides a description of how the SPR inhibitors of the invention may be therapeutically administered to a subject in need thereof.

One of the therapeutic embodiments of the invention is the provision, to a subject in need thereof, compositions comprising one or more SPR inhibitors. In one aspect, the SPR inhibitor formulation for therapy in a subject is selected based on the route of administration and in certain aspects includes liposome and micelle formulations as well as classic pharmaceutical preparations.

In various aspects, administration of the compositions is systemic or local, and in still other aspects comprises a single site injection of a therapeutically-effective amount of the SPR inhibitor composition. Any route known to those of skill in the art for the administration of a therapeutic composition of the invention is contemplated including, for example, intravenous, intramuscular, subcutaneous, oral, or a catheter for long-term administration.

Combination Therapy:

In addition to therapies based solely on the delivery of the SPR inhibitor composition, combination therapy is specifically contemplated. In the context of the invention, it is contemplated that the SPR inhibitor composition therapy is used similarly in conjunction with other agents commonly used for the treatment of elevated levels of BH4 and/or SPR.

The combination therapy compositions are provided in a combined amount effective to produce the desired therapeutic outcome in the treatment of reduced levels of BH4 and/or make a detectable change in an indication as described herein. This process involves administering the SPR inhibitor and the second agent(s) or factor(s) at the same time. Methods thus include administering a single composition or pharmacological formulation that includes both agents, or administering two distinct compositions or formulations, at the same time, wherein one composition includes the SPR inhibitor therapeutic composition and the other includes the second therapeutic agent.

Alternatively, the SPR inhibitor treatment precedes or follows the second therapeutic agent treatment by intervals ranging from minutes to weeks. In embodiments where the second therapeutic agent and the SPR inhibitor are administered separately, one generally ensures that a significant period of time did not transpire between the times of each delivery, such that the second therapeutic agent and the SPR inhibitor are able to exert an advantageously combined effect. In such instances, it is contemplated that one administers both modalities within about 12-24 hours of each other, or alternately, within about 6-12 hours of each other, or alternately, with a delay time of only about 12 hours. However, in some situations, it is desirable to extend the time period for treatment significantly, where several days (2, 3, 4, 5, 6 or 7) to several weeks (1, 2, 3, 4, 5, 6, 7 or 8) lapse between the respective administrations.

Systemic delivery of SPR inhibitors to patients is a very efficient method for delivering a therapeutically effective amount of the compound to counteract the immediate clinical manifestations of a disease or disorder. Alternatively, local delivery of the SPR inhibitor and/or the second therapeutic agent is appropriate in certain circumstances. In a certain embodiment, it is contemplated that the SPR inhibitor is delivered to a patient for an extended period of time. It is further contemplated that the SPR inhibitor is taken throughout a patient's lifetime to lower SPR activity levels.

Dosing and Pharmaceutical Formulations

Also provided herein are pharmaceutical compositions that includes a compound as disclosed herein, together with a pharmaceutically acceptable excipient such as a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all cases the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some cases, all the necessary components for the treatment of an SPR-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

Synthesis of Compounds Disclosed Herein

The compounds disclosed herein can be prepared following the methods outlined in detail in the Examples, using suitable modifications to the starting reagents. One of skill in the art, in view of the teachings of the Examples and using typical organic chemistry techniques, can synthesize a compound as disclosed herein.

In some cases, compounds of formula I can be prepared by converting an appropriate thiouracil to a hydrazine intermediate, coupling the hydrazine intermediate with an appropriate enamine reagent to form a compound of formula I or an intermediate having a pyrazolyl moiety, and further reacting the intermediate having a pyrazolyl moiety so as to couple with an appropriate amine (for example, using reagents such as HATU or HATU/HOAt) to provide a compound of formula I as shown in the Scheme 1 and Scheme 2.

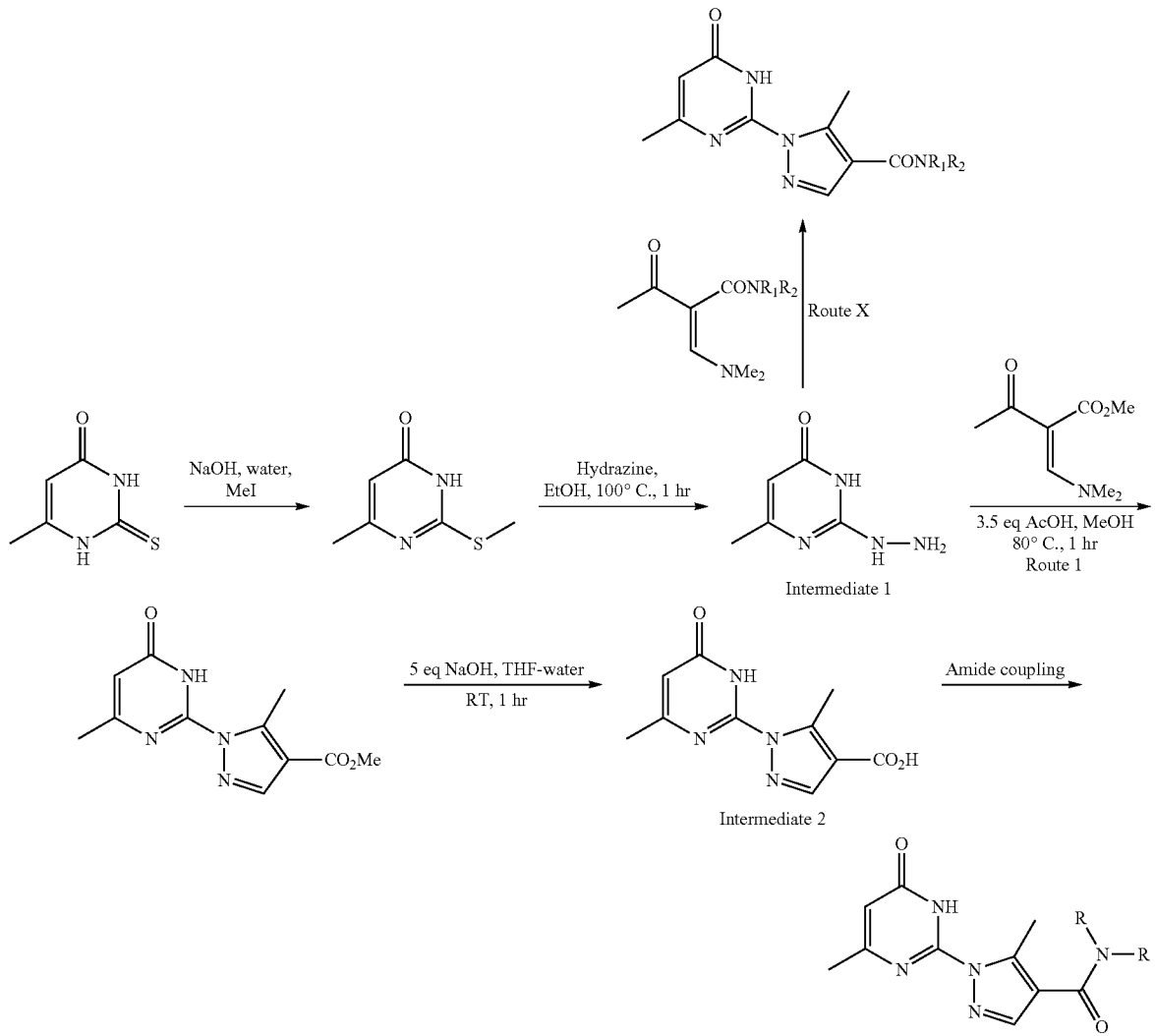

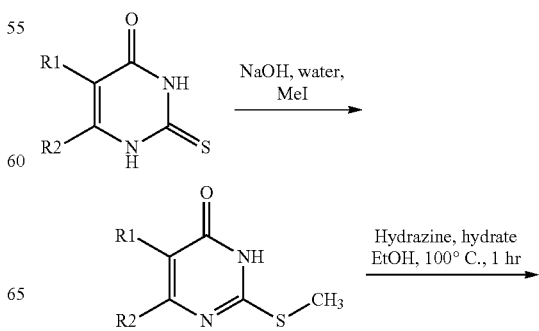

547
-continued

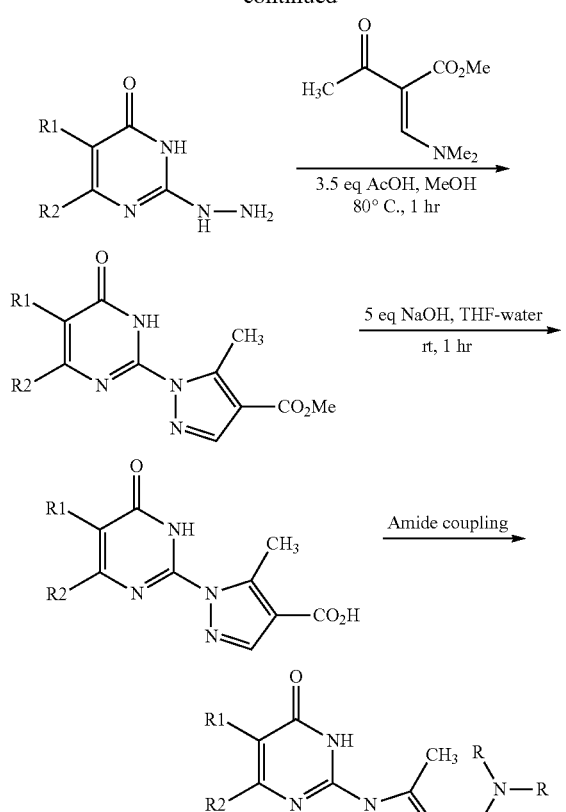

In some cases, compounds of formula I can be prepared by converting an appropriate dichloropyrimidine to a hydrazine intermediate, coupling the hydrazine intermediate with an appropriate enamine reagent to form an intermediate having a pyrazolyl moiety, and further reacting the intermediate having a pyrazolyl moiety so as to couple with an appropriate amine (for example, using reagents such as HATU or HATU/HOAt) to provide a compound of formula I as shown in Schemes 3 and 4.

Scheme 3

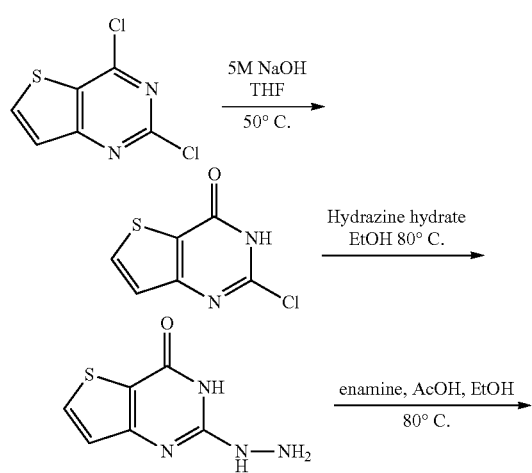

548
-continued

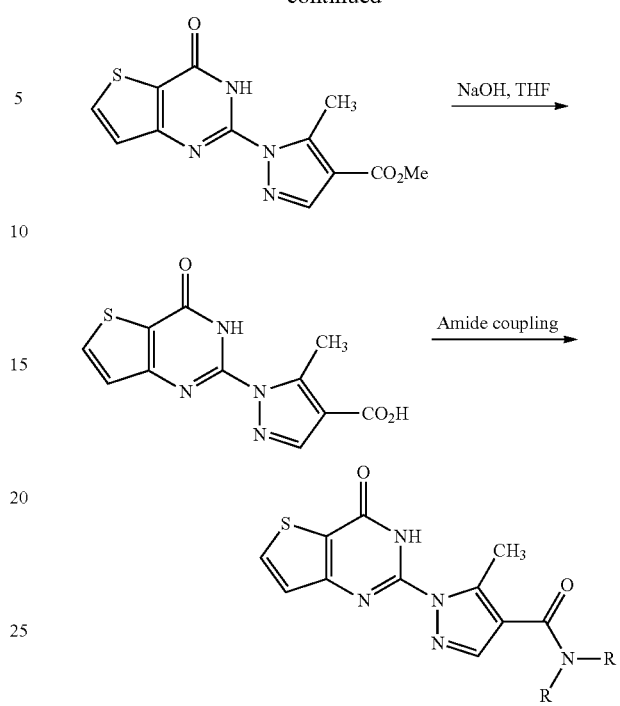

Scheme 4

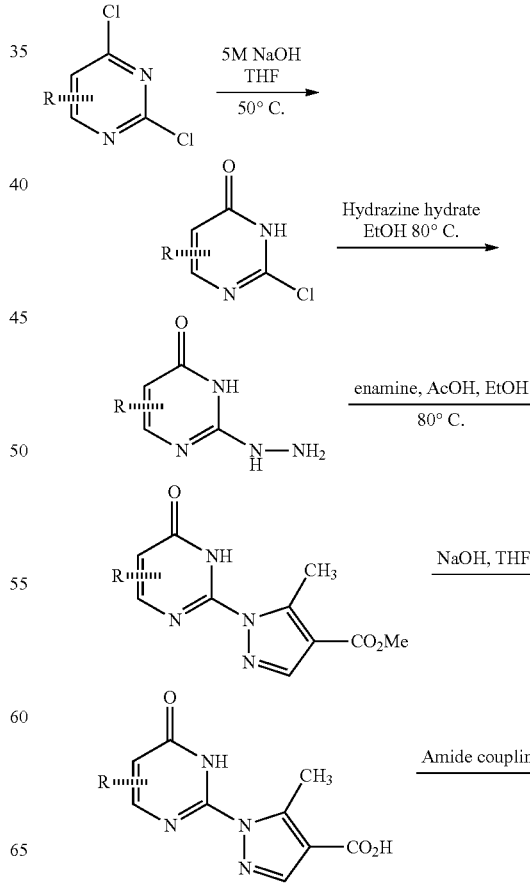

-continued

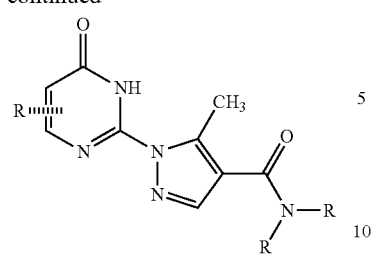

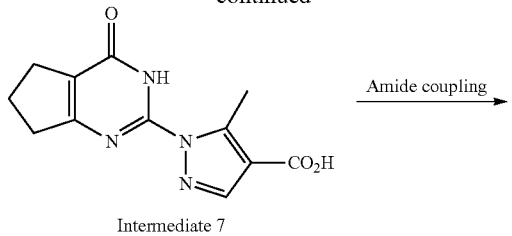

Intermediate 7

In some cases, compounds of formula I can be prepared by converting an appropriate cyclopentanone to a hydrazine intermediate, coupling the hydrazine intermediate with an appropriate enamine reagent to form an intermediate having a pyrazolyl moiety, and further reacting the intermediate having a pyrazolyl moiety so as to couple with an appropriate amine (for example, using reagents such as HATU or HATU/HOAt) to provide a compound of formula I as shown in Scheme 5.

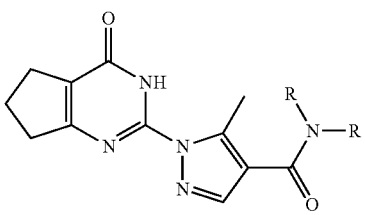

In some cases, compounds of formula I can be prepared by coupling an appropriate hydrazine intermediate with an appropriate enamine, enol ether, aldehyde, or ketone reagent to form an intermediate having a pyrazolyl moiety, and further reacting the intermediate having a pyrazolyl moiety so as to couple with an appropriate amine (for example, using reagents such as HATU or HATU/HOAt) to provide a compound of formula I as shown in Scheme 6.

Scheme 5

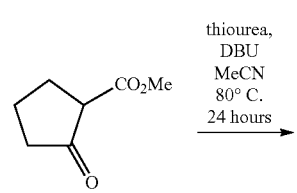

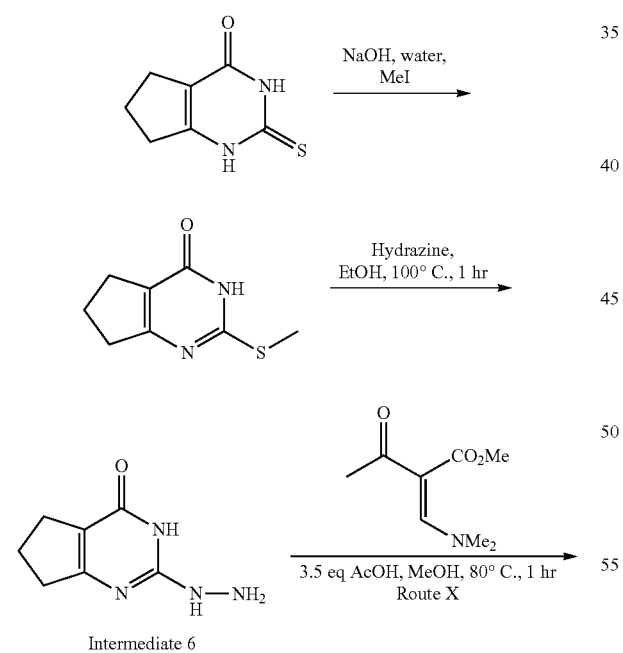

Intermediate 6

Scheme 6

One of:

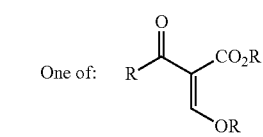

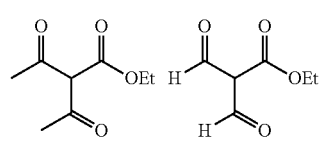

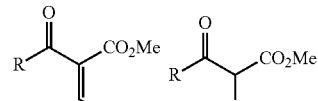

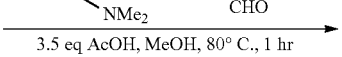

3.5 eq AcOH, MeOH, 80° C., 1 hr

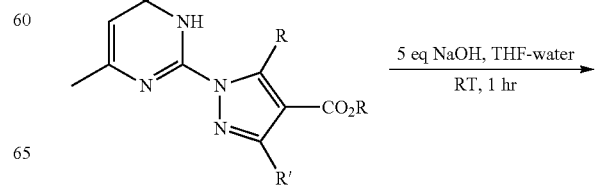

5 eq NaOH, THF-water
RT, 1 hr

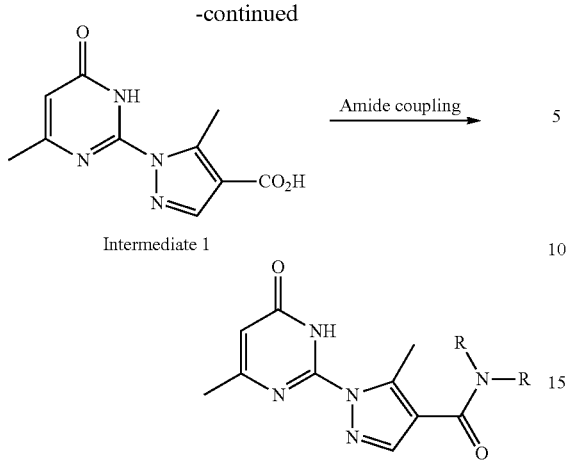

Intermediate 1

In some cases, compounds of formula I can be prepared by coupling an appropriate hydrazine intermediate with an appropriate dialdehyde reagent to form an intermediate having a pyrazolyl moiety, and further reacting the intermediate having a pyrazolyl moiety so as to couple with an appropriate amine (for example, using reagents such as HATU or HATU/HOAt) to provide a compound of formula I as shown in Scheme 7.

Scheme 7

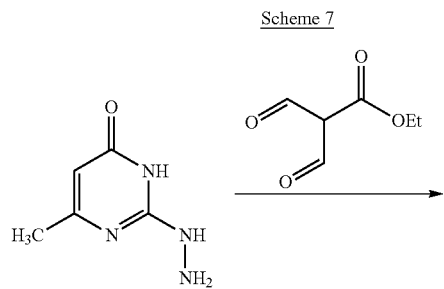

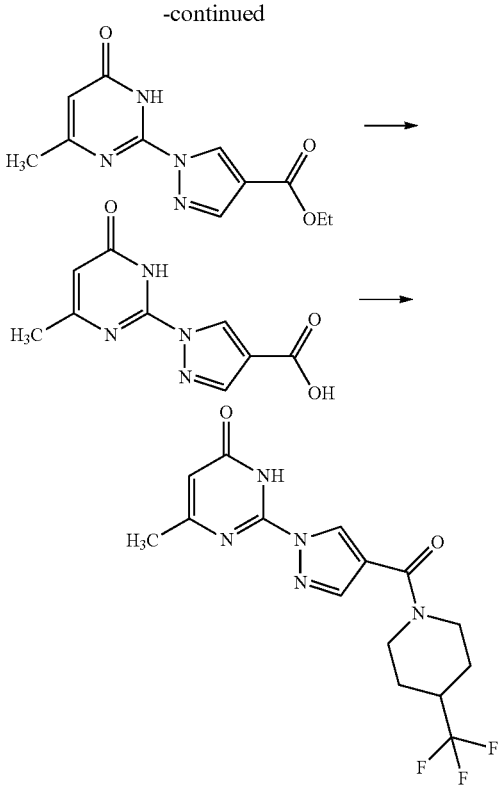

In some cases, compounds of formula I can be prepared by coupling an appropriate chloropyrimidine or sulfonyl pyrimidine with an appropriate pyrazolyl moiety to form a compound of formula I or an intermediate having a pyrazolyl moiety, and further reacting the intermediate having a pyrazolyl moiety so as to couple with an appropriate amine (for example, using reagents such as HATU or HATU/HOAt) to provide a compound of formula I as shown in Schemes 8, 9, 10 and 11.

Scheme 8

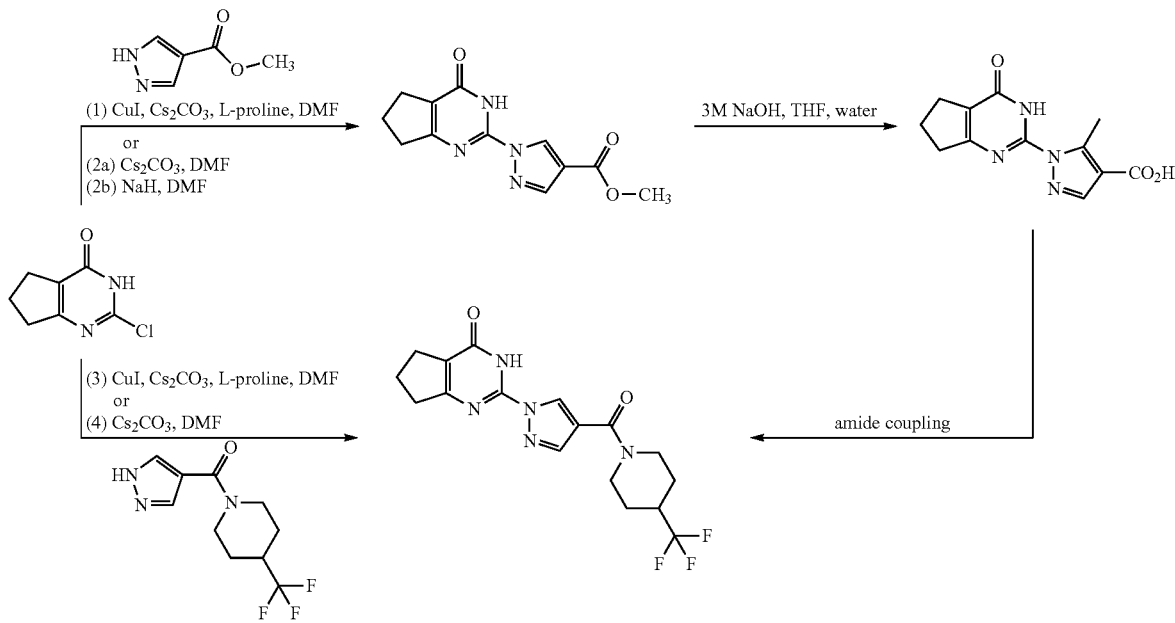

553
Scheme 9
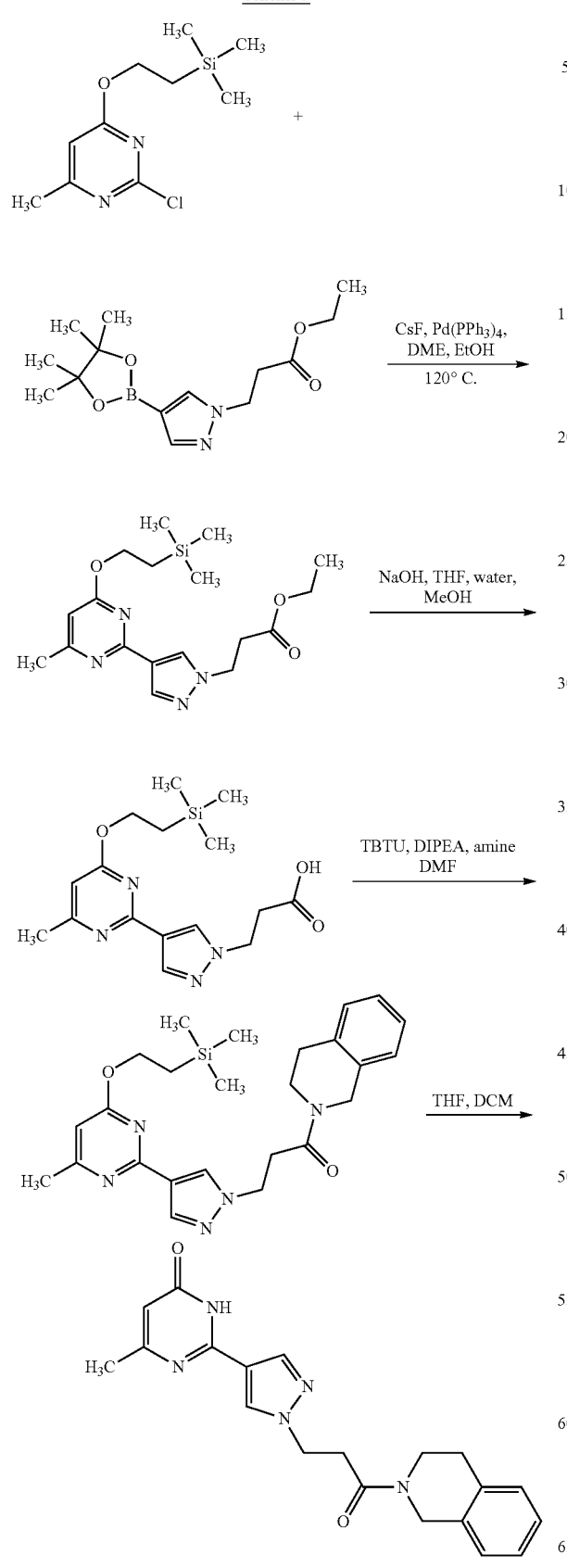
554
Scheme 10
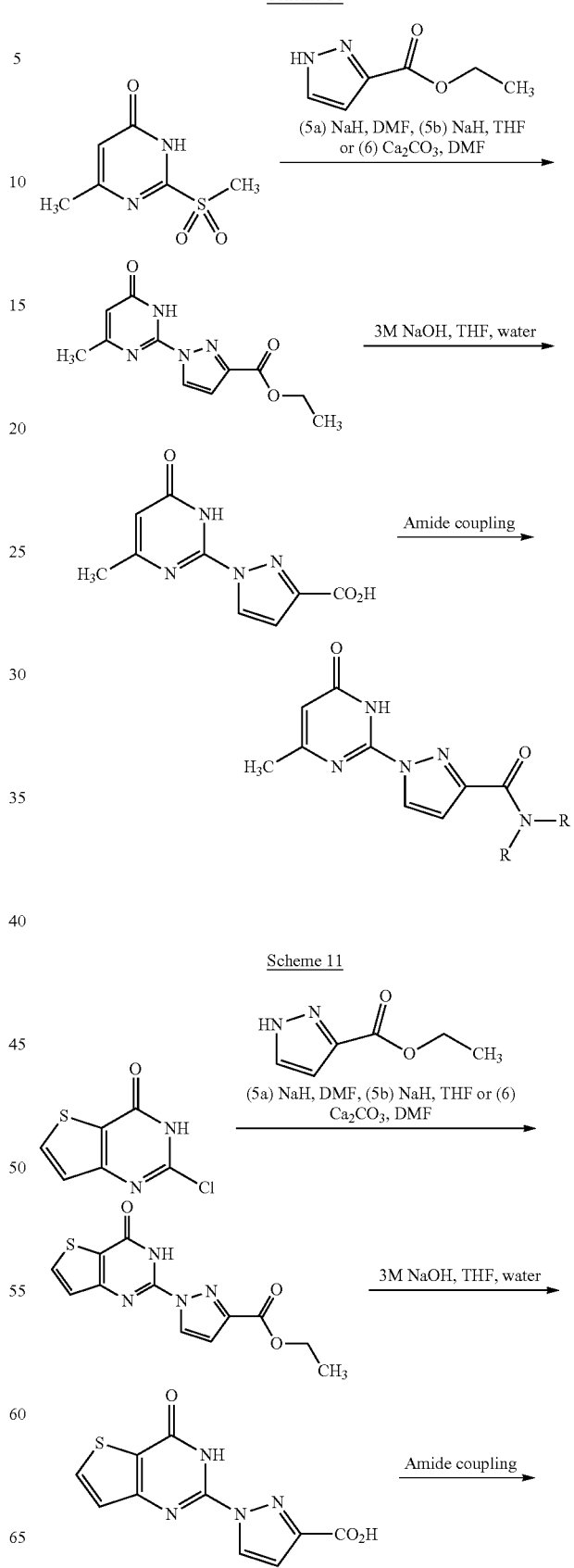
Scheme 11
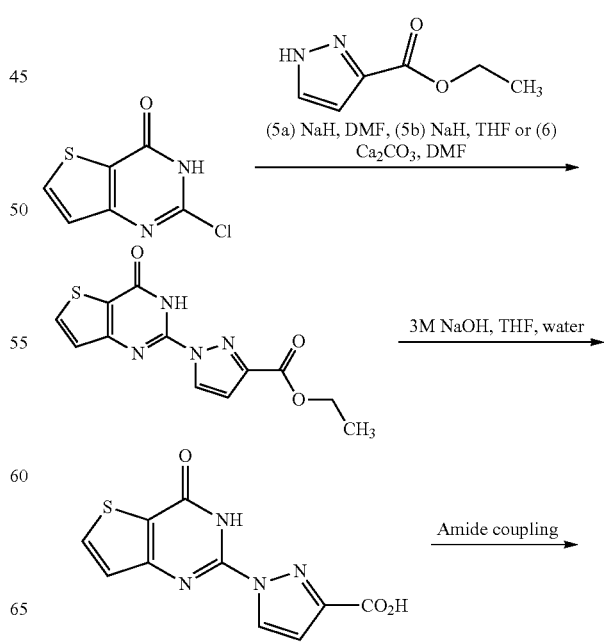

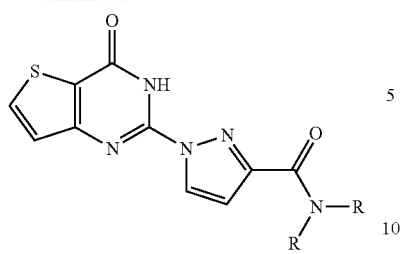

In some cases, compounds of formula I can be prepared by coupling an appropriate bromo-cyclopropylideneacetate with an appropriate pyrazolyl moiety to form an intermediate having a pyrazolyl moiety, and further reacting the intermediate having a pyrazolyl moiety so as to couple with an appropriate amine (for example, using reagents such as HATU or HATU/HOAt) to provide a compound of formula I as shown in Scheme 12.

Scheme 12

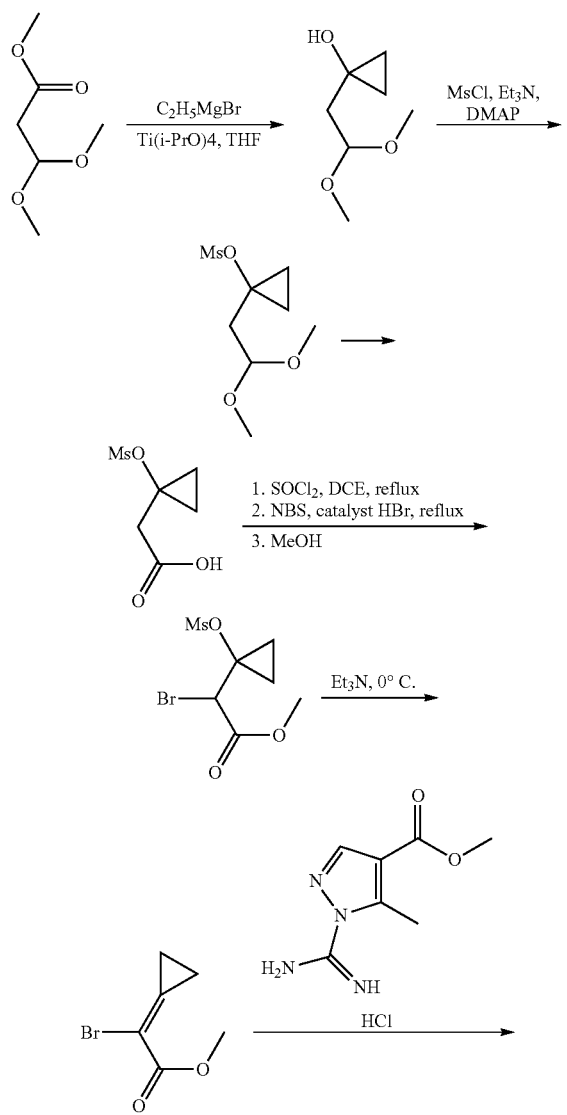

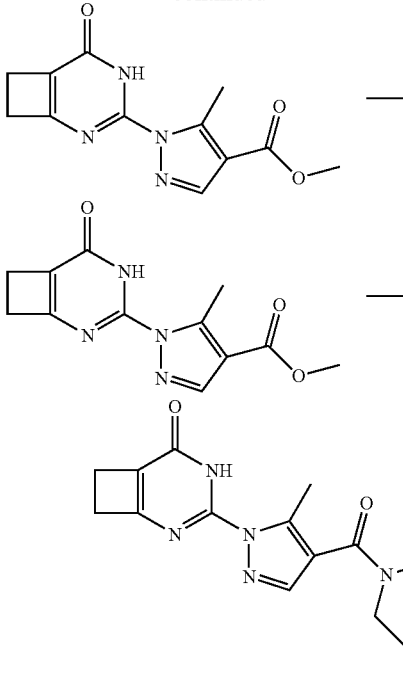

In some cases, compounds of formula I can be prepared by coupling an appropriate azide with an appropriate β-keto ester to form an intermediate having a triazolyl moiety, and further reacting the intermediate having a triazolyl moiety so as to couple with an appropriate amine (for example, using reagents such as HATU or HATU/HOAt) to provide a compound of formula I as shown in Scheme 13.

Scheme 13

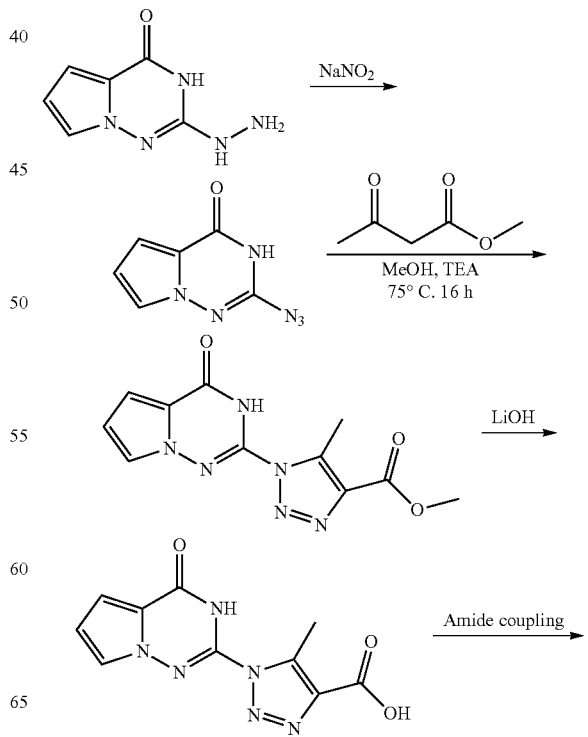

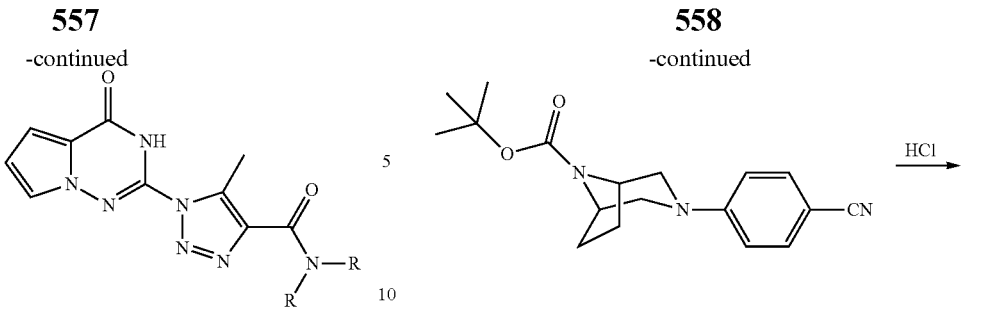

Amines that are not commercially available can be prepared by standard procedures. In some cases, amines that are not commercially available can be prepared by coupling an appropriate aryl bromide with a mono-protected cyclic diamine, followed by deprotection of the amine protecting group to obtain the amine, for example, as shown in Scheme 14.

Scheme 14

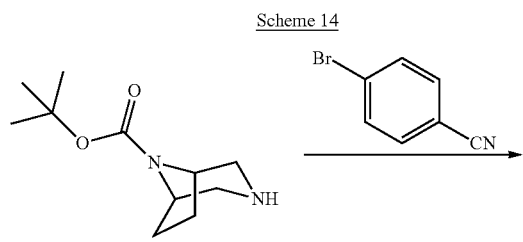

In some cases, amines that are not commercially available can be prepared by reducing an appropriate protected aminoketone to obtain the corresponding alcohol, protecting the alcohol with an appropriate protecting group, further reacting with an appropriate reagent so as to convert the protected alcohol to a desired functional group (e.g., a cyano group), followed by deprotection of the amine protecting group to obtain the amine, for example, as shown in Scheme 15.

Scheme 15

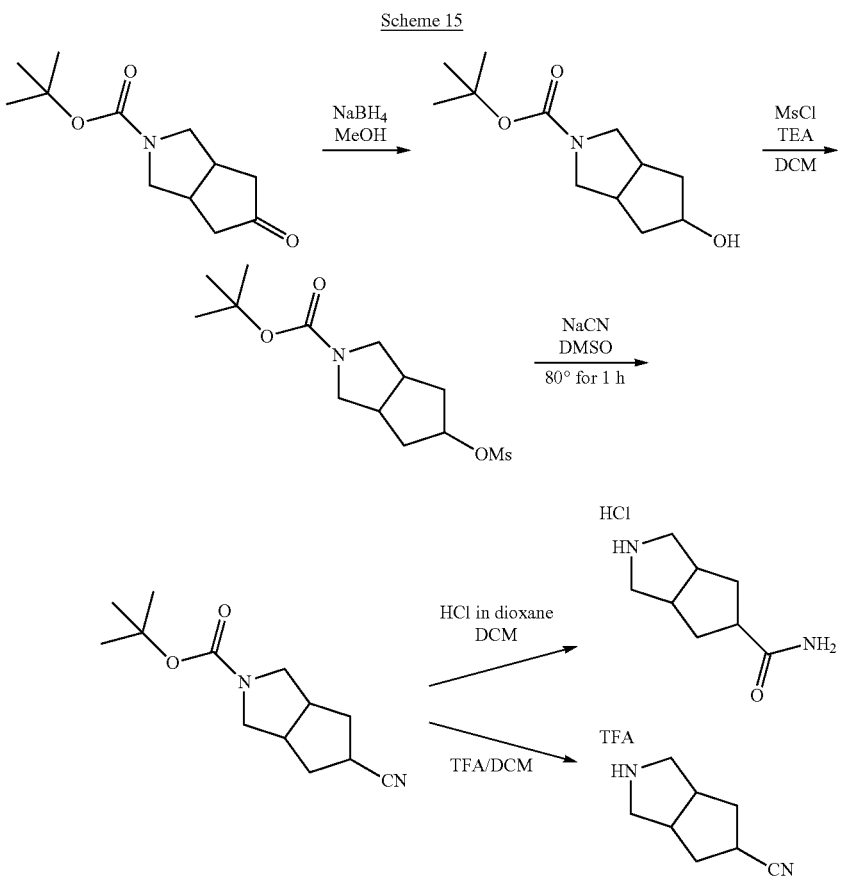

Assessment of SPR Inhibitory Activity

The compounds disclosed herein can be assessed for SPR inhibitory activity. Typically, a compound is assayed by an enzymatic assay (e.g., a TR-FRET assay) and/or a cellular assay (e.g., SKN-N-BE(2) cells or human PBMC (Peripheral Blood Mononuclear Cells)) as described below.

TR-FRET Assay: A TR-FRET (homogeneous, time-resolved, fluorescence resonance energy transfer) assay was used to assess activity of compounds following standard assay conditions. Terbium labeled SNAP-hSPR and SSZ (sulfasalazine) labeled SNAP-EGFP were used as the protein pair in this assay according to the procedure described in Haruki et al., Science, 430:987 (2013). Compounds were screened at different concentrations and IC50 values calculated.

SKN-N-BE(2) Cellular Assay: SK-N-BE (2) cells were seeded in sterile, 96-well plates and incubated for 12-24 hours at 37° C. with 5% $CO_2$ supply. Media was removed and fresh DMEM/F-12 media (containing Glutamine & Pen/Strep but no FBS) was added. Compounds (at different concentrations) were added to different wells. The plates were then incubated for 6-48 hours at 37° C. with 5% $CO_2$ supply. Plates were then centrifuged and the supernatant was removed. The plates were then optionally washed once with PBS. They were then sealed and stored at −80° C. or immediately used. The cells were lysed and the level of BH4 was assessed by LC-MS.

hPBMC Assay: PBMCs were either purchased or isolated from fresh human blood and used either as a fresh preparation or frozen for later use. The assay system was prepared by pre-treating the assay plates overnight with a solution containing anti-human CD3 antibody. Human PBMCs were suspended in assay medium and plated into the assay plates at a density of 1-4×$10^5$ cells per well. The desired concentration of the test compound was added to each well. A solution of human anti-CD28 antibody was also added to each well. Plates were incubated for 12-48 hours at 37° C. and 5% $CO_2$. Assay plates were centrifuged for 5-15 minutes at 1-3000 RMP and supernatants were removed. The cells were lysed, sealed and used directly or frozen at −80° C. LC-MS was used to quantify the amount of inhibition of BH4 production.

Assessment of Pain Behavior

The compounds disclosed herein can be assessed for effect on pain behavior. Typically, a compound is assayed by a behavioral pharmacology model as described below.

Behavioral Pharmacology Model: Compounds were administered by oral gavage to rats that had undergone one of two nerve injury surgeries: spared nerve injury to injure two of the three peripheral branches of the sciatic nerve or chronic constriction injury of the sciatic nerve. Paw withdrawal thresholds to mechanical stimulation using calibrated von Frey filaments were used as measurement of neuropathic pain-like behaviors.

EXAMPLES

In the examples and throughout the specification, the following abbreviations are used.

| | |
|---|---|
| conc. | concentrated |
| DCM | dichloromethane |
| DMF | N,N-dimethylformamide |
| DMSO | dimethylsulfoxide |
| $Et_2O$ | diethyl ether |
| EtOAc or EA | ethyl acetate |
| MeOH | methanol |
| EtOH | ethanol |
| THF | tetrahydrofuran |
| DIPEA | N,N-diisopropylethylamine |
| DAST | diethylaminosulfur trifluoride |
| LDA | lithium diisopropylamide |
| mCPBA | 3-chloroperoxybenzoic acid |
| $Pd(OAc)_2$ | palladium(II) acetate |
| TEA | triethylamine |
| DIAD | diisopropyl azodicarboxylate |
| $NaHCO_3$ | Sodium bicarbonate |
| $Na_2CO_3$ | Sodium Carbonate |
| $MgSO_4$ | Magnesium sulphate |
| $Na_2SO_4$ | Sodium Sulphate |
| $SiO_2$ | silica |
| h | hour |
| r.t. | room temperature |
| RT | retention time |
| br | broad |
| M | mass |
| HPLC | High Performance Liquid Chromatography |
| LC-MS | Liquid Chromatography Mass Spectrometry |
| ES+ | Electrospray Positive Ionisation |
| ES− | Electrospray Negative Ionisation |
| brine | aqueous sodium chloride solution |
| EDC | 1-(3-dimethylaminopropyl)-3-ethylcarbodiimide hydrochloride |
| HATU | O-(7-azabenzotriazol-1-yl)-N,N,N',N'-tetramethyluronium hexafluorophosphate |
| $Pd(PPh_3)_4$ | tetrakis(triphenylphosphine)palladium(0) |
| HOAt | 1-Hydroxy-7-azabenzotriazole |
| PE | Petroleum ether |
| SGC | Silica gel chromatography |
| TLC | Thin layer chromatography |
| GC-MS | Gas chromatography mass spectrometry |
| $PdCl_2(dppf)$ | [1,1'-bis(diphenylphosphino)ferrocene]dichloropalladium(II) |
| T3P | Propylphosphonic anhydride |
| COMU | (1-Cyano-2-ethoxy-2-oxoethylidenaminooxy)dimethylamino-morpholino-carbenium hexafluorophosphate |
| SCX | propylsulfonic acid bonded sorbent purification cartridge |

General Procedures

The following analytical LC-MS methods were used.

Method A: (2 min IPC)
MET/CR/1673
Column: Supelco Ascentis Express C18, 30 mm × 2.1 mm, 2.7 µm
Flow rate: 1.0 ml/min
Mobile Phase: A, Formic acid (aqueous) 0.1% and B, Formic acid (MeCN) 0.1%
Injection Vol: 3 µl
Temp.: 40° C.
Detection: 215 nm (nominal)
Gradient Time (minutes) - % B
0.00-5
1.50-100
1.60-100
1.61-5
Method B: (1.7 min IPC)
MET/CR/1410
Column: Kinetex Core-Shell C18, 50 mm × 2.1 mm, 5.0 µm
Flow rate: 1.2 ml/min
Mobile Phase: A, Formic acid (aqueous) 0.1% and B, Formic acid (MeCN) 0.1%
Injection Vol: 3 µl
Temp.: 40° C.
Detection: 215 nm (nominal)
Gradient Time (minutes) - % B
0.00-5
1.20-100
1.30-100
1.31-5

Method C: (7 min IPC)
MET/u-HPLC (low pH 7 min method)
Column: Phenomenex Kinetex-XB C18, 2.1 mm × 100 mm, 1.7 μm
Flow rate: 0.6 ml/min
Mobile Phase: A, Formic acid (aqueous) 0.1% and B, Formic acid (MeCN) 0.1%
Injection Vol: 3 μl
Temp.: 40° C.
Detection: 215 nm (nominal)
Gradient Time (minutes) - % B
0.00-5
5.30-100
5.80-100
5.82-5

The following preparative HPLC and SFC methods were used.

Method D:
SFC: 10% Methanol: 90% $CO_2$ on a 25 cm OJ-H Column, at 15 ml/min.
Method E:
Generic high pH prep method (Gilson 3 and Gilson 5)
Column: Waters Xbridge C18 (30 × 100 mm, 10 um)
Flow rate: 40 ml/min
Mobile Phase: A, Water + 0.2% Ammonium hydroxide, B, Acetonitrile + 0.2% Ammonium hydroxide
Injection Vol.: 1500 μl
Temperature: r.t.
Detection: 215 nm
Gradient Time (minutes) - % B
0.0-5
2.5-5
16.05-95
18.2-95
19.1-5
20-5
Method F:
Generic neutral pH prep method (Waters 1)
Column: Waters Sunfire C18 (30 × 100 mm, 10 um), Part no. 186003971
Flow rate: 40 ml/min
Mobile Phase: A, Water, B, Acetonitrile
Injection Vol: 1500 μl
Temperature: r.t.
Detection: 215 nm
Gradient Time (minutes) - % B
0-10
2-10
2.5-15
14.5-100
15.5-100
16-10
17-10
Method G:
Generic low pH prep method (Waters 2)
Column: Waters Sunfire C18 (30 × 100 mm, 10 um), Part no. 186003971
Flow rate: 40 ml/min
Mobile Phase: A, Water + 0.1% Formic acid, B, Acetonitrile + 0.1% Formic acid
Injection Vol.: 1500 μl
Temperature: r.t.
Detection: 215 nm
Gradient Time (minutes) - % B
0-5
2-5
2.5-10
14.5-10
15.5-100
16-5

The following preparative chiral separation and analysis methods were used.

Method H:
Separation
Column: SFC ChiralPak AS (250 mm × 20 mm, 5 um)
Flow rate: 50 mL/min
Eluent: MeOH/$CO_2$ 50% (TFA was added as a modifier)
Injection Vol: 0.7 mL (7 mg)
Detection: 218 nm
Method I:
Analysis
Column: SFC ChiralPak AS (250 mm × 4.6 mm, 5 um)
Flow rate: 4 mL/min
Eluent: MeOH/CO2 45% (TFA was added as a modifier)
Method J:
Separation
Column: HPLC Lux C1 (20 mm × 250 mm, 5 um)
Flow rate: 21 mL/min
Eluent: HEPT/EtOH (50:50) (TFA was added as a modifier)
Injection Vol: 0.5 mL (10 mg)
Detection: 210 nm
Method K:
Analysis
Column: HPLC Lux C1 (4.6 mm × 250 mm, 5 um)
Eluent: HEPT/EtOH (40:60) (TFA was added as a modifier)
Flow rate: 4 mL/min.
Method L:
Separation
Column: ChiralPak AD (20 mm × 250 mm, 20 um)
Eluent: EtOH (TFA was added as a modifier)
Flow rate was 21 mL/min
Method M:
Analysis
Column: HPLC using a YMC AMY-C (4.6 mm × 250 mm, 5 um)
Eluent EtOH (TFA was added as a modifier)
Flow rate: 1 mL/min
Method N:
Separation
Column: HPLC Chiralcel OD-H 25 cm
Eluent: ethanol + 0.1% formic acid
Flow rate: 5 ml/min
Method O:
Separation
Column: Lux A2 (20 mm × 250 mm, 5 um)
Eluent: EtOH (TFA was added as a modifier)
Flow rate: 21 mL/min
Detection: 210 nm The following LC-MS methods were used.

Method A':
Column: SunFire C18 (4.6 × 50 mm, 3.5 um)
Mobile phase: $H_2O$ (0.05% TFA) (A)/ACN (0.05% TFA) (B)
Elution program: Gradient from 5 to 100% of B in 1.3 min at 2 mL/min
Temperature: 50° C.
Detection: UV (214, 254 nm) and MS (ESI, Pos mode, 110 to 1000 amu)
Method B':
Column: Chromolith Fast Gradien RP-18e, 50-3 mm
Mobile Phase: A: Water (0.01% TFA) B: ACN (0.01% TFA)
Gradient: 5% B increase to 100% B within 0.8 min, 100% B for 1.1 min.
Flow Rate: 1.5 mL/min
Column Temperature: 40° C.
Mass Range: 103-1100
Method C':
Column: Sunfire C18 4.6 × 50 mm, 3.5 um
Mobile phase: $H_2O$ (0.01% TFA) (A)/ACN (0.01% TFA) (B)
Elution program: Gradient from 5 to 95% of B in 1.4 min at 2.0 ml/min
Temperature: 45° C.
Detection: UV (214, 254 nm) and MS (ESI, POS mode, 113 to 1200 amu)
Method D':
Column: Sunfire C18 2.5 um3 * 30 mm
Mobile Phase: A: water (0.01% TFA) B: ACN (0.01% TFA)
Gradient: 5%-95% B in 1.5 min
Flow Rate: 1.5 mL/min
Mass Range: 110-1000 UV: 214 nm; 254 nm
Oven Temperature: 50° C.
Method E':
Column: SunFire C18, 4.6 * 50 mm, 3.5 um
Mobile Phase: A: Water (0.01% TFA) B: ACN (0.01% TFA)
Gradient: 5% B increase to 95% B within 1.2 min, 95% B for 1.3 min, back to 5% B within 0.01 min.
Flow Rate: 2.0 mL/min -continued Column Temperature: 50° C.
Method F':
Column: Xbridge C18 (4.6 × 50 mm, 3.5 um)
Mobile phase: H2O (10 mmol NH₄HCO₃) (A)/ACN(B)
Elution program: Gradient from 5 to 95% of B in 1.3 min at 1.8 ml/min
Temperature: 50° C.
Detection: UV (214, 254 nm) and MS (ESI, POS mode, 110 to 1000 amu)
Method G':
Column: Xbridge, 3.5um, 50 * 4.6 mm
Mobile Phase: A: 10 m mol/L NH₄HCO₃ in water B: ACN
Gradient: 5% B increase to 95% B within 1.5 min, 95% B for 1.0 min, back to 5% B within 0.01 min.
Flow Rate: 2 mL/min
Oven Temperature: 50° C.
Method H':
Column: Xbridge C18 4.6 * 50 mm 3.5 um
Mobile Phase: A: 10 mM NH₄HCO₃ in water B: ACN
Gradient: 5% B increase to 95% B within 1.2 min, 95% B for 1.3 min, back to 5% B within 0.01 min.
Flow Rate: 2.0 mL/min
Oven Temperature: 50° C.

-continued

Method I':
Column: Gemini-NX 3u C18 (4.6 × 50 mm, 3 um)
Mobile phase: H₂O (10 mmol NH₄HCO₃) (A)/ACN (B)
Elution program: Gradient from 10 to 95% of B in 1.5 min at 1.8 mL/min
Temperature: 50° C.
Detection: UV (214, 254 nm) and MS (ESI, Pos mode, 70 to 900 amu)
Method J':
Column: Xbridge C18(2) (4.6 × 50 mm, 3.5 um)
Mobile phase: H₂O (10 mmol NH4HCO3) (A)/ACN (B)
Elution program: Gradient from 10 to 95% of B in 1.5 min at 1.8 mL/min
Temperature: 50° C.
Detection: UV (214, 254 nm) and MS (ESI, Pos mode, 110 to 1100 amu)
Method K':
Column: YMC C18 Plus, 4.6 * 50 mm, 3 um, 12 nm
Mobile Phase: A: water (10 mM Ammonium hydrogen carbonate) B: ACN
Gradient: 5%-95% B in 1.6 min
Flow Rate: 1.6 mL/min
Oven Temperature: 50° C.
MS Range: 110-1100

Preparative Example 1—Method 1: Formation of Intermediates from Corresponding Thiouracils

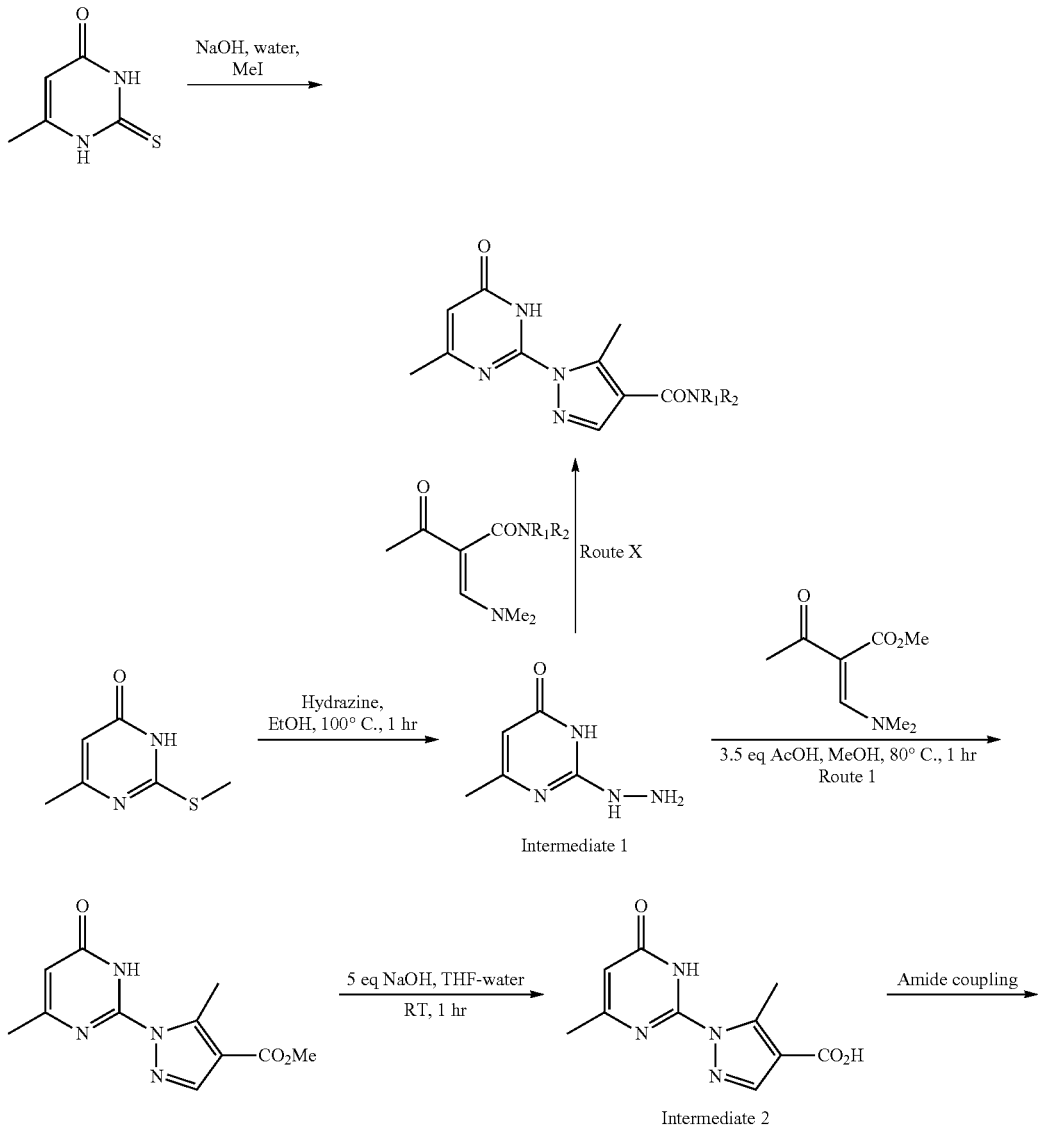

-continued

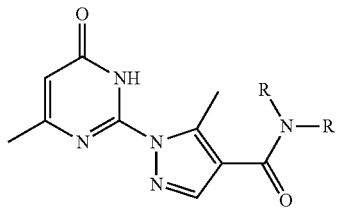

Intermediate 1: Preparation of 2-hydrazinyl-6-methyl-3,4-dihydropyrimidin-4-one

Step 1: Synthesis of 6-methyl-2-(methylsulfanyl)-3,4-dihydropyrimidin-4-one

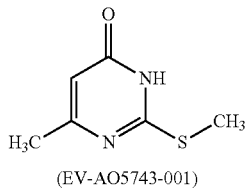

(EV-AO5743-001)

To water (500 mL) was added NaOH (97%, 15.7 g, 381 mmol) and the suspension stirred at r.t. for 10 mins. 6-methyl-2-sulfanylidene-1,2,3,4-tetrahydropyrimidin-4-one (98%, 53.5 g, 369 mmol) was added and the mixture stirred until fully dissolved for 10 mins. Iodomethane (28.99 mL, 461 mmol) was added dropwise and the mixture stirred at r.t. for 4 h. The colorless solid was filtered, washed with ice cold water (2×100 mL) and dried under vacuum at 60° C. to afford the title compound (57 g, 98%) as a colorless solid.

Method A: LC-MS m/z=156.9 [M+H]$^+$; RT=0.61 min.

Step 2: Synthesis of 2-hydrazinyl-6-methyl-3,4-dihydropyrimidin-4-one (Intermediate 1)

(Intermediate 1)

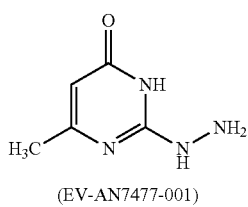

(EV-AN7477-001)

To a stirred solution of 6-methyl-2-(methylsulfanyl)-3,4-dihydropyrimidin-4-one (11.9 g, 76.18 mmol) in EtOH (30 mL) was added hydrazine hydrate (15.75 mL, 0.32 mol) and stirred at 80° C. for 5.5 h. The reaction mixture was allowed to cool to r.t. and the resulting precipitate was collected and dried by vacuum filtration, washing with water (3 mL) to afford the title compound (9.20 g, 85%) as an off white powder.

Method A: LC-MS m/z=140.90 [M+H]$^+$; RT=0.18 min.

Intermediate 2: Preparation of 5-methyl-1-(4-methyl-6-oxo-1,6-dihydropyrimidin-2-yl)-1H-pyrazole-4-carboxylic acid

Step 1: Synthesis of methyl-5-methyl-1-(4-methyl-6-oxo-1,6-dihydropyrimidin-2-yl)-1H-pyrazole-4-carboxylate

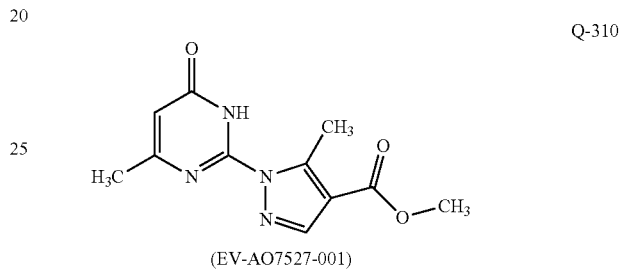

Q-310

(EV-AO7527-001)

To a stirred suspension of hydrazinyl-6-methyl-3,4-dihydropyrimidin-4-one (Intermediate 1, 6.82 g, 48.66 mmol) in EtOH (70 mL) was added methyl (2Z)-2-[(dimethylamino)methylidene]-3-oxobutanoate (8.33 g, 48.66 mmol) (Intermediate 3) followed by addition of AcOH (9.75 mL) and stirred at 80° C. for 1 h. The reaction mixture was cooled to r.t., at which point the product precipitated out of solution, and was filtered under vacuum, washing sparingly with EtOH, to afford the title compound (6.02 g, 50%) as a fluffy pale peach powder.

Method A: LC-MS m/z=248.95 [M+H]$^+$; RT=1.01 min.

Step 2: Synthesis of 5-methyl-1-(4-methyl-6-oxo-1,6-dihydropyrimidin-2-yl)-1H-pyrazole-4-carboxylic acid (Intermediate 2)

(Intermediate 2)

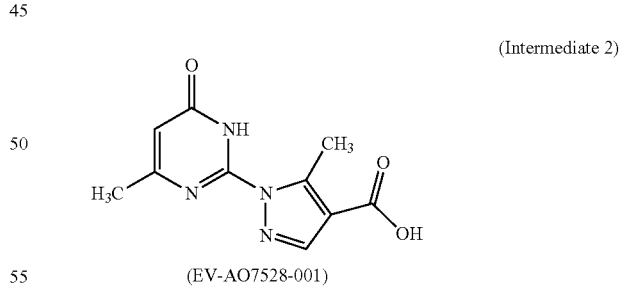

(EV-AO7528-001)

To a stirred suspension of methyl-5-methyl-1-(4-methyl-6-oxo-1,6-dihydropyrimidin-2-yl)-1H-pyrazole-4-carboxylate (6.02 g, 24.25 mmol) in THF (40 mL) was added 3M aq NaOH solution (40.42 mL), followed by water (20 mL) to aid dissolution and stirred at r.t. for 1 h. The reaction mixture was concentrated in vacuo to remove the THF and then acidified to pH 6 using 1M aq HCl solution. The resultant white solid was filtered under vacuum, washing with Et$_2$O, and dried to afford the title compound (5.45 g, 96%) as an off white powder.

Method A: LC-MS m/z=234.9 [M+H]$^+$; RT=0.84 min.

Intermediate 3: Preparation of methyl-2-[(dimethylamino)methylidene]-3-oxobutanoate

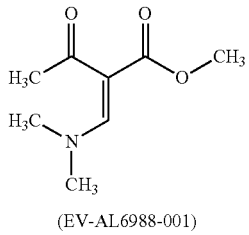

(Intermediate 3)

(EV-AL6988-001)

Methyl 3-oxobutanoate (40 g, 0.34 mol) and 1,1-dimethoxy-N,N-dimethylmethanamine (54.92 mL, 0.41 mol) were combined and stirred at 80° C. for 2 hours. The reaction mixture was concentrated in vacuo and the resulting oil was dried for 24 hours under vacuum to afford 56.53 g (86.3%) of the title compound as a dark red solid: $^1$H NMR (500 MHz, DMSO-d6) δ 7.62 (s, 1H), 3.63 (s, 3H), 3.24-2.96 (m, 3H), 2.90-2.58 (m, 3H), 2.13 (s, 3H).

Intermediate 4: Preparation of 2-ethyl-2,3-dihydro-1H-indole

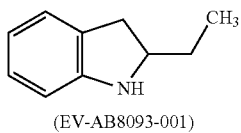

(Intermediate 4)

(EV-AB8093-001)

The intermediate was formed using the procedure from US Patent Publication 2011/0021500.

A solution of 2-ethyl-1H-indole (1 g, 6.89 mmol) in acetic acid (15 ml) at r.t. was treated portion wise with sodium cyanoborohydride (2.03 g, 32.37 mmol); addition caused effervescence and a slight exotherm. The resultant suspension was stirred at r.t. for 20 h. The reaction mixture was concentrated in vacuo and the residue treated with 4M aq HCl solution (30 mL) with scrubbing. The mixture was stirred at r.t. for 1 h, then cooled to 0° C. and treated with 4M aq NaOH solution (40 mL). Once the addition was complete the mixture was extracted with EtOAc (×2). The extracts were washed with brine, dried over MgSO$_4$ and concentrated in vacuo to afford the title compound (1.1 g, 97%) as a pale yellow mobile oil.

Method A: LC-MS m/z=147.9 [M+H]$^+$; RT=0.96 min.

Example 1—Synthesis of 6-methyl-2-[5-methyl-4-(1,2,3,4-tetrahydroisoquinoline-2-carbonyl)-1H-pyrazol-1-yl]-3,4-dihydropyrimidin-4-one

Q-279

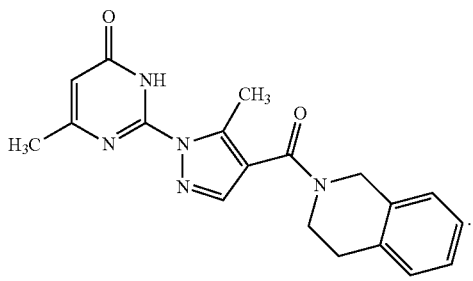

(EV-AO7529-002)

To a stirred solution of 5-methyl-1-(4-methyl-6-oxo-1,6-dihydropyrimidin-2-yl)-1H-pyrazole-4-carboxylic acid (Intermediate 2, 6.60 g, 28.18 mmol) in DMF (80 mL) was added COMU (13.28 g, 31.00 mmol), DIPEA (12.06 mL, 70.45 mmol) and 1,2,3,4-tetrahydroisoquinoline (3.93 mL, 31.00 mmol) and stirred at r.t. for 1 h. The reaction mixture was quenched by addition of saturated NaHCO$_3$ solution (20 mL) and water (20 mL) and extracted with DCM (4×100 mL). The combined organic extracts were dried over sodium sulphate, concentrated in vacuo and triturated using MeCN to afford the title compound (4.71 g, 48%) as an off white powder.

Method C: LC-MS m/z=350.1 [M+H]$^+$; RT=2.54 min.

Examples 2-39—Synthesis of Dihydropyrimidinones

Examples 2-39 were prepared according to the procedure described in Example 1 by reacting Intermediate 2 (5-methyl-1-(4-methyl-6-oxo-1,6-dihydropyrimidin-2-yl)-1H-pyrazole-4-carboxylic acid) with the appropriate amine and the coupling agent specified in Table 1. All amines used in Table 1 were commercially available except for example 38 which was synthesized using Intermediate 4 (2-ethyl-2,3-dihydro-1H-indole).

TABLE 1

| Example No. | Ref. No. | LBN | Structure | LC-MS (RT) Method C | MS (M + H)$^+$ Method C | Coupling Agent |
|---|---|---|---|---|---|---|
| 2 | Q-328 | EV-AP2301-002 | 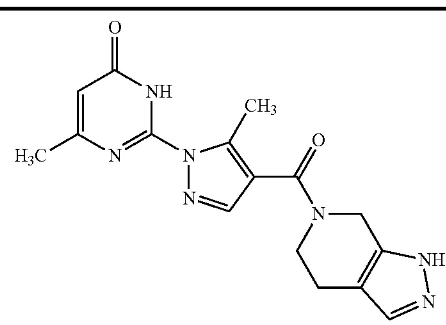 | 1.54 | 340.1 | COMU |

TABLE 1-continued

| Example No. | Ref. No. | LBN | Structure | LC-MS (RT) Method C | MS (M + H)+ Method C | Coupling Agent |
|---|---|---|---|---|---|---|
| 3 | Q-341 | EV-AP2305-001 | 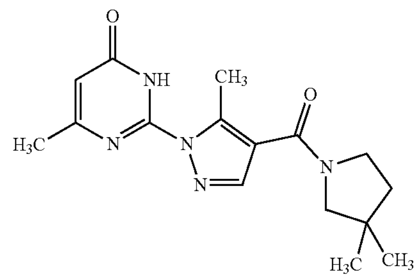 [SMILES: Cc1cc(=O)[nH]c(-n2ncc(C(=O)N3CCC(C)(C)C3)c2C)n1] | 2.27 | 316.2 | TBTU |
| 4 | Q-346 | EV-AP2309-001 | 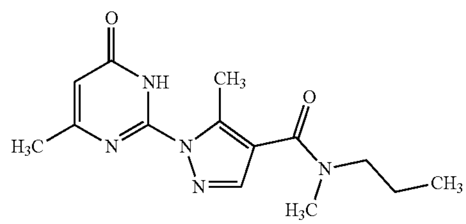 [SMILES: CCCN(C)C(=O)c1cnn(-c2nc(C)cc(=O)[nH]2)c1C] | 1.97 | 290.2 | TBTU |
| 5 | Q-347 | EV-AP2310-001 | 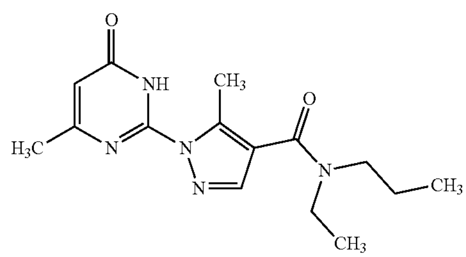 [SMILES: CCCN(CC)C(=O)c1cnn(-c2nc(C)cc(=O)[nH]2)c1C] | 2.25 | 304.2 | TBTU |
| 6 | Q-348 | EV-AP2311-001 | 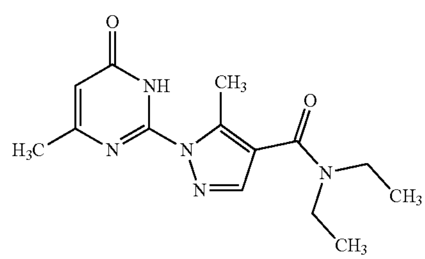 [SMILES: CCN(CC)C(=O)c1cnn(-c2nc(C)cc(=O)[nH]2)c1C] | 1.94 | 290.2 | TBTU |
| 7 | Q-359 | EV-AP2325-001 | 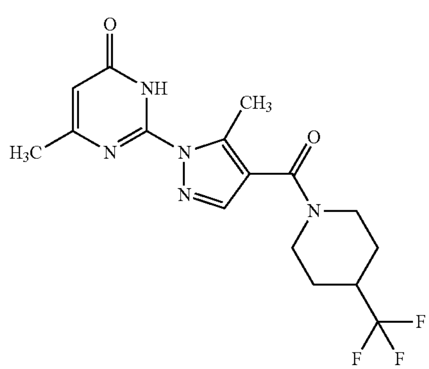 [SMILES: Cc1cc(=O)[nH]c(-n2ncc(C(=O)N3CCC(C(F)(F)F)CC3)c2C)n1] | 2.65 | 370.2 | COMU |

TABLE 1-continued

| Example No. | Ref. No. | LBN | Structure | LC-MS (RT) Method C | MS (M + H)+ Method C | Coupling Agent |
|---|---|---|---|---|---|---|
| 8 | Q-368 | EV-AP2328-001 | 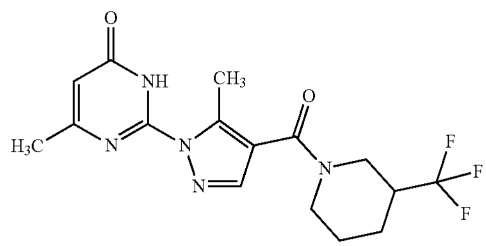 [SMILES: Cc1cc(=O)[nH]c(-n2ncc(C(=O)N3CCCC(C(F)(F)F)C3)c2C)n1] | 2.50 | 370.2 | COMU |
| 9 | Q-329 | EV-AP2300-002 | 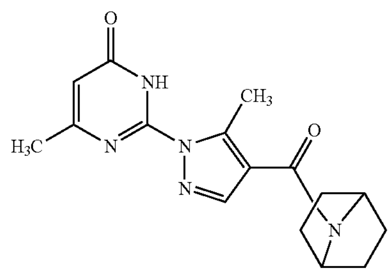 [SMILES: Cc1cc(=O)[nH]c(-n2ncc(C(=O)CN3C4CCC3CC4)c2C)n1] | 2.12 | 314.1 | COMU |
| 10 | Q-344 | EV-AN7494-001 | 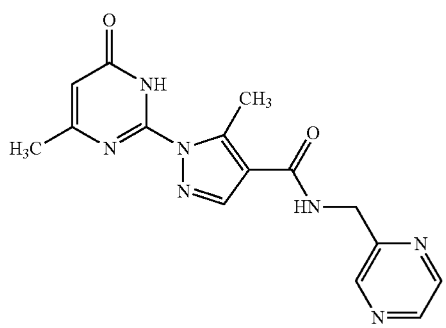 [SMILES: Cc1cc(=O)[nH]c(-n2ncc(C(=O)NCc3cnccn3)c2C)n1] | 1.45 | 326.1 | COMU |
| 11 | Q-345 | EV-AN7496-002 | 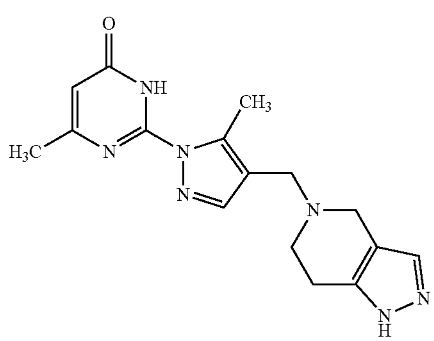 [SMILES: Cc1cc(=O)[nH]c(-n2ncc(CN3CCc4[nH]ncc4C3)c2C)n1] | 1.44 | 340.1 | COMU |
| 12 | Q-327 | EV-AP2502-001 | 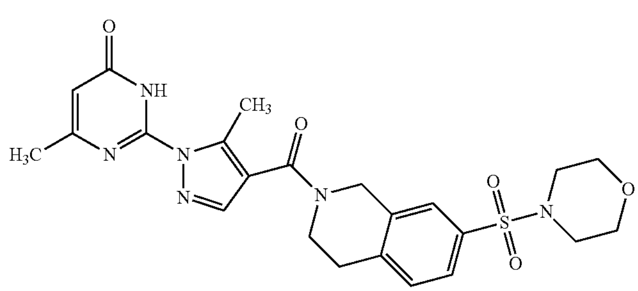 [SMILES: Cc1cc(=O)[nH]c(-n2ncc(C(=O)N3CCc4ccc(S(=O)(=O)N5CCOCC5)cc4C3)c2C)n1] | 2.34 | 499.2 | TBTU |

TABLE 1-continued

| Example No. | Ref. No. | LBN | Structure | LC-MS (RT) Method C | MS (M + H)+ Method C | Coupling Agent |
|---|---|---|---|---|---|---|
| 13 | Q-350 | EV-AP2503-001 | 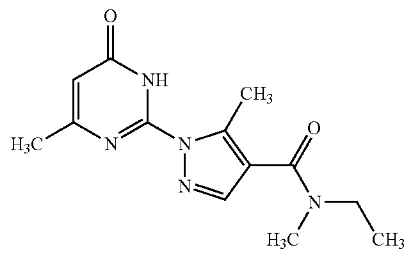 [SMILES: CCN(C)C(=O)c1cnn(-c2nc(C)cc(=O)[nH]2)c1C] | 1.70 | 276.2 | COMU |
| 14 | Q-351 | EV-AP2504-001 | 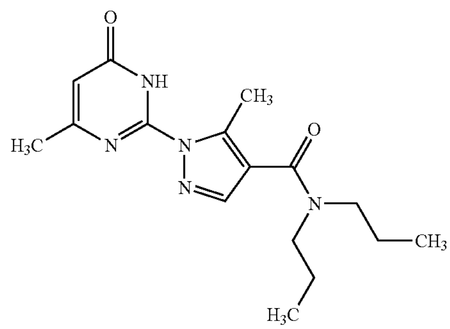 [SMILES: CCCN(CCC)C(=O)c1cnn(-c2nc(C)cc(=O)[nH]2)c1C] | 2.56 | 318.2 | COMU |
| 15 | Q-352 | EV-AP2508-001 | 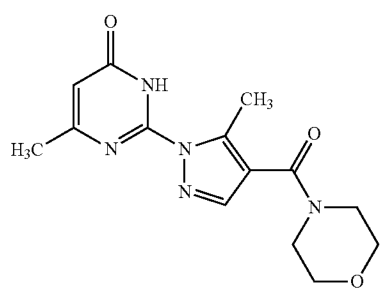 [SMILES: Cc1cc(=O)[nH]c(-n2ncc(C(=O)N3CCOCC3)c2C)n1] | 1.47 | 304.2 | COMU |
| 16 | Q-302 | EV-AO7503-002 | 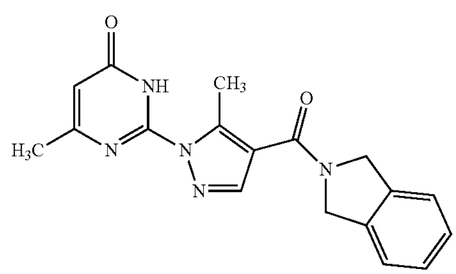 [SMILES: Cc1cc(=O)[nH]c(-n2ncc(C(=O)N3Cc4ccccc4C3)c2C)n1] | 2.39 | 336.1 | HATU |
| 17 | Q-303 | EV-AO7504-002 | 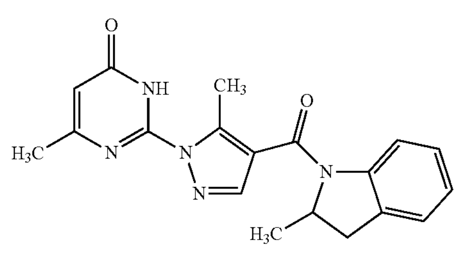 | 2.88 | 350.2 | HATU |

TABLE 1-continued

| Example No. | Ref. No. | LBN | Structure | LC-MS (RT) Method C | MS (M + H)+ Method C | Coupling Agent |
|---|---|---|---|---|---|---|
| 18 | Q-304 | EV-AO7506-002 | 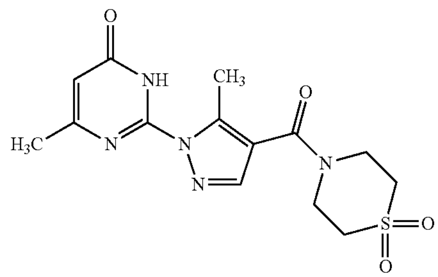 [SMILES: Cc1cc(=O)[nH]c(-n2ncc(C(=O)N3CCS(=O)(=O)CC3)c2C)n1] | 1.48 | 352.1 | HATU |
| 19 | Q-305 | EV-AO7508-002 | 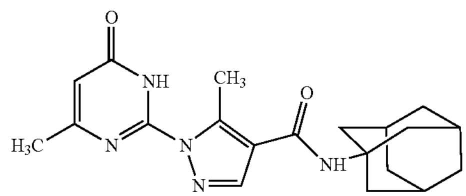 [SMILES: Cc1cc(=O)[nH]c(-n2ncc(C(=O)NC34CC5CC(CC(C5)C3)C4)c2C)n1] | 3.32 | 368.2 | HATU |
| 20 | Q-318 | EV-AO7513-002 | 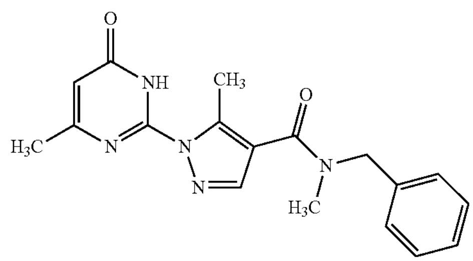 [SMILES: Cc1cc(=O)[nH]c(-n2ncc(C(=O)N(C)Cc3ccccc3)c2C)n1] | 2.44 | 338.1 | COMU |
| 21 | Q-362 | EV-AO7565-002 | 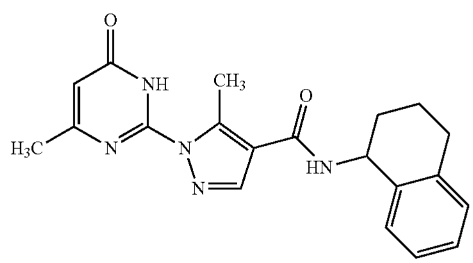 [SMILES: Cc1cc(=O)[nH]c(-n2ncc(C(=O)NC3CCCc4ccccc43)c2C)n1] | 2.94 | 364.2 | COMU |
| 22 | Q-363 | EV-AO7566-002 | 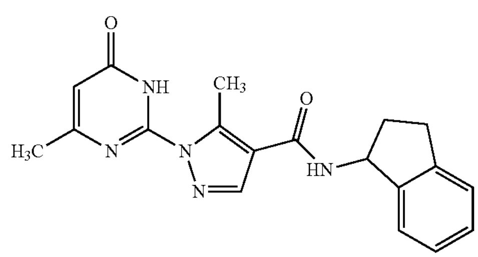 [SMILES: Cc1cc(=O)[nH]c(-n2ncc(C(=O)NC3CCc4ccccc43)c2C)n1] | 2.66 | 350.2 | COMU |
| 23 | Q-364 | EV-AO7567-002 | 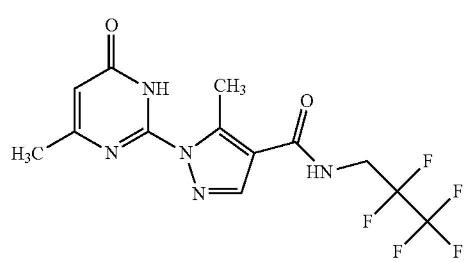 [SMILES: Cc1cc(=O)[nH]c(-n2ncc(C(=O)NCC(F)(F)C(F)(F)F)c2C)n1] | 2.47 | 366.1 | COMU |

TABLE 1-continued

| Example No. | Ref. No. | LBN | Structure | LC-MS (RT) Method C | MS (M + H)+ Method C | Coupling Agent |
|---|---|---|---|---|---|---|
| 24 | Q-367 | EV-AO7570-002 | 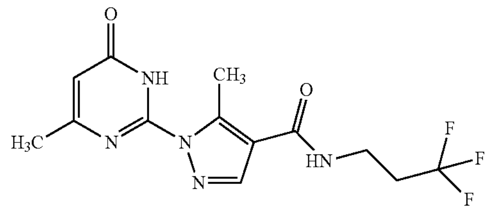 [SMILES: Cc1cc(=O)[nH]c(-n2ncc(C(=O)NCCC(F)(F)F)c2C)n1] | 2.09 | 330.1 | COMU |
| 25 | Q-385 | EV-AO7572-002 | 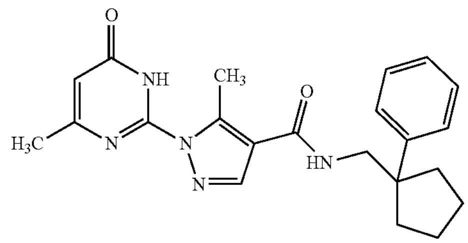 [SMILES: Cc1cc(=O)[nH]c(-n2ncc(C(=O)NCC3(c4ccccc4)CCCC3)c2C)n1] | 3.26 | 392.2 | COMU |
| 26 | Q-373 | EV-AO7573-002 | 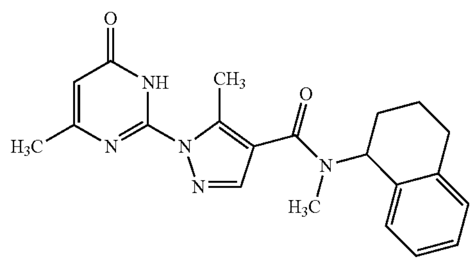 [SMILES: Cc1cc(=O)[nH]c(-n2ncc(C(=O)N(C)C3CCCc4ccccc43)c2C)n1] | 2.96 | 378.2 | COMU |
| 27 | Q-374 | EV-AO7574-002 | 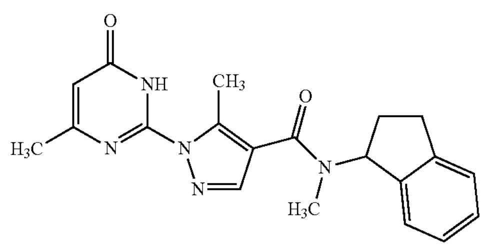 [SMILES: Cc1cc(=O)[nH]c(-n2ncc(C(=O)N(C)C3CCc4ccccc43)c2C)n1] | 2.774 | 364.2 | COMU |
| 28 | Q-286 | EV-AN0091-004 | 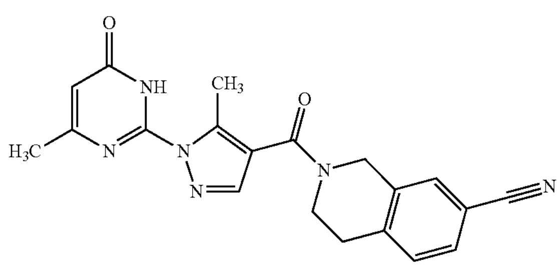 [SMILES: Cc1cc(=O)[nH]c(-n2ncc(C(=O)N3CCc4ccc(C#N)cc4C3)c2C)n1] | 2.34 | 375.1 | TBTU |
| 29 | Q-287 | EV-AN0093-003 | 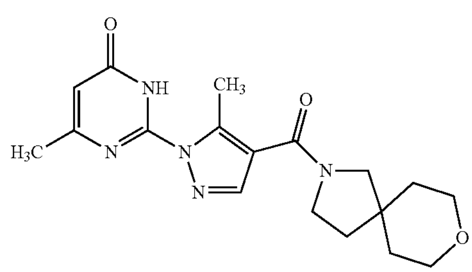 [SMILES: Cc1cc(=O)[nH]c(-n2ncc(C(=O)N3CCC4(CCOCC4)C3)c2C)n1] | 1.77 | 358.2 | TBTU |

TABLE 1-continued

| Example No. | Ref. No. | LBN | Structure | LC-MS (RT) Method C | MS (M + H)+ Method C | Coupling Agent |
|---|---|---|---|---|---|---|
| 30 | Q-300 | EV-AN0094-002 | 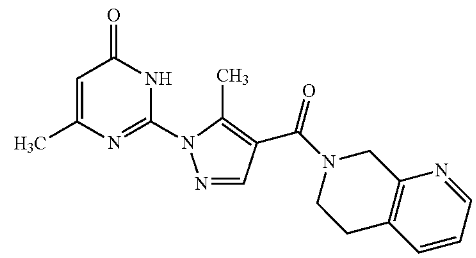 [SMILES: Cc1cc(=O)[nH]c(-n2ncc(C(=O)N3CCc4cccnc4C3)c2C)n1] | 1.36 | 351.1 | TBTU |
| 31 | Q-307 | EV-AN0099-002 | 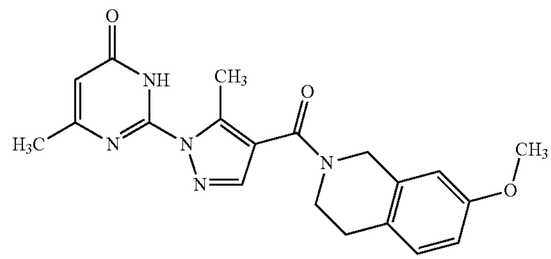 | 2.68 | 380.2 | COMU |
| 32 | Q-313 | EV-AO8802-002 | 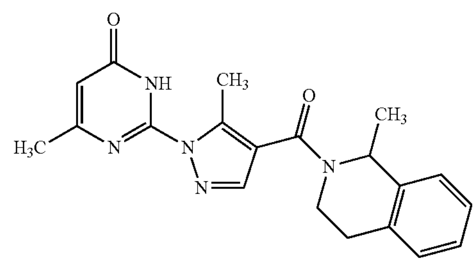 | 2.75 | 364.2 | COMU |
| 33 | Q-322 | EV-AO8803-002 | 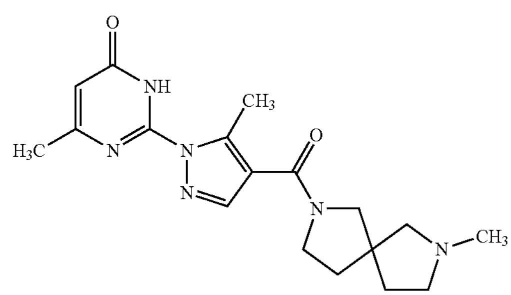 | 0.87 | 357.2 | COMU |
| 34 | Q-317 | EV-AO5736-002 | 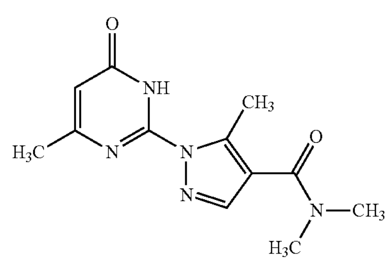 | 1.45 | 262.1 | COMU |
| 35 | Q-316 | EV-AO5735-002 | 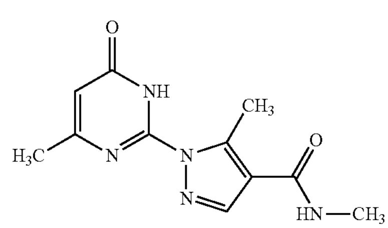 | 1.31 | 248.1 | COMU |

TABLE 1-continued

| Example No. | Ref. No. | LBN | Structure | LC-MS (RT) Method C | MS (M + H)+ Method C | Coupling Agent |
|---|---|---|---|---|---|---|
| 36 | Q-298 | EV-AO5715-002 | 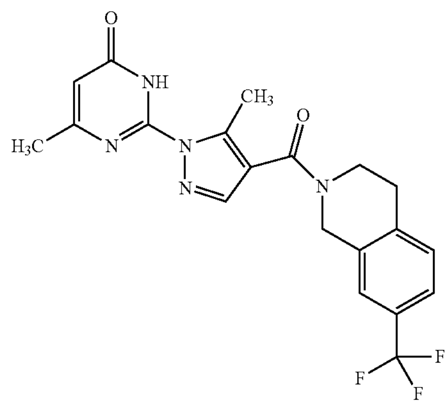 [SMILES: Cc1cc(=O)[nH]c(-n2ncc(C(=O)N3CCc4ccc(C(F)(F)F)cc4C3)c2C)n1] | 3.03 | 418.2 | HATU (Et₃N) |
| 37 | Q-299 | EV-AO5716-002 | 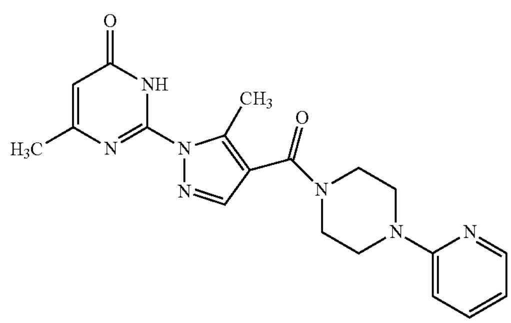 [SMILES: Cc1cc(=O)[nH]c(-n2ncc(C(=O)N3CCN(c4ccccn4)CC3)c2C)n1] | 1.11 | 380.2 | HATU (Et₃N) |
| 38 | Q-420 | EV-AB8097-002 | 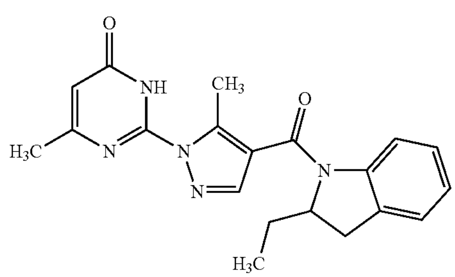 [SMILES: CCC1Cc2ccccc2N1C(=O)c1cnn(-c2nc(C)cc(=O)[nH]2)c1C] | 3.07 | 364.3 | COMU |
| 39 | Q-347 | EV-AP2310-001 | 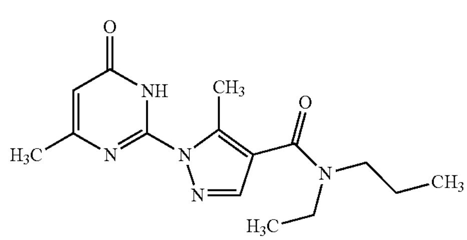 [SMILES: CCCN(CC)C(=O)c1cnn(-c2nc(C)cc(=O)[nH]2)c1C] | 2.25 | 304.2 | TBTU |

Examples 40-43—Chiral Separation

Examples 40-43 in Table 2 were prepared by chiral separation of racemic compounds in Table 1. The stereochemistry was arbitrarily assigned.

TABLE 2

| Ex. No. | Ref. No. | LBN | Structure | LC-MS (RT) Method C | MS (M + H)⁺ Method C | Column Retention* (min) | Separation Method |
|---|---|---|---|---|---|---|---|
| 40 | Q-339 | EV-AO8802-004 | 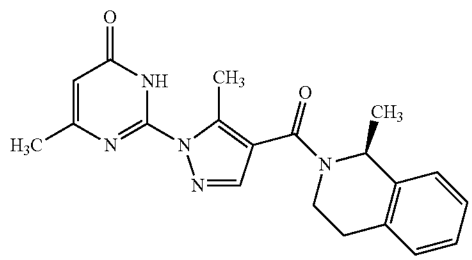 [SMILES: Cc1cc(=O)[nH]c(-n2ncc(C(=O)N3CCc4ccccc4[C@@H]3C)c2C)n1] | 2.75 | 364.2 | 3.09 Method I | H |
| 41 | Q-340 | EV-AO8802-005 | 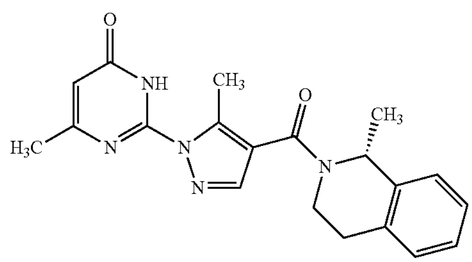 [SMILES: Cc1cc(=O)[nH]c(-n2ncc(C(=O)N3CCc4ccccc4[C@H]3C)c2C)n1] | 2.75 | 364.2 | 5.09 Method I | H |
| 42 | Q-372 | EV-AO7553-002 | 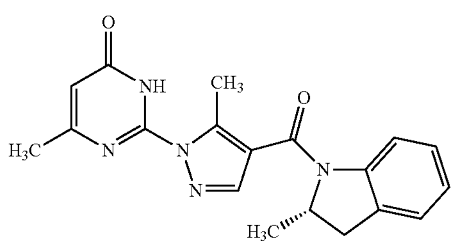 [SMILES: Cc1cc(=O)[nH]c(-n2ncc(C(=O)N3c4ccccc4C[C@@H]3C)c2C)n1] | 2.58 | 350.2 | 6.69 Method K | J |
| 43 | Q-361 | EV-AO7553-003 | 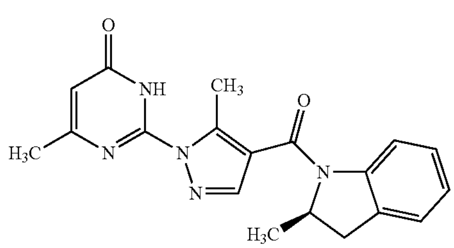 [SMILES: Cc1cc(=O)[nH]c(-n2ncc(C(=O)N3c4ccccc4C[C@H]3C)c2C)n1] | 2.81 | 350.2 | 8.35 Method K | J |

Example 44—Synthesis of 5-chloro-6-methyl-2-[5-methyl-4-(1,2,3,4-tetrahydroisoquinoline-2-carbonyl)-1H-pyrazol-1-yl]-3,4-dihydropyrimidin-4-one

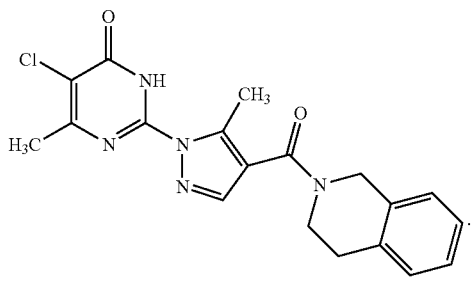

Q-456

(EV-AO7571-002)

To a solution of 6-methyl-2-[5-methyl-4-(1,2,3,4-tetrahydroisoquinoline-2-carbonyl)-1H-pyrazol-1-yl]-3,4-dihydropyrimidin-4-one (Example 1, Q-279 (EV-AO7529-002), 100 mg, 0.286 mmol) in AcOH (2 mL) was added NCS (40 mg, 0.301 mmol) and stirred at 90° C. for 1 h. The reaction mixture was concentrated in vacuo and triturated using MeCN to afford the title compound (60 mg, 54%) as a white powder.

Method C: LC-MS m/z=384.2 [M+H]$^+$; RT=2.99 min.

Example 45—Synthesis of 5-chloro-6-methyl-2-[5-methyl-4-(1,2,3,4-tetrahydroisoquinoline-2-carbonyl)-1H-pyrazol-1-yl]-3,4-dihydropyrimidin-4-one

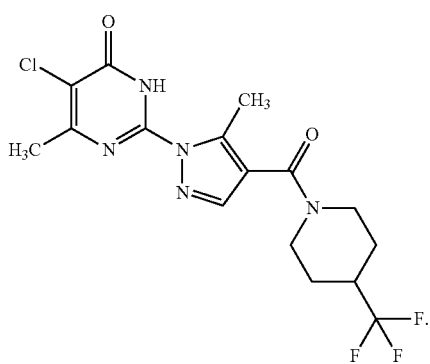

Q-421

(EV-AQ0223-002)

Chlorination of 6-methyl-2-[5-methyl-4-(1,2,3,4-tetrahydroisoquinoline-2-carbonyl)-1H-pyrazol-1-yl]-3,4-dihydropyrimidin-4-one (Example 7, Q-359 (EV-AP2325-001) using the procedure described in Example 44 afforded the title compound (54 mg, 42%) as a white powder.

Method C: LC-MS m/z=404.2 [M+H]$^+$; RT=2.88 min.

Example 46—Synthesis of 6-methyl-2-[5-methyl-4-(1,2,3,4-tetrahydroisoquinolin-2-ylmethyl)-1H-pyrazol-1-yl]-3,4-dihydropyrimidin-4-one

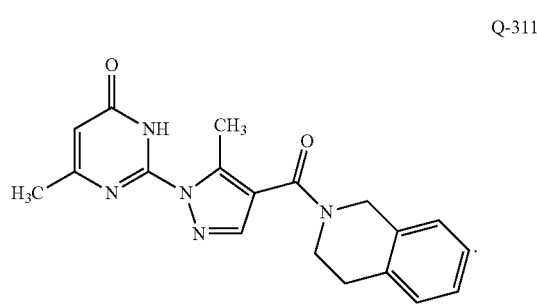

Q-311

(EV-AO7520-002)

To a stirred solution of 6-methyl-2-[5-methyl-4-(1,2,3,4-tetrahydroisoquinoline-2-carbonyl)-1H-pyrazol-1-yl]-3,4-dihydropyrimidin-4-one (Example 1, Q-279 (EV-AO7529-002), 165 mg, 0.472 mmol) in THF (3 mL) at 0° C. was added LiAlH$_4$ (216 µl, 0.519 mmol) and stirred at r.t. for 1 h. The reaction mixture was quenched by the addition of water (4 mL), NaOH (4 mL) and then further water (4 mL). The reaction mixture was acidified to pH 5 using acetic acid and then neutralized to pH 7 using saturated sodium bicarbonate solution. The reaction mixture was extracted with DCM (3×40 mL) and the combined organic extracts dried over Na$_2$SO$_4$, concentrated in vacuo and triturated using MeCN (3 mL) to afford the title compound (57 mg, 35%) as a white powder.

Method C: LC-MS m/z=336.1 [M+H]$^+$; RT=1.29 min.

Preparative Example 2—Preparation of Intermediate Thiouracils and Thio Ethers

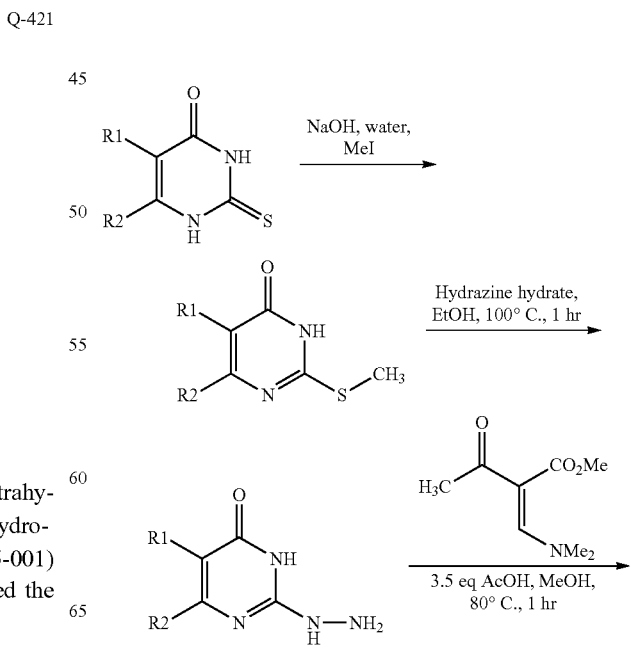

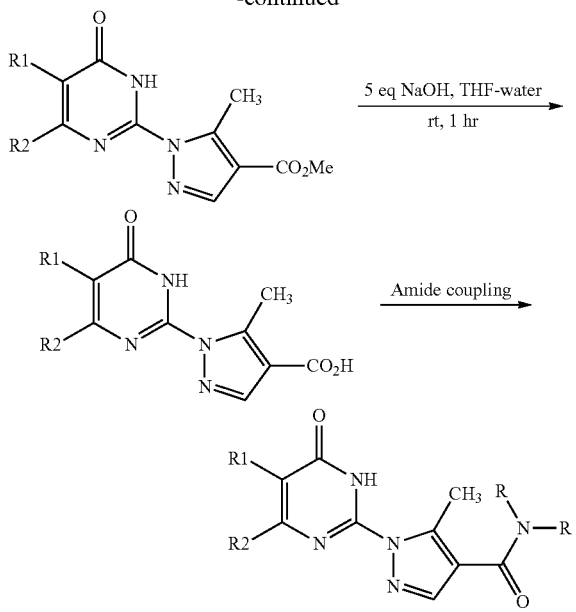

Intermediate 5: Preparation of 2-sulfanylidene-1H, 2H,3H,4H-pyrazolo[1,5-a][1,3,5]triazin-4-one Step 1: Synthesis of ethyl N-[(1H-pyrazol-5-yl)carbamothioyl]carbamate

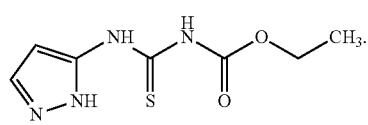

(EV-AQ3814-001)

To a solution of 1H-pyrazol-5-amine (3 g, 36.1 mmol) in acetone (50 ml) was added over 5 mins (slight exotherm) ethyl N-carbothioylcarbamate (3.96 ml, 0.03 mol) and stirred at r.t. for 2 h. The yellow solution was treated with ice cold water (50 ml) which caused a transient precipitation. The flask was cooled in ice and a precipitate formed. The solid was collected by filtration, washed with water and dried under vacuum to afford the title compound (5.0 g, 46%) as a yellow solid.

Method A: LC-MS m/z=214.90 [M+H]$^+$; RT=0.94.

Step 2: Synthesis of 2-sulfanylidene-1H,2H,3H,4H-pyrazolo[1,5-a][1,3,5]triazin-4-one (Intermediate 5)

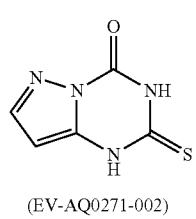

(EV-AQ0271-002)

To ethyl N-[(1H-pyrazol-5-yl)carbamothioyl]carbamate (2.5 g, 11.67 mmol) was added 2M aq NaOH solution (23.3 ml) and stirred at r.t. for 2 h. The solution was acidified with concentrated H$_2$SO$_4$ and the resultant precipitate filtered under vacuum to afford a pale yellow powder. Purification by recrystallisation using water afforded the title compound (1.54 g, 94%) as a pale yellow powder.

Method A: LC-MS m/z=168.95 [M+H]$^+$; RT=0.19.

Intermediate 6: Preparation of 2-sulfanylidene-1,2, 3,4,5,6,7,8-octahydroquinazolin-4-one

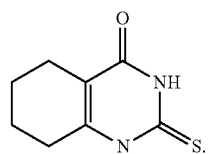

(EV-AQ0232-001)

To a solution of ethyl 2-oxocyclohexane-1-carboxylate (9.40 ml, 58.75 mmol) in MeCN (40 ml) was added thiourea (5.37 g, 70.5 mmol) and DBU (13.15 ml, 88.13 mmol) and stirred at 80° C. overnight.

The reaction mixture was concentrated in vacuo and the residue redissolved in water. The reaction mixture was acidified to pH 3/4 using 5M aq HCl solution, the precipitate filtered, washing with H$_2$O and Et$_2$O, and dried under vacuum to afford the title compound (10.70 g, 98%) as an off white powder.

Method A: LC-MS: m/z=183.0 (M+H)$^+$; RT=0.71.

Intermediate 7: Synthesis of 6-methyl-4-sulfanylidene-1,2,3,4-tetrahydropyrimidin-2-one (Intermediate 7)

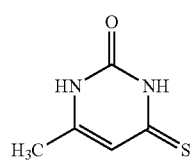

(EV-AQ0296-002)

To a solution of 6-methyl-1,2,3,4-tetrahydropyrimidine-2,4-dione (2.0 g, 15.86 mmol) in dioxane (30 ml) was added 2,4-bis(4-methoxyphenyl)-1,3,2,4-dithiadiphosphetane 2,4-disulfide (6.41 g, 15.86 mmol) and stirred at 100° C. for 2 h. The reaction mixture was cooled to r.t. and the white precipitate filtered under vacuum, washing with dioxane (20 ml), to afford the title compound (1.85 g, 82%) as an off white powder.

Method B: LC-MS: m/z=142.85 (M+H)$^+$; RT=0.36.

Intermediate 8: Synthesis of 3,6-dimethyl-2-(methylsulfanyl)-3,4-dihydropyrimidin-4-one

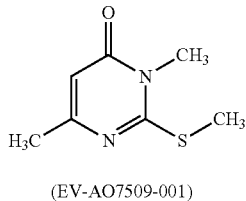

(Intermediate 8)

(EV-AO7509-001)

3,6-dimethyl-2-(methylsulfanyl)-3,4-dihydropyrimidin-4-one was prepared from (3E)-1,1,1-trichloro-4-methoxypent-3-en-2-one using the procedure found in: Zanatta, Nilo; Madruga, Claudia C.; Marisco, Patricia C.; Da Rosa, Luciana S.; Da Silva, Fabio M.; Bonacorso, Helio G.; Martins, Marcos A. P.; Journal of Heterocyclic Chemistry; vol. 47; nb. 5; (2010); p. 1234-1239, affording the title compound (4.68 g, 78%) as a brown powder.

Method A: LC-MS: m/z=170.95 (M+H)$^+$; RT=0.97 min.

Examples 47-54

Examples 47-54 in Table 3 were prepared in an analogous fashion to Example 1 starting with the corresponding commercial thiouracil, methyl thioether or the specified intermediate, and coupling the intermediate acid with the appropriate amine using the specified coupling conditions.

TABLE 3

| Ex. No. | Ref. No. | LBN | Structure | LC-MS (RT) Method C | MS (M + H)$^+$ Method C | Coupling Agent | Comments |
|---|---|---|---|---|---|---|---|
| 47 | Q-447 | EV-AQ0294-002 | 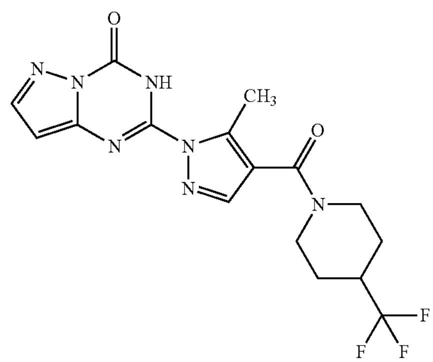 [SMILES: Cc1c(C(=O)N2CCC(C(F)(F)F)CC2)cnn1-c1nc2ccnn2c(=O)[nH]1] | 2.53 | 396.2 | T3P | Intermediate 5 |
| 48 | Q-454 | EV-AR5305-002 | 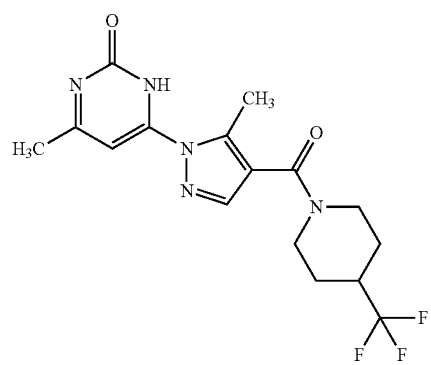 [SMILES: Cc1cc(-n2ncc(C(=O)N3CCC(C(F)(F)F)CC3)c2C)[nH]c(=O)n1] | 2.19 | 370.0 | T3P | Intermediate 7 |
| 49 | Q-455 | EV-AO7537-002 | 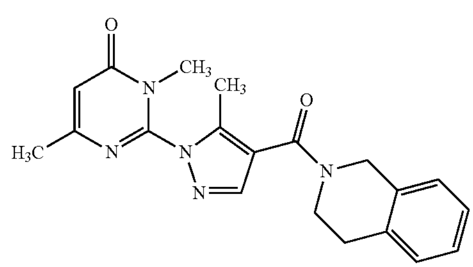 [SMILES: Cc1cc(=O)n(C)c(-n2ncc(C(=O)N3CCc4ccccc4C3)c2C)n1] | 2.58 | 364.1 | COMU | Intermediate 8 |

TABLE 3-continued
| Ex. No. | Ref. No. | LBN | Structure | LC-MS (RT) Method C | MS (M + H)+ Method C | Coupling Agent | Comments |
|---|---|---|---|---|---|---|---|
| 50 | Q-427 | EV-AQ0240-002 | 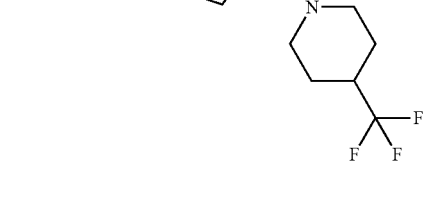 | 2.35 | 395.1 | COMU | |
| 51 | Q-425 | EV-AQ0230-002 | 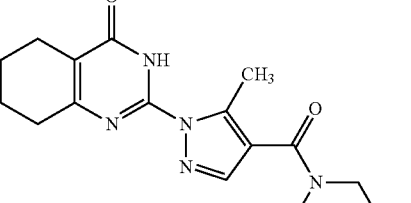 | 3.04 | 410.2 | COMU | Intermediate 6 |
| 52 | Q-404 | EV-AP2566-003 | 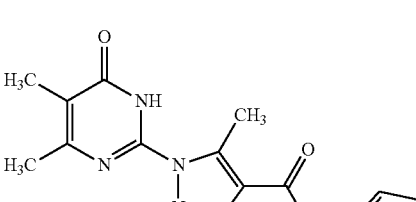 | 3.10 | 364.3 | COMU | |
| 53 | Q-383 | EV-AP2542-001 | 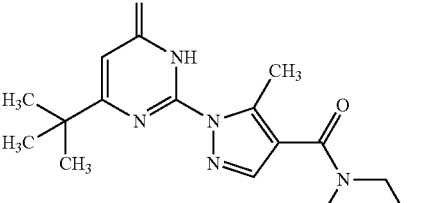 | 3.48 | 392.3 | COMU | |

TABLE 3-continued

| Ex. No. | Ref. No. | LBN | Structure | LC-MS (RT) Method C | MS (M + H)+ Method C | Coupling Agent | Comments |
|---|---|---|---|---|---|---|---|
| 54 | Q-488 | EV-AR5353-002 | 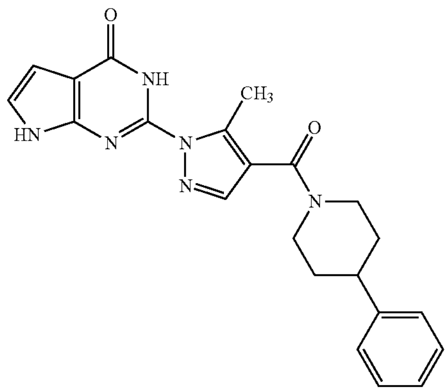 [SMILES: Cc1c(C(=O)N2CCC(c3ccccc3)CC2)cnn1-c1nc2[nH]ccc2c(=O)[nH]1] | 2.75 | 403.2 | T3P | |

Examples 55-56—Chiral Separation

Examples 55-56 in Table 4 were prepared by chiral separation of racemic compounds in Table 3. The stereochemistry was arbitrarily assigned.

TABLE 4

| Ex. No. | Ref. No. | LBN | Structure | LC-MS (RT) Method C | MS (M + H)+ Method C | Column Retention* (min) | Separation Method |
|---|---|---|---|---|---|---|---|
| 55 | Q-416 | EV-AP2566-004 | 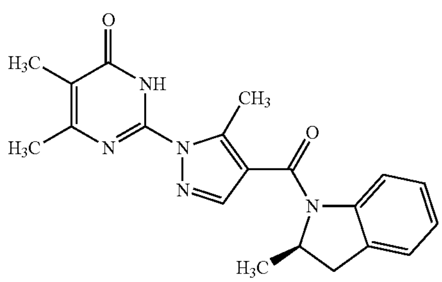 [SMILES: Cc1nc(-n2ncc(C(=O)N3c4ccccc4C[C@H]3C)c2C)[nH]c(=O)c1C] | 3.11 | 364.3 | 5.134 | L |
| 56 | Q-457 | EV-AP2566-005 | 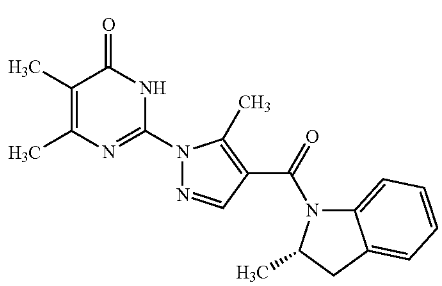 [SMILES: Cc1nc(-n2ncc(C(=O)N3c4ccccc4C[C@@H]3C)c2C)[nH]c(=O)c1C] | 3.10 | 364.2 | 7.20 | L |

Preparative Example 3—Formation of Intermediates from the Corresponding Dichloropyrimidines

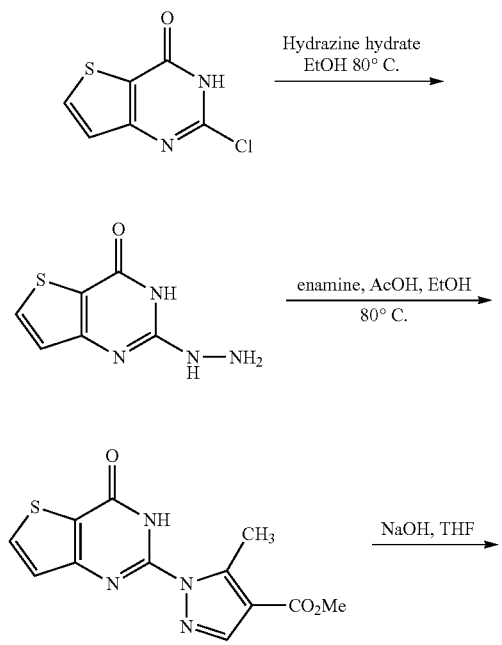

Intermediate 9: Preparation of 2-chloro-3H,4H-thieno[3,2-d]pyrimidin-4-one

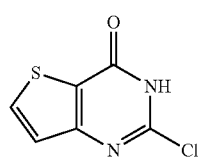

(EV-AP2383-001)

To a stirred solution of 2,4-dichlorothieno[3,2-d]pyrimidine (20 g, 97.5 mmol) in THF (80 mL) was added 5M aq NaOH solution (98 mL, 488 mmol) and stirred at 50° C. for 6 h. The reaction mixture was acidified to pH 5 using acetic acid. The solution was then extracted with EtOAc (2×50 mL) and the combined organics were dried over $Na_2SO_4$, filtered and concentrated in vacuo to yield the title compound (11.3 g, 60.5 mmol, 62%) as a yellow powder.

Method A: LC-MS m/z=186.9 [M+H]$^+$; RT=0.77 min.

Intermediate 10: Preparation of 2-hydrazinyl-3H,4H-thieno[3,2-d]pyrimidin-4-one

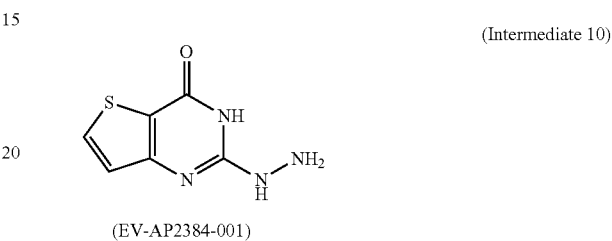

(Intermediate 10)

(EV-AP2384-001)

To a stirred solution of 2-chloro-3H,4H-thieno[3,2-d]pyrimidin-4-one (11.34 g, 60.8 mmol) in EtOH (90 mL) was added hydrazine hydrate (5.91 mL, 121.5 mmol) and stirred at 80° C. overnight. The reaction mixture was cooled to r.t. and the resultant precipitate was collected via filtration, and washed with water (15 mL) to yield the title compound (7.4 g, 40.6 mmol, 67%) as a pale yellow powder.

Method A: LC-MS m/z=182.9 [M+H]$^+$; RT=0.18 min.

Intermediate 11: 5-methyl-1-{4-oxo-3H,4H-thieno[3,2-d]pyrimidin-2-yl}-1H-pyrazole-4-carboxylic acid Step 1: Synthesis of methyl-5-methyl-1-{4-oxo-3H,4H-thieno[3,2-d]pyrimidin-2-yl}-1H-pyrazole-4-carboxylate

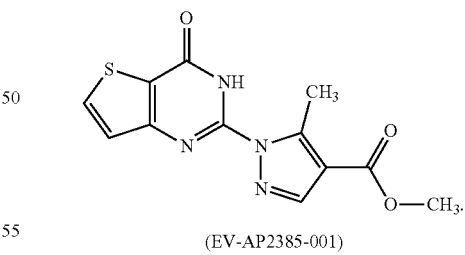

(EV-AP2385-001)

To a stirred solution of 2-hydrazinyl-3H,4H-thieno[3,2-d]pyrimidin-4-one (7 g, 38.4 mmol) in EtOH (75 mL) and AcOH (7.70 mL, 134.5 mmol) was added (2Z)-2-[(dimethylamino)methylidene]-3-oxobutanoate (7.89 g, 46.1 mmol) and stirred at 50° C. for 3 h. The reaction mixture was cooled to r.t. and the resulting precipitate was isolated via filtration to yield the title compound (11.2 g, 22.5 mmol, 59%) as a pale yellow powder.

Method A: LC-MS m/z=291.0 [M+H]$^+$; RT=1.15 min.

Step 2: Synthesis of 5-Methyl-1-{4-oxo-3H,4H-thieno[3,2-d]pyrimidin-2-yl}-1H-pyrazole-4-carboxylic acid

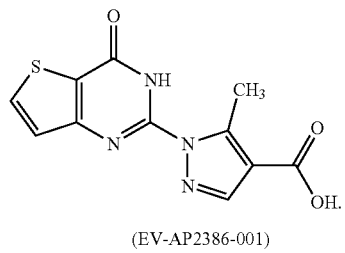

(Intermediate 11)

(EV-AP2386-001)

To a solution of methyl-5-methyl-1-{4-oxo-3H,4H-thieno[3,2-d]pyrimidin-2-yl}-1H-pyrazole-4-carboxylate (6.53 g, 22.5 mmol) in 2:1 THF/methanol (37 mL) was added 2.5M aq NaOH solution (54 mL, 135 mmol) and stirred at r.t. for 2 h. The organics were removed in vacuo, the residue acidified to pH 5 with 2M aq HCl solution and the resulting precipitate was collected via filtration to yield the title compound (6.22 g, 19.9 mmol, 89%) as a beige powder.

Method A: LC-MS m/z=277.0 [M+H]$^+$; RT=0.97 min.

Intermediate 12: Preparation of 2-methyl-4-(trifluoromethyl)piperidine (4:1 Mixture of Diastereoisomers)

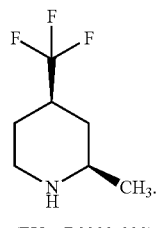

(Intermediate 12)

(EV-AB8098-002)

A solution of 2-methyl-4-(trifluoromethyl)pyridine (800 mg, 4.97 mmol) in 25% acetic acid in MeOH (100 ml) [0.05M] was reacted on the H-Cube [10% Pt on C cartridge, 90 bar and 80° C., 1 ml/min. Upon completion, the reaction mixture was treated with a solution of 4M HCl in dioxane (2 ml, 8 mmol) and then concentrated in vacuo to yield a white solid. The solid was dissolved in MeOH, treated with ammonia (7M in MeOH) and concentrated in vacuo to afford the title compound (270 mg, 32%) as a white solid.

Method A: LC-MS m/z=168.00 [M+H]$^+$; RT=0.17 min.

Intermediate 13: Preparation of 4-(1-cyano-1-methylethyl)piperidin-1-ium chloride

Step 1: Synthesis of tert-butyl 4-(1-cyano-1-methylethyl)piperidine-1-carboxylate

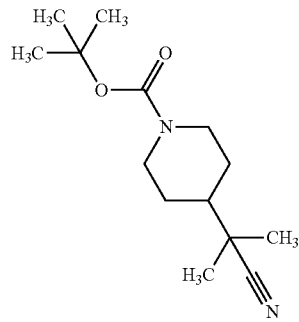

(EV-AQ8828-001)

To a stirred solution of tert-butyl 4-(cyanomethyl)piperidine-1-carboxylate (0.2 g, 8.13 mmol) in dry THF (2 mL) at 0° C. was added slowly KHMDS (1 M in toluene, 2.68 mL, 2.68 mmol). The reaction mixture was allowed to stir for 10 minutes, after which a solution of iodomethane (0.11 mL, 1.78 mmol) in dry THF (2 mL) was added slowly. The reaction was warmed to room temperature and stirred overnight. The reaction mixture was quenched with aqueous ammonium chloride and extracted with ethyl acetate. The extracts were dried (Na$_2$SO$_4$) and concentrated in vacuo to afford the title compound (246 mg, 98%) as a yellow powder: $^1$H NMR (250 MHz, Chloroform-d) δ 4.20 (s, 2H), 2.63 (m, 2H), 1.80 (m, 2H), 1.47 (s, 3H), 1.46 (s, 9H), 1.33 (s, 6H).

Step 2: Synthesis of 4-(1-cyano-1-methylethyl)piperidin-1-ium chloride (Intermediate 13)

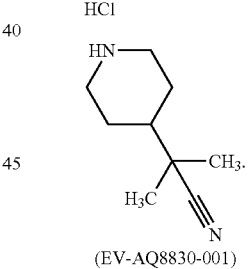

(EV-AQ8830-001)

Tert-butyl 4-(1-cyano-1-methylethyl)piperidine-1-carboxylate (EV-AQ8828-001, 243 mg, 0.963 mmol) was suspended in HCl (4 M in dioxane, 7 mL) and the reaction was stirred at room temperature for 3 hours. The resultant precipitate was filtered and washed with ether to afford the title compound (95 mg, 51%) as a yellow powder: $^1$H NMR (500 MHz, DMSO-d6) δ 8.96 (s, 1H), 8.51 (s, 1H), 2.87-2.78 (m, 2H), 1.95-1.87 (m, 2H), 1.72-1.63 (m, 1H), 1.54-1.45 (m, 2H), 1.29 (s, 6H).

Examples 57-74—Synthesis of Thienopyrimidines

Examples 57-74 in Table 5 were prepared using the method described in Example 1 reacting intermediate 11 (5-methyl-1-{4-oxo-3H,4H-thieno[3,2-d]pyrimidin-2-yl}-1H-pyrazole-4-carboxylic acid) with the appropriate amine using the specified coupling reagent.

TABLE 5

| Example No | Ref. No. | LBN | Structure | LC-MS (RT) Method C | MS (M + H)+ Method C | Coupling Agent |
|---|---|---|---|---|---|---|
| 57 | Q-403 | EV-AP2371-001 | 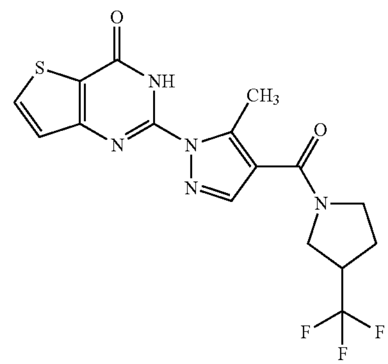 [SMILES: Cc1c(C(=O)N2CCC(C(F)(F)F)C2)cnn1-c1nc2ccsc2c(=O)[nH]1] | 2.68 | 398.2 | COMU |
| 58 | Q-402 | EV-AP2366-001 | 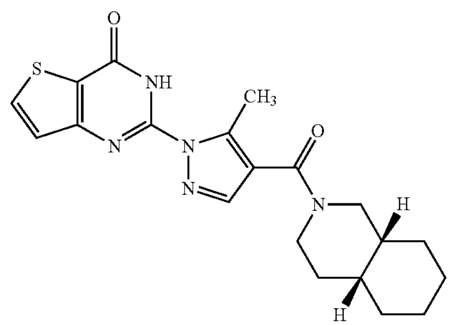 [SMILES: Cc1c(C(=O)N2CC[C@H]3CCCC[C@H]3C2)cnn1-c1nc2ccsc2c(=O)[nH]1] | 3.43 | 398.3 | T3P |
| 59 | Q-495 | EV-AQ8852-001 | 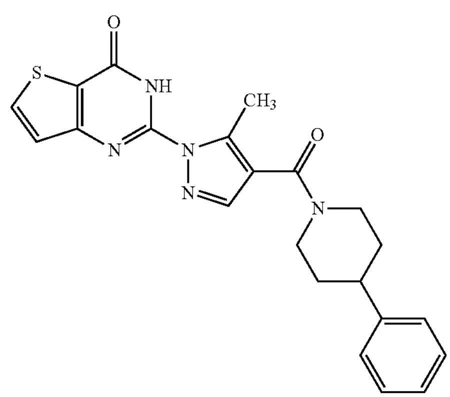 [SMILES: Cc1c(C(=O)N2CCC(c3ccccc3)CC2)cnn1-c1nc2ccsc2c(=O)[nH]1] | 3.31 | 420.1 | T3P |
| 60 | Q-395 | EV-AP2364-001 | 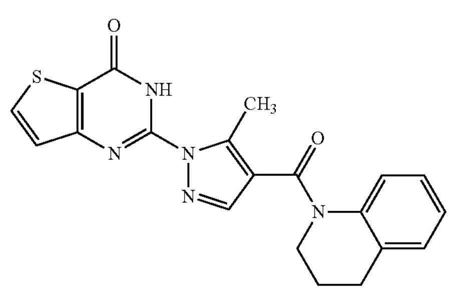 [SMILES: Cc1c(C(=O)N2CCCc3ccccc32)cnn1-c1nc2ccsc2c(=O)[nH]1] | 3.16 | 392.2 | T3P |

TABLE 5-continued
| Example No | Ref. No. | LBN | Structure | LC-MS (RT) Method C | MS (M + H)+ Method C | Coupling Agent |
|---|---|---|---|---|---|---|
| 61 | Q-380 | EV-AP2536-001 | 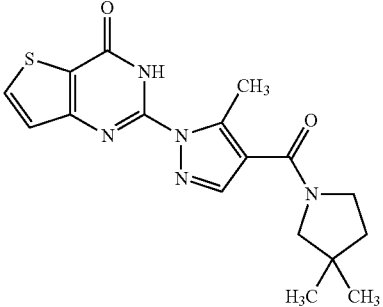 [SMILES: Cc1c(C(=O)N2CCC(C)(C)C2)cnn1-c1nc2ccsc2c(=O)[nH]1] | 2.79 | 358.2 | COMU |
| 62 | Q-397 | EV-AP2562-001 | 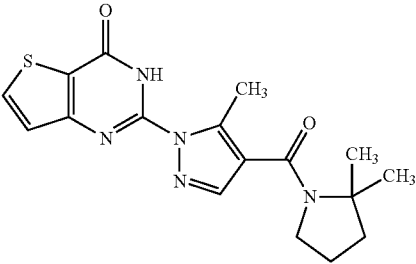 [SMILES: Cc1c(C(=O)N2CCCC2(C)C)cnn1-c1nc2ccsc2c(=O)[nH]1] | 2.85 | 358.2 | COMU |
| 63 | Q-405 | EV-AP2570-001 | 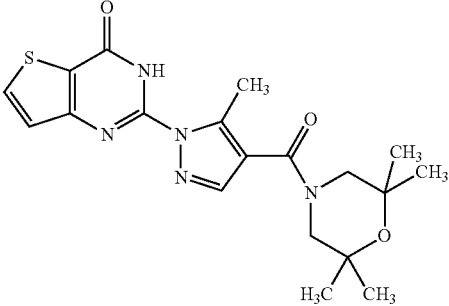 [SMILES: Cc1c(C(=O)N2CC(C)(C)OC(C)(C)C2)cnn1-c1nc2ccsc2c(=O)[nH]1] | 2.74 | 402.3 | COMU |
| 64 | Q-398 | EV-AP2563-001 | 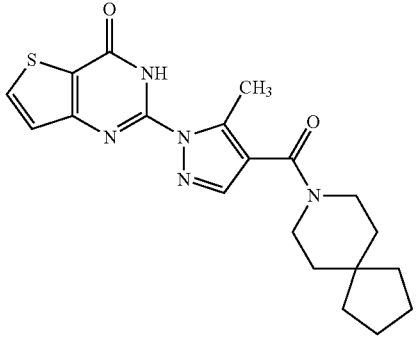 [SMILES: Cc1c(C(=O)N2CCC3(CCCC3)CC2)cnn1-c1nc2ccsc2c(=O)[nH]1] | 3.51 | 398.2 | COMU |

TABLE 5-continued

| Example No | Ref. No. | LBN | Structure | LC-MS (RT) Method C | MS (M + H)+ Method C | Coupling Agent |
|---|---|---|---|---|---|---|
| 65 | Q-354 | EV-AP2517-001 | 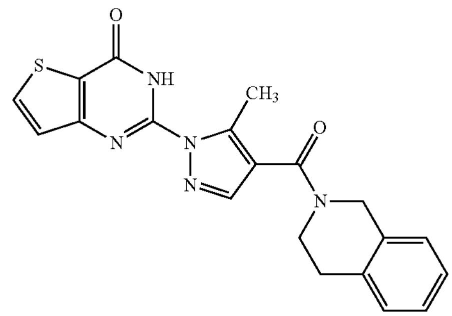 [SMILES: Cc1c(C(=O)N2CCc3ccccc3C2)cnn1-c1nc2ccsc2c(=O)[nH]1] | 3.00 | 392.2 | COMU |
| 66 | Q-399 | EV-AQ0205-002 | 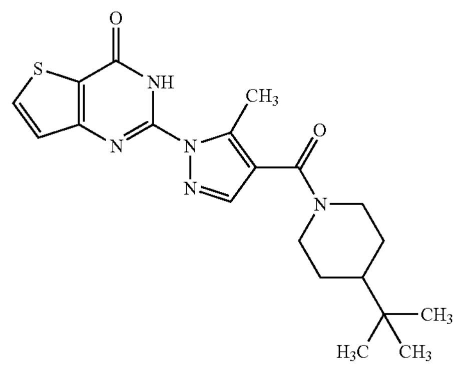 [SMILES: Cc1c(C(=O)N2CCC(C(C)(C)C)CC2)cnn1-c1nc2ccsc2c(=O)[nH]1] | 3.64 | 400.2 | T3P |
| 67 | Q-400 | EV-AQ0207-002 | 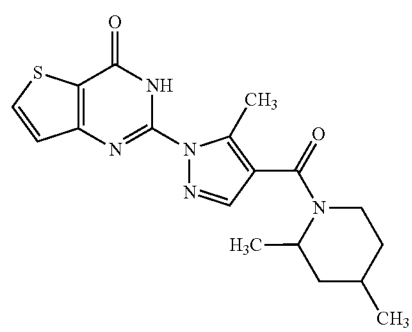 [SMILES: Cc1c(C(=O)N2CCC(C)CC2C)cnn1-c1nc2ccsc2c(=O)[nH]1] | 3.08 | 372.2 | COMU |
| 68 | Q-406 | EV-AQ0208-002 | 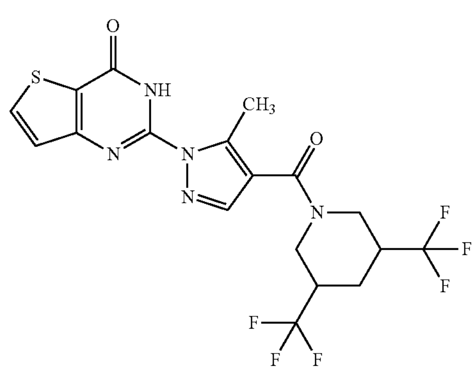 [SMILES: Cc1c(C(=O)N2CC(C(F)(F)F)CC(C(F)(F)F)C2)cnn1-c1nc2ccsc2c(=O)[nH]1] | 3.21 | 480.2 | T3P |

TABLE 5-continued

| Example No | Ref. No. | LBN | Structure | LC-MS (RT) Method C | MS (M + H)+ Method C | Coupling Agent |
|---|---|---|---|---|---|---|
| 69 | Q-408 | EV-AQ0210-002 | | 3.54 | 398.3 | COMU |
| 70 | Q-412 | EV-AQ0216-002 | 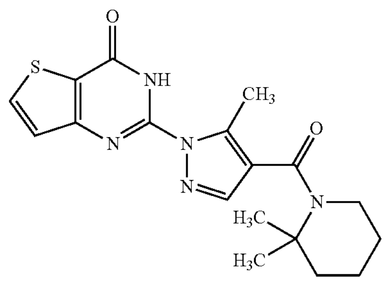 [SMILES: Cc1c(C(=O)N2CCCCC2(C)C)cnn1-c1nc2ccsc2c(=O)[nH]1] | 3.28 | 372.2 | COMU |
| 71 | Q-401 | EV-AB8083-002 | 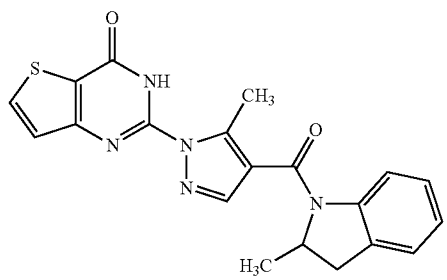 [SMILES: Cc1c(C(=O)N2c3ccccc3CC2C)cnn1-c1nc2ccsc2c(=O)[nH]1] | 3.28 | 392.2 | T3P |
| 72 | Q-422 | EV-AQ3802-003 | 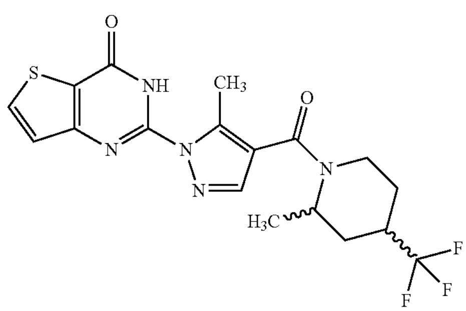 [SMILES: Cc1c(C(=O)N2CCC(C(F)(F)F)CC2C)cnn1-c1nc2ccsc2c(=O)[nH]1] | 3.10, 28% 3.14 63% | 425.0 | COMU Intermediate 12 |
| 73 | Q-379 | EV-AP2394-001 | 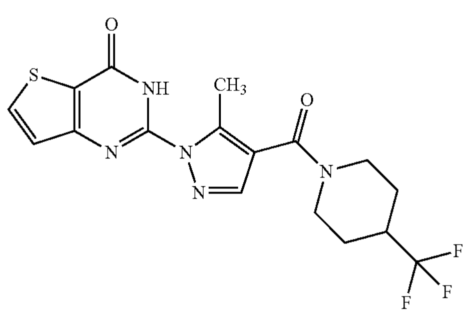 [SMILES: Cc1c(C(=O)N2CCC(C(F)(F)F)CC2)cnn1-c1nc2ccsc2c(=O)[nH]1] | 2.90 | 412.1 | T3P |

TABLE 5-continued

| Example No | Ref. No. | LBN | Structure | LC-MS (RT) Method C | MS (M + H)+ Method C | Coupling Agent |
|---|---|---|---|---|---|---|
| 74 | Q-531 | EV-AS3708-002 | 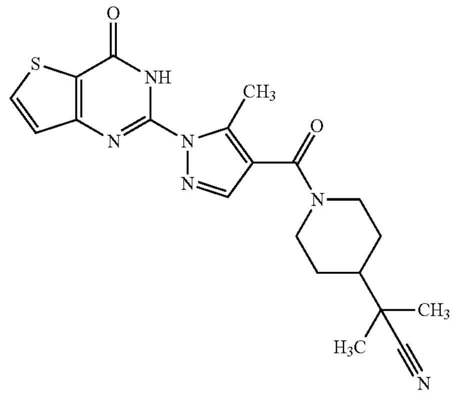 [SMILES: Cc1c(C(=O)N2CCC(C(C)(C)C#N)CC2)cnn1-c1nc2ccsc2c(=O)[nH]1] | 2.58 | 411.1 | T3P Intermediate 13 |

Example 75—Preparation of 2-{4-[(2R,6S)-2,6-dimethylpiperidine-1-carbonyl]-5-methyl-1H-pyrazol-1-yl}-3H,4H-thieno[3,2-d]pyrimidin-4-one

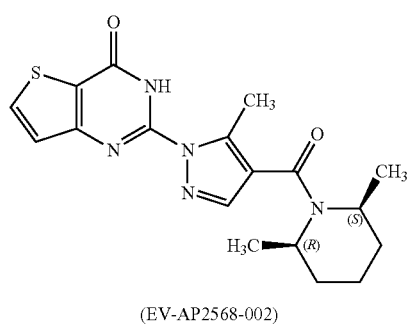

Q-417

(EV-AP2568-002)

To a solution of 5-methyl-1-{4-oxo-3H,4H-thieno[3,2-d]pyrimidin-2-yl}-1H-pyrazole-4-carboxylic acid (Intermediate 11, (EV-AP2386-001), 75 mg, 0.27 mmol) in DCM (5 ml) was added thionyl chloride (0.2 ml, 2.71 mmol) followed by DMF (cat, 1 drop) and stirred at 50° C. for 2 h. The reaction mixture was concentrated in vacuo and DCM added and the concentration repeated (×2). The crude acid chloride (assume 0.271 mmol) was suspended in more DCM (5 ml) at 0° C. and (cis)-2,6-dimethylpiperidine (0.04 ml, 0.41 mmol) and triethylamine (0.09 ml, 0.68 mmol) were added dropwise. The reaction mixture was stirred at r.t. for 2 h. The reaction mixture was washed with water (5 mL) and brine solution (5 mL) and the organic fraction was concentrated in vacuo. The crude residue was dissolved in THF: 1M NaOH (1:1, 2 mL) and stirred at r.t. Methanol (0.5 ml) was added. The organics from the reaction mixture were removed in vacuo and the reaction mixture acidified to pH 5 using 1M aq HCl solution. The aqueous was extracted using DCM (2×5 mL) and the combined organic extracts were dried over $Na_2SO_4$, filtered and concentrated in vacuo. The crude residue was purified by prep HPLC (Method G) to afford the title compound (14.2 mg, 14%) as an off-white powder.

Method A: LC-MS m/z=372.2 [M+H]+; RT=3.05 min.

Examples 76-77

Examples in Table 6 were prepared by chiral separation of racemic compounds in Table 5. The stereochemistry was arbitrarily assigned.

TABLE 6

| Example No | Ref. No. | LBN | Structure | LC-MS (RT) Method C | MS (M + H)+ Method C | Column Retention* (min) | Separation Method |
|---|---|---|---|---|---|---|---|
| 76 | Q-414 | EV-AQ0229-001 | 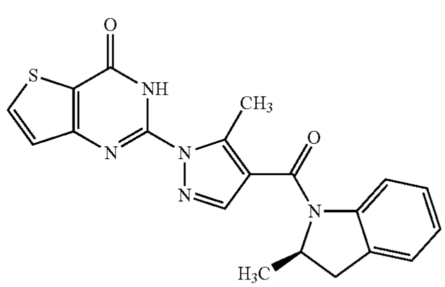 [SMILES: Cc1c(C(=O)N2c3ccccc3C[C@H]2C)cnn1-c1nc2ccsc2c(=O)[nH]1] | 3.29 | 392.2 | 6.43 Method M | L |

TABLE 6-continued

| Example No | Ref. No. | LBN | Structure | LC-MS (RT) Method C | MS (M + H)+ Method C | Column Retention* (min) | Separation Method |
|---|---|---|---|---|---|---|---|
| 77 | Q-415 | EV-AQ0229-002 | 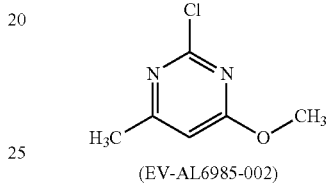 | 3.29 | 392.2 | 8.41 Method M | L |

Preparative Example 4—Formation of Intermediates from the Corresponding Dichloropyrimidines Intermediate 14: Preparation of 2-chloro-4-methoxy-6-methylpyrimidine

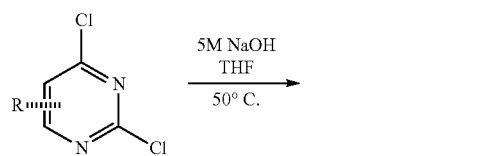

(EV-AL6985-002)

To a solution of 2,4-dichloro-6-methylpyrimidine (1 g, 6.14 mmol) in THF (10 ml) was added 0.5M NaOMe in MeOH (18.4 ml, 9.20 mmol) at 0° C. and stirred at r.t. overnight. A further 0.5 equivalents of 0.5 M NaOMe in MeOH (6.14 ml, 3.07 mmol) were added at 0° C. and the reaction stirred at r.t. for 1 h. The reaction mixture was diluted with water (30 ml) and extracted with EtOAc (2×50 ml). The combined organic extracts were washed with brine (20 ml), dried and concentrated in vacuo and the residue purified via column chromatography (100:0-75:25 Heptane-EtOAc) to afford the title compound (275 mg, 28%) as a colourless crystalline solid.

Method A: LC-MS m/z=158.9 [M+H]+; RT=1.05 min.

Intermediate 15: Preparation of 5-chloro-6H,7H-[1,3]thiazolo[5,4-d]pyrimidin-7-one (EV-AQ0263-001)

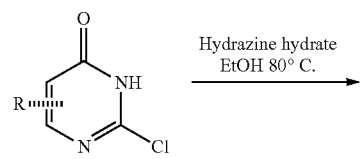

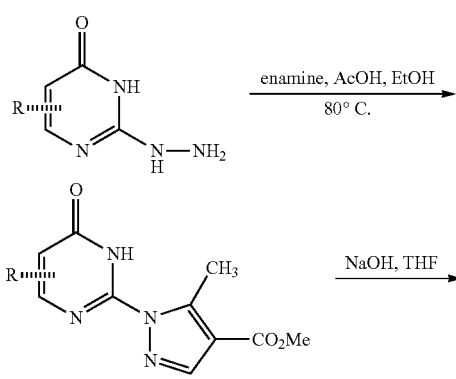

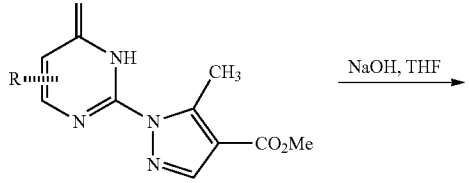

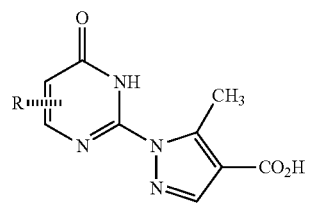

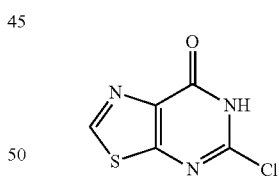

Step 1: Synthesis of 7-(benzyloxy)-5-chloro-[1,3]thiazolo[5,4-d]pyrimidine

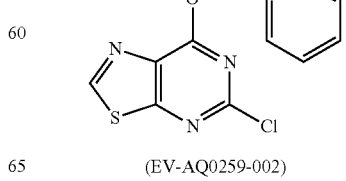

(EV-AQ0259-002)

To a solution of 5,7-dichloro-[1,3]thiazolo[5,4-d]pyrimidine (980 mg, 4.76 mmol) in THF (20 mL) at 0° C. was added benzyl alcohol (495 µl, 4.76 mmol) and sodium hydride (114 mg, 4.76 mmol, 60% in mineral oil) and stirred at r.t. for 22 h. To the reaction mixture was added water (20 ml) and extracted with EtOAc (2×50 ml). The combined organic extracts were washed with brine, dried over sodium sulfate and concentrated in vacuo. Purification by chromatography on $SiO_2$ (gradient 100:0-90:10, Heptane-EtOAc) afforded the title compound (708 mg, 47%) as a white powder.

Method A: LC-MS m/z=277.85 [M+H]$^+$; RT=1.39 min.

Step 2: Synthesis of 5-chloro-6H,7H-[1,3]thiazolo[5,4-d]pyrimidin-7-one

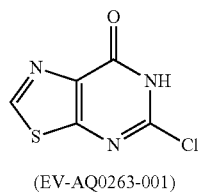

(EV-AQ0263-001)

7-(benzyloxy)-5-chloro-[1,3]thiazolo[5,4-d]pyrimidine (EV-AQ0259-002, 708 mg, 2.24 mmol) was dissolved in a 1:1 mixture of 37% aq HCl-THF (10 mL) and stirred at room temperature for 18 h. The reaction mixture was filtered under vacuum, washing with THF and $Et_2O$, to afford 5-chloro-6H,7H-[1,3]thiazolo[5,4-d]pyrimidin-7-one (246 mg, 58%) as a pale yellow powder.

Method A: LC-MS m/z=187.80 [M+H]$^+$; RT=0.49 min.

Intermediate 16: Synthesis of 2,4-dichloro-7-methyl-7H-pyrrolo[2,3-d]pyrimidine

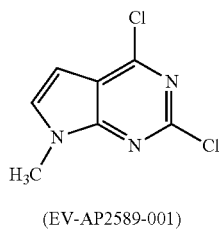

(EV-AP2589-001)

To a solution of 2,4-dichloro-7H-pyrrolo[2,3-d]pyrimidine (1.5 g, 7.98 mmol) in THF (30 ml) at 0° C. was added sodium hydride (60% oil suspension, 383 mg, 9.57 mmol) and stirred at 0° C. to r.t. for 20 mins. Iodomethane (0.6 ml, 9.57 mmol) was added and stirred at r.t. for 3 h.

The mixture was quenched by addition of saturated ammonium chloride solution (20 mL). EtOAc was then added resulting in formation of a precipitate. The precipitate was filtered and the filtrate extracted with EtOAc (×2). The combined organic fractions were washed with water, dried over $Na_2SO_4$, filtered and concentrated in vacuo to afford the title compound (1.65 g, 97.2%) as a yellow powder.

Method A: LC-MS m/z=201.90, 203.90 [M+H]+; RT=1.21 min.

Examples 78-88

Examples 78-88 in Table 7 were synthesized following the procedure described for Example 57 starting from the corresponding dichloropyrimidine or specified intermediate and coupling the intermediate acid with the appropriate amine using the specified coupling conditions.

TABLE 7

| Example No | Ref. No. | LBN | Structure | LC-MS (RT) Method C | MS (M + H)$^+$ Method C | Coupling Agent | Comments |
|---|---|---|---|---|---|---|---|
| 78 | Q-410 | EV-AP2378-001 | 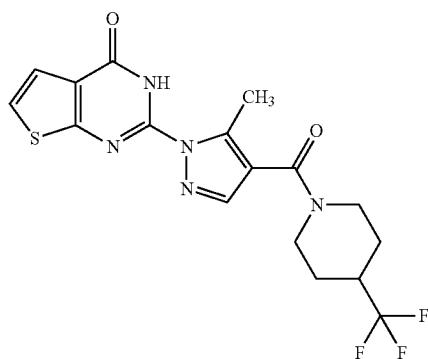 [SMILES: Cc1c(C(=O)N2CCC(C(F)(F)F)CC2)cnn1-c1nc2sccc2c(=O)[nH]1] | 3.02 | 412.2 | COMU | |

TABLE 7-continued

| Example No | Ref. No. | LBN | Structure | LC-MS (RT) Method C | MS (M + H)+ Method C | Coupling Agent | Comments |
|---|---|---|---|---|---|---|---|
| 79 | Q-426 | EV-AP2597-002 | 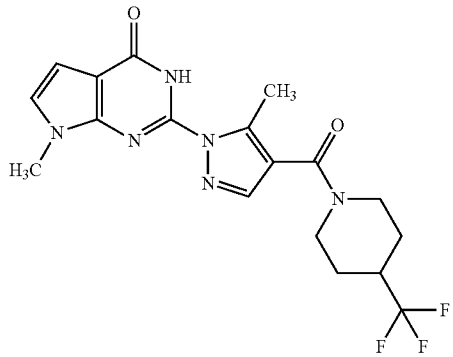 [SMILES: Cc1c(C(=O)N2CCC(C(F)(F)F)CC2)cnn1-c1nc2c(ccn2C)c(=O)[nH]1] | 2.72 | 409.2 | T3P | |
| 80 | Q-323 | EV-AN7481-001 | 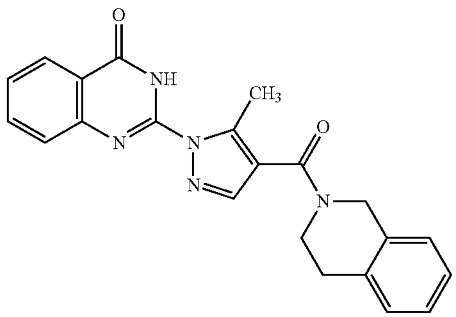 [SMILES: Cc1c(C(=O)N2CCc3ccccc3C2)cnn1-c1nc2ccccc2c(=O)[nH]1] | 3.26 | 386.2 | COMU | |
| 81 | Q-320 | EV-AO8806-002 | 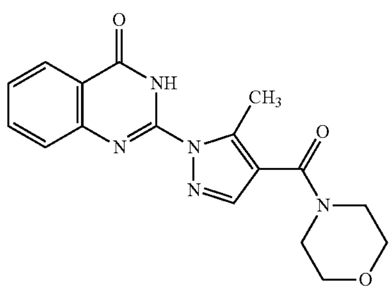 [SMILES: Cc1c(C(=O)N2CCOCC2)cnn1-c1nc2ccccc2c(=O)[nH]1] | 340.1 | 2.17 | COMU | |
| 82 | Q-321 | EV-AO8807-002 | 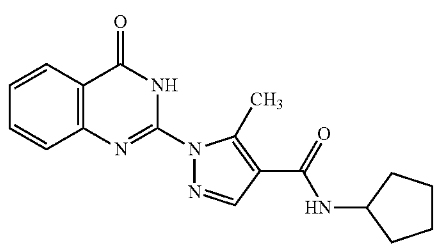 [SMILES: Cc1c(C(=O)NC2CCCC2)cnn1-c1nc2ccccc2c(=O)[nH]1] | 338.2 | 2.96 | COMU | |
| 83 | Q-429 | EV-AQ0246-002 | 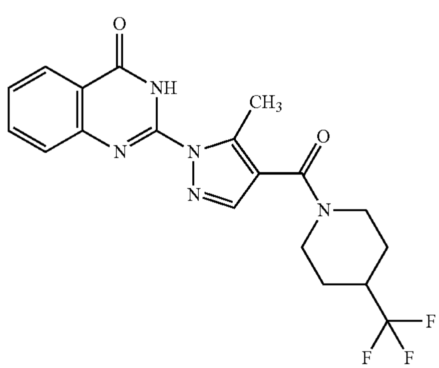 [SMILES: Cc1c(C(=O)N2CCC(C(F)(F)F)CC2)cnn1-c1nc2ccccc2c(=O)[nH]1] | 406.2 | 3.16 | T3P | |

TABLE 7-continued

| Example No | Ref. No. | LBN | Structure | LC-MS (RT) Method C | MS (M + H)+ Method C | Coupling Agent | Comments |
|---|---|---|---|---|---|---|---|
| 84 | Q-378 | EV-AP2343-001 | 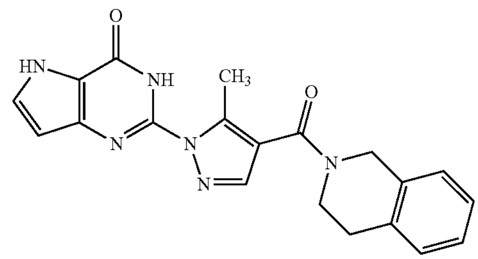 [SMILES: Cc1c(C(=O)N2CCc3ccccc3C2)cnn1-c1nc2cc[nH]c2c(=O)[nH]1] | 375.2 | 2.62 | TBTU | |
| 85 | Q-436 | EV-AQ7107-002 | 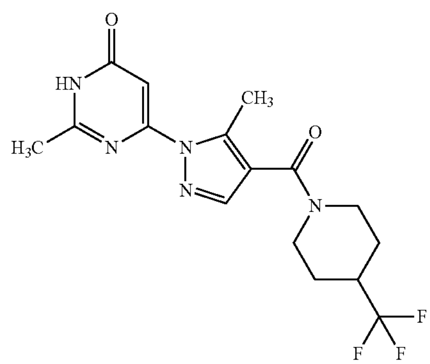 [SMILES: Cc1nc(-n2ncc(C(=O)N3CCC(C(F)(F)F)CC3)c2C)cc(=O)[nH]1] | 2.23 | 370.2 | T3P | Commerical chloro-pyrimidone |
| 86 | Q-413 | EV-AQ0227-002 | 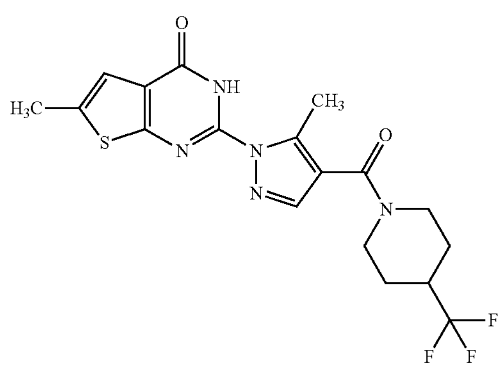 [SMILES: Cc1cc2c(=O)[nH]c(-n3ncc(C(=O)N4CCC(C(F)(F)F)CC4)c3C)nc2s1] | 426.2 | 3.29 | COMU | |
| 87 | Q-441 | EV-AQ0268-002 | 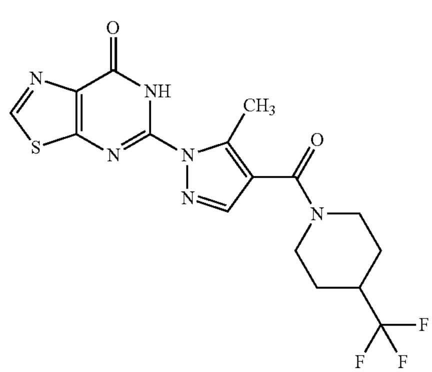 [SMILES: Cc1c(C(=O)N2CCC(C(F)(F)F)CC2)cnn1-c1nc2scnc2c(=O)[nH]1] | 2.53 | 413.2 | T3P | Intermediate 15 |

Preparative Example 5

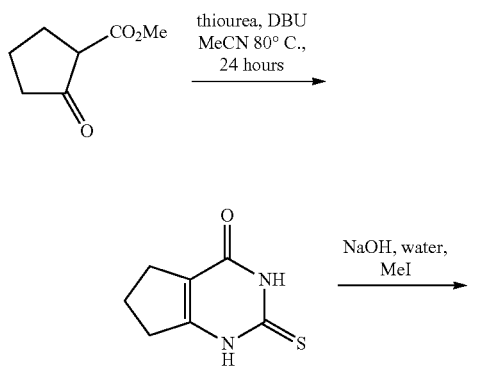

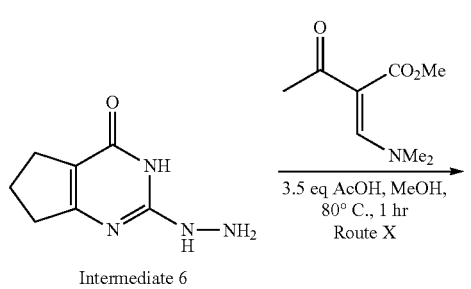

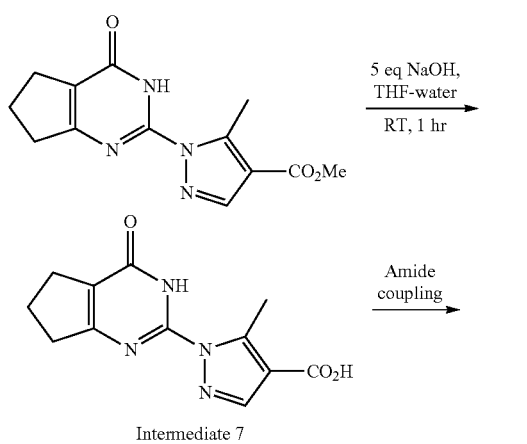

Intermediate 6

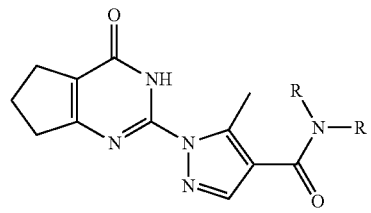

Intermediate 7

Intermediate 17: Preparation of 2-hydrazinyl-3H,4H,5H,6H,7H-cyclopenta[d]pyrimidin-4-one (EV-AQ7134-001)

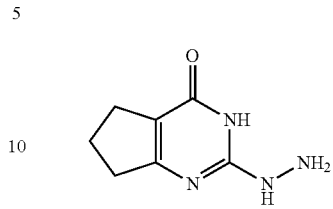

Step 1: Synthesis of 2-sulfanylidene-1H,2H,3H,4H,5H,6H,7H-cyclopenta[d]pyrimidin-4-one

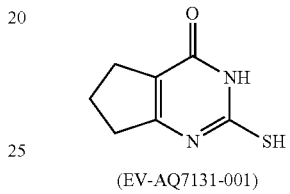

(EV-AQ7131-001)

To a solution of methyl 2-oxocyclopentanecarboxylate (17.83 mL, 143.65 mmol) in acetonitrile (150 mL) was added thiourea (16.4 g, 215.47 mmol) followed by DBU (25.73 mL, 172.38 mmol) and stirred at 80° C. for 24 h. The reaction mixture was concentrated in vacuo and dissolved in water. The solution was acidified to pH3/4 using 5M aq HCl solution and the resulting precipitate was collected and dried under vacuum after washing with water and diethyl ether. The solid was dried further at 40° C. under vacuum overnight to afford the title compound (17.81 g, 73.7%) as a beige powder.

Method A: LC-MS: m/z=168.9 (M+H)+, RT=0.2-0.45 min.

Step 2: Synthesis of 2-(methylsulfanyl)-3H,4H,5H,6H,7H-cyclopenta[d]pyrimidin-4-one

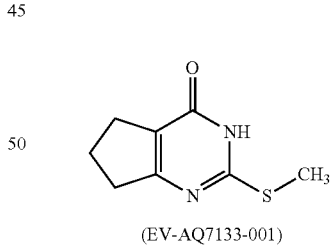

(EV-AQ7133-001)

To a suspension of 2-sulfanylidene-1H,2H,3H,4H,5H,6H,7H-cyclopenta[d]pyrimidin-4-one (EV-AS7131-001, 17.81 g, 105.88 mmol) in water (100 mL) was added NaOH (4.66 g, 116.46 mmol) followed by the drop wise addition of iodomethane (7.25 mL, 116.46 mmol). The reaction mixture was stirred at room temperature for 1.5 h, then cooled to 5° C. and the resultant precipitate was collected by vacuum filtration. The solid was washed with ice cold water (50 mL) water and diethyl ether (50 mL) and dried further under vacuum at 40° C. to afford the title compound (17.78 g, 89.4%) as an off white powder.

Method A: LC-MS: m/z=182.9 (M+H)+; RT=0.89 min.

Step 3: Synthesis of 2-hydrazinyl-3H,4H,5H,6H,7H-cyclopenta[d]pyrimidin-4-one

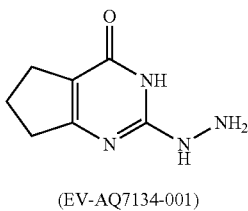 [SMILES: NNc1nc2c(c(=O)[nH]1)CCC2]

(EV-AQ7134-001)

To a solution of 2-(methylsulfanyl)-3H,4H,5H,6H,7H-cyclopenta[d]pyrimidin-4-one (EV-AQ7133-001, 17.78 g, 97.56 mmol) in EtOH (30 mL) was added hydrazine hydrate (23.73 mL, 487.81 mmol). The reaction mixture was stirred at 90° C. for 24 h and then at 85° C. for a further 7 h. The cooled reaction mixture was filtered and washed with EtOH (15 mL) and water (10 mL) to afford the title compound (13.1 g, 80.8%) as a white powder.

Method B: LC-MS: m/z=166.9 (M+H)+, RT=0.19 min.

Intermediate 18: Preparation of 5-methyl-1-{4-oxo-3H,4H,5H,6H,7H-cyclopenta[d]pyrimidin-2-yl}-1H-pyrazole-4-carboxylic acid (Q-481, EV-AQ7139-001)

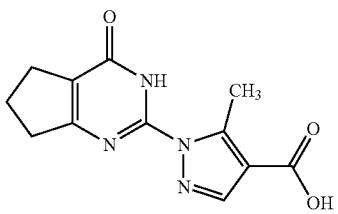 [SMILES: Cc1c(C(=O)O)cnn1-c1nc2c(c(=O)[nH]1)CCC2]

Step 1: Synthesis of 2-{5-methyl-4-[4-(trifluoromethyl)piperidine-1-carbonyl]-1H-pyrazol-1-yl}-3H,4H,5H,6H,7H-cyclopenta[d]pyrimidin-4-one

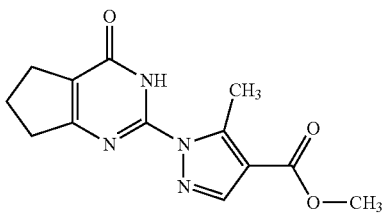

(EV-AQ7137-001)

To a solution of 2-hydrazinyl-3H,4H,5H,6H,7H-cyclopenta[d]pyrimidin-4-one (EV-AQ7134-001, 19 g, 114.33 mmol) in ethanol (120 mL) was added methyl 2-[(dimethylamino)methylidene]-3-oxobutanoate (EV-AL6988-001, 21.53 g, 125.77 mmol) followed by acetic acid (22.91 mL, 400.17 mmol). The reaction mixture was stirred at 50° C. for 3.5 h. After 15 mins additional ethanol (170 mL) was added to maintain stirring. The reaction mixture was cooled and the solvent volume reduced to approximately half. The resultant precipitate was collected and dried by vacuum filtration to afford the title compound (21.84 g, 69.6%) as a beige powder.

Method B: LC-MS: m/z=275.0 (M+H)+, RT=0.98 min.

Step 2: Synthesis of 5-methyl-1-{4-oxo-3H,4H,5H,6H,7H-cyclopenta[d]pyrimidin-2-yl}-1H-pyrazole-4-carboxylic acid (Q-481, EV-AQ7139-001)

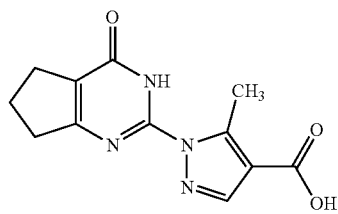

(EV-AQ7139-001)

Methyl 5-methyl-1-{4-oxo-3H,4H,5H,6H,7H-cyclopenta[d]pyrimidin-2-yl}-1H-pyrazole-4-carboxylate (EV-AQ7137-001, 21.84 g, 79.63 mmol) was suspended in 3:2:1 water/THF/methanol (300 mL) and 2.5M aq NaOH solution (191 mL) was added. The reaction mixture was stirred at r.t. for 3 h. The organics from the reaction mixture were removed in vacuo. The residue was acidified with 5M aq HCl solution and the resulting precipitate was collected and dried under vacuum filtration at 45° C. for 5 days to afford the title compound (21.6 g, 100%) as a beige powder.

Method C: LC-MS: m/z=261.1 (M+H)+, RT=1.81 min.

Intermediate 19: Preparation of +(syn)-2-methyl-4-(trifluoromethyl)piperidine hydrochloride

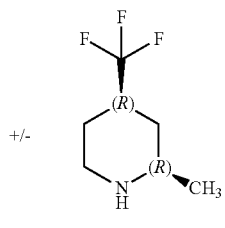

(EV-AQ3807-001)

A solution of 2-methyl-4-(trifluoromethyl)pyridine (3 g, 18.62 mmol) in MeOH (100 ml) was treated with a solution of 4M HCl in dioxane (5.6 ml, 22.3 mmol) followed by platinum (iv) oxide (253 mg, 1.12 mmol) and the resultant suspension was hydrogenated in a pressure vessel at 50 psi and r.t. for 4 h. The catalyst was cautiously removed by filtration over Celite and the filtrate concentrated in vacuo to afford the title compound (3.7 g, 99%) as a white solid.

Method A: LC-MS m/z=168.0 [M+H]+; RT=0.21 min.

Intermediate 20: Synthesis of 2-methyl-4-phenylpiperidin-4-ol hydrochloride EV-AQ7159-002 used in (EV-AQ7163-003)

Step 1: Synthesis of tert-butyl 4-hydroxy-2-methyl-4-phenylpiperidine-1-carboxylate formation using phenyllithium

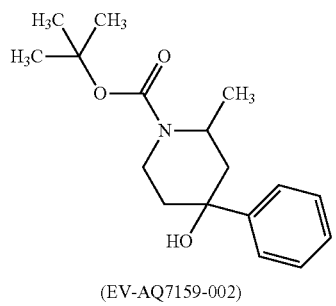 [SMILES: CC1CC(O)(c2ccccc2)CCN1C(=O)OC(C)(C)C]

(EV-AQ7159-002)

To a solution of phenyllithium (1.8M in Bu2O, 7.16 ml, 12.89 mmol) in THF (15 mL) at −78° C. was added dropwise 1-boc-2-methyl-4-piperidinone (2.5 g, 11.72 mmol) in more THF (5 mL). The reaction mixture was warmed to room temperature and stirred for 3 hours. The reaction was quenched by pouring onto ice water. EtOAc (2×25 mL) was added and the product extracted. The combined organics were dried (Na$_2$SO$_4$), filtered and concentrated in vacuo. The crude residue was purified by chromatography on SiO$_2$ Eluting with 0-100% EtOAc in heptane to afford the title compound (2.97 g, 73.9%) as a yellow oil Method B: LC-MS: m/z=192.0 (M-Boc)+, RT=1.19 min.

Step 2: Synthesis of 2-methyl-4-phenylpiperidin-4-ol hydrochloride

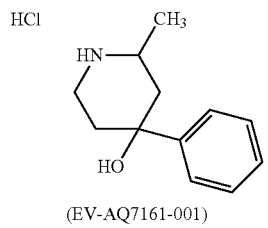

(EV-AQ7161-001)

To a solution of tert-butyl 4-hydroxy-2-methyl-4-phenylpiperidine-1-carboxylate (EV-AQ7159-002, 1.5 g, 5.15 mmol) in dioxane (3 mL) was added HCl in dioxane (4M, 6.43 mL, 25.74) and the reaction mixture stirred at room temperature for 1 hour. The reaction mixture was concentrated in vacuo re-dissolved in DCM and concentrated again to afford 1.22 g (83.3%) of the title compound as an orange gum.

Method B: LC-MS: m/z=192.0 (M+H)+, RT=0.21 min.

Intermediate 21: Synthesis of 2-(4-{3-hydroxy-3-phenyl-8-azabicyclo[3.2.1]octane-8-carbonyl}-5-methyl-1H-pyrazol-1-yl)-3H,4H,5H,6H,7H-cyclopenta[d]pyrimidin-4-one

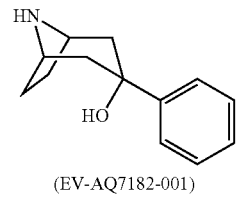 [SMILES: OC1(c2ccccc2)CC2CCC(C1)N2]

(EV-AQ7182-001)

2-(4-{3-hydroxy-3-phenyl-8-azabicyclo[3.2.1]octane-8-carbonyl}-5-methyl-1H-pyrazol-1-yl)-3H,4H,5H,6H,7H-cyclopenta[d]pyrimidin-4-one was prepared by the procedure described for Intermediate 21 (EV-AQ7161-001) substituting 1-boc-2-methyl-4-piperidinone with tert-butyl 3-oxo-8-azabicyclo[3.2.1]octane-8-carboxylate, affording the title compound (505 mg, 35%) as a an off white powder.

Method B: LC-MS: m/z=203.9 (M+H)+, RT=0.27 mins.

Intermediate 22: Synthesis of 3-phenyl-8-azabicyclo[3.2.1]octane hydrochloride EV-AQ7185-002

Step 1: Synthesis of tert-butyl 3-phenyl-8-azabicyclo[3.2.1]oct-2-ene-8-carboxylate

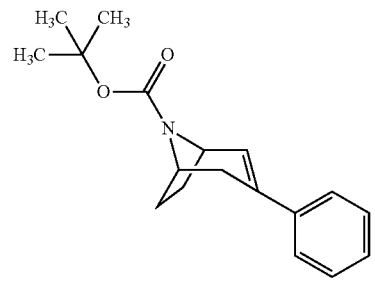

(EV-AQ7180-002)

To a solution of phenyllithium (2.0M in Bu2O, 3.66 ml, 7.32 mmol) in THF (15 mL) at −78° C. was added dropwise tert-butyl 3-oxo-8-azabicyclo[3.2.1]octane-8-carboxylate (1.5 g, 6.66 mmol) in THF (5 mL). The reaction was warmed to r.t. over 1 h and stirred for another 1 h. 1/3 of the reaction mixture was removed for an analogous chemistry and the remaining 2/3 of the reaction mixture was cooled to −78° C. and treated with methanesulfonyl chloride (1.03 mL, 13.32 mmol) followed by triethylamine (3.06 mL, 21.97 mmol). The reaction mixture was then warmed to r.t. and stirred overnight. The reaction mixture was cooled to −78° C. again and more methanesulfonyl chloride (2.06 mL, 26.64 mmol) and triethylamine (6.12 mL, 43.94 mmol) were added. The reaction mixture was then warmed to r.t. and stirred for 3.5 h. The reaction was diluted with water and extracted with EtOAc (3×20 mL). The combined organics were washed with water (10 mL) and brine (10 mL), dried over Na$_2$SO$_4$ and concentrated in vacuo. The crude residue was purified by chromatography on SiO$_2$ eluenting with Heptane/EtOAc (0-100%) to afford the title compound (480 mg, 36.8%) as an off-white solid.

Method B: LC-MS: m/z=229.95 (M−$^t$Bu)+, RT=1.37 min.

Step 2: Synthesis of 3-phenyl-8-azabicyclo[3.2.1]oct-2-ene hydrochloride

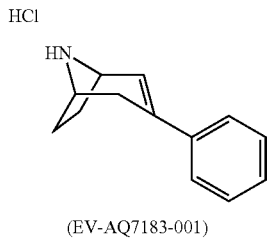 [SMILES: Cl ; C1=C(c2ccccc2)CC2CCC1N2]

(EV-AQ7183-001)

To a solution of tert-butyl 3-phenyl-8-azabicyclo[3.2.1]oct-2-ene-8-carboxylate (EV-AQ7180-002, 97%, 480 mg, 1.63 mmol) in dioxane (3 mL) was added HCl in dioxane (4M, 2.04 mL, 8.16 mmol) and the mixture was stirred at r.t. for 4 h. The reaction mixture was concentrated in vacuo re-dissolved in DCM and concentrated again to afford the title compound (355 mg, 93.2%) as an off white powder.
Method B: LC-MS: m/z=186.0 (M+H)+, RT=0.79 min.

Step 3: Synthesis of 3-phenyl-8-azabicyclo[3.2.1]octane hydrochloride

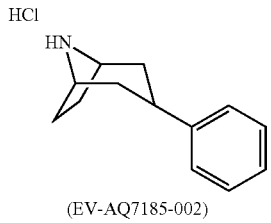 [SMILES: Cl ; c1ccc(C2CC3CCC(C2)N3)cc1]

(EV-AQ7185-002)

3-phenyl-8-azabicyclo[3.2.1]oct-2-ene hydrochloride (EV-AQ7183-001, 355 mg, 1.92 mmol) was dissolved in MeOH: EtOAc (1:1, 45 mL) and subjected to H-cube hydrogenation (1 mL/min, 20 bar, 60° C., controlled $H_2$ mode) over an Pd/C (10%) cat cart. The procedure was repeated at 40 bar, 60° C. and again at 60 bar, 60° C. The reaction mixture was concentrated in vacuo to afford the title compound (305 mg, 76%) as an off white powder.
Method B: LC-MS: m/z=188.0 (M+H)+, RT=0.74 mins.

Intermediate 23: Synthesis of 4-methoxy-4-phenylpiperidin-1-ium chloride EV-AQ8865-001

Step 1: Synthesis of tert-butyl-4-hydroxy-4-phenylpiperidine-1-carboxylate

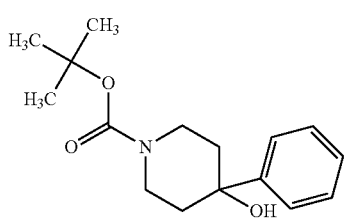 [SMILES: CC(C)(C)OC(=O)N1CCC(O)(c2ccccc2)CC1]

A solution 1-Boc-4-piperidinone (1 g, 5.02 mmol) in THF (5 mL) was added dropwise to a solution of phenyllithium (1.8M in $Bu_2O$, 3.07 mL, 5.52 mmol) in THF (5 mL) at −78° C. The reaction was warmed to r.t. and stirred for 4 h. The reaction was quenched by pouring onto ice water and extracted with EtOAc (2×25 mL). The combined organic extracts were dried over $MgSO_4$ and concentrated in vacuo. The crude residue was purified by chromatography on $SiO_2$, eluenting with Heptane/EtOAc (gradient 100:0-20:80) to afford the title compound (1.095 g, 79%) as a yellow powder.
Method B: LC-MS: m/z=177.9 (M-Boc)+, RT=1.15 min.

Step 2: Synthesis of tert-butyl 4-methoxy-4-phenylpiperidine-1-carboxylate

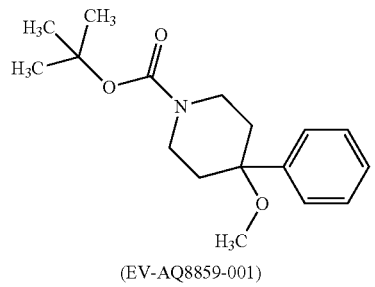 [SMILES: COC1(c2ccccc2)CCN(C(=O)OC(C)(C)C)CC1]

(EV-AQ8859-001)

To a stirred solution of 4-hydroxy-4-phenyl-piperidine-1-carboxylic acid tert-butyl ester (1.08 g, 3.91 mmol) in dry THF (25 mL) was added NaH (60% in oil, 0.17 g, 4.30 mmol) and stirred for 1 h before methyl iodide (0.37 mL, 5.86 mmol) was added and stirred overnight. The mixture was retreated with NaH (60%, 0.17 g, 4.30 mmol), followed by methyl iodide (0.37 mL, 5.86 mmol) and stirred overnight. The mixture was retreated for a third time with NaH (60%, 0.17 g, 4.30 mmol), followed by methyl iodide (0.37 mL, 5.86 mmol) and stirred for 4 h. Brine (40 mL) was added and the product extracted with EtOAc (2×50 mL). The combined organic extracts were dried over $MgSO_4$, concentrated in vacuo and purified by chromatography, eluting with Heptane/EtOAc (gradient 100:0-85:15) to afford the title compound (610 mg, 54%) as an off-white powder.
Method B: LC-MS: m/z=192.02 (M-Boc)+, RT=1.30 mins.

Step 3: Synthesis of 4-methoxy-4-phenylpiperidin-1-ium chloride

(EV-AQ8862-001)

4-methoxy-4-phenylpiperidine-1-carboxylate (603 mg, 2.07 mmol) was dissolved in HCl in dioxane (4M, 6 mL, 24.0 mmol) and stirred at r.t. overnight. The reaction mixture was concentrated in vacuo and triturated with ether to afford the title compound (391 mg, 83%) as a colourless powder.
Method B: LC-MS: m/z=191.9 (M+H)+, RT=0.64 mins.

Intermediate 24: Synthesis of 4-(2,2,2-trifluoroethoxy) piperidine

Step 1: Synthesis of 4-(2,2,2-trifluoroethoxy)pyridine

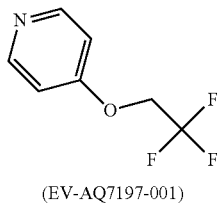 [SMILES: FC(F)(F)COc1ccncc1]

(EV-AQ7197-001)

To a solution of 2,2,2-trifluoroethanol (0.96 mL, 13.33 mmol) and NaH (60% in oil, 533.26 mg, 13.33 mmol) was added 4-chloropyridine hydrochloride (1 g, 6.67 mmol) in anhydrous DMSO (20 mL). The reaction mixture was stirred at 0° C. to r.t. overnight. Water (10 mL) was added and the product extracted with DCM (2×50 mL). The combined organic extracts were washed with water (10 mL) and brine (10 mL), dried over Na$_2$SO$_4$, filtered and concentrated in vacuo to afford the title compound (510 mg, 38.9%) as a tan gum.
Method B: LC-MS: m/z=178.0 (M+H)+, RT=0.31 min.

Step 2: Synthesis of 4-(2,2,2-trifluoroethoxy) piperidine

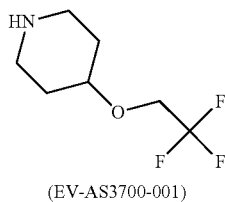

(EV-AS3700-001)

4-(2,2,2-trifluoroethoxy)pyridine (EV-AQ7197-001, 510 mg, 2.88 mmol) was dissolved in EtOH: acetic acid (3:1, 60 mL) and subjected to H-cube hydrogenation (1 ml/min, 90 bar, 80° C.) over a 5% Rh/C cat cart. The reaction mixture was concentrated in vacuo to afford the title compound (104 mg, 11.9%) as a tan gum.
Method B: LC-MS: m/z=184.0 (M+H)+, RT=0.21-0.33 min.

Intermediate 25: Synthesis of +(syn)-4-methyl-2-(trifluoromethyl)piperidine hydrochloride

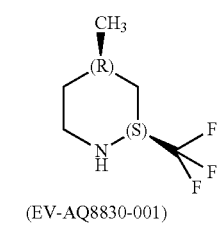

(EV-AQ8830-001)

A solution of 4-methyl-2-(trifluoromethyl)pyridine (1 g, 6.21 mmol) in MeOH (20 ml) was treated with HCl (4M in dioxane, 1.9 mL), followed by platinum (iv) oxide (85 mg, 0.37 mmol) and the resultant suspension was hydrogenated in a pressure vessel at 50 psi and r.t. for 20 h. More platinum (iv) oxide (85 mg, 0.37 mmol) was added along with AcOH (10 ml) and the hydrogenation was continued for 20 h.

The catalyst was removed by filtration over Celite and the filtrate evaporated under vacuum, the residue was triturated with ether to provide the title compound (460 mg, 36%) as a white solid.
Method B: LC-MS m/z=167.95 [M+H]$^+$; RT=0.18 min.

Examples 89-141

Examples in Table 8 were prepared using Method 1 reacting Intermediate 18 (5-methyl-1-{4-oxo-3H,4H,5H,6H,7H-cyclopenta[d]pyrimidin-2-yl}-1H-pyrazole-4-carboxylic acid) with the appropriate amine using the specified coupling reagent.

TABLE 8

| Example No | Ref. No. | LBN | Structure | LC-MS (RT) Method C | MS (M + H) Method C | Coupling Agent | Comments |
|---|---|---|---|---|---|---|---|
| 89 | Q-431 | EV-AQ7102-002 | 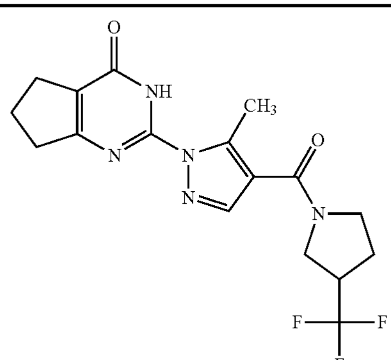 | 2.55 | 382.2 | T3P | |

TABLE 8-continued
| Example No | Ref. No | LBN | Structure | LC-MS (RT) Method C | MS (M + H) Method C | Coupling Agent | Comments |
|---|---|---|---|---|---|---|---|
| 90 | Q-435 | EV-AQ7103-002 | 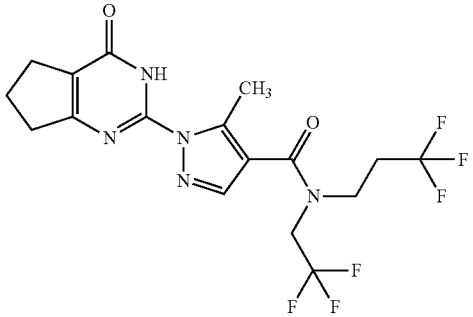 [SMILES: Cc1c(C(=O)N(CCC(F)(F)F)CC(F)(F)F)cnn1-c1nc2c(c(=O)[nH]1)CCC2] | 3.17 | 438.2 | T3P, SOCl$_2$ | |
| 91 | Q-446 | EV-AQ7126-004 | 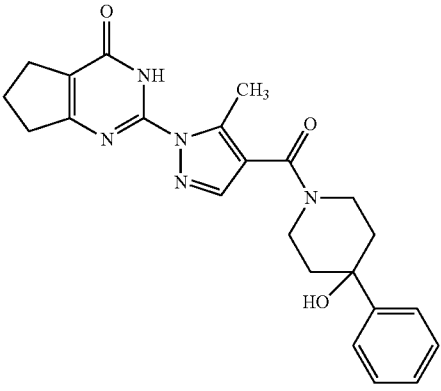 [SMILES: Cc1c(C(=O)N2CCC(O)(c3ccccc3)CC2)cnn1-c1nc2c(c(=O)[nH]1)CCC2] | 2.47 | 420.2 | T3P | |
| 92 | Q-449 | EV-AQ7132-002 | 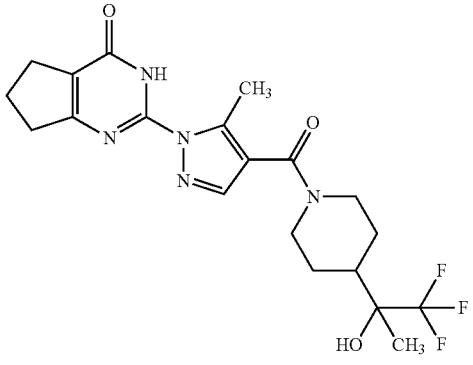 [SMILES: Cc1c(C(=O)N2CCC(C(C)(O)C(F)(F)F)CC2)cnn1-c1nc2c(c(=O)[nH]1)CCC2] | 2.48 | 440.2 | T3P | |
| 93 | Q-461 | EV-AQ7145-002 | 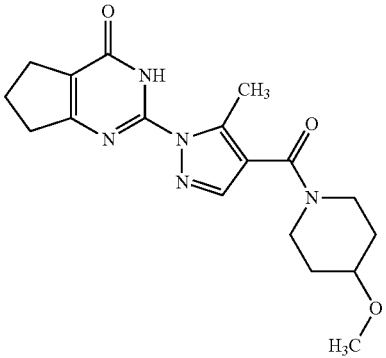 [SMILES: COC1CCN(C(=O)c2cnn(-c3nc4c(c(=O)[nH]3)CCC4)c2C)CC1] | 2.1 | 358.3 | T3P | |

TABLE 8-continued
| Example No | Ref. No | LBN | Structure | LC-MS (RT) Method C | MS (M + H) Method C | Coupling Agent | Comments |
|---|---|---|---|---|---|---|---|
| 94 | Q-462 | EV-AQ7146-002 | 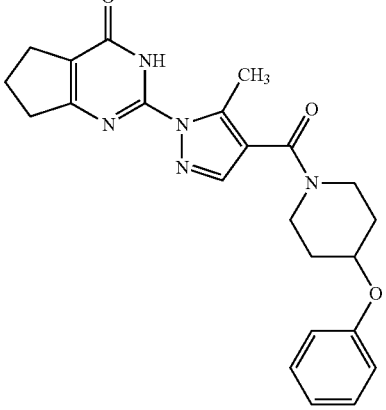 | 3.13 | 420.2 | T3P | |
| 95 | Q-505 | EV-AQ7172-001 | 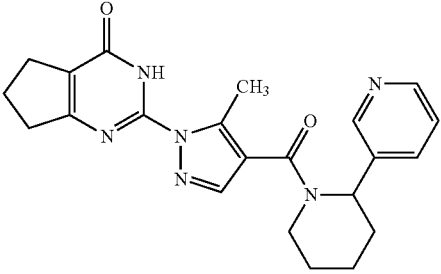 [SMILES: Cc1c(C(=O)N2CCCCC2c2cccnc2)cnn1-c1nc2c(c(=O)[nH]1)CCC2] | 1.67 | 405.2 | T3P | |
| 96 | Q-496 | EV-AQ7172-002 | 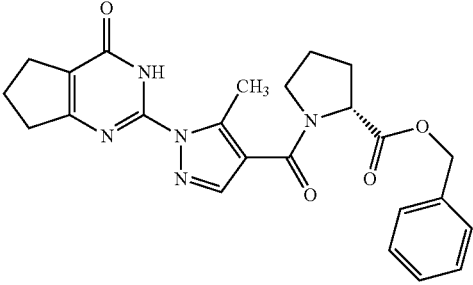 [SMILES: Cc1c(C(=O)N2CCC[C@@H]2C(=O)OCc2ccccc2)cnn1-c1nc2c(c(=O)[nH]1)CCC2] | 3.03 | 448.1 | T3P | |
| 97 | Q-418 | EV-AQ8866-003 | 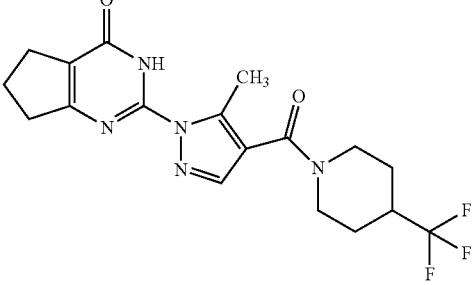 | 2.72 | 396.2 | T3P | |
| 98 | Q-497 | EV-AQ7172-003 | 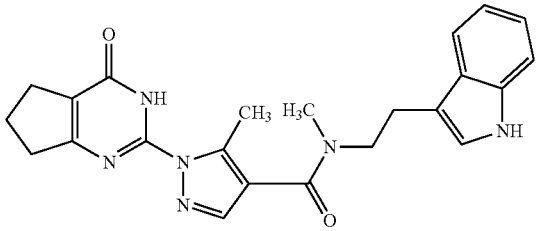 [SMILES: Cc1c(C(=O)N(C)CCc2c[nH]c3ccccc23)cnn1-c1nc2c(c(=O)[nH]1)CCC2] | 2.63 | 417.2 | T3P | |

TABLE 8-continued
| Example No | Ref. No | LBN | Structure | LC-MS (RT) Method C | MS (M + H) Method C | Coupling Agent | Comments |
|---|---|---|---|---|---|---|---|
| 99 | Q-498 | EV-AQ7172-004 | 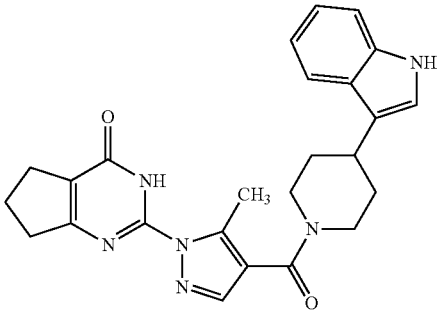 [SMILES: Cc1c(C(=O)N2CCC(c3c[nH]c4ccccc34)CC2)cnn1-c1nc2c(c(=O)[nH]1)CCC2] | 3.06 | 443.2 | T3P | |
| 100 | Q-499 | EV-AQ7173-001 | 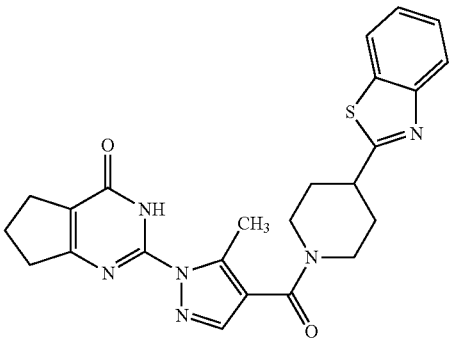 [SMILES: Cc1c(C(=O)N2CCC(c3nc4ccccc4s3)CC2)cnn1-c1nc2c(c(=O)[nH]1)CCC2] | 3.04 | 461.1 | T3P | |
| 101 | Q-500 | EV-AQ7173-002 | 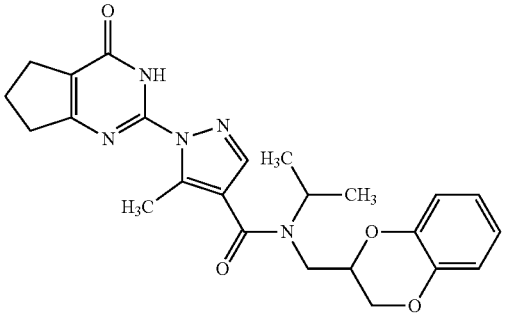 [SMILES: Cc1c(C(=O)N(CC2COc3ccccc3O2)C(C)C)cnn1-c1nc2c(c(=O)[nH]1)CCC2] | 3.45 | 450.2 | T3P | |
| 102 | Q-501 | EV-AQ7173-003 | 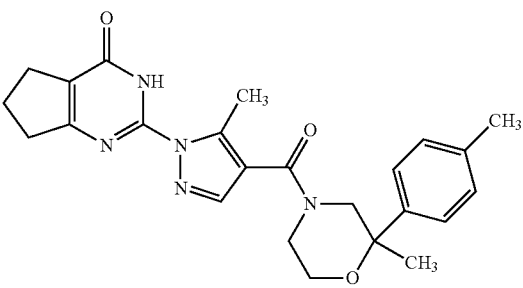 [SMILES: Cc1ccc(C2(C)CN(C(=O)c3cnn(-c4nc5c(c(=O)[nH]4)CCC5)c3C)CCO2)cc1] | 3.18 | 434.2 | T3P | |

TABLE 8-continued
| Example No | Ref. No. | LBN | Structure | LC-MS (RT) Method C | MS (M + H) Method C | Coupling Agent | Comments |
|---|---|---|---|---|---|---|---|
| 103 | Q-502 | EV-AQ7176-001 | 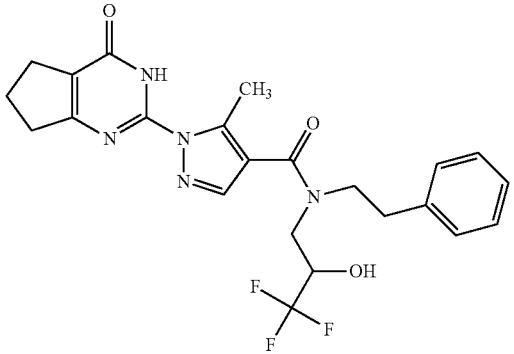 [SMILES: Cc1c(C(=O)N(CCc2ccccc2)CC(O)C(F)(F)F)cnn1-c1nc2c(c(=O)[nH]1)CCC2] | 3.14 | 476.1 | T3P | |
| 104 | Q-464 | EV-AQ8829-001 | 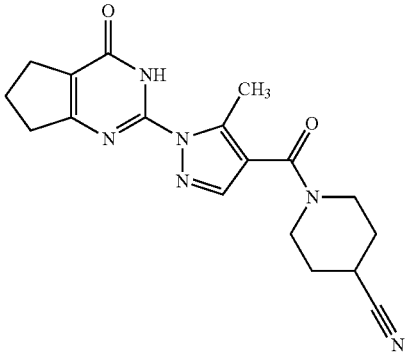 [SMILES: Cc1c(C(=O)N2CCC(C#N)CC2)cnn1-c1nc2c(c(=O)[nH]1)CCC2] | 2.02 | 353.1 | T3P | |
| 105 | Q-470 | EV-AQ8832-001 | 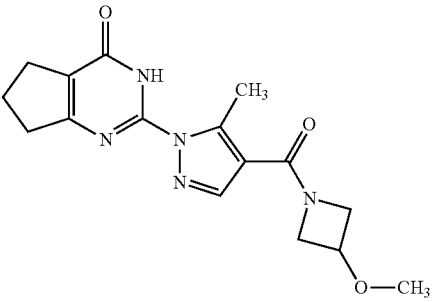 [SMILES: COC1CN(C(=O)c2cnn(-c3nc4c(c(=O)[nH]3)CCC4)c2C)C1] | 1.9 | 330.1 | T3P | |
| 106 | Q-477 | EV-AQ8837-001 | 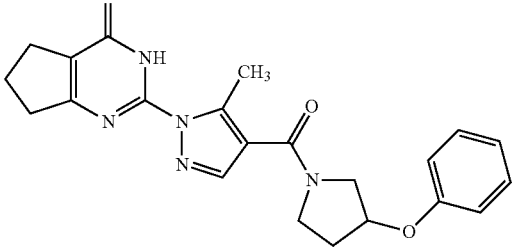 | 2.86 | 406.2 | T3P | |

TABLE 8-continued

| Example No | Ref. No. | LBN | Structure | LC-MS (RT) Method C | MS (M + H) Method C | Coupling Agent | Comments |
|---|---|---|---|---|---|---|---|
| 107 | Q-478 | EV-AQ8838-001 | 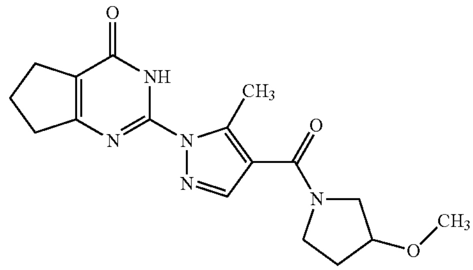 [SMILES: COC1CCN(C(=O)c2cnn(-c3nc4c(c(=O)[nH]3)CCC4)c2C)C1] | 1.92 | 344.2 | T3P | |
| 108 | Q-504 | EV-AQ8853-001 | 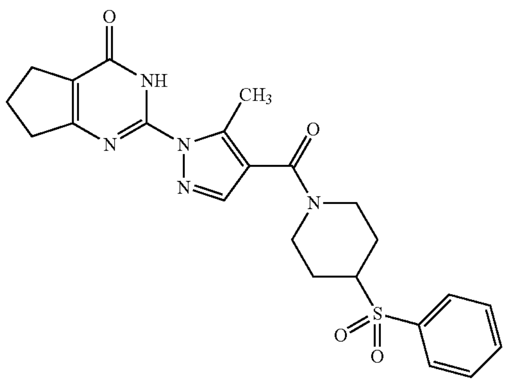 [SMILES: Cc1c(C(=O)N2CCC(S(=O)(=O)c3ccccc3)CC2)cnn1-c1nc2c(c(=O)[nH]1)CCC2] | 2.5 | 468.1 | T3P | |
| 109 | Q-424 | EV-AQ0237-002 | 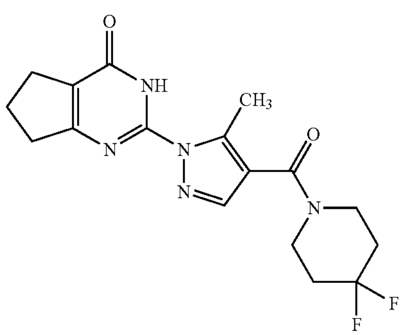 [SMILES: Cc1c(C(=O)N2CCC(F)(F)CC2)cnn1-c1nc2c(c(=O)[nH]1)CCC2] | 2.47 | 364.2 | COMU | |
| 110 | Q-428 | EV-AQ0241-002 | 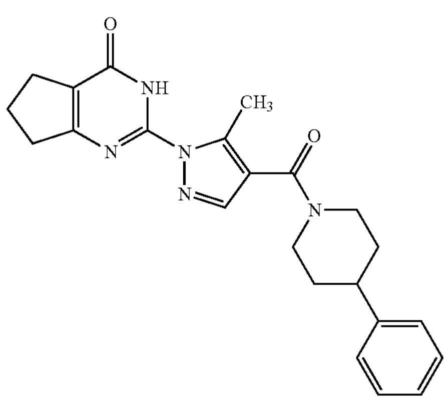 [SMILES: Cc1c(C(=O)N2CCC(c3ccccc3)CC2)cnn1-c1nc2c(c(=O)[nH]1)CCC2] | 3.22 | 404.2 | T3P | |

TABLE 8-continued

| Example No | Ref. No. | LBN | Structure | LC-MS (RT) Method C | MS (M + H) Method C | Coupling Agent | Comments |
|---|---|---|---|---|---|---|---|
| 111 | Q-473 | EV-AR5330-002 | 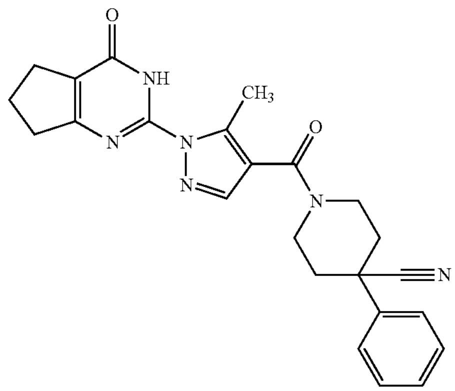 [SMILES: Cc1c(C(=O)N2CCC(C#N)(c3ccccc3)CC2)cnn1-c1nc2c(c(=O)[nH]1)CCC2] | 2.98 | 429.2 | T3P | |
| 112 | Q-479 | EV-AR5333-002 | 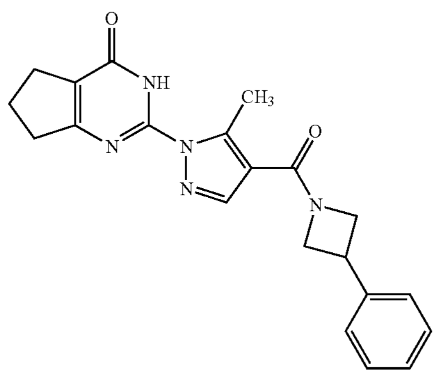 [SMILES: Cc1c(C(=O)N2CC(c3ccccc3)C2)cnn1-c1nc2c(c(=O)[nH]1)CCC2] | 2.83 | 376.2 | T3P | |
| 113 | Q-490 | EV-AR5335-002 | 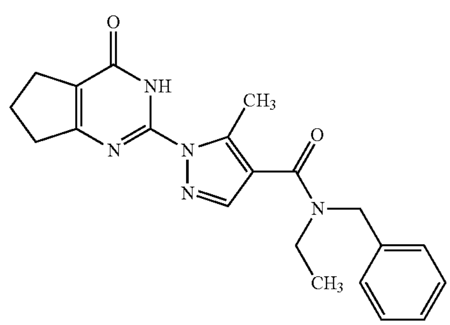 [SMILES: CCN(Cc1ccccc1)C(=O)c1cnn(-c2nc3c(c(=O)[nH]2)CCC3)c1C] | 3.00 | 378.2 | T3P | |
| 114 | Q-491 | EV-AR5343-002 | 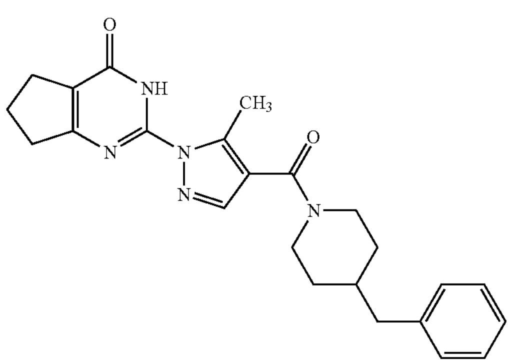 [SMILES: Cc1c(C(=O)N2CCC(Cc3ccccc3)CC2)cnn1-c1nc2c(c(=O)[nH]1)CCC2] | 3.46 | 418.2 | T3P | |

TABLE 8-continued

| Example No | Ref. No. | LBN | Structure | LC-MS (RT) Method C | MS (M + H) Method C | Coupling Agent | Comments |
|---|---|---|---|---|---|---|---|
| 115 | Q-492 | EV-AR5344-002 | 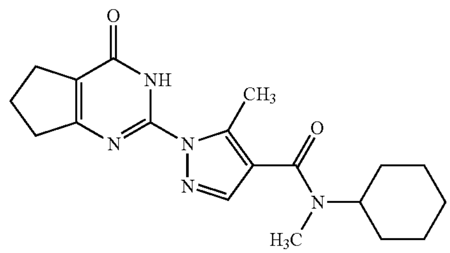 [SMILES: Cc1c(C(=O)N(C)C2CCCCC2)cnn1-c1nc2c(c(=O)[nH]1)CCC2] | 2.94 | 356.2 | T3P | |
| 116 | Q-489 | EV-AR5345-002 | 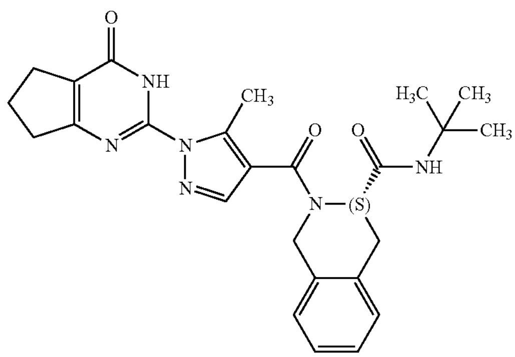 | 3.01 | 475.2 | T3P | |
| 117 | Q-487 | EV-AR5346-002 | 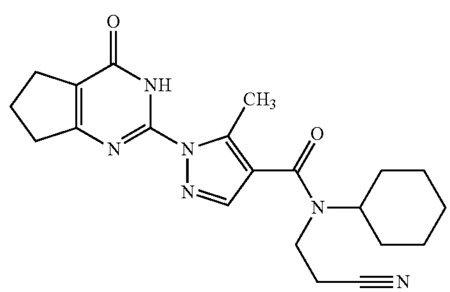 [SMILES: Cc1c(C(=O)N(CCC#N)C2CCCCC2)cnn1-c1nc2c(c(=O)[nH]1)CCC2] | 2.87 | 395.2 | T3P | |
| 118 | Q-493 | EV-AR5347-002 | 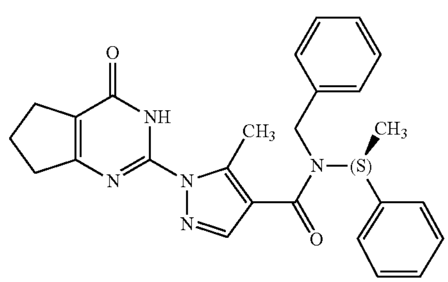 | 3.73 | 454.2 | T3P | |
| 119 | Q-485 | EV-AR5351-002 | 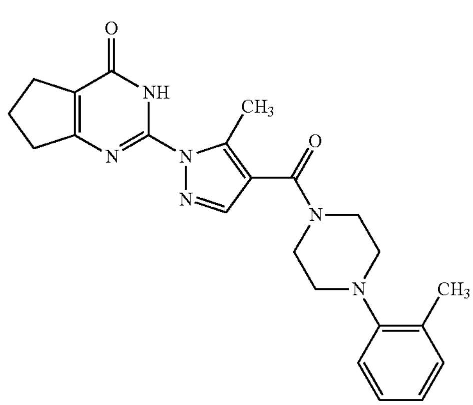 [SMILES: Cc1ccccc1N1CCN(C(=O)c2cnn(-c3nc4c(c(=O)[nH]3)CCC4)c2C)CC1] | 3.36 | 419.2 | T3P | |

TABLE 8-continued
| Example No | Ref. No. | LBN | Structure | LC-MS (RT) Method C | MS (M + H) Method C | Coupling Agent | Comments |
|---|---|---|---|---|---|---|---|
| 120 | Q-486 | EV-AR5352-002 | 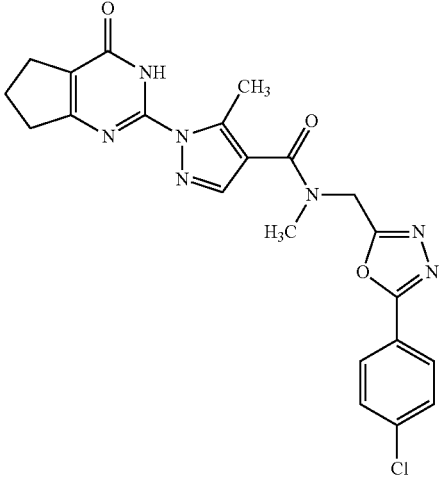 [SMILES: Cc1c(C(=O)N(C)Cc2nnc(-c3ccc(Cl)cc3)o2)cnn1-c1nc2c(c(=O)[nH]1)CCC2] | 2.9 | 466.1 | T3P | |
| 121 | Q-506 | EV-AR5357-002 | 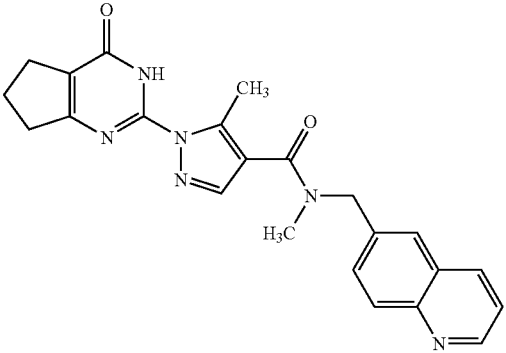 [SMILES: Cc1c(C(=O)N(C)Cc2ccc3ncccc3c2)cnn1-c1nc2c(c(=O)[nH]1)CCC2] | 1.68 | 415.1 | T3P | |
| 122 | Q-507 | EV-AR5363-002 | 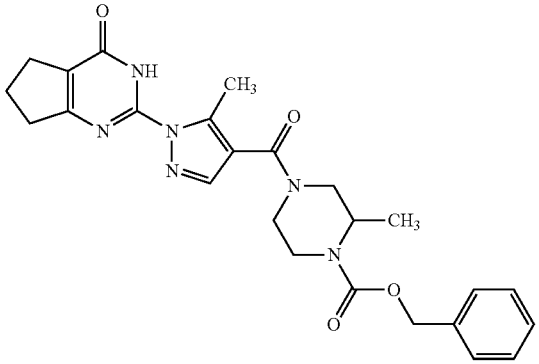 [SMILES: Cc1c(C(=O)N2CCN(C(=O)OCc3ccccc3)C(C)C2)cnn1-c1nc2c(c(=O)[nH]1)CCC2] | 2.97 | 477.2 | T3P | |
| 123 | Q-468 | EV-AQ3828-001 | 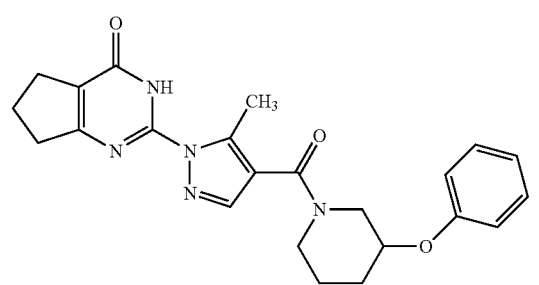 [SMILES: Cc1c(C(=O)N2CCCC(Oc3ccccc3)C2)cnn1-c1nc2c(c(=O)[nH]1)CCC2] | 3.07 | 420.2 | T3P | |

TABLE 8-continued

| Example No | Ref. No. | LBN | Structure | LC-MS (RT) Method C | MS (M + H) Method C | Coupling Agent | Comments |
|---|---|---|---|---|---|---|---|
| 124 | Q-476 | EV-AQ3831-001 | 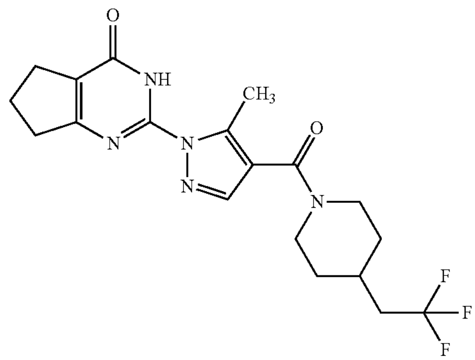 [SMILES: Cc1c(C(=O)N2CCC(CC(F)(F)F)CC2)cnn1-c1nc2c(c(=O)[nH]1)CCC2] | 2.93 | 410.2 | T3P | |
| 125 | Q-450 | EV-AN9592-005 | 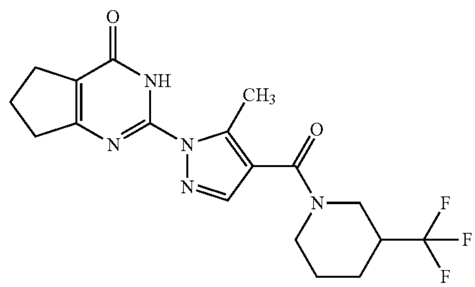 [SMILES: Cc1c(C(=O)N2CCCC(C(F)(F)F)C2)cnn1-c1nc2c(c(=O)[nH]1)CCC2] | 2.85 | 396.2 | T3P | |
| 126 | Q-423 | EV-AQ3801-003 | 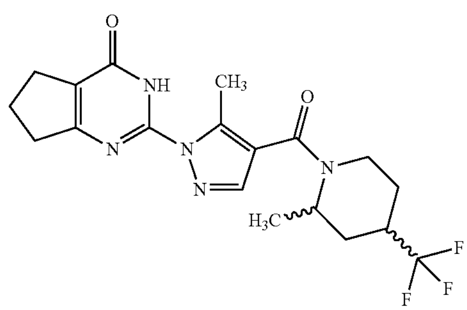 [SMILES: Cc1c(C(=O)N2CCC(C(F)(F)F)CC2C)cnn1-c1nc2c(c(=O)[nH]1)CCC2] | 2.99 min, 18%, 3.02 min, 74%. | 409.0 | COMU | |
| 127 | Q-434 | EV-AQ3808-002 | +/− | 3.02 | 409.0 | T3P | |
| 128 | Q-482 | EV-AQ3835-002 | 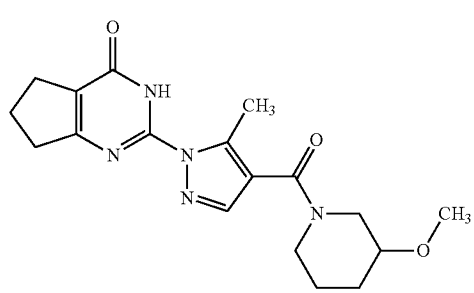 [SMILES: COC1CCCN(C(=O)c2cnn(-c3nc4c(c(=O)[nH]3)CCC4)c2C)C1] | 2.16 | 358.2 | T3P | |

TABLE 8-continued
| Example No | Ref. No. | LBN | Structure | LC-MS (RT) Method C | MS (M + H) Method C | Coupling Agent | Comments |
|---|---|---|---|---|---|---|---|
| 129 | Q-518 | EV-AQ7198-001 | 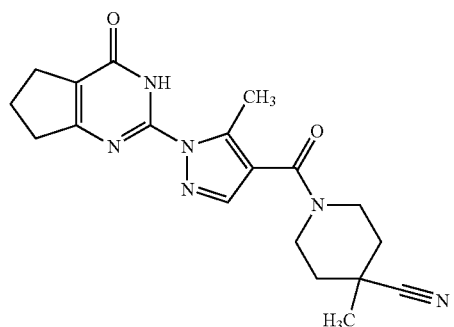 | 367.2 | 2.23 | T3P | |
| 130 | Q-519 | EV-AQ7198-002 | 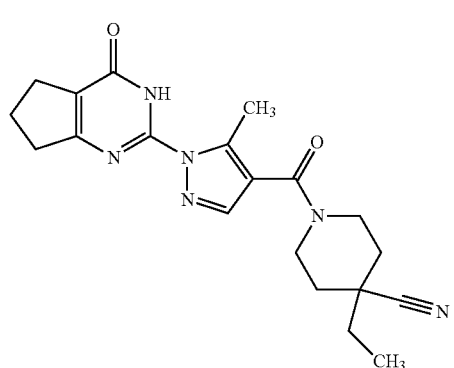 | 381.2 | 2.48 | T3P | |
| 131 | Q-520 | EV-AQ7199-001 | 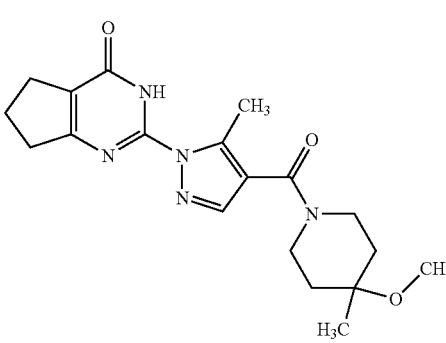 [SMILES: Cc1c(C(=O)N2CCC(C)(C#N)CC2)cnn1-c1nc2c(c(=O)[nH]1)CCC2] | 372.2 | 2.29 | T3P | |
| 132 | Q-451 | EV-AN9594-002 | 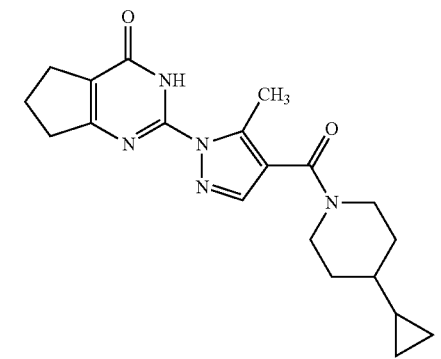 [SMILES: Cc1c(C(=O)N2CCC(C3CC3)CC2)cnn1-c1nc2c(c(=O)[nH]1)CCC2] | 368.2 | 3.10 | T3P | |

TABLE 8-continued

| Example No | Ref. No | LBN | Structure | LC-MS (RT) Method C | MS (M + H) Method C | Coupling Agent | Comments |
|---|---|---|---|---|---|---|---|
| 133 | Q-532 | EV-AS5411-002 | 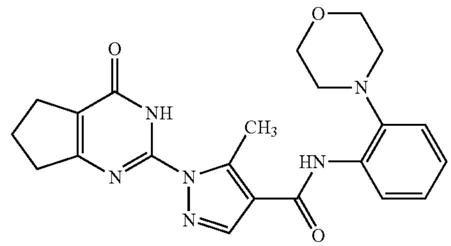 [SMILES: Cc1c(C(=O)Nc2ccccc2N2CCOCC2)cnn1-c1nc2c(c(=O)[nH]1)CCC2] | 421.1 | 3.05 | T3P | |
| 134 | Q-510 | EV-AR7006-003 | 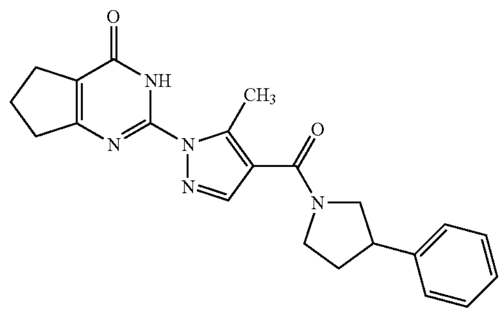 [SMILES: Cc1c(C(=O)N2CCC(c3ccccc3)C2)cnn1-c1nc2c(c(=O)[nH]1)CCC2] | 390.3 | 2.91 | T3P | |
| 135 | Q-469 | EV-AQ8831-001 | 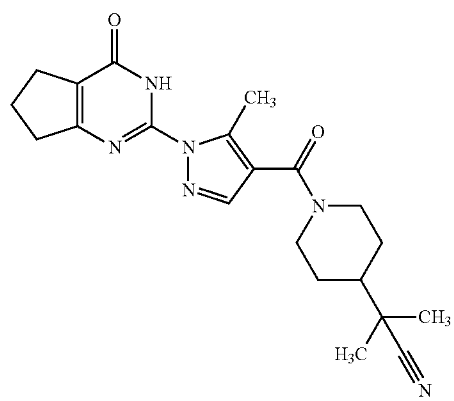 [SMILES: Cc1c(C(=O)N2CCC(C(C)(C)C#N)CC2)cnn1-c1nc2c(c(=O)[nH]1)CCC2] | 395.2 | 2.52 | T3P | Intermediate 13 |
| 136 | Q-514 | EV-AQ8865-001 | 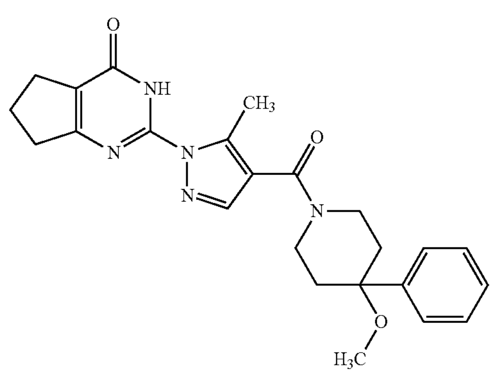 [SMILES: COC1(c2ccccc2)CCN(C(=O)c2cnn(-c3nc4c(c(=O)[nH]3)CCC4)c2C)CC1] | 434.2 | 3.07 | T3P | |

TABLE 8-continued
| Example No | Ref. No. | LBN | Structure | LC-MS (RT) Method C | MS (M + H) Method C | Coupling Agent | Comments |
|---|---|---|---|---|---|---|---|
| 137 | Q-521 | EV-AS3701-002 | 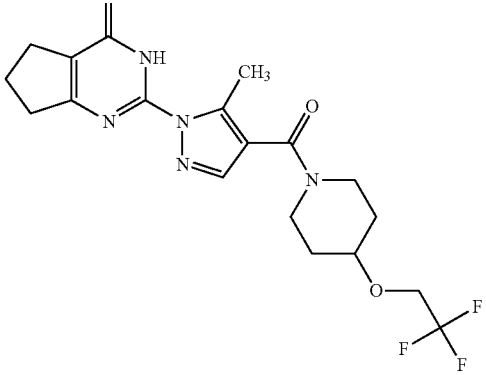 | 426.1 | 2.73 | T3P | Intermediate 24 |
| 138 | Q-509 | EV-AQ7187-002 | 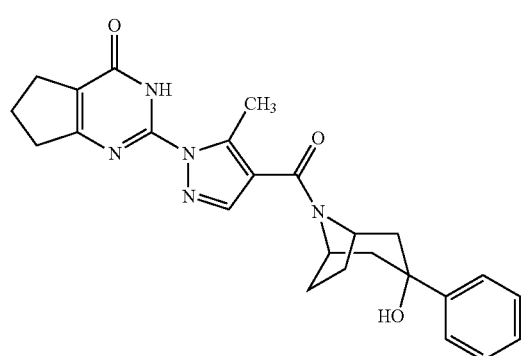 | 446.2 | 2.56 | T3P | Intermediate 21 |
| 139 | Q-513 | EV-AQ7190-002 | 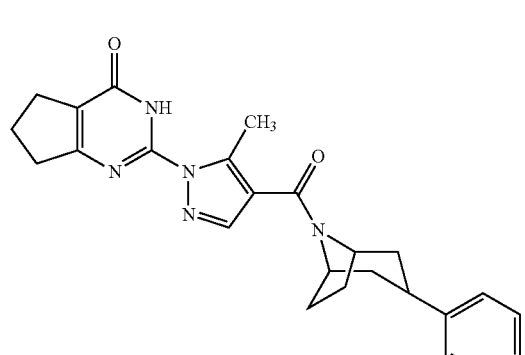 | 430.3 | 3.31 | T3P | Intermediate 22 |
| 140 | Q-483 | EV-AQ7163-003 | 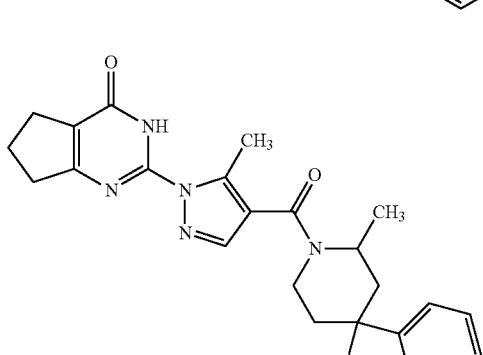 | 434.2 | 2.63 | SOCl$_2$ | Intermediate 20 |

TABLE 8-continued

| Example No | Ref. No. | LBN | Structure | LC-MS (RT) Method C | MS (M + H) Method C | Coupling Agent | Comments |
|---|---|---|---|---|---|---|---|
| 141 | Q-480 | EV-AR5334-002 | 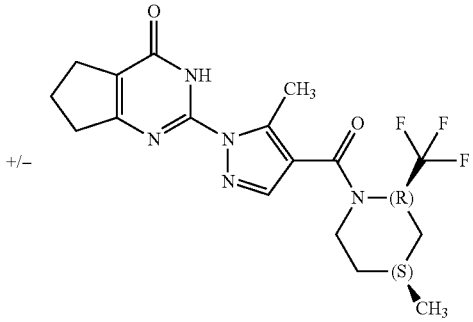 | 410.1 | 3.36 | SOCl$_2$ | Intermediate 25 |

Examples 142-145

Examples in Table 9 were prepared by chiral separation of racemic compounds in Table 8. The stereochemistry was arbitrarily assigned.

TABLE 9

| Example No | Ref. No. | LBN | Structure | LC-MS (RT) Method C | MS (M + H)$^+$ Method C | Column Retention* (min) | Separation method |
|---|---|---|---|---|---|---|---|
| 142 | Q-442 | EV-AQ3808-004 | 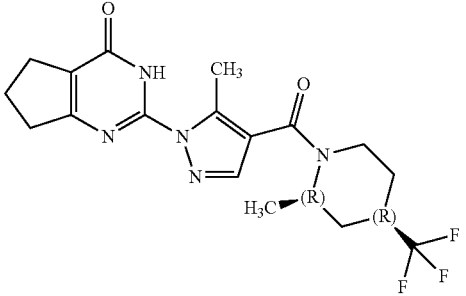 | 3.01 94% | 409.0 | 16.3 Method N | N |
| 143 | Q-459 | EV-AQ3808-005 | 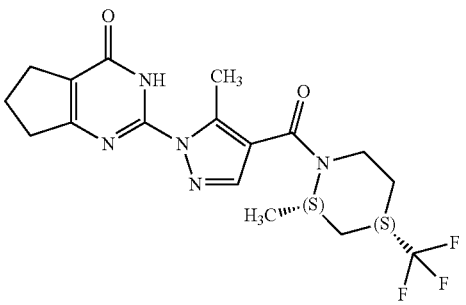 | 3.01 95% | 409.0 | 21.3 Method N | N |
| 144 | Q-474 | EV-AN9592-006 | 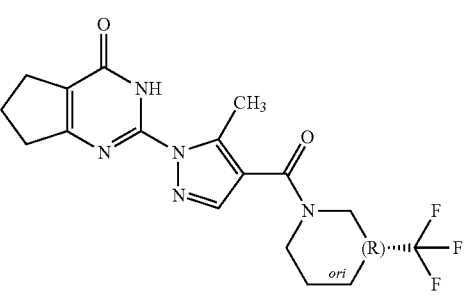 | 2.84 | 396.2 | 7.47 Method O | O |

TABLE 9-continued

| Example No | Ref. No. | LBN | Structure | LC-MS (RT) Method C | MS (M + H)+ Method C | Column Retention* (min) | Separation method |
|---|---|---|---|---|---|---|---|
| 145 | Q-475 | EV-AN9592-007 | 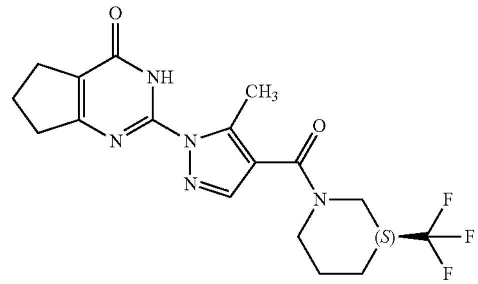 | 2.84 | 396.2 | 12.48 Method O | O |

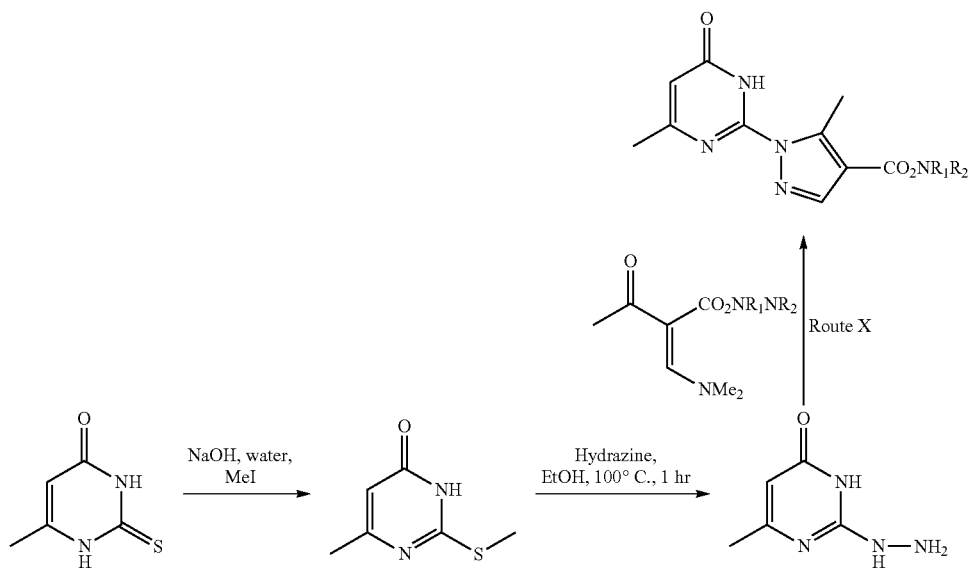

Preparative Example 6—Direct Cyclisation of Hydrazines

Intermediate 26: Preparation of methyl-2-[(dimethylamino)methylidene]-3-oxobutanoate

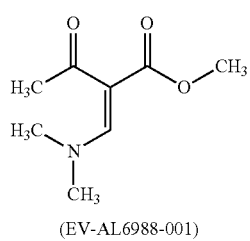

(EV-AL6988-001)

Methyl 3-oxobutanoate (40 g, 0.34 mol) and 1,1-dimethoxy-N,N-dimethylmethanamine (54.92 mL, 0.41 mol) were combined and stirred at 80° C. for 2 h. The reaction mixture was concentrated in vacuo and the resulting oil was dried for 24 h under vacuum to afford the title compound (56.53 g, 86.3%) as a dark red solid.

¹H NMR (500 MHz, DMSO-d6) δ 7.62 (s, 1H), 3.63 (s, 3H), 3.24-2.96 (m, 3H), 2.90-2.58 (m, 3H), 2.13 (s, 3H).

Intermediate 27: Preparation of 2-[(dimethylamino)methylidene]-1-(1,2,3,4-tetrahydroisoquinolin-2-yl)butane-1,3-dione (EV-AP2538-001)

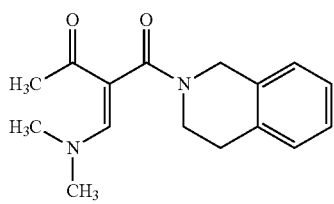

Step 1: Synthesis of 1-(1,2,3,4-tetrahydroisoquinolin-2-yl)butane-1,3-dione

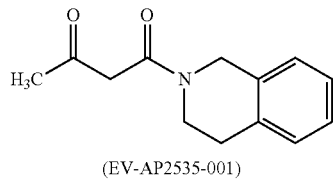

(EV-AP2535-001)

To a solution of 1,2,3,4-tetrahydroisoquinoline (10.0 mL, 78.83 mmol) in toluene (80 mL) was added methyl 3-oxobutanoate (12.76 mL, 118.25 mmol) and triethylamine (13.19 mL, 94.6 mmol) and stirred at 105° C. for 15.5 hours. Water (15 mL) was added to the cooled reaction mixture and the organic phase was extracted. The organics were dried over $Na_2SO_4$, filtered and concentrated in vacuo. The crude residue was purified by chromatography on $SiO_2$, eluting with 0-100% EtOAc in heptane to afford the title compound (12.8 g, 70.2%) as viscous yellow oil.

Method A: LC-MS: m/z=218.0 (M+H)+; RT=1.03 min.

Step 2: Synthesis of 2-[(dimethylamino)methylidene]-1-(1,2,3,4-tetrahydroisoquinolin-2-yl)butane-1,3-dione

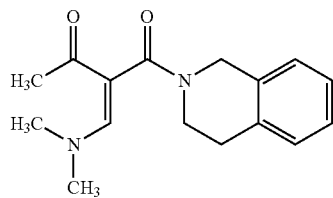 [SMILES: CC(=O)/C(=C\N(C)C)C(=O)N1CCc2ccccc2C1]

(EV-AP2538-001)

1-(1,2,3,4-tetrahydroisoquinolin-2-yl)butane-1,3-dione (EV-AP2535-001, 2 g, 9.21 mmol) and 1,1-dimethoxy-N,N-dimethylmethanamine (1.47 mL, 11.1 mmol) were combined and stirred at 80° C. for 15 h. The reaction mixture was concentrated in vacuo to afford the title compound (2.51 g, 96.1%) as a beige powder.

Method A: LC-MS: m/z=273.0 (M+H)+; RT=0.99 min.

Intermediate 28: Preparation of (2E)-2-[(dimethylamino)methylidene]-1-[4-(trifluoromethyl)piperidin-1-yl]butane-1,3-dione (EV-AP2553-001)

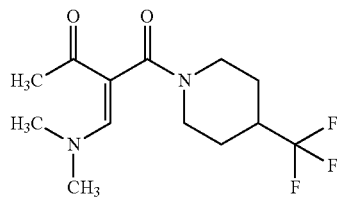

The title compound was prepared in an analogous manner to intermediate EV-AP2535-001 starting with 4-trifluoromethylpiperidine hydrochloride (10.5 g, 55.4 mm) to afford the title compound (13.4 g, 87%) as a dark orange powder.

Method A: LC-MS: m/z=293.0 (M+H); RT=0.97 min.

Intermediate 29: Preparation of 1-(1H-pyrazole-4-carbonyl)-4-(trifluoromethyl)piperidine (EV-AQ8818-001)

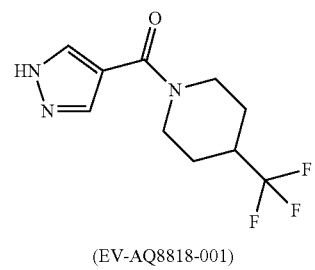 [SMILES: O=C(c1cn[nH]c1)N1CCC(C(F)(F)F)CC1]

(EV-AQ8818-001)

To a stirred solution of 1H-pyrazole-4-carboxylic acid (1.0 g, 8.92 mmol) and DIPEA (5.4 mL, 31.2 mmol) in THF (15 mL) was added T3P (50% in EtOAc, 10.5 mL, 17.8 mmol) and stirred at r.t. for 5 mins. 4-(trifluoromethyl)piperidine hydrochloride (2.03 g, 10.7 mmol) was then added and the solution was stirred at r.t. overnight. The reaction mixture was cooled, partitioned between DCM (30 mL) and saturated $NaHCO_3$ solution (40 mL) and the aqueous fraction extracted with DCM (2×30 mL). The combined organic fractions were dried over $MgSO_4$ and the solvent removed in vacuo. The resulting oil was purified via chromatography on $SiO_2$ MeOH/DCM (gradient 100:0-90:10) to afford the title compound (673 mg, 61%) as a yellow powder.

Method A: LC-MS m/z=248.0 [M+H]+; RT=0.98 min.

Intermediate 30: Preparation of Synthesis of 6-chloro-2-hydrazinyl-3H,4H-thieno[3,2-d]pyrimidin-4-one Step 1: Synthesis of methyl 1H,2H,3H,4H-thieno[3,2-d]pyrimidine-2,4-dione

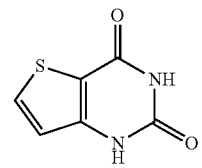

(EV-AP2346-001)

A mixture of methyl 3-aminothiophene-2-carboxylate (3.5 g, 22.3 mmol) and urea (8.75 mL, 144.7 mmol) was heated at 180° C. for 5 h. The mixture was cooled to ~90° C. and water (40 mL) was added. The mixture was stirred at r.t. overnight and the resulting precipitate isolated via filtration to afford the title compound (3.66 mg, 98%) as an off-white powder.

Method A: LC-MS m/z=214.0 [M+H]+; RT=0.79 min.

Step 2: Synthesis of 6-nitro-1H,2H,3H,4H-thieno[3,2-d]pyrimidine-2,4-dione

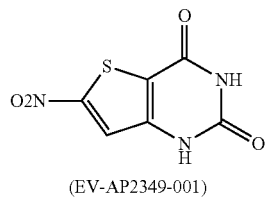

(EV-AP2349-001)

1H,2H,3H,4H-thieno[3,2-d]pyrimidine-2,4-dione (EV-AP2346-001, 3.65 g, 21.7 mmol) was added portion wise to a stirred solution of fuming $HNO_3$ (12 mL) and $H_2SO_4$ (95%, 12 mL) at 0° C. The reaction was warmed to r.t. and stirred for 1 h. The precipitated solid was collected via filtration to afford the title compound (1.28 g, 28%) as an orange powder.
Method A: LC-MS m/z=214.0 [M+H]$^+$; RT=0.79 min.

Step 3: Synthesis of 2,4,6-trichlorothieno[3,2-d]pyrimidine

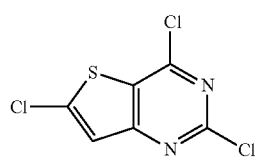

(EV-AP2352-001)

A stirred suspension of 6-nitro-1H,2H,3H,4H-thieno[3,2-d]pyrimidine-2,4-dione (EV-AP2349-001, 1.2 g, 21.7 mmol) in phenylphosphonic dichloride (5 mL, 35.3 mmol) was stirred at 180° C. for 4 h. The mixture was cooled to ~100° C. and transferred slowly onto vigorously stirred ice/water (40 mL). The resulting suspension was stirred at r.t. for 30 mins and was then extracted with DCM (2×40 mL). The combined organic fractions were dried over $Na_2SO_4$, concentrated in vacuo, and purified via chromatography on $SiO_2$ (0:100-10:90 MeOH-DCM) followed by further chromatography on $SiO_2$ (0:100-50:50 EtOAc-heptane) to yield the title compound (752 mg, 55%) as a colourless powder.
Method A: LC-MS m/z=240.7 [M+H]$^+$; RT=1.43 min.

Step 4: Synthesis of 2,6-dichloro-3H,4H-thieno[3,2-d]pyrimidin-4-one

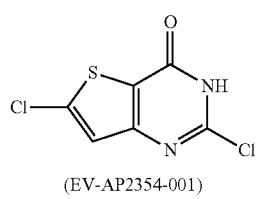 [SMILES: O=c1[nH]c(Cl)nc2cc(Cl)sc12]

(EV-AP2354-001)

To a stirred solution of 2,4,6-trichlorothieno[3,2-d]pyrimidine (EV-AP2352-001, 749 mg, 3.13 mmol) in THF (12 mL) was added 1M aq NaOH solution (16 mL, 16 mmol) and stirred at r.t. overnight. The solution was acidified to pH ~5 with 5M aq HCl solution and the resulting precipitate isolated via filtration to afford the title compound (400 mg, 58%) as a colourless powder.
Method A: LC-MS m/z=220.8 [M+H]$^+$; RT=1.02 min.

Step 5: Synthesis of 6-chloro-2-hydrazinyl-3H,4H-thieno[3,2-d]pyrimidin-4-one

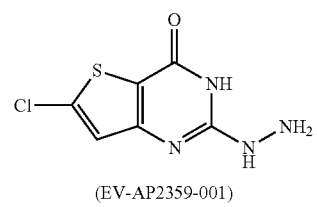 [SMILES: NNc1nc2cc(Cl)sc2c(=O)[nH]1]

(EV-AP2359-001)

To a stirred solution of 2,6-dichloro-3H,4H-thieno[3,2-d]pyrimidin-4-one (EV-AP2354-001, 361 mg, 1.63 mmol) in ethanol (5 mL) was added hydrazine hydrate (199 µL, 4.08 mmol) and stirred at 80° C. overnight. The reaction mixture was cooled, the precipitate was collected via filtration and the solid washed with water to afford the title compound (247 mg, 70%) as a yellow powder.
Method A: LC-MS m/z=216.9 [M+H]$^+$; RT=0.74 min.

Intermediate 31: Preparation of 5-chloro-2-hydrazinyl-3,4-dihydropyrimidin-4-one

Step 1: Synthesis of 5-chloro-2-hydrazinyl-3,4-dihydropyrimidin-4-one

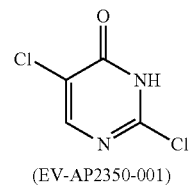

(EV-AP2350-001)

To a solution of 2,4,5-trichloropyrimidine (5.00 g, 27.3 mmol) in THF (12 mL) was added 1M aq NaOH (35.4 mL, 35.4 mmol) and stirred at r.t. for 3 days. The solution was acidified to pH ~5 with 5M aq HCl and extracted with DCM (2×40 mL). The combined organic fractions were dried over $Na_2SO_4$, concentrated in vacuo and triturated with 1:4 DCM-heptane to afford the title compound (2.33 g, 52%) as an orange powder.
Method A: LC-MS m/z=164.8 [M+H]$^+$; RT=0.38 min.

Step 2: Synthesis of 5-chloro-2-hydrazinyl-3,4-dihydropyrimidin-4-one

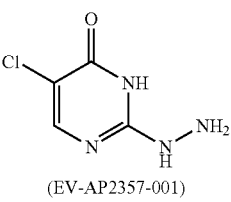

(EV-AP2357-001)

To a solution of 2,5-dichloro-3,4-dihydropyrimidin-4-one (EV-AP2350-001, 200 mg, 1.21 mmol) in ethanol (3 mL) was added hydrazine hydrate (148 µL, 3.03 mmol) and stirred at 50° C. overnight. The reaction mixture was cooled to r.t. and the resulting precipitate isolated via filtration to afford the title compound (88 mg, 45%) as an off-white powder.

Method A: LC-MS m/z=160.9 [M+H]$^+$; RT=0.17 min.

Intermediate 32: Preparation of 5-tert-butyl-2-hydrazinyl-3,4-dihydropyrimidin-4-one Step 1: Synthesis of ethyl 2-formyl-3,3-dimethylbutanoate

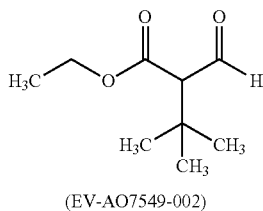

(EV-AO7549-002)

To a solution of ethyl 3,3-dimethylbutanoate (5.814 ml, 34.67 mmol) and ethyl formate (8.366 ml, 104.01 mmol) in DCM (60 ml) at 0° C. under nitrogen was added TiCl$_4$ (52.01 ml, 52.01 mmol) and Et$_3$N (11.61 mL, 83.21 mmol) and stirred at 0° C.—r.t. overnight. To the reaction mixture was added water, which was then extracted with DCM (2×50 ml). The combined organic extracts were washed with brine, dried over Na$_2$SO$_4$, concentrated in vacuo and purified via column chromatography (100:0-0:100 Heptane-EtOAc) to afford the title compound (2.72 mg, 42%) as a free flowing orange oil.

$^1$H NMR (500 MHz, DMSO-d6) δ 9.74 (d, J=3.6 Hz, 1H), 4.21-4.10 (m, 2H), 3.07 (d, J=3.6 Hz, 1H), 1.21 (t, J=7.1 Hz, 3H), 1.07 (s, 9H).

Step 2: Synthesis of 5-tert-butyl-2-(methylsulfanyl)-3,4,5,6-tetrahydropyrimidin-4-one

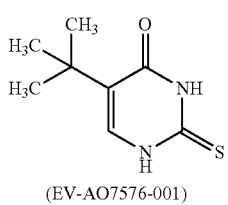

(EV-AO7576-001)

To a solution of ethyl 2-formyl-3,3-dimethylbutanoate (EV-AO7549-002, 92%, 100 mg, 0.534 mmol) in water (2 ml) was added 1M aq NaOH solution (534 µl, 0.534 mmol) and thiourea (122 mg, 1.603 mmol) and stirred at 100° C. for 1 h. The reaction mixture was allowed to cool to r.t. and acidified to pH 2-3 using 1M aq HCl solution to afford a white precipitate. The reaction mixture was filtered, washing with MeCN, to afford the title compound (72 mg, 73%) as a pearly white solid.

Method A: LC-MS m/z=184.9 [M+H]$^+$; RT=0.93 min.

Step 3: Synthesis of 3,6-dimethyl-2-(methylsulfanyl)-3,4-dihydropyrimidin-4-one

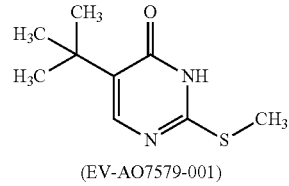

(EV-AO7579-001)

To water (20 ml) was added NaOH (97%, 286 mg, 6.925 mmol). After the sodium hydroxide had dissolved 5-tert-butyl-2-sulfanylidene-1,2,3,4-tetrahydropyrimidin-4-one (EV-A07576-001, 1.16 g, 6.295 mmol) was added and the mixture stirred until dissolved. Iodomethane (435 µl, 6.925 mmol) was added dropwise and the mixture stirred at r.t. overnight. The solid was filtered and washed with ice cold water (2×10 ml) to afford the title compound (686 mg, 54%) as an off white solid.

Method A: LC-MS m/z=198.9 [M+H]$^+$; RT=1.09 min.

Step 4: Synthesis of 5-tert-butyl-2-hydrazinyl-3,4-dihydropyrimidin-4-one

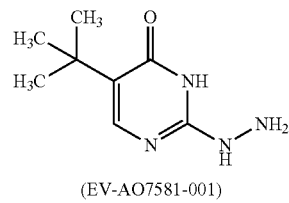

(EV-AO7581-001)

To a solution of 5-tert-butyl-2-(methylsulfanyl)-3,4-dihydropyrimidin-4-one (EV-A07579-001, 600 mg, 3.026 mmol) in pyridine (5 ml) was added hydrazine hydrate (1.47 ml, 30.26 mmol) and stirred at 100° C. overnight. The reaction mixture was concentrated in vacuo and triturated using Et$_2$O to afford the title compound (331 mg, 60%) as an off white powder.

Method A: LC-MS m/z=183.0 [M+H]$^+$; RT=0.40 min.

Intermediate 33: Preparation of 2-hydrazinyl-6-(trifluoromethyl)-3,4-dihydropyrimidin-4-one (EV-AO7596-001)

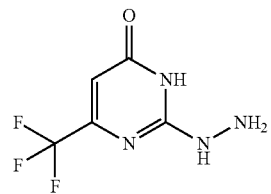 [SMILES: NNc1nc(C(F)(F)F)cc(=O)[nH]1]

2-hydrazinyl-6-(trifluoromethyl)-3,4-dihydropyrimidin-4-one was prepared by an analogous route to Intermediate 32 substituting with 2-sulfanylidene-6-(trifluoromethyl)-1,2,3,4-tetrahydropyrimidin-4-one, which afforded the title compound (212 mg, 31%) as an off white powder.

Method A: LC-MS m/z=194.9 [M+H]$^+$; RT=0.52 min.

Intermediate 34: Preparation of 6-hydrazinyl-1H,4H,5H-pyrazolo[3,4-d]pyrimidin-4-one (EV-AQ7120-001)

Step 1: Synthesis of 4-(benzyloxy)-6-chloro-1H-pyrazolo[3,4-d]pyrimidine

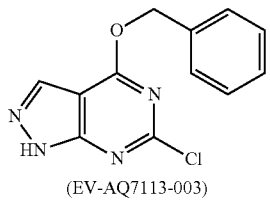 [SMILES: Clc1nc(OCc2ccccc2)c2cn[nH]c2n1]

(EV-AQ7113-003)

To a solution of benzyl alcohol (0.19 mL, 1.85 mmol) in dioxane (3 mL) at 0° C. was added potassium t-butoxide (436.38 mg, 3.89 mmol) followed by 4,6-dichloro-1H-pyrazolo[3,4-d]pyrimidine (350 mg, 1.85 mmol). The reaction mixture was warmed to r.t. over 15 mins and then stirred for 21 h. The reaction mixture was quenched by the addition of sat aq NH$_4$Cl solution (2 mL) and extracted with EtOAc (2×5 mL). The combined organic fractions were dried over Na$_2$SO$_4$, filtered and concentrated in vacuo. The crude material was purified by chromatography on SiO$_2$, eluting with 0-50% EtOAc in heptane to afford the title compound (325 mg, 41.1%) as a white solid.

Method A: LC-MS: m/z=+261.0, 262.9 (M+H)+; RT=1.28 min.

Step 2: Synthesis of 6-chloro-1H,4H,5H-pyrazolo[3,4-d]pyrimidin-4-one

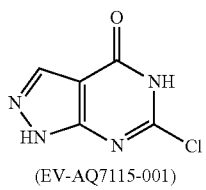 [SMILES: O=c1[nH]c(Cl)nc2[nH]ncc12]

(EV-AQ7115-001)

To a solution of 4-(benzyloxy)-6-chloro-1H-pyrazolo[3,4-d]pyrimidine (EV-AQ7113-003, 61%, 325 mg, 0.76 mmol) in THF (2.5 mL) was added 4M HCl in dioxane (1.9 mL) and stirred at r.t. for 1.5 h. Conc. HCl (2.5 mL) was then added and the reaction stirred for a further 2 h. The resulting precipitate was collected and dried under vacuum filtration to afford the title compound (128 mg, 98.7%) as a white powder.

Method A: LC-MS: m/z=+170.9, 172.8 (M+H)+; RT=0.20

Step 3: Synthesis of 6-hydrazinyl-1H,4H,5H-pyrazolo[3,4-d]pyrimidin-4-one

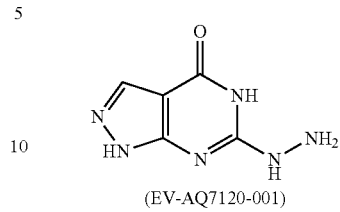

(EV-AQ7120-001)

To a solution of 6-chloro-1H,4H,5H-pyrazolo[3,4-d]pyrimidin-4-one (EV-AQ7115-001, 128 mg, 0.75 mmol) in ethanol (2 mL) was added hydrazine hydrate (0.18 mL, 3.75 mmol). The reaction vessel was sealed and the reaction mixture irradiated in the microwave at 100° C. for 30 mins. The reaction mixture was cooled and the resulting precipitate was collected and dried under vacuum to afford the title compound (90 mg, 72.2%) as a white powder.

Method A: LC-MS: m/z=+166.9 (M+H)+; RT=0.17 min.

Intermediate 35: Preparation of 2-hydrazinyl-5,6-dimethyl-3,4-dihydropyrimidin-4-one (EV-AP2534-001)

Step 1: Synthesis of 5,6-dimethyl-2-(methylsulfanyl)-3,4-dihydropyrimidin-4-one

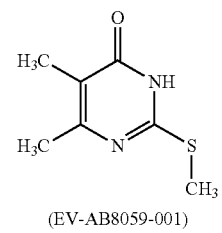

(EV-AB8059-001)

To a suspension of 5,6-dimethyl-2-sulfanylidene-1,2,3,4-tetrahydropyrimidin-4-one (2 g, 12.8 mmol) in water (15 mL) was added sodium hydroxide (527.47 mg, 13.19 mmol) followed by iodomethane (1 mL, 16 mmol) and stirred at r.t. overnight. The reaction mixture was cooled to 5° C. and the resulting precipitate was collected by vacuum filtration. The solid was washed with water and dried under vacuum at 40° C. to afford the title compound (1.67 g, 76%) as a white powder.

Method A: LC-MS m/z=170.9 [M+H]$^+$; RT=0.83 min.

Step 2: Synthesis of 2-hydrazinyl-5,6-dimethyl-3,4-dihydropyrimidin-4-one

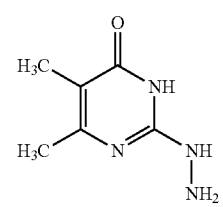

(EV-AP2534-001)

To 5,6-dimethyl-2-(methylsulfanyl)-3,4-dihydropyrimidin-4-one (EV-AB8059-001, 1 g, 5.87 mmol) was added hydrazine hydrate (1.43 mL, 29.37 mmol) and stirred at 100° C. for 1.5 h. The reaction was then allowed to stand at r.t. over the weekend. A further portion of hydrazine hydrate (1.43 mL, 29.37 mmol) was added and stirred at 100° C. for 1 h. The reaction mixture was cooled to r.t. and ice cold methanol (3 mL) was added. The resultant precipitate was collected by vacuum filtration and washed with more ice cold methanol (5 mL). The solid was dried further under vacuum to afford the title compound (618 mg, 68.2%) as a white powder.

Method A: LC-MS m/z=154.9 [M+H]$^+$; RT=0.17 min.

Intermediate 36: Preparation of 5-chloro-6H,7H-[1,3]thiazolo[4,5-d]pyrimidin-7-one (EV-AQ0249-001)

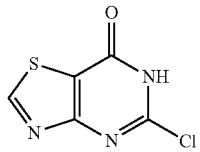 [SMILES: O=c1[nH]c(Cl)nc2ncsc12]

EV-AQ0249-001 was synthesized in an analogous method to the synthesis of EV-AQ0263-001, affording the title compound (190 mg, 56%) as a yellow powder.

Method A: LC-MS m/z=187.85 [M+H]$^+$; RT=0.37 min.

Intermediate 37a: Synthesis of 2-hydrazinyl-3H,4H-pyrrolo[2,1-f][1,2,4]triazin-4-one Step 1: Synthesis of 2-chloro-3H,4H-pyrrolo[2,1-f][1,2,4]triazin-4-one

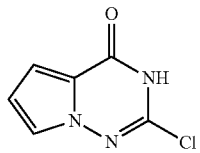

EV-AQ3861

To a solution of 2,4-dichloropyrrolo[2,1-f][1,2,4]triazine (2 g, 10.6 mmol) in THF (100 ml) was added sodium hydroxide (5M, 10.64 ml, 53.2 mmol) and the reaction mixture was stirred at room temperature for 16 hours and at 50° C. for 4 hours.

The yellow solution was cooled to room temperature and concentrated in vacuo and acidified (pH 3-4, 2M HCl). The resultant precipitate was collected by filtration, washed with water followed by ether, to afford the title compound (1.79 g, 99%) as a pale yellow powder after drying under vacuum.

Method B: LC-MS m/z=160.0 [M+H]$^+$; RT=0.79 min.

Step 2: Synthesis of 2-hydrazinyl-3H,4H-pyrrolo[2,1-f][1,2,4]triazin-4-one

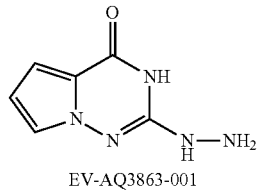 [SMILES: NNc1nn2cccc2c(=O)[nH]1]

EV-AQ3863-001

Hydrazine hydrate (43.04 µl, 0.88 mmol) was added to a stirred solution of 2-chloro-3H,4H-pyrrolo[2,1-f][1,2,4]triazin-4-one (100 mg, 0.59 mmol) in EtOH (2 ml) and the reaction was stirred at room temperature for 18 hours before the suspension was heated at 80° C. for 40 hours.

More hydrazine hydrate (43.04 µl, 0.88 mmol) was added and the reaction mixture was heated at 80° C. for 16 hours The yellow suspension was cooled to 4° C., the solid was collected by filtration, washed with cold water (~0.5 ml) and dried under vacuum to provide the title compound (64 mg, 65%) as a yellow solid.

Method B: LC-MS m/z=166.9 [M+H]$^+$; RT=0.20 min.

Preparation of 2-[5-methyl-4-(1,2,3,4-tetrahydroisoquinoline-2-carbonyl)-1H-pyrazol-1-yl]-3H,4H-thieno[2,3-d]pyrimidin-4-one

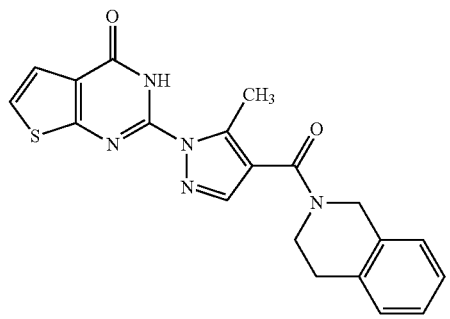

Q-382

(EV-AP2544-001)

To a solution of 2-hydrazinyl-3H,4H-thieno[2,3-d]pyrimidin-4-one (formed in an analogous manner to Intermediate 4) (EV-AP2372-001, 120 mg, 0.66 mmol) in ethanol (3 mL) was added 2-[(dimethylamino)methylidene]-1-(1,2,3,4-tetrahydroisoquinolin-2-yl)butane-1,3-dione (Intermediate 27, 90%, 199.3 mg, 0.66 mmol) followed by acetic acid (0.13 mL, 2.31 mmol). The vessel was sealed and the reaction mixture stirred at r.t. for 5 mins and then heated at 80° C. for 5 h. The reaction mixture was concentrated in vacuo. The crude residue was purified by chromatography on SiO$_2$ eluting with 0-10% methanol in DCM. The material was purified further by PREP-HPLC (Method G) to afford the title compound (20.9 mg, 8.1%) as an off white powder.

Method C: LC-MS m/z=392.1 [M+H]+; RT=3.12 min.

Examples 146-156 and 157a

The examples in Table 10 were synthesized by cyclizing the corresponding hydrazine intermediate with either intermediate 27 or intermediate 28 using the procedure described in example 1.

TABLE 10

| Example No | Ref. No. | LBN | Structure | LC-MS (RT) Method C | MS (M + H)+ Method C | Comments |
|---|---|---|---|---|---|---|
| 146 | Q-438 | EV-AQ7122-002 | 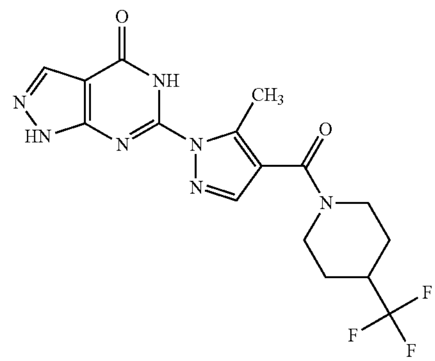 [SMILES: Cc1c(C(=O)N2CCC(C(F)(F)F)CC2)cnn1-c1nc2[nH]ncc2c(=O)[nH]1] | 2.19 | 396.2 | Intermediate 34 |
| 147 | Q-407 | EV-AQ0209-002 | 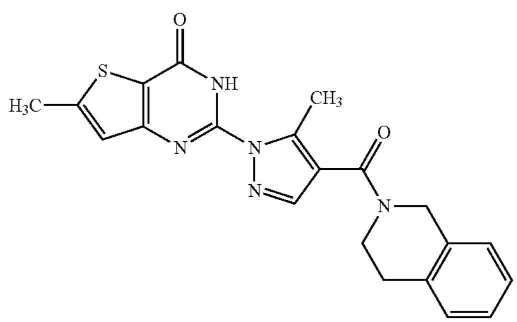 [SMILES: Cc1cc2nc(-n3ncc(C(=O)N4CCc5ccccc5C4)c3C)[nH]c(=O)c2s1] | 3.25 | 406.2 | |
| 148 | Q-409 | EV-AQ0218-002 | 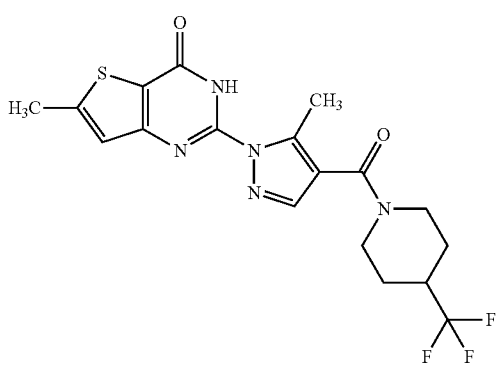 [SMILES: Cc1cc2nc(-n3ncc(C(=O)N4CCC(C(F)(F)F)CC4)c3C)[nH]c(=O)c2s1] | 3.14 | 426.2 | |
| 149 | Q-448 | EV-AQ0295-002 | 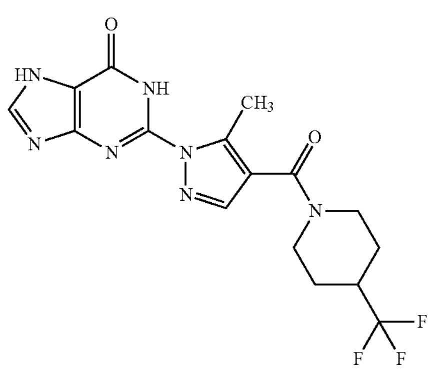 [SMILES: Cc1c(C(=O)N2CCC(C(F)(F)F)CC2)cnn1-c1nc2nc[nH]c2c(=O)[nH]1] | 2.02 | 396.2 | |

TABLE 10-continued

| Example No | Ref. No. | LBN | Structure | LC-MS (RT) Method C | MS (M + H)+ Method C | Comments |
|---|---|---|---|---|---|---|
| 150 | Q-384 | EV-AO7582-002 | 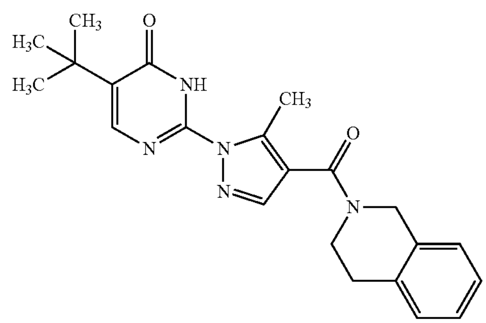 [SMILES: Cc1c(C(=O)N2CCc3ccccc3C2)cnn1-c1ncc(C(C)(C)C)c(=O)[nH]1] | 3.55 | 391.5 | Intermediate 32 |
| 151 | Q-393 | EV-AO7599-002 | 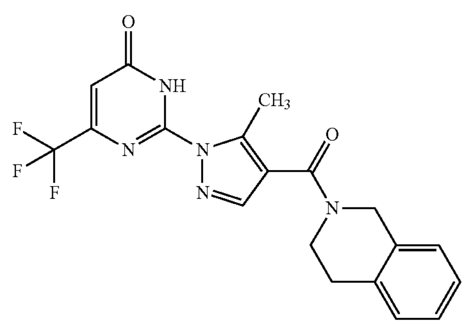 [SMILES: Cc1c(C(=O)N2CCc3ccccc3C2)cnn1-c1nc(C(F)(F)F)cc(=O)[nH]1] | 3.29 | 404.2 | Intermediate 33 |
| 152 | Q-533 | EV-AQ3864-005 | 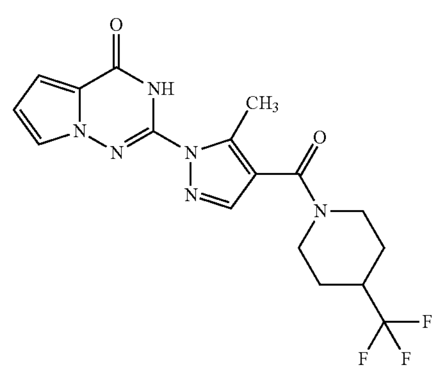 [SMILES: Cc1c(C(=O)N2CCC(C(F)(F)F)CC2)cnn1-c1nn2cccc2c(=O)[nH]1] | 2.80 | 394.0 | Intermediate 37a |
| 153 | Q-433 | EV-AQ0254-002 | 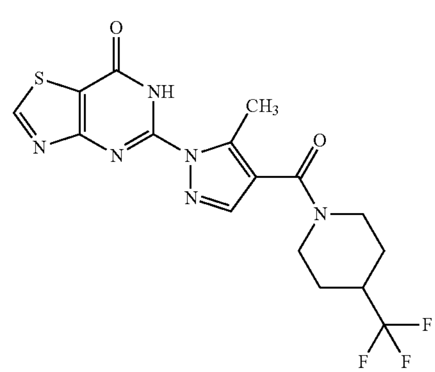 [SMILES: Cc1c(C(=O)N2CCC(C(F)(F)F)CC2)cnn1-c1nc2ncsc2c(=O)[nH]1] | 2.53 | 412.1 | Intermediate 36 |

TABLE 10-continued

| Example No | Ref. No. | LBN | Structure | LC-MS (RT) Method C | MS (M + H)+ Method C | Comments |
|---|---|---|---|---|---|---|
| 154 | Q-394 | EV-AP2362-001 | 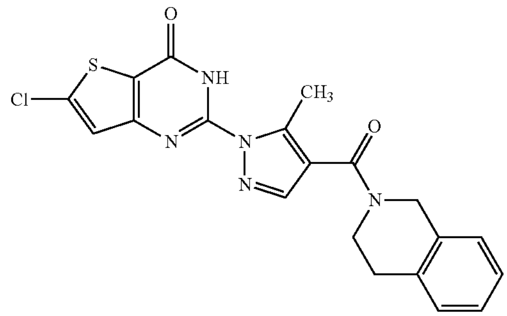 [SMILES: Cc1c(C(=O)N2CCc3ccccc3C2)cnn1-c1nc2cc(Cl)sc2c(=O)[nH]1] | 3.56 | 426.1 | Intermediate 30 |
| 155 | Q-396 | EV-AP2556-002 | 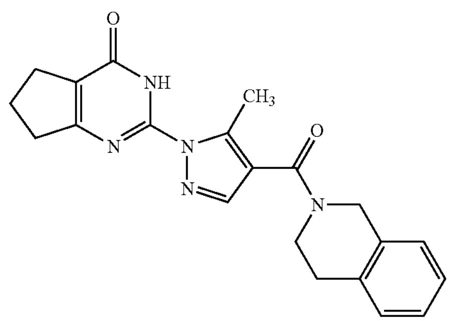 [SMILES: Cc1c(C(=O)N2CCc3ccccc3C2)cnn1-c1nc2c(c(=O)[nH]1)CCC2] | 2.89 | 376.2 | Intermediate 17 |
| 156 | Q-387 | EV-AP2358-001 | 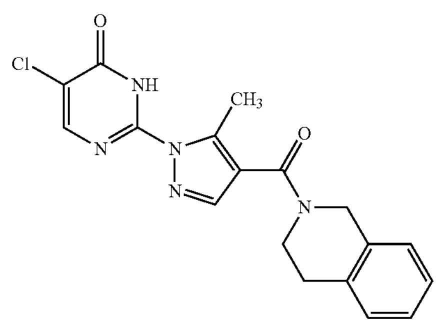 [SMILES: Cc1c(C(=O)N2CCc3ccccc3C2)cnn1-c1ncc(Cl)c(=O)[nH]1] | 2.75 | 370.1 | Intermediate 31 |
| 157a | Q-381 | EV-AP2539-002 | 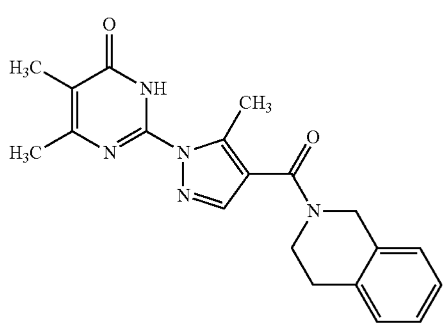 [SMILES: Cc1nc(-n2ncc(C(=O)N3CCc4ccccc4C3)c2C)[nH]c(=O)c1C] | 2.81 | 364.2 | Intermediate 35 |

Intermediate 37b: Synthesis of ethyl 2-formyl-3-oxopropanoate EV-AQ8817-001

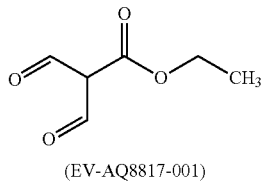

(EV-AQ8817-001)

To a stirred suspension of sodium hydride (60%, 1.68 g, 42.1 mmol) in THF (20 mL) was added ethyl formate (8.5 mL, 105.7 mmol). The solution was cooled to 0° C. and a solution of ethyl 3,3-diethoxypropanoate (4 g, 21.0 mmol) in THF (10 mL) was added dropwise over 30 mins and the reaction mixture stirred at r.t. overnight. 2M aq HCl (30 mL) was added under whilst cooling with ice and the reaction stirred at r.t. for 30 mins. The reaction mixture was extracted with diethyl ether (2×50 mL) and the combined organic extracts were dried over MgSO$_4$ and concentrated in vacuo to afford the title compound (3.02 g, 99.7%) as an amber liquid.

$^1$H NMR (250 MHz, Chloroform-d) δ 9.13 (s, 2H), 4.29 (q, J=7.1 Hz, 2H), 1.37-1.28 (m, 3H).

Example 158a—Preparation of 6-methyl-2-[5-methyl-3-(1,2,3,4-tetrahydroisoquinoline-2-carbonyl)-1H-pyrazol-1-yl]-3,4-dihydropyrimidin-4-one Q-432 (EV-AQ0253-002)

Step 1: Synthesis of methyl 3-[2-(4-methyl-6-oxo-1,6-dihydropyrimidin-2-yl)hydrazin-1-ylidene]butanoate

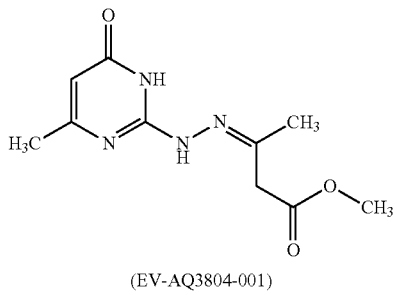

(EV-AQ3804-001)

A solution of 2-hydrazinyl-6-methyl-3,4-dihydropyrimidin-4-one (Intermediate 1, EV-AO5744-001, 826 mg, 5.89 mmol) and methyl 3-oxobutanoate (763 µl, 7.07 mmol) in EtOH (20 ml) was heated at reflux for 3 h. The reaction mixture was cooled to r.t., concentrated in vacuo and triturated with EtOH, washing with EtOH followed by Et$_2$O, to afford the title compound (886 mg, 63%) as a pink solid.

Method A: LC-MS m/z=239.00 [M+H]$^+$; RT=0.71 min.

Step 2: Synthesis of methyl 3-methyl-1-(4-methyl-6-oxo-1,6-dihydropyrimidin-2-yl)-1H-pyrazole-4-carboxylate

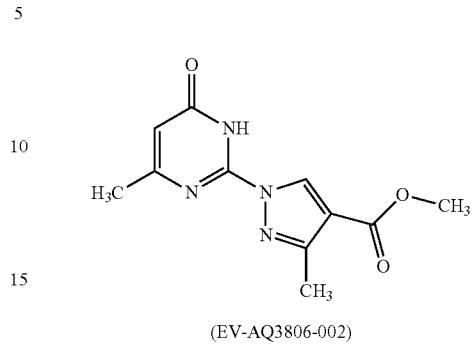

(EV-AQ3806-002)

A solution of methyl 3-[2-(4-methyl-6-oxo-1,6-dihydropyrimidin-2-yl)hydrazin-1-ylidene]butanoate (EV-AQ3804-001, 300 mg, 1.26 mmol) in anhydrous DMF (4 ml) at 0° C. was treated dropwise with phosphoric trichloride (352 µl, 3.78 mmol) and stirred at 0° C. for 2 h. The reaction mixture was quenched by the addition of water (1 ml), poured onto crushed ice and left to stand for 30 mins. The solution was neutralised with 1M aq NaOH solution and then concentrated in vacuo. The residue was dissolved in water (20 ml) and extracted with EtOAc (3×50 ml). The organic extracts were washed with brine, dried over magnesium sulfate, concentrated in vacuo and triturated using Et$_2$O to afford methyl 3-methyl-1-(4-methyl-6-oxo-1,6-dihydropyrimidin-2-yl)-1H-pyrazole-4-carboxylate (119 mg, 38%) as a pink solid.

Method A: LC-MS m/z=249.00 [M+H]$^+$; RT=1.01 min.

Step 3: Synthesis of 3-methyl-1-(4-methyl-6-oxo-1,6-dihydropyrimidin-2-yl)-1H-pyrazole-4-carboxylic acid

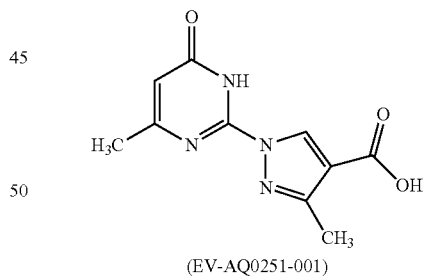

(EV-AQ0251-001)

To a solution of methyl 3-methyl-1-(4-methyl-6-oxo-1,6-dihydropyrimidin-2-yl)-1H-pyrazole-4-carboxylate (EV-AQ3806-002, 120 mg, 0.44 mmol) in THF (3 mL) was added 3M aq NaOH solution (0.97 ml) and stirred at r.t. for 2 h. The reaction mixture was concentrated in vacuo to remove the organic solvent and the aqueous solution acidified to pH 3 using 5M aq HCl solution. A beige precipitate formed which was filtered washing with H$_2$O and Et$_2$O to afford 3-methyl-1-(4-methyl-6-oxo-1,6-dihydropyrimidin-2-yl)-1H-pyrazole-4-carboxylic acid (110 mg, 95%) as a beige powder.

Method A: LC-MS m/z=235.0 [M+H]$^+$; RT=0.83 min.

Step 4: Synthesis of 6-methyl-2-{3-methyl-4-[4-(trifluoromethyl)piperidine-1-carbonyl]-1H-pyrazol-1-yl}-3,4-dihydropyrimidin-4-one

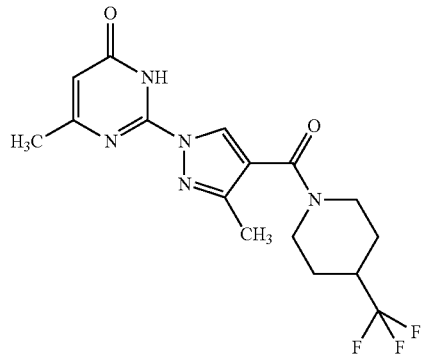

Q-432

(EV-AQ0253-002)

To a suspension of 3-methyl-1-(4-methyl-6-oxo-1,6-dihydropyrimidin-2-yl)-1H-pyrazole-4-carboxylic acid (EV-AQ0251-001, 35 mg, 0.15 mmol) in THF (2 ml) was added DIPEA (91 µl, 0.52 mmol), T3P (50% in EtOAc) (176 µl, 0.30 mmol) and 4-(trifluoromethyl)piperidine hydrochloride (34 mg, 0.18 mmol) and stirred at r.t. for 3 h. The reaction mixture was concentrated in vacuo, redissolved in water (10 ml) and extracted with EtOAc (3×20 ml). The combined organic extracts were dried over sodium sulfate, concentrated in vacuo and purified via chromatography on SiO$_2$ (gradient 100:0-80:20, DCM-MeOH) to afford 6-methyl-2-{3-methyl-4-[4-(trifluoromethyl)piperidine-1-carbonyl]-1H-pyrazol-1-yl}-3,4-dihydropyrimidin-4-one (16 mg, 29%) as an off white powder.

Method C: LC-MS m/z=370.2 [M+H]$^+$; RT=2.40 min.

Preparative Example 7—Formation of Products Via Cyclization to Form Substituted Pyrazoles

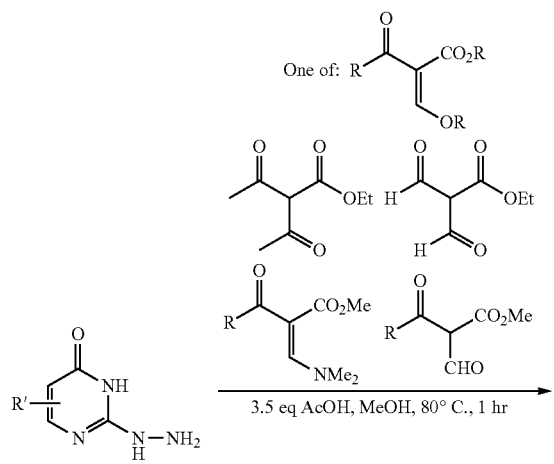

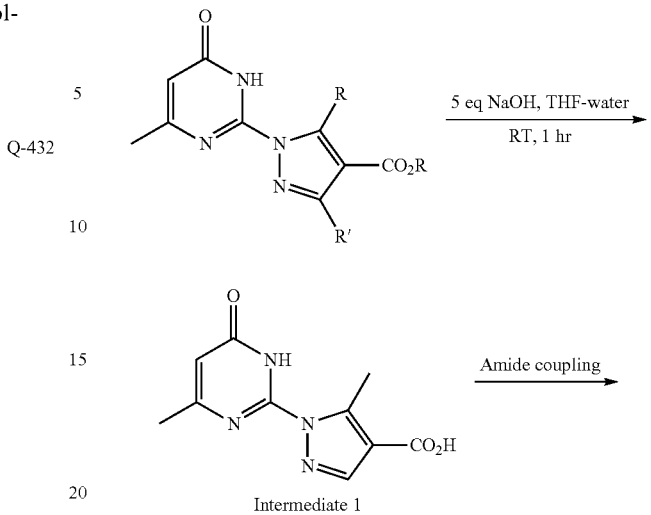

Synthesis of Intermediates

Intermediate 38: Synthesis of 2,4-dichloro-7-methyl-7H-pyrrolo[2,3-d]pyrimidine

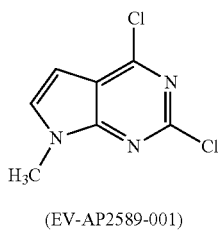

(EV-AP2589-001)

To a solution of 2,4-dichloro-7H-pyrrolo[2,3-d]pyrimidine (1.5 g, 7.98 mmol) in THF (30 ml) at 0° C. was added sodium hydride (60% oil suspension, 383 mg, 9.57 mmol) and stirred at 0° C.—r.t. for 20 mins. Iodomethane (0.6 ml, 9.57 mmol) was added and stirred at r.t. for 3 h. The mixture was quenched by addition of saturated ammonium chloride solution (20 mL). EtOAc was then added resulting in formation of a precipitate. The precipitate was filtered and the filtrate extracted with EtOAc (×2). The combined organic fractions were washed with water, dried over Na$_2$SO$_4$, filtered and concentrated in vacuo to afford the title compound (1.65 g, 97.2%) as a yellow powder.

Method A: LC-MS m/z=201.90, 203.90 [M+H]+; RT=1.21

Intermediate 39: Synthesis of 5-chloro-6H,7H-[1,3]thiazolo[5,4-d]pyrimidin-7-one

Step 1: Synthesis of 7-(benzyloxy)-5-chloro-[1,3]thiazolo[5,4-d]pyrimidine

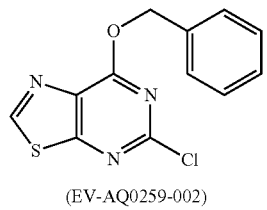 [SMILES: Clc1nc(OCc2ccccc2)c2ncsc2n1]

(EV-AQ0259-002)

To a solution of 5,7-dichloro-[1,3]thiazolo[5,4-d]pyrimidine (980 mg, 4.76 mmol) in THF (20 mL) at 0° C. was added benzyl alcohol (495 µl, 4.76 mmol) and sodium hydride (114 mg, 4.76 mmol, 60% in mineral oil) and stirred at r.t. for 22 h. To the reaction mixture was added water (20 ml) and extracted with EtOAc (2×50 ml). The combined organic extracts were washed with brine, dried over sodium sulfate and concentrated in vacuo. Purification by chromatography on SiO$_2$ (gradient 100:0-90:10, Heptane-EtOAc) afforded the title compound (708 mg, 47%) as a white powder.

Method A: LC-MS m/z=277.85 [M+H]$^+$; RT=1.39 min.

Step 2: Synthesis of 5-chloro-6H,7H-[1,3]thiazolo[5,4-d]pyrimidin-7-one

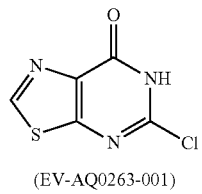

(EV-AQ0263-001)

7-(benzyloxy)-5-chloro-[1,3]thiazolo[5,4-d]pyrimidine (EV-AQ0259-002, 708 mg, 2.24 mmol) was dissolved in a 1:1 mixture of 37% aq HCl-THF (10 mL) and stirred at r.t. for 18 h. The reaction mixture was filtered under vacuum, washing with THF and Et$_2$O, to afford the title compound (246 mg, 58%) as a pale yellow powder.

Method A: LC-MS m/z=187.80 [M+H]$^+$; RT=0.49 min.

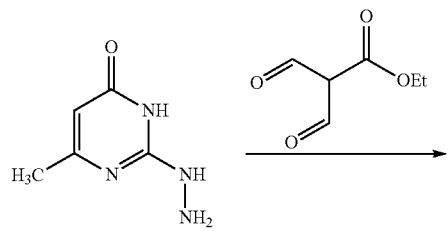

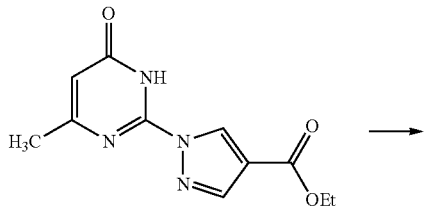

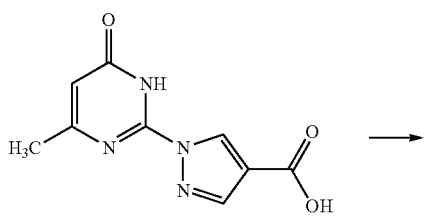

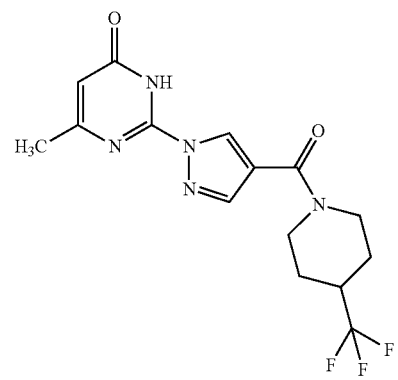

Intermediate 40: Methyl-2-[(dimethylamino)methylidene]-4-methyl-3-oxopentanoate

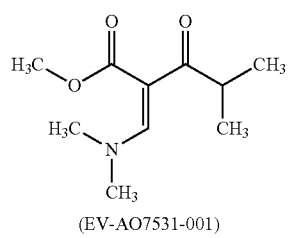

(EV-AO7531-001)

To methyl 4-methyl-3-oxopentanoate (1.98 ml, 13.87 mmol) was added 1,1-dimethoxy-N,N-dimethylmethanamine (2.21 ml, 16.65 mmol) and the solution was stirred at 80° C. for 1 h. The reaction mixture was concentrated in vacuo to afford methyl-2-[(dimethylamino)methylidene]-4-methyl-3-oxopentanoate (2.76 g, 95%) as an orange oil.

Method A: LC-MS m/z=200.0 [M+H]$^+$; RT=1.00

Intermediate 41: Methyl-2-[(dimethylamino)methylidene]-4-methyl-3-oxopentanoate

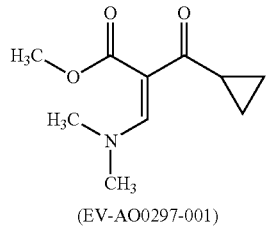

(EV-AO0297-001)

To methyl 4-methyl-3-oxopentanoate (1.98 ml, 13.87 mmol) was added 1,1-dimethoxy-N,N-dimethylmethanamine (2.21 ml, 16.65 mmol) and the solution was stirred at 80° C. for 1 h. The reaction mixture was concentrated in vacuo to afford methyl-2-[(dimethylamino)methylidene]-4-methyl-3-oxopentanoate (2.76 g, 95%) as an orange oil.

Method A: LC-MS m/z=200.0 [M+H]$^+$; RT=1.00

Examples 157b, 158b, and 159-180

The compounds in Table 11 were prepared by cyclization of the intermediate hydrazine with the appropriate enamine followed by coupling using the specified reagent.

TABLE 11

| Example No | Enamine | Ref. No. | LBN | Structure | LC-MS (RT) Method C | MS (M + H)$^+$ Method C | Coupling Agent |
|---|---|---|---|---|---|---|---|
| 157b | | Q-444 | EV-AQ0282-002 | 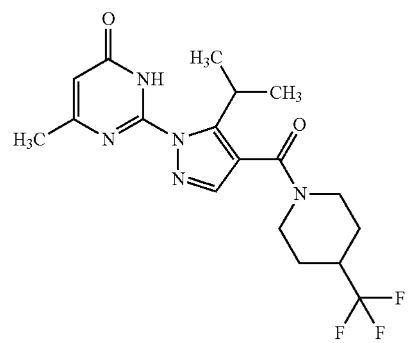 [SMILES: Cc1cc(=O)[nH]c(-n2ncc(C(=O)N3CCC(C(F)(F)F)CC3)c2C(C)C)n1] | 2.87 | 398.2 | T3P |
| 158b | | Q-445 | EV-AQ0286-002 | 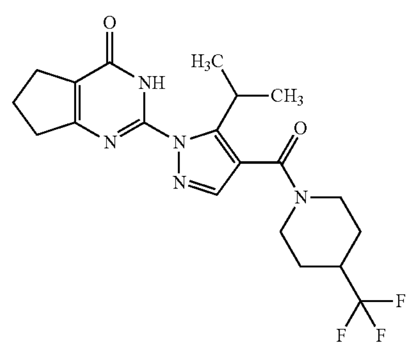 [SMILES: CC(C)c1c(C(=O)N2CCC(C(F)(F)F)CC2)cnn1-c1nc2c(c(=O)[nH]1)CCC2] | 3.20 | 424.2 | T3P |
| 159 | | Q-330 | EV-AO7546-002 | 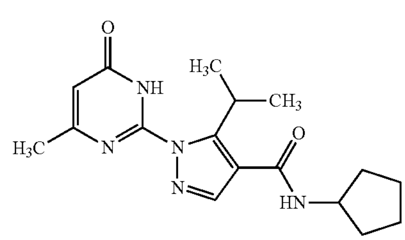 [SMILES: Cc1cc(=O)[nH]c(-n2ncc(C(=O)NC3CCCC3)c2C(C)C)n1] | 2.61 | 330.2 | COMU |

TABLE 11-continued

| Example No | Enamine | Ref. No. | LBN | Structure | LC-MS (RT) Method C | MS (M + H)+ Method C | Coupling Agent |
|---|---|---|---|---|---|---|---|
| 160 | | Q-319 | EV-AQ0281-002 | 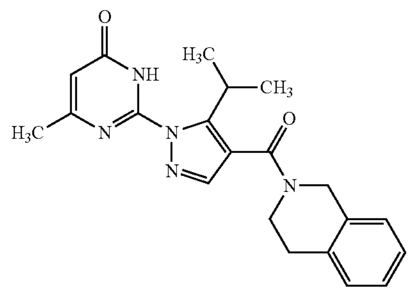 [SMILES: Cc1cc(=O)[nH]c(-n2ncc(C(=O)N3CCc4ccccc4C3)c2C(C)C)n1] | 2.95 | 377.4 | T3P |
| 161 | | Q-463 | EV-AR5315-002 | 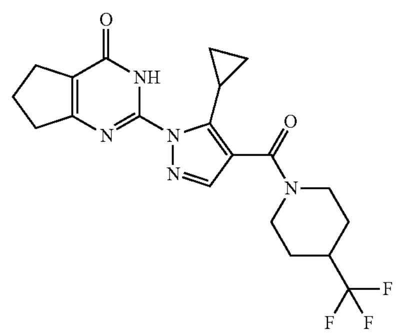 [SMILES: O=C(c1cnn(-c2nc3c(c(=O)[nH]2)CCC3)c1C1CC1)N1CCC(C(F)(F)F)CC1] | 2.91 | 422.2 | T3P |
| 162 | | Q-353 | EV-AP2516-001 | 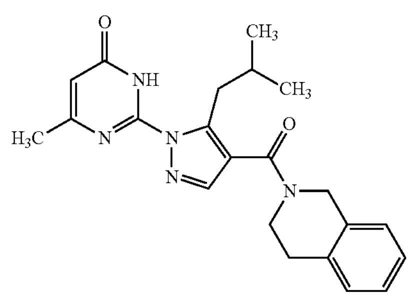 [SMILES: Cc1cc(=O)[nH]c(-n2ncc(C(=O)N3CCc4ccccc4C3)c2CC(C)C)n1] | 3.27 | 392.3 | COMU |
| 163 | | Q-371 | EV-AP2521-001 | 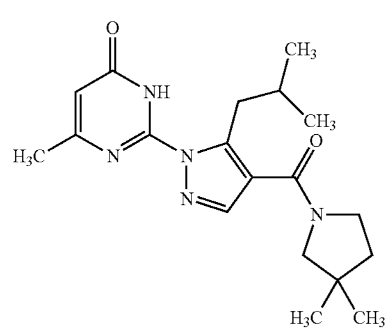 [SMILES: Cc1cc(=O)[nH]c(-n2ncc(C(=O)N3CCC(C)(C)C3)c2CC(C)C)n1] | 3.04 | 358.2 | COMU |

TABLE 11-continued

| Example No | Enamine | Ref. No. | LBN | Structure | LC-MS (RT) Method C | MS (M + H)+ Method C | Coupling Agent |
|---|---|---|---|---|---|---|---|
| 164 | *Angew Chem Int Ed* 53(3), 757-760, 2014. | Q-358 | EV-AP2324-001 | 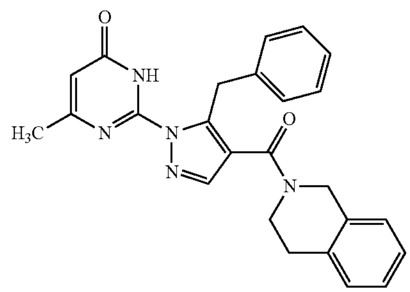 [SMILES: Cc1cc(=O)[nH]c(-n2ncc(C(=O)N3CCc4ccccc4C3)c2Cc2ccccc2)n1] | 3.40 | 426.2 | COMU |
| 165 | *Angew Chem Int Ed* 53(3), 757-760, 2014. | Q-369 | EV-AP2329-001 | 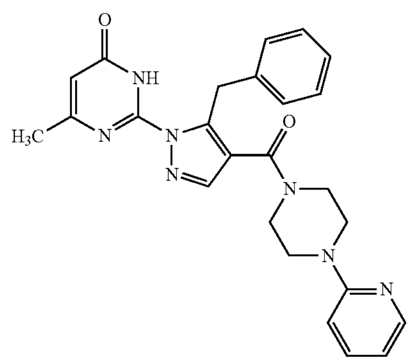 [SMILES: Cc1cc(=O)[nH]c(-n2ncc(C(=O)N3CCN(c4ccccn4)CC3)c2Cc2ccccc2)n1] | 1.72 | 456.2 | COMU |
| 166 | *Angew Chem Int Ed* 53(3), 757-760, 2014. | Q-370 | EV-AP2333-001 | 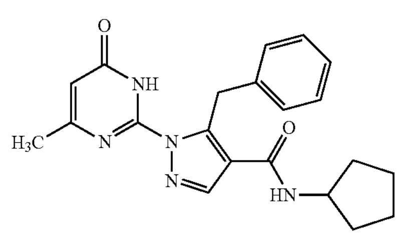 [SMILES: Cc1cc(=O)[nH]c(-n2ncc(C(=O)NC3CCCC3)c2Cc2ccccc2)n1] | 3.03 | 378.2 | COMU |
| 167 | WO2008053043 | Q-332 | EV-AN7498-001 | 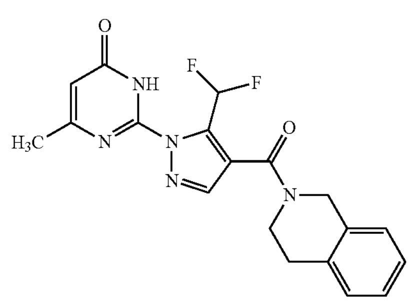 [SMILES: Cc1cc(=O)[nH]c(-n2ncc(C(=O)N3CCc4ccccc4C3)c2C(F)F)n1] | 2.71 | 386.12 | COMU |

TABLE 11-continued

| Example No | Enamine | Ref. No. | LBN | Structure | LC-MS (RT) Method C | MS (M + H)+ Method C | Coupling Agent |
|---|---|---|---|---|---|---|---|
| 168 | (structure) WO2008053043 | Q-331 | EV-AN7499-001 | (structure) | 2.36 | 338.1 | COMU |
| 169 | (structure) WO2008053043 | Q-349 | EV-AP2500-001 | (structure) | 1.69 | 340.1 | COMU |
| 170 | (structure) WO2008053043 | Q-342 | EV-AN7486-001 | (structure) | 2.95 | 404.1 | COMU |
| 171 | (structure) WO2008053043 | Q-334 | EV-AN7489-001 | (structure) | 2.56 | 356.1 | TBTU |
| 172 | (structure) | Q-375 | EV-AP2332-001 | (structure) | 2.67 | 364.2 | COMU |

TABLE 11-continued

| Example No | Enamine | Ref. No. | LBN | Structure | LC-MS (RT) Method C | MS (M + H)+ Method C | Coupling Agent |
|---|---|---|---|---|---|---|---|
| 173 | | Q-419 | EV-AP2578-001 | 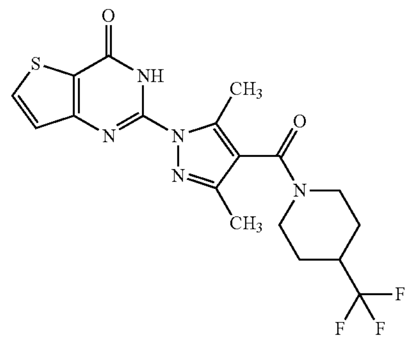 [SMILES: Cc1nn(-c2nc3ccsc3c(=O)[nH]2)c(C)c1C(=O)N1CCC(C(F)(F)F)CC1] | 3.04 | 426.2 | COMU |
| 174 | | Q-458 | EV-AP2577-001 | 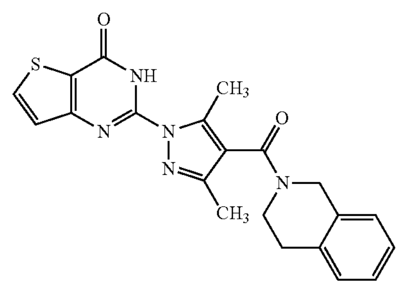 [SMILES: Cc1nn(-c2nc3ccsc3c(=O)[nH]2)c(C)c1C(=O)N1CCc2ccccc2C1] | 3.15 | 406.2 | COMU |
| 175 | | Q-411 | EV-AP2579-001 | 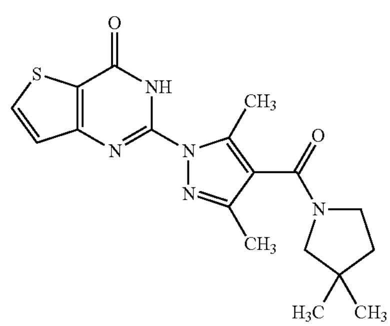 [SMILES: Cc1nn(-c2nc3ccsc3c(=O)[nH]2)c(C)c1C(=O)N1CCC(C)(C)C1] | 2.91 | 372.2 | COMU |
| 176 | | Q-443 | EV-AQ4752-003 | 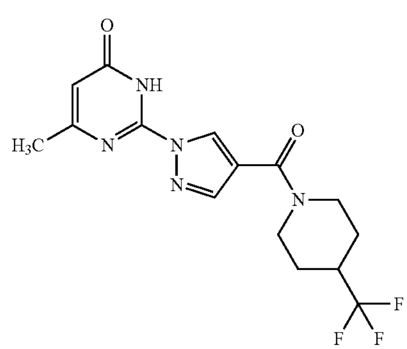 [SMILES: Cc1cc(=O)[nH]c(-n2cc(C(=O)N3CCC(C(F)(F)F)CC3)cn2)n1] | 2.28 | 356.2 | T3P |

WO2009148004

TABLE 11-continued

| Example No | Enamine | Ref. No. | LBN | Structure | LC-MS (RT) Method C | MS (M + H)+ Method C | Coupling Agent |
|---|---|---|---|---|---|---|---|
| 177 | (structure) WO2009148004 | Q-537 | EV-AQ3868-002 | (structure) | 2.95 | 446.1 | T3P |
| 178 | (structure) WO2009148004 | Q-536 | EV-AQ3869-002 | (structure) | 2.97 | 428.3 | T3P |
| 179 | (structure) WO2009148004 | Q-535 | EV-AS5419-002 | (structure) | 2.42 | 453.0 | T3P |

TABLE 11-continued
| Example No | Enamine | Ref. No. | LBN | Structure | LC-MS (RT) Method C | MS (M + H)+ Method C | Coupling Agent |
|---|---|---|---|---|---|---|---|
| 180 | 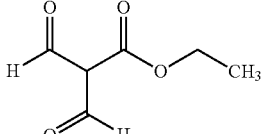 | Q-534 | EV-AS5418-002 | 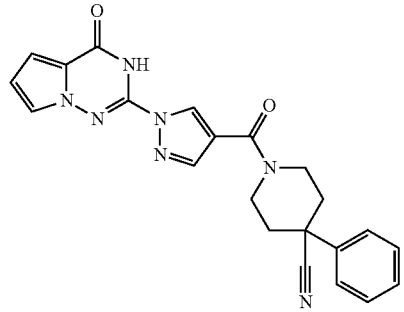 [SMILES: N#CC1(c2ccccc2)CCN(C(=O)c2cnn(-c3nn4cccc4c(=O)[nH]3)c2)CC1] | 2.89 | 414.1 | T3P |
WO2009148004
Preparative Example 8—Formation of Intermediates Via SNAr
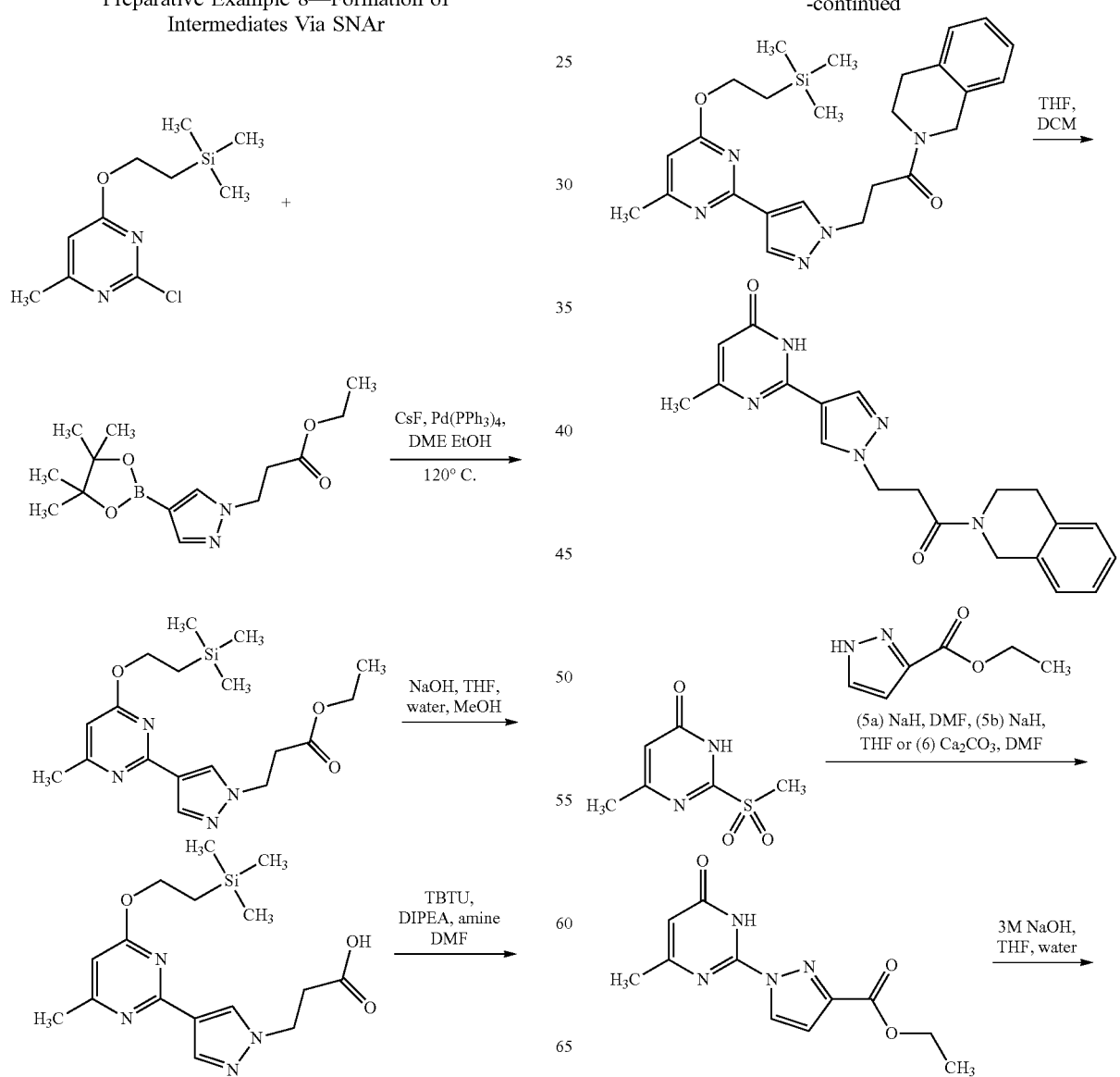

691
-continued

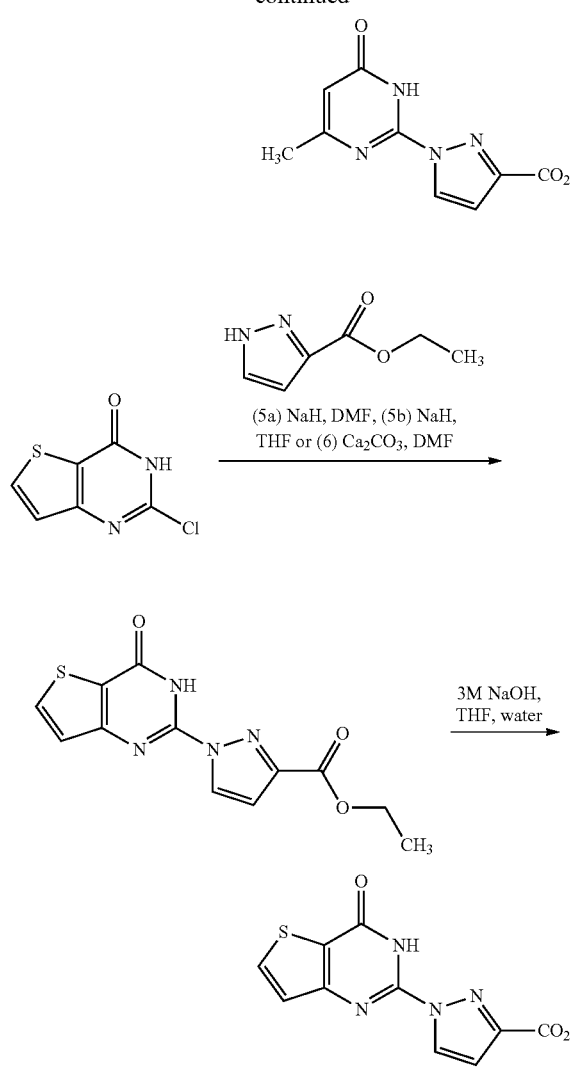

(5a) NaH, DMF, (5b) NaH, THF or (6) Ca₂CO₃, DMF

3M NaOH, THF, water

Example 181—Preparation of 1-(1-{4-oxo-3H,4H-thieno[3,2-d]pyrimidin-2-yl}-1H-pyrazole-4-carbonyl)-4-phenylpiperidine-4-carbonitrile EV-AR5394-002)

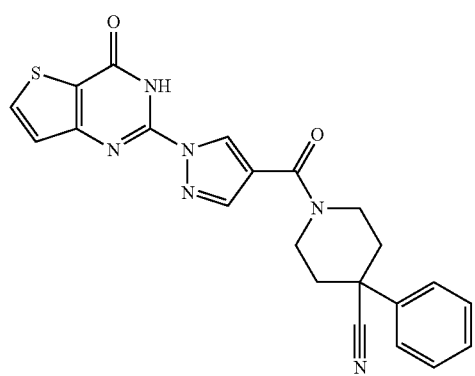 [SMILES: N#CC1(c2ccccc2)CCN(C(=O)c2cnn(-c3nc4ccsc4c(=O)[nH]3)c2)CC1]

692

Step 1: Synthesis of ethyl 1-{4-oxo-3H,4H-thieno[3,2-d]pyrimidin-2-yl}-1H-pyrazole-4-carboxylate

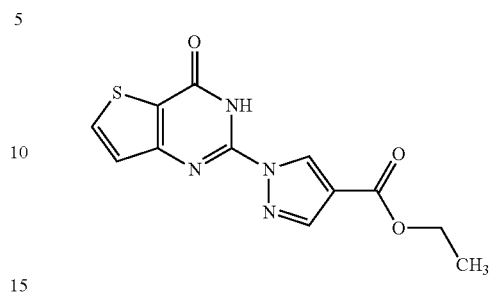

(EV-AR5386-001)

To a solution of 2-chloro-3H,4H-thieno[3,2-d]pyrimidin-4-one (Intermediate 9, 647 mg, 3.47 mmol) in DMF (2 ml) was added ethyl 1H-pyrazole-4-carboxylate (Intermediate Y, 437 mg, 3.12 mmol), caesium carbonate (1.69 g, 5.20 mmol), L-proline (160 mg, 1.39 mmol) and copper (I) iodide (132 mg, 0.69 mmol). The reaction mixture was then degassed and stirred at 120° C. overnight. The reaction mixture was concentrated in vacuo and a 0.2M aq EDTA solution (20 ml) and DCM (30 ml) were added and the mixture was stirred at r.t. overnight. The organic phase was separated and the aqueous phase was extracted with DCM (10 ml). The combined organic phases were washed with water, dried over sodium sulfate and concentrated in vacuo to afford the title compound (559, 44%) as a beige powder.

Method B: LC-MS m/z=290.95 [M+H]⁺; RT=1.02 min.

Step 2: Synthesis of 1-{4-oxo-3H,4H-thieno[3,2-d]pyrimidin-2-yl}-1H-pyrazole-4-carboxylic acid. Intermediate 42

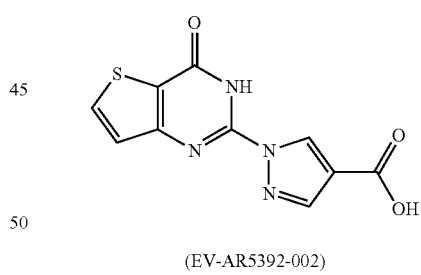

(EV-AR5392-002)

To a solution of methyl ethyl 1-{4-oxo-3H,4H-thieno[3,2-d]pyrimidin-2-yl}-1H-pyrazole-4-carboxylate (EV-AR5386-001, 80%, 559 mg, 1.54 mmol) in THF (5 mL) and water (5 ml) was added 6M aqueous NaOH solution (2.57 ml) and the reaction mixture stirred at r.t. for 4 h. The reaction mixture was concentrated in vacuo to remove the organic solvent and the aqueous mixture acidified to pH 4 using 5M aq HCl solution. The reaction mixture was extracted with EtOAc (2×50 ml) and the combined organic extracts dried over sodium sulfate and concentrated in vacuo to afford the title compound (307 mg, 72%) as a pale grey powder.

Method B: LC-MS m/z=262.95 [M+H]⁺; RT=0.82 min.

Step 3: Synthesis of 1-(1-{4-oxo-3H,4H-thieno[3,2-d]pyrimidin-2-yl}-1H-pyrazole-4-carbonyl)-4-phenylpiperidine-4-carbonitrile

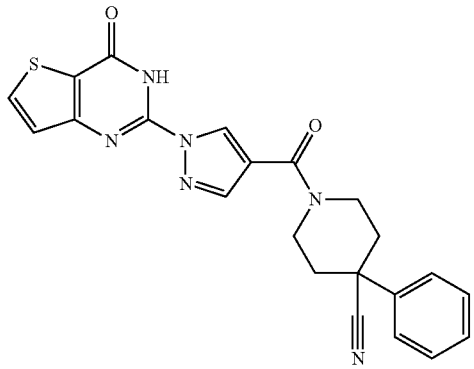

Q-523

(EV-AR5387-002)

To a suspension of 1-{4-oxo-3H,4H-thieno[3,2-d]pyrimidin-2-yl}-1H-pyrazole-4-carboxylic acid (EV-AR5392-001, 80%, 52 mg, 0.159 mmol) in THF (2 ml) was added DIPEA (69 μl, 0.40 mmol), T3P (50% in EtOAc) (234 μl, 0.40 mmol) and 4-phenylpiperidine-4-carbonitrile (33 mg, 0.17 mmol) and the reaction mixture stirred at r.t. for 2 h. The reaction mixture was concentrated in vacuo and to the crude sample added DCM (2 ml) and saturated NaHCO$_3$ solution (1 ml). The solution was then passed through a phase separator cartridge and concentrated in vacuo. Purification using an SCX cartridge followed by trituration with MeOH afforded the title compound (31 mg, 45%) as an off white powder.

Method C: LC-MS m/z=431.0 [M+H]$^+$; RT=2.83 min.

Examples 182-184

The compounds in Table 12 were prepared in an analogous manner to Example 181 by coupling the appropriate amine with intermediate 42

TABLE 12

| Example No | Route | Ref. No. | LBN | Structure | LC-MS (RT) Method C | MS (M + H)$^+$ Method C |
|---|---|---|---|---|---|---|
| 182 | 1 | Q-524 | EV-AR5388-002 | 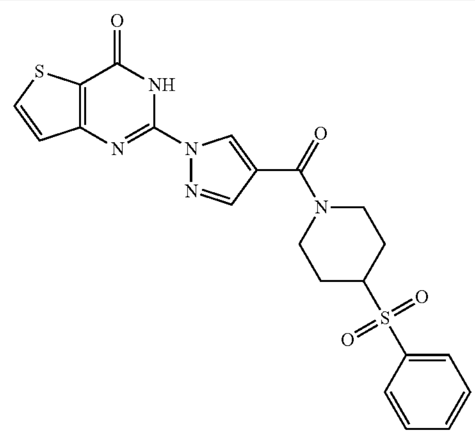 [SMILES: O=C(c1cnn(-c2nc3ccsc3c(=O)[nH]2)c1)N1CCC(S(=O)(=O)c2ccccc2)CC1] | 2.36 | 470.0 |
| 183 | 1 | Q-528 | EV-AR5394-002 | 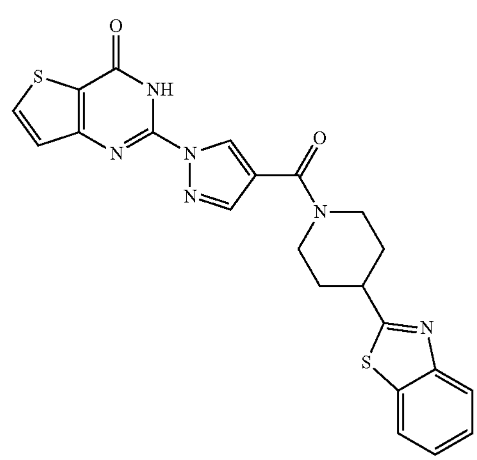 [SMILES: O=C(c1cnn(-c2nc3ccsc3c(=O)[nH]2)c1)N1CCC(c2nc3ccccc3s2)CC1] | 2.88 | 463.0 |

TABLE 12-continued

| Example No | Route | Ref. No. | LBN | Structure | LC-MS (RT) Method C | MS (M + H)+ Method C |
|---|---|---|---|---|---|---|
| 184 | 1 | Q-527 | EV-AR5395-002 | 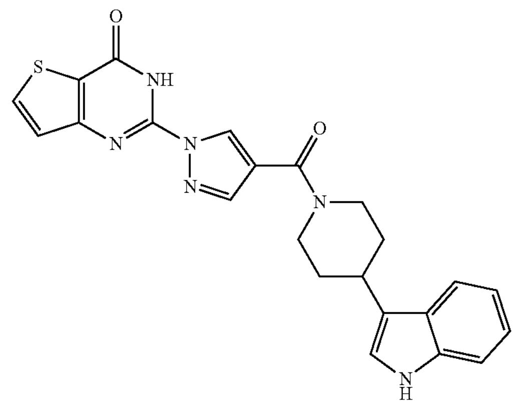 [SMILES: O=C(c1cnn(-c2nc3ccsc3c(=O)[nH]2)c1)N1CCC(c2c[nH]c3ccccc23)CC1] | 2.91 | 445.1 |

Intermediate 43: Synthesis of 1-{4-oxo-3H,4H-thieno[3,2-d]pyrimidin-2-yl}-1H-pyrazole-3-carboxylic acid

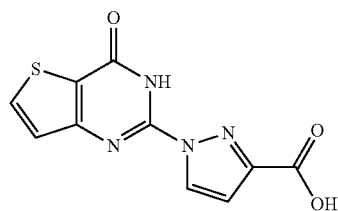 [SMILES: O=C(O)c1ccn(-c2nc3ccsc3c(=O)[nH]2)n1]

Step 1: Synthesis of 2-chloro-4-[(2-methoxyethoxy)methoxy]thieno[3,2-d]pyrimidine

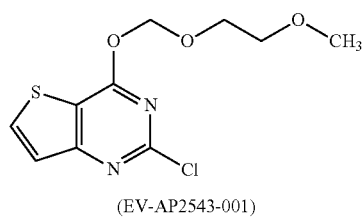 [SMILES: COCCOCOc1nc(Cl)nc2ccsc12]

(EV-AP2543-001)

To a solution of 2-chloro-3H,4H-thieno[3,2-d]pyrimidin-4-one (EV-AP2531-001, 750 mg, 4.02 mmol) and DIPEA (1.03 mL, 6.03 mmol) in THF (15 mL) was added dropwise 1-(chloromethoxy)-2-methoxyethane (0.5 ml, 4.42 mmol) and stirred at r.t. overnight. To the reaction mixture was added EtOAc (50 mL) washed with water (2×15 mL) and brine solution (15 mL). The organic fraction was dried over $Na_2SO_4$ and concentrated in vacuo to afford the title compound (1.09, 87.9%) (as a mixture of N and O alkylation products) as a tan oil.

Method A: LC-MS: m/z=274.9, 276.9 (M+H)+; RT=1.03, 1.19 min, A=52 and 37% respectively.

Step 2: Synthesis of ethyl 1-{4-oxo-3H,4H-thieno[3,2-d]pyrimidin-2-yl}-1H-pyrazole-3-carboxylate

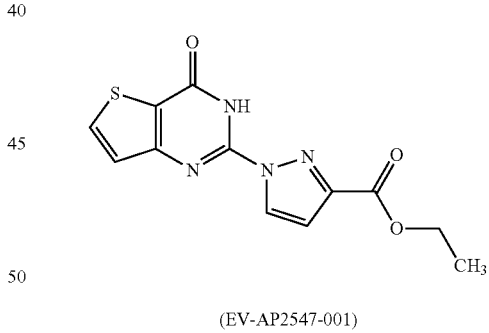

(EV-AP2547-001)

To a solution of 2-chloro-4-[(2-methoxyethoxy)methoxy]thieno[3,2-d]pyrimidine (EV-AP2543-001, 902 mg, 3.28 mmol) in DMF (20 mL) was added caesium carbonate (1.71 g, 5.25 mmol) and ethyl 1H-pyrazole-5-carboxylate (506.13 mg, 3.61 mmol) and stirred at 120° C. for 30 mins. The reaction mixture was cooled to 0° C., diluted with 1M aqueous HCl solution (45 mL) and stirred at 0° C. to r.t. for 30 mins. The resulting precipitate was filtered under vacuum and dried to afford the title compound (275 mg, 28%) as a pale brown powder.

Method A: LC-MS: m/z=+291.1 (M+H)+; RT=1.12 min.

Step 3: Synthesis of 1-{4-oxo-3H,4H-thieno[3,2-d]pyrimidin-2-yl}-1H-pyrazole-3-carboxylic acid Intermediate 43

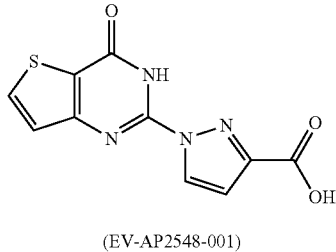 [SMILES: O=C(O)c1ccn(-c2nc3ccsc3c(=O)[nH]2)n1]

(EV-AP2548-001)

Ethyl 1-{4-oxo-3H,4H-thieno[3,2-d]pyrimidin-2-yl}-1H-pyrazole-3-carboxylate (EV-AP2547-001, 310 mg, 1.07 mmol) was suspended in 2:2:1 THF/water/methanol (10 mL) and 2.5M aq NaOH solution (2.6 mL) was added. The reaction mixture was stirred at r.t. for 1.5 h. The reaction mixture was concentrated in vacuo and the aqueous solution acidified to pH 4 with 2M aq HCl solution. The resulting precipitate was filtered and dried under vacuum filtration to afford the title compound (260 mg, 91%) as a pale brown powder.

Method A: LC-MS: m/z=+262.9 (M+H)+; RT=0.92 min.

Example 185—2-[3-(1,2,3,4-tetrahydroisoquinoline-2-carbonyl)-1H-pyrazol-1-yl]-3H,4H-thieno[3,2-d]pyrimidin-4-one

Q-388

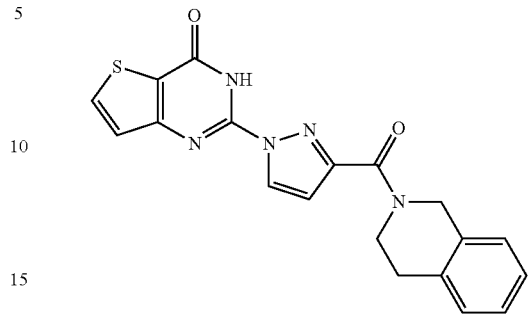

(EV-AP2549-002)

To a solution of 1-{4-oxo-3H,4H-thieno[3,2-d]pyrimidin-2-yl}-1H-pyrazole-3-carboxylic acid (Intermediate 43) (EV-AP2548-001, 80 mg, 0.31 mmol) in DMF (1.0 mL) was added COMU (143.71 mg, 0.34 mmol), DIPEA (0.13 mL, 0.76 mmol) and 1,2,3,4-tetrahydroisoquinoline (0.04 mL, 0.34 mmol) and stirred at r.t. for 2 h. The reaction mixture was concentrated in vacuo and the crude material was purified by PREP-HPLC (Method G) to afford the title compound (28.7 mg, 24.9%) as a fluffy pale yellow solid.

Method C: LC-MS: m/z=+378.1 (M+H)+; RT=2.98 min.

Examples 186-187

The examples in Table 13 were prepared analogously to example 181 coupling intermediate 43

TABLE 13

| Example No | Ref. No. | LBN | Structure | LC-MS (RT) Method C | MS (M + H)+ Method C |
|---|---|---|---|---|---|
| 186 | Q-389 | EV-AP2550-001 | 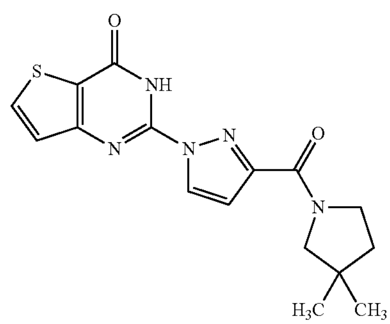 [SMILES: CC1(C)CCN(C(=O)c2ccn(-c3nc4ccsc4c(=O)[nH]3)n2)C1] | 2.74 | 344.1 |
| 187 | Q-390 | EV-AP2551-001 | 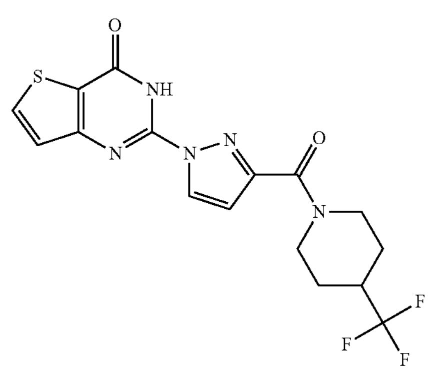 [SMILES: O=C(c1ccn(-c2nc3ccsc3c(=O)[nH]2)n1)N1CCC(C(F)(F)F)CC1] | 2.88 | 398.1 |

Example 188—Preparation of 2-methyl-6-{3-[4-(trifluoromethyl)piperidine-1-carbonyl]-1H-pyrazol-1-yl}-3,4-dihydropyrimidin-4-one (Q-437, EV-AQ7121-003)

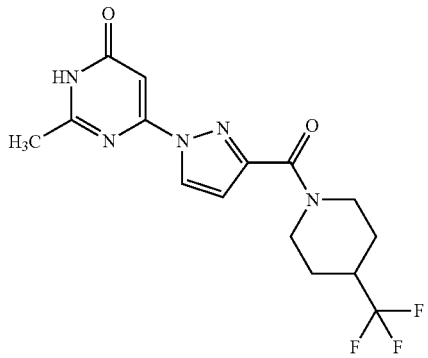 [SMILES: Cc1nc(-n2ccc(C(=O)N3CCC(C(F)(F)F)CC3)n2)cc(=O)[nH]1]

Step 1: Synthesis of ethyl 1-(2-methyl-6-oxo-1,6-dihydropyrimidin-4-yl)-1H-pyrazole-3-carboxylate

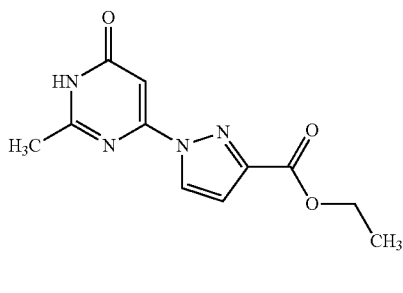

(EV-AQ7119-001)

To a microwave vessel was added 6-chloro-2-methyl-3,4-dihydropyrimidin-4-one (450 mg, 3.11 mmol), ethyl 1H-pyrazole-5-carboxylate (610.74 mg, 4.36 mmol), caesium carbonate (1.72 g, 5.29 mmol), L-proline (143.36 mg, 1.25 mmol) and copper (I) iodide (118.57 mg, 0.62 mmol) in DMF (10 mL). The reaction mixture was de-gassed by bubbling through nitrogen gas for 5 mins and then irradiated in the microwave at 140° C. for 4 h. Additional 6-chloro-2-methyl-3,4-dihydropyrimidin-4-one (150 mg, 1.04 mmol) was added and the reaction irradiated at 140° C. for a further 1.5 h. EtOAc was added to the cooled reaction mixture and the organic layer washed with brine (×2). The organics were dried over $Na_2SO_4$, concentrated in vacuo and purified by chromatography on $SiO_2$, eluting with 0-100% EtOAc in heptane followed by a flush with 50% methanol in EtOAc to afford the title compound (294 mg, 11.4%) as a beige powder.

Method A: LC-MS: m/z=+249.0 (M+H)+; RT=1.00 min.

Step 2: Synthesis of 1-(2-methyl-6-oxo-1,6-dihydropyrimidin-4-yl)-1H-pyrazole-3-carboxylic acid

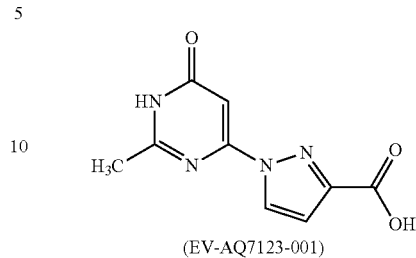

(EV-AQ7123-001)

Ethyl 1-(2-methyl-6-oxo-1,6-dihydropyrimidin-4-yl)-1H-pyrazole-3-carboxylate (EV-AQ7119-001, 30%, 240 mg, 0.29 mmol) was suspended in 2:2:1 THF/water/methanol (10 mL) and 2.5M aq NaOH (1.7 mL) was added. The reaction mixture was stirred at r.t. for 25 mins. The organics from the reaction mixture were removed in vacuo. The residue was acidified with 2M aq HCl solution and the resulting precipitate was collected and dried under vacuum filtration to afford the title compound (55 mg, 86.1%) as a beige powder:

Method A: LC-MS: m/z=+221.0 (M+H)+; RT=0.78.

Step 3: Synthesis of 2-methyl-6-{3-[4-(trifluoromethyl)piperidine-1-carbonyl]-1H-pyrazol-1-yl}-3,4-dihydropyrimidin-4-one

Q-437

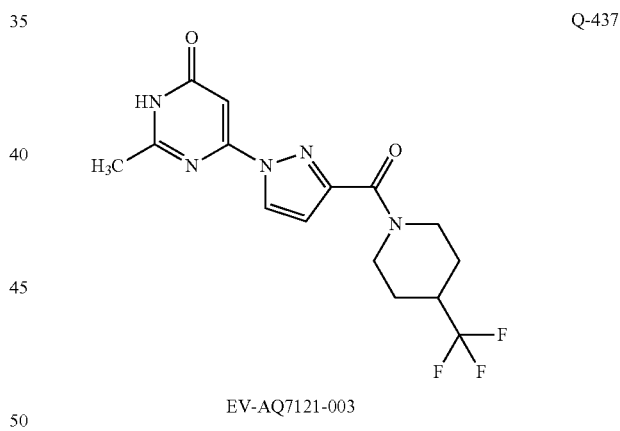

EV-AQ7121-003

To a solution of 1-(2-methyl-6-oxo-1,6-dihydropyrimidin-4-yl)-1H-pyrazole-3-carboxylic acid (EV-AQ7123-001 75 mg, 0.34 mmol) in THF (2 mL) was added DIPEA (0.20 mL, 1.19 mmol) and T3P 50% in EtOAc (0.40 mL, 0.68 mmol). The reaction mixture was stirred at r.t. for 10 mins and 4-(trifluoromethyl)piperidin-1-ium. HCl (77.5 mg, 0.41 mmol) was added before stirring for a further 14 h. The reaction mixture concentrated in vacuo and the crude residue partitioned between water (1 mL) and DCM (5 mL). The organic phase was extracted, washed with saturated $NaHCO_3$ solution (1 ml), water (1 mL) and brine solution (5 mL) and dried over $Na_2SO_4$ and concentrated in vacuo. The crude residue was purified by Prep HPLC (method G) to afford the title compound (43.2 mg, 35.7%) as an off white powder.

Method C: LC-MS: m/z=+356.2 (M+H)+; RT=2.32 min.

Intermediate 44 Synthesis of 1-(4-methyl-6-oxo-1,6-dihydropyrimidin-2-yL)-1H-pyrazole-3-carboxylic acid

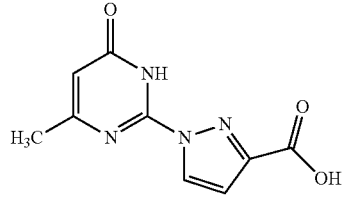 [SMILES: Cc1cc(=O)[nH]c(-n2ccc(C(=O)O)n2)n1]

Step 1: Synthesis of 2-chloro-4-[(4-methoxyphenyL)methoxy]-6-methylpyrimidine

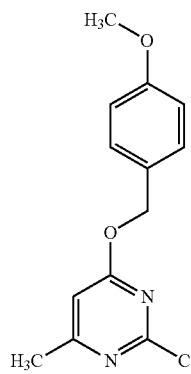

(EV-AP2317-001)

To a stirred solution of (4-methoxyphenyL)methanol (3.39 g, 3.05 mL, 24.5 mmol) in THF (40 mL) at 0° C. was added NaH (60% in oil, 1.47 g, 36.8 mmol). After 1 h, a solution of 2,4-dichloro-6-methylpyrimidine (4.0 g, 24.5 mmol) in THF (15 mL) was added dropwise and stirred at 0° C. to r.t. overnight. The reaction mixture was quenched by the addition of saturated aq NH$_4$Cl solution (40 mL) and extracted with EtOAc (3×75 mL). The combined organic fractions were washed with brine solution (40 mL), dried over Na$_2$SO$_4$ and concentrated in vacuo. The resulting residue was purified via chromatography on SiO$_2$, eluent Heptane/EtOAc (gradient 100:0-75:25), to afford the title compound (2.37 g, 36%) as a colourless crystalline solid.

Method A: LC-MS m/z=256.0 [M+H]$^+$; RT=1.39 min.

Step 2: Synthesis of ethyl-1-{4-[(4-methoxyphenyL)methoxy]-6-methylpyrimidin-2-yl}-1H-pyrazole-3-carboxylate

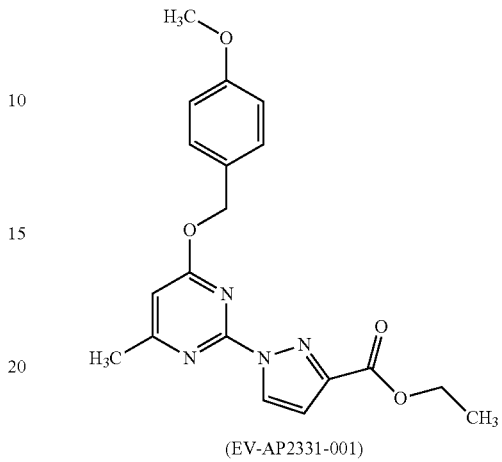

(EV-AP2331-001)

To a stirred solution of ethyl-1H-pyrazole-5-carboxylate (0.945 g, 6.74 mmol) in THF (65 mL) at 0° C. was added NaH (60%, 290 mg, 7.25 mmol) and stirred at 0° C. for 30 mins. 2-chloro-4-[(4-methoxyphenyL)methoxy]-6-methylpyrimidine (1.70 g, 6.42 mmol) was then added and the reaction mixture stirred at reflux for 4 days. The cooled reaction mixture was quenched with saturated NH$_4$Cl aqueous solution (40 mL) and extracted with EtOAc (2×40 mL). The combined organic fractions were dried (Na$_2$SO$_4$), concentrated in vacuo and purified via chromatography on SiO$_2$, eluting with Heptane/EtOAc (gradient 100:0-70:30) to afford the title compound (1.23 g, 52%) as a colourless powder.

Method A: LC-MS m/z=369.1 [M+H]$^+$; RT=1.43 min.

Step 3: Synthesis of ethyl-1-(4-methyl-6-oxo-1,6-dihydropyrimidin-2-yL)-1H-pyrazole-3-carboxylate

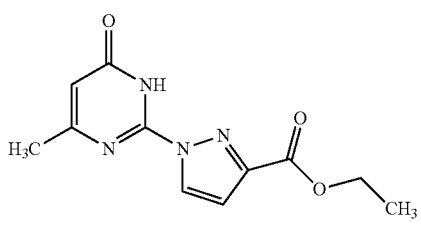

(EV-AP2334-001)

To a stirred solution of ethyl-1-{4-[(4-methoxyphenyL)methoxy]-6-methylpyrimidin-2-yl}-1H-pyrazole-3-carboxylate (1.06 g, 2.73 mmol) in EtOAc (25 mL) was added Pd on carbon (10%, 100 mg) and the solution exposed to an atmosphere of H$_2$ (g) overnight. The solution was filtered through celite, washing with EtOAc, the filtrate concentrated in vacuo and the residue purified via chromatography, eluting with Heptane/EtOAc (gradient 100:0-20:80) to afford the title compound (400 mg, 59%) as a colourless powder.

Method A: LC-MS m/z=249.0 [M+H]$^+$; RT=1.01 min.

Step 4: Synthesis of 1-(4-methyl-6-oxo-1,6-dihydropyrimidin-2-yL)-1H-pyrazole-3-carboxylic acid

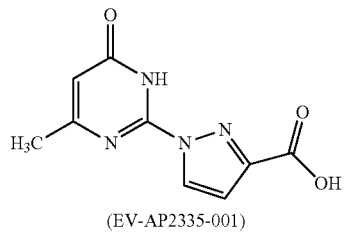

(EV-AP2335-001)

To a stirred solution of ethyl-1-(4-methyl-6-oxo-1,6-dihydropyrimidin-2-yL)-1H-pyrazole-3-carboxylate (386 mg, 1.56 mmol) in 2:1 THF/methanol (8 mL) was added 3M aqueous NaOH solution (3.1 mL) and the reaction mixture was stirred at r.t. for 2 h. The organics were removed in vacuo, the residue acidified to pH 4/5 with 2M aqueous HCl solution and extracted with EtOAc (3×20 mL). The combined organics were dried over $Na_2SO_4$ and concentrated in vacuo to afford the title compound (337 mg, 98%) as a colourless powder.

Method A: LC-MS m/z=220.9 [M+H]$^+$; RT=0.79 min.

Examples 189-190

The examples in Table 14 were prepared by coupling intermediate 44 with the appropriate amine using COMU as the coupling agent.

Example 191—7-{4-[4-(trifluoromethyl)piperidine-1-carbonyl]-1H-pyrazol-1-yl}-5H,6H-imidazo[1,2-c]pyrimidin-5-one

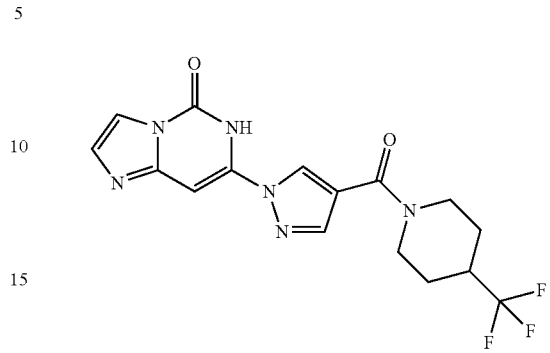

Step 1: Synthesis of 7-chloro-5-(methylsulfanyL)imidazo[1,2-c]pyrimidine hydrochloride

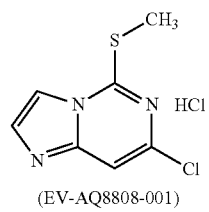

(EV-AQ8808-001)

To a stirred solution of 6-chloro-2-(methylsulfanyL)pyrimidin-4-amine (1.5 g, 8.54 mmol) in dioxane (4 mL) was added chloroacetaldehyde (50%, 1.63 mL, 12.8 mmol) and stirred at 95° C. overnight. The reaction mixture was cooled

TABLE 14

| Example No. | Ref. No. | LBN | Structure | LC-MS (RT) Method C | MS (M + H)$^+$ Method C |
|---|---|---|---|---|---|
| 189 | Q-376 | EV-AP2337-001 | 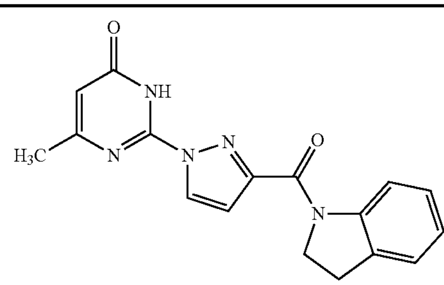 | 2.63 | 322.2 |
| 190 | Q-377 | EV-AP2338-001 | | 2.84 | 336.2 | in an ice bath and the resulting precipitate filtered and washed with dioxane to afford the title compound (1.41 g, 70%) as a colourless powder.

Method A: LC-MS m/z=199.8 [M+H]+; RT=0.93 min

Step 2: Synthesis of 7-chloro-5H,6H-imidazo[1,2-c]pyrimidin-5-one

(EV-AQ8809-001)

To a stirred solution of methyl 7-chloro-5-(methylsulfanyL)imidazo[1,2-c]pyrimidine hydrochloride (EV-AQ8808-001, 1.32 g, 5.59 mmol) in methanol (4 mL) was added 2M aqueous KOH solution (10 mL, 20 mmol) and stirred at reflux overnight. The solution was cooled to r.t. and acidified to pH 5/6 using 5M aq HCl solution. The resulting precipitate was isolated via vacuum filtration to afford the title compound (704 mg, 74%) as a tan powder.

Method A: LC-MS m/z=169.9 [M+H]+; RT=0.23 min

Step 3: 7-{4-[4-(trifluoromethyl)piperidine-1-carbonyl]-1H-pyrazol-1-yl}-5H,6H-imidazo[1,2-c]pyrimidin-5-one

Q-452

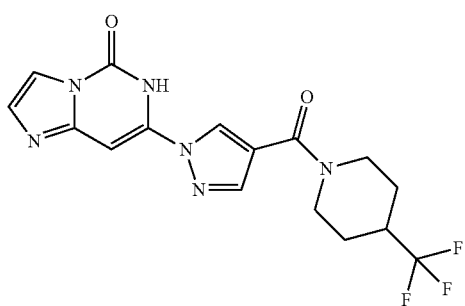 [SMILES: O=C(c1cnn(-c2cc3nccn3c(=O)[nH]2)c1)N1CCC(C(F)(F)F)CC1]

(EV-AQ8822-001)

To a stirred solution of 7-chloro-5H,6H-imidazo[1,2-c]pyrimidin-5-one (EV-AQ8809-001,100 mg, 0.59 mmol) and cesium carbonate (288 mg, 0.89 mmol) in DMF (3 mL) was added 1-(1H-pyrazole-4-carbonyL)-4-(trifluoromethyL)piperidine (intermediate 29, EV-AQ8818-001,175 mg, 0.71 mmol) and the reaction was stirred at 70° C. for 2 h and 100° C. for 3 h. Copper iodide (22 mg, 0.12 mmol) and L-proline (27 mg, 0.24 mmol) were added the reaction heated at 100° C. overnight. The reaction was transferred to the microwave at heated at 150° C. for 6 hours. The reaction was cooled to r.t., concentrated in vacuo and purified via PREP-HPLC (Method G) to yield the title compound (70 mg, 31%) as a colourless powder.

Method C: LC-MS m/z=379.2 [M+H]+; RT=2.00 min.

Example 192—Preparation of 2-chloro-7-fluoro-3H,4H-pyrrolo[2,1-f][1,2,4]triazin-4-one

Q-525 (EV-AS3703-002)

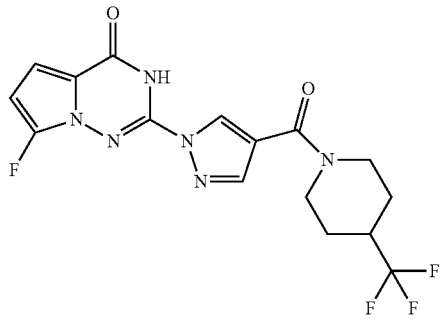 [SMILES: O=C(c1cnn(-c2nn3c(F)ccc3c(=O)[nH]2)c1)N1CCC(C(F)(F)F)CC1]

Step 1: Synthesis of 2-chloro-7-fluoro-3H,4H-pyrrolo[2,1-f][1,2,4]triazin-4-one

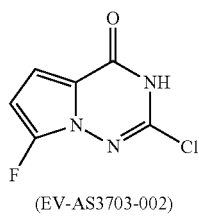 [SMILES: O=c1[nH]c(Cl)nn2c(F)ccc12]

(EV-AS3703-002)

To a solution of 2,4-dichloro-7-fluoropyrrolo[2,1-f][1,2,4]triazine (WO2011/88045 A1, 2011) (446 mg, 2.16 mmol) in THF (20 ml) was added 5M aq NaOH solution (2.16 ml, 10.82 mmol) and stirred at r.t. for 22 h. The reaction mixture was concentrated in vacuo and the residue acidified to pH 5 using 2M aq HCl solution. The resulting precipitate was collected under vacuum filtration, washing with diethyl ether, to afford the title compound (283 mg, 35%) as an off-white powder.

Method B: LC-MS m/z=187.9 [M+H]+; RT=0.86 min.

Step 2: Synthesis of 7-fluoro-2-{4-[4-(trifluoromethyl)piperidine-1-carbonyl]-1H-pyrazol-1-yl}-3H,4H-pyrrolo[2,1-f][1,2,4]triazin-4-one

Q-525

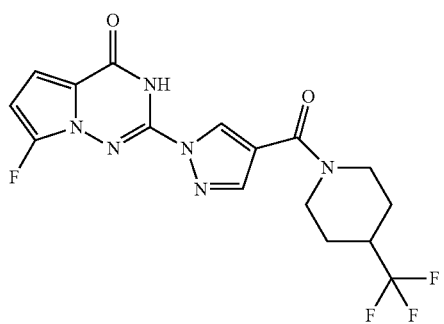

(EV-AS3703-002)

The title compound was prepared in an analogous manner to Example 191 using 2-chloro-7-fluoro-3H,4H-pyrrolo[2,1-f][1,2,4]triazin-4-one (140 mg, 0.75 mmol) and purifying by preparative HPLC [method G] to give 7-fluoro-2-{4-[4-(trifluoromethyl)piperidine-1-carbonyl]-1H-pyrazol-1-yl}-3H,4H-pyrrolo[2,1-f][1,2,4]triazin-4-one one (42 mg, 14%) as an off white powder.

Method C: LC-MS m/z=398.0 [M+H]⁺; RT=2.82 min.

Example 193—Preparation of 2-{4-[4-(trifluoromethyl)piperidine-1-carbonyl]-1H-pyrazol-1-yl}-3H,4H,5H,6H,7H-cyclopenta[d]pyrimidin-4-one (Q-526, EV-AR5391-002)

Step 1: Synthesis of 2-chloro-3H,4H,5H,6H,7H-cyclopenta[d]pyrimidin-4-one

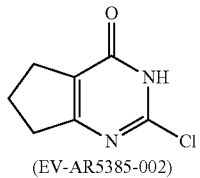

(EV-AR5385-002)

To a solution of 2,4-dichloro-5H,6H,7H-cyclopenta[d]pyrimidine (3 g, 15.87 mmol) in THF (15 mL) was added 6M aq NaOH solution (10 eq, 26.45 ml) and the reaction stirred at 50° C. for 48 h. The reaction mixture was concentrated in vacuo to remove the organic solvent. The resulting aqueous solution was acidified to pH 4 with 5M aq HCl solution and extracted with EtOAc (2×50 ml), dried over sodium sulfate and concentrated in vacuo to afford the title compound (2.09 g, 75%) as a pale orange powder.

Method B: LC-MS m/z=170.9 [M+H]⁺; RT=0.68 min.

Step 2: Synthesis of 2-{4-[4-(trifluoromethyl)piperidine-1-carbonyl]-1H-pyrazol-1-yl}-3H,4H,5H,6H,7H-cyclopenta[d]pyrimidin-4-one

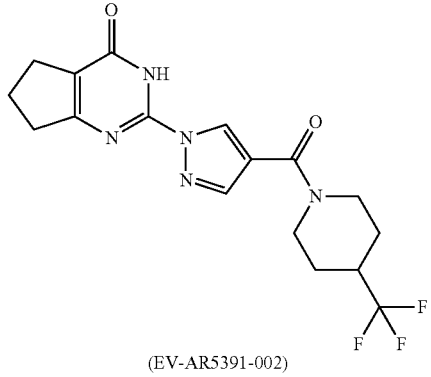 [SMILES: O=C(c1cnn(-c2nc3c(c(=O)[nH]2)CCC3)c1)N1CCC(C(F)(F)F)CC1]

(EV-AR5391-002)

To a solution of 2-chloro-3H,4H,5H,6H,7H-cyclopenta[d]pyrimidin-4-one (EV-AR5385-002, 200 mg, 1.17 mmol) in DMF (2 ml) was added 1-(1H-pyrazole-4-carbonyl)-4-(trifluoromethyl)piperidine (EV-AQ8818-001, 319 mg, 1.29 mmol), caesium carbonate (573 mg, 1.76 mmol), L-proline (54 mg, 0.47 mmol) and copper (I) iodide (45 mg, 0.23 mmol). The reaction mixture was then de-gassed and stirred at 120° C. for 20 h. The reaction mixture was concentrated in vacuo and then a 0.2M aq solution of EDTA (20 ml) and DCM (30 ml) were added and the mixture stirred at r.t. for 4 h. The organic phase was separated and the aqueous phase extracted with DCM (20 ml). The combined organic extracts were washed with water (10 ml), dried over sodium sulfate and concentrated in vacuo. Purification by PREP-HPLC (Method G) afforded the title compound (140 mg, 31%) as a beige powder.

Method C: LC-MS m/z=382.1 [M+H]⁺; RT=2.51 min

Example 194

The example in Table 15 was prepared by the procedure described in Example 192, starting instead with 2,4-dichlorothieno[3,2-d]pyrimidine.

TABLE 15

| Example No | Ref. No. | LBN | Structure | LC-MS (RT) Method C | MS (M + H)⁺ Method C |
|---|---|---|---|---|---|
| 194 | Q-517 | EV-AR5376-002 | 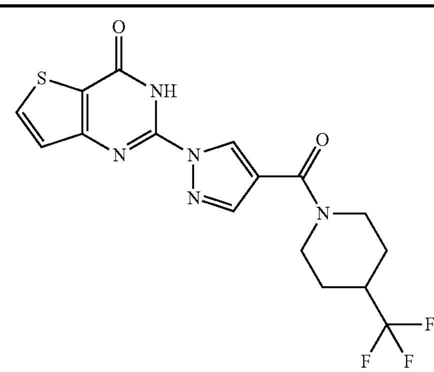 | 2.67 | 397.1 |

Example 195—Preparation of 2-{4-[4-(trifluoromethyL)piperidine-1-carbonyl]-1H-pyrazol-1-yl}-3H,4H,5H,7H-furo[3,4-d]pyrimidin-4-one (Q-453, EV-AQ8825-001)

Step 1: Synthesis of 2-chloro-3H,4H,5H,7H-furo[3,4-d]pyrimidin-4-one

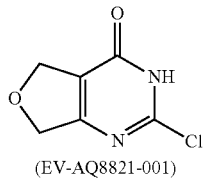 [SMILES: O=c1[nH]c(Cl)nc2c1COC2]

(EV-AQ8821-001)

To a stirred solution of 2,4-dichloro-5H,7H-furo[3,4-d]pyrimidine (EV-AQ8821-001, 1 g, 5.24 mmol) in THF (10 mL) was added 1M aq NaOH solution (10.5 mL, 10.5 mmol) and stirred at r.t. overnight. The solution was acidified to pH 4/5 with acetic acid and extracted with DCM (3×30 mL). The combined organic extracts were dried over MgSO₄ and concentrated in vacuo to afford the title compound (890 mg, 99%) as an orange powder.

1H NMR (500 MHz, DMSO-d6) δ 4.88 (t, J=3.3 Hz, 2H), 4.81 (t, J=3.3 Hz, 2H).

Step 2: Synthesis of 2-{4-[4-(trifluoromethyL)piperidine-1-carbonyl]-1H-pyrazol-1-yl}-3H,4H,5H,7H-furo[3,4-d]pyrimidin-4-one

Q-453

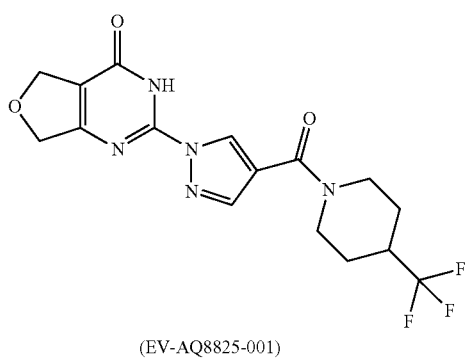

(EV-AQ8825-001)

To a stirred solution of 7-chloro-5H,6H-imidazo[1,2-c]pyrimidin-5-one (EV-AQ8821-001, 100 mg, 0.58 mmol) and caesium carbonate (283 mg, 0.87 mmol) in DMF (3 mL) was added 1-(1H-pyrazole-4-carbonyL)-4-(trifluoromethyL)piperidine (Intermediate V, EV-AQ8818-001, 143 mg, 0.58 mmol) and stirred under microwave conditions at 120° C. for 5 h. The reaction was cooled to r.t., concentrated in vacuo and purified via PREP-HPLC (Method G) to afford (59 mg, 27%) as a colourless powder.

Method C: LC-MS m/z=382.2 [M−H]⁺; RT=2.28 min

Example 196—Preparation of 6-methyl-2-[3-(1,2,3,4-tetrahydroisoquinoline-2-carbonyl)-1H-pyrazol-1-yl]-3,4-dihydropyrimidin-4-one (Q-308, EV-AN7470-001)

Step 1: Synthesis of 4-[(4-methoxyphenyl)methoxy]-6-methyl-2-(methylsulfanyl)pyrimidine

(EV-AN0086-002)

To solution of 6-methyl-2-(methylsulfanyl)-3,4-dihydropyrimidin-4-one Intermediate 1 Step 1 (EV-AO5743-001, 7 g, 44.8 mmol) in water (50 ml) and dioxane (100 ml) was added NaOH (2.15 g, 53.8 mmol) followed by 1-(chloromethyl)-4-methoxybenzene (8.42 g, 53.8 mmol) and stirred at 50° C. for 1 h. The reaction mixture was cooled to r.t. and the resultant precipitate filtered under vacuum and purified by chromatography on SiO₂, eluting with Heptane/EtOAc (gradient 100:0-0:100) to afford the title compound (1.54 g, 11.4%) as an oil.

Method A: LC-MS: m/z=+277.0 (M+H)+; RT=1.40 min.

Step 2: Synthesis of 2-methanesulfonyl-4-[(4-methoxyphenyl)methoxy]-6-methylpyrimidine

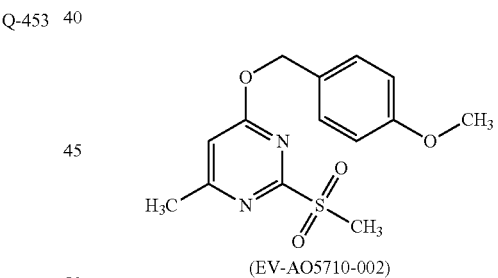

(EV-AO5710-002)

To a solution of 4-[(4-methoxyphenyl)methoxy]-6-methyl-2-(methylsulfanyl)pyrimidine (EV-AN0086-002, 1.5 g, 5.43 mmol) in DCM (15 mL) under nitrogen at 0° C. was added mCPBA (75%, 2.50 g, 10.86 mmol) and stirred at r.t. for 1 h. The reaction was diluted with chloroform (50 mL) and more mCPBA (200 mg, 0.87 mmol) was added and the reaction stirred at r.t. for a further 1 h. The reaction was quenched by addition of 0.5M aq sodium thiosulfate solution (20 mL). The organic layer was extracted and washed with saturated NaHCO₃ solution (3×20 mL), dried over Na₂SO₄ and concentrated in vacuo to afford the title compound (1.64 g, 104%) as a pale yellow oil.

Method A: LC-MS: m/z=+331.1 (M+Na)+, RT=1.23 min.

Step 3: Synthesis of ethyl 1-{4-[(4-methoxyphenyl)methoxy]-6-methylpyrimidin-2-yl}-1H-pyrazole-3-carboxylate

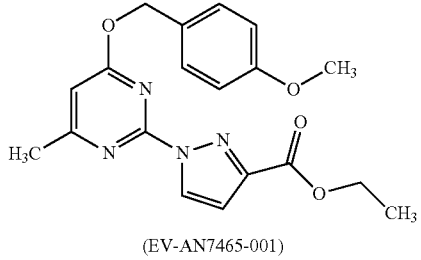 [SMILES: CCOC(=O)c1ccn(-c2nc(C)cc(OCc3ccc(OC)cc3)n2)n1]

(EV-AN7465-001)

To a solution of ethyl 1H-pyrazole-5-carboxylate (95.44 mg, 0.68 mmol) in DMF (5 mL) at 0° C. was added NaH (60% in oil, 31.13 mg, 0.78 mmol) and stirred at 0° C.—r.t. for 30 mins. 2-methanesulfonyl-4-[(4-methoxyphenyl)methoxy]-6-methylpyrimidine (EV-A05710-002, 200 mg, 0.65 mmol) in DMF (5 mL) was added and the reaction mixture stirred at r.t. for 1.5 h. The reaction mixture was quenched by the addition of water (10 mL) and extracted with EtOAc (3×15 mL). The combined organic fractions were washed with water (3×10 mL), brine solution (10 mL), dried over $Na_2SO_4$, and concentrated in vacuo. Purification by chromatography on $SiO_2$ eluting with Heptane/EtOAc (gradient 100:0-0:100) to afford the title compound (154 mg, 62.5%) as a clear oil.

Method A: LC-MS: m/z=391.1 (M+Na)+; RT=1.43.

Step 4: Intermediate 46 Synthesis of 1-{4-[(4-methoxyphenyl)methoxy]-6-methylpyrimidin-2-yl}-1H-pyrazole-3-carboxylic acid

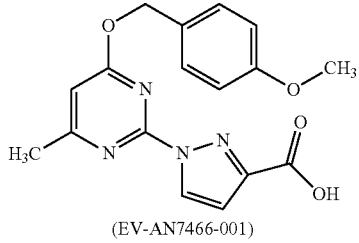

(EV-AN7466-001)

Ethyl 1-{4-[(4-methoxyphenyl)methoxy]-6-methylpyrimidin-2-yl}-1H-pyrazole-3-carboxylate (EV-AN7466-001, 125 mg, 0.34 mmol) was suspended in 2:2:1 THF/water/methanol (7.5 mL) and 2.5M aq NaOH solution (0.81 mL) was added. The reaction mixture was stirred at r.t. for 30 mins. The organics were removed in vacuo and the aqueous solution acidified with 2M aq HCl solution. The resultant precipitate was collected and dried under vacuum filtration. The filtrate was then extracted with EtOAc (2×10 mL) and the combined extracts dried over $Na_2SO_4$, concentrated in vacuo and combined with the precipitate to afford the title compound (115 mg, 93.6%) as an off white powder.

Method A: LC-MS: m/z=363.1 (M+Na)+; RT=1.24 min.

Step 5: Synthesis of 2-(1-{4-[(4-methoxyphenyl)methoxy]-6-methylpyrimidin-2-yl}-1H-pyrazole-3-carbonyl)-1,2,3,4-tetrahydroisoquinoline

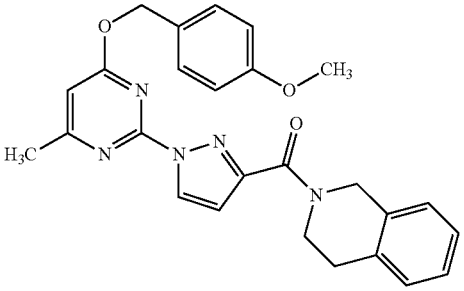

(EV-AN7468-001)

To a solution of 1-{4-[(4-methoxyphenyl)methoxy]-6-methylpyrimidin-2-yl}-1H-pyrazole-3-carboxylic acid (EV-AN7466-001, 115 mg, 0.34 mmol) in DMF (1.5 mL) was added COMU (159.18 mg, 0.37 mmol), DIPEA (0.14 mL, 0.84 mmol) and 1,2,3,4-tetrahydroisoquinoline (0.05 mL, 0.37 mmol) and stirred at r.t. overnight. To the reaction mixture was added ice water and extracted with EtOAc (2×5 mL). The combined organic extracts were washed with saturated $NaHCO_3$ solution (5 mL), brine solution (5 mL), dried over $Na_2SO_4$ and concentrated in vacuo. Purification by chromatography on $SiO_2$, eluting with Heptane/EtOAc (gradient 100:0-0:100), afforded the title compound (119 mg, 70.4%) as an opaque gum.

Method A: LC-MS: m/z=+456.0 (M+H)+; RT=1.52 min.

Step 6: Synthesis of 6-methyl-2-[3-(1,2,3,4-tetrahydroisoquinoline-2-carbonyl)-1H-pyrazol-1-yl]-3,4-dihydropyrimidin-4-one

Q-308

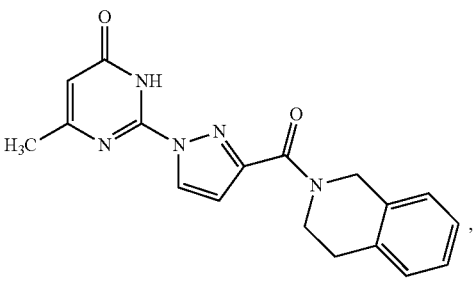

EV-AN7470-001

To a solution of 2-(1-{4-[(4-methoxyphenyl)methoxy]-6-methylpyrimidin-2-yl}-1H-pyrazole-3-carbonyl)-1,2,3,4-tetrahydroisoquinoline (EV-AN7468-001, 89 mg, 0.2 mmol) in DCM (2 mL) was added TFA (0.16 mL) and stirred at r.t. for 2 h. The reaction mixture was concentrated in vacuo, re-dissolved in DCM, washed with saturated $NaHCO_3$ solution, dried over $Na_2SO_4$ and concentrated in vacuo. Purification by PREP-HPLC (Method G) method followed by a free base with saturated $NaHCO_3$ solution afforded the title compound (35.7 mg, 54.5%) as an off white solid.

Method A: LC-MS: m/z=+336.1 (M+H)+; RT=2.50.

Examples 197-198

The examples in Table 16 were made in an analogous manner to example 197 coupling Intermediate 46 with the appropriate amine followed by deprotection.

TABLE 16

| Example No | Route | Ref. No. | LBN | Structure | LC-MS (RT) Method C | MS (M + H)+ Method C |
|---|---|---|---|---|---|---|
| 197 | 5a | Q-343 | EV-AN7493-001 | 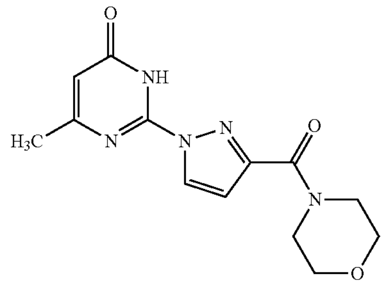 [SMILES: Cc1cc(=O)[nH]c(-n2ccc(C(=O)N3CCOCC3)n2)n1] | 1.48 | 290.1 |
| 198 | 5a | Q-333 | EV-AN7492-001 | 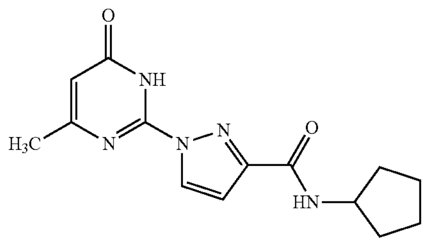 [SMILES: Cc1cc(=O)[nH]c(-n2ccc(C(=O)NC3CCCC3)n2)n1] | 2.24 | 288.1 |

Example 199—2-{3,5-dimethyl-4-[2-oxo-2-(pyrrolidin-1-yl)ethyl]-1H-pyrazol-1-yl}-6-methyl-3,4-dihydropyrimidin-4-one EV-AN7461-001

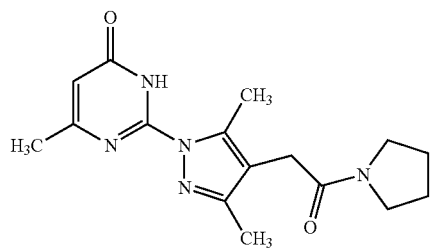

Q-301

The title compound (20.1 mg, 25.6%) was prepared in an analogous manner to Example 196, reacting ethyl 2-(3,5-dimethyl-1H-pyrazol-4-yl)acetate with Example 196 step 2 using HATU for the coupling with pyrrolidine.

Method C: LC-MS: m/z=316.2 (M+H)+; RT=2.05 min.

Example 200—Preparation of 6-methyl-2-[5-methyl-3-(1,2,3,4-tetrahydroisoquinoline-2-carbonyl)-1H-pyrazol-1-yl]-3,4-dihydropyrimidin-4-one (Q-365, EV-AO7568-002)

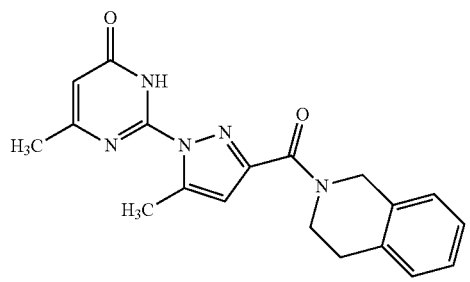 [SMILES: Cc1cc(=O)[nH]c(-n2nc(C(=O)N3CCc4ccccc4C3)cc2C)n1]

Step 1: Synthesis of ethyl-1-{4-[(4-methoxyphenyl)methoxy]-6-methylpyrimidin-2-yl}-5-methyl-1H-pyrazole-3-carboxylate

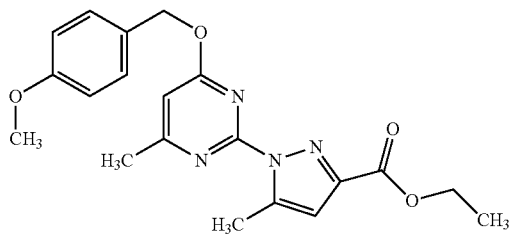

(EV-AO7559-002)

To a solution of 2-methanesulfonyl-4-[(4-methoxyphenyl)methoxy]-6-methylpyrimidine (Example 196 Step 2, 500 mg, 1.622 mmol) in DMF (10 mL) at 0° C. was added NaH (60% in oil) (60%, 78 mg, 1.946 mmol) and then ethyl 5-methyl-1H-pyrazole-3-carboxylate (275 mg, 1.784 mmol) and the reaction mixture stirred at r.t. for 2 h. The reaction mixture was quenched by the addition of water (10 mL) and extracted with EtOAc (3×20 mL). The combined organic extracts were washed with water (2×10 mL), brine solution (10 mL), dried over $Na_2SO_4$, concentrated in vacuo and purified via chromatography on $SiO_2$ (gradient 100:0-0:100, Heptane-EtOAc), to afford the title compound (406 mg, 65%) as a colourless oil.

Method A: LC-MS m/z=383.1 [M+H]+; RT=1.45 min.

Step 2: Synthesis of 1-{4-[(4-methoxyphenyl)methoxy]-6-methylpyrimidin-2-yl}-5-methyl-1H-pyrazole-3-carboxylic acid

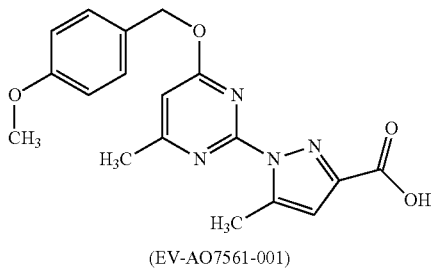 [SMILES: COc1ccc(COc2cc(C)nc(-n3nc(C(=O)O)cc3C)n2)cc1]

(EV-AO7561-001)

To a solution of ethyl 1-{4-[(4-methoxyphenyl)methoxy]-6-methylpyrimidin-2-yl}-5-methyl-1H-pyrazole-3-carboxylate (EV-AO7559-002, 406 mg, 1.062 mmol) in 2:2:1 THF/water/methanol (25 mL) was added 2.5M aqueous NaOH (2.55 ml) and the reaction mixture stirred at r.t. overnight. The reaction mixture was concentrated in vacuo and the residue acidified with 2M aq HCl solution to pH 6 to afford a white precipitate which was filtered and dried under vacuum to give the title compound (340 mg, 90%) as a white powder.

Method A: LC-MS m/z=377.0 [M+H]$^+$; RT=1.26 min.

Step 3: Synthesis of 2-(1-{4-[(4-methoxyphenyl)methoxy]-6-methylpyrimidin-2-yl}-5-methyl-1H-pyrazole-3-carbonyl)-1,2,3,4-tetrahydroisoquinoline

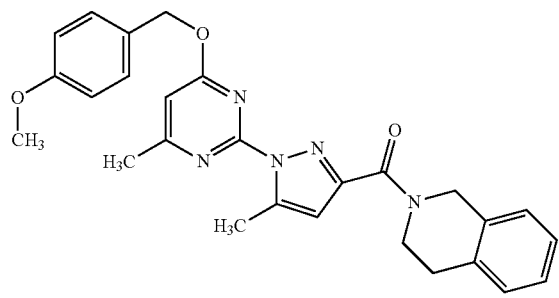

(EV-AO7563-002)

To a stirred solution of 5-methyl-1-(4-methyl-6-oxo-1,6-dihydropyrimidin-2-yl)-1H-pyrazole-4-carboxylic acid (EV-AO7561-001, 150 mg, 0.423 mmol) in DMF (2 ml) were added COMU (199 mg, 0.466 mmol), DIPEA (181 μl, 1.058 mmol) and 1,2,3,4-tetrahydroisoquinoline (59 μl, 0.466 mmol). The resulting mixture was stirred at r.t. for 2 h. The reaction mixture was concentrated in vacuo to remove the DMF and the crude residue redissolved in water (50 ml). The reaction mixture was quenched by addition of saturated sodium bicarbonate solution (20 ml) extracted with DCM (3×100 ml). The combined organic extracts were dried over sodium sulphate, concentrated in vacuo and purified via chromatography on SiO$_2$ (gradient 100:0-0:100, Heptane-EtOAc) to afford the title compound (152 mg, 61%) as a yellow viscous oil.

Method A: LC-MS m/z=470.2 [M+H]$^+$; RT=1.51 min.

Step 4: Synthesis of 6-methyl-2-[5-methyl-3-(1,2,3,4-tetrahydroisoquinoline-2-carbonyl)-1H-pyrazol-1-yl]-3,4-dihydropyrimidin-4-one

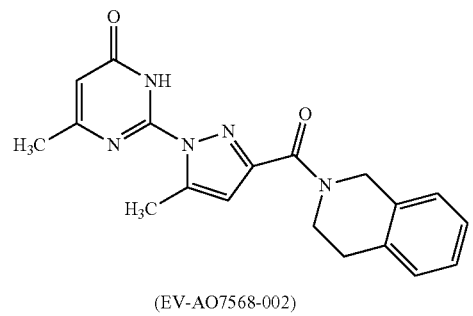

Q-365

(EV-AO7568-002)

2-(1-{4-[(4-methoxyphenyl)methoxy]-6-methylpyrimidin-2-yl}-5-methyl-1H-pyrazole-3-carbonyl)-1,2,3,4-tetrahydroisoquinoline (EV-AO7563-002, 80%, 152 mg, 0.259 mmol) was dissolved in MeOH (10 mL) and subjected to H-cube conditions (1 ml/min, 1 bar, 50° C., Full H2 mode) over a Pd/C (10%) cat cartridge. The solvent was then removed in vacuo and the residue purified by trituration using MeCN to afford the title compound (61 mg, 67%) as a white powder.

Method C: LC-MS m/z=350.2 [M+H]$^+$; RT=2.81 min

Example 201—Synthesis of 6-methyl-2-[5-methyl-3-(1,2,3,4-tetrahydroisoquinoline-2-carbonyl)-1H-pyrazol-1-yl]-3,4-dihydropyrimidin-4-one

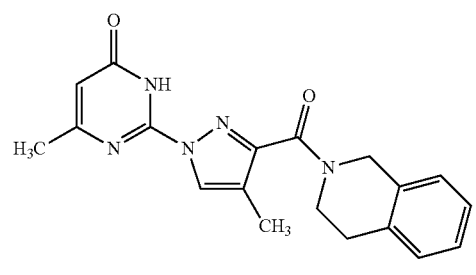

Q-366

(EV-AO7569-002)

The title compound was prepared analogously to Example 200 using ethyl 4-methyl-1H-pyrazole-3-carboxylate in place of ethyl 5-methyl-1H-pyrazole-3-carboxylate.

Method C: LC-MS m/z=350.2 [M+H]$^+$; RT=2.81 min.

Example 203—Preparation of 2-{4-[4-(trifluoromethyl)piperidine-1-carbonyl]-1H-pyrazol-1-yl}-3H,4H-pyrrolo[2,1-f][1,2,4]triazin-4-one (Q-467, EV-AQ3851-002)

Step 1: Synthesis of 2-methanesulfonyl-3H,4H-pyrrolo[2,1-f][1,2,4]triazin-4-one

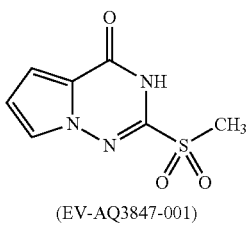

(EV-AQ3847-001)

To 2-(methylsulfanyl)-3H,4H-pyrrolo[2,1-f][1,2,4] triazin-4-one (900 mg, 4.97 mmol) in AcOH (18 ml) was added hydrogen peroxide (35%, 8.7 ml, 0.1 mol) and the resultant suspension was stirred r.t. for 39 h, during which time the suspension dissolved and a precipitate formed. The precipitate was collected by vacuum filtration, washed with water followed by ether to afford the title compound (950 mg, 88%) as a white solid.

Method B: LC-MS m/z=213.9 [M+H]$^+$; RT=0.73 min.

Step 2: Synthesis of 2-{4-[4-(trifluoromethyl)piperidine-1-carbonyl]-1H-pyrazol-1-yl}-3H,4H-pyrrolo[2,1-f][1,2,4]triazin-4-one

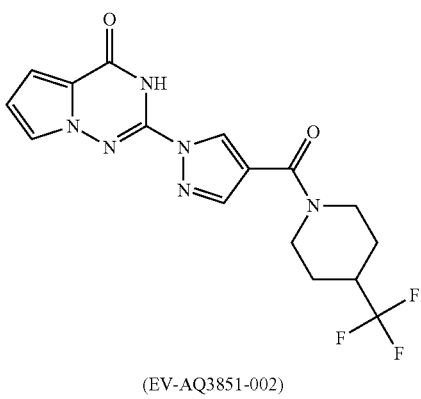 [SMILES: O=C(c1cnn(-c2nn3cccc3c(=O)[nH]2)c1)N1CCC(C(F)(F)F)CC1]

(EV-AQ3851-002)

1-(1H-pyrazole-4-carbonyl)-4-(trifluoromethyl)piperidine (EV-AQ3840-001, 243.49 mg, 0.98 mmol) was added to a solution of 2-methanesulfonyl-3H,4H-pyrrolo[2,1-f][1,2,4]triazin-4-one (200 mg, 0.94 mmol) and caesium carbonate (458.44 mg, 1.41 mmol) in DMF (4 ml) and stirred under microwave conditions at 175° C. for 9 h. The reaction mixture was concentrated in vacuo, redissolved in water and extracted with EtOAc (×2). The combined organic extracts were washed with brine, dried over MgSO$_4$ and concentrated in vacuo to afford a clear gum. Purification by PREP-HPLC afforded the title compound (37 mg, 10%) as a white solid. Meanwhile a solid had precipitated from the aqueous, the solid was collected under vacuum filtration, washed with water followed by ether and dried under vacuum overnight to afford a further batch of the title compound (113 mg, 32%) as a white solid.

Method C: LC-MS m/z=380.0 [M+H]$^+$; RT=2.66 min.

Example 204—Preparation of 6-methyl-2-{1-[3-oxo-3-(1,2,3,4-tetrahydroisoquinolin-2-yl)propyl]-1H-pyrazol-4-yl}-3,4-dihydropyrimidin-4-one (Q-291, EV-AN7447-001) and Example 205—4-methyl-6-{1-[3-oxo-3-(1,2,3,4-tetrahydroisoquinolin-2-yl)propyl]-1H-pyrazol-4-yl}-1,2-dihydropyrimidin-2-one (Q-292, EV-AN7447-002)

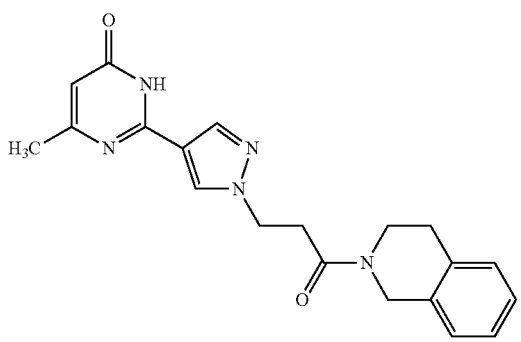

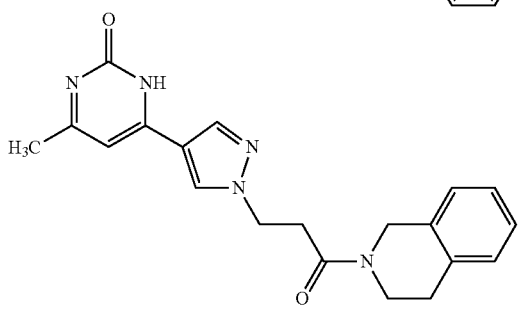

Step 1: Synthesis of ethyl 3-[3,5-dimethyl-4-(tetramethyl-1,3,2-dioxaborolan-2-yl)-1H-pyrazol-1-yl]propanoate

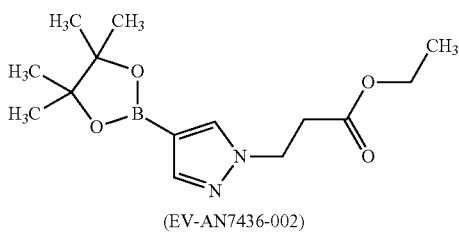 [SMILES: CCOC(=O)CCn1cc(B2OC(C)(C)C(C)(C)O2)cn1]

(EV-AN7436-002)

To a solution of pyrazole-4-boronic acid pinacol ester (500 mg, 2.58 mmol) in acetonitrile (10 mL) was added ethyl acrylate (0.42 mL, 3.87 mmol), followed by DBU (0.39 mL, 2.58 mmol) and stirred at r.t. for 15.5 h. The reaction mixture was concentrated in vacuo and purified by chromatography on SiO$_2$, eluting with Heptane/EtOAc (gradient 100:0-0:100) to afford the title compound (310 mg, 38%) as a clear oil.

Method A: LC-MS: m/z=+295.0 (M+H)+; RT=1.25 min.

Step 2: Synthesis of 2-chloro-4-methyl-6-[2-(trimethylsilyl)ethoxy]pyrimidine and 4-chloro-6-methyl-2-[2-(trimethylsilyl)ethoxy]pyrimidine

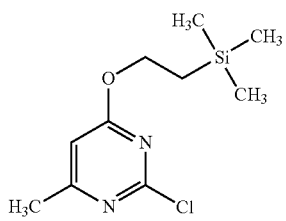

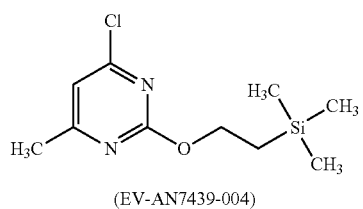

(EV-AN7439-004)

To a stirred solution of 2-(trimethylsilyl)ethanol (3.5 mL) in THF (7 mL) at 0° C. was added NaH (60% in oil, 490.74 mg, 12.27 mmol). The reaction mixture was warmed to r.t. over 15 mins and then cooled again to 0° C. To the reaction mixture was added 2,4-dichloro-6-methylpyrimidine (2 g, 12.27 mmol) in THF (8 mL) and stirred at 0° C. for 1.5 h. The reaction mixture was quenched by the addition of saturated NH$_4$Cl aqueous solution (10 mL) and extracted with EtOAc (3×25 mL). The combined organic extracts were washed with brine solution (10 mL), dried over Na$_2$SO$_4$ and concentrated in vacuo. Purification by chromatography on SiO$_2$, eluting with Heptane/EtOAc (gradient 100:0-50:50) to afford the title compound (2.21 g, 72.2%, 2.7:1 mixture of regioisomers) as a white solid.

Method A: LC-MS: m/z=216.9, 218.9 (M+H)+; RT=1.62 min.

Step 3: Synthesis of ethyl 3-(4-{4-methyl-6-[2-(trimethylsilyl)ethoxy]pyrimidin-2-yl}-1H-pyrazol-1-yl)propanoate and ethyl 3-(4-{6-methyl-2-[2-(trimethylsilyl)ethoxy]pyrimidin-4-yl}-1H-pyrazol-1-yl)propanoate

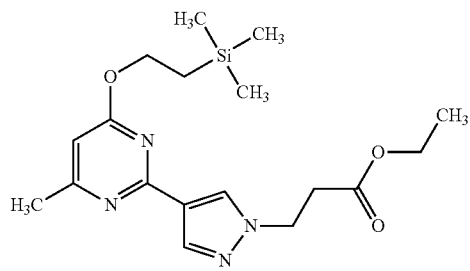

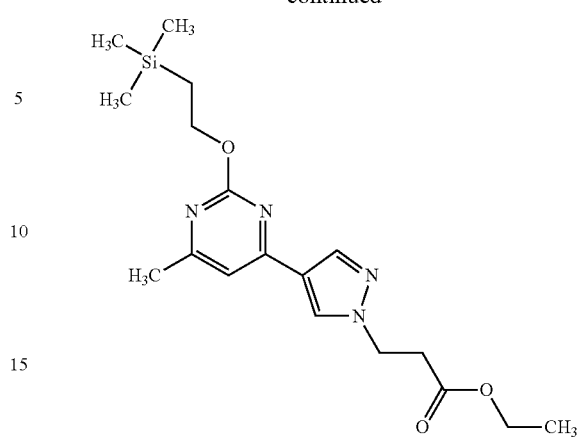

(EV-AN7442-001)

To a solution of 2-chloro-4-methyl-6-[2-(trimethylsilyl)ethoxy]pyrimidine (EV-AN7439-004,185 mg as a mixture of regioisomers, 0.76 mmol), ethyl 3-[4-(tetramethyl-1,3,2-dioxaborolan-2-yl)-1H-pyrazol-1-yl]propanoate (EV-AN7436-002, 93%, 358.56 mg, 1.13 mmol) and CsF (172.2 mg, 1.13 mmol) in DME, ethanol (2:1, 7.5 mL) was added Pd(PPh$_3$)$_4$ (87.33 mg, 0.08 mmol) and stirred under microwave conditions at 120° C. for 15 mins. The reaction mixture was cooled to r.t. and water (10 mL) and EtOAc (15 mL) were added. The organic fraction was extracted and the aqueous phase re-extracted with more EtOAc (2×5 mL). The combined organics were washed with brine solution (5 mL), dried over Na$_2$SO$_4$ and concentrated in vacuo. Purification by chromatography on SiO$_2$ eluting with Heptane/EtOAc (gradient 100:0-0:100) to afford the title compound (285 mg, 81.1%, 2:1 mixture of regioisomers) as a clear oil.

Method A: LC-MS: m/z=+377.2 (M+H)+; RT=1.45 min.

Step 4: Synthesis 3-(4-{4-methyl-6-[2-(trimethylsilyl)ethoxy]pyrimidin-2-yl}-1H-pyrazol-1-yl)propanoic acid and 3-(4-{6-methyl-2-[2-(trimethylsilyl)ethoxy]pyrimidin-4-yl}-1H-pyrazol-1-yl)propanoic acid

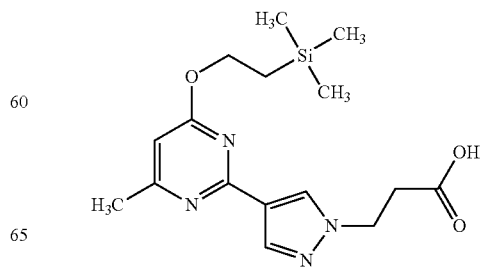

-continued

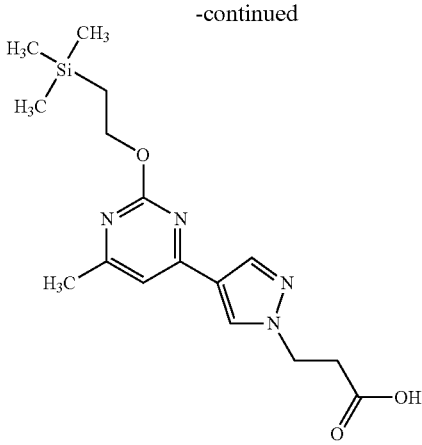

(EV-AN7445-001)

Ethyl 3-(4-{4-methyl-6-[2-(trimethylsilyl)ethoxy]pyrimidin-2-yl}-1H-pyrazol-1-yl)propanoate (EV-AN7442-001, 285 mg (as a mixture of regioisomers), 0.76 mmol) was suspended in 2:2:1 THF/water/methanol (12.5 mL) and sodium hydroxide (147.13 mg, 3.68 mmol) was added. The reaction mixture was stirred at r.t. for 1 h. The organics were removed in vacuo and the aqueous solution acidified with 2M aq HCl solution and extracted with EtOAc (2×10 mL). The combined organics were dried over $Na_2SO_4$ and concentrated in vacuo to afford the title compound (239 mg, 94%, 2:1 mixture of regioisomers) as a colourless oil.

Method A: LC-MS: m/z=+349.2 (M+H)+; RT=1.27 min.

Step 5: Synthesis of 3-(4-{4-methyl-6-[2-(trimethylsilyl)ethoxy]pyrimidin-2-yl}-1H-pyrazol-1-yl)-1-(1,2,3,4-tetrahydroisoquinolin-2-yl)propan-1-one and 3-(4-{6-methyl-2-[2-(trimethylsilyl)ethoxy]pyrimidin-4-yl}-1H-pyrazol-1-yl)-1-(1,2,3,4-tetrahydroisoquinolin-2-yl)propan-1-one

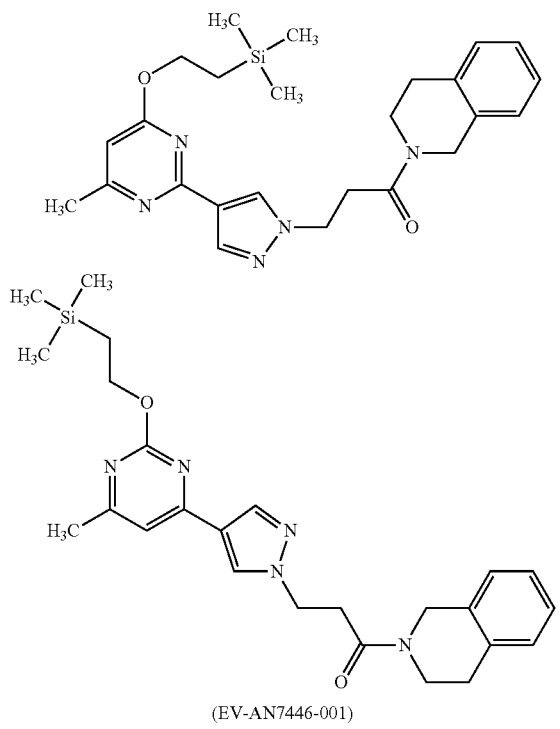

(EV-AN7446-001)

To a solution of 3-(4-{4-methyl-6-[2-(trimethylsilyl)ethoxy]pyrimidin-2-yl}-1H-pyrazol-1-yl)propanoic acid (EV-AN7445-001, 120 mg (as a mixture of regioisomers), 0.29 mmol) in DMF (4 ml) was added TBTU (278.63 mg, 0.87 mmol), DIPEA (0.12 mL, 0.72 mmol) and 1,2,3,4-tetrahydroisoquinoline (0.06 mL, 0.43 mmol) and stirred at r.t. for 15 h. To the reaction mixture was added ice water and extracted with EtOAc (2×5 mL). The combined organic extracts were washed with brine (5 mL), dried over $Na_2SO_4$ and concentrated in vacuo to afford the title compound (162 mg, 87%, as a mixture of regioisomers) as a colourless oil.

Method: LC-MS: m/z=+464.2 (M+H)+; RT=1.47 min.

Step 6: Synthesis of 6-methyl-2-{1-[3-oxo-3-(1,2,3,4-tetrahydroisoquinolin-2-yl)propyl]-1H-pyrazol-4-yl}-3,4-dihydropyrimidin-4-one (Q-291, EV-AN7447-001) and 4-methyl-6-{1-[3-oxo-3-(1,2,3,4-tetrahydroisoquinolin-2-yl)propyl]-1H-pyrazol-4-yl}-1,2-dihydropyrimidin-2-one 3-(4-{4-methyl-6-[2-(trimethylsilyl)ethoxy]pyrimidin-2-yl}-1H-pyrazol-1-yl)-1-(1,2,3,4-tetrahydroisoquinolin-2-yl)propan-1-one (EV-AN7446-001, 162 mg (as a mixture of regioisomers), 0.25 mmol) was dissolved in DCM (4 mL) and TFA (1 mL) was added. The reaction mixture was stirred for 1.5 h and then concentrated in vacuo. The crude residue was re-dissolved in DCM and washed with saturated $NaHCO_3$ solution, dried over $Na_2SO_4$ and concentrated in vacuo afforded the title compounds as a mixture of regioisomers.

Purification by PREP-HPLC (Method G) afforded the first eluting isomer 6-methyl-2-{1-[3-oxo-3-(1,2,3,4-tetrahydroisoquinolin-2-yl)propyl]-1H-pyrazol-4-yl}-3,4-dihydropyrimidin-4-one, Example 204 (Q-291, EV-AN7447-001) (20.2 mg, 22.1%) as an off white powder.

Method C: LC-MS: m/z=364.2 (M+H)+; RT=2.02

The second eluting isomer 4-methyl-6-{1-[3-oxo-3-(1,2,3,4-tetrahydroisoquinolin-2-yl)propyl]-1H-pyrazol-4-yl}-1, 2-dihydropyrimidin-2-one Example 205 (Q-292, EV-AN7447-002) (12.2 mg, 12.5%) was isolated as a beige powder.

Example 206—6-methyl-2-{1-[3-oxo-3-(pyrrolidin-1-yl)propyl]-1H-pyrazol-4-yl}-3,4-dihydropyrimidin-4-one (Q-283, EV-AN7448-001)

The title compound was prepared in an analogous manner to Example 204 provide the title compound (12.02 mg, 16.6%). The regioisomer could not be obtained in sufficient purity for testing.
Method C: LC-MS: m/z=302.1 (M+H)+; RT=1.40

Example 207—2-{3,5-dimethyl-1-[3-oxo-3-(1,2,3,4-tetrahydroisoquinolin-2-yl)propyl]-1H-pyrazol-4-yl}-6-methyl-3,4-dihydropyrimidin-4-one

Q-284

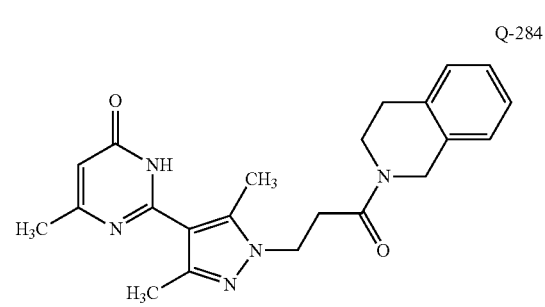 [SMILES: Cc1cc(=O)[nH]c(-c2c(C)nn(CCC(=O)N3CCc4ccccc4C3)c2C)n1]

The title compound was prepared in an analogous fashion to Example 204 using 3,5-dimethyl-4-(tetramethyl-1,3,2-dioxaborolan-2-yl)-1H-pyrazole in step 1 to provide the title compound (21.9 mg, 38.5).
Method C: LC-MS: m/z=392.2 (M+H)+; RT=2.15

Example 208—4-{3,5-dimethyl-1-[3-oxo-3-(1,2,3,4-tetrahydroisoquinolin-2-yl)propyl]-1H-pyrazol-4-yl}-6-methyl-1,2-dihydropyrimidin-2-one (Q-285, EV-AN7453-002)

The title compound was prepared in an analogous fashion to Example 204 using 3,5-dimethyl-4-(tetramethyl-1,3,2-dioxaborolan-2-yl)-1H-pyrazole in step 1 to provide the title compound (17.5 mg, 31.1).
Method C: LC-MS: m/z=392.2 (M+H)+; RT=1.82 min.

Example 209—2-{3,5-dimethyl-1-[3-oxo-3-(pyrrolidin-1-yl)propyl]-1H-pyrazol-4-yl}-6-methyl-3,4-dihydropyrimidin-4-one

Q-306

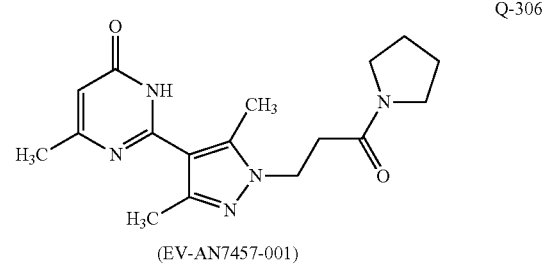 [SMILES: Cc1cc(=O)[nH]c(-c2c(C)nn(CCC(=O)N3CCCC3)c2C)n1]

(EV-AN7457-001)

The title compound (20.1 mg, 25.6%) was prepared in an analogous manner to Example 208 coupling with pyrrolidine.
Method C: LC-MS: m/z=330.2 (M+H)+; RT=1.57 min.

Example 210—Preparation of 4-methyl-6-{5-methyl-4-[4-(trifluoromethyl)piperidine-1-carbonyl]-1H-pyrazol-1-yl}-1,2-dihydropyridin-2-one (Q-439, EV-AQ8815-001) and Example 211—4-methyl-6-{3-methyl-4-[4-(trifluoromethyL)piperidine-1-carbonyl]-1H-pyrazol-1-yl}-1,2-dihydropyridin-2-one (Q-440, EV-AQ8815-002)

Step 1: Synthesis of 6-chloro-2-hydrazinylidene-4-methyl-1,2-dihydropyridine

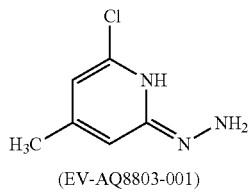

(EV-AQ8803-001)

2,6-dichloro-4-methylpyridine (102 mg, 0.63 mmol) was heated to ~110° C. in hydrazine hydrate (1 mL) for 3 hours. The solution was cooled to 0° C. and water (3 mL) was added. The resulting precipitate was isolated via filtration and washed with ice-cold water to yield 6-chloro-2-hydrazinylidene-4-methyl-1,2-dihydropyridine (32 mg, 32%) as a pale yellow powder.
LC-MS m/z=157.9 [M+H]+; RT=0.42 min.

Step 2: Synthesis of 2-chloro-4-methyl-6-{5-methyl-4-[4-(trifluoromethyL)piperidine-1-carbonyl]-1H-pyrazol-1-yl}pyridine and 2-chloro-4-methyl-6-{3-methyl-4-[4-(trifluoromethyl)piperidine-1-carbonyl]-1H-pyrazol-1-yl}pyridine

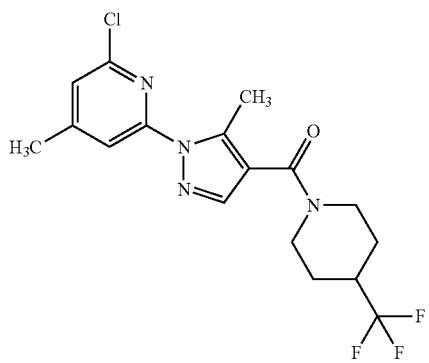

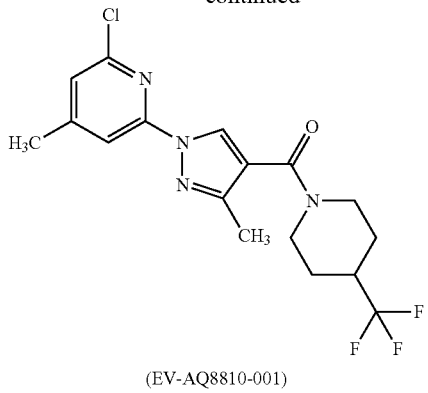

(EV-AQ8810-001)

To a stirred solution of (2E)-2-[(dimethylamino)methylidene]-1-[4-(trifluoromethyL)piperidin-1-yl]butane-1,3-dione (EV-AP2353-001, 927 mg, 3.17 mmol) in EtOH (7 mL) and AcOH (635 µL 11.1 mmol) was added 2-chloro-6-hydrazinyl-4-methylpyridine (500 mg, 3.17 mmol) and the reaction mixture was stirred at 80° C. overnight. The reaction was cooled ant the solvent removed in vacuo, the resulting residue was partitioned between DCM (50 mL) and sat. NaHCO₃ (60 mL), the aqueous fraction was extracted with DCM (2×50 mL) and the combined organic fractions were dried (MgSO₄) and concentrated in vacuo to yield 2-chloro-4-methyl-6-{5-methyl-4-[4-(trifluoromethyL)piperidine-1-carbonyl]-1H-pyrazol-1-yl}pyridine (1.08 g, 88%, mixture of regioisomers) as a yellow powder.

LC-MS m/z=387.1 [M+H]⁺; RT=1.41-1.43 min.

Step 3: Synthesis of 2-(benzyloxy)-4-methyl-6-{5-methyl-4-[4-(trifluoromethyL)piperidine-1-carbonyl]-1H-pyrazol-1-yl}pyridine and 2-(benzyloxy)-4-methyl-6-{3-methyl-4-[4-(trifluoromethyl)piperidine-1-carbonyl]-1H-pyrazol-1-yl}pyridine

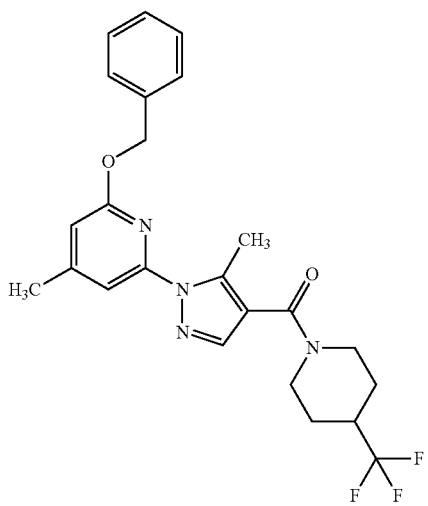

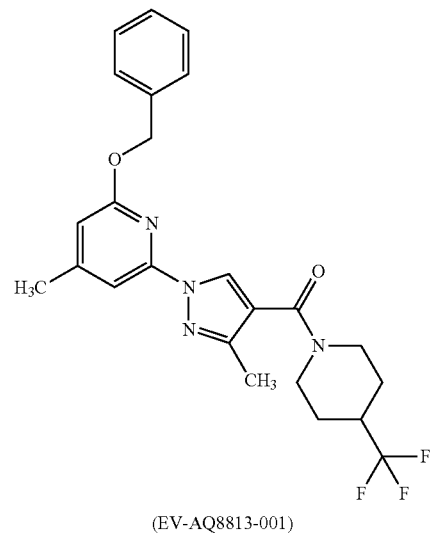

(EV-AQ8813-001)

To a stirred solution of 2-chloro-4-methyl-6-{5-methyl-4-[4-(trifluoromethyL)piperidine-1-carbonyl]-1H-pyrazol-1-yl}pyridine (1.08 g, 2.79 mmol) (Crude mixture from containing regioisomers) in dioxane (15 mL) was added phenylmethanol (0.32 mL, 3.07 mmol), followed by t-BuOK (345 mg, 3.07 mmol) and the solution was heated to reflux overnight. A further 1.1 equivalents of t-BuOK (345 mg, 3.07 mmol) and phenylmethanol (0.32 mL, 3.07 mmol) were added and the reaction was refluxed for a further 3 hours. Saturated NH₄Cl (50 mL) was added to the cooled solution and the mixture was extracted with EtOAc (2×80 mL), the combined organic fractions were dried over MgSO₄, the solvent removed in vacuo and the resulting residue purified via chromatography on SiO₂ eluting with 0:100-100:0 EtOAc-heptane) to afford the title compounds (593 mg, 82%, mixture of isomers) as an off-white powder.

LC-MS m/z=459.2 [M+H]⁺; RT=1.56-1.60 min.

Step 4: Synthesis of 4-methyl-6-{5-methyl-4-[4-(trifluoromethyL)piperidine-1-carbonyl]-1H-pyrazol-1-yl}-1,2-dihydropyridin-2-one and 4-methyl-6-{3-methyl-4-[4-(trifluoromethyl)piperidine-1-carbonyl]-1H-pyrazol-1-yl}-1,2-dihydropyridin-2-one

Q-439

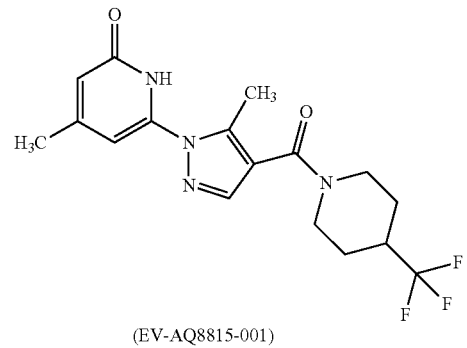

(EV-AQ8815-001)

-continued

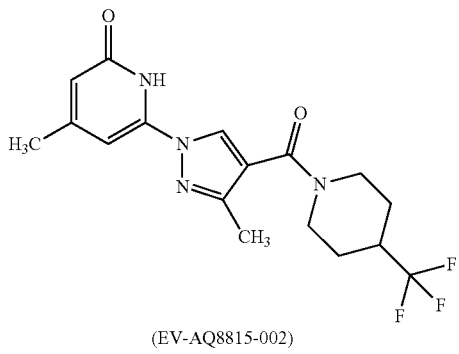

(EV-AQ8815-002)

To a stirred solution of 2-(benzyloxy)-4-methyl-6-{5-methyl-4-[4-(trifluoromethyL)piperidine-1-carbonyl]-1H-pyrazol-1-yl}pyridine (530 mg, 1.16 mmol, as a mixture of regioisomers) in EtOAc (25 mL) was added Pd on carbon (10%, 100 mg) and the solution exposed to an atmosphere of H$_2$ (g) overnight. The solution was filtered through celite washing with EtOAc, the filtrate concentrated in vacuo and the residue purified via PREP-HPLC (Method G) to yield 4-methyl-6-{5-methyl-4-[4-(trifluoromethyL)piperidine-1-carbonyl]-1H-pyrazol-1-yl}-1,2-dihydropyridin-2-one (42 mg, 10%) as a yellow powder and 4-methyl-6-{3-methyl-4-[4-(trifluoromethyL)piperidine-1-carbonyl]-1H-pyrazol-1-yl}-1,2-dihydropyridin-2-one (118 mg, 28%) as a yellow powder.

LC-MS m/z=369.1 [M+H]$^+$; RT=3.46 min.

Q-440

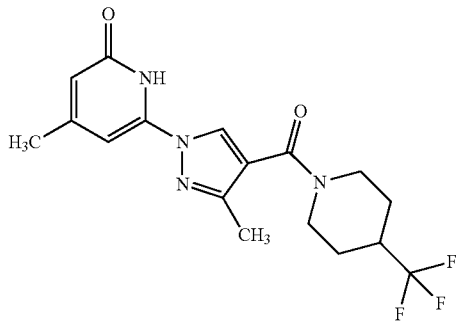

(EV-AQ8815-002)

LC-MS m/z=369.1 [M+H]$^+$; RT=3.67 min

Example 212—Preparation of 4-methyl-6-{4-[4-(trifluoromethyl)piperidine-1-carbonyl]-1H-pyrazol-1-yl}-1,2-dihydropyridin-2-one, Q-460, EV-AQ7135-001

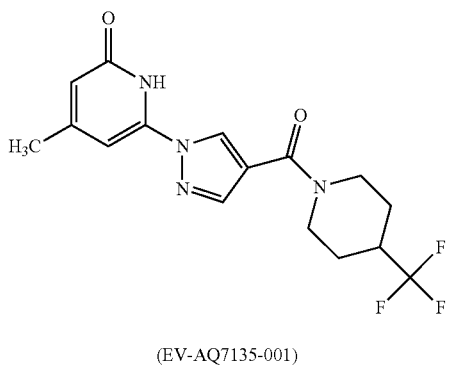 [SMILES: Cc1cc(-n2cc(C(=O)N3CCC(C(F)(F)F)CC3)cn2)[nH]c(=O)c1]

(EV-AQ7135-001)

Step 1: Synthesis of 2-chloro-4-methyl-6-{4-[4-(trifluoromethyl)piperidine-1-carbonyl]-1H-pyrazol-1-yl}pyridine

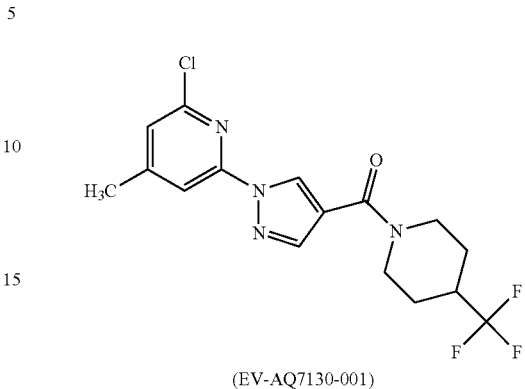

(EV-AQ7130-001)

To a solution of 1-(1H-pyrazole-4-carbonyl)-4-(trifluoromethyl)piperidine (EV-AQ8818-001, 91.55 mg, 0.37 mmol) and caesium carbonate (150.83 mg, 0.46 mmol) in DMF (2 mL) was added 2,6-dichloro-4-methylpyridine (50 mg, 0.31 mmol). The reaction mixture was stirred at 100° C. for 6 h. The reaction mixture was concentrated under vacuum. The residue was diluted with water and extracted with EtOAc. The organics were washed with brine (×2), dried over Na$_2$SO$_4$ and concentrated under vacuum. The crude residue was purified by chromatography on SiO$_2$ eluting with 0-100% EtOAc in heptane to afford the title compound (45 mg, 39.1%) as an off-white powder.

Method A: LC-MS: m/z=373.1 (M+H)+; RT=1.43 min.

Step 2: Synthesis of 2-(benzyloxy)-4-methyl-6-{4-[4-(trifluoromethyl)piperidine-1-carbonyl]-1H-pyrazol-1-yl}pyridine

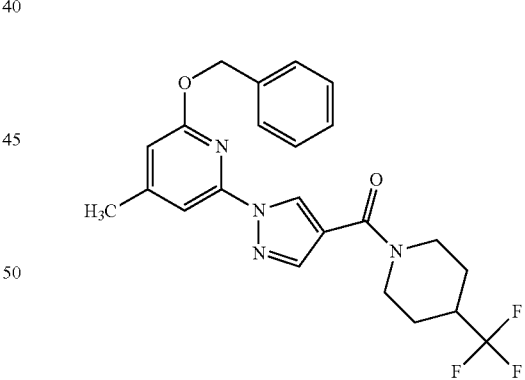

(EV-AQ7129-002)

To a solution of 2-chloro-4-methyl-6-{4-[4-(trifluoromethyl)piperidine-1-carbonyl]-1H-pyrazol-1-yl}pyridine (EV-AQ7130-001, 45 mg, 0.12 mmol) in dioxane (2 mL) was added benzyl alcohol (0.01 mL, 0.13 mmol) and potassium tert-butoxide (14.9 mg, 0.13 mmol) and the solution was heated at 90° C. for 4 h. The reaction mixture was concentrated under vacuum and purified by chromatography on SiO$_2$ eluting with 0-100% EtOAc in heptane to afford the title compound (72 mg, 33.5%).

Method A: LC-MS: m/z=445.1 (M+H)+; RT=1.60 min.

Step 3: Synthesis of 4-methyl-6-{4-[4-(trifluoromethyl)piperidine-1-carbonyl]-1H-pyrazol-1-yl}-1,2-dihydropyridin-2-one, Q-460, EV-AQ7135-001

Pd on carbon (10%, 17 mg) was added to a stirred solution of 2-(benzyloxy)-4-methyl-6-{4-[4-(trifluoromethyl)piperidine-1-carbonyl]-1H-pyrazol-1-yl}pyridine (EV-AQ7129-002, 72 mg, 0.16 mmol) in ethanol (5.0 mL) and the solution was stirred under an atmosphere of $H_2$ overnight. More Pd on carbon (10%, 17 mg) was added to the reaction and the stir under an atmosphere of $H_2$ was continued for a further 5 h. The solution was filtered through Celite, washing with EtOAc. The filtrate was concentrated under vacuum and the residue purified by Prep-HPLC (Method G) to afford the title compound (8.2 mg, 14.3%) as an off-white powder Method C: LC-MS: m/z=355.2 (M+H)+; RT=2.84 min.

Example 213—Preparation of 6-{5-methyl-4-[4-(trifluoromethyl)piperidine-1-carbonyl]-1H-pyrazol-1-yl}-4-(trifluoromethyl)-1,2-dihydropyridin-2-one

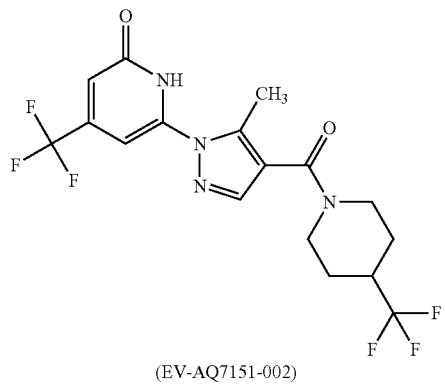 [SMILES: Cc1c(C(=O)N2CCC(C(F)(F)F)CC2)cnn1-c1cc(C(F)(F)F)cc(=O)[nH]1]

(EV-AQ7151-002)

Step 1: Synthesis of 2-chloro-6-hydrazinyl-4-(trifluoromethyl)pyridine

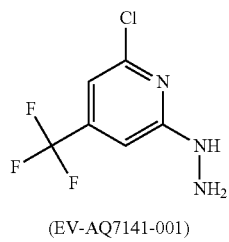 [SMILES: NNc1cc(C(F)(F)F)cc(Cl)n1]

(EV-AQ7141-001)

Hydrazine hydrate (0.05 mL, 0.93 mmol) was added to a suspension of 2,6-dichloro-4-(trifluoromethyl)pyridine (100 mg, 0.46 mmol) in ethanol (2 mL) and the reaction vessel was sealed and heated at 40° C. for 1.5 h and then at 70° C. for another 5.5 h.

The solution was concentrated and the resulting solid was triturated with water to afford the title compound (70 mg, 51.5%) as a pale brown solid.

Method B: LC-MS: m/z=211.9 (M+H)+; RT=0.91 min.

Step 2: Synthesis of methyl 1-[6-chloro-4-(trifluoromethyl)pyridin-2-yl]-5-methyl-1H-pyrazole-4-carboxylate

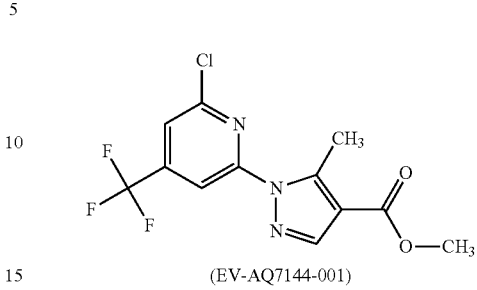

(EV-AQ7144-001)

To a solution of 2-chloro-6-hydrazinyl-4-(trifluoromethyl)pyridine (EV-AQ7141-001, 770 mg, 3.64 mmol) and methyl 2-[(dimethylamino)methylidene]-3-oxobutanoate (90%, 934.57 mg, 4.91 mmol) in ethanol (22 mL) was added acetic acid (0.729 mL, 12.74 mmol) and the reaction mixture was stirred at r.t. for 5 mins and then heated at 50° C. for 1 h. The mixture was concentrated under vacuum and purified by chromatography on SiO2 Eluting with 0-100% EtOAc in heptane to afford the title compound (1.04 g, 88.5%) as a white powder.

Method B: LC-MS: m/z=320.0 (M+H)+; RT=1.35 min.

Step 3: Synthesis of methyl 1-[6-(benzyloxy)-4-(trifluoromethyl)pyridin-2-yl]-5-methyl-1H-pyrazole-4-carboxylate

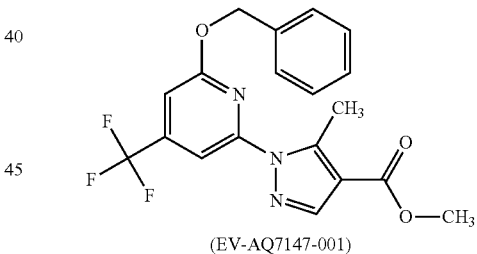

(EV-AQ7147-001)

To a solution of methyl 1-[6-chloro-4-(trifluoromethyl)pyridin-2-yl]-5-methyl-1H-pyrazole-4-carboxylate (EV-AQ7144-001, 600 mg, 1.88 mmol) in dioxane (10 mL) was added benzyl alcohol (0.21 mL, 2.06 mmol) and potassium tert-butoxide (231.68 mg, 2.06 mmol). The reaction mixture was stirred at 60° C. for 0.5 h. The reaction mixture was concentrated under vacuum, diluted with water (10 mL), and extracted with EtOAc (25 mL). The organics were washed with brine, dried ($Na_2SO_4$) and concentrated under vacuum. The crude material was purified by chromatography on $SiO_2$ eluting with 0-50% EtOAc in heptane to afford the title compound (629 mg, 48%) (mixture with the benzyl ester) of as a clear oil.

Method B: LC-MS: m/z=392.1 (M+H)+; RT=1.39 min.

Step 3: Synthesis of 5-methyl-1-[6-oxo-4-(trifluoromethyl)-1,6-dihydropyridin-2-yl]-1H-pyrazole-4-carboxylic acid

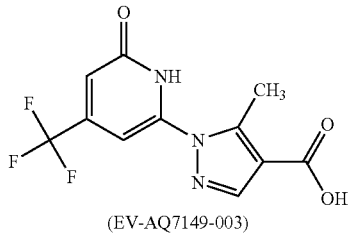 [SMILES: Cc1c(C(=O)O)cnn1-c1cc(C(F)(F)F)cc(=O)[nH]1]

(EV-AQ7149-003)

Pd on carbon (10%, 86 mg) was added to a stirred solution of methyl 1-[6-(benzyloxy)-4-(trifluoromethyl)pyridin-2-yl]-5-methyl-1H-pyrazole-4-carboxylate (EV-AQ7147-001, (mixture with the benzyl ester) (629 mg, 1.61 mmol)) in ethyl acetate (15.0 mL) and the solution was stirred under an atmosphere of $H_2$ overnight. The reaction mixture was filtered through Celite, washing with EtOAc. The filtrate was concentrated in vacuo and purified by chromatography on $SiO_2$ Eluting with 0-100% EtOAc in heptane to afford the title compound (107 mg, 21.6%) as an off white powder.
Method B: LC-MS: m/z=287.9 (M+H)+; RT=1.01

Step 4: Synthesis of 6-{5-methyl-4-[4-(trifluoromethyl)piperidine-1-carbonyl]-1H-pyrazol-1-yl}-4-(trifluoromethyl)-1,2-dihydropyridin-2-one, Q-466, EV-AQ7151-002

To a solution of 5-methyl-1-[6-oxo-4-(trifluoromethyl)-1,6-dihydropyridin-2-yl]-1H-pyrazole-4-carboxylic acid (200 mg, 0.70 mmol) in THF (6.0 mL) was added DIPEA (0.417 mL, 2.44 mmol) and T3P 50% in EtOAc (0.821 ml, 1.39 mmol). The reaction mixture was stirred at r.t. for 10 mins and 4-(trifluoromethyl)piperidin-1-ium. HCl (158.45 mg, 0.84 mmol) was added before stirring for a further 1 h. The reaction mixture concentrated in vacuo and the crude residue was then suspended in water (5 mL) and DCM (10 mL). The organics were extracted and the aqueous phase was then acidified to pH3-4 and extracted with more DCM (5 mL). The combined organics were dried ($Na_2SO_4$), filtered and concentrated in vacuo. The crude material was purified by PREP-HPLC (Method G) method) to afford the title compound (19.1 mg, 6.4%) of as an off-white powder.
Method C: LC-MS: m/z=423.1 (M+H)+; RT=3.41

Example 214—Preparation of 5-{4-[4-(trifluoromethyl)piperidine-1-carbonyl]-1H-pyrazol-1-yl}-6H,7H-thieno[2,3-c]pyridin-7-one (Q-511, EV-AR5370-002)

Step 1: Synthesis of 5-chloro-7-[(4-methoxyphenyl)methoxy]-6H,7H-thieno[2,3-c]pyridine

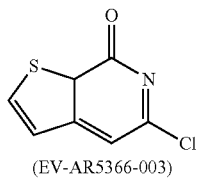 [SMILES: O=C1N=C(Cl)C=C2C=CSC12]

(EV-AR5366-003)

To a solution of 5-chloro-7-[(4-methoxyphenyl)methoxy]thieno[2,3-c]pyridine (EV-AR5360-001, 200 mg, 0.65 mmol) in DMF (3 ml) was added caesium carbonate (341 mg, 1.05 mmol) and 1-(1H-pyrazole-4-carbonyl)-4-(trifluoromethyl)piperidine (Intermediate 29, EV-AQ8818-001, 178 mg, 0.719 mmol) and stirred at 140° C. for 5 h. The reaction mixture was concentrated in vacuo and purified by PREP-HPLC (Method G) to afford the title compound (56 mg, 44%) as an off white powder.
Method B: LC-MS m/z=185.8 [M+H]+; RT=0.86 min.

Step 2: Synthesis of 5-{4-[4-(trifluoromethyl)piperidine-1-carbonyl]-1H-pyrazol-1-yl}-6H,7H-thieno[2,3-c]pyridin-7-one

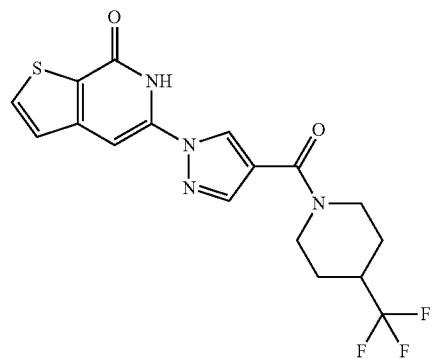

(EV-AR5370-002)

To a solution of 5-chloro-7-[(4-methoxyphenyl)methoxy]-6H,7H-thieno[2,3-c]pyridine (EV-AR5366-003, 56 mg, 0.302 mmol) in DMF (1 ml) was added 1-(1H-pyrazole-4-carbonyl)-4-(trifluoromethyl)piperidine (Intermediate 29, 89 mg, 0.362 mmol), caesium carbonate (147 mg, 0.453 mmol), L-proline (14 mg, 0.121 mmol) and copper (I) iodide (11 mg, 0.06 mmol). The reaction mixture was then de-gassed and stirred at 140° C. for 16 h. The reaction mixture was cooled to r.t., diluted with EtOAc (20 ml) and washed with brine (2×10 ml). The organic extracts were dried over sodium sulfate, concentrated in vacuo and purified by PREP-HPLC (Method G) followed by trituration using MeCN, to afford the title compound (32 mg, 27%) as an off white powder.
Method C: LC-MS m/z=397.1 [M+H]+; RT=2.67 min.

Example 216—Preparation of 2-{5-[4-(trifluoromethyl)piperidine-1-carbonyl]-1,3-thiazol-2-yl}-3H,4H-thieno[3,2-d]pyrimidin-4-one Step 1: Synthesis of 2-(ethoxycarbonyl)-1,3-thiazole-5-carboxylic acid

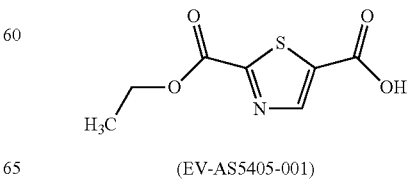

(EV-AS5405-001)

To a solution of bromopyruvic acid (2.0 g, 11.98 mmol) in anhydrous 1,4-dioxane (20 ml) was added ethyl amino(thioxo)acetate (1.60 g, 11.98 mmol) and stirred at 100° C. overnight. The reaction mixture was cooled to room temperature, basified with saturated NaHCO₃ solution and extracted with EtOAc (2×20 ml). The organic extracts were discarded. The aqueous extracts were then acidified to pH 3/4 using 5M aq HCl solution and extracted with EtOAc (2×50 ml). The organic extracts were dried over sodium sulfate and concentrated in vacuo to afford the title compound (1.34 g, 54%) as an orange powder.

Method B: LC-MS m/z=201.85 [M+H]⁺; RT=0.80 min.

Step 2: Synthesis of ethyl 5-[4-(trifluoromethyl)piperidine-1-carbonyl]-1,3-thiazole-2-carboxylate

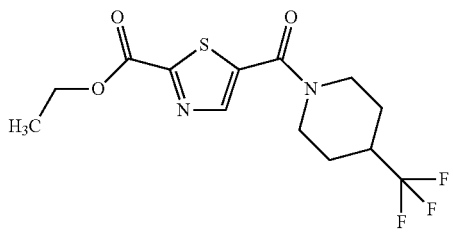

(EV-AS5406-001)

To a suspension of 2-(ethoxycarbonyl)-1,3-thiazole-5-carboxylic acid (EV-AS5405-001, 1.34 g, 6.66 mmol) in THF (15 ml) was added DIPEA (2.9 ml, 16.7 mmol), T3P (50% in EtOAc) (9.8 ml, 16.7 mmol) and 4-(trifluoromethyl)piperidine hydrochloride (1.39 g, 7.33 mmol) and stirred at r.t. for 2 h. The reaction mixture was concentrated in vacuo and to the crude residue added DCM (40 ml) and saturated NaHCO₃ solution (20 ml). The organic layer was extracted, washed with water (10 ml), dried over sodium sulfate and concentrated in vacuo to afford the title compound (2.13 g, 75%) as a brown powder.

Method B: LC-MS m/z=337.0 [M+H]⁺; RT=1.09 min.

Step 3: Synthesis of 5-[4-(trifluoromethyl)piperidine-1-carbonyl]-1,3-thiazole-2-carboxylic acid

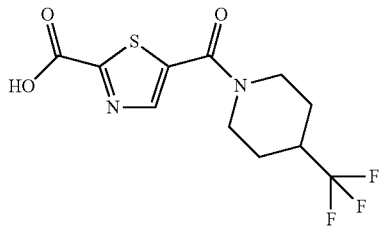

(EV-AS5407-001)

To a solution of ethyl 5-[4-(trifluoromethyl)piperidine-1-carbonyl]-1,3-thiazole-2-carboxylate (EV-AS5406-001, 79%, 2.10 g, 4.93 mmol) in THF (10 mL) and water (5 ml) was added 3M aqueous NaOH solution (8.22 ml) and stirred at r.t. for 2 h. The reaction mixture was concentrated in vacuo to remove the organic solvent and the aqueous mixture acidified to pH 2/3 using 5M aq HCl solution. The reaction mixture was extracted with EtOAc (2×50 ml) and the combined organic extracts dried over sodium sulfate and concentrated in vacuo to afford the title compound (874 mg, 40%) as a brown solid.

Method B: LC-MS m/z=308.85 [M+H]⁺; RT=0.87 min.

Step 4: Synthesis of N-(2-carbamoylthiophen-3-yl)-5-[4-(trifluoromethyl)piperidine-1-carbonyl]-1,3-thiazole-2-carboxamide

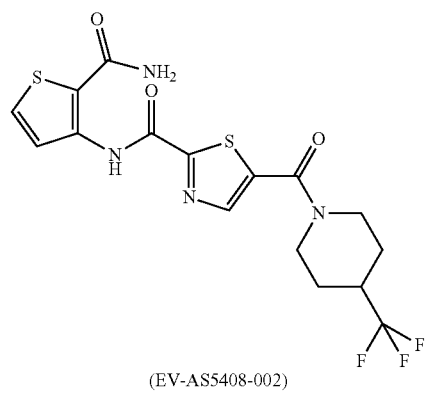 [SMILES: NC(=O)c1sccc1NC(=O)c1ncc(C(=O)N2CCC(C(F)(F)F)CC2)s1]

(EV-AS5408-002)

To a solution of 5-[4-(trifluoromethyl)piperidine-1-carbonyl]-1,3-thiazole-2-carboxylic acid (EV-AS5407-001, 70%, 872 mg, 1.98 mmol) in THF (10 ml) was added HATU (904 mg, 2.38 mmol), DIPEA (848 μl, 4.95 mmol) and 3-aminothiophene-2-carboxamide (310 mg, 2.18 mmol) and stirred at r.t. for 2 h. The reaction mixture was concentrated in vacuo and redissolved in DCM (2 ml) and water (1 ml). The reaction mixture was filtered through a phase separator cartridge, concentrated in vacuo and purified by chromatography, eluting with DCM/MeOH (gradient 100:0-95:5) to afford the title compound (1.03 g, 88%) as an orange oil.

Method B: LC-MS m/z=432.90 [M+H]⁺; RT=1.09 min.

Step 5: Synthesis of 2-{5-[4-(trifluoromethyl)piperidine-1-carbonyl]-1,3-thiazol-2-yl}-3H,4H-thieno[3,2-d]pyrimidin-4-one

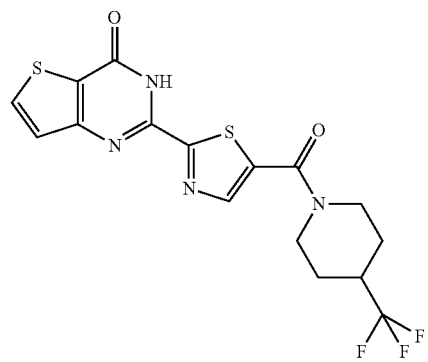

Q-530 (EV-AS5409-002)

To a solution of N-(2-carbamoylthiophen-3-yl)-5-[4-(trifluoromethyl)piperidine-1-carbonyl]-1,3-thiazole-2-carboxamide (EV-AS5408-002, 73%, 45 mg, 0.076 mmol) in MeOH (3 ml) was added 1M aq NaOH solution (380 μl, 0.38 mmol) and stirred at 70° C. for 2 h. The reaction mixture was filtered to remove the precipitate, the filtrate extracted with EtOAc (2×10 ml) and the organic extracts discarded. The aqueous extracts were then acidified to pH 4/5 using 2M aq HCl solution. A white precipitate formed which was filtered, washing with water and purified by PREP-HPLC (Method G) to afford the title compound (12 mg, 38%) as a white powder.

Method C: LC-MS m/z=415.0 [M+H]$^+$; RT=2.84 min.

Example 218—Preparation of 2-(5-methyl-4-{2,2,2-trifluoro-1-[4-(trifluoromethyl)piperidin-1-yl]ethyl}-1H-pyrazol-1-yl)-3H,4H,5H,6H,7H-cyclopenta[d]pyrimidin-4-one (Q-503, EV-AQ7177-001)

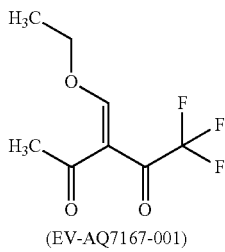

(EV-AQ7167-001)

Step 1: Synthesis of 2-[5-methyl-4-(trifluoroacetyl)-1H-pyrazol-1-yl]-3H,4H,5H,6H,7H-cyclopenta[d]pyrimidin-4-one

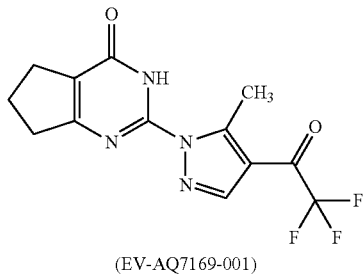 [SMILES: Cc1c(C(=O)C(F)(F)F)cnn1-c1nc2c(c(=O)[nH]1)CCC2]

(EV-AQ7169-001)

To a solution of 2-hydrazinyl-3H,4H,5H,6H,7H-cyclopenta[d]pyrimidin-4-one (EV-AQ7134-001, 150 mg, 0.9 mmol, Intermediate 17) in THF (15 mL) at −10° C. was added dropwise 3-(ethoxymethylidene)-1,1,1-trifluoropentane-2,4-dione (prepared using the procedure described in *Journal of Fluorine Chemistry*. 136, 38-42; 2012) (EV-AQ7167-001, 199.17 mg, 0.95 mmol) in THF (5 mL) over 20 mins and stirred at −10° C. for 30 mins and at r.t. for a further 1 h. The reaction mixture was concentrated in vacuo and dissolved in DCM. The organics were washed with brine, dried over Na$_2$SO$_4$ and concentrated in vacuo to afford the title compound (310 mg, 92.4%) as an orange powder, which ionised in the LC-MS as a mixture of ketone and dehydrate.

Method B: LC-MS m/z=331.0 [M+H]$^+$; RT=0.98 min; 313.0 [M+H]$^+$; RT=1.14 min

Step 2: Synthesis of 2-[5-methyl-4-(2,2,2-trifluoro-1-hydroxyethyl)-1H-pyrazol-1-yl]-3H,4H,5H,6H,7H-cyclopenta[d]pyrimidin-4-one

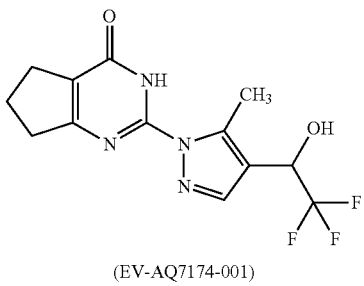 [SMILES: Cc1c(C(O)C(F)(F)F)cnn1-c1nc2c(c(=O)[nH]1)CCC2]

(EV-AQ7174-001)

To a solution of NaBH$_4$ (49.68 mg, 1.31 mmol) in MeOH (1 mL) was added 1M aqueous NaOH solution (0.1 mL) followed by 2-[5-methyl-4-(trifluoroacetyl)-1H-pyrazol-1-yl]-3H,4H,5H,6H,7H-cyclopenta[d]pyrimidin-4-one (EV-AQ7169-001, 100 mg, 0.32 mmol) in MeOH (2 mL) and stirred at r.t. for 1 h. The reaction mixture was quenched with water (~2 mL) and concentrated in vacuo. The residue was dissolved in EtOAc, washed with water (3 mL) and brine (3 mL), dried over Na$_2$SO$_4$ and concentrated in vacuo to afford the title compound (95 mg, 94.4%) as an orange powder.

Method B: LC-MS m/z=315.0 [M+H]$^+$; RT=0.99 min

Step 3: Synthesis of 2-(5-methyl-4-{2,2,2-trifluoro-1-[4-(trifluoromethyl)piperidin-1-yl]ethyl}-1H-pyrazol-1-yl)-3H,4H,5H,6H,7H-cyclopenta[d]pyrimidin-4-one

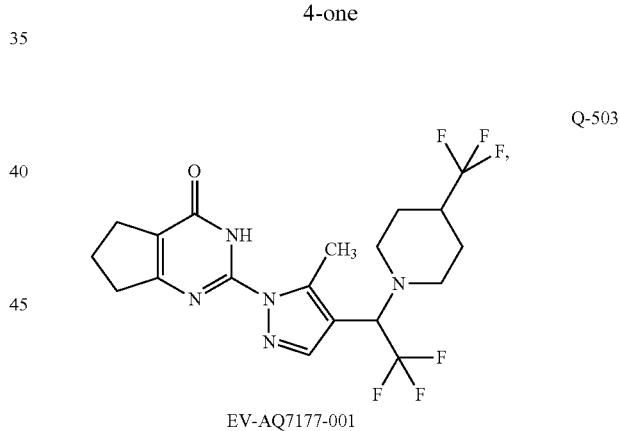

EV-AQ7177-001

To a solution of 2-[5-methyl-4-(2,2,2-trifluoro-1-hydroxyethyl)-1H-pyrazol-1-yl]-3H,4H,5H,6H,7H-cyclopenta[d]pyrimidin-4-one (EV-AQ7174-001, 90 mg, 0.29 mmol) in DCM (3.5 mL) at −10° C. was added Et$_3$N (0.12 mL, 0.86 mmol) followed by triflic anhydride (0.08 mL, 0.50 mmol) and stirred at −10° C. for 1 h. The reaction mixture was washed with cold saturated NaHCO$_3$ solution (3 mL) and water (3 mL). The organic extracts were then dried over Na$_2$SO$_4$ and concentrated in vacuo. The residue was dissolved in THF (3 mL), cooled to 0° C., added to a stirred solution of 4-(trifluoromethyl)piperidin-1-ium HCl (108.6 mg, 0.57 mmol) and potassium carbonate (118.74 mg, 0.86 mmol) and stirred at 0° C.—r.t. for 15 h. The reaction mixture was concentrated in vacuo and partitioned between DCM (2 mL) and water (1 mL). The organics were isolated using a phase separator cartridge, concentrated in vacuo and purified by PREP-HPLC (Method G) to afford the title compound (21 mg, 16.3%) as brown powder.

Method C: LC-MS m/z=450.1 [M+H]⁺; RT=2.98 min

Example 219—Preparation of 3-methyl-5-{5-methyl-4-[4-(trifluoromethyL)piperidine-1-carbonyl]-1H-pyrazol-1-yl}phenol (Q-494, EV-AR5355-002)

Step 1: Synthesis of 2-[4-(hydroxymethyL)-5-methyl-1H-pyrazol-1-yl]-3H,4H,5H,6H,7H-cyclopenta[d]pyrimidin-4-one

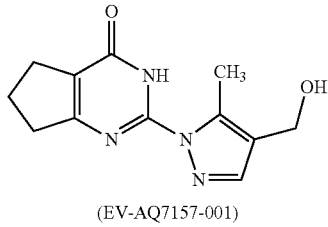 [SMILES: Cc1c(CO)cnn1-c1nc2c(c(=O)[nH]1)CCC2]

(EV-AQ7157-001)

To a solution of methyl 5-methyl-1-{4-oxo-3H,4H,5H,6H,7H-cyclopenta[d]pyrimidin-2-yl}-1H-pyrazole-4-carboxylate (Intermediate 18 step 1, EV-AQ7137-001, 1 g, 3.65 mmol) in THF (20 mL) at 0° C. was added dropwise lithium aluminium hydride (2.4 M solution in THF, 1.82 mL, 4.35 mmol) and stirred at r.t. for 15 h. The reaction mixture was quenched by the addition of water (15 mL) and filtered through Celite, washing with methanol (15 mL). The filtrate was concentrated in vacuo to afford the title compound (650 mg, 62%) as a pale yellow powder:

Method B: LC-MS m/z=245 [M+H]⁺; RT=0.89 min

Step 2: Synthesis of 5-methyl-1-{4-oxo-3H,4H,5H,6H,7H-cyclopenta[d]pyrimidin-2-yl}-1H-pyrazole-4-carbaldehyde

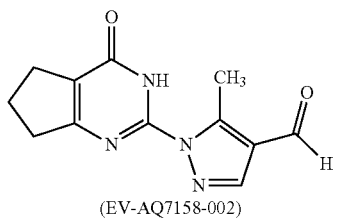 [SMILES: Cc1c(C=O)cnn1-c1nc2c(c(=O)[nH]1)CCC2]

(EV-AQ7158-002)

To a solution of 2-[4-(hydroxymethyL)-5-methyl-1H-pyrazol-1-yl]-3H,4H,5H,6H,7H-cyclopenta[d]pyrimidin-4-one (EV-AQ7157-001, 650 mg, 2.64 mmol) in DCM (20 mL) and MeOH (10 mL) was added manganese (IV) oxide (1.84 g, 21.12 mmol) and stirred at r.t. for 15 h. A further portion of manganese (IV) oxide (1.84 g, 21.12 mmol) was added and stirred at r.t. for 6 h. A further portion of manganese (IV) oxide (0.92 g, 10.56 mmol) was added and stirred at r.t. for 4 days. The reaction mixture was filtered through Celite, washing with DCM and MeOH, and the filtrate concentrated in vacuo to afford the title compound (558 mg, 68%) as a beige powder.

Method B: LC-MS m/z=245 [M+H]⁺; RT=0.89 min

Step 3: Synthesis of 1-[(5-methyl-1-{4-oxo-3H,4H,5H,6H,7H-cyclopenta[d]pyrimidin-2-yl}-1H-pyrazol-4-yL)methyl]piperidin-2-one

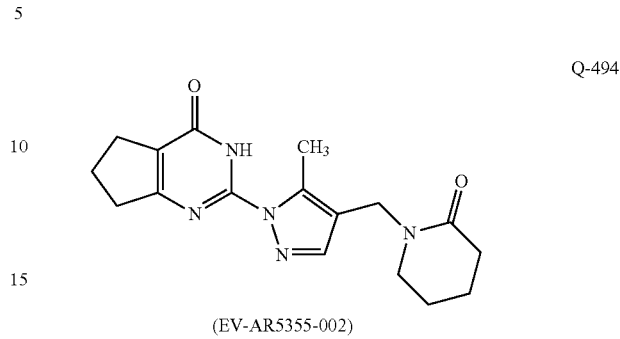

Q-494

(EV-AR5355-002)

To a solution of 5-methyl-1-{4-oxo-3H,4H,5H,6H,7H-cyclopenta[d]pyrimidin-2-yl}-1H-pyrazole-4-carbaldehyde (EV-AQ7158-001, 80%, 90 mg, 0.295 mmol) in anhydrous MeOH (3 mL) was added ethyl 5-aminopentanoate hydrochloride (59 mg, 0.324 mmol) and Et₃N (164 µl, 1.179 mmol) and stirred at r.t. for 1 h. To the reaction mixture was added NaBH₄ (13 mg, 0.354 mmol) and stirred at 45° C. for 16 h. The reaction mixture was stirred at 50° C. for a further 3 h. The reaction mixture was cooled to r.t. and diluted with water (10 mL). The aqueous mixture was then acidified to pH 4 using 5 M aq HCl solution and extracted with EtOAc (2×30 mL). The combined extracts were dried over sodium sulfate, concentrated in vacuo and purified via PREP-HPLC (Method G) to afford the title compound (5 mg, 5%) as an off white powder.

Method C: LC-MS m/z=328.1 [M+H]⁺; RT=2.19 min.

Example 220

Step 1: Synthesis of ethyl 1-{4-[(4-methoxyphenyl)methoxy]-6-methylpyrimidin-2-yl}-1H-pyrazole-4-carboxylate

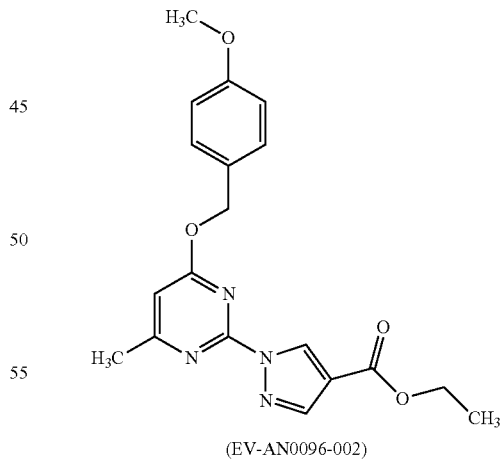

(EV-AN0096-002)

To a solution of ethyl 1H-pyrazole-4-carboxylate (143 m g, 1.022 mol) in DMF (5 mL) at 0° C. was added NaH (60% in oil) (60%, 45 mg, 1.12 mmol). The reaction mixture was warmed to r.t. over 30 minutes before 2-methanesulfonyl-4-[(4-methoxyphenyl)methoxy]-6-methylpyrimidine (Example 196 step 2, EV-AO5710-002, 300 mg, 0.97 mmol) was added in more DMF (1 mL). The reaction mixture was stirred at r.t. for 3 h. The reaction mixture was quenched by the addition of water (20 mL) and extracted with EtOAc (3×30 mL). The combined organic fractions were washed with brine (20 mL), dried (Na$_2$SO$_4$) and concentrated under vacuum to an opaque gum which was purified by chromatography on SiO$_2$ eluting with 12-100% EtOAc in heptane to afford the title compound (266 mg, 66% yield) as a white powder.

Method A: LC-MS: m/z=+391.10 (M+Na)$^+$ 1.41 min

Step 2: Synthesis of 1-{4-[(4-methoxyphenyl) methoxy]-6-methylpyrimidin-2-yl}-1H-pyrazole-4-carboxylic acid

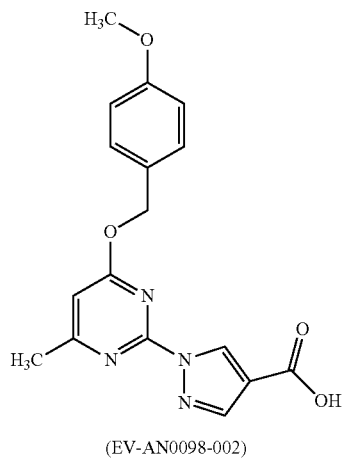 [SMILES: COc1ccc(COc2cc(C)nc(-n3cc(C(=O)O)cn3)n2)cc1]

(EV-AN0098-002)

To a solution of ethyl 1-{4-[(4-methoxyphenyl)methoxy]-6-methylpyrimidin-2-yl}-1H-pyrazole-4-carboxylate (EV-AN0096-002 (266 mg, 0.64 mmol) in THF (10 ml) was added NaOH (3M, 1 ml) and the reaction was stirred at room temperature for 18 h. More NaOH (2.5M, 1.5 ml) was added along with MeOH (1 ml) and the reaction stirred for a further 7 h. The Organic solvent was evaporated in vacuo and the aqueous phase acidified to pH1 with HCl (1M). The mixture was extracted with EtOAc (3×30 ml), washed with brine (2×20 ml), dried (Na$_2$SO$_4$) and evaporated to afford the title compound (199 mg, 64%) as a colourless gum.

Method A: LC-MS: m/z=+363.0 (M+Na)$^+$ 1.20 min

Step 3: Synthesis of 2-(1-{4-[(4-methoxyphenyl) methoxy]-6-methylpyrimidin-2-yl}-1H-pyrazole-4-carbonyl)-1,2,3,4-tetrahydroisoquinoline

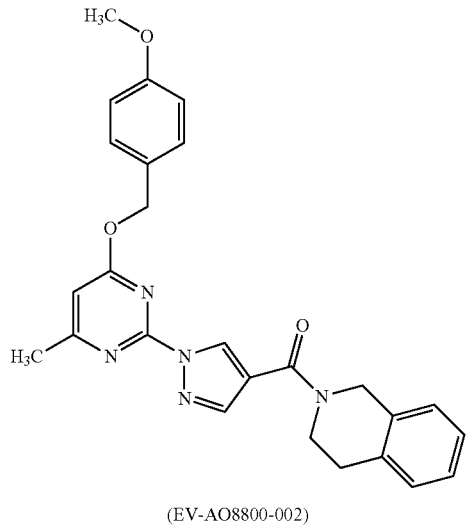 [SMILES: COc1ccc(COc2cc(C)nc(-n3cc(C(=O)N4CCc5ccccc5C4)cn3)n2)cc1]

(EV-AO8800-002)

To a stirred solution of 1-{4-[(4-methoxyphenyl) methoxy]-6-methylpyrimidin-2-yl}-1H-pyrazole-4-carboxylic acid (EV-AN0090-001, 199 mg, 0.58 mmol) in DMF (1 ml) was added DIPEA (255 µl, 1.46 mmol) followed by TBTU (225 mg, 0.7 mmol). The reaction was stirred for 3 min after which time 1,2,3,4-tetrahydroisoquinoline (101 mg, 0.76 mmol) was added and then the reaction was placed under N$_2$. The reaction was stirred for 16 hours and then quenched with water (20 ml) and extracted with DCM (3×30 ml). The organics were washed with brine (2×50 ml), dried (Na$_2$SO$_4$) and evaporated under vacuum, followed by azeotrope with heptane (2×50 mL) to remove residual DMF. The crude product was purified by chromatography on SiO$_2$ eluting with 25-100% EtOAc in heptane gradient to afford the title compound (220 mg, 72%) as a colourless gum.

Method C: LC-MS: m/z=456.2 (M+H)$^+$ 1.40 min

Step 4: Synthesis of 6-methyl-2-[4-(1,2,3,4-tetrahydroisoquinoline-2-carbonyl)-1H-pyrazol-1-yl]-3,4-dihydropyrimidin-4-one

Q-314

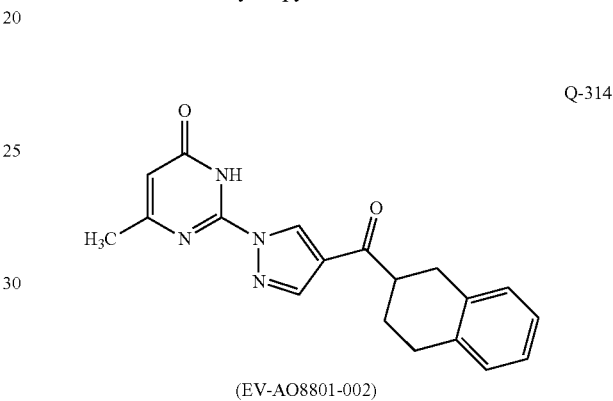

(EV-AO8801-002)

2-(1-{4-[(4-methoxyphenyl)methoxy]-6-methylpyrimidin-2-yl}-1H-pyrazole-4-carbonyl)-1,2,3,4-tetrahydroisoquinoline (EV-AO8800-002, 220 mg, 0.42 mmol) was dissolved in DCM (3 mL) and TFA (0.35 mL) was added. The reaction mixture was stirred for 1 hour and 30 minutes and then concentrated under vacuum. The crude residue was then re-dissolved in DCM (30 ml) and washed with sodium bicarbonate solution (sat, 2×10 ml), dried (Na$_2$SO$_4$) and concentrated under vacuum. The crude material was purified by preparative HPLC (Method G) to afford the title compound (46 mg, 33%) as an off white solid Method C: LC-MS: m/z=336.1 (M+H)$^+$ 2.38 min Example 221—Preparation of 6-methyl-2-[4-(1,2,3,4-tetrahydroisoquinoline-2-carbonyl)-1H-1,2,3-triazol-1-yl]-3,4-dihydropyrimidin-4-one (Q-312, EV-A05730-002)

Step 1: Synthesis of 5-methyl-3H,7H-[1,2,3,4]tetrazolo[1,5-a]pyrimidin-7-one

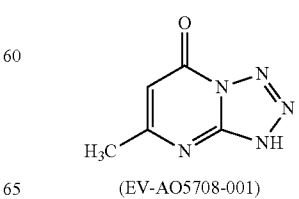

(EV-AO5708-001)

To a solution of hydrazinyl-6-methyl-3,4-dihydropyrimidin-4-one (Intermediate 1, EV-AN7477-001, 0.5 g, 3.6 mmol) in ice cold acetic acid (3 mL) was added dropwise a solution of sodium nitrite (0.37 g, 5.4 mmol) in water (0.4 mL). The reaction mixture was stirred at 5° C. for 1 hour and then concentrated in vacuo. The residue was triturated from water, filtered and dried in vacuo to afford the title compound (335 mg, 59%) as a colourless solid.

Method A: LC-MS m/z=152.1 [M+H]+; RT=0.24 min

Step 2: Synthesis of methyl 1-(4-methyl-6-oxo-1,6-dihydropyrimidin-2-yl)-1H-1,2,3-triazole-4-carboxylate

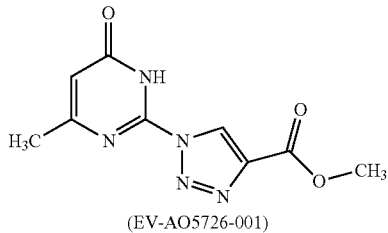

(EV-AO5726-001)

A solution of tert-butanol-water 1:1 (4 mL) was degassed with a stream of nitrogen for 5 minutes and methyl-3H,7H-[1,2,3,4]tetrazolo[1,5-a]pyrimidin-7-one (EV-AO05708-001, 200 mg, 1.32 mmol), copper (I) chloride (26 mg, 0.26 mmol) and methyl propionate (98%, 227 mg, 2.65 mmol) were added. The reaction mixture was stirred at 70° C. for 6 hours. The reaction mixture was diluted with CHCl3-10% IPA (5 mL) and washed with water (5 mL) and brine (5 mL). The aqueous phase was re-extracted with CHCl3-10% IPA (3×5 mL) and the combined organics were dried (Na$_2$SO$_4$) and concentrated in vacuo. Purification by chromatography on SiO2, eluting with DCM/Ammonia (7M in methanol) 0-100%) afforded the title compound (183 mg, 53%) as a pale solid.

Method A: LC-MS m/z=235.9 [M+H]+; RT=0.90 min

Step 3: Synthesis of 1-(4-methyl-6-oxo-1,6-dihydropyrimidin-2-yl)-1H-1,2,3-triazole-4-carboxylic acid

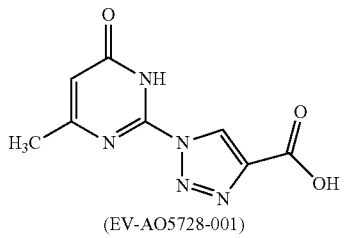 [SMILES: Cc1cc(=O)[nH]c(-n2cc(C(=O)O)nn2)n1]

(EV-AO5728-001)

To a solution of methyl 1-(4-methyl-6-oxo-1,6-dihydropyrimidin-2-yl)-1H-1,2,3-triazole-4-carboxylate (EV-AO5726-001, 190 mg, 0.71 mmol) in methanol (3 mL) was added 1M KOH (1.25 mL, 1.25 mmol) and the mixture was stirred at r.t. for 4 hours. The reaction mixture was concentrated in vacuo and acidified with HCl (3M, 0.4 mL). The resulting precipitate was collected by filtration, washed with water (2×1 mL) and dried under vacuum to afford the title compound (137 mg, 83%) as a light brown solid.

Method A: LC-MS m/z=221.9 [M+H]+; RT=0.70 min.

Step 4: Synthesis of 6-methyl-2-[4-(1,2,3,4-tetrahydroisoquinoline-2-carbonyl)-1H-1,2,3-triazol-1-yl]-3,4-dihydropyrimidin-4-one, Q-312, EV-A05730-002

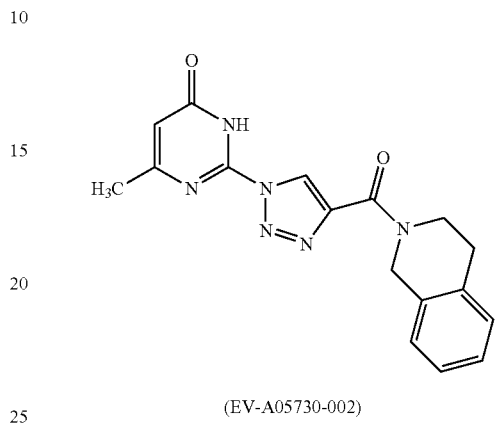

(EV-A05730-002)

To a solution of 1-(4-methyl-6-oxo-1,6-dihydropyrimidin-2-yl)-1H-1,2,3-triazole-4-carboxylic acid (EV-A05728-001 (130 mg, 0.56 mmol) in DMF (2 mL) was added DIPEA (233.05 µl, 1.4 mmol and COMU (98%, 268.42 mg, 0.61 mmol). The reaction mixture was stirred at r.t. for 2 minutes and 1,2,3,4-tetrahydroisoquinoline (98%, 83.48 mg, 0.61 mmol) was added and the reaction stirred at r.t. for a further 24 hours. Further COMU (98%, 268.42 mg, 0.61 mmol) and 1,2,3,4-tetrahydroisoquinoline (98%, 83.48 mg, 0.61 mmol) were added and the mixture stirred at r.t. for 2 hr.

The reaction mixture was concentrated in vacuo and diluted with DCM (10 ml). The mixture was washed with HCl (1 M 2×5 mL), water (5 mL) and brine (5 mL), dried (Na$_2$SO$_4$) and concentrated in vacuo. Purification by chromatography on SiO2 eluting with DCM/methanol (0-2%) followed by preparative HPLC (Method G) afforded the title compound (36 mg, 19%) as a colourless solid.

Method C: LC-MS: m/z=337.1 (M+H)+; RT=2.56 min

Example 222—Preparation of 2-{5-[4-(trifluoromethyl)piperidine-1-carbonyl]pyridin-2-yl}-3H,4H,5H,6H,7H-cyclopenta[d]pyrimidin-4-one 0-472 (EV-AR5325-002)

Step 1: Preparation of 2-(5-bromopyridin-2-yl)-1H,2H,3H,4H,5H,6H,7H-cyclopenta[d]pyrimidin-4-one

Q-465

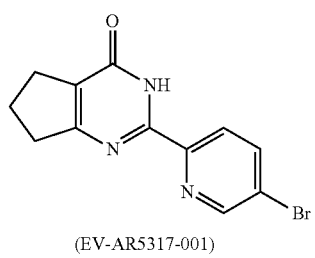

(EV-AR5317-001)

To a solution of 5-bromopyridine-2-carboximidamide (917 mg, 4.584 mmol) in dry MeOH (10 ml) was added methyl-2-oxocyclopentane-1-carboxylate (1.1 eq, 569 µl, 4.584 mmol), followed by NaOMe (5.4 M in MeOH) (1.1 eq, 934 µl, 5.043 mmol) and stirred at 60° C. for 20 h. A further portion of methyl-2-oxocyclopentane-1-carboxylate (0.1 eq, 57 µl, 0.458 mmol) and NaOMe (5.4 M in MeOH) (0.1 eq, 85 µl, 0.458 mmol) was added and stirred at 60° C. for 1 h. The reaction mixture was concentrated in vacuo, the residue redissolved in water and the solution acidified to pH 3 using 2 M aqueous HCl solution. The precipitate was filtered under vacuum filtration, washed with water and Et₂O, and dried to afford the title compound (832 mg, 62%) as a cream powder.

Method C: LC-MS m/z=295.0 [M+H]⁺; RT=2.53 min.

Step 2: Preparation of methyl-6-{4-oxo-3H,4H,5H,6H,7H-cyclopenta[d]pyrimidin-2-yl}pyridine-3-carboxylate

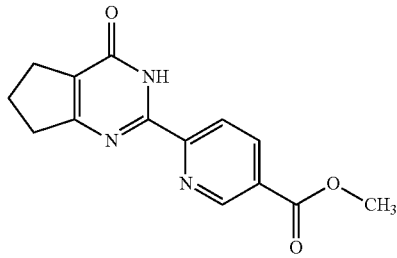

(EV-AR5321-002)

Q-471

To a suspension of 2-(5-bromopyridin-2-yl)-3H,4H,5H,6H,7H-cyclopenta[d]pyrimidin-4-one (EV-AR5317-001, 690 mg, 2.36 mmol) in THF (3 ml) was added MeOH (3 ml), Mo(CO)₆ (249 mg, 0.945 mmol), Pd(OAc)₂ (53 mg, 0.236 mmol), ᵗBu₃P (96 mg, 0.472 mmol) and DBU (705 µl, 4.724 mmol) and stirred at 120° C. overnight. The reaction mixture was diluted with water (10 mL) and extracted with EtOAc (3×20 mL). The combined organic extracts were washed with saturated brine solution (10 mL), dried over Na₂SO₄, concentrated in vacuo and purified via chromatography on SiO₂ eluting with (100:0-95:5, DCM-MeOH) followed by trituration using THF to afford the title compound (109 mg, 17%) as an off white powder.

Method C: LC-MS m/z=272.1 [M+H]⁺; RT=2.27 min.

Step 3: Preparation of 5-cyclopropyl-1-{4-oxo-3H,4H,5H,6H,7H-cyclopenta[d]pyrimidin-2-yl}-1H-pyrazole-4-carboxylic acid

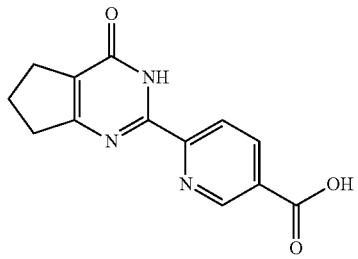

(EV-AR5324-001)

To a solution of methyl 6-{4-oxo-3H,4H,5H,6H,7H-cyclopenta[d]pyrimidin-2-yl}pyridine-3-carboxylate (EV-AR5321-002, 100 mg, 0.369 mmol) in THF (5 mL) was added 3M aqueous NaOH solution (737 µl, 2.21 mmol) and stirred at r.t. for 1 h. The reaction mixture was concentrated in vacuo to remove the organic solvent and the aqueous mixture acidified to pH 4 using 5M aq HCl solution; a white precipitate formed. The reaction mixture was filtered under vacuum to afford the title compound (65 mg, 53%) as an off white powder.

Method B: LC-MS m/z=258.0 [M+H]⁺; RT=0.84 min.

Step 4: Preparation of 2-{5-[4-(trifluoromethyl)piperidine-1-carbonyl]pyridin-2-yl}-3H,4H,5H,6H,7H-cyclopenta[d]pyrimidin-4-one

Q-472

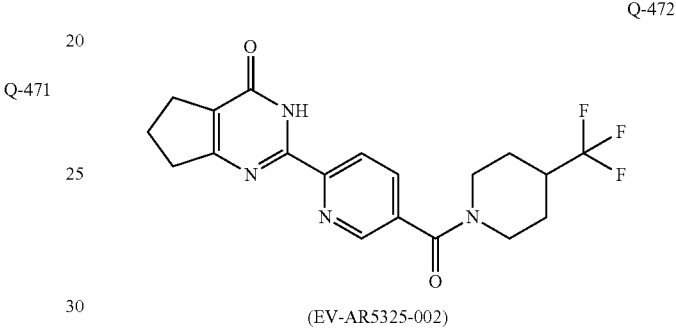

(EV-AR5325-002)

To a suspension of 6-{4-oxo-3H,4H,5H,6H,7H-cyclopenta[d]pyrimidin-2-yl}pyridine-3-carboxylic acid (EV-AR5324-001, 64 mg, 0.249 mmol) in THF (3 ml) was added DIPEA (130 µl, 0.746 mmol), T3P (50% in EtOAc) (440 µl, 0.746 mmol) and 4-(trifluoromethyl)piperidine hydrochloride (52 mg, 0.274 mmol) and stirred at r.t. for 2 h. The reaction mixture was concentrated in vacuo and redissolved in EtOAc (20 ml). The reaction mixture was then washed with water (10 ml), the organic extracts dried over sodium sulfate, concentrated in vacuo and purified via PREP-HPLC (Method G) to afford the title compound (45 mg, 46%) as a white powder.

Method C: LC-MS m/z=393.2 [M+H]⁺; RT=2.65 min.

Example 223—Synthesis of 2-{4-[4-(trifluoromethyl)piperidine-1-carbonyl]pyridin-2-yl}-3H,4H,5H,6H,7H-cyclopenta[d]pyrimidin-4-one Step 1: Preparation of 4-bromopyridine-2-carboxamidine hydrochloride

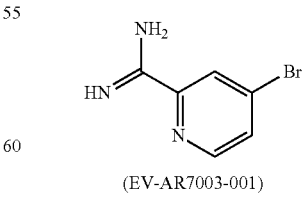

(EV-AR7003-001)

To a solution of 4-bromopyridine-2-carbonitrile (1 g, 5.46 mmol) in anhydrous MeOH (4 mL) was added sodium methoxide in MeOH (0.5 M, 2.19 mL, 1.1 mmol) and stirred at r.t. for 4 h. To the reaction mixture was added ammonium chloride (0.32 g, 6 mmol) and stirred at r.t. overnight. The reaction was diluted with ether (10 mL) and stirred at r.t. for 30 mins. A precipitate formed that was collected by filtration, washed with ether (2×4 mL) and dried under vacuum to afford the title compound (967 mg, 74.8%) as a white powder.

Method B: LC-MS m/z=199.8, 201.9 [M+H]$^+$; RT=0.2 min.

Step 2: Preparation of 2-(4-bromopyridin-2-yl)-3H,4H,5H,6H,7H-cyclopenta[d]pyrimidin-4-one

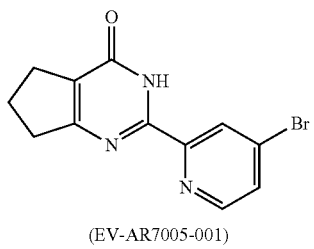 [SMILES: O=c1[nH]c(-c2cc(Br)ccn2)nc2c1CCC2]

(EV-AR7005-001)

Methyl 2-oxocyclopentane-1-carboxylate (609.16 µl, 4.91 mmol) and 4-bromopyridine-2-carboxamidine hydrochloride (0.97 g, 4.09 mmol) were dissolved in NaOMe in MeOH (0.5 M, 9.8 mL, 4.9 mmol) at r.t. under an atmosphere of nitrogen, and stirred at 60° C. overnight. The reaction mixture was concentrated in vacuo, the residue re-dissolved in water and the solution acidified to pH 3 using 2 M aq HCl solution. The precipitate was collected by filtration, washed with water and diethyl ether, and dried to afford the title compound (783 mg, 65.6%) as a brown powder.

Method B: LC-MS m/z=293.85/295 [M+H]$^+$; RT=1.04 min.

Step 3: Synthesis of 2-{4-[4-(trifluoromethyl)piperidine-1-carbonyl]pyridin-2-yl}-3H,4H,5H,6H,7H-cyclopenta[d]pyrimidin-4-one

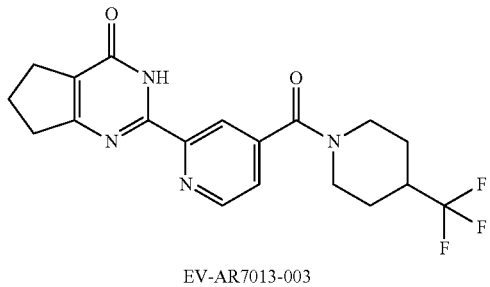 [SMILES: O=C(c1ccnc(-c2nc3c(c(=O)[nH]2)CCC3)c1)N1CCC(C(F)(F)F)CC1]

EV-AR7013-003

To a solution of 2-(4-bromopyridin-2-yl)-3H,4H,5H,6H,7H-cyclopenta[d]pyrimidin-4-one (50 mg, 0.17 mmol) in anhydrous 1,4-dioxane (2 mL) under nitrogen was added 4-(trifluoromethyl)piperidin-1-ium chloride (97.36 mg, 0.51 mmol), palladium acetate (2.88 mg, 0.01 mmol), (9,9-dimethyl-9H-xanthene-4,5-diyl)bis(diphenylphosphane) (14.86 mg, 0.03 mmol), tripotassium phosphate (0.09 ml, 1.03 mmol), hexakis(oxomethylidene)molybdenum (18.07 mg, 0.07 mmol) and N,N-dimethylpyridin-4-amine (41.82 mg, 0.34 mmol). The reaction vessel was de-gassed and back filled with nitrogen (×3), sealed and heated at 140° C. for 45 mins. The reaction mixture was diluted with EtOAc, concentrated on to silica and purified by chromatography on SiO$_2$ eluting with 0-5% MeOH/DCM then 5-15% rapid flush to yield a brown gum. The crude material was dissolved in IPA (0.3 mL) and treated with (2E)-but-2-enedioic acid (0.01 ml, 0.09 mmol) solution in IPA and stirred at r.t. for 4 mins before diethyl ether (1 mL) was added. A precipitate slowly formed over 3 h and was left standing overnight. The precipitate was collected by filtration, washed with ether (2×1 mL) and dried under vacuum to provide the title compound (9.7 mg, 14.2%) as a pale beige solid.

Method C: LC-MS m/z=393.1 [M+H]$^+$; RT=2.59 min.

Example 224—Synthesis of 2-{4-[4-(trifluoromethyl)piperidine-1-carbonyl]pyridin-2-yl}-3H,4H-thieno[3,2-d]pyrimidin-4-one Step 1: Preparation of phenyl 2-cyanopyridine-4-carboxylate

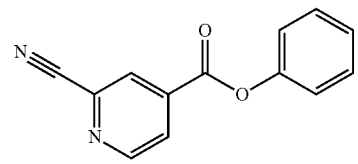

(EV-AR7020-001)

4-bromopyridine-2-carbonitrile (150 mg, 0.82 mmol), phenyl formate (0.12 ml, 1.07 mmol), palladium(II) acetate (5.52 mg, 0.02 mmol), tri-tert-butylphosphonium tetrafluoroborate (28.54 mg, 0.1 mmol) and N,N-diethylethanamine (0.15 ml, 1.07 mmol) were added to a microwave vessel under an atmosphere of nitrogen. The reaction vessel was de-gassed and back filled with nitrogen (×3), sealed and heated at 140° C. for 20 mins under microwave irradiation. A further portion of palladium(II) acetate (5.52 mg, 0.02 mmol) and tri-tert-butylphosphonium tetrafluoroborate (28.54 mg, 0.1 mmol) was added and the reaction vessel de-gassed and back filled with nitrogen (×3), sealed and heated at 140° C. for 45 mins under microwave irradiation. The resultant mixture was diluted with water (4 mL) and DCM (3 mL), stirred vigorously and the phases separated using a phase separator cartridge. The aqueous was re-extracted with DCM (×2) and the organic extracts separated using a phase separator. The combined organic extracts were concentrated in vacuo and purified by chromatography on SiO$_2$, eluting with Heptane/EtOAc (gradient 100:0-55:45) to afford the title compound (94 mg, 51%) as a pale yellow gum that solidified on standing.

Method B: LC-MS m/z=224.9 [M+H]$^+$; RT=1.11 min.

Step 2: Preparation of 4-[4-(trifluoromethyl)piperidine-1-carbonyl]pyridine-2-carbonitrile

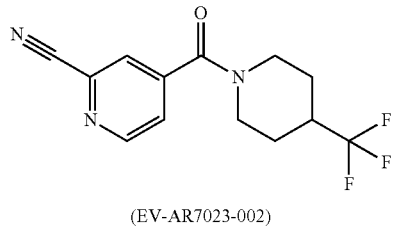 [SMILES: N#Cc1cc(C(=O)N2CCC(C(F)(F)F)CC2)ccn1]

(EV-AR7023-002)

To a solution of phenyl 2-cyanopyridine-4-carboxylate (101 mg, 0.45 mmol) in anhydrous THF (1 mL), under an atmosphere of nitrogen, was added 4-(trifluoromethyl)piperidin-1-ium chloride (128.12 mg, 0.68 mmol), N,N-diethylethanamine (0.13 ml, 0.9 mmol) and N,N-dimethylpyridin-4-amine (2.75 mg, 0.02 mmol) and the suspension stirred at 45° C. for 4-5 h. The reaction mixture was diluted with DCM, concentrated on to silica (1.5 g) and purified by chromatography on $SiO_2$ eluting with Heptane/EtOAc (gradient 100:0-70:30), followed by DCM/MeOH (gradient 100:0-45:55), to afford the title compound (102 mg, 80%) as a colourless glass.

Method B: LC-MS m/z=284.0 [M+H]$^+$; RT=1.02 min

Step 3: Synthesis of 2-{4-[4-(trifluoromethyl)piperidine-1-carbonyl]pyridin-2-yl}-3H,4H-thieno[3,2-d]pyrimidin-4-one

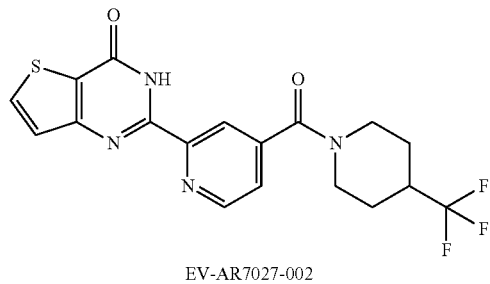 [SMILES: O=C(c1ccnc(-c2nc3ccsc3c(=O)[nH]2)c1)N1CCC(C(F)(F)F)CC1]

EV-AR7027-002

To a solution of 4-[4-(trifluoromethyl)piperidine-1-carbonyl]pyridine-2-carbonitrile (0.1 g, 0.36 mmol) and methyl 3-aminothiophene-2-carboxylate (0.06 g, 0.4 mmol) in THF (2.5 mL) at 0° C. under an atmosphere of nitrogen was added potassium tert-butoxide (0.04 g, 0.4 mmol) and stirred at 0° C.—r.t. for 3 h. The reaction mixture was concentrated in vacuo, diluted with saturated ammonium chloride (5 mL) and water and stirred at r.t. The mixture was extracted with DCM (×2), followed by EtOAc, and the combined organic extracts dried over $Na_2SO_4$ and concentrated in vacuo. The crude residue was stirred in diethyl ether (9 mL) for 30 mins at r.t. and the resultant solid was filtered, washing with diethyl ether (×2) and dried under vacuum to yield the title compound (58 mg, 38.6%) as a white solid.

Method C: LC-MS m/z=409.1 [M+H]$^+$; RT=2.75 min

Example 225—Synthesis of 2-(4-{[4-(trifluoromethyl)piperidin-1-yl]sulfonyl}pyridin-2-yl)-3H,4H,5H,6H,7H-cyclopenta[d]pyrimidin-4-one

Q-522

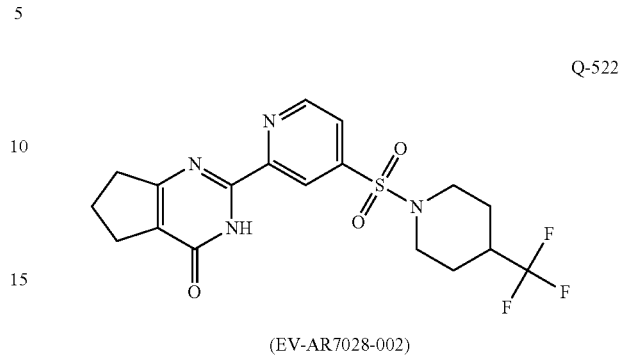

(EV-AR7028-002)

In a pressure tube palladium(II) acetate (0.01 g, 0.03 mmol), N,N,N-tributylbutan-1-aminium bromide (182 mg, 0.56 mmol), triphenylphosphine (20 mg, 0.08 mmol), sodium formate (77 mg, 1.13 mmol), 1,10-phenanthroline hydrate (1:1) (0.02 g, 0.08 mmol) and dipotassium oxidosulfanesulfonate oxide (0.23 g, 1.03 mmol) were stirred vigorously in anhydrous DMSO (3 mL), under an atmosphere of nitrogen before 2-(4-bromopyridin-2-yl)-3H,4H,5H,6H,7H-cyclopenta[d]pyrimidin-4-one (Example 223 step 2)(0.15 g, 0.51 mmol) was added and the vessel sealed and heated at 70° C. for 3 h. The reaction mixture was cooled to r.t., diluted with MeOH (5 mL) and stirred for 5-10 mins. The mixture was filtered through a small pad of Celite®, washing with MeOH (3×2 mL), concentrated in vacuo and triturated with diethyl ether (2×4 mL). The resulting solid was azeotroped with toluene, cooled to 0° C. and treated with 4-(trifluoromethyl)piperidin-1-ium chloride (0.11 g, 0.56 mmol), DIPEA (223.59 µl, 1.28 mmol) and 1-chloropyrrolidine-2,5-dione (41.55 µl, 0.51 mmol) in DMF (1 mL) and stirred at r.t. for 72 h. The reaction mixture was diluted with water (10 mL), extracted with EtOAc (3×25 mL) and the combined extracts washed with water (×4) and brine. The organics were dried over $Na_2SO_4$, concentrated in vacuo and triturated with ether. The solid was suspended in MeOH (~4-5 mL) and heated to dissolution. The solution was concentrated in vacuo and triturated with ether to afford the title compound (96 mg, 44%) as a pale yellow solid.

Method C: LC-MS m/z=429.1 [M+H]$^+$; RT=3.15 min

Example 226—Synthesis of 2-[4-(cyclopentyloxy)-1H-pyrazol-1-yl]-3H,4H,5H,6H,7H-cyclopenta[d]pyrimidin-4-one

Q-529

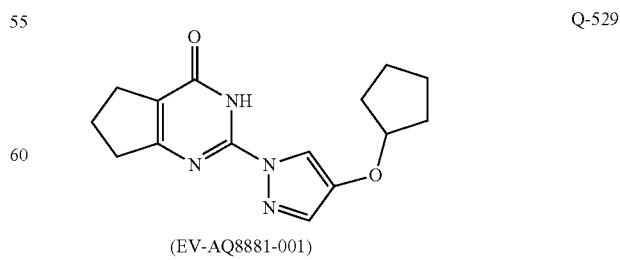

(EV-AQ8881-001)

To a solution of 2-chloro-3H,4H,5H,6H,7H-cyclopenta[d]pyrimidin-4-one (Example 193 step 1, 74 mg, 0.43 mmol)

and 4-(cyclopentyloxy)-1H-pyrazole (85 mg, 0.46 mmol) in DMF (3 mL) was added cesium carbonate (434 mg, 1.33 mmol). The mixture was irradiated at 170° C. in the microwave for an hour. After a further 1 hour under these conditions the cooled reaction mixture was diluted with HCl (1M 20 mL) and extracted with EtOAc (20 mL), the organic fraction was dried (MgSO$_4$), concentrated under vacuum and purified by PERP-HPLC (method G) to yield the title compound (32 mg, 26%) as a as a colourless powder.

Method C: LC-MS m/z=287.1 [M+H]$^+$; RT=3.10 min

Example 227—Synthesis of 2-(piperidin-4-yl)butanenitrile hydrochloride

Step 1: Synthesis of tert-butyl 4-(1-cyanopropyl)piperidine-1-carboxylate

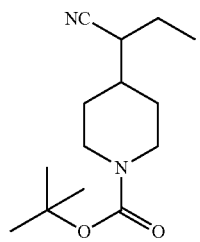 [SMILES: CCC(C#N)C1CCN(C(=O)OC(C)(C)C)CC1]

2.5 M n-BuLi in THF (0.28 mL, 0.7 mmol) was added to a solution of diisopropylamine (54 mg, 0.536 mmol) in THF (2 mL) at −78° C. The solution was stirred for 30 min and then a solution of tert-butyl 4-(cyanomethyl)piperidine-1-carboxylate (100 mg, 0.446 mmol) was added dropwise at −78° C. The resulting solution was stirred for 1 h and iodoethane (83.6 mg, 0.536 mmol) was added. The reaction mixture was stirred overnight. The reaction was quenched with sat. NH$_4$Cl (5 mL), extracted with EtOAc (30 mL×2), the combined organics were dried over Na$_2$SO$_4$, concentrated to yield the product (110 mg, 98% yield) which was used in the next step without purification.

LC-MS: m/z=197 (M−55)+, RT=1.70 min.

Step 2: Synthesis of 2-(piperidin-4-yl)butanenitrile hydrochloride

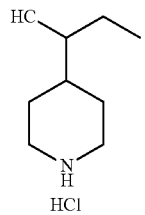

4.0 M HCl in dioxane (2 mL) was added to a solution of tert-butyl 4-(1-cyanopropyl) piperidine-1-carboxylate (110 mg, 0.436 mmol) in DCM (2 mL). The solution was stirred at r.t for 4 h. Then the reaction was removed the solvent to yield the product (85 mg, 99%) as white solid.

LC-MS: m/z=153 (M+H)+

Example 228—Synthesis of 4-ethylpiperidine-4-carbonitrile hydrochloride

Step 1: Synthesis of tert-butyl 4-cyano-4-ethylpiperidine-1-carboxylate

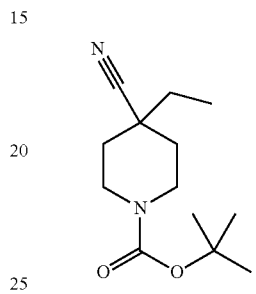

2.5 M n-BuLi in THF (7.2 mL, 18 mmol) was added to a solution of diisopropylamine (1.818 g, 18 mmol) in THF (20 mL) at −78° C. The solution was stirred for 30 min and then the solution was added to the solution of tert-butyl 4-cyanopiperidine-1-carboxylate (3.15 g, 15 mmol) in THF (40 mL) dropwise at −78° C. The resulting solution was stirred for 1 h and iodoethane (83.6 mg, 0.536 mmol) was added. The reaction mixture was stirred overnight. The reaction was quenched with sat. NH$_4$Cl (10 mL) and water (20 mL), extracted with EtOAc (50 mL×2), the combined organics were dried over Na$_2$SO$_4$, concentrated to yield the product (3.4 g, 95.2% yield) which used in the next step without purification.

LC-MS: m/z=183 (M−55)+, RT=1.879 min.

Step 2: Synthesis of 4-ethylpiperidine-4-carbonitrile hydrochloride

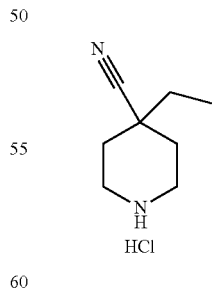

4.0 M HCl in dioxane (10 mL) was added to the solution of tert-butyl 4-cyano-4-ethylpiperidine-1-carboxylate (3.4 g, 14.3 mmol) in DCM (10 mL). The solution was stirred at r.t. overnight. Then the reaction was removed the solvent to yield the product (2.48 g, 99%) as pale white solid.

LC-MS: m/z=139 (M+H)+, RT=1.076 min.

Example 229—Synthesis of 2-(5-(4-(trifluoromethyl)piperidine-1-carbonyl)thiophen-2-yl)-6,7-dihydro-3H-cyclopenta[d]pyrimidin-4(5H)-one (Q-609)

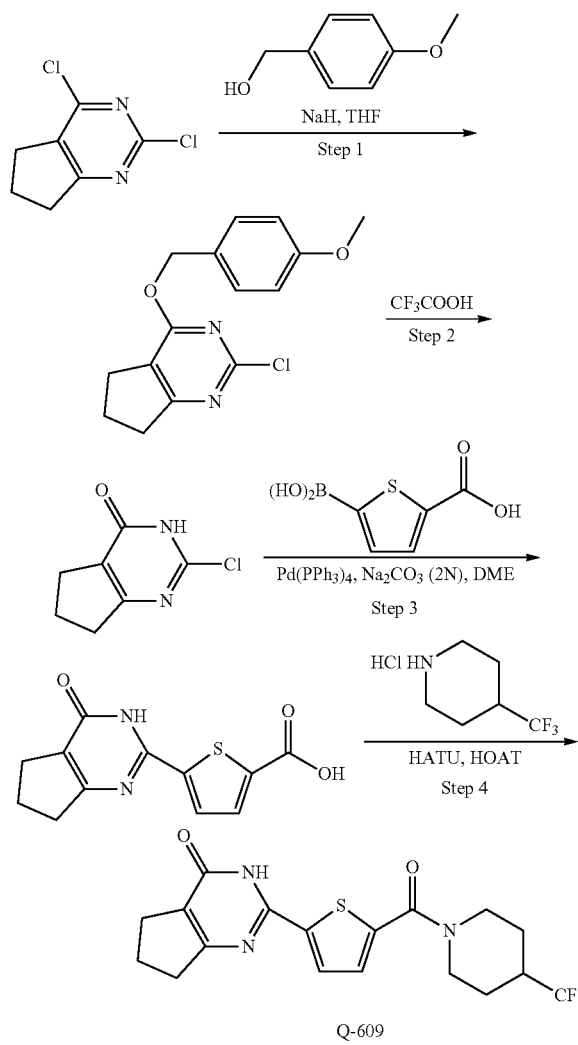

Step 1: Synthesis of 2-chloro-4-(4-methoxybenzyloxy)-6,7-dihydro-5H-cyclopenta[d]pyrimidine

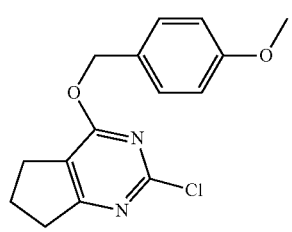 [SMILES: COc1ccc(COc2nc(Cl)nc3c2CCC3)cc1]

To a 100 mL of RBF was added (4-methoxyphenyl) methanol (460 mg, 3.33 mmol), 15 mL of THF and NaH (60%) (160 mg, 4.0 mmol). The mixture was stirred at r.t. for 30 min. Then 2,4-dichloro-6,7-dihydro-5H-cyclopenta[d] pyrimidine (600 mg, 3.19 mmol) was added and the mixture was stirred at r.t. for 3 h. The reaction mixture was treated with water (20 ml) and extracted with EtOAc (100 ml). The organic layer was concentrated and purified by combiflash (isco, silica gel, UV 254, 40 g, EA/PE=1/10) to give product. LC-MS: m/z=291 (M+H)+, RT=2.012 min.

Step 2: Synthesis of 2-chloro-6,7-dihydro-3H-cyclopenta[d]pyrimidin-4(5H)-one

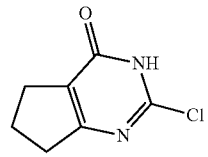 [SMILES: O=c1[nH]c(Cl)nc2c1CCC2]

To a 100 mL of RBF was added 2-chloro-4-(4-methoxybenzyloxy)-6,7-dihydro-5H-cyclopenta[d]pyrimidine (350 mg, 1.2 mmol), 8 mL of DCM and 2 ml of CF3COOH. The mixture was stirred at r.t. for 3 h. The reaction mixture was treated with TEA until pH=8 and then purified by combiflash (isco, silica gel, UV 254, 40 g, EA/PE=1/1) to give product. LC-MS: m/z=171 (M+H)+, RT=1.246 min.

Step 3: Synthesis of 5-(4-oxo-4,5,6,7-tetrahydro-3H-cyclopenta[d]pyrimidin-2-yl)thiophene-2-carboxylic acid

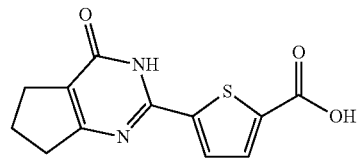 [SMILES: O=C(O)c1ccc(-c2nc3c(c(=O)[nH]2)CCC3)s1]

To a 100 mL of RBF was added 2-chloro-6,7-dihydro-3H-cyclopenta[d]pyrimidin-4(5H)-one (100 mg, 0.58 mmol), 5-boronothiophene-2-carboxylic acid (350 mg, 2.03 mmol), 3 mL of DME, 1.5 mL of EtOH, 0.5 mL of Na$_2$CO$_3$ (2N) and Pd(PPh$_3$)$_4$ (100 mg, 0.086 mmol). The mixture was stirred at 110° C. for 1 h. Then the reaction mixture was purified by combi flash (isco, silica gel, UV 254, 20 g, MeOH/DCM=1/20) to give product LC-MS: m/z=263 (M+H)+, RT=1.358 min.

Step 4: Synthesis of 2-(5-(4-(trifluoromethyl)piperidine-1-carbonyl)thiophen-2-yl)-6,7-dihydro-3H-cyclopenta[d]pyrimidin-4(5H)-one

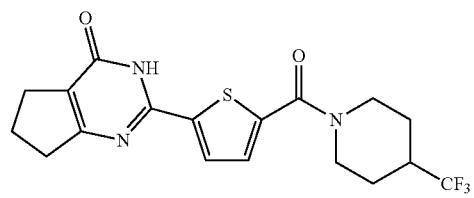 [SMILES: O=C(c1ccc(-c2nc3c(c(=O)[nH]2)CCC3)s1)N1CCC(C(F)(F)F)CC1]

To a 100 mL of RBF was added 5-(4-oxo-4, 5,6,7-tetrahydro-3H-cyclopenta[d]pyrimidin-2-yl)thiophene-2- carboxylic acid (80 mg, 0.30 mmol), 4-(trifluoromethyl) piperidine hydrochloride (60 mg, 0.31 mmol), HOAT (40 mg, 0.30 mmol), HATU (80 mg, 0.34 mmol), 5 ml of THF and 0.05 ml of TEA. The mixture was stirred at r.t. for 16 h. Then the reaction mixture was purified by combi flash (isco, silica gel, UV 254, 20 g, MeOH/DCM=1/20) to give product. LC-MS (method C'): m/z=398 (M+H)+, RT=1.703 min.

Example 230—Synthesis of 2-(3-(4-(trifluoromethyl) piperidine-1-carbonyl) phenyl)-6,7-dihydro-3H-cyclopenta[d]pyrimidin-4(5H)-one (Q-593)

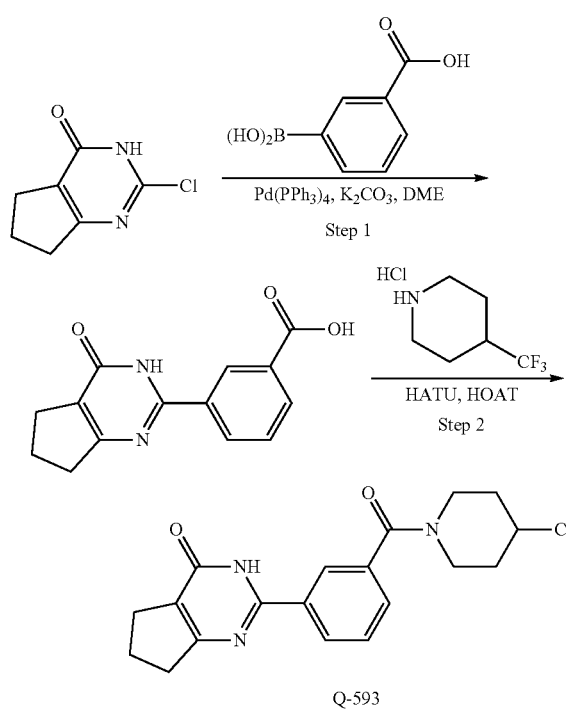

Step 1: Synthesis of 3-(4-oxo-4,5,6,7-tetrahydro-3H-cyclopenta[d]pyrimidin-2-yl)benzoic acid

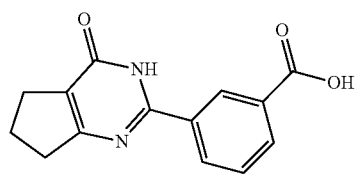 [SMILES: O=C(O)c1cccc(-c2nc3c(c(=O)[nH]2)CCC3)c1]

To a 100 mL of RBF was added 2-chloro-6,7-dihydro-3H-cyclopenta[d]pyrimidin-4(5H)-one (90 mg, 0.53 mmol), 3-boronobenzoic acid (200 mg, 1.20 mmol), $K_2CO_3$ (120 mg, 0.87 mmol), 5 mL of dioxane, 1 mL of water and Pd(PPh$_3$)$_4$ (40 mg, 0.034 mmol). The mixture was stirred at 100° C. for 40 h. Then the reaction mixture was purified by combiflash (isco, silica gel, UV 254, 20 g, MeOH/DCM=1/10) to give product. LC-MS: m/z=257 (M+H)+, RT=0.994 min.

Step 2: Synthesis of 2-(3-(4-(trifluoromethyl)piperidine-1-carbonyl)phenyl)-6,7-dihydro-3H-cyclopenta[d]pyrimidin-4(5H)-one

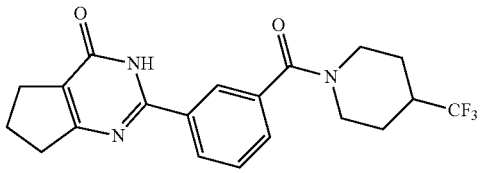 [SMILES: O=C(c1cccc(-c2nc3c(c(=O)[nH]2)CCC3)c1)N1CCC(C(F)(F)F)CC1]

To a 100 mL of RBF was added 3-(4-oxo-4,5,6,7-tetrahydro-3H-cyclopenta[d]pyrimidin-2-yl)benzoic acid (60 mg, 0.23 mmol), 4-(trifluoromethyl)piperidine hydrochloride (50 mg, 0.26 mmol), HOAT (40 mg, 0.30 mmol), HATU (60 mg, 0.25 mmol), 3 ml of THF and 0.05 ml of TEA. The mixture was stirred at r.t. for 16 h. Then the reaction mixture was purified by combiflash (isco, silica gel, UV 254, 20 g, MeOH/DCM=1/20) to give product. LC-MS (method G'): m/z=392 (M+H)+, RT=1.608 min.

Example 231—Synthesis of 2-(4-(3-(3,3-difluoropyrrolidin-1-yl)azetidine-1-carbonyl)-5-methyl-1H-pyrazol-1-yl)-6,6-dimethyl-6,7-dihydro-3H-cyclopenta[d]pyrimidin-4(5H)-one (Q-1564)

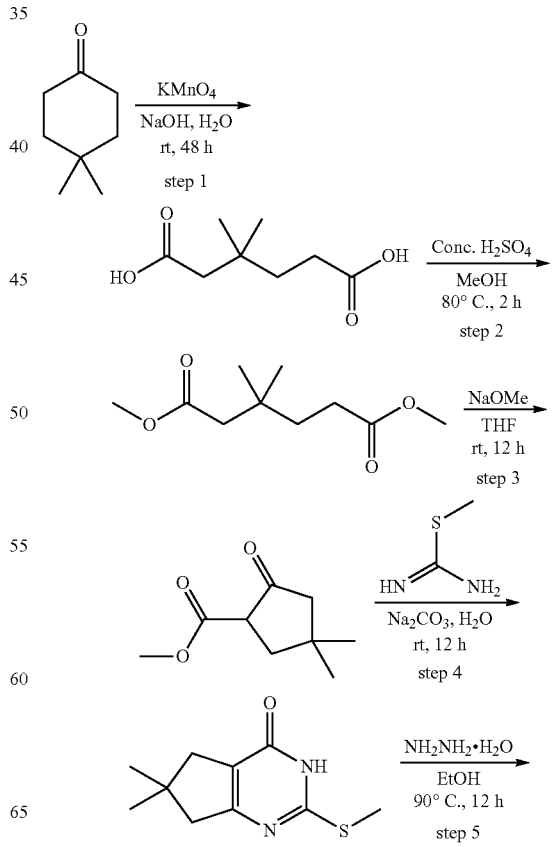

756

Step 2: Synthesis of dimethyl 3,3-dimethylhexanedioate

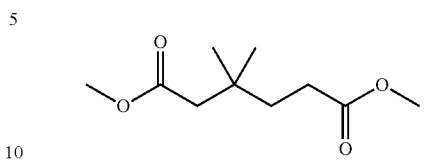

To a solution of 3,3-dimethylhexanedioic acid (7.8 g, 44.8 mmol) in MeOH (100 mL) was added conc. $H_2SO_4$ (1 g, 10 mmol). The mixture was stirred at 80° C. for 2 hrs and concentrated. $NaHCO_3$ solution was added to the residue to pH=7. The mixture was extracted with EtOAc (50 mL×2). The combined organic layers were dried over $Na_2SO_4$ and concentrated under vacuum to yield the product. LC-MS: m/z=203.1 (M+H)+, RT=1.89 min.

Step 3: Synthesis of methyl 4,4-dimethyl-2-oxocyclopentanecarboxylate

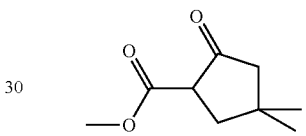

The mixture of Na (230 mg, 10 mmol) in MeOH (8 mL) was stirred at r.t. for 5 minutes. Dimethyl 3,3-dimethylhexanedioate (1 g, 5 mmol) was added. The mixture was stirred at r.t. for 30 minutes and concentrated under vacuum to remove MeOH. THF (8 mL) was added to the residue, and the mixture was stirred at r.t. for 12 hrs. The mixture was poured into $H_2O$ (20 mL). HCl (2N) was added to pH=7. The mixture was extracted with EtOAc (50 mL×2). The organic layers were concentrated and purified by column (silica gel, PE/EtOAc=1/1) to yield the product. LC-MS: m/z=171.1 (M+H)+, RT=1.77 min.

Step 4: Synthesis of 6,6-dimethyl-2-(methylthio)-6,7-dihydro-3H-cyclopenta[d]pyrimidin-4(5H)-one

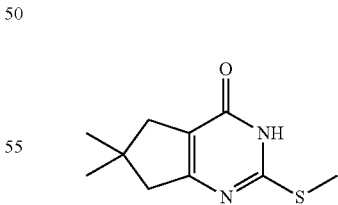

To a solution of methyl 4,4-dimethyl-2-oxocyclopentanecarboxylate (750 mg, 4.4 mmol) in $H_2O$ (20 mL) was added methyl carbamimidothioate (594 mg, 6.6 mmol) and $Na_2CO_3$ (1.87 g, 17.6 mmol). The mixture was stirred at r.t. for 12 hrs. The mixture was extracted with EtOAc (20 mL×2). The organic layers were concentrated and purified by column (silica gel, PE/EtOAc=2/1) to yield the product. LC-MS: m/z=211.1 (M+H)+, RT=1.61 min.

755
-continued

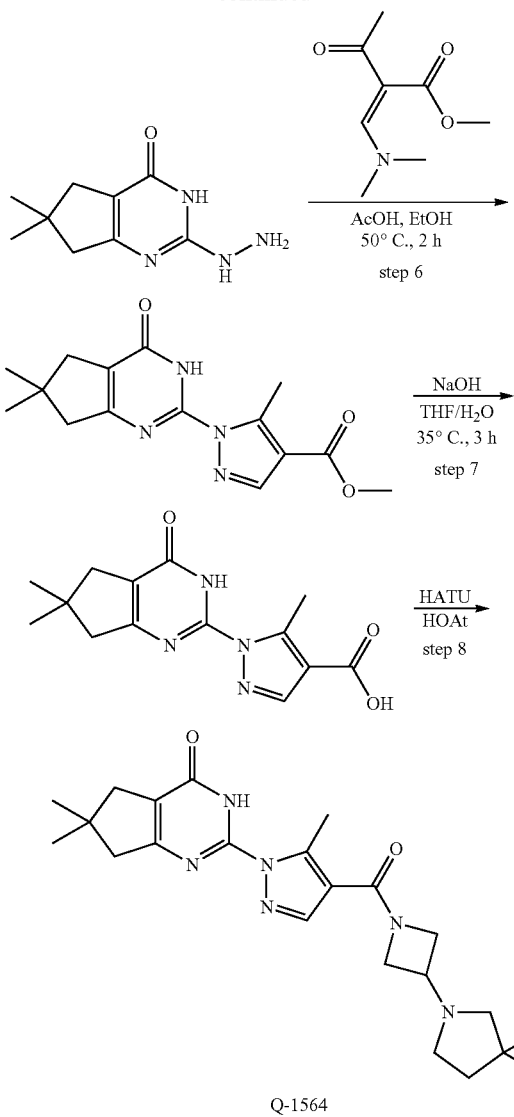

Q-1564

Step 1: Synthesis of 3,3-dimethylhexanedioic acid

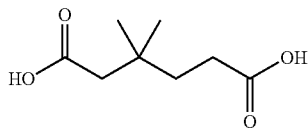

4,4-dimethylcyclohexanone (9 g, 71.3 mmol) and $KMnO_4$ (22.5 g, 142.6 mmol) were taken up in 450 mL of $H_2O$. To this, an aqueous solution of NaOH (1 g, 25 mmol) in 10 mL of $H_2O$ was added at r.t. This mixture was stirred at r.t. for 48 hrs. Aqueous sodium bisulfate was then added until the purple color disappeared. A brown solid was filtered off, and the filtrate was brought to pH=2 with conc. HCl. The solution was extracted with EtOAc (150 mL×2). The combined organics were dried and concentrated to yield the product. LC-MS: m/z=175.1 (M+H)+, RT=0.35 min.

Step 5: Synthesis of 2-hydrazinyl-6,6-dimethyl-6,7-dihydro-3H-cyclopenta[d]pyrimidin-4(5H)-one

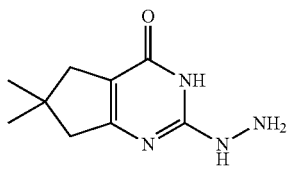

To a solution of 6,6-dimethyl-2-(methylthio)-6,7-dihydro-3H-cyclopenta[d]pyrimidin-4(5H)-one (250 mg, 1.2 mmol) in EtOH (5 mL) was added NH$_2$NH$_2$.H2O (1 mL). The mixture was stirred at 90° C. for 12 hrs and concentrated under vacuum to yield the product which was used in next step directly without purification. LC-MS: m/z=195.2 (M+H)+, RT=1.23 min.

Step 6: Synthesis of methyl 1-(6,6-dimethyl-4-oxo-4,5,6,7-tetrahydro-3H-cyclopenta[d]pyrimidin-2-yl)-5-methyl-1H-pyrazole-4-carboxylate

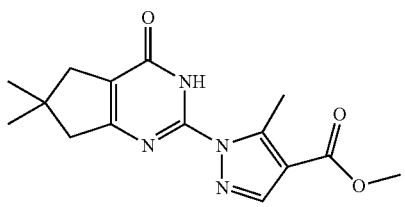

To a solution of 2-hydrazinyl-6,6-dimethyl-6,7-dihydro-3H-cyclopenta[d]pyrimidin-4(5H)-one (230 mg, 1.2 mmol) in EtOH (5 mL) was added (Z)-methyl 2-((dimethylamino)methylene)-3-oxobutanoate (246 mg, 1.4 mmol) and AcOH (0.5 mL). The mixture was stirred at 50° C. for 2 hrs and concentrated under vacuum. The crude residue was purified by column (silica gel, PE/EtOAc=1/3) to yield the product. LC-MS: m/z=303.1 (M+H)+, RT=1.99 min.

Step 7: Synthesis of 1-(6,6-dimethyl-4-oxo-4,5,6,7-tetrahydro-3H-cyclopenta[d]pyrimidin-2-yl)-5-methyl-1H-pyrazole-4-carboxylic acid

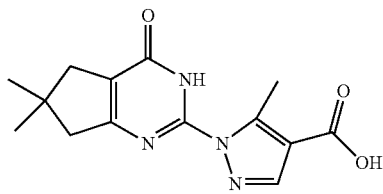 [SMILES: Cc1c(C(=O)O)cnn1-c1nc2c(c(=O)[nH]1)CC(C)(C)C2]

To a solution of methyl 1-(6,6-dimethyl-4-oxo-4,5,6,7-tetrahydro-3H-cyclopenta[d] pyrimidin-2-yl)-5-methyl-1H-pyrazole-4-carboxylate (140 mg, 0.5 mmol) in THF (5 mL) was added a solution of NaOH (60 mg, 1.5 mmol) in H$_2$O (3 mL). The mixture was stirred at 35° C. for 3 hrs and concentrated under vacuum to remove THF. EtOAc (10 mL) was added to extract the impurity. The aqueous phase was adjusted to pH=4 with HCl (2N). The solid was filtered to yield the product. LC-MS: m/z=289.1 (M+H)+, RT=1.11 min.

Step 8: Synthesis of 2-(4-(3-(3,3-difluoropyrrolidin-1-yl)azetidine-1-carbonyl)-5-methyl-1H-pyrazol-1-yl)-6,6-dimethyl-6,7-dihydro-3H-cyclopenta[d]pyrimidin-4(5H)-one

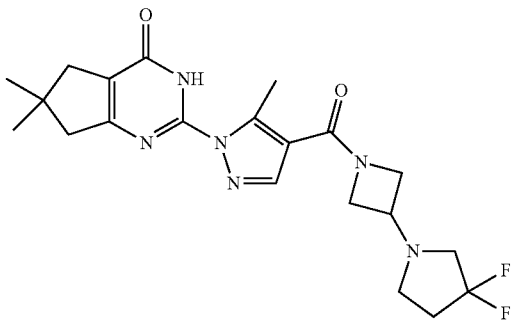 [SMILES: Cc1c(C(=O)N2CC(N3CCC(F)(F)C3)C2)cnn1-c1nc2c(c(=O)[nH]1)CC(C)(C)C2]

To a solution of 1-(6,6-dimethyl-4-oxo-4,5,6,7-tetrahydro-3H-cyclopenta[d]pyrimidin-2-yl)-5-methyl-1H-pyrazole-4-carboxylic acid (49 mg, 0.17 mmol) in THF (6 mL) was added NMM (68 mg, 0.68 mmol), HATU (76 mg, 0.2 mmol), HOAt (26 mg, 0.2 mmol) and 1-(azetidin-3-yl)-3,3-difluoropyrrolidine (46 mg, 0.2 mmol). The mixture was stirred at r.t. for 2 hrs and concentrated under vacuum. The residue was purified by Prep-HPLC (NH$_4$HCO$_3$) to yield the product. LC-MS (method J'): m/z=433.2 (M+H)+, RT=1.46 min.

Example 232—Synthesis of 2-(2-methyl-3-(4-(trifluoromethyl) piperidine-1-carbonyl)-1H-pyrrol-1-yl)-6,7-dihydro-3H-cyclopenta[d]pyrimidin-4(5H)-one) (Q-622

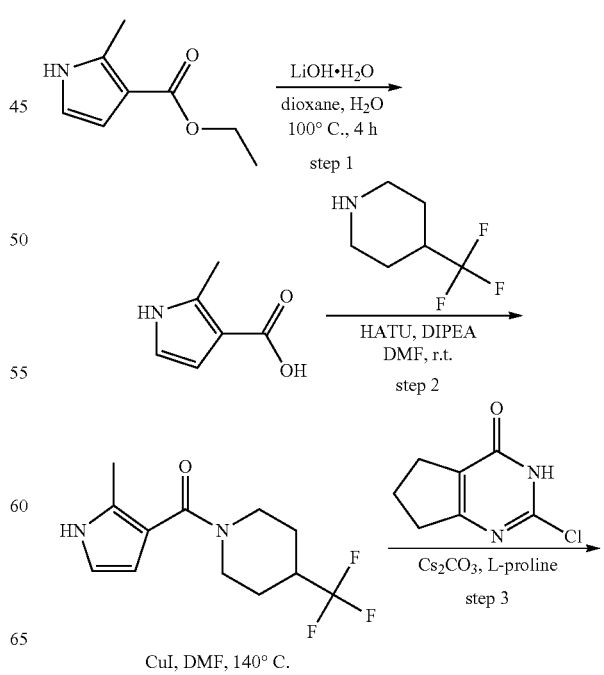

-continued

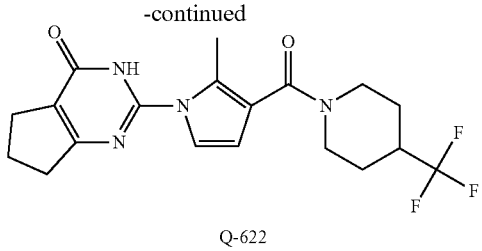

Q-622

Step 1: Synthesis of 2-methyl-1H-pyrrole-3-carboxylic acid

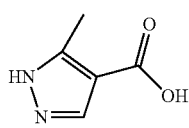

To the solution of ethyl 2-methyl-1H-pyrrole-3-carboxylate (785 mg, 5.12 mmol) in dioxane (8 mL) was added a solution of lithium hydroxide (1.08 g, 25.62 mmol) in H₂O (8 mL). After addition, the reaction mixture was stirred under refluxed for 4 h. The mixture was partitioned with EtOAc and HCl (1M, a.q.). The organic phase was washed with brine, dried over Na₂SO₄ and concentrated to get the title compound. LC-MS: m/z=126.2 (M+H)+, RT=0.32 min.

Step 2: Synthesis of (2-methyl-1H-pyrrol-3-yl)(4-(trifluoromethyl)piperidin-1-yl)methanone

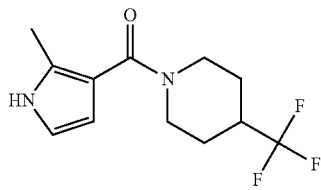 [SMILES: Cc1[nH]ccc1C(=O)N1CCC(C(F)(F)F)CC1]

To the solution of 2-methyl-1H-pyrrole-3-carboxylic acid (100 mg, 0.8 mmol) and 4-(trifluoromethyl)piperidine (147 mg, 0.96 mmol) in DMF (2 mL) were added HATU (456 mg, 1.2 mmol) and DIPEA (206 mg, 1.6 mmol). The reaction mixture was stirred at r.t. for 15 h. The mixture was concentrated and purified by SGC (eluting with PE/EtOAc=1/2, silica gel) to give the title compound. LC-MS: m/z=261.1 (M+H)+, RT=1.62 min.

Step 3: Synthesis of 2-(2-methyl-3-(4-(trifluoromethyl)piperidine-1-carbonyl)-1H-pyrrol-1-yl)-6,7-dihydro-3H-cyclopenta[d]pyrimidin-4(5H)-one

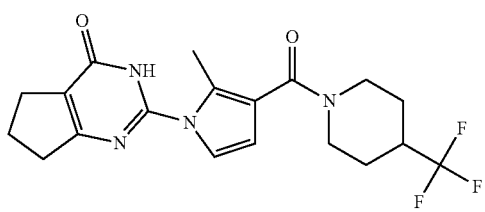 [SMILES: Cc1c(C(=O)N2CCC(C(F)(F)F)CC2)ccn1-c1nc2c(c(=O)[nH]1)CCC2]

To the solution of 2-chloro-6,7-dihydro-3H-cyclopenta[d]pyrimidin-4(5H)-one (90 mg, 0.53 mmol) and (2-methyl-1H-pyrrol-3-yl)(4-(trifluoromethyl)piperidin-1-yl)methanone (164 mg, 0.63 mmol) in DMF (2 mL) were added Cs₂CO₃ (344 mg, 1.06 mmol), L-proline (30 mg, 0.26 mmol) and CuI (50 mg, 0.26 mmol). The reaction mixture was stirred at 140° C. for 15 h. The mixture was purified by pre-HPLC (high pH) to give the title compound. LC-MS (method G'): m/z=395.0 (M+H)+, RT=1.42 min.

Example 233—Synthesis of 5-methyl-1-(4-oxo-4, 5, 6, 7-tetrahydro-3H-cyclopenta[d]pyrimidin-2-yl)-4-(4-(trifluoromethyl) piperidine-1-carbonyl)-1H-pyrazole-3-carboxamide (Q-1884)

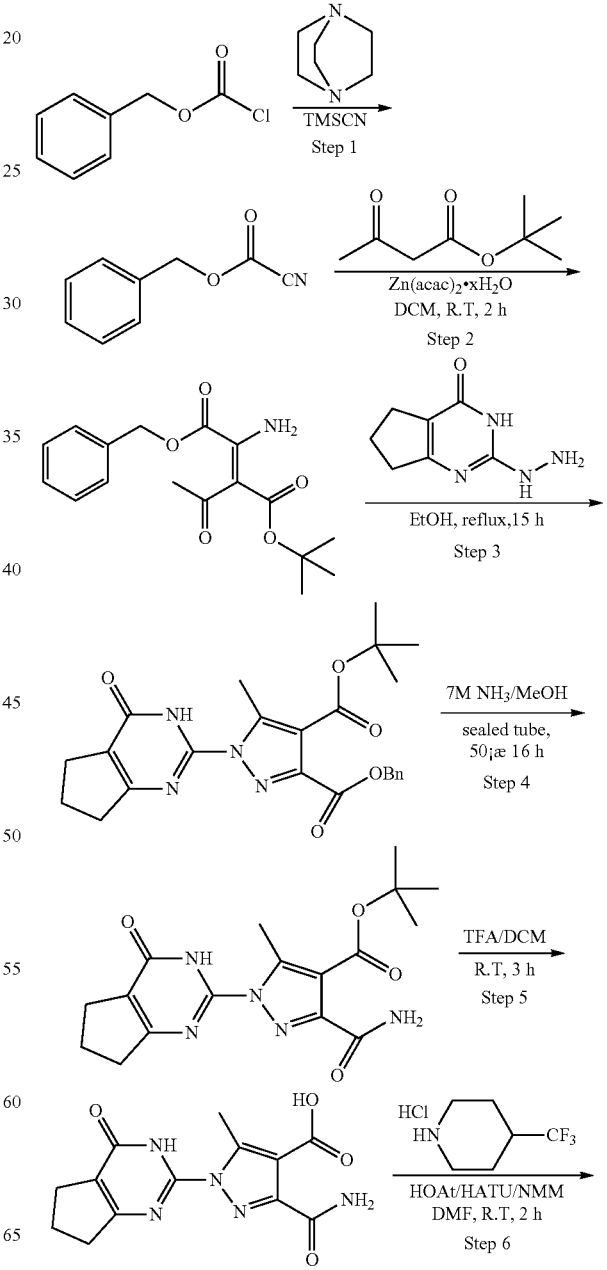

-continued

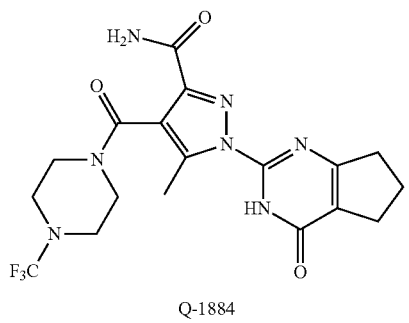

Q-1884

Step 1: Synthesis of Benzyl Cyanoformate

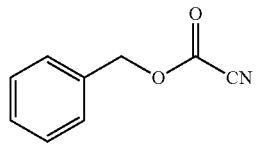 [SMILES: N#CC(=O)OCc1ccccc1]

Benzyl chloroformate (5 g, 0.029 mol) and 1, 4-diazabicyclo [2.2.2] octane (22 mg; 0.20 mmol) were added to a dry reaction vessel under a dry nitrogen atmosphere. Trimethylsilyl nitrile (2.9 g, 0.029 mol) was added dropwise over about 1 hr. The mixture was maintained at between 20° C.-30° C. until the reaction reached completion in about 3 hr. After distilling off the trimethylsilyl chloride, 4.3 g of crude product was obtained, which was used directly in the next step. GC-MS: m/z=161 M+, RT=9.249 min.

Step 2: Synthesis of 4-benzyl 1-tert-butyl 2-acetyl-3-aminofumarate

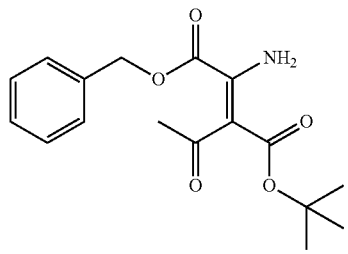 [SMILES: CC(=O)/C(C(=O)OC(C)(C)C)=C(/N)C(=O)OCc1ccccc1]

To a solution of tert-butyl 3-oxobutanoate (982 mg, 6.22 mmol and benzyl cyanoformate (1 g, 6.21 mmol) in DCM (3 mL) was added zinc(II) acetyl acetonate (82 mg, 0.31 mmol) and the reaction mixture was stirred at r.t. for 2 h. The reaction mixture was evaporated, and the residue was taken up in Et$_2$O (20 mL) and the suspension was filtered over celite. The cake was washed with Et$_2$O (15 mL) and the filtrate evaporated. The residue was purified by silica gel chromatography (PE/EA=12/1) to afford the title compound. LC-MS: m/z=342 (M+Na)+, RT=1.596 min.

Step 3: Synthesis of 3-benzyl 4-tert-butyl 5-methyl-1-(4-oxo-4, 5, 6, 7-tetrahydro-3H-cyclo-penta[d]pyrimidin-2-yl)-1H-pyrazole-3, 4-dicarboxylate

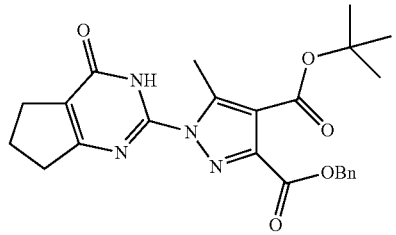 [SMILES: Cc1c(C(=O)OC(C)(C)C)c(C(=O)OCc2ccccc2)nn1-c1nc2c(c(=O)[nH]1)CCC2]

To a solution of 4-benzyl 1-tert-butyl 2-acetyl-3-aminofumarate (575 mg, 1.80 mmol) in 5 mL of EtOH was added 2-hydrazinyl-6,7-dihydro-3H-cyclopenta[d]pyrimidin-4(5H)-one (300 mg, 1.81 mmol). The suspension was heated to reflux for 15 h. After being cooled to r.t., the suspension was filtered and the filtrate was concentrated. The residue was purified by silica gel chromatography using (PE/EA=12/1) to afford the title compound. LC-MS: m/z=395 (M−55)+, RT=2.188 min.

Step 4: Synthesis of tert-butyl 3-carbamoyl-5-methyl-1-(4-oxo-4, 5, 6, 7-tetrahydro-3H-cyclopenta [d]pyrimidin-2-yl)-1H-pyrazole-4-carboxylate A solution of 3-benzyl 4-tert-butyl 5-methyl-1-(4-oxo-4, 5, 6, 7-tetrahydro-3H-cyclopenta[d]pyrimidin-2-yl)-1H-pyrazole-3,4-dicarboxylate (440 mg, 0.98 mmol) in 8 mL of 7 M NH$_3$ solution in MeOH was put into a sealed tube and heated at 50° C. for 15 h. After being cooled to r.t., the solution was concentrated to give title compound. LC-MS: m/z=304 (M−55)+, RT=1.504 min.

Step 5: Synthesis of 3-carbamoyl-5-methyl-1-(4-oxo-4, 5, 6, 7-tetrahydro-3H-cyclopenta[d]-pyrimidin-2-yl)-1H-pyrazole-4-carboxylic acid

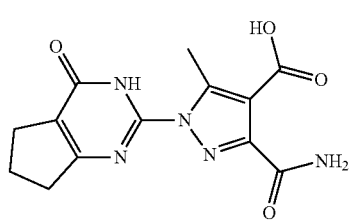 [SMILES: Cc1c(C(=O)O)c(C(N)=O)nn1-c1nc2c(c(=O)[nH]1)CCC2]

To a solution of tert-butyl 3-carbamoyl-5-methyl-1-(4-oxo-4,5,6,7-tetrahydro-3H-cyclopenta-[d]pyrimidin-2-yl)-1H-pyrazole-4-carboxylate (30 mg, 0.084 mmol) in 2 mL of DCM was added 1 mL of TFA and the mixture was stirred at r.t. for 3 h. Then the reaction mixture was diluted with toluene and concentrated to give the desired product. LC-MS: m/z=304 (M+H)+, RT=0.407 min.

Step 6: Synthesis of 5-methyl-1-(4-oxo-4, 5, 6, 7-tetrahydro-3H-cyclopenta[d]pyrimidin-2-yl)-4-(4-(trifluoromethyl) piperidine-1-carbonyl)-1H-pyrazole-3-carboxamide

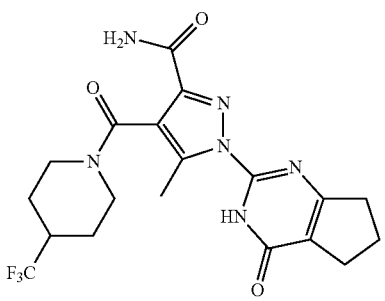 [SMILES: Cc1c(C(=O)N2CCC(C(F)(F)F)CC2)c(C(N)=O)nn1-c1nc2c(c(=O)[nH]1)CCC2]

To a mixture of 3-carbamoyl-5-methyl-1-(4-oxo-4, 5, 6, 7-tetrahydro-3H-cyclopenta[d]pyrimidin-2-yl)-1H-pyrazole-4-carboxylic acid (26 mg, 0.084 mmol) and 4-(trifluoromethyl) piperidine hydrochloride (16 mg, 0.084 mmol) in 2 mL of DMF was added NMM (0.05 mL, 0.45 mmol), HOAt (14 mg, 0.10 mmol) and HATU (38 mg, 0.10 mmol). The reaction mixture was stirred at r.t. for 2 h and filtered. The filtrate was purified by prepared HPLC (NH$_4$HCO$_3$) to give the desired product. LC-MS (method F'): m/z=439 (M+H)+, RT=1.356 min.

Example 234—Synthesis of 6-fluoro-2-(4-(4-(trifluoromethyl)piperidine-1-carbonyl)-1H-pyrazol-1-yl)pyrrolo[1,2-f][1,2,4]triazin-4(3H)-one (Q-616)

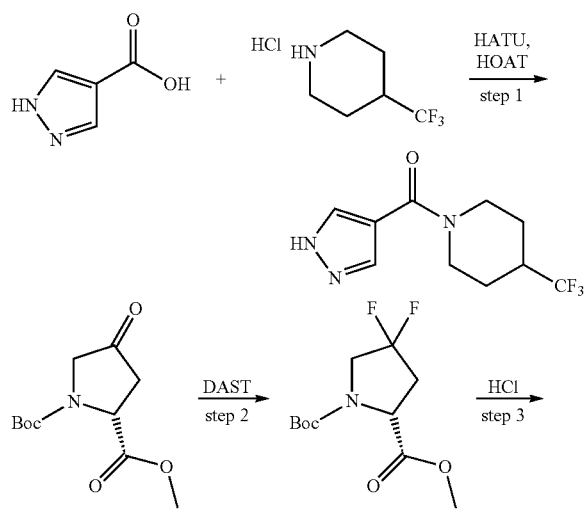

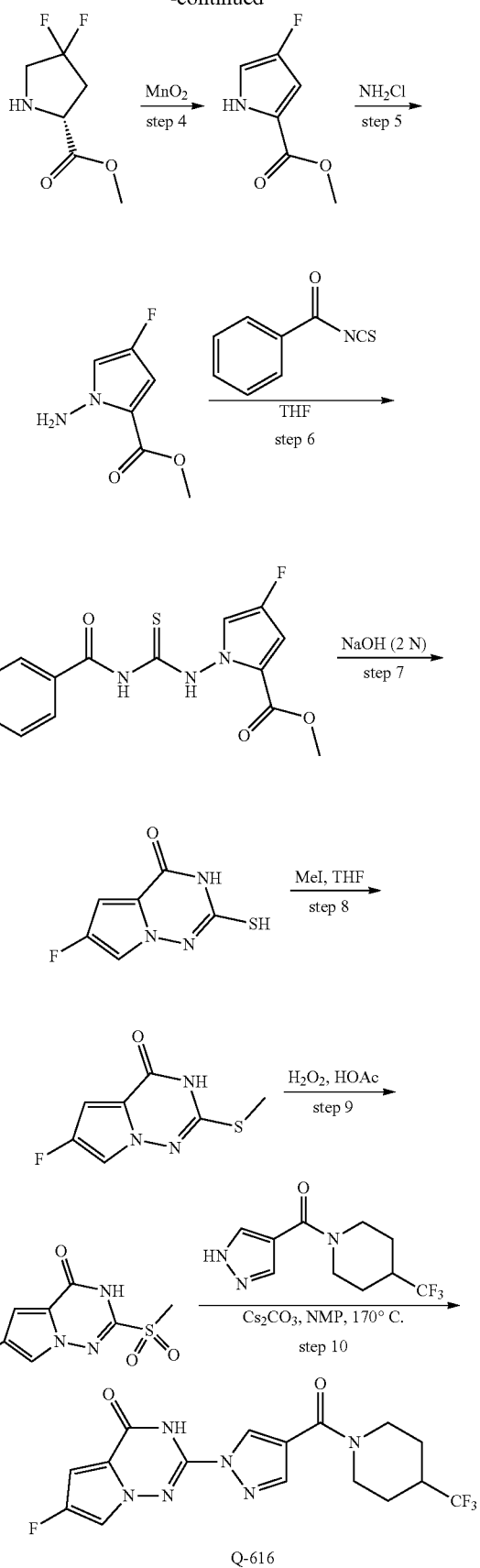

Q-616

Step 1: (1H-pyrazol-4-yl)(4-(trifluoromethyl)piperidin-1-yl)methanone

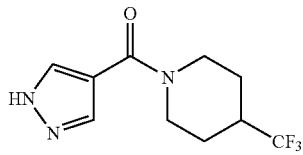 [SMILES: O=C(c1cn[nH]c1)N1CCC(C(F)(F)F)CC1]

To a 100 mL of RBF was added 1H-pyrazole-4-carboxylic acid (500 mg, 4.46 mmol), 4-(trifluoromethyl)piperidine hydrochloride (1.0 g, 5.29 mmol), HATU (1.2 g, 5.10 mmol), HOAT (700 mg, 5.14 mmol), 40 mL of THF and 2 mL of TEA. The mixture was stirred at RT for 16 h. The reaction mixture was concentrated and purified by combiflash (isco, silica gel, UV 254, 40 g, MeOH/DCM=1/10) to give product LC-MS: m/z=248 (M+H)+, RT=1.434 min.

Step 2: Synthesis of (R)-1-tert-butyl 2-methyl 4,4-difluoropyrrolidine-1,2-dicarboxylate

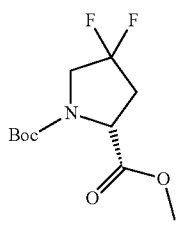

To a 500 mL of RBF was added (R)-1-tert-butyl 2-methyl 4-oxopyrrolidine-1,2-dicarboxylate (4.0 g, 16.4 mmol) and 200 mL of DCM. The mixture was cooled to 0° C. and DAST (24.0 g, 150.0 mmol) in 100 ml of DCM was added drop wise over 1 h. Then the mixture was stirred at r.t. for 16 h. The reaction mixture was treated with NaHCO₃ (aq) and extracted with DCM (300 ml), the organic layer was concentrated to give product. LC-MS: m/z=166 (M−100)+, RT=0.344 min.

Step 3: Synthesis of (R)-methyl 4,4-difluoropyrrolidine-2-carboxylate

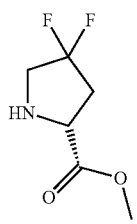

To a 100 mL of RBF was added (R)-1-tert-butyl 2-methyl 4,4-difluoropyrrolidine-1,2-dicarboxylate (4.0 g, 15.1 mmol) and 40 mL of HCl (4 M in dioxane). The mixture was stirred at RT for 16 h. Then the reaction mixture was concentrated to give product. LC-MS: m/z=166 (M+H)+, RT=0.347 min.

Step 4: Synthesis of methyl 1-amino-4-fluoro-1H-pyrrole-2-carboxylate

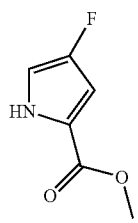

To a 250 mL of RBF was added (R)-methyl 4,4-difluoropyrrolidine-2-carboxylate (2.4 g, 14.5 mmol) in 80 ml of THF was added 24 g of MnO₂. The mixture was stirred at 70° C. for 16 h. The reaction mixture was filtered and the filtrate was concentrated and purified by combiflash (isco, silica gel, UV 254, 40 g, EA/PE=1/3) to give product. LC-MS: m/z=144 (M+H)+, RT=1.528 min.

Step 5: Synthesis of methyl 1-amino-4-fluoro-1H-pyrrole-2-carboxylate

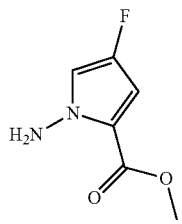

To a 500 mL of RBF was added NH₄Cl (6.0 g, 112 mmol) in 200 ml of Et₂O. The mixture was cooled to −5° C. and 9.4 ml of NH₄OH was added drop wise with vigorous stirring. Then 145 ml of NaClO was added drop wise over 2 h. The mixture was stirred for 15 min and the layer was separated. The organic layer was washed with brine and dried with CaCl₂ and used in the next step without further purification. Then to a 100 ml of RBF was added methyl 4-fluoro-1H-pyrrole-2-carboxylate (1.7 g, 11.8 mmol) and 30 ml of DMF. The mixture was cooled to 0° C. and NaH (60%) (600 mg, 15.0 mmol) was added. After 45 min, the previously prepared NH₂Cl (100 ml) was added dropwise. The mixture was stirred at r.t. for 2 h. The reaction mixture was extracted with EtOAc (200 ml), the organic layer was concentrated and purified by combiflash (isco, silica gel, UV 254, 40 g, EA/PE=1/5) to give product. LC-MS: m/z=159 (M+H)+, RT=1.49 min.

Step 6: Synthesis of methyl 1-(3-benzoylthioureido)-4-fluoro-1H-pyrrole-2-carboxylate

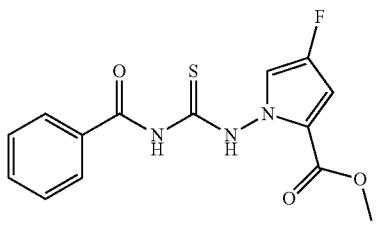 [SMILES: COC(=O)c1cc(F)cn1NC(=S)NC(=O)c1ccccc1]

To a 250 mL of RBF was added methyl 1-amino-4-fluoro-1H-pyrrole-2-carboxylate (1.7 g, 10.76 mmol), 80 ml of THF and benzoyl isothiocyanate (1.8 g, 11.04 mmol). The mixture was stirred at RT under $N_2$ for 16 h. The reaction mixture was concentrated and purified by combi flash (isco, silica gel, UV 254, 40 g, EA/PE=1/4) to give product. LC-MS: m/z=322 (M+H)+, RT=1.823 min.

Step 7: Synthesis of 6-fluoro-2-mercaptopyrrolo[1,2-f][1,2,4]triazin-4(3H)-one

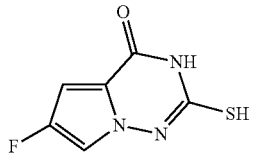

To a 100 mL of RBF was added methyl 1-(3-benzoylthioureido)-4-fluoro-1H-pyrrole-2-carboxylate (1.5 g, 4.67 mmol) and 10 ml of NaOH (2N). The mixture was stirred at 85° C. under $N_2$ for 1.5 h. The reaction mixture was cooled to 0° C. and EtOH (5 ml), HOAc (2 ml) was added and stirred at r.t. for 30 min. The reaction mixture was filtered and washed with $Et_2O$ (20 ml) to give product. LC-MS: m/z=186 (M+H)+, RT=0.67 min.

Step 8: Synthesis of 6-fluoro-2-(methylthio)pyrrolo[1,2-f][1,2,4]triazin-4(3H)-one

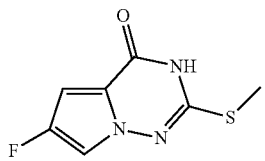

To a 100 mL of RBF was added 6-fluoro-2-mercaptopyrrolo[1,2-f][1,2,4]triazin-4(3H)-one (700 mg, 3.78 mmol) and 20 ml of THF was added MeI (700 mg, 4.92 mmol). The mixture was stirred at 45° C. under $N_2$ for 1 h. The reaction mixture was treated with $NaHCO_3$ (aq) and filtered to give product. LC-MS: m/z=200 (M+H)+, RT=1.551 min.

Step 9: Synthesis of 6-fluoro-2-(methylsulfonyl)pyrrolo[1,2-f][1,2,4]triazin-4(3H)-one

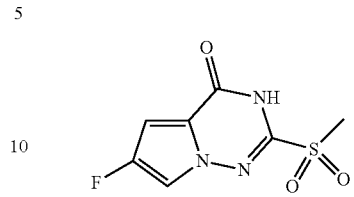

To a 50 mL of RBF was added 6-fluoro-2-(methylthio)pyrrolo[1,2-f][1,2,4]triazin-4(3H)-one (100 mg, 0.50 mmol) and 4 ml of HOAc was added 2 ml of $H_2O_2$. The mixture was stirred at 170° C. in a microwave for 15 h. The reaction mixture was filtered to give product. LC-MS: m/z=232 (M+H)+, RT=1.368 min.

Step 10: Synthesis of 6-fluoro-2-(4-(4-(trifluoromethyl) piperidine-1-carbonyl)-1H-pyrazol-1-yl)pyrrolo[1,2-f][1,2,4]triazin-4(3H)-one

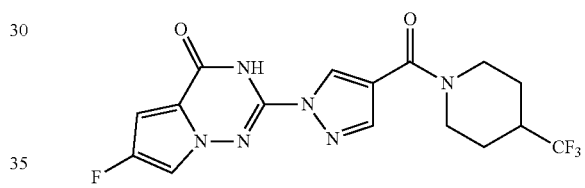

To a microwave tube was added 6-fluoro-2-(methylsulfonyl)pyrrolo[1,2-f][1,2,4]triazin-4(3H)-one (100 mg, 0.43 mmol), (1H-pyrazol-4-yl)(4-(trifluoromethyl)piperidin-1-yl)methanone (110 mg, 0.44 mmol), $Cs_2CO_3$ (160 mg, 0.49 mmol) and 2 ml of NMP. The mixture was stirred at r.t. for 2 days. The reaction mixture was concentrated and purified by combi flash (isco, silica gel, UV 254, 20 g, MeOH/DCM=1/10) to give product. LC-MS (method G'): m/z=399 (M+H)+, RT=1.399 min.

Examples 235-236

Examples 235-236 in Table 17 were prepared in an analogous fashion to Example 234 starting with the corresponding starting materials.

TABLE 17

| Ex. No. | Ref. No. | LC-MS (Retention Time) | MS (M + H)+ | LC-MS Method |
|---|---|---|---|---|
| 235 | Q-741 | 1.565 | 413.1 | F' |
| 236 | Q-746 | 1.497 | 384.1 | F' |

Example 237—Synthesis of 7-fluoro-2-(4-(4-(trifluoromethyl)piperidine-1-carbonyl)-1H-pyrazol-1-yl)pyrrolo[1,2-f][1,2,4]triazin-4(3H)-one (Q-525)

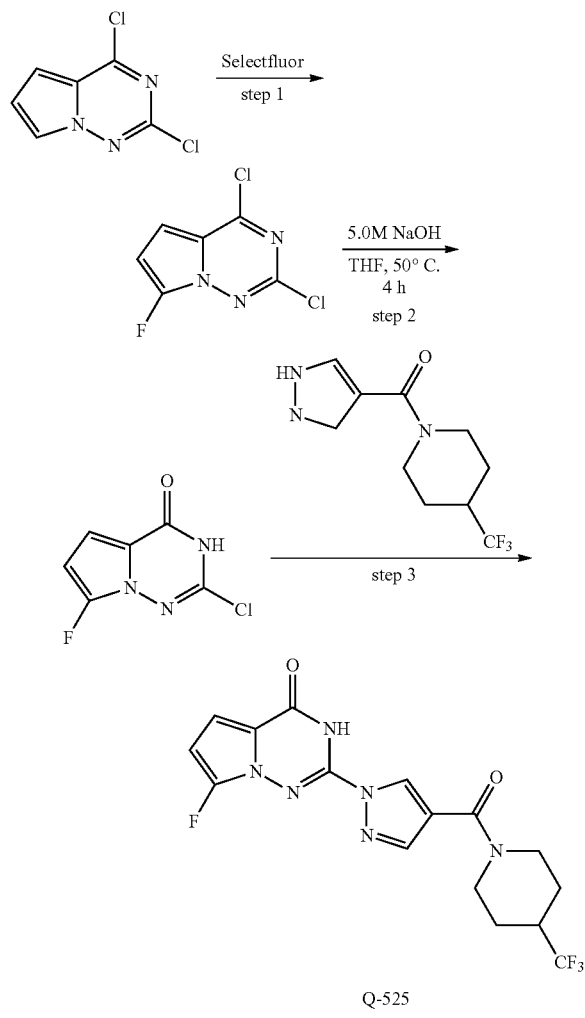

Q-525

Step 1: Synthesis of 2,4-dichloro-7-fluoropyrrolo[1,2-f][1,2,4]triazine

A mixture of 2,4-dichloropyrrolo[1,2-f][1,2,4]triazine (6.0 g, 31.9 mmol) and 1-(chloromethyl)-4-fluoro-1,4-diazonia-bicyclo[2.2.2]octane tetrafluoroborate (22.6 g, 63.8 mmol) in acetonitrile (250 mL) was stirred at 45° C. for 16 h under N₂ atmosphere. The mixture was concentrated, the residue was diluted with DCM (400 mL), washed with H₂O (50 mL×3), and dried over Na₂SO₄. The filtrate was concentrated to give the crude product. LC-MS: m/z=206.0 (M+H)+, RT=1.873 min.

Step 2: Synthesis of 2-chloro-7-fluoropyrrolo[1,2-f][1,2,4]triazin-4(3H)-one

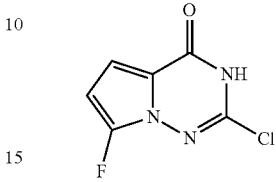

To a mixture of 2,4-dichloro-7-fluoropyrrolo[1,2-f][1,2,4]triazine (6.33 g, 30.7 mmol) in THF/H₂O (30 ml/30 mL) was added sodium hydroxide (6.16 g, 154 mmol). The mixture was stirred at 50° C. for 4 h, and cooled to r.t. The mixture was adjusted to pH=3-4 with 4N HCl and extracted with EtOAc (100 mL×4). The combined organics were dried over Na₂SO₄ and concentrated to give 5.2 g of the crude product. 2 g of the crude product was purified by prep-HPLC (TFA/CH₃CN/H₂O) to give the product. LC-MS: m/z=188.0 (M+H)+, RT=1.486 min.

Step 3: Synthesis of 7-fluoro-2-(4-(4-(trifluoromethyl)piperidine-1-carbonyl)-1H-pyrazol-1-yl)pyrrolo[1,2-f][1,2,4]triazin-4(3H)-one

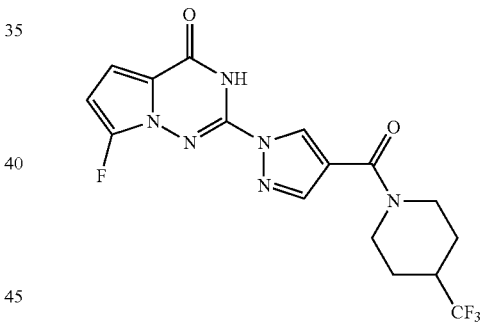

To a mixture of 2-chloro-7-fluoropyrrolo[1,2-f][1,2,4]triazin-4(3H)-one (302 mg, 1.61 mmol), (1H-pyrazol-4-yl)(4-(trifluoromethyl)piperidin-1-yl)methanone (398 mg, 1.61 mmol) and Cs₂CO₃ (1049 mg, 3.22 mmol) in dry DMF (20 mL) were added L-proline (93 mg, 0.8 mmol) and CuI (152 mg, 0.8 mmol) under N₂ atmosphere. The mixture was stirred at 140° C. for 20 h. The mixture was cooled to r.t., diluted with H₂O (100 mL), pH adjusted to 3-4 with 1N HCl, and extracted with EtOAc (100 mL×5). The combined organics were dried over Na₂SO₄ and concentrated. The residue was purified by prep-HPLC (TFA/CH₃CN/H₂O) to give the crude product which was further purified by prep-HPLC (NH₄HCO₃/CH₃CN/H₂O) to give the product. LC-MS (method D'): m/z=399.2 (M+H)+, RT=1.002 min.

Examples 238-239

Examples 238-239 in Table 18 were prepared in an analogous fashion to Example 237 starting with the corresponding starting materials.

TABLE 18

| Ex. No. | Ref. No. | LC-MS (Retention Time) | MS (M + H)+ | LC-MS Method |
|---|---|---|---|---|
| 238 | Q-732 | 1.429 | 381.2 | F' |
| 239 | Q-738 | 1.479 | 380.2 | F' |

Example 240—Synthesis of 2-(5-methyl-4-(4-(4-(trifluoromethoxy)phenylsulfonyl)piperazine-1-carbonyl)-1H-pyrazol-1-yl)pyrrolo[1,2-f][1,2,4]triazin-4(3H)-one (Q-1798)

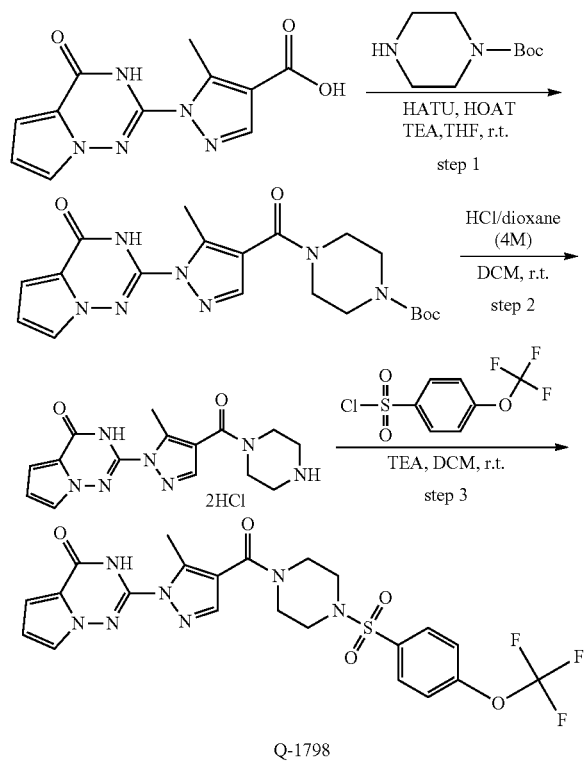

Q-1798

Step 1: Synthesis of tert-butyl-4-(5-methyl-1-(4-oxo-3,4-dihydropyrrolo[1,2-f][1,2,4]triazin-2-yl)-1H-pyrazole-4-carbonyl)piperazine-1-carboxylate

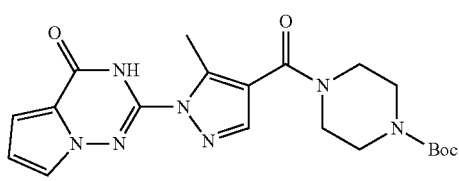 [SMILES: Cc1c(C(=O)N2CCN(C(=O)OC(C)(C)C)CC2)cnn1-c1nn2cccc2c(=O)[nH]1]

To the solution of 5-methyl-1-(4-oxo-3,4-dihydropyrrolo[1,2-f][1,2,4]triazin-2-yl)-1H-pyrazole-4-carboxylic acid (2 g, 7.715 mmol) and tert-butyl-piperazine-1-carboxylate (1.6 g, 8.487 mmol) in THF (40 mL) were added HATU (3.52 g, 9.258 mmol), HOAT (1.05 g, 7.715 mmol) and TEA (2.34 g, 23.146 mmol), the reaction mixture was stirred at r.t. for 15 h. The mixture was concentrated and purified by SGC (eluting with DCM/MeOH=20/1) to give the title compound. LC-MS: m/z=428.3 (M+H)+, RT=1.535 min.

Step 2: Synthesis of 2-(5-methyl-4-(piperazine-1-carbonyl)-1H-pyrazol-1-yl)pyrrolo[1,2-f][1,2,4]triazin-4(3H)-one dihydrochloride

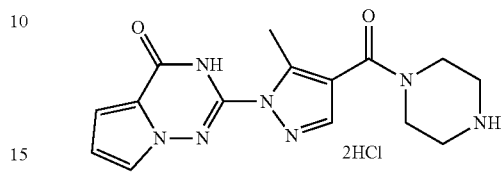

To the solution of tert-butyl-4-(5-methyl-1-(4-oxo-3,4-dihydropyrrolo[1,2-f][1,2,4]triazin-2-yl)-1H-pyrazole-4-carbonyl)piperazine-1-carboxylate (3.88 g, 9.077 mmol) in DCM (50 mL) was added HCl (20 mL, 4 M in dioxane). The reaction mixture was stirred at r.t. for 15 h. The mixture was concentrated to give the title compound. LC-MS: m/z=328.2 (M+H)+, RT=1.146 min.

Step 3: Synthesis of 2-(5-methyl-4-(4-(4-(trifluoromethoxy)phenylsulfonyl)piperazine-1-carbonyl)-1H-pyrazol-1-yl)pyrrolo[1,2-f][1,2,4]triazin-4(3H)-one

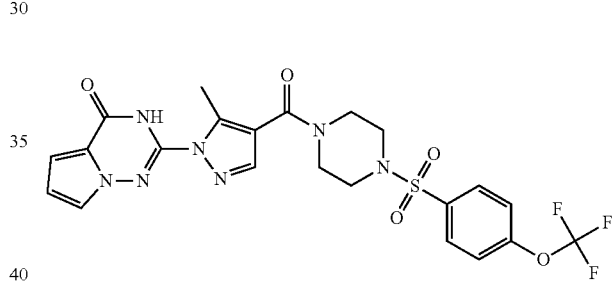

To the solution of 2-(5-methyl-4-(piperazine-1-carbonyl)-1H-pyrazol-1-yl)pyrrolo[1,2-f][1,2,4]triazin-4(3H)-one dihydrochloride (50 mg, 0.125 mmol) and TEA (51 mg, 0.50 mmol) in DCM (3 mL) was added 4-(trifluoromethoxy)benzene-1-sulfonyl chloride (39 mg, 0.15 mmol). The reaction mixture was stirred at r.t. for 15 h. The mixture was purified by prep-HPLC (high pH) to give the title compound. LC-MS (method J'): m/z=552.2 (M+H)+, RT=1.671 min.

Examples 241-289

Examples 241-289 in Table 19 were prepared in an analogous fashion to Example 240 starting with the corresponding starting materials.

TABLE 19

| Ex. No. | Ref. No. | LC-MS (Retention Time) | MS (M + H)+ | LC-MS Method |
|---|---|---|---|---|
| 241 | Q-1794 | 1.51 | 493.2 | J' |
| 243 | Q-1796 | 1.62 | 536.2 | J' |
| 243 | Q-1797 | 1.436 | 434.2 | J' |
| 244 | Q-1798 | 1.671 | 552.2 | J' |
| 245 | Q-1799 | 1.524 | 486.2 | J' |
| 246 | Q-1800 | 1.719 | 524.3 | J' |
| 247 | Q-1801 | 1.630 | 520.2 | J' |

TABLE 19-continued

| Ex. No. | Ref. No. | LC-MS (Retention Time) | MS (M + H)+ | LC-MS Method |
|---|---|---|---|---|
| 248 | Q-1804 | 1.84 | 498.1 | C' |
| 249 | Q-1805 | 1.488 | 503.2 | J' |
| 250 | Q-1807 | 1.86 | 486.1 | C' |
| 251 | Q-1814 | 1.695 | 542.1 | J' |
| 252 | Q-1815 | 1.701 | 561.3 | J' |
| 253 | Q-1819 | 1.562 | 502.2 | J' |
| 254 | Q-1820 | 1.691 | 510.2 | J' |
| 255 | Q-1821 | 1.502 | 474.2 | J' |
| 256 | Q-1822 | 1.606 | 502.2 | J' |
| 257 | Q-1823 | 1.553 | 486.2 | J' |
| 258 | Q-1824 | 1.51 | 493.2 | J' |
| 259 | Q-1825 | 1.648 | 536.1 | J' |
| 260 | Q-1826 | 1.646 | 536.2 | J' |
| 261 | Q-1827 | 1.461 | 546.2 | J' |
| 262 | Q-1829 | 1.527 | 512.2 | J' |
| 263 | Q-1830 | 1.681 | 536.2 | J' |
| 264 | Q-1831 | 1.623 | 518.2 | J' |
| 265 | Q-1832 | 1.6 | 472 | C' |
| 266 | Q-1833 | 1.72 | 525.1 | C' |
| 267 | Q-1834 | 1.647 | 536.2 | J' |
| 268 | Q-1835 | 1.757 | 604.2 | J' |
| 269 | Q-1836 | 1.73 | 536 | A' |
| 270 | Q-1837 | 1.62 | 546.2 | J' |
| 271 | Q-1838 | 1.51 | 493.2 | J' |
| 272 | Q-1839 | 1.84 | 528.1 | C' |
| 273 | Q-1840 | 1.82 | 570 | A' |
| 274 | Q-1841 | 1.961 | 518.1 | C' |
| 275 | Q-1842 | 1.955 | 508.0 | C' |
| 276 | Q-1845 | 1.748 | 512.1 | C' |
| 277 | Q-1846 | 1.720 | 435.1 | C' |
| 278 | Q-1847 | 1.498 | 493.2 | J' |
| 279 | Q-1848 | 1.511 | 487.2 | J' |
| 280 | Q-1857 | 1.7 | 469.1 | C' |
| 281 | Q-1858 | 1.680 | 542.1 | J' |
| 282 | Q-1859 | 1.508 | 519.2 | J' |
| 283 | Q-1861 | 1.966 | 552.1 | C' |
| 284 | Q-1862 | 1.850 | 503.0 | C' |
| 285 | Q-1864 | 1.56 | 519.2 | E' |
| 286 | Q-1875 | 1.823 | 532.1 | C' |
| 287 | Q-1876 | 1.93 | 520 | C' |
| 288 | Q-1882 | 1.832 | 526.5 | C' |
| 289 | Q-1885 | 1.940 | 544.0 | C' |

Example 290—Synthesis of 2-(5-methyl-4-(2,6-diazaspiro[4.5]decane-2-carbonyl)-1H-pyrazol-1-yl)-6,7-dihydro-3H-cyclopenta[d]pyrimidin-4(5H)-one (Q-577)

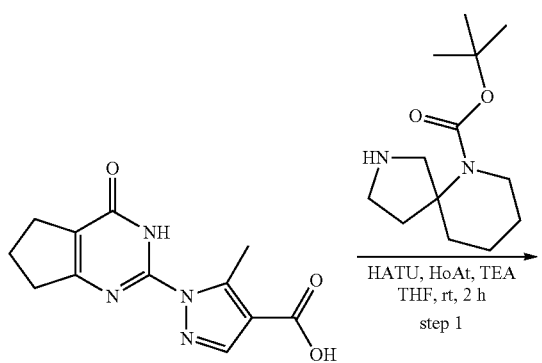

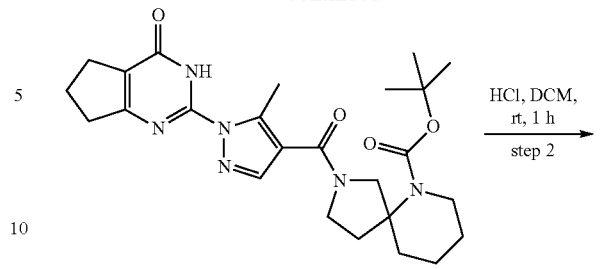

Step 1: Synthesis of tert-butyl 2-(5-methyl-1-(4-oxo-4,5,6,7-tetrahydro-3H-cyclopenta[d]pyrimidin-2-yl)-1H-pyrazole-4-carbonyl)-2,6-diazaspiro[4.5]decane-6-carboxylate

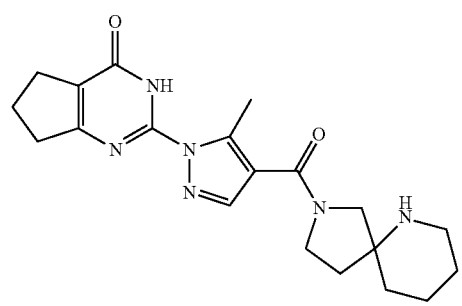 [SMILES: Cc1c(C(=O)N2CCC3(CCCCN3)C2)cnn1-c1nc2c(c(=O)[nH]1)CCC2]

The mixture of 5-methyl-1-(4-oxo-4,5,6,7-tetrahydro-3H-cyclopenta[d]pyrimidin-2-yl)-1H-pyrazole-4-carboxylic acid (50 mg, 0.19 mmol), tert-butyl 2,6-diazaspiro[4.5]decane-6-carboxylate (55 mg, 0.19 mmol), HATU (109.6 mg, 0.29 mmol), HOAt (39 mg, 0.29 mmol) and TEA (0.05 mL, 0.38 mmol) was stirred at r.t. for 2 h. The reaction was concentrated. The residue was purified by prep-TLC (DCM/MeOH=15/1, silica, UV254) to get the title compound. LC-MS: m/z=483 (M+H)+, RT=1.544 min.

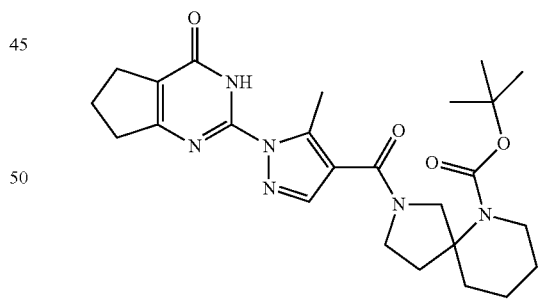

Step 2: Synthesis of 2-(5-methyl-4-(2,6-diazaspiro[4.5]decane-2-carbonyl)-1H-pyrazol-1-yl)-6,7-dihydro-3H-cyclopenta[d]pyrimidin-4(5H)-one

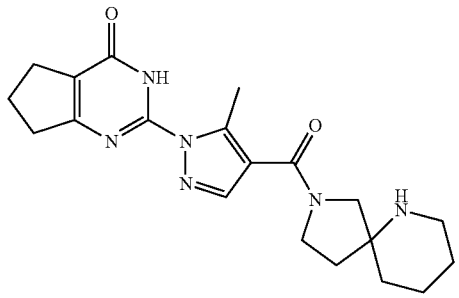

To a solution of tert-butyl 2-(5-methyl-1-(4-oxo-4,5,6,7-tetrahydro-3H-cyclo penta[d]pyrimidin-2-yl)-1H-pyrazole-4-carbonyl)-2,6-diazaspiro[4.5]decane-6-carboxylate (50 mg, 0.1 mmol) in DCM (1 mL) was added HCl (4M in dioxane, 1 mL). The mixture was stirred at r.t. for 1 h. The reaction was concentrated. The residue was purified by prep-HPLC (high pH) to get the title compound. LC-MS (method C'): m/z=383 (M+H)+, RT=1.21 min.

Examples 291-292

Examples 291-292 in Table 20 were prepared in an analogous fashion to Example 290 starting with the corresponding starting materials.

TABLE 20

| Ex. No. | Ref. No. | LC-MS (Retention Time) | MS (M + H)+ | LC-MS Method |
|---|---|---|---|---|
| 291 | Q-595 | 1.069 | 399 | H' |
| 292 | Q-714 | 1.185 | 329.1 | A' |

Example 293—Synthesis of 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carboxylic acid (Q-627)

Example 293—Synthesis of 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carbonitrile (Q-632)

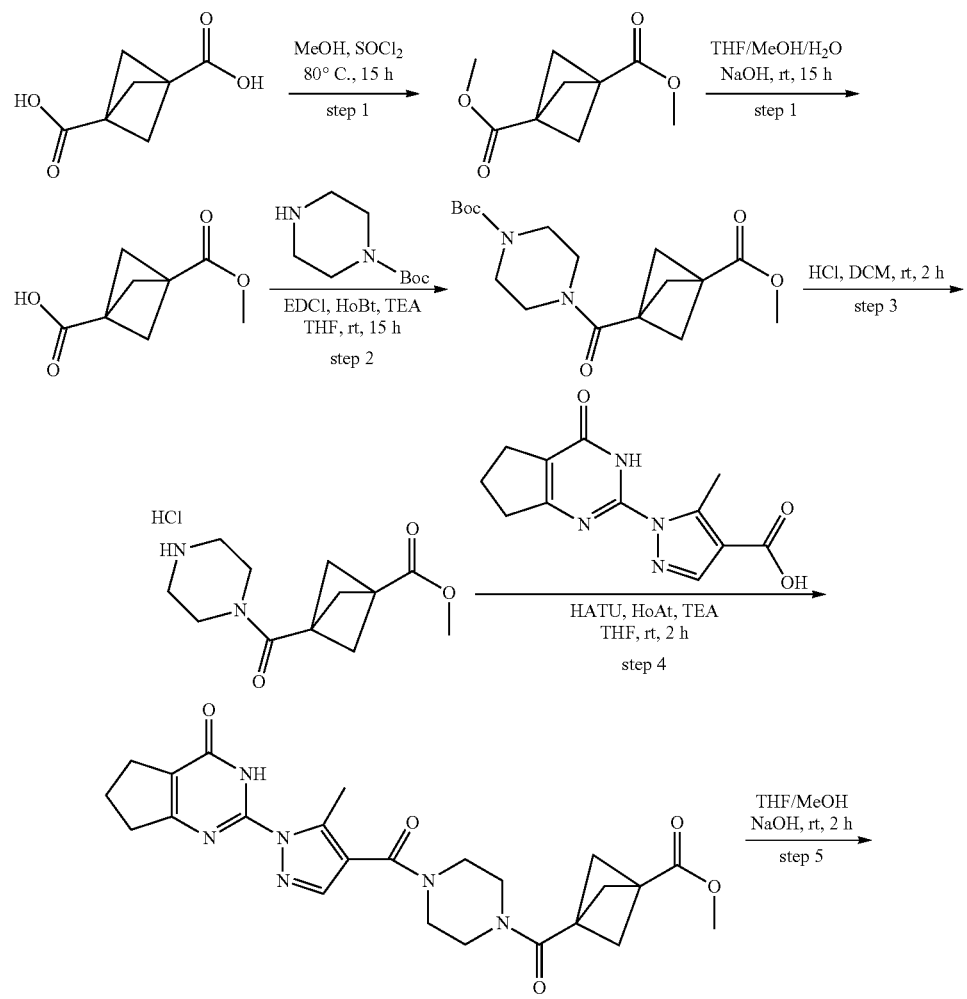

Q-612

-continued

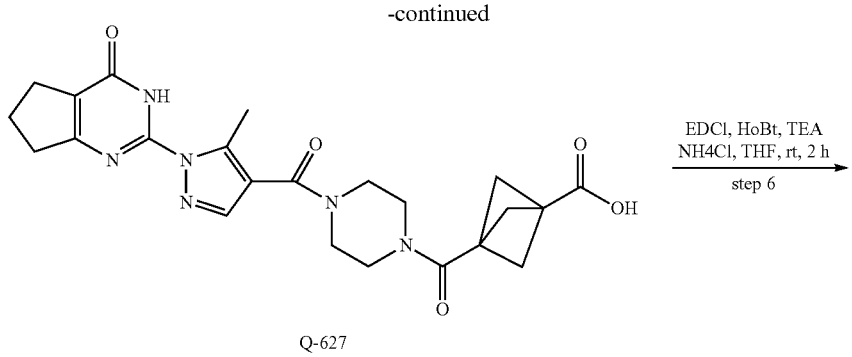

Q-627

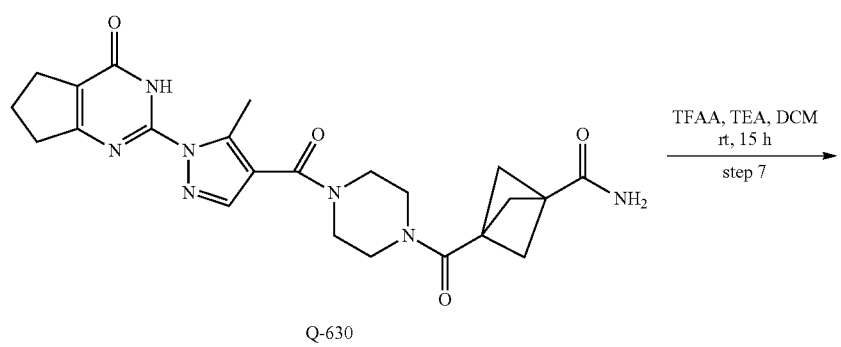

Q-630

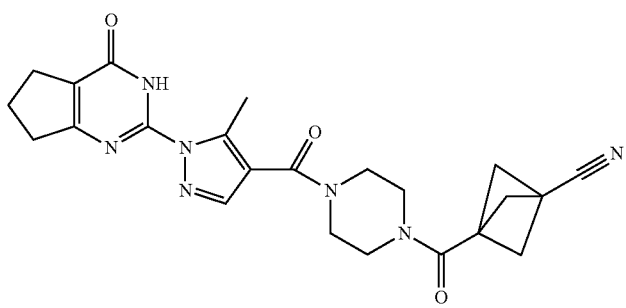

Q-632

Step 1: Synthesis of dimethyl bicyclo[1.1.1]pentane-1,3-dicarboxylate

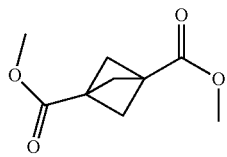

Step 2: Synthesis of 3-(methoxycarbonyl)bicyclo[1.1.1]pentane-1-carboxylic acid

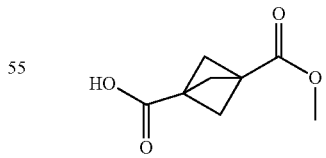

To a solution of bicyclo[1.1.1]pentane-1,3-dicarboxylic acid (1 g, 6.4 mmol) in MeOH (50 mL) was added SOCl₂ (6 mL) dropwise. The reaction was stirred at 80° C. for 15 h. The reaction was concentrated. The residue was treated with aq. NaHCO₃ (80 mL) and extracted with DCM (2×60 mL). The combined organic layers were concentrated to get the title compound.

To a solution of dimethyl bicyclo[1.1.1]pentane-1,3-dicarboxylate (1.1 g, 5.98 mmol) in THF/MeOH (1/1, 10 mL) was added NaOH (2M, 3 mL). The reaction was stirred at r.t. for 15 h. The reaction was concentrated. The residue was treated with water (50 mL), adjusted pH=5 with HCl (2M), and extracted with DCM (2×50 mL). The combined organic layers were concentrated to get the title compound.

Step 3: Synthesis of tert-butyl 4-(3-(methoxycarbonyl)bicyclo[1.1.1]pentane-1-carbonyl) piperazine-1-carboxylate

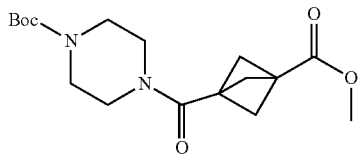 [SMILES: COC(=O)C12CC(C(=O)N3CCN(C(=O)OC(C)(C)C)CC3)(C1)C2]

The mixture of 3-(methoxycarbonyl)bicyclo[1.1.1]pentane-1-carboxylic acid (600 mg, 3.53 mmol), tert-butyl piperazine-1-carboxylate (656 mg, 3.53 mmol), EDCI (1.01 g, 5.29 mmol), HOBt (715 mg, 5.29 mmol) and TEA (1 mL, 7.06 mmol) in THF (30 mL) was stirred at room temperature for 15 h. The reaction was treated with water (50 mL), extracted with EtOAc (2×50 mL). The combined organic layers were concentrated to get the title compound. LC-MS: m/z=283 (M−56+H)+; RT=1.68 min.

Step 4: Synthesis of methyl 3-(piperazine-1-carbonyl)bicyclo[1.1.1]pentane-1-carboxylate hydrochloride

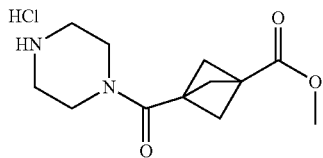 [SMILES: Cl ; COC(=O)C12CC(C(=O)N3CCNCC3)(C1)C2]

To a solution of tert-butyl 4-(3-(methoxycarbonyl)bicyclo[1.1.1]pentane-1-carbonyl)piperazine-1-carboxylate (1.05 g, 3.1 mmol) in DCM (10 mL) was added HCl (4M in dioxane, 10 mL). The mixture was stirred at r.t. for 2 h. The reaction was concentrated to get the title compound (850 mg, 99%). LC-MS: m/z=239 (M+H)+, RT=0.92 min.

Step 5: Synthesis of methyl 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carboxylate (Q-612)

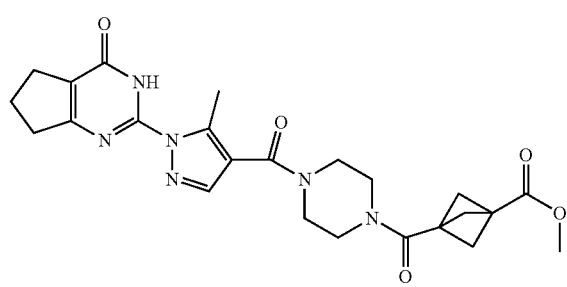

The mixture of 5-methyl-1-(4-oxo-4,5,6,7-tetrahydro-3H-cyclopenta[d]pyrimidin-2-yl)-1H-pyrazole-4-carboxylic acid (585 mg, 2.25 mmol), methyl 3-(piperazine-1-carbonyl) bicyclo[1.1.1]pentane-1-carboxylate hydrochloride (850 mg, 3.1 mmol), HATU (1.28 g, 3.37 mmol), HOAt (460 mg, 3.37 mmol) and TEA (1 mL) in THF (30 mL) was stirred at r.t. for 15 h. The reaction was concentrated. The residue was purified by combi-flash (40 g, DCM/MeOH=20/1, silica, UV254) to get the title compound. LC-MS: m/z=481 (M+H)+, RT=1.48 min.

Step 6: Synthesis of 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carboxylic acid (Q-627)

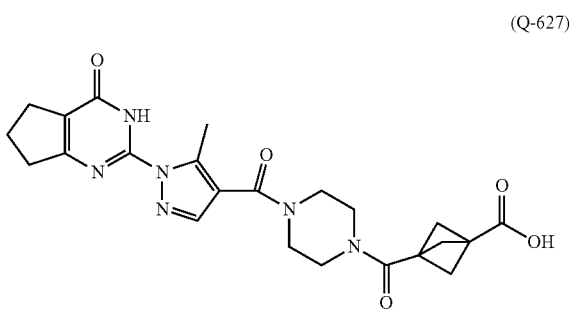 [SMILES: Cc1c(C(=O)N2CCN(C(=O)C34CC(C(=O)O)(C3)C4)CC2)cnn1-c1nc2c(c(=O)[nH]1)CCC2]

To a solution of methyl 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carboxylate (120 mg, 0.25 mmol) in THF/MeOH (1/1, 4 mL) was added LiOH (2 M, 1 mL). The reaction mixture was stirred at r.t. for 1 h. The reaction was treated with water (20 mL), adjust pH=5 with HCl (2M). The mixture was extracted with EtOAc (2×30 mL). The combined organic layers were concentrated. The residue was purified by prep-HPLC (low pH) to get the title compound. LC-MS (method C'): m/z=467 (M+H)+, RT=1.34 min.

Step 7: Synthesis of 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carboxamide (Q-630)

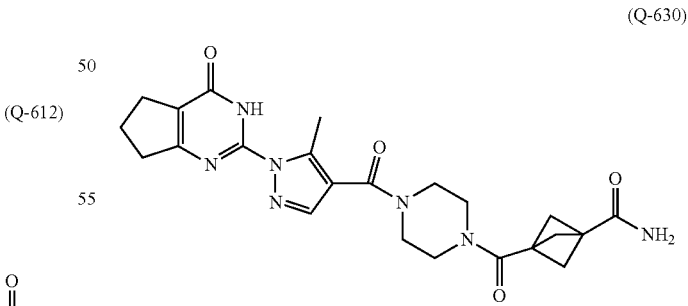

The mixture of 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carboxylic acid (80 mg, 0.17 mmol), NH4Cl (13.6 mg, 0.26 mmol), HOBt (49.2 mg, 0.26 mmol), EDCI (34.7 mg, 0.26 mmol) and TEA (0.07 mL) in THF (5 mL) was stirred at r.t. for 15 h. The reaction was concentrated. The residue was purified by prep-HPLC (low pH) to get the title compound. LC-MS: m/z=466 (M+H)+, RT=1.28 min.

Step 8: Synthesis of 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carbonitrile (Q-632)

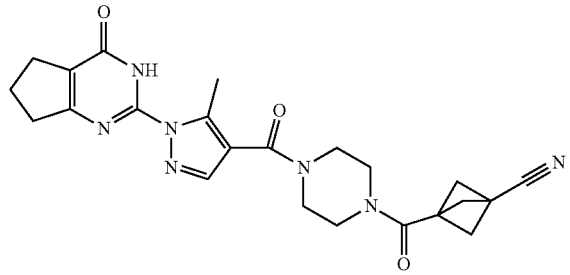

To a solution of 3-(4-(5-methyl-1-(4-oxo-4,5,6,7-tetrahydro-3H-cyclopenta[d]pyrimidin-2-yl)-1H-pyrazole-4-carbonyl)piperazine-1-carbonyl)bicyclo[1.1.1]pentane-1-carboxamide (45 mg, 0.1 mmol) in DCM (3 mL) was added TEA (0.6 mL) and trifluoroacetic anhydride (0.4 mL). The mixture was stirred at r.t. for 15 h. The reaction was concentrated. The residue was purified by prep-HPLC (high pH) to get the title compound. LC-MS (method F'): m/z=448 (M+H)+, RT=1.35 min.

Example 295—Synthesis of 2-(4-(2,2-dimethyl-4-(2,2,2-trifluoroethyl)piperazine-1-carbonyl)-5-methyl-1H-pyrazol-1-yl)pyrrolo[1,2-f][1,2,4]triazin-4(3H)-one (Q-949)

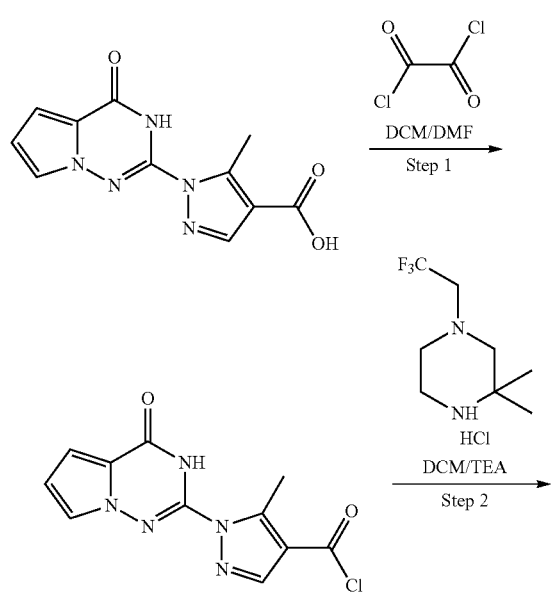

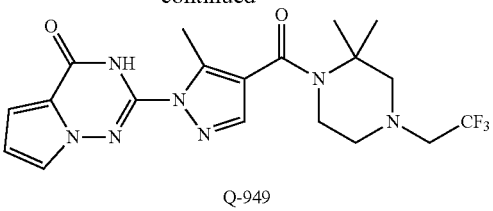

Q-949

Step 1: Preparation of 5-methyl-1-(4-oxo-3,4-dihydropyrrolo[1,2-f][1,2,4]triazin-2-yl)-1H-pyrazole-4-carbonyl chloride

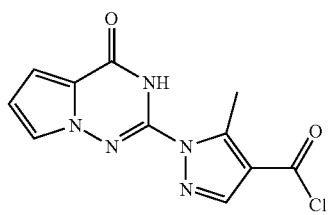 [SMILES: Cc1c(C(=O)Cl)cnn1-c1nn2cccc2c(=O)[nH]1]

To a solution of 5-methyl-1-(4-oxo-3,4-dihydropyrrolo[1,2-f][1,2,4]triazin-2-yl)-1H-pyrazole-4-carboxylic acid (50 mg, 0.193 mmol) and oxalyl dichloride (74 mg, 0.579 mmol) in DCM (8 mL) was added DMF (3 drops) at r.t. The mixture was stirred at r.t. for 2 h until the reaction was completed. The mixture was concentrated to give the crude product (80 mg) which was used to next step directly.

Step 2: Preparation of 2-(4-(2,2-dimethyl-4-(2,2,2-trifluoroethyl)piperazine-1-carbonyl)-5-methyl-1H-pyrazol-1-yl)pyrrolo[1,2-f][1,2,4]triazin-4(3H)-one

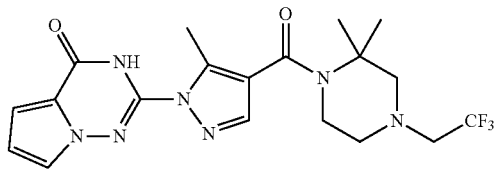 [SMILES: Cc1c(C(=O)N2CCN(CC(F)(F)F)CC2(C)C)cnn1-c1nn2cccc2c(=O)[nH]1]

A solution of 5-methyl-1-(4-oxo-3,4-dihydropyrrolo[1,2-f][1,2,4]triazin-2-yl)-1H-pyrazole-4-carbonyl chloride (80 mg, 0.288 mmol), 3,3-dimethyl-1-(2,2,2-trifluoroethyl)piperazine hydrochloride (74 mg, 0.317 mmol) and TEA (87 mg, 0.864 mmol) in DCM (8 mL) was stirred at r.t. overnight. The mixture was concentrated to remove solvent, and the residue was purified with prep-HPLC (high pH) to the target. LC-MS (method F'): m/z=438.1 (M+H)+, RT=1.67 min.

Examples 296-299

Examples 296-299 in Table 21 were prepared in an analogous fashion to Example 295 starting with the corresponding starting materials.

TABLE 21

| Ex. No. | Ref. No. | LC-MS (Retention Time) | MS (M + H)+ | LC-MS Method |
|---|---|---|---|---|
| 296 | Q-1142 | 1.388 | 479.3 | J' |
| 297 | Q-1143 | 1.516 | 461.3 | J' |
| 298 | Q-1295 | 1.29 | 376.3 | D' |
| 299 | Q-1345 | 1.57 | 405.1 | K' |

Examples 300-946

Examples 300-946 in Table 22 were prepared according to the methods described herein starting with appropriate starting materials.

TABLE 22

| Ex. No. | Ref. No. | LC-MS (Retention Time) | MS (M + H)+ | LC-MS Method | Coupling Agent |
|---|---|---|---|---|---|
| 300 | Q-0540 | 1.108 | 308.0 | B' | |
| 301 | Q-0541 | 0.937 | 277.2 | B' | |
| 302 | Q-0542 | 0.958 | 277.2 | B' | |
| 303 | Q-0543 | 1.43 | 413 | G' | HATU/HOAt |
| 304 | Q-0544 | 0.932 | 287.3 | B' | |
| 305 | Q-0545 | 1.389 | 405.1 | G' | HATU/HOAt |
| 306 | Q-0546 | 1.087 | 487.2 | F' | HATU/HOAt |
| 307 | Q-0547 | 1.033 | 274.0 | H' | |
| 308 | Q-0548 | 1.765 | 474.0 | C' | HATU/HOAt |
| 309 | Q-0549 | 1.007 | 459.1 | F' | HATU/HOAt |
| 310 | Q-0550 | 1.389 | 445 | H' | HATU/HOAt |
| 311 | Q-0551 | 1.469 | 459.0 | G' | HATU/HOAt |
| 312 | Q-0552 | 1.496 | 483.0 | G' | HATU/HOAt |
| 313 | Q-0553 | 1.32 | 421 | G' | HATU/HOAt |
| 314 | Q-0555 | 1.755 | 456.1 | C' | HATU/HOAt |
| 315 | Q-0556 | 1.185 | 385 | G' | HATU/HOAt |
| 316 | Q-0557 | 1.237 | 400 | G' | HATU/HOAt |
| 317 | Q-0558 | 1.014 | 258.2 | B' | |
| 318 | Q-0559 | 1.455 | 477 | G' | HATU/HOAt |
| 319 | Q-0560 | 1.462 | 459 | G' | HATU/HOAt |
| 320 | Q-0561 | 1.768 | 445.1 | C' | HATU/HOAt |
| 321 | Q-0562 | 1.286 | 397 | G' | HATU/HOAt |
| 322 | Q-0563 | 1.34 | 397 | G' | HATU/HOAt |
| 323 | Q-0564 | 1.61 | 423 | G' | HATU/HOAt |
| 324 | Q-0565 | 1.164 | 461.3 | B' | HATU/HOAt |
| 325 | Q-0566 | 1.449 | 274.02 | C' | |
| 326 | Q-0567 | 1.103 | 441.3 | B' | HATU/HOAt |
| 327 | Q-0568 | 1.104 | 429.4 | B' | HATU/HOAt |
| 328 | Q-0569 | 1.218 | 370.1 | H' | HATU/HOAt |
| 329 | Q-0570 | 1.540 | 439.1 | H' | HATU/HOAt |
| 330 | Q-0571 | 1.408 | 443.2 | H' | HATU/HOAt |
| 331 | Q-0572 | 1.343 | 395 | G' | HATU/HOAt |
| 332 | Q-0573 | 1.483 | 459 | G' | HATU/HOAt |
| 333 | Q-0574 | 1.469 | 477 | G' | HATU/HOAt |
| 334 | Q-0575 | 1.171 | 369.2 | C' | HATU/HOAt |
| 335 | Q-0576 | 1.288 | 384.1 | H' | HATU/HOAt |
| 336 | Q-0578 | 1.29 | 407.2 | H' | HATU/HOAt |
| 337 | Q-0579 | 1.489 | 499 | G' | HATU/HOAt |
| 338 | Q-0580 | 1.603 | 384.2 | H' | HATU/HOAt |
| 339 | Q-0582 | 1.284 | 445 | G' | HATU/HOAt |
| 340 | Q-0583 | 0.938 | 345 | G' | HATU/HOAt |
| 341 | Q-0584 | 0.969 | 359 | H' | HATU/HOAt |
| 342 | Q-0585 | 1.475 | 442.0 | G' | HATU/HOAt |
| 343 | Q-0586 | 1.380 | 380.0 | G' | HATU/HOAt |
| 344 | Q-0587 | 1.484 | 479 | H' | HATU/HOAt |
| 345 | Q-0588 | 1.029 | 343.1 | G' | HATU/HOAt |
| 346 | Q-0589 | 0.934 | 329.0 | G' | HATU/HOAt |
| 347 | Q-0590 | 1.489 | 479.0 | H' | HATU/HOAt |
| 348 | Q-0591 | 1.42 | 502.9 | G' | HATU/HOAt |
| 349 | Q-0592 | 1.515 | 457 | G' | HATU |
| 350 | Q-0594 | 1.675 | 470 | G' | HATU/HOAt |
| 351 | Q-0596 | 1.668 | 362.1 | C' | HATU/HOAt |
| 352 | Q-0597 | 1.089 | 520.2 | B' | HATU |
| 353 | Q-0598 | 1.396 | 493.9 | G' | HATU/HOAt |
| 354 | Q-0599 | 1.458 | 427.9 | G' | HATU/HOAt |
| 355 | Q-0600 | 1.349 | 394.0 | G' | HATU/HOAt |
| 356 | Q-0601 | 1.444 | 475.0 | G' | HATU/HOAt |
| 357 | Q-0602 | 1.171 | 386.0 | G' | HATU/HOAt |
| 358 | Q-0603 | 1.804 | 495 | C' | HATU/HOAt |
| 359 | Q-0604 | 1.494 | 478.0 | G' | HATU/HOAt |
| 360 | Q-0605 | 1.584 | 488 | H' | HATU/HOAt |
| 361 | Q-0606 | 1.441 | 412.9 | G' | HATU/HOAt |
| 362 | Q-0607 | 1.502 | 477.9 | G' | HATU/HOAt |
| 363 | Q-0608 | 1.477 | 460.0 | G' | HATU/HOAt |
| 364 | Q-0610 | 0.723 | 369.2 | B' | HATU/HOAt |
| 365 | Q-0611 | 0.975 | 457.2 | B' | HATU/HOAt |
| 366 | Q-0612 | 1.481 | 481.1 | C' | HATU/HOAt |
| 367 | Q-0614 | 1.046 | 342.1 | H' | HATU/HOAt |
| 368 | Q-0615 | 0.951 | 443.3 | B' | HATU |
| 369 | Q-0617 | 1.092 | 358.0 | H' | HATU/HOAt |
| 370 | Q-0618 | 1.246 | 318.1 | H' | |
| 371 | Q-0619 | 1.612 | 292.1 | E' | |
| 372 | Q-0620 | 1.026 | 439.3 | B' | HATU/HOAt |
| 373 | Q-0621 | 1.050 | 358.1 | H' | HATU/HOAt |
| 374 | Q-0623 | 1.277 | 398.1 | H' | HATU/HOAt |
| 375 | Q-0624 | 1.410 | 460.1 | H' | HATU/HOAt |
| 376 | Q-0626 | 1.56 | 423.2 | F' | HATU/HOAt |
| 377 | Q-0630 | 1.280 | 466.2 | A' | EDCI/HOBt |
| 378 | Q-0633 | 1.405 | 328.2 | F' | HATU/HOAt |
| 379 | Q-0634 | 1.463 | 327.2 | F' | HATU/HOAt |
| 380 | Q-0635 | 1.504 | 354.1 | F' | HATU/HOAt |
| 381 | Q-0681 | 1.557 | 353.1 | F' | HATU/HOAt |
| 382 | Q-0690 | 2 | 403 | F' | HATU/HOAt |
| 383 | Q-0691 | 1.559 | 404.1 | E' | HATU/HOAt |
| 384 | Q-0693 | 1.399 | 368.1 | F' | HATU/HOAt |
| 385 | Q-0696 | 1.609 | 497.2 | F' | HATU/HOAt |
| 386 | Q-0697 | 1.568 | 498.2 | F' | HATU/HOAt |
| 387 | Q-0698 | 1.584 | 384.2 | F' | HATU/HOAt |
| 388 | Q-0700 | 1.698 | 384.1 | E' | HATU/HOAt |
| 389 | Q-0701 | 1.519 | 480.1 | F' | HATU/HOAt |
| 390 | Q-0702 | 1.56 | 429.2 | F' | HATU/HOAt |
| 391 | Q-0703 | 1.341 | 354.2 | F' | HATU/HOAt |
| 392 | Q-0704 | 1.547 | 426.1 | F' | HATU/HOAt |
| 393 | Q-0705 | 1.476 | 340.1 | F' | HATU/HOAt |
| 394 | Q-0706 | 1.543 | 354.2 | F' | HATU/HOAt |
| 395 | Q-0707 | 1.576 | 465.1 | F' | HATU/HOAt |
| 396 | Q-0708 | 1.505 | 339.1 | F' | HATU/HOAt |
| 397 | Q-0709 | 2 | 353 | F' | HATU/HOAt |
| 398 | Q-0710 | 1.426 | 381.2 | F' | HATU/HOAt |
| 399 | Q-0711 | 1.541 | 370.1 | F' | HATU/HOAt |
| 400 | Q-0712 | 1.408 | 412.1 | F' | HATU/HOAt |
| 401 | Q-0713 | 1.555 | 395.1 | F' | HATU/HOAt |
| 402 | Q-0715 | 1.518 | 440.2 | F' | HATU/HOAt |
| 403 | Q-0716 | 1.547 | 489.1 | F' | HATU/HOAt |
| 404 | Q-0718 | 1.580 | 465.1 | E' | HATU/HOAt |
| 405 | Q-0719 | 1.429 | 479.2 | F' | HATU/HOAt |
| 406 | Q-0720 | 1.337 | 380.3 | F' | HATU/HOAt |
| 407 | Q-0721 | 1.473 | 493.2 | F' | HATU/HOAt |
| 408 | Q-0722 | 1.156 | 343.2 | F' | HATU/HOAt |
| 409 | Q-0723 | 1.4 | 429.3 | F' | HATU/HOAt |
| 410 | Q-0724 | 1.598 | 426.1 | F' | HATU/HOAt |
| 411 | Q-0725 | 1.607 | 367.1 | A' | HATU/HOAt |
| 412 | Q-0726 | 1.712 | 415.1 | A' | HATU/HOAt |
| 413 | Q-0727 | 1.625 | 367.2 | F' | HATU/HOAt |
| 414 | Q-0730 | 1.717 | 372.1 (M − 55)+ | A' | HATU/HOAt |
| 415 | Q-0731 | 1.617 | 391.2 | E' | HATU/HOAt |
| 416 | Q-0734 | 1.566 | 426.1 | F' | HATU, HOAt |
| 417 | Q-0735 | 1.397 | 427.1 | C' | HATU/HOAt |
| 418 | Q-0736 | 1.378 | 442.3 | C' | HATU/HOAt |
| 419 | Q-0737 | 1.664 | 411.1 | A' | HATU/HOAt |
| 420 | Q-0739 | 1.494 | 454.3 | F' | HATU/HOAt |
| 421 | Q-0743 | 1.311 | 355.2 | F' | HATU/HOAt |
| 422 | Q-0744 | 1.802 | 396.1 | F' | HATU/HOAt |
| 423 | Q-0745 | 1.758 | 455.2 | A' | HATU/HOAt |
| 424 | Q-0747 | 1.617 | 427.1 | F' | HATU/HOAt |
| 425 | Q-0748 | 1.474 | 454.3 | F' | HATU/HOAt |
| 426 | Q-0749 | 1.526 | 412.1 | F' | HATU/HOAt |
| 427 | Q-0750 | 1 | 428 | F' | HATU/HOAt |
| 428 | Q-0751 | 1.437 | 369.8 | I' | HATU/HOAt |
| 429 | Q-0752 | 1.424 | 411.7 | I' | HATU/HOAt |
| 430 | Q-0753 | 1.525 | 398 | F' | HATU/HOAt |
| 431 | Q-0754 | 1.589 | 445.1 | F' | HATU/HOAt |

TABLE 22-continued

| Ex. No. | Ref. No. | LC-MS (Retention Time) | MS (M + H)+ | LC-MS Method | Coupling Agent |
|---|---|---|---|---|---|
| 432 | Q-0755 | 1.356 | 371.1 | F' | HATU/HOAt |
| 433 | Q-0756 | 1 | 342 | F' | HATU/HOAt |
| 434 | Q-0757 | 1.584 | 421.1 | F' | HATU/HOAt |
| 435 | Q-0758 | 1.768 | 413.1 | A' | HATU/HOAt |
| 436 | Q-0759 | 1.575 | 390.1 | F' | HATU/HOAt |
| 437 | Q-0760 | 1.404 | 410.2 | F' | HATU/HOAt |
| 438 | Q-0761 | 1.539 | 389.1 | F' | HATU/HOAt |
| 439 | Q-0762 | 1.702 | 398.1 (M − 55)+ | A' | HATU/HOAt |
| 440 | Q-0764 | 1.425 | 368.1 | F' | HATU/HOAt |
| 441 | Q-0768 | 1.593 | 412.1 (M − 55)+ | F' | HATU/HOAt |
| 442 | Q-0770 | 1.53 | 412.1 | F' | HATU/HOAt |
| 443 | Q-0771 | 1.584 | 411.1 | F' | HATU/HOAt |
| 444 | Q-0772 | 1.595 | 468.2 | F' | HATU/HOAt |
| 445 | Q-0773 | 1.432 | 462 (M + Na)+ | F' | HATU/HOAt |
| 446 | Q-0774 | 1.327 | 247 | A' | |
| 447 | Q-0775 | 1.464 | 367.1 | F' | HATU/HOAt |
| 448 | Q-0777 | 1.487 | 381.1 | F' | HATU/HOAt |
| 449 | Q-0779 | 1.398 | 261.0 | A' | |
| 450 | Q-0780 | 1.434 | 289.1 | F' | |
| 451 | Q-0781 | 1.528 | 382.1 | F' | HATU/HOAt |
| 452 | Q-0782 | 1.490 | 439.1 | F' | HATU/HOAt |
| 453 | Q-0783 | 1.518 | 411.1 | F' | HATU/HOAt |
| 454 | Q-0784 | 1.562 | 425.1 | F' | HATU/HOAt |
| 455 | Q-0785 | 1.537 | 454.2 | F' | HATU/HOAt |
| 456 | Q-0788 | 1.525 | 454.2 | F' | HATU/HOAt |
| 457 | Q-0789 | 1.393 | 335.1 | F' | HATU/HOAt |
| 458 | Q-0790 | 1.53 | 454.2 | F' | HATU/HOAt |
| 459 | Q-0791 | 1.378 | 325.1 | F' | HATU/HOAt |
| 460 | Q-0792 | 1.482 | 437.1 | F' | HATU/HOAt |
| 461 | Q-0793 | 1.347 | 369.2 | E' | HATU/HOAt |
| 462 | Q-0794 | 1.353 | 299.2 | E' | HATU/HOAt |
| 463 | Q-0795 | 1.371 | 385.1 | F' | HATU/HOAt |
| 464 | Q-0796 | 1.475 | 389.1 | F' | HATU/HOAt |
| 465 | Q-0797 | 1.485 | 445.2 | F' | HATU/HOAt |
| 466 | Q-0798 | 1.658 | 468.2 | F' | HATU/HOAt |
| 467 | Q-0799 | 1.439 | 375.1 | F' | HATU/HOAt |
| 468 | Q-0800 | 1.41 | 366.2 | F' | HATU/HOAt |
| 469 | Q-0802 | 1.558 | 404.2 | F' | HATU/HOAt |
| 470 | Q-0803 | 1.560 | 411.0 | A' | HATU/HOAt |
| 471 | Q-0804 | 1.444 | 375.1 | F' | HATU/HOAt |
| 472 | Q-0805 | 1.415 | 423.1 | F' | HATU/HOAt |
| 473 | Q-0806 | 1.504 | 384.1 (M − 55)+ | F' | HATU/HOAt |
| 474 | Q-0807 | 1.420 | 361.1 | F' | HATU/HOAt |
| 475 | Q-0808 | 1.577 | 367.2 | F' | HATU/HOAt |
| 476 | Q-0809 | 1.537 | 398.1 (M − 55)+ | F' | HATU/HOAt |
| 477 | Q-0812 | 1.411 | 404.2 | F' | HATU/HOAt |
| 478 | Q-0813 | 1.533 | 353.1 | F' | HATU/HOAt |
| 479 | Q-0814 | 1.340 | 355.1 | F' | HATU/HOAt |
| 480 | Q-0815 | 1.401 | 383.1 | F' | HATU/HOAt |
| 481 | Q-0816 | 1.467 | 375.1 | F' | HATU/HOAt |
| 482 | Q-0817 | 1.459 | 392.2 | F' | HATU/HOAt |
| 483 | Q-0818 | 1.460 | 418.1 | F' | HATU/HOAt |
| 484 | Q-0819 | 1.534 | 353.1 | F' | HATU/HOAt |
| 485 | Q-0820 | 1.664 | 468.2 | F' | HATU/HOAt |
| 486 | Q-0821 | 1.301 | 382.1 | A' | HATU/HOAt |
| 487 | Q-0822 | 1.585 | 357 | A' | HATU/HOAt |
| 488 | Q-0823 | 1.597 | 422.2 | E' | HATU/HOAt |
| 489 | Q-0824 | 1.3 | 367.1 | F' | HATU/HOAt |
| 490 | Q-0825 | 1.365 | 366.1 | F' | HATU/HOAt |
| 491 | Q-0826 | 1.503 | 394.1 | F' | HATU/HOAt |
| 492 | Q-0827 | 1.651 | 438.0 | F' | HATU/HOAt |
| 493 | Q-0828 | 1.715 | 472.1 | F' | HATU/HOAt |
| 494 | Q-0829 | 1.509 | 429.2 | F' | HATU/HOAt |
| 495 | Q-0830 | 1.651 | 438.1 | F' | HATU/HOAt |
| 496 | Q-0831 | 1.367 | 406.1 | F' | HATU/HOAt |
| 497 | Q-0832 | 1.535 | 396.1 | F' | HATU/HOAt |
| 498 | Q-0833 | 1.703 | 472.1 | F' | HATU/HOAt |
| 499 | Q-0835 | 1.593 | 439.1 | F' | HATU/HOAt |
| 500 | Q-0836 | 1.647 | 473.1 | F' | HATU/HOAt |
| 501 | Q-0837 | 1.635 | 437.1 | A' | HATU/HOAt |
| 502 | Q-0839 | 1.389 | 275.1 | F' | |
| 503 | Q-0840 | 1.702 | 472.1 | F' | |
| 504 | Q-0842 | 1.501 | 384.1 (M − 55)+ | F' | HATU/HOAt |
| 505 | Q-0843 | 1.305 | 405.1 | A' | HATU/HOAt |
| 506 | Q-0844 | 1.510 | 407.1 | F' | HATU/HOAt |
| 507 | Q-0845 | 1.389 | 430.2 | F' | HATU/HOAt |
| 508 | Q-0846 | 1.611 | 430.2 | F' | HATU/HOAt |
| 509 | Q-0847 | 1.088 | 368.2 | E' | HATU/HOAt |
| 510 | Q-0848 | 1.411 | 396.1 | A' | HATU/HOAt |
| 511 | Q-0849 | 1.413 | 380.2 | F' | HATU/HOAt |
| 512 | Q-0850 | 1.507 | 428.2 | F' | HATU/HOAt |
| 513 | Q-0851 | 1.566 | 442.2 | F' | HATU/HOAt |
| 514 | Q-0852 | 1.600 | 496.2 | F' | HATU/HOAt |
| 515 | Q-0853 | 1.333 | 366.1 | A' | HATU/HOAt |
| 516 | Q-0854 | 1.674 | 499.2 | F' | HATU/HOAt |
| 517 | Q-0855 | 1.502 | 406.2 | F' | HATU/HOAt |
| 518 | Q-0856 | 1.348 | 368.1 | F' | HATU/HOAt |
| 519 | Q-0857 | 1.499 | 384.1 (M − 55)+ | F' | HATU/HOAt |
| 520 | Q-0858 | 1.556 | 408.2 | F' | HATU/HOAt |
| 521 | Q-0859 | 1.367 | 434.1 | F' | HATU/HOAt |
| 522 | Q-0860 | 1.506 | 440.1 | F' | HATU/HOAt |
| 523 | Q-0861 | 1.534 | 464.1 (M + Na)+ | F' | HATU/HOAt |
| 524 | Q-0862 | 1.267 | 382.1 | F' | HATU/HOAt |
| 525 | Q-0863 | 1.386 | 343.1 | F' | HATU/HOAt |
| 526 | Q-0865 | 1.580 | 412.1 (M − 55)+ | F' | HATU/HOAt |
| 527 | Q-0866 | 1.270 | 365.1 | F' | HATU/HOAt |
| 528 | Q-0867 | 1.497 | 428.2 | F' | HATU/HOAt |
| 529 | Q-0868 | 1.287 | 406.2 | F' | HATU/HOAt |
| 530 | Q-0869 | 1.560 | 455.1 | F' | HATU/HOAt |
| 531 | Q-0870 | 1.738 | 498.1 | F' | HATU/HOAt |
| 532 | Q-0871 | 1.443 | 433.1 | F' | HATU/HOAt |
| 533 | Q-0872 | 1.261 | 382.1 | F' | HATU/HOAt |
| 534 | Q-0873 | 1.245 | 365.1 | F' | HATU/HOAt |
| 535 | Q-0874 | 1.54 | 378.1 | A' | HATU/HOAt |
| 536 | Q-0875 | 1.654 | 430.1 | F' | HATU/HOAt |
| 537 | Q-0876 | 1.65 | 448.2 | F' | HATU/HOAt |
| 538 | Q-0877 | 1.511 | 456.2 | F' | HATU/HOAt |
| 539 | Q-0878 | 1.509 | 476.2 (M + Na)+ | F' | HATU/HOAt |
| 540 | Q-0879 | 1.264 | 396.1 | F' | HATU/HOAt |
| 541 | Q-0880 | 1.548 | 448.3 | F' | HATU/HOAt |
| 542 | Q-0881 | 1.346 | 382.1 | F' | HATU/HOAt |
| 543 | Q-0882 | 1.507 | 431.2 | F' | HATU/HOAt |
| 544 | Q-0883 | 1.365 | 352.1 | F' | HATU/HOAt |
| 545 | Q-0884 | 1.616 | 436.1 | F' | HATU/HOAt |
| 546 | Q-0885 | 1.631 | 442.2 | F' | HATU/HOAt |
| 547 | Q-0886 | 1.325 | 396.2 | F' | HATU/HOAt |
| 548 | Q-0887 | 1.57 | 442.2 | F' | HATU/HOAt |
| 549 | Q-0888 | 1.32 | 384.2 | A' | HATU/HOAt |
| 550 | Q-0890 | 1.618 | 260.1 | C' | |
| 551 | Q-0891 | 1.341 | 422.2 | F' | HATU/HOAt |
| 552 | Q-0892 | 1.558 | 442 | F' | HATU/HOAt |
| 553 | Q-0893 | 2 | 451 | F' | HATU/HOAt |
| 554 | Q-0894 | 1.704 | 464.1 | F' | HATU/HOAt |
| 555 | Q-0895 | 1.223 | 381.2 | F' | HATU/HOAt |
| 556 | Q-0896 | 1.474 | 389.1 | F' | HATU/HOAt |
| 557 | Q-0897 | 1.54 | 476.1 (M + Na)+ | F' | HATU/HOAt |
| 558 | Q-0899 | 1.569 | 442.1 | F' | HATU/HOAt |
| 559 | Q-0900 | 1.499 | 375.1 | F' | HATU/HOAt |
| 560 | Q-0901 | 1.275 | 434.1 | F' | HATU/HOAt |
| 561 | Q-0902 | 1.557 | 421.1 | F' | HATU/HOAt |
| 562 | Q-0905 | 1.597 | 515.2 | F' | HATU/HOAt |
| 563 | Q-0906 | 1.688 | 404.1 | D' | HATU/HOAt |
| 564 | Q-0907 | 1.598 | 411.1 | D' | HATU/HOAt |
| 565 | Q-0908 | 1.538 | 424.1 | F' | HATU/HOAt |
| 566 | Q-0909 | 1.569 | 431.1 | F' | HATU/HOAt |
| 567 | Q-0910 | 1.818 | 389 | D' | HATU/HOAt |
| 568 | Q-0911 | 1.419 | 450.2 | F' | HATU/HOAt |
| 569 | Q-0912 | 1.642 | 482 | F' | HATU/HOAt |
| 570 | Q-0913 | 1.512 | 450.2 | F' | HATU/HOAt |
| 571 | 'Q-0914 | 1.538 | 476.1 (M + Na)+ | F' | HATU/HOAt |
| 572 | Q-0915 | 1.577 | 442.3 | J' | HATU/HOAt |
| 573 | Q-0916 | 2 | 456 | F' | HATU/HOAt |
| 574 | Q-0917 | 1.745 | 383.2 | C' | HATU/HOAt |
| 575 | Q-0918 | 1.293 | 367.1 | F' | HATU/HOAt |
| 576 | Q-0919 | 1.284 | 394.2 | J' | HATU/HOAt |
| 577 | Q-0920 | 1.925 | 395.1 | D' | HATU/HOAt |
| 578 | Q-0921 | 1.435 | 339.2 | J' | HATU/HOAt |
| 579 | Q-0922 | 1.332 | 369.1 | F' | HATU/HOAt |
| 580 | Q-0923 | 1.388 | 366.1 | F' | HATU/HOAt |
| 581 | Q-0924 | 1.528 | 469.3 | J' | HATU/HOAt |
| 582 | Q-0925 | 4.538 | 438.1 | F' | HATU/HOAt |
| 583 | Q-0926 | 1.463 | 377.1 | F' | HATU/HOAt |

TABLE 22-continued

| Ex. No. | Ref. No. | LC-MS (Retention Time) | MS (M + H)+ | LC-MS Method | Coupling Agent |
|---|---|---|---|---|---|
| 584 | Q-0927 | 1.525 | 353.1 | F' | HATU/HOAt |
| 585 | Q-0928 | 1.520 | 469.3 | J' | HATU/HOAt |
| 586 | Q-0929 | 1.504 | 454.1 | F' | HATU/HOAt |
| 587 | Q-0930 | 1.467 | 450.2 | F' | HATU/HOAt |
| 588 | Q-0931 | 1.890 | 354.2 | C' | HATU/HOAt |
| 589 | Q-0932 | 1.515 | 498.3 | F' | HATU/HOAt |
| 590 | Q-0933 | 1.402 | 422.2 | C' | HATU/HOAt |
| 591 | Q-0934 | 1.553 | 367.2 | J' | HATU/HOAt |
| 592 | Q-0935 | 1.298 | 410.2 | J' | HATU/HOAt |
| 593 | Q-0936 | 1.889 | 461.1 | C' | HATU/HOAt |
| 594 | Q-0937 | 1.330 | 405.2 | J' | HATU/HOAt |
| 595 | Q-0938 | 1.5 | 397.1 | F' | HATU/HOAt |
| 596 | Q-0939 | 1.680 | 486.2 | J' | HATU/HOAt |
| 597 | Q-0940 | 1.667 | 457.2 | J' | HATU/HOAt |
| 598 | Q-0941 | 1.500 | 392.2 | J' | HATU/HOAt |
| 599 | Q-0942 | 1.287 | 393.2 | J' | HATU/HOAt |
| 600 | Q-0943 | 1.980 | 436.2 | C' | HATU/HOAt |
| 601 | Q-0944 | 1.989 | 435.2 | C' | HATU/HOAt |
| 602 | Q-0945 | 1.322 | 404.1 | C' | HATU/HOAt |
| 603 | Q-0946 | 1.502 | 452 | J' | HATU/HOAt |
| 604 | Q-0947 | 1.828 | 381 | C' | HATU/HOAt |
| 605 | Q-0948 | 1.379 | 393.2 | F' | HATU/HOAt |
| 606 | Q-0950 | 1.298 | 398.2 | F' | HATU/HOAt |
| 607 | Q-0951 | 1.518 | 450.2 | F' | HATU/HOAt |
| 608 | Q-0952 | 1.453 | 429.1 | F' | HATU/HOAt |
| 609 | Q-0953 | 1.479 | 435.3 | J' | HATU/HOAt |
| 610 | Q-0954 | 1.328 | 436.3 | J' | HATU/HOAt |
| 611 | Q-0955 | 1.352 | 434.3 | J' | HATU/HOAt |
| 612 | Q-0956 | 1.609 | 424.2 | J' | HATU/HOAt |
| 613 | Q-0957 | 1.391 | 396.2 | J' | HATU/HOAt |
| 614 | Q-0958 | 1.331 | 434.2 | F' | HATU/HOAt |
| 615 | Q-0959 | 1.61 | 409.1 | F' | HATU/HOAt |
| 616 | Q-0960 | 1.647 | 435.2 | J' | HATU/HOAt |
| 617 | Q-0961 | 1.406 | 357.2 | J' | HATU/HOAt |
| 618 | Q-0962 | 1.498 | 422.2 | J' | HATU/HOAt |
| 619 | Q-0963 | 1.585 | 461.2 | J' | HATU/HOAt |
| 620 | Q-0964 | 1.555 | 449.2 | J' | HATU/HOAt |
| 621 | Q-0965 | 1.572 | 401.2 | J' | HATU/HOAt |
| 622 | Q-0966 | 1.501 | 395.2 | J' | HATU/HOAt |
| 623 | Q-0967 | 1.605 | 463.2 | J' | HATU/HOAt |
| 624 | Q-0968 | 1.612 | 456.3 | J' | HATU/HOAt |
| 625 | Q-0969 | 1.420 | 410.2 | J' | HATU/HOAt |
| 626 | Q-0970 | 1.781 | 486.2 | C' | HATU/HOAt |
| 627 | Q-0971 | 1.253 | 403.2 | J' | HATU/HOAt |
| 628 | Q-0972 | 1.993 | 490.1 (M + Na)+ | C' | HATU/HOAt |
| 629 | Q-0973 | 1.329 | 371.2 | F' | HATU/HOAt |
| 630 | Q-0974 | 2.082 | 459.3 | C' | HATU/HOAt |
| 631 | Q-0975 | 1.520 | 480.2 | J' | HATU/HOAt |
| 632 | Q-0976 | 1.695 | 357.2 | C' | HATU/HOAt |
| 633 | Q-0977 | 1.282 | 433.2 | F' | HATU/HOAt |
| 634 | Q-0978 | 1.853 | 406.2 | C' | HATU/HOAt |
| 635 | Q-0979 | 1.745 | 379.1 | C' | HATU/HOAt |
| 636 | Q-0980 | 1.708 | 424.1 | C' | HATU/HOAt |
| 637 | Q-0981 | 1 | 372 | J' | HATU/HOAt |
| 638 | Q-0982 | 1.519 | 409.3 | J' | HATU/HOAt |
| 639 | Q-0983 | 1.425 | 434.2 | C' | HATU/HOAt |
| 640 | Q-0984 | 1.958 | 461.2 | C' | HATU/HOAt |
| 641 | Q-0985 | 1.279 | 354.2 | J' | HATU/HOAt |
| 642 | Q-0986 | 1.852 | 434.2 | C' | HATU/HOAt |
| 643 | Q-0987 | 1.424 | 397.1 | F' | HATU/HOAt |
| 644 | Q-0988 | 1.515 | 420.2 | F' | HATU/HOAt |
| 645 | Q-0989 | 1.619 | 458.3 | J' | HATU/HOAt |
| 646 | Q-0990 | 1.746 | 455.1 | F' | HATU/HOAt |
| 647 | Q-0991 | 1.928 | 415.1 | C' | HATU/HOAt |
| 648 | Q-0992 | 1.871 | 424.2 | C' | HATU/HOAt |
| 649 | Q-0993 | 1.348 | 418.2 | F' | HATU/HOAt |
| 650 | Q-0994 | 1.587 | 418.2 | D' | HATU/HOAt |
| 651 | Q-0995 | 1 | 446 | C' | HATU/HOAt |
| 652 | Q-0996 | 1.576 | 425.1 | F' | HATU/HOAt |
| 653 | Q-0997 | 1.448 | 460.1 | F' | HATU/HOAt |
| 654 | Q-0998 | 1.539 | 385.1 | F' | HATU/HOAt |
| 655 | Q-0999 | 1.472 | 406.1 | F' | HATU/HOAt |
| 656 | Q-1000 | 1.562 | 441.1 | F' | HATU/HOAt |
| 657 | Q-1001 | 1.643 | 364.2 | C' | HATU/HOAt |
| 658 | Q-1002 | 1.667 | 364.2 | C' | HATU/HOAt |
| 659 | Q-1003 | 1.812 | 422.1 | C' | HATU/HOAt |
| 660 | Q-1004 | 1.863 | 430.1 | C' | HATU/HOAt |
| 661 | Q-1005 | 1.474 | 354 | F' | HATU/HOAt |
| 662 | Q-1006 | 1.523 | 425.1 | F' | HATU/HOAt |
| 663 | Q-1007 | 1.448 | 411.1 | F' | HATU/HOAt |
| 664 | Q-1008 | 1.552 | 411.1 | F' | HATU/HOAt |
| 665 | Q-1009 | 1.280 | 386.2 | A' | HATU/HOAt |
| 666 | Q-1010 | 1.321 | 400.2 | D' | HATU/HOAt |
| 667 | Q-1011 | 1.447 | 460.1 | F' | HATU/HOAt |
| 668 | Q-1012 | 1.429 | 464.2 | F' | HATU/HOAt |
| 669 | Q-1013 | 1.42 | 396 | F' | HATU/HOAt |
| 670 | Q-1014 | 1.513 | 425.1 | F' | HATU/HOAt |
| 671 | Q-1015 | 1.584 | 478.2 | F' | HATU/HOAt |
| 672 | Q-1016 | 1.37 | 414.2 | F' | HATU/HOAt |
| 673 | Q-1017 | 1.819 | 395.2 | C' | HATU/HOAt |
| 674 | Q-1018 | 1.528 | 478.2 | D' | HATU/HOAt |
| 675 | Q-1019 | 1.832 | 464.2 | C' | HATU/HOAt |
| 676 | Q-1020 | 1.540 | 410.2 | F' | HATU/HOAt |
| 677 | Q-1021 | 1.355 | 400.1 | F' | HATU/HOAt |
| 678 | Q-1022 | 1.33 | 369.2 | F' | HATU/HOAt |
| 679 | Q-1023 | 1.772 | 376.2 | C' | HATU/HOAt |
| 680 | Q-1024 | 1.832 | 376.1 | C' | HATU/HOAt |
| 681 | Q-1025 | 1.35 | 400.2 | F' | HATU/HOAt |
| 682 | Q-1026 | 1.367 | 414.2 | F' | HATU/HOAt |
| 683 | Q-1027 | 1.331 | 414.2 | C' | HATU/HOAt |
| 684 | Q-1028 | 2 | 437 | D' | HATU/HOAt |
| 685 | Q-1029 | 1.810 | 464.2 | C' | HATU/HOAt |
| 686 | Q-1030 | 1.339 | 400.2 | J' | HATU/HOAt |
| 687 | Q-1031 | 1.315 | 386.2 | J' | HATU/HOAt |
| 688 | Q-1032 | 1.326 | 438.2 | J' | HATU/HOAt |
| 689 | Q-1033 | 1.483 | 428.1 (M − H)− | F' | HATU/HOAt |
| 690 | Q-1034 | 1.461 | 390.2 | F' | HATU/HoAt |
| 691 | Q-1035 | 1.589 | 450.2 | J' | HATU/HOAt |
| 692 | Q-1036 | 1.566 | 464.2 | J' | HATU/HOAt |
| 693 | Q-1037 | 1.844 | 481.1 | F' | HATU/HOAt |
| 694 | Q-1038 | 1.934 | 393.2 | C' | HATU/HOAt |
| 695 | Q-1039 | 1.427 | 359.1 | F' | HATU/HOAt |
| 696 | Q-1040 | 1.494 | 341.1 | F' | HATU/HOAt |
| 697 | Q-1041 | 1.416 | 395.2 | J' | HATU/HOAt |
| 698 | Q-1042 | 1.803 | 440.1 | D' | HATU/HOAt |
| 699 | Q-1043 | 1.474 | 455.2 | J' | HATU/HOAt |
| 700 | Q-1044 | 1.556 | 425.1 | F' | HATU/HOAt |
| 701 | Q-1045 | 1.545 | 469.3 | J' | HATU/HOAt |
| 702 | Q-1046 | 1.505 | 492.2 | F' | HATU/HOAt |
| 703 | Q-1047 | 1.866 | 412 | J' | HATU/HOAt |
| 704 | Q-1048 | 1.891 | 354.2 | C' | HATU/HOAt |
| 705 | Q-1049 | 1.786 | 378.2 | C' | HATU/HOAt |
| 706 | Q-1050 | 1.747 | 349.1 | D' | HATU/HOAt |
| 707 | Q-1051 | 1.680 | 437.2 | J' | HATU/HOAt |
| 708 | Q-1052 | 1.949 | 453.2 | J' | HATU/HOAt |
| 709 | Q-1053 | 1.487 | 406.1 | F' | HATU/HOAt |
| 710 | Q-1054 | 1.903 | 425.2 | C' | HATU/HOAt |
| 711 | Q-1055 | 1 | 410 | J' | HATU/HOAt |
| 712 | Q-1056 | 2.054 | 487.2 | C' | HATU/HOAt |
| 713 | Q-1057 | 1.401 | 464.3 | F' | HATU/HOAt |
| 714 | Q-1058 | 1.381 | 465.2 | F' | HATU/HOAt |
| 715 | Q-1059 | 1.373 | 356.1 | J' | HATU/HOAt |
| 716 | Q-1060 | 1.472 | 424.2 | J' | HATU/HOAt |
| 717 | Q-1061 | 1.696 | 451.2 | C' | HATU/HOAt |
| 718 | Q-1062 | 1.773 | 412.2 | C' | HATU/HOAt |
| 719 | Q-1063 | 1.745 | 413.2 | C' | HATU/HOAt |
| 720 | Q-1064 | 2.066 | 435.2 | C' | HATU/HOAt |
| 721 | Q-1065 | 2.049 | 435.2 | C' | HATU/HOAt |
| 722 | Q-1066 | 1.425 | 425.2 | J' | HATU/HOAt |
| 723 | Q-1067 | 1.390 | 426.2 | J' | HATU/HOAt |
| 724 | Q-1070 | 1.271 | 466.2 | F' | HATU/HOAt |
| 725 | Q-1071 | 1.991 | 409.1 | C' | HATU/HOAt |
| 726 | Q-1072 | 1.802 | 395.2 | C' | HATU/HOAt |
| 727 | Q-1073 | 1.431 | 407.2 | J' | HATU/HOAt |
| 728 | Q-1074 | 1.563 | 463.1 | F' | HATU/HOAt |
| 729 | Q-1075 | 1.517 | 464.1 | F' | HATU/HOAt |
| 730 | Q-1076 | 1.7 | 411.2 | C' | HATU/HOAt |
| 731 | Q-1077 | 1.284 | 467.3 | F' | HATU/HOAt |
| 732 | Q-1078 | 1.945 | 450.1 | C' | HATU/HOAt |
| 733 | Q-1079 | 1.486 | 471.2 | I' | HATU/HOAt |
| 734 | Q-1080 | 1.522 | 470.2 | I' | HATU/HOAt |
| 735 | Q-1081 | 1.759 | 451.2 | A' | HATU/HOAt |

TABLE 22-continued

| Ex. No. | Ref. No. | LC-MS (Retention Time) | MS (M + H)+ | LC-MS Method | Coupling Agent |
|---|---|---|---|---|---|
| 736 | Q-1082 | 1.490 | 422.1 | C' | HATU/HOAt |
| 737 | Q-1083 | 1.691 | 422.1 | A' | HATU/HOAt |
| 738 | Q-1084 | 1.551 | 488.1 | C' | HATU/HOAt |
| 739 | Q-1085 | 1.401 | 478.2 | F' | HATU/HOAt |
| 740 | Q-1086 | 1.533 | 506.3 | F' | HATU/HOAt |
| 741 | Q-1087 | 1.430 | 407.1 | F' | HATU/HOAt |
| 742 | Q-1088 | 1.373 | 436.3 | F' | HATU/HOAt |
| 743 | Q-1089 | 1.344 | 437.3 | F' | HATU/HOAt |
| 744 | Q-1090 | 1.617 | 453.2 | C' | HATU/HOAt |
| 745 | Q-1091 | 1.35 | 454.2 | J' | HATU/HOAt |
| 746 | Q-1092 | 1.387 | 408.3 | E' | HATU/HOAt |
| 747 | Q-1093 | 1.446 | 435.1 | J' | HATU/HOAt |
| 748 | Q-1094 | 1.499 | 394.2 | C' | HATU/HOAt |
| 749 | Q-1095 | 1.614 | 421.2 | J' | HATU/HOAt |
| 750 | Q-1096 | 1.572 | 422.2 | J' | HATU/HOAt |
| 751 | Q-1097 | 1.570 | 487.2 | C' | HATU/HOAt |
| 752 | Q-1098 | 1.466 | 373.2 | J' | HATU/HOAt |
| 753 | Q-1099 | 1.669 | 487.2 | C' | HATU/HOAt |
| 754 | Q-1100 | 1.648 | 488.2 | C' | HATU/HOAt |
| 755 | Q-1101 | 1.490 | 487.2 | C' | HATU/HOAt |
| 756 | Q-1102 | 1.82 | 413.3 | C' | HATU/HOAt |
| 757 | Q-1103 | 1.799 | 393.2 | C' | HATU/HOAt |
| 758 | Q-1104 | 1.41 | 436.2 | J' | HATU/HOAt |
| 759 | Q-1105 | 1.494 | 422.2 | J' | HATU/HOAt |
| 760 | Q-1106 | 1.752 | 422.2 | C' | HATU/HOAt |
| 761 | Q-1107 | 1 | 437 | J' | HATU/HOAt |
| 762 | Q-1108 | 2 | 478.2 | J' | HATU/HOAt |
| 763 | Q-1109 | 1.349 | 451.2 | F' | HATU/HOAt |
| 764 | Q-1110 | 1.986 | 446.3 | C' | HATU/HOAt |
| 765 | Q-1111 | 1.851 | 438.2 | C' | HATU/HOAt |
| 766 | Q-1112 | 1.792 | 383.2 | C' | HATU/HOAt |
| 767 | Q-1113 | 1.753 | 384.2 | C' | HATU/HOAt |
| 768 | Q-1114 | 1.422 | 408.2 | C' | HATU/HOAt |
| 769 | Q-1115 | 1.584 | 422.2 | A' | HATU/HOAt |
| 770 | Q-1116 | 1.866 | 438.1 | C' | HATU/HOAt |
| 771 | Q-1117 | 1.469 | 422.2 | C' | HATU/HOAt |
| 772 | Q-1118 | 1.755 | 425.1 | C' | HATU/HOAt |
| 773 | Q-1119 | 1.437 | 377.2 | J' | HATU/HOAt |
| 774 | Q-1120 | 1.640 | 418.1 | C' | HATU/HOAt |
| 775 | Q-1121 | 1.396 | 394.1 | J' | HATU/HOAt |
| 776 | Q-1122 | 1.923 | 421.1 | C' | HATU/HOAt |
| 777 | Q-1123 | 1.545 | 435.2 | F' | HATU/HOAt |
| 778 | Q-1124 | 1.921 | 409.2 | C' | HATU/HOAt |
| 779 | Q-1125 | 1.398 | 410.2 | J' | HATU/HOAt |
| 780 | Q-1126 | 1.549 | 379.2 | J' | HATU/HOAt |
| 781 | Q-1128 | 1.781 | 394.1 | C' | HATU/HOAt |
| 782 | Q-1129 | 1.312 | 394.1 | J' | HATU/HOAt |
| 783 | Q-1130 | 1.517 | 421.1 | F' | HATU/HOAt |
| 784 | Q-1131 | 1.704 | 459.2 | J' | HATU/HOAt |
| 785 | Q-1132 | 1.657 | 423.2 | F' | HATU/HOAt |
| 786 | Q-1134 | 1.974 | 479.1 | C' | HATU/HOAt |
| 787 | Q-1135 | 1.637 | 505.2 | J' | HATU/HOAt |
| 788 | Q-1136 | 1.35 | 488.2 | F' | HATU/HOAt |
| 789 | Q-1137 | 1.896 | 463.1 | C' | HATU/HOAt |
| 790 | Q-1138 | 2.162 | 521.1 | C' | HATU/HOAt |
| 791 | Q-1139 | 2.191 | 555.1 | C' | HATU/HOAt |
| 792 | Q-1140 | 1.894 | 506.1 | C' | HATU/HOAt |
| 793 | Q-1141 | 1.571 | 455.2 | J' | HATU/HOAt |
| 794 | Q-1144 | 1.731 | 394.1 | C' | HATU/HOAt |
| 795 | Q-1145 | 1.820 | 464.1 | C' | HATU/HOAt |
| 796 | Q-1146 | 2.125 | 492.1 | C' | HATU/HOAt |
| 797 | Q-1147 | 2.069 | 492.1 | C' | HATU/HOAt |
| 798 | Q-1148 | 2.135 | 526.1 | C' | HATU/HOAt |
| 799 | Q-1149 | 1.566 | 489.2 | J' | HATU/HOAt |
| 800 | Q-1150 | 1.588 | 473.1 | C' | HATU/HOAt |
| 801 | Q-1151 | 1.602 | 505.2 | J' | HATU/HOAt |
| 802 | Q-1152 | 1.753 | 521.2 | J' | HATU/HOAt |
| 803 | Q-1153 | 2.078 | 555.1 | C' | HATU/HOAt |
| 804 | Q-1154 | 1.912 | 506.1 | C' | HATU/HOAt |
| 805 | Q-1155 | 1.748 | 521.2 | J' | HATU/HOAt |
| 806 | Q-1156 | 1.683 | 505.2 | J' | HATU/HOAt |
| 807 | Q-1157 | 1.919 | 489.2 | D' | HATU/HOAt |
| 808 | Q-1158 | 1.842 | 459.1 | D' | HATU/HOAt |
| 809 | Q-1159 | 2.031 | 539.1 | C' | HATU/HOAt |
| 810 | Q-1160 | 2.009 | 476.1 | C' | HATU/HOAt |
| 811 | Q-1161 | 1.350 | 472.2 | J' | HATU/HOAt |
| 812 | Q-1162 | 1.366 | 472.2 | J' | HATU/HOAt |
| 813 | Q-1163 | 1.886 | 522.1 | C' | HATU/HOAt |
| 814 | Q-1164 | 1.593 | 488.2 | D' | HATU/HOAt |
| 815 | Q-1165 | 2.043 | 505.1 | C' | HATU/HOAt |
| 816 | Q-1166 | 2.114 | 492.0 | C' | HATU/HOAt |
| 817 | Q-1167 | 2.139 | 526.1 | C' | HATU/HOAt |
| 818 | Q-1168 | 1.383 | 394.2 | C' | HATU/HOAt |
| 819 | Q-1170 | 1.482 | 440.2 | J' | HATU/HOAt |
| 820 | Q-1171 | 1.648 | 539.2 | J' | HATU/HOAt |
| 821 | Q-1172 | 1.989 | 512.1 | C' | HATU/HOAt |
| 822 | Q-1173 | 2.183 | 555.1 | C' | HATU/HOAt |
| 823 | Q-1174 | 1.683 | 447.2 | J' | HATU/HOAt |
| 824 | Q-1175 | 1.668 | 539.2 | J' | HATU/HOAt |
| 825 | Q-1176 | 1.63 | 505.2 | J' | HATU/HOAt |
| 826 | Q-1177 | 1.521 | 349.1 | E' | HATU/HOAt |
| 827 | Q-1178 | 1.838 | 541.1 | C' | HATU/HOAt |
| 828 | Q-1179 | 1.997 | 522 | C' | HATU/HOAt |
| 829 | Q-1180 | 1.937 | 506.2 | C' | HATU/HOAt |
| 830 | Q-1181 | 2.010 | 512.1 | C' | HATU/HOAt |
| 831 | Q-1182 | 1.477 | 488.1 | C' | HATU/HOAt |
| 832 | Q-1183 | 1.469 | 438.2 | J' | HATU/HOAt |
| 833 | Q-1184 | 1.959 | 368.1 | C' | HATU/HOAt |
| 834 | Q-1185 | 1.689 | 405.1 | C' | HATU/HOAt |
| 835 | Q-1186 | 2.022 | 449.1 | C' | HATU/HOAt |
| 836 | Q-1187 | 1.550 | 459.1 | C' | HATU/HOAt |
| 837 | Q-1188 | 1.856 | 506.1 | C' | HATU/HOAt |
| 838 | Q-1189 | 1.41 | 396.3 | J' | HATU/HOAt |
| 839 | Q-1190 | 1.524 | 506.2 | J' | HATU/HOAt |
| 840 | Q-1191 | 1.402 | 383.2 | J' | HATU/HOAt |
| 841 | Q-1192 | 1.78 | 395.2 | C' | HATU/HOAt |
| 842 | Q-1193 | 1.863 | 490.1 | C' | HATU/HOAt |
| 843 | Q-1194 | 1.456 | 436.1 | C' | HATU/HOAt |
| 844 | Q-1196 | 1.963 | 506.1 | C' | HATU/HOAt |
| 845 | Q-1197 | 1.865 | 506.1 | C' | HATU/HOAt |
| 846 | Q-1198 | 1.537 | 453.2 | J' | HATU/HOAt |
| 847 | Q-1199 | 2.083 | 449.2 | C' | HATU/HOAt |
| 848 | Q-1200 | 2.004 | 450.2 | C' | HATU/HOAt |
| 849 | Q-1201 | 1.405 | 369.2 | C' | HATU/HOAt |
| 850 | Q-1202 | 1.575 | 489.2 | J' | HATU/HOAt |
| 851 | Q-1203 | 1.525 | 496.2 | J' | HATU/HOAt |
| 852 | Q-1205 | 1.366 | 382.3 | J' | HATU/HOAt |
| 853 | Q-1206 | 1.690 | 459.1 | C' | HATU/HOAt |
| 854 | Q-1207 | 1.857 | 397.2 | C' | HATU/HOAt |
| 855 | Q-1208 | 1.786 | 395.1 | C' | HATU/HOAt |
| 856 | Q-1209 | 1.377 | 381.2 | J' | HATU/HOAt |
| 857 | Q-1210 | 2.026 | 512.2 | C' | HATU/HOAt |
| 858 | Q-1211 | 1.928 | 512.2 | C' | HATU/HOAt |
| 859 | Q-1212 | 1.559 | 496.3 | J' | HATU/HOAt |
| 860 | Q-1213 | 1.318 | 396.2 | J' | HATU/HOAt |
| 861 | Q-1214 | 1.615 | 384.2 | J' | HATU/HOAt |
| 862 | Q-1215 | 1.926 | 445.2 | C' | HATU/HOAt |
| 863 | Q-1216 | 2 | 458.3 | J' | HATU/HOAt |
| 864 | Q-1217 | 1.780 | 394.1 | C' | HATU/HOAt |
| 865 | Q-1218 | 1.584 | 438.2 | J' | HATU/HOAt |
| 866 | Q-1219 | 1.88 | 417.1 | C' | HATU/HOAt |
| 867 | Q-1220 | 1.847 | 409.2 | C' | HATU/HOAt |
| 868 | Q-1221 | 1.331 | 355.2 | C' | HATU/HOAt |
| 869 | Q-1222 | 1.516 | 354.2 | J' | HATU/HOAt |
| 870 | Q-1223 | 1.427 | 397.2 | J' | HATU/HOAt |
| 871 | Q-1224 | 1.645 | 391.1 | C' | HATU/HOAt |
| 872 | Q-1225 | 1.759 | 423.1 | C' | HATU/HOAt |
| 873 | Q-1226 | 1.708 | 409.1 | C' | HATU/HOAt |
| 874 | Q-1227 | 1.895 | 451.1 | C' | HATU/HOAt |
| 875 | Q-1228 | 1.767 | 439.1 | C' | HATU/HOAt |
| 876 | Q-1229 | 1.418 | 461.2 | J' | HATU/HOAt |
| 877 | Q-1230 | 1.626 | 505.2 | J' | HATU/HOAt |
| 878 | Q-1231 | 1.874 | 506.1 | C' | HATU/HOAt |
| 879 | Q-1232 | 1.668 | 427.1 | C' | HATU/HOAt |
| 880 | Q-1233 | 1.578 | 426.2 | J' | HATU/HOAt |
| 881 | Q-1234 | 1.792 | 461.1 | C' | HATU/HOAt |
| 882 | Q-1235 | 1.474 | 488.1 | C' | HATU/HOAt |
| 883 | Q-1236 | 1.924 | 522.1 | C' | HATU/HOAt |
| 884 | Q-1237 | 1.762 | 362.1 | C' | HATU/HOAt |
| 885 | Q-1238 | 2.05 | 460.1 | C' | HATU/HOAt |
| 886 | Q-1239 | 1.404 | 375.2 | J' | HATU/HOAt |
| 887 | Q-1240 | 1.542 | 436.2 | J' | HATU/HOAt |

TABLE 22-continued

| Ex. No. | Ref. No. | LC-MS (Retention Time) | MS (M + H)+ | LC-MS Method | Coupling Agent |
|---|---|---|---|---|---|
| 888 | Q-1241 | 1.272 | 382.1 | C' | HATU/HOAt |
| 889 | Q-1243 | 1.368 | 404.2 | J' | HATU/HOAt |
| 890 | Q-1244 | 1.254 | 369.1 | C' | HATU/HOAt |
| 891 | Q-1246 | 1.646 | 390.1 | C' | HATU/HOAt |
| 892 | Q-1247 | 1.401 | 405.2 | J' | HATU/HOAt |
| 893 | Q-1249 | 1.388 | 386.2 | J' | HATU/HOAt |
| 894 | Q-1250 | 1.786 | 417.1 | C' | HATU/HOAt |
| 895 | Q-1251 | 1.162 | 328.2 | J' | HATU/HOAt |
| 896 | Q-1254 | 1.35 | 404.2 | J' | HATU/HOAt |
| 897 | Q-1255 | 1.537 | 404.1 |  | HATU/HOAt |
| 898 | Q-1256 | 1.477 | 410.2 | J' | HATU/HOAt |
| 899 | Q-1259 | 1.677 | 375.1 | C' | HATU/HOAt |
| 900 | Q-1260 | 1.719 | 410.1 | C' | HATU/HOAt |
| 901 | Q-1263 | 1.409 | 375.2 | J' | HATU/HOAt |
| 902 | Q-1266 | 1.778 | 424.1 | C' | HATU/HOAt |
| 903 | Q-1269 | 1.699 | 394.1 | C' | HATU/HOAt |
| 904 | Q-1288 | 2 | 524.1 | C' | HATU/HOAt |
| 905 | Q-1289 | 2 | 524.2 | J' | HATU/HOAt |
| 906 | Q-1291 | 1.603 | 422.1 | C' | HATU/HOAt |
| 907 | Q-1292 | 4.560 | 438.2 | E' | HATU/HOAt |
| 908 | Q-1296 | 1.345 | 411.2 | J' | HATU/HOAt |
| 909 | Q-1301 | 1.400 | 394.3 | D' | HATU/HOAt |
| 910 | Q-1305 | 1.461 | 422.2 | F' | HATU/HOAt |
| 911 | Q-1306 | 1.485 | 389.2 | E' | HATU/HOAt |
| 912 | Q-1311 | 1.680 | 432.1 | C' | HATU/HOAt |
| 913 | Q-1313 | 1.537 | 403.2 | E' | HATU/HOAt |
| 914 | Q-1320 | 1.753 | 394.1 | C' | HATU/HOAt |
| 915 | Q-1322 | 1.612 | 418.2 | C' | HATU/HOAt |
| 916 | Q-1341 | 1.450 | 450.2 | E' | HATU/HOAt |
| 917 | Q-1343 | 1.256 | 407.2 | J' | HATU/HOAt |
| 918 | Q-1344 | 1.709 | 413.1 | C' | HATU/HOAt |
| 919 | Q-1346 | 1.673 | 378.1 | C' | HATU/HOAt |
| 920 | Q-1362 | 1.462 | 432.2 | J' | HATU/HOAt |
| 921 | Q-1365 | 1.547 | 436.2 | J' | HATU/HOAt |
| 922 | Q-1483 | 1.633 | 425.1 | C' | HATU |
| 923 | Q-1535 | 1.506 | 468.2 | J' | HOAt/HATU |
| 924 | Q-1539 | 1.607 | 406.1 | C' | HATU/HOAt |
| 925 | Q-1558 | 1.402 | 434.2 | J' | HATU/HOAt |
| 926 | Q-1560 | 1.493 | 423.0 | C' | HATU/HOAt |
| 927 | Q-1563 | 1.524 | 439.2 | J' | HATU/HOAt |
| 928 | Q-1565 | 1.479 | 404.2 | J' | HATU/HOAt |
| 929 | Q-1581 | 1.663 | 420.1 | C' | HATU/HOAt |
| 930 | Q-1591 | 1.494 | 482.2 | J' | HOAt/HATU |
| 931 | Q-1597 | 1.757 | 289.1 | C' |  |
| 932 | Q-1641 | 1.424 | 303.2 | J' |  |
| 933 | Q-1728 | 1.448 | 488.1 | F' | HATU/HOAt |
| 934 | Q-1818 | 1.561 | 474.3 | J' | HATU/HOAt |
| 935 | Q-1866 | 1.889 | 504.1 | C' | HATU/HOAt |
| 936 | Q-1886 | 1.573 | 460.1 | J' | HATU/HOAt |
| 937 | Q-1889 | 1.925 | 425.1 | C' | HATU/HOAt |
| 938 | Q-1925 | 1.343 | 364.1 | D' | HATU/HOAt |
| 939 | Q-1932 | 1.381 | 365.0 | J' | HATU/HOAt |
| 940 | Q-1984 | 1.784 | 467.0 | C' | HATU/HOAt |
| 941 | Q-1985 | 1.561 | 405.1 | C' | HATU/HOAt |
| 942 | Q-2007 | 1.285 | 460.3 | D' | HATU/HOAt |
| 943 | Q-2008 | 1.756 | 426.0 | C' | HATU/HOAt |
| 944 | Q-2009 | 1.850 | 444.0 | C' | HATU/HOAt |
| 945 | Q-2016 | 1.509 | 412.1 | J' | HATU/HOAt |
| 946 | Q-2017 | 1.556 | 439.0 | J' | HATU/HOAt |

Preparative Example 9—Formation of Amines

Preparation of 4-(azetidin-3-yl)-2-fluoropyridine TFA salt

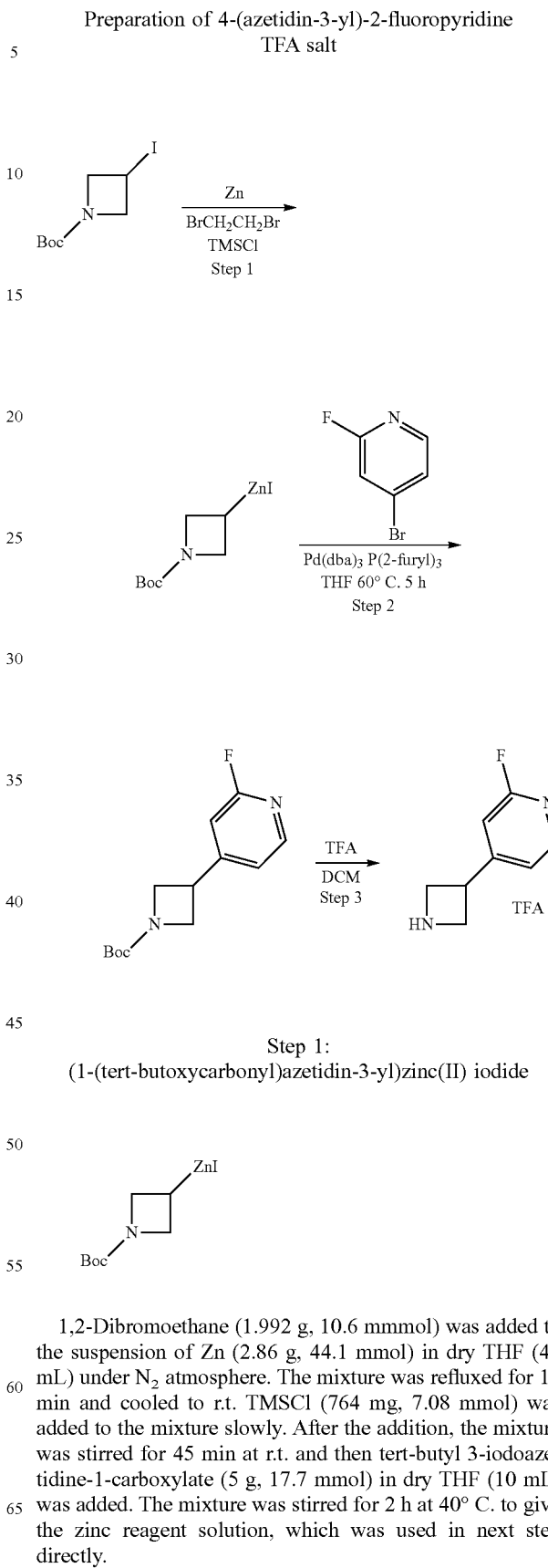

Step 1:
(1-(tert-butoxycarbonyl)azetidin-3-yl)zinc(II) iodide 1,2-Dibromoethane (1.992 g, 10.6 mmmol) was added to the suspension of Zn (2.86 g, 44.1 mmol) in dry THF (40 mL) under $N_2$ atmosphere. The mixture was refluxed for 15 min and cooled to r.t. TMSCl (764 mg, 7.08 mmol) was added to the mixture slowly. After the addition, the mixture was stirred for 45 min at r.t. and then tert-butyl 3-iodoazetidine-1-carboxylate (5 g, 17.7 mmol) in dry THF (10 mL) was added. The mixture was stirred for 2 h at 40° C. to give the zinc reagent solution, which was used in next step directly.

Step 2: Synthesis of tert-butyl 3-(2-fluoropyridin-4-yl)azetidine-1-carboxylate

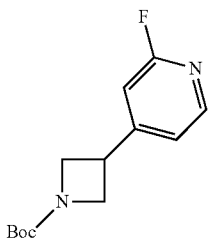 [SMILES: CC(C)(C)OC(=O)N1CC(c2ccnc(F)c2)C1]

4-Bromo-2-fluoropyridine (3 g, 17.142 mmol) in THF (10 ml) was added to the mixture of Pd(dba)₃ (1.57 g, 1.714 mmol) and Pd(2-furyl)₃ (1.2 g, 5.143 mmol) under N₂ atmosphere. Then (1-(tert-butoxycarbonyl)azetidin-3-yl)zinc(II) iodide (7.2 g, 20.571 mmol) solution in THF (50 mL) was added. The mixture was stirred at 60° C. for 5 h. The reaction was quenched with H₂O (10 mL). The precipitate was filtered. The filtrate was extracted with EtOAc (30 mL×2) and washed with water (200 mL). The combined organics were dried over Na₂SO₄. The solvent was then removed and the residue was purified by silica gel chromatography with CH₂Cl₂/MeOH: 50/1 to yield the product. LC-MS: m/z=253 (M+H)+, RT=1.457 min.

Step 3: Synthesis of 4-(azetidin-3-yl)-2-fluoropyridine TFA salt

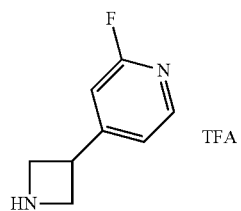

TFA (5 mL) was added to a solution of tert-butyl 3-(2-fluoropyridin-4-yl)azetidine-1-carboxylate (1.926 g, 7.634 mmol) in DCM (5 mL). The solution was stirred at r.t. for 3 h. The solvent was removed from the reaction to yield the product which was used in the next step without further purification. LC-MS: m/z=153 (M+H)+.

Preparation 1-(3,3-difluorocyclobutyl)piperazine

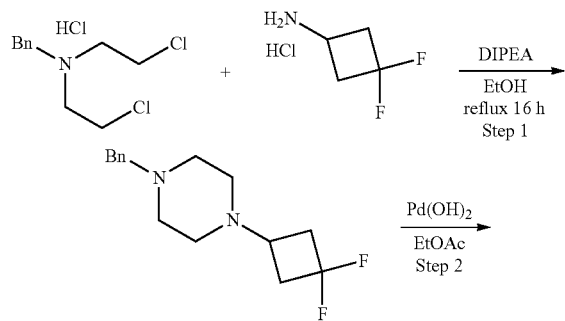

Step 1: Synthesis of 1-benzyl-4-(3,3-difluorocyclobutyl)piperazine.

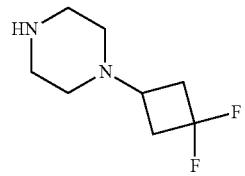 [SMILES: FC1(F)CC(N2CCNCC2)C1]

To a 100 mL of RBF was added N-benzyl-2-chloro-N-(2-chloroethyl)ethanamine hydrochloride (2.3 g, 8.61 mmol), 3,3-difluorocyclobutanamine hydrochloride (1.0 g, 6.99 mmol), 20 mL of EtOH, and 6 mL of DIPEA. The mixture was stirred at reflux under N₂ for 16 h. The reaction mixture was concentrated and purified by combi flash (isco, silica gel, UV 254, 40 g, EA/PE=1/3) to give the product. LC-MS (UV 214) 267.2 (M+H)+, RT=2.01 min.

Step 2: Synthesis of 1-(3,3-difluorocyclobutyl)piperazine

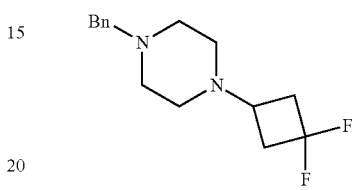

To a 100 mL of RBF was added 1-benzyl-4-(3,3-difluorocyclobutyl)piperazine (1.0 g, 3.76 mmol), 30 mL of EtOAc, 0.05 mL of HOAc, and 400 mg of Pd(OH)₂. The mixture was stirred at r.t. under H₂ (2 atm) for 16 h. The reaction mixture was filtered and the filtrate was concentrated to give the title product. LC-MS (UV 214) 177.2 (M+H)+, RT=1.17 min.

Preparation of 1-(2,2-difluorocyclobutyl)piperazine hydrochloride

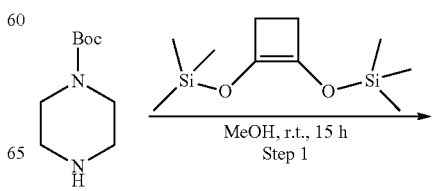

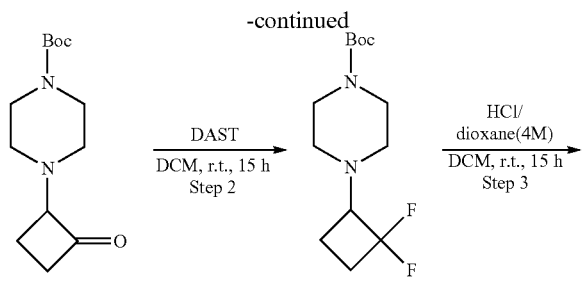

Step 1: Synthesis of tert-butyl-4-(2-oxocyclobutyl) piperazine-1-carboxylate

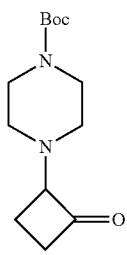

To the solution of 1,2-bis(trimethylsilyloxy)cyclobut-1-ene (12.5 g, 54.24 mmol) in MeOH (40 mL) was added dropwise a solution of tert-butyl-piperazine-1-carboxylate (10.1 g, 54.24 mmol) in MeOH (60 mL) over 30 min. After addition, the reaction mixture was stirred at r.t. for 15 h. The mixture was concentrated and purified by SGC (eluting with DCM/MeOH=20/1) to get the title compound. LC-MS: m/z=199.1 (M−56)+, RT=1.80 min.

Step 2: Synthesis of tert-butyl-4-(2,2-difluorocyclobutyl)piperazine-1-carboxylate

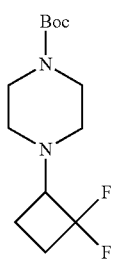

To the solution of tert-butyl-4-(2-oxocyclobutyl)piperazine-1-carboxylate (7.2 g, 28.31 mmol) in DCM (50 mL) was added DAST (13.69 g, 84.93 mmol). The reaction mixture was stirred at r.t. for 15 h. It was then quenched with sat. NaHCO₃ (100 mL), extracted with DCM (80 mL×3), and the combined organics were dried over Na₂SO₄ and concentrated. The residue was purified by SGC (eluting with PE/EtOAc=10/1-1/1) to give the title compound. LC-MS: m/z=277.2 (M+H)+, RT=2.01 min.

Step 3: Synthesis of 1-(2,2-difluorocyclobutyl)piperazine hydrochloride

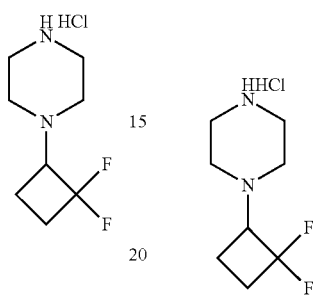

To a solution of tert-butyl-4-(2,2-difluorocyclobutyl)piperazine-1-carboxylate (950 mg, 3.44 mmol) in DCM (10 mL) was added HCl (4 mL, 4 M in dioxane). The reaction mixture was stirred at r.t. for 15 h, concentrated, and washed with EtOAc (40 mL) to give the title compound. LC-MS: m/z=177.2 (M+H)+, RT=1.15 min.

Preparation of 2-(piperidin-4-yl)oxazole-4-carbonitrile hydrochloride

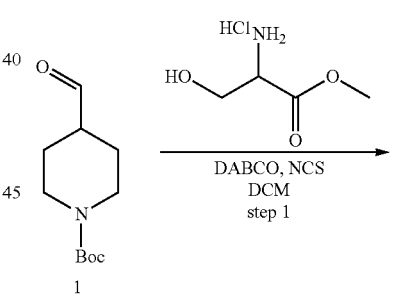

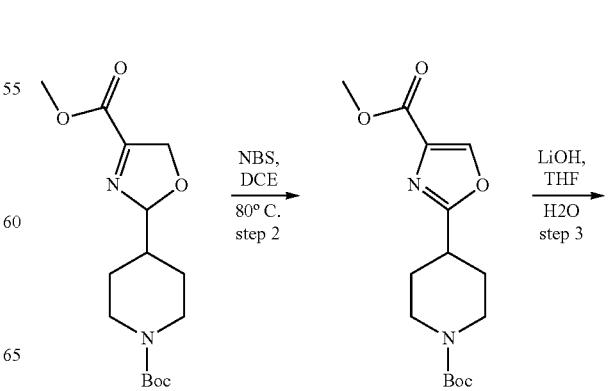

-continued

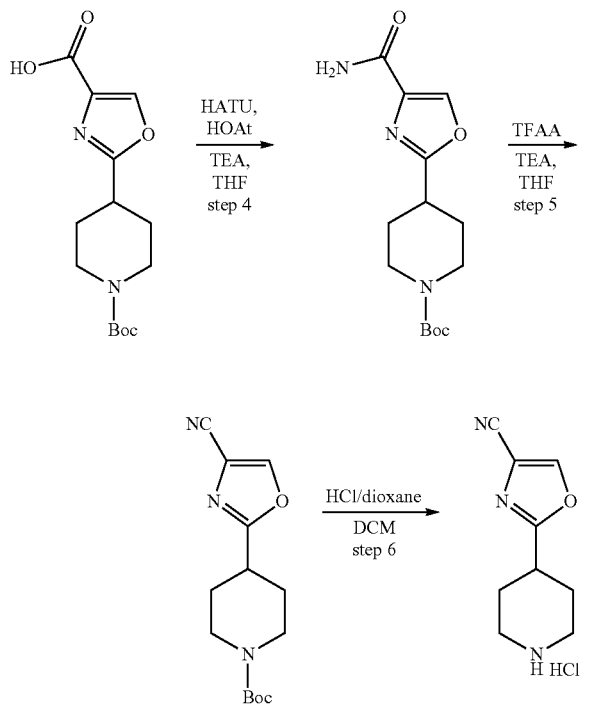

Step 1: Synthesis of methyl 2-(1-(tert-butoxycarbonyl)piperidin-4-yl)-2,5-dihydrooxazole-4-carboxylate

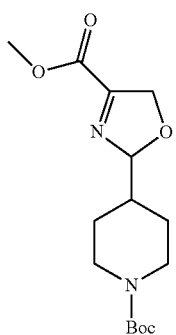 [SMILES: COC(=O)C1=NC(C2CCN(C(=O)OC(C)(C)C)CC2)OC1]

The mixture of methyl 2-amino-3-hydroxypropanoate (80 g, 516.4 mmol) and DABCO (157.74 g, 1408.45 mmol) in 2 liters of DCM was stirred for 40 min. Then tert-butyl 4-formylpiperidine-1-carboxylate (100 g, 469.48 mmol) was added to the mixture and stirred for 40 min at r.t. The mixture was cooled to 0° C. and then NBS (68.68 g, 516.4 mmol) in 500 mL of DCM was added dropwise to the mixture. The mixture was warmed to r.t. and stirred overnight. The reaction was quenched with sat. aq. Na₂S₂O₅, extracted with DCM (300 Ml×2), and washed with aq. NaHCO₃. The combined organics were dried over Na₂SO₄, concentrated and purified by SGC (PE/EA=3/2) to get the title compound. LC-MS: m/z=335 (M+23)+, RT=1.97 min.

Step 2: Synthesis of methyl 2-(1-(tert-butoxycarbonyl)piperidin-4-yl)oxazole-4-carboxylate

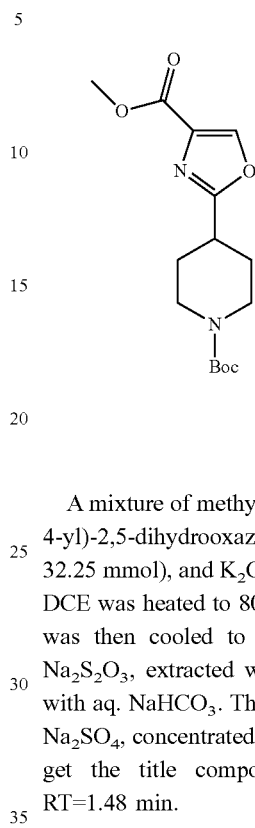

A mixture of methyl 2-(1-(tert-butoxycarbonyl)piperidin-4-yl)-2,5-dihydrooxazole (10 g, 32.25 mmol), NBS (5.74 g, 32.25 mmol), and K₂CO₃ (5.34 g, 38.7 mmol) in 100 mL of DCE was heated to 80° C. and stirred for 2 h. The mixture was then cooled to 0° C. and quenched with sat. aq. Na₂S₂O₃, extracted with DCM (100 mL×3), and washed with aq. NaHCO₃. The combined organics were dried over Na₂SO₄, concentrated and purified by SGC (PE/EA=3/2) to get the title compound. LC-MS: m/z=333 (M+23)+, RT=1.48 min.

Step 3: Synthesis of 2-(1-(tert-butoxycarbonyl)piperidin-4-yl)oxazole-4-carboxylic acid

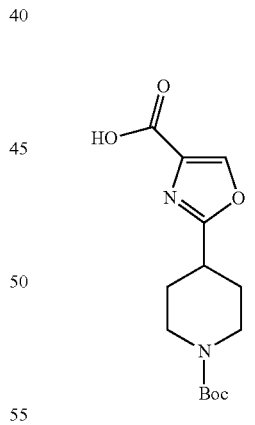

A solution of methyl 2-(1-(tert-butoxycarbonyl)piperidin-4-yl) oxazole-4-carboxylate (6 g, 19.35 mmol) and LiOH·H₂O (2.438 g, 58.06 mmol) in THF/H₂O (40 mL, v/v=1/1) was stirred for 16 h at 25° C. The mixture was adjusted to pH=3 with 1N HCl and then extracted with EA (60 mL×3). The combined organics were dried over Na₂SO₄. The solvent was removed under reduced pressure. The residue was used for the next step directly. LC-MS: m/z=319 (M+23)+, RT=1.34 min.

Step 4: Synthesis of tert-butyl 4-(4-carbamoyloxazol-2-yl)piperidine-1-carboxylate

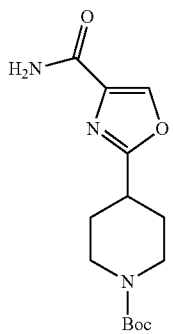

The mixture of 2-(1-(tert-butoxycarbonyl)piperidin-4-yl)oxazole-4-carboxylic acid (4 g, 13.51 mmol), NH₄Cl (1.702 g, 27.02 mmol), HATU (6.16 g, 16.212 mmol), HOAt (2.204 g, 16.212 mmol) and TEA (4.093 g, 40.53 mmol) in 50 mL of THF was stirred overnight at r.t. The reaction was quenched with water, extracted with EA (60 mL×3), and washed with aq. NaCl. The combined organics were dried over Na₂SO₄, concentrated, and purified by SGC (PE/EA=1/4) to get the title compound. LC-MS: m/z=318 (M+23)+, RT=1.77 min.

Step 5: Synthesis of tert-butyl 4-(4-cyanooxazol-2-yl) piperidine-1-carboxylate

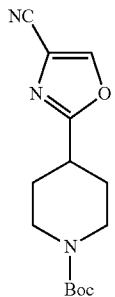

To a solution of tert-butyl 4-(4-carbamoyloxazol-2-yl)piperidine-1-carboxylate (2.5 g, 8.474 mmol) in TEA (10 mL) and THF (10 mL) was added TFAA (4 mL) dropwise at 0° C. The reaction mixture was stirred at room temperature overnight. The solvent was removed under reduced pressure, and the residue was purified by SGC (PE/EA=2/1) to get the title compound. LC-MS: m/z=300 (M+23)+; RT=2.01 min.

Step 6: 2-(piperidin-4-yl) oxazole-4-carbonitrile hydrochloride

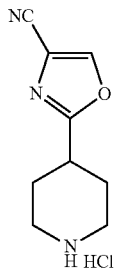

To a solution of tert-butyl 4-(4-cyanooxazol-2-yl)piperidine-1-carboxylate (1.3 g, 4.693 mmol) in EA (5 mL) was added 3N HCl/EA (5 mL). The mixture was stirred for 1 h at r.t. The resulting precipitate was collected and dried under vacuum after washing with diethyl ether to afford the title compound. LC-MS: m/z=178 (M+1)+, RT=0.21 min.

Preparation of 5-(azetidin-2-yl)-2-fluoropyridine hydrochloride

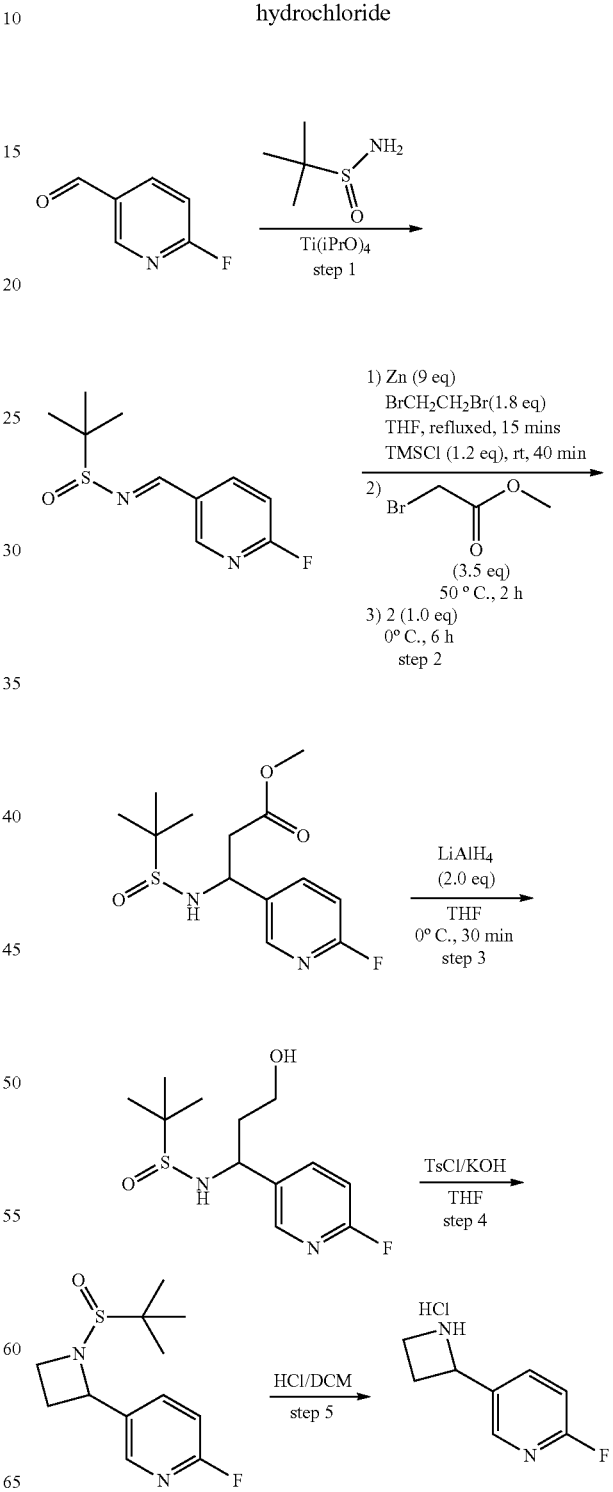

801

Step 1: Synthesis of (E)-N-((6-fluoropyridin-3-yl) methylene)-2-methylpropane-2-sulfinamide

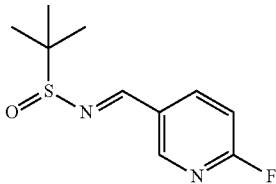

A mixture of 6-fluoronicotinaldehyde (4.7 g, 37.6 mmol) and titanium isopropoxide (1.37 g, 75.2 mmol) in dry THF (90 mL) was stirred at r.t. for 30 mins under nitrogen. Then a solution of 2-methyl-2-propanesulfinamide (4.56 g, 37.6 mmol) in dry THF (10 mL) was added. The reaction mixture was stirred at r.t. for 16 h, diluted with EtOAc (200 mL) and MeOH (50 mL), and then brine (100 mL) was added slowly. The mixture was stirred at r.t. for 30 mins and filtered. The solid was washed with EtOAc (200 mL×2). The filtrate was extracted with EtOAc (200 mL×3). The combined organics were washed with brine (50 mL×2), dried over $Na_2SO_4$, and concentrated. The residue was purified by SGC (PE/EtOAc=5/1) to give the title compound. LC-MS: m/z=303 (M+H)+, RT=1.61 min.

Step 2: Synthesis of methyl 3-(1,1-dimethylethyl-sulfinamido)-3-(6-fluoropyridin-3-yl) propanoate

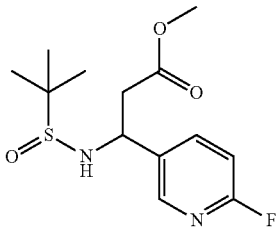 [SMILES: COC(=O)CC(NS(=O)C(C)(C)C)c1ccc(F)nc1]

To a suspension of Zn dust (13.13 g, 200.7 mmol) in dry THF (130 mL) was added 1, 2-Dibromoethane (7.53 g, 40.1 mmol). The mixture was stirred at reflux for 20 mins and then was cooled to r.t. TMSCl (2.91 g, 26.8 mmol) was added and stirred for 1 h at r.t. Then methyl 2-bromoacetate (10.05 g, 66.9 mmol) was added and stirred for 2 h at 50° C. The mixture was cooled to r.t. The resulting solution was dropped into a solution of (E)-N-((6-fluoropyridin-3-yl) methylene)-2-methylpropane-2-sulfinamide (5.09 g, 22.3 mmol) in dry THF (20 mL) at 0° C. The mixture was stirred at 0° C. for 6 h, diluted with DCM (100 mL), washed with 0.25 M aq. citric acid (200 mL×2), sat. aq. NaHCO₃ (50 mL×2), brine (50 mL×2), dried over $Na_2SO_4$, and concentrated to give the title compound. LC-MS: m/z=303 (M+H)+, RT=1.61 min.

802

Step 3: Synthesis of N-(1-(6-fluoropyridin-3-yl)-3-hydroxypropyl)-2-methylpropane-2-sulfinamide

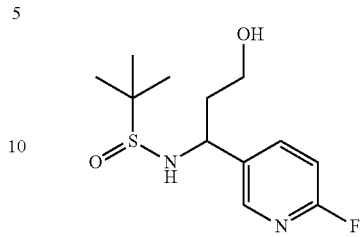

To a solution of methyl 3-(1,1-dimethylethylsulfinamido)-3-(6-fluoropyridin-3-yl)propanoate (3.32 g, 11.0 mmol) in dry THF (50 mL) was added 1 M LiAlH₄ THF solution (22 mL, 22 mol) at 0° C. The mixture was stirred at 0° C. for 30 mins, diluted with EtOAc (200 mL), quenched with $Na_2SO_4 \cdot 10H_2O$ (22 g) in portions. The mixture was stirred at r.t. for 30 mins and filtered. The solid was washed with MeOH (20 mL). The filtrate was dried over $Na_2SO_4$ and concentrated to give the crude title compound. LC-MS: m/z=275 (M+H)+; RT=1.60 min.

Step 4: Synthesis of 5-(1-(tert-butylsulfinyl) azetidin-2-yl)-2-fluoropyridine

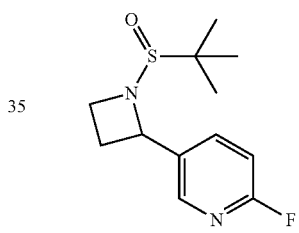

To a solution of N-(1-(6-fluoropyridin-3-yl)-3-hydroxypropyl)-2-methylpropane-2-sulfinamide (2.7 g, 9.85 mmol) in dry THF (50 mL) was added potassium hydroxide (1.65 g, 29.55 mmol) and 4-methylbenzene-1-sulfonyl chloride (2.25 g, 11.82 mmol). The mixture was stirred at reflux for 5 h and cooled to r.t. The mixture was diluted with DCM (200 mL), washed with brine (20 mL×2), dried over $Na_2SO_4$ and concentrated. The residue was purified by SGC (PE/EtOAc=2/1) to give the title compound. LC-MS: m/z=257 (M+H)+; RT=1.61 min.

Step 5: Synthesis of 5-(azetidin-2-yl)-2-fluoropyridine hydrochloride

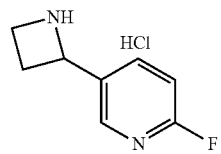 [SMILES: Fc1ccc(C2CCN2)cn1 ; Cl]

To a solution of 5-(1-(tert-butylsulfinyl)azetidin-2-yl)-2-fluoropyridine (1.14 g, 4.45 mmol) in DCM (20 mL) was added 4 M HCl/Dixoane solution (16.7 mL, 66.8 mmol) at 0° C. The mixture was stirred at r.t. for 30 mins then concentrated to give the title compound. LC-MS: m/z=124 (M−28)+, RT=0.308 min.

Preparation 6-cyclopropyl-3,6-diaza-bicyclo[3.1.1]heptane dihydrochloride

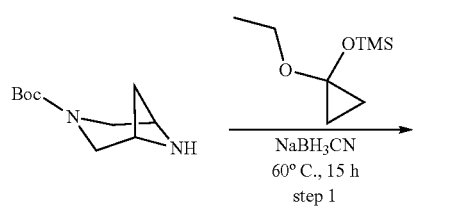

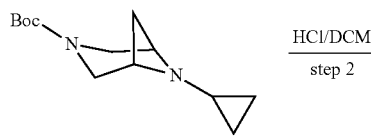

Step 1: Synthesis of tert-butyl 6-cyclopropyl-3,6-diaza-bicyclo[3.1.1]heptane-3-carboxylate

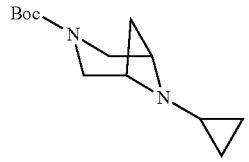

To a solution of tert-butyl 3,6-diaza-bicyclo[3.1.1]heptane-3-carboxylate (1.5 g, 7.58 mmol) and (1-ethoxycyclopropoxy)trimethylsilane (3.1 ml, 15.45 mmol) in 10 ml of MeOH and 10 ml of THF were added sodium cyanoborohydride (715 mg, 11.35 mmol) and acetic acid (2.2 ml, 38.50 mmol). The mixture was stirred at 60° C. under N₂ for 12 h. After cooling to r.t., 1 ml of water was added and the mixture was stirred for 5 min. It was then treated with 1N NaOH (2.5 ml) and stirred for 15 min. The mixture was concentrated and the aqueous phase was extracted with DCM (100 ml). The organic phase was washed with 1N NaOH (50 ml). The combined aqueous phase was extracted with DCM (2×100 ml). The combined organics were washed with brine, dried over sodium sulphate and concentrated to give crude product which was used for the next step without further purification. LC-MS: m/z=239 (M+H)+, RT=2.26 min.

Step 2: Synthesis of 6-cyclopropyl-3,6-diaza-bicyclo[3.1.1]heptane dihydrochloride

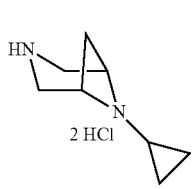

To a solution of tert-butyl 6-cyclopropyl-3,6-diaza-bicyclo[3.1.1]heptane-3-carboxylate (1.8 g crude, 7.56 mmol) in 40 mL of dichloromethane was added 25 mL of 4N HCl solution in 1,4-dioxane. The mixture was stirred at r.t. for 7 h and then stirred at 4° C. overnight. The upper clear solution was poured out and the sticky solid on the bottom of the flask was dried under vacuum to give the product. LC-MS: m/z=139 (M+H)+, RT=0.44 min.

Preparative Example 10—Formation of 4-(2,2,2-trifluoroethyl)piperidine

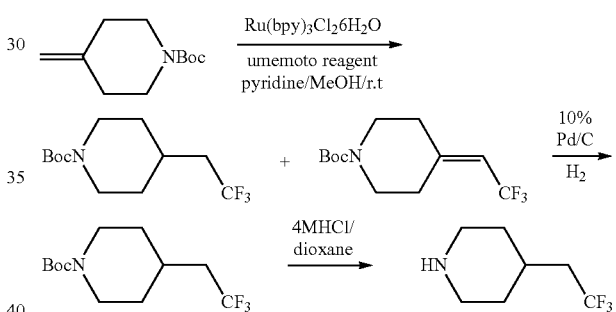

Preparative Example 11—Formation of (1R,5S)-3-azabicyclo[3.1.0]hexan-1-ol

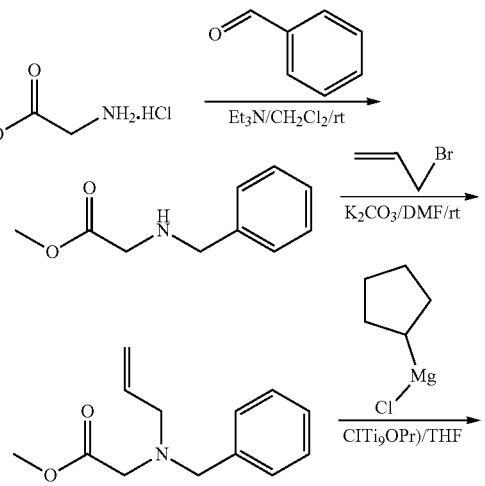

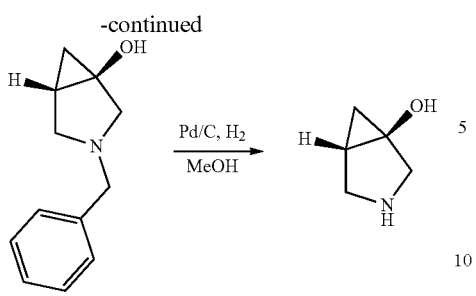
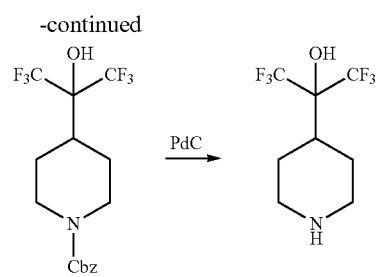
Preparative Example 12—Formation of tert-butyl 4-(1H-indol-4-yl)piperidine-1-carboxylate
Preparative Example 14—Formation of 4-((3,4-difluorophenyl)sulfonyl)piperidine
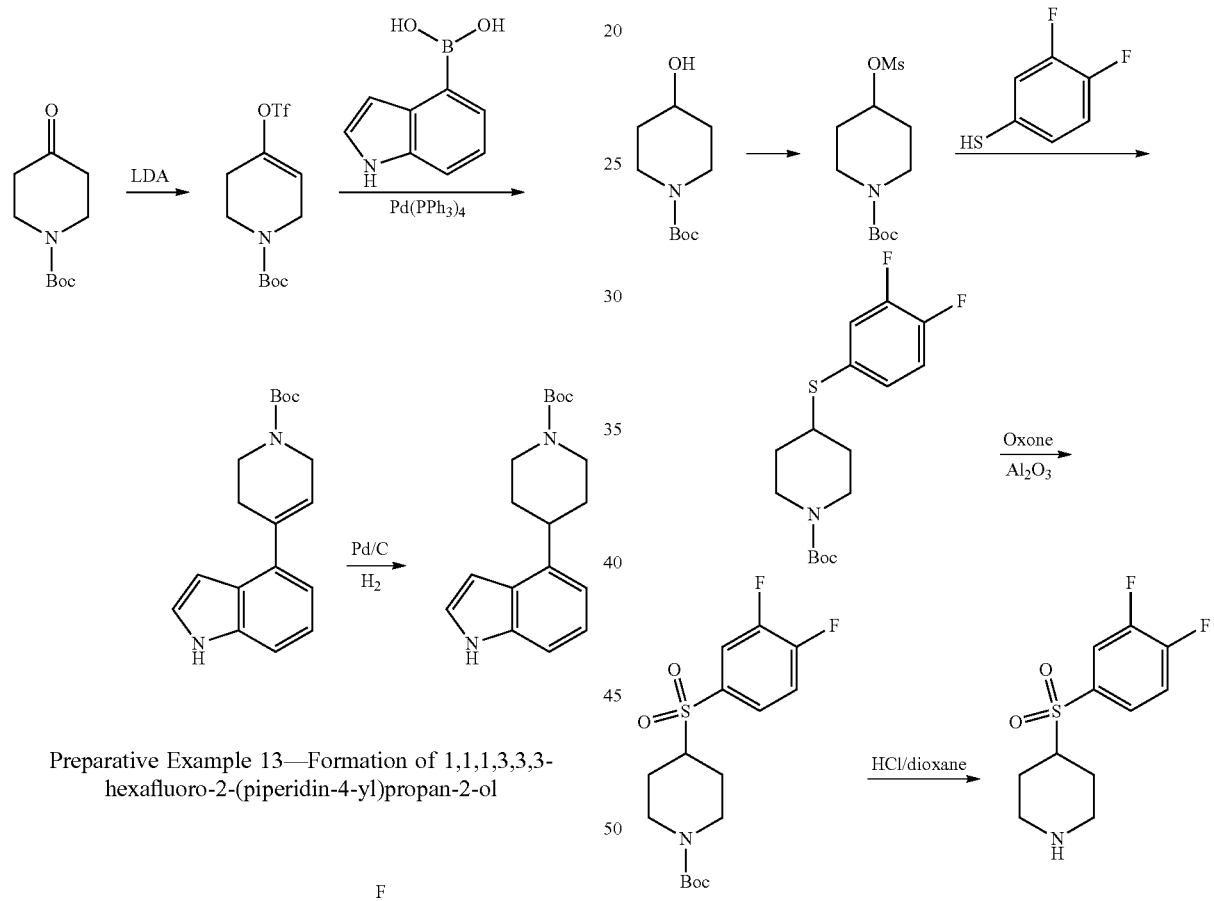
Preparative Example 13—Formation of 1,1,1,3,3,3-hexafluoro-2-(piperidin-4-yl)propan-2-ol
Preparative Example 15—Formation of 1-(2,2-difluorocyclopentyl)piperazine
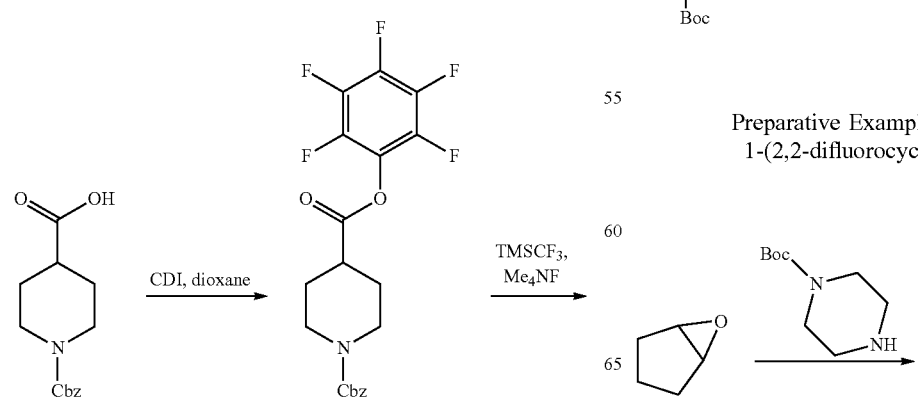

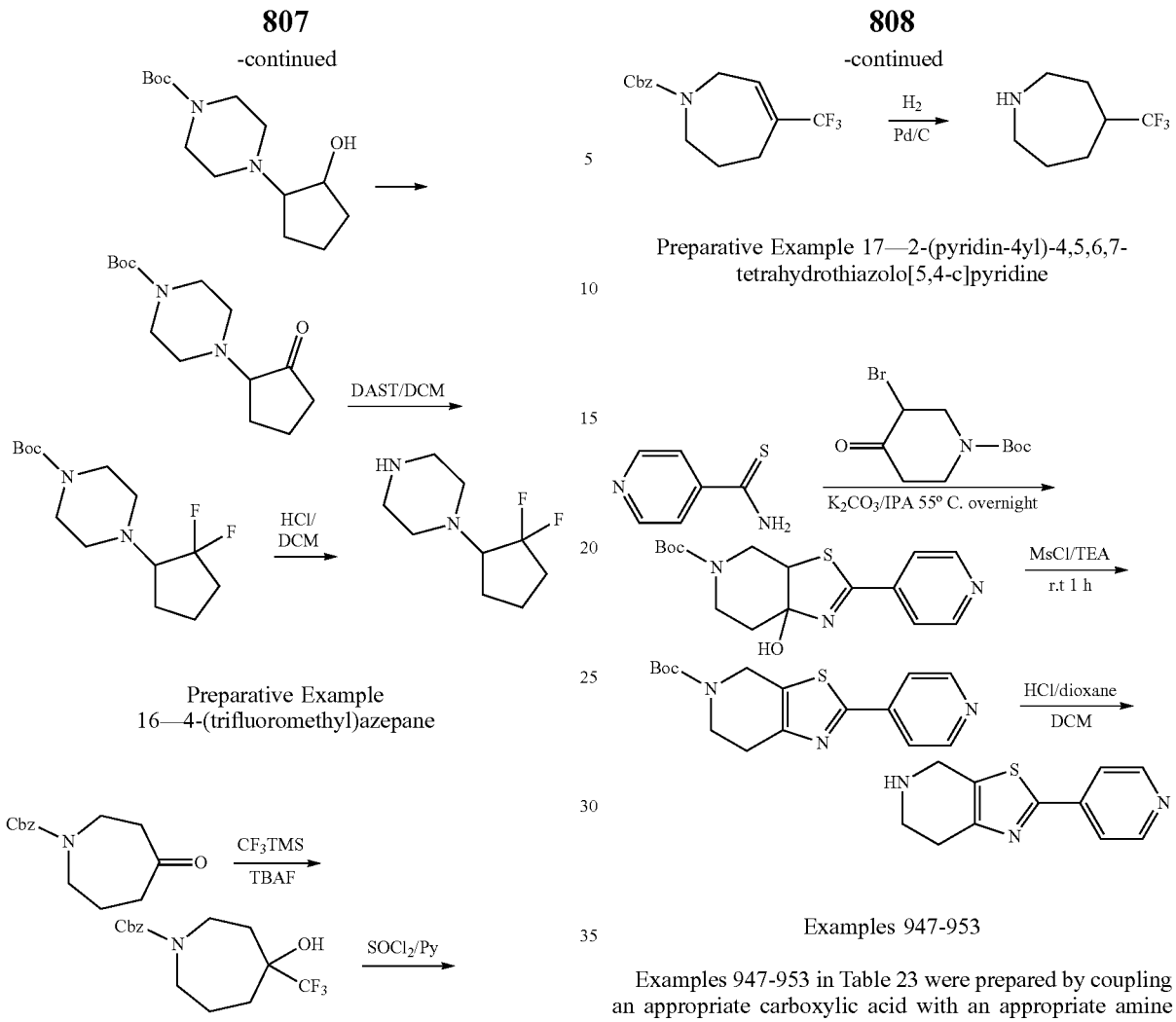

Preparative Example 16—4-(trifluoromethyl)azepane

Preparative Example 17—2-(pyridin-4yl)-4,5,6,7-tetrahydrothiazolo[5,4-c]pyridine Examples 947-953

Examples 947-953 in Table 23 were prepared by coupling an appropriate carboxylic acid with an appropriate amine using the specified reaction conditions.

TABLE 23

| Ex. No. | Ref. No. | LC-MS (Retention Time) | MS (M + H)+ | LC-MS Method | Reaction Conditions | Acid Scale |
|---|---|---|---|---|---|---|
| 947 | Q-1127 | 1.553 | 419.2 | A' | Acid (1 eqv.), amine (1.1 eqv.), HATU (1.2 eqv.), HOAt (1.2 eqv.), NMM (3 eqv.), THF, room temperature, 16 h | 2.1 g |
| 948 | Q-1133 | 1.749 | 394.1 | C' | Acid (1 eqv.), amine (1.1 eqv.), HATU (1 eqv.), HOAt (1 eqv.), TEA (4 eqv.), THF, room temperature, 2 h | 1 g |
| 949 | Q-1169 | 1.514 | 418.2 | F' | Acid (1 eqv.), amine (1.1 eqv.), HATU (1 eqv.), HOAt (1 eqv.), NMM (4 eqv.), THF, room temperature, 16 h | 820 mg |
| 950 | Q-1195 | 1.302 | 380.2 | J' | Acid (1 eqv.), amine (1eqv.), HATU (1.2 eqv.), HOAt (1.2 eqv.), NMM (7 eqv.), DMF, room temperature, 3 h | 1.9 g |
| 951 | Q-1204 | 1.579 | 419.1 | C' | Acid (1 eqv.), amine (1.1 eqv.), HATU (1.1 eqv.), HOAt (1 eqv.), NMM (2.6 eqv.), THF, 60 C., 16h | 700 mg |
| 952 | Q-1242 | 1.771 | 394.1 | C' | Acid (1 eqv.), amine (1.1 eqv.), HATU (1.1 eqv.), HOAt (1 eqv.), NMM (4 eqv.), THF, room temperature, 16 h | 1 g |

TABLE 23-continued

| Ex. No. | Ref. No. | LC-MS (Retention Time) | MS (M + H)+ | LC-MS Method | Reaction Conditions | Acid Scale |
|---|---|---|---|---|---|---|
| 953 | Q-1245 | 1.455 | 419.1 | C' | Acid (1 eqv.), amine (1.1 eqv.), HATU (1 eqv.), HOAt (1 eqv.), NMM (4 eqv.), THF, room temperature, 16 h | 800 mg |

Example 954—Assays of SPR Inhibitory Activity

Compounds were assayed for SPR inhibitory activity using a TR-FRET (homogeneous, time-resolved, fluorescence resonance energy transfer) assay according to the procedure described in Haruki et al., Science, 430:987 (2013). Terbium labelled SNAP-hSPR and SSZ (sulfasalazine) labelled SNAP-EGFP were used as the protein pair in this assay. Compounds were screened at different concentrations, and 1050 and Kd values calculated. SPR inhibitory activity of the compounds is provided in Table 24.

Compounds were assayed for SPR inhibitory activity using a SKN-N-BE (2) cellular assay according to the following procedure. SK-N-BE (2) cells were seeded in sterile, 96-well plates and incubated for 12-24 hours at 37° C. with 5% $CO_2$ supply. Media was removed and fresh DMEM/F-12 media (containing Glutamine & Pen/Strep but no FBS) was added. Compounds (at different concentrations) were added to different wells. The plates were then incubated for 6-48 hours at 37° C. with 5% $CO_2$ supply. Plates were then centrifuged and the supernatant was removed. The plates were then optionally washed once with PBS. They were then sealed and stored at −80° C. or immediately used in the next step. The cells were lysed and the levels of BH4 were assessed by LC-MS. SPR inhibitory activity of the compounds is provided in Table 24.

Compounds were assayed for inhibition of BH4 production using human peripheral blood mononuclear cells (PBMCs) according to the following procedure. PBMCs were either purchased or isolated from fresh human blood and used either as a fresh preparation or frozen for later use. The assay system was prepared by pre-treating the assay plates overnight with a solution containing anti-human CD3 antibody. Human PBMCs were suspended in assay medium and plated into the assay plates at a density of $1-4\times10^5$ cells per well. The desired concentration of the test compound was added to each well. A solution of human anti-CD28 antibody was also added to each well. Plates are incubated for 12-48 hours at 37° C. and 5% $CO_2$. Assay plates were centrifuged for 5-15 minutes at 1-3000 RMP and supernatants were removed. The cells were lysed, sealed and used directly or frozen at −80° C. LC-MS was used to quantify the amount of inhibition of BH4 production and is provided in Table 24.

TABLE 24

| Compound | hTR-FRET IC50 (µM) | SK-N-BE(2) IC50 (µM) | hPBMC IC50 (µM) | TR FRET Kd (nM) |
|---|---|---|---|---|
| Q-0001 | 0.02 | 2.7 | | |
| Q-0002 | 0.03 | | | |
| Q-0003 | | | | 14 |
| Q-0004 | 0.07 | | | |
| Q-0005 | | | | 33 |
| Q-0006 | | | | 41 |
| Q-0007 | 0.10 | | | |
| Q-0008 | | | | 48 |
| Q-0009 | 0.3 | 22 | | |
| Q-0010 | | | | 72 |
| Q-0011 | | | | 77 |
| Q-0012 | | | | 81 |
| Q-0013 | | | | 88 |
| Q-0014 | | | | 88 |
| Q-0015 | | | | 100 |
| Q-0016 | | | | 101 |
| Q-0017 | | | | 118 |
| Q-0018 | | | | 125 |
| Q-0019 | | | | 129 |
| Q-0020 | | | | 129 |
| Q-0021 | | | | 133 |
| Q-0022 | | | | 139 |
| Q-0023 | | | | 141 |
| Q-0024 | | | | 153 |
| Q-0025 | | | | 268 |
| Q-0026 | | | | 295 |
| Q-0027 | | | | 326 |
| Q-0028 | | | | 364 |
| Q-0029 | | | | 406 |
| Q-0030 | | | | 484 |
| Q-0031 | | | | 495 |
| Q-0055 | | | | 7 |
| Q-0214 | | | | 1123 |
| Q-0248 | 0.6 | | | 575 |
| Q-0279 | 0.007 | 1.0 | 2.2 | |
| Q-0280 | 0.06 | 16 | | |
| Q-0281 | 0.06 | 9.0 | | |
| Q-0282 | 0.03 | 4.4 | | |
| Q-0283 | 1.5 | | | |
| Q-0284 | 2.9 | | | |
| Q-0285 | 40 | | | |
| Q-0286 | 0.01 | | | |
| Q-0287 | 0.02 | | | |
| Q-0290 | 2.0 | | | |
| Q-0291 | 2.7 | | | |
| Q-0292 | 40 | | | |
| Q-0298 | 0.02 | 1.5 | | |
| Q-0299 | 0.005 | 1.2 | | |
| Q-0300 | 0.009 | 5.0 | | |
| Q-0301 | 0.2 | | | |
| Q-0302 | 0.009 | 1.2 | | |
| Q-0303 | 0.007 | 0.9 | | |
| Q-0304 | 0.04 | 67 | | |
| Q-0305 | 0.03 | 4.6 | | |
| Q-0306 | 25 | | | |
| Q-0307 | 0.009 | 4.2 | | |
| Q-0308 | 0.02 | 2.0 | | |
| Q-0310 | 0.06 | 12 | | |
| Q-0311 | 0.04 | 11 | | |
| Q-0312 | 0.02 | 10 | | |
| Q-0313 | 0.006 | 1.5 | | |
| Q-0314 | 0.02 | 5.8 | | |
| Q-0316 | 0.3 | | | |
| Q-0317 | 0.06 | 20 | | |
| Q-0318 | 0.006 | 2.1 | | |
| Q-0319 | 0.01 | 2.2 | | |
| Q-0320 | 1.3 | | | |
| Q-0321 | 0.9 | | | |
| Q-0322 | 0.2 | | | |
| Q-0323 | 0.3 | 35 | | |

TABLE 24-continued

| Compound | hTR-FRET IC50 (μM) | SK-N-BE(2) IC50 (μM) | hPBMC IC50 (μM) | TR FRET Kd (nM) |
|---|---|---|---|---|
| Q-0327 | 0.007 | 12 | | |
| Q-0328 | 0.01 | 53 | | |
| Q-0329 | 0.01 | 3.5 | | |
| Q-0330 | 0.02 | 6.1 | | |
| Q-0331 | 0.08 | 15 | | |
| Q-0332 | 0.01 | 2.5 | | |
| Q-0333 | 0.02 | 12 | | |
| Q-0334 | 0.08 | 49 | | |
| Q-0339 | 0.009 | 1.5 | | |
| Q-0340 | 0.007 | 1.1 | | |
| Q-0341 | 0.005 | 1.8 | | |
| Q-0342 | 0.01 | 2.4 | | |
| Q-0343 | 0.1 | 40 | | |
| Q-0344 | 0.07 | 23 | | |
| Q-0345 | 0.01 | 78 | | |
| Q-0346 | 0.008 | 5.3 | | |
| Q-0347 | 0.01 | 7.5 | | |
| Q-0348 | 0.01 | 6.4 | | |
| Q-0349 | 0.03 | 57 | | |
| Q-0350 | 0.02 | 11 | | |
| Q-0351 | 0.01 | 4.6 | | |
| Q-0352 | 0.02 | 13 | | |
| Q-0353 | 0.05 | 15 | | |
| Q-0354 | 0.002 | 0.1 | 0.38 | |
| Q-0358 | 0.1 | 22 | | |
| Q-0359 | 0.003 | 1.1 | | |
| Q-0361 | 0.01 | 0.6 | | |
| Q-0362 | 0.02 | 2.9 | | |
| Q-0363 | 0.03 | 5.8 | | |
| Q-0364 | 0.07 | 16 | | |
| Q-0365 | 0.05 | 12 | | |
| Q-0366 | 0.4 | 128 | | |
| Q-0367 | 0.07 | 11 | | |
| Q-0368 | 0.01 | 2.9 | | |
| Q-0369 | 0.2 | 28 | | |
| Q-0370 | 0.1 | 22 | | |
| Q-0371 | 0.07 | 14 | | |
| Q-0372 | 0.005 | 0.3 | | |
| Q-0373 | 0.02 | 1.5 | | |
| Q-0374 | 0.009 | 1.2 | | |
| Q-0375 | 0.02 | 2.5 | | |
| Q-0376 | 0.03 | 8.2 | | |
| Q-0377 | 0.04 | 6.3 | | |
| Q-0378 | 0.03 | 4.1 | 0.74 | |
| Q-0379 | 0.002 | 0.084 | 0.28 | |
| Q-0380 | 0.007 | 2.7 | | |
| Q-0381 | 0.01 | 2.1 | | |
| Q-0382 | 0.003 | 0.1 | | |
| Q-0383 | 0.3 | 69 | | |
| Q-0384 | 14 | | | |
| Q-0385 | 0.03 | 3.8 | | |
| Q-0387 | 0.01 | 3.7 | | |
| Q-0388 | 0.1 | 36 | | |
| Q-0389 | 0.02 | 5.6 | | |
| Q-0390 | 0.02 | 12 | | |
| Q-0393 | 0.006 | 0.8 | | |
| Q-0394 | 1.5 | | | |
| Q-0395 | 0.02 | 0.5 | | |
| Q-0396 | 0.002 | 0.061 | | |
| Q-0397 | 0.02 | 2.3 | | |
| Q-0398 | 0.01 | 0.072 | | |
| Q-0399 | 0.003 | 0.024 | | |
| Q-0400 | 0.004 | 0.2 | | |
| Q-0401 | 0.03 | 0.4 | | |
| Q-0402 | 0.01 | 0.041 | | |
| Q-0403 | 0.009 | 1.1 | | |
| Q-0404 | 0.04 | 4.3 | | |
| Q-0405 | 0.01 | 1.5 | | |
| Q-0406 | 0.05 | 2.0 | | |
| Q-0407 | 1.7 | | | |
| Q-0408 | 0.01 | 0.075 | | |
| Q-0409 | 0.2 | 25 | | |
| Q-0410 | 0.002 | 0.2 | | |
| Q-0411 | 0.009 | 2.7 | | |
| Q-0412 | 0.009 | 0.5 | | |
| Q-0413 | 2.2 | | | |
| Q-0414 | 0.006 | 0.3 | | |
| Q-0415 | 0.03 | 1.2 | | |
| Q-0416 | 0.02 | 2.8 | | |
| Q-0417 | 0.004 | 0.9 | | |
| Q-0418 | 0.002 | 0.05 | 0.032 | |
| Q-0419 | 0.005 | 0.7 | | |
| Q-0420 | 0.007 | | | |
| Q-0421 | 0.003 | 0.7 | | |
| Q-0422 | 0.003 | 0.2 | | |
| Q-0423 | 0.005 | 0.1 | 0.41 | |
| Q-0424 | 0.004 | 1.1 | | |
| Q-0425 | 0.03 | 2.1 | | |
| Q-0426 | 0.1 | 16 | | |
| Q-0427 | 0.009 | 3.1 | 1.1 | |
| Q-0428 | 0.003 | 0.019 | | |
| Q-0429 | 0.1 | 49 | | |
| Q-0431 | 0.003 | 0.5 | | |
| Q-0432 | 0.04 | 6.5 | | |
| Q-0433 | 0.2 | 58 | | |
| Q-0434 | 0.005 | 0.2 | | |
| Q-0435 | 0.02 | 1.2 | | |
| Q-0436 | 4.6 | | | |
| Q-0437 | 5.0 | | | |
| Q-0438 | 0.10 | 35 | | |
| Q-0439 | 0.001 | 0.096 | | |
| Q-0440 | 0.009 | 1.4 | | |
| Q-0441 | 0.1 | 31 | | |
| Q-0442 | 0.004 | 0.2 | | |
| Q-0443 | 0.009 | 3.9 | | |
| Q-0444 | 0.01 | 2.7 | | |
| Q-0445 | 0.01 | 0.9 | | |
| Q-0446 | 0.007 | 0.096 | | |
| Q-0447 | 0.4 | | | |
| Q-0448 | 1.5 | | | |
| Q-0449 | 0.003 | 0.078 | | |
| Q-0450 | 0.005 | 0.3 | | |
| Q-0451 | 0.002 | 0.019 | 0.013 | |
| Q-0452 | 0.8 | | | |
| Q-0453 | 0.006 | 1.6 | 1.3 | |
| Q-0454 | 0.3 | | | |
| Q-0455 | 16 | | | |
| Q-0456 | 0.008 | 0.5 | | |
| Q-0457 | 0.1 | | | |
| Q-0458 | 0.006 | 0.4 | | |
| Q-0459 | 0.002 | 0.059 | | |
| Q-0460 | 0.003 | 0.6 | | |
| Q-0461 | 0.003 | 0.4 | | |
| Q-0462 | 0.005 | 0.094 | | |
| Q-0463 | 0.004 | 0.3 | | |
| Q-0464 | 0.003 | 0.3 | | |
| Q-0465 | 0.3 | 150 | | |
| Q-0466 | 0.001 | 0.059 | | |
| Q-0467 | 0.002 | 0.082 | 0.1 | |
| Q-0468 | 0.007 | 0.2 | | |
| Q-0469 | 0.004 | 0.037 | | |
| Q-0470 | 0.005 | 1.0 | | |
| Q-0471 | 0.08 | 16 | | |
| Q-0472 | 0.2 | 17 | | |
| Q-0473 | 0.006 | 0.092 | | |
| Q-0474 | 0.007 | 0.6 | | |
| Q-0475 | 0.005 | 0.3 | | |
| Q-0476 | 0.003 | 0.056 | | |
| Q-0477 | 0.005 | 0.091 | | |
| Q-0478 | 0.006 | 1.4 | | |
| Q-0479 | 0.006 | 0.1 | | |
| Q-0480 | 0.009 | 0.3 | | |
| Q-0481 | 0.03 | 95 | | |
| Q-0482 | 0.008 | 1.0 | | |
| Q-0483 | 0.004 | 0.049 | | |
| Q-0485 | 0.009 | 0.062 | | |
| Q-0486 | 0.006 | 0.1 | | |
| Q-0487 | 0.003 | 0.6 | | |
| Q-0488 | 0.02 | 1.2 | | |
| Q-0489 | 0.008 | 0.053 | | |
| Q-0490 | 0.007 | 0.1 | | |
| Q-0491 | 0.02 | 0.037 | | |

TABLE 24-continued

| Compound | hTR-FRET IC50 (μM) | SK-N-BE(2) IC50 (μM) | hPBMC IC50 (μM) | TR FRET Kd (nM) |
|---|---|---|---|---|
| Q-0492 | 0.008 | 0.2 | | |
| Q-0493 | 0.03 | 0.029 | | |
| Q-0494 | 0.006 | 0.3 | | |
| Q-0495 | 0.005 | 0.051 | | |
| Q-0496 | 0.007 | 0.4 | | |
| Q-0497 | 0.009 | 0.4 | | |
| Q-0498 | 0.02 | 0.03 | | |
| Q-0499 | 0.02 | 0.044 | | |
| Q-0500 | 0.03 | 0.097 | | |
| Q-0501 | 0.009 | 0.2 | | |
| Q-0502 | 0.02 | 0.4 | | |
| Q-0503 | 4.0 | | | |
| Q-0504 | 0.004 | 0.058 | | |
| Q-0505 | 0.004 | 0.1 | | |
| Q-0506 | 0.003 | 0.2 | | |
| Q-0507 | 0.01 | 0.2 | | |
| Q-0508 | 0.03 | 2.0 | | |
| Q-0509 | 0.003 | 0.068 | | |
| Q-0510 | 0.005 | 0.1 | | |
| Q-0511 | 0.003 | 0.3 | | |
| Q-0513 | 0.01 | 0.047 | | |
| Q-0514 | 0.007 | 0.057 | | |
| Q-0515 | 0.04 | 5.3 | | |
| Q-0517 | 0.002 | 0.1 | | |
| Q-0518 | 0.003 | 0.5 | 0.032 | |
| Q-0519 | 0.003 | 0.053 | 0.12 | |
| Q-0520 | 0.003 | 0.2 | | |
| Q-0521 | 0.008 | 0.1 | | |
| Q-0522 | 0.3 | 10 | | |
| Q-0523 | 0.02 | 0.1 | | |
| Q-0524 | 0.004 | 1.1 | | |
| Q-0525 | 0.001 | 0.019 | 0.024 | |
| Q-0526 | 0.003 | 0.028 | | |
| Q-0527 | 0.03 | 0.045 | | |
| Q-0528 | 0.07 | 0.8 | | |
| Q-0529 | 0.01 | 0.1 | | |
| Q-0530 | 0.03 | 1.8 | | |
| Q-0531 | 0.004 | 0.062 | | |
| Q-0532 | 0.02 | 0.044 | | |
| Q-0533 | 0.002 | 0.069 | | |
| Q-0534 | 0.003 | 0.1 | | |
| Q-0535 | 0.004 | 0.4 | | |
| Q-0536 | 0.007 | 0.059 | | |
| Q-0537 | 0.04 | 0.2 | | |
| Q-0540 | 0.3 | | | |
| Q-0541 | 0.2 | | | |
| Q-0542 | 0.1 | | | |
| Q-0543 | 0.003 | 0.4 | | |
| Q-0544 | 0.03 | | | |
| Q-0545 | 0.002 | 0.041 | | |
| Q-0546 | 0.009 | 0.084 | | |
| Q-0547 | 2.3 | 10 | | |
| Q-0548 | 0.02 | 2.1 | | |
| Q-0549 | 0.004 | 0.4 | | |
| Q-0550 | 0.002 | 0.1 | | |
| Q-0551 | 0.006 | 0.5 | | |
| Q-0552 | 0.007 | 0.038 | | |
| Q-0553 | 0.006 | 0.2 | | |
| Q-0555 | 0.02 | 0.7 | | |
| Q-0556 | 0.007 | 0.6 | | |
| Q-0557 | 0.008 | 0.6 | | |
| Q-0558 | 5.0 | 10 | | |
| Q-0559 | 0.007 | 0.038 | | |
| Q-0560 | 0.003 | 0.012 | | |
| Q-0561 | 0.004 | 0.011 | | |
| Q-0562 | 0.004 | 0.2 | | |
| Q-0563 | 0.005 | 0.3 | | |
| Q-0564 | 0.2 | 4.0 | | |
| Q-0565 | 0.006 | 0.011 | | |
| Q-0566 | 5.0 | 10 | | |
| Q-0567 | 0.003 | 0.02 | | |
| Q-0568 | 0.006 | 0.2 | | |
| Q-0569 | 0.01 | 0.3 | | |
| Q-0570 | 0.003 | 0.023 | | |
| Q-0571 | 0.003 | 0.073 | 0.067 | |
| Q-0572 | 0.002 | 0.036 | 0.024 | |
| Q-0573 | 0.003 | 0.035 | | |
| Q-0574 | 0.006 | 0.047 | | |
| Q-0575 | 0.003 | 0.2 | | |
| Q-0576 | 0.006 | 0.1 | | |
| Q-0577 | 0.04 | 2.1 | | |
| Q-0578 | 0.008 | 0.7 | | |
| Q-0579 | 0.005 | 0.1 | | |
| Q-0580 | 0.003 | 0.022 | | |
| Q-0582 | 0.02 | 1.0 | | |
| Q-0583 | 0.1 | 3.7 | | |
| Q-0584 | 0.2 | 10 | | |
| Q-0585 | 0.006 | 0.033 | | |
| Q-0586 | 0.002 | 0.2 | 0.13 | |
| Q-0587 | 0.01 | 0.021 | | |
| Q-0588 | 0.07 | 4.7 | | |
| Q-0589 | 0.06 | 1.7 | | |
| Q-0590 | 0.003 | 0.015 | | |
| Q-0591 | 0.003 | 0.1 | 0.045 | |
| Q-0592 | 0.02 | 0.076 | | |
| Q-0593 | 0.2 | 7.4 | | |
| Q-0594 | 0.3 | 3.6 | | |
| Q-0595 | 0.07 | 4.4 | | |
| Q-0596 | 0.004 | 0.016 | | |
| Q-0597 | 0.003 | 0.053 | | |
| Q-0598 | 0.004 | 0.01 | | |
| Q-0599 | 0.002 | 0.012 | | |
| Q-0600 | 0.001 | 0.057 | | |
| Q-0601 | 0.005 | 0.1 | | |
| Q-0602 | 0.02 | 1.2 | | |
| Q-0603 | 0.006 | 0.1 | | |
| Q-0604 | 0.007 | 0.072 | | |
| Q-0605 | 0.2 | 10 | | |
| Q-0606 | 0.002 | 0.051 | | |
| Q-0607 | 0.005 | 0.087 | | |
| Q-0608 | 0.002 | 0.056 | | |
| Q-0609 | 0.001 | 0.084 | | |
| Q-0610 | 0.01 | 10 | | |
| Q-0611 | 0.004 | 0.029 | | |
| Q-0612 | 0.01 | 2.6 | | |
| Q-0614 | 0.01 | 1.6 | | |
| Q-0615 | 0.003 | 0.019 | | |
| Q-0616 | 0.002 | 0.1 | | |
| Q-0617 | 0.02 | 3.0 | | |
| Q-0618 | 0.001 | 0.025 | | |
| Q-0619 | 0.003 | 0.3 | | |
| Q-0620 | 0.001 | 0.1 | | |
| Q-0621 | 0.02 | 5.2 | | |
| Q-0622 | 0.001 | 0.058 | | |
| Q-0623 | 0.001 | 0.078 | | |
| Q-0624 | 0.002 | 0.032 | | |
| Q-0626 | 0.001 | 0.014 | | |
| Q-0627 | 0.009 | 10 | | |
| Q-0630 | 0.009 | 10 | | |
| Q-0632 | 0.004 | 7.3 | | |
| Q-0633 | 0.005 | 0.4 | | |
| Q-0634 | 0.003 | 0.7 | | |
| Q-0635 | 0.002 | 0.1 | 0.054 | |
| Q-0681 | 0.001 | 0.2 | | |
| Q-0690 | 0.002 | 0.2 | 0.072 | |
| Q-0691 | 0.002 | 0.091 | | |
| Q-0693 | 0.003 | 0.8 | 0.45 | |
| Q-0696 | 0.004 | 0.4 | | |
| Q-0697 | 0.004 | 0.2 | | |
| Q-0698 | 0.001 | 0.071 | | |
| Q-0700 | 0.002 | 0.1 | | |
| Q-0701 | 0.002 | 0.082 | | |
| Q-0702 | 0.002 | 0.032 | | |
| Q-0703 | 0.004 | 0.6 | 0.19 | |
| Q-0704 | 0.002 | 0.2 | | |
| Q-0705 | 0.002 | 0.043 | | |
| Q-0706 | 0.002 | 0.03 | | |
| Q-0707 | 0.005 | 0.3 | | |
| Q-0708 | 0.001 | 0.097 | | |
| Q-0709 | 0.001 | 0.028 | | |
| Q-0710 | 0.002 | 0.2 | | |
| Q-0711 | 0.002 | 0.086 | | |

TABLE 24-continued

| Compound | hTR-FRET IC50 (μM) | SK-N-BE(2) IC50 (μM) | hPBMC IC50 (μM) | TR FRET Kd (nM) |
|---|---|---|---|---|
| Q-0712 | 0.002 | 0.3 | | |
| Q-0713 | 0.001 | 0.2 | | |
| Q-0714 | 0.03 | 8.1 | | |
| Q-0715 | 0.002 | 0.097 | | |
| Q-0716 | 0.002 | 0.4 | | |
| Q-0718 | 0.004 | 0.2 | | |
| Q-0719 | 0.002 | 0.2 | | |
| Q-0720 | 0.001 | 0.3 | | |
| Q-0721 | 0.001 | 0.035 | 0.026 | |
| Q-0722 | 0.02 | 3.3 | | |
| Q-0723 | 0.003 | 0.2 | | |
| Q-0724 | 0.002 | 0.2 | | |
| Q-0725 | 0.001 | 0.1 | | |
| Q-0726 | 0.001 | 0.074 | | |
| Q-0727 | 0.001 | 0.081 | | |
| Q-0730 | 0.001 | 0.2 | | |
| Q-0731 | 0.002 | 0.053 | | |
| Q-0732 | 0.001 | 0.1 | | |
| Q-0734 | 0.004 | 0.3 | | |
| Q-0735 | 0.003 | 0.095 | | |
| Q-0736 | 0.002 | 0.2 | | |
| Q-0737 | 0.005 | 0.2 | 0.037 | |
| Q-0738 | 0.001 | 0.1 | | |
| Q-0739 | 0.002 | 0.3 | | |
| Q-0741 | 0.004 | 0.4 | | |
| Q-0743 | 0.004 | 0.4 | | |
| Q-0744 | 0.003 | 0.1 | | |
| Q-0745 | 0.004 | 0.2 | | |
| Q-0746 | 0.004 | 0.6 | | |
| Q-0747 | 0.008 | 0.8 | | |
| Q-0748 | 0.004 | 0.9 | | |
| Q-0749 | 0.003 | 0.05 | | |
| Q-0750 | 0.003 | 0.5 | 0.18 | |
| Q-0751 | 0.003 | 0.2 | | |
| Q-0752 | 0.004 | 0.5 | | |
| Q-0753 | 0.002 | 0.2 | | |
| Q-0754 | 0.009 | 0.1 | | |
| Q-0755 | 0.004 | 0.5 | | |
| Q-0756 | 0.004 | 0.8 | | |
| Q-0757 | 0.002 | 0.2 | | |
| Q-0758 | 0.002 | 0.09 | | |
| Q-0759 | 0.001 | 0.2 | | |
| Q-0760 | 0.001 | 0.4 | 0.075 | |
| Q-0761 | 0.002 | 0.2 | 0.14 | |
| Q-0762 | 0.002 | 0.2 | | |
| Q-0764 | 0.002 | 0.3 | 0.10 | |
| Q-0765 | 0.005 | 0.3 | | |
| Q-0768 | 0.002 | 0.2 | 0.045 | |
| Q-0770 | 0.002 | 0.2 | | |
| Q-0771 | 0.001 | 0.2 | | |
| Q-0772 | 0.001 | 0.2 | 0.072 | |
| Q-0773 | 0.006 | 1.7 | | |
| Q-0774 | 0.2 | 10 | | |
| Q-0775 | 0.002 | 1.0 | | |
| Q-0777 | 0.001 | 0.3 | 0.055 | |
| Q-0779 | 0.02 | 10 | | |
| Q-0780 | 0.001 | 0.2 | | |
| Q-0781 | 0.001 | 0.2 | | |
| Q-0782 | 0.001 | 0.1 | 0.038 | |
| Q-0783 | 0.002 | 0.3 | | |
| Q-0784 | 0.001 | 0.3 | 0.12 | |
| Q-0785 | 0.001 | 0.2 | | |
| Q-0788 | 0.01 | 3.6 | | |
| Q-0789 | 0.008 | 2.5 | 0.44 | |
| Q-0790 | 0.007 | 1.4 | | |
| Q-0791 | 0.002 | 0.6 | | |
| Q-0792 | 0.006 | 2.1 | | |
| Q-0793 | 0.003 | 1.0 | | |
| Q-0794 | 0.01 | 3.5 | 0.41 | |
| Q-0795 | 0.002 | 0.5 | | |
| Q-0796 | 0.001 | 0.2 | | |
| Q-0797 | 0.001 | 0.1 | 0.027 | |
| Q-0798 | 0.002 | 0.3 | | |
| Q-0799 | 0.001 | 0.3 | | |
| Q-0800 | 0.002 | 0.6 | 0.047 | |
| Q-0802 | 0.001 | 0.067 | | |
| Q-0803 | 0.001 | 0.2 | | |
| Q-0804 | 0.001 | 0.3 | 0.094 | |
| Q-0805 | 0.004 | 2.3 | | |
| Q-0806 | 0.003 | 1.2 | | |
| Q-0807 | 0.002 | 0.4 | | |
| Q-0808 | 0.001 | 0.2 | | |
| Q-0809 | 0.006 | 0.9 | | |
| Q-0812 | 0.003 | 1.0 | 0.15 | |
| Q-0813 | 0.001 | 0.1 | 0.065 | |
| Q-0814 | 0.002 | 0.4 | | |
| Q-0815 | 0.001 | 0.1 | 0.072 | |
| Q-0816 | 0.001 | 0.6 | 0.17 | |
| Q-0817 | 0.001 | 0.2 | 0.044 | |
| Q-0818 | 0.002 | 0.9 | | |
| Q-0819 | 0.001 | 0.2 | | |
| Q-0820 | 0.001 | 0.04 | | |
| Q-0821 | 0.001 | 0.1 | 0.051 | |
| Q-0822 | 0.002 | 0.4 | 0.13 | |
| Q-0823 | 0.001 | 0.066 | | |
| Q-0824 | 0.005 | 1.8 | | |
| Q-0825 | 0.002 | 0.4 | 0.15 | |
| Q-0826 | 0.001 | 0.1 | | |
| Q-0827 | 0.002 | 0.065 | | |
| Q-0828 | 0.004 | 0.05 | | |
| Q-0829 | 0.001 | 0.08 | | |
| Q-0830 | 0.001 | 0.041 | | |
| Q-0831 | 0.002 | 0.4 | | |
| Q-0832 | 0.001 | 0.2 | | |
| Q-0833 | 0.006 | 0.2 | | |
| Q-0835 | 0.002 | 0.1 | 0.039 | |
| Q-0836 | 0.005 | 0.3 | 0.052 | |
| Q-0837 | 0.001 | 0.2 | 0.063 | |
| Q-0839 | 0.008 | 1.5 | | |
| Q-0840 | 0.003 | 0.2 | | |
| Q-0842 | 0.002 | 0.7 | | |
| Q-0843 | 0.001 | 0.2 | | |
| Q-0844 | 0.001 | 0.2 | | |
| Q-0845 | 0.003 | 0.4 | | |
| Q-0846 | 0.002 | 0.2 | | |
| Q-0847 | 0.02 | 8.8 | | |
| Q-0848 | 0.002 | 10 | | |
| Q-0849 | 0.001 | 0.3 | 0.044 | |
| Q-0850 | 0.001 | 0.3 | 0.074 | |
| Q-0851 | 0.002 | 0.5 | 0.13 | |
| Q-0852 | 0.002 | 0.8 | | |
| Q-0853 | 0.03 | 10 | | |
| Q-0854 | 0.003 | 0.2 | | |
| Q-0855 | 0.001 | 0.1 | | |
| Q-0856 | 0.004 | 1.1 | | |
| Q-0857 | 0.003 | 0.8 | | |
| Q-0858 | | 0.044 | | |
| Q-0859 | 0.02 | 8.3 | | |
| Q-0860 | | 1.0 | | |
| Q-0861 | | 0.4 | | |
| Q-0862 | | 10 | | |
| Q-0863 | | 0.6 | | |
| Q-0865 | | 0.1 | | |
| Q-0866 | | 6.7 | | |
| Q-0867 | 0.002 | 0.4 | 0.07 | |
| Q-0868 | | 10 | | |
| Q-0869 | | 0.1 | | |
| Q-0870 | | 0.3 | | |
| Q-0871 | | 4.0 | | |
| Q-0872 | | 10 | | |
| Q-0873 | | 10 | | |
| Q-0874 | | 1.1 | | |
| Q-0875 | | 0.076 | | |
| Q-0876 | | 0.088 | | |
| Q-0877 | | 0.2 | | |
| Q-0878 | | 0.8 | | |
| Q-0879 | | 10 | | |
| Q-0880 | | 0.087 | | |
| Q-0881 | | 2.3 | | |
| Q-0882 | | 0.2 | | |
| Q-0883 | | 1.3 | | |
| Q-0884 | | 0.2 | | |

TABLE 24-continued

| Compound | hTR-FRET IC50 (μM) | SK-N-BE(2) IC50 (μM) | hPBMC IC50 (μM) | TR FRET Kd (nM) |
|---|---|---|---|---|
| Q-0885 | | 0.4 | | |
| Q-0886 | | 5.4 | | |
| Q-0887 | 0.001 | 0.2 | 0.057 | |
| Q-0888 | 0.005 | 0.4 | 0.24 | |
| Q-0890 | | | | |
| Q-0891 | 0.004 | 0.9 | 0.24 | |
| Q-0892 | 0.002 | 0.4 | 0.076 | |
| Q-0893 | | 0.3 | | |
| Q-0894 | | 0.1 | | |
| Q-0895 | | 1.4 | | |
| Q-0896 | 0.001 | 0.3 | 0.049 | |
| Q-0897 | | 0.5 | | |
| Q-0899 | 0.001 | 0.3 | 0.048 | |
| Q-0900 | | 2.3 | | |
| Q-0901 | | 10 | | |
| Q-0902 | | 0.1 | | |
| Q-0905 | | 0.6 | | |
| Q-0906 | 0.003 | 0.8 | 0.19 | |
| Q-0907 | | 0.4 | | |
| Q-0908 | 0.001 | 0.3 | 0.13 | |
| Q-0909 | | 0.1 | | |
| Q-0910 | 0.002 | 0.5 | 0.074 | |
| Q-0911 | 0.002 | 0.4 | 0.11 | |
| Q-0912 | | 0.9 | | |
| Q-0913 | 0.002 | 0.5 | 0.087 | |
| Q-0914 | | 0.6 | | |
| Q-0915 | 0.002 | 0.5 | 0.092 | |
| Q-0916 | | 0.7 | | |
| Q-0917 | 0.003 | 0.7 | 0.10 | |
| Q-0918 | 0.002 | 0.6 | 0.12 | |
| Q-0919 | | 1.7 | | |
| Q-0920 | | 0.5 | | |
| Q-0921 | 0.002 | 0.4 | 0.047 | |
| Q-0922 | | 1.0 | | |
| Q-0923 | | 1.3 | | |
| Q-0924 | 0.002 | 0.2 | 0.051 | |
| Q-0925 | | 0.5 | | |
| Q-0926 | 0.001 | 0.2 | 0.045 | |
| Q-0927 | 0.001 | 0.2 | 0.081 | |
| Q-0928 | | 0.2 | | |
| Q-0929 | | 2.0 | | |
| Q-0930 | 0.001 | 0.3 | 0.058 | |
| Q-0931 | | 0.2 | | |
| Q-0932 | | 0.7 | | |
| Q-0933 | | 0.2 | | |
| Q-0934 | | 0.3 | | |
| Q-0935 | | 1.6 | | |
| Q-0936 | | 0.2 | | |
| Q-0937 | 0.004 | 0.8 | 0.13 | |
| Q-0938 | | 0.1 | | |
| Q-0939 | | 0.083 | | |
| Q-0940 | | 0.8 | | |
| Q-0941 | 0.001 | 0.3 | 0.013 | |
| Q-0942 | | 9.1 | | |
| Q-0943 | 0.002 | 0.018 | 0.038 | |
| Q-0944 | 0.001 | 0.028 | 0.036 | |
| Q-0945 | | 1.0 | | |
| Q-0946 | | 1.1 | | |
| Q-0947 | | 1.0 | | |
| Q-0948 | 0.001 | 0.1 | 0.053 | |
| Q-0949 | | 0.2 | | |
| Q-0950 | | 6.2 | | |
| Q-0951 | 0.002 | 0.4 | 0.045 | |
| Q-0952 | 0.001 | 0.3 | 0.083 | |
| Q-0953 | 0.001 | 0.058 | 0.021 | |
| Q-0954 | | 9.0 | | |
| Q-0955 | | 10 | | |
| Q-0956 | 0.001 | 0.086 | 0.014 | |
| Q-0957 | | 1.0 | | |
| Q-0958 | | 10 | | |
| Q-0959 | | 1.0 | | |
| Q-0960 | | 0.2 | | |
| Q-0961 | | 0.7 | | |
| Q-0962 | | 0.3 | | |
| Q-0963 | | 4.0 | | |
| Q-0964 | | 8.9 | | |
| Q-0965 | | 0.1 | | |
| Q-0966 | | 1.3 | | |
| Q-0967 | | 1.9 | | |
| Q-0968 | | 0.4 | | |
| Q-0969 | 0.001 | 0.2 | 0.16 | |
| Q-0970 | | 0.4 | | |
| Q-0971 | | 7.2 | | |
| Q-0972 | 0.001 | 0.065 | 0.014 | |
| Q-0973 | 0.001 | 0.7 | 0.08 | |
| Q-0974 | | 0.1 | | |
| Q-0975 | | 1.3 | | |
| Q-0976 | | 1.1 | | |
| Q-0977 | 0.001 | 0.5 | 0.086 | |
| Q-0978 | 0.001 | 0.081 | 0.059 | |
| Q-0979 | | 1.4 | | |
| Q-0980 | | 1.3 | | |
| Q-0981 | | 1.4 | | |
| Q-0982 | | 10 | | |
| Q-0983 | | 10 | | |
| Q-0984 | | 0.4 | | |
| Q-0985 | | 9.2 | | |
| Q-0986 | 0.002 | 0.7 | 0.11 | |
| Q-0987 | | 1.1 | | |
| Q-0988 | | 0.069 | | |
| Q-0989 | | 0.9 | | |
| Q-0990 | | 0.2 | | |
| Q-0991 | | 0.1 | | |
| Q-0992 | 0.003 | 0.8 | 0.098 | |
| Q-0993 | 0.003 | 1.1 | 0.16 | |
| Q-0994 | | 3.0 | | |
| Q-0995 | 0.002 | 0.6 | 0.18 | |
| Q-0996 | | 1.9 | | |
| Q-0997 | | 1.0 | | |
| Q-0998 | 0.001 | 0.3 | 0.092 | |
| Q-0999 | | 0.2 | | |
| Q-1000 | | 0.9 | | |
| Q-1001 | | 1.8 | | |
| Q-1002 | | 3.4 | | |
| Q-1003 | 0.001 | 0.1 | 0.051 | |
| Q-1004 | | 3.1 | | |
| Q-1005 | 0.001 | 0.3 | 0.1 | |
| Q-1006 | | 1.4 | | |
| Q-1007 | 0.001 | 0.5 | 0.12 | |
| Q-1008 | | 0.3 | | |
| Q-1009 | | 2.0 | | |
| Q-1010 | | 4.0 | | |
| Q-1011 | | 0.8 | | |
| Q-1012 | | 1.3 | | |
| Q-1013 | | 1.5 | | |
| Q-1014 | | 1.4 | | |
| Q-1015 | | 0.4 | | |
| Q-1016 | | 2.4 | | |
| Q-1017 | | 0.3 | | |
| Q-1018 | | 0.7 | | |
| Q-1019 | | 0.4 | | |
| Q-1020 | 0.002 | 0.3 | 0.20 | |
| Q-1021 | | 1.0 | | |
| Q-1022 | 0.002 | 0.1 | 0.041 | |
| Q-1023 | | 0.7 | | |
| Q-1024 | 0.001 | 0.3 | 0.056 | |
| Q-1025 | | 1.2 | | |
| Q-1026 | | 1.7 | | |
| Q-1027 | | 3.1 | | |
| Q-1028 | | 1.1 | | |
| Q-1029 | | 1.0 | | |
| Q-1030 | | 3.1 | | |
| Q-1031 | | 2.3 | | |
| Q-1032 | | 10 | | |
| Q-1033 | 0.008 | 0.4 | 0.26 | |
| Q-1034 | 0.002 | 0.2 | 0.16 | |
| Q-1035 | | 0.1 | | |
| Q-1036 | | 0.07 | | |
| Q-1037 | | 0.071 | | |
| Q-1038 | 0.002 | 0.3 | 0.34 | |
| Q-1039 | | 0.3 | | |
| Q-1040 | | 0.3 | | |

TABLE 24-continued

| Compound | hTR-FRET IC50 (µM) | SK-N-BE(2) IC50 (µM) | hPBMC IC50 (µM) | TR FRET Kd (nM) |
|---|---|---|---|---|
| Q-1041 | 0.001 | 0.046 | 0.028 | |
| Q-1042 | | 1.0 | | |
| Q-1043 | | 1.4 | | |
| Q-1044 | | 1.0 | | |
| Q-1045 | | 0.1 | | |
| Q-1046 | 0.001 | 0.1 | 0.083 | |
| Q-1047 | 0.001 | 0.2 | 0.066 | |
| Q-1048 | 0.001 | 0.2 | 0.05 | |
| Q-1049 | 0.002 | 0.072 | 0.025 | |
| Q-1050 | | 1.4 | | |
| Q-1051 | 0.001 | 0.053 | 0.027 | |
| Q-1052 | 0.001 | 0.044 | 0.083 | |
| Q-1053 | 0.001 | 0.2 | 0.23 | |
| Q-1054 | 0.001 | 0.028 | 0.06 | |
| Q-1055 | 0.001 | 0.7 | 0.16 | |
| Q-1056 | 0.003 | 0.016 | 0.055 | |
| Q-1057 | 0.001 | 0.1 | 0.067 | |
| Q-1058 | 0.002 | 0.093 | 0.15 | |
| Q-1059 | 0.002 | 1.3 | 2.1 | |
| Q-1060 | 0.002 | 0.2 | 0.22 | |
| Q-1061 | 0.003 | 0.4 | 0.21 | |
| Q-1062 | 0.001 | 0.1 | 0.097 | |
| Q-1063 | 0.002 | 0.055 | 0.12 | |
| Q-1064 | 0.002 | 0.2 | 0.22 | |
| Q-1065 | 0.001 | 0.058 | 0.074 | |
| Q-1066 | 0.001 | 0.3 | 0.082 | |
| Q-1067 | 0.002 | 0.1 | 0.16 | |
| Q-1070 | 0.002 | | 0.20 | |
| Q-1071 | 0.006 | | 0.032 | |
| Q-1072 | 0.002 | | 0.055 | |
| Q-1073 | 0.003 | | 0.055 | |
| Q-1074 | 0.001 | | 0.022 | |
| Q-1075 | 0.002 | | 0.017 | |
| Q-1076 | 0.001 | | 0.035 | |
| Q-1077 | 0.005 | | 0.16 | |
| Q-1078 | 0.005 | | 0.036 | |
| Q-1079 | 0.003 | | 0.074 | |
| Q-1080 | 0.002 | | 0.025 | |
| Q-1081 | 0.002 | | 0.13 | |
| Q-1082 | 0.004 | | 0.12 | |
| Q-1083 | 0.001 | | 0.068 | |
| Q-1084 | 0.002 | | 0.013 | |
| Q-1085 | 0.001 | | 0.063 | |
| Q-1086 | 0.001 | | 0.084 | |
| Q-1087 | 0.002 | | 0.029 | |
| Q-1088 | 0.004 | | 0.29 | |
| Q-1089 | 0.003 | | 0.35 | |
| Q-1090 | 0.001 | | | |
| Q-1091 | 0.002 | | 0.13 | |
| Q-1092 | 0.001 | | 0.33 | |
| Q-1093 | 0.001 | | 0.095 | |
| Q-1094 | 0.001 | | 0.099 | |
| Q-1095 | 0.001 | | 0.027 | |
| Q-1096 | 0.001 | | 0.018 | |
| Q-1097 | 0.001 | | 0.024 | |
| Q-1098 | 0.001 | | 0.21 | |
| Q-1099 | 0.001 | | 0.06 | |
| Q-1100 | 0.001 | | 0.031 | |
| Q-1101 | 0.001 | | 0.041 | |
| Q-1102 | 0.001 | | 0.058 | |
| Q-1103 | 0.001 | | 0.10 | |
| Q-1104 | 0.003 | | 0.11 | |
| Q-1105 | 0.001 | | 0.018 | |
| Q-1106 | 0.001 | | 0.093 | |
| Q-1107 | 0.001 | | 0.058 | |
| Q-1108 | 0.001 | | 0.05 | |
| Q-1109 | 0.001 | | 0.046 | |
| Q-1110 | 0.002 | | 0.043 | |
| Q-1111 | 0.001 | | 0.015 | |
| Q-1112 | 0.001 | | 0.037 | |
| Q-1113 | 0.001 | | 0.016 | |
| Q-1114 | 0.001 | | 0.024 | |
| Q-1115 | 0.001 | | 0.045 | |
| Q-1116 | 0.001 | | 0.076 | |
| Q-1117 | 0.001 | | 0.02 | |
| Q-1118 | 0.001 | | 0.11 | |
| Q-1119 | 0.002 | | 0.37 | |
| Q-1120 | 0.001 | | 0.097 | |
| Q-1121 | 0.001 | | 0.07 | |
| Q-1122 | 0.001 | | 0.025 | |
| Q-1123 | 0.001 | | 0.057 | |
| Q-1124 | 0.001 | | 0.035 | |
| Q-1125 | 0.006 | | 0.1 | |
| Q-1126 | 0.001 | | 0.048 | |
| Q-1127 | 0.001 | | 0.015 | |
| Q-1128 | 0.002 | | 0.048 | |
| Q-1129 | 0.002 | | 0.05 | |
| Q-1130 | 0.001 | | 0.057 | |
| Q-1131 | 0.001 | | 0.027 | |
| Q-1132 | 0.001 | | 0.04 | |
| Q-1133 | 0.002 | | 0.022 | |
| Q-1134 | 0.003 | | 0.025 | |
| Q-1135 | 0.01 | | 0.045 | |
| Q-1136 | 0.002 | | 0.014 | |
| Q-1137 | 0.003 | | 0.16 | |
| Q-1138 | 0.02 | | 0.36 | |
| Q-1139 | 0.02 | | 0.42 | |
| Q-1140 | 0.008 | | 0.23 | |
| Q-1141 | 0.001 | | 0.019 | |
| Q-1142 | 0.001 | | 0.075 | |
| Q-1143 | 0.003 | | 0.31 | |
| Q-1144 | 0.001 | | 0.07 | |
| Q-1145 | 0.003 | | 0.19 | |
| Q-1146 | 0.005 | | 0.38 | |
| Q-1147 | 0.007 | | 0.52 | |
| Q-1148 | 0.01 | | 0.54 | |
| Q-1149 | 0.005 | | 0.21 | |
| Q-1150 | 0.001 | | | |
| Q-1151 | 0.008 | | 0.31 | |
| Q-1152 | 0.008 | | 0.38 | |
| Q-1153 | 0.008 | | 0.63 | |
| Q-1154 | 0.005 | | 0.35 | |
| Q-1155 | 0.01 | | 0.27 | |
| Q-1156 | 0.006 | | 0.11 | |
| Q-1157 | 0.004 | | 0.49 | |
| Q-1158 | 0.002 | | 0.13 | |
| Q-1159 | 0.02 | | 0.60 | |
| Q-1160 | 0.003 | | 0.11 | |
| Q-1161 | 0.003 | | 0.31 | |
| Q-1162 | 0.001 | | 0.095 | |
| Q-1163 | 0.002 | | 0.068 | |
| Q-1164 | 0.001 | | 0.037 | |
| Q-1165 | 0.006 | | 0.19 | |
| Q-1166 | 0.005 | | 0.02 | |
| Q-1167 | 0.01 | | 0.081 | |
| Q-1168 | 0.003 | | 0.058 | |
| Q-1169 | 0.001 | | 0.077 | |
| Q-1170 | 0.001 | | 0.16 | |
| Q-1171 | 0.01 | | 0.14 | |
| Q-1172 | 0.003 | | 0.18 | |
| Q-1173 | 0.02 | | 0.29 | |
| Q-1174 | 0.001 | | 0.022 | |
| Q-1175 | 0.02 | | 0.45 | |
| Q-1176 | 0.009 | | 0.28 | |
| Q-1177 | 0.009 | | 1.3 | |
| Q-1178 | 0.009 | | 2.6 | |
| Q-1179 | 0.002 | | 0.11 | |
| Q-1180 | 0.002 | | 0.047 | |
| Q-1181 | 0.002 | | 0.011 | |
| Q-1182 | 0.001 | | 0.048 | |
| Q-1183 | 0.004 | | 0.11 | |
| Q-1184 | 0.002 | | 0.037 | |
| Q-1185 | 0.001 | | 0.11 | |
| Q-1186 | 0.001 | | 0.036 | |
| Q-1187 | 0.004 | | 0.19 | |
| Q-1188 | 0.006 | | 0.29 | |
| Q-1189 | | | | |
| Q-1190 | 0.01 | | 0.059 | |
| Q-1191 | 0.001 | | 0.02 | |
| Q-1192 | 0.001 | | 0.04 | |
| Q-1193 | 0.007 | | 0.16 | |
| Q-1194 | 0.002 | | 0.06 | |

TABLE 24-continued

| Compound | hTR-FRET IC50 (µM) | SK-N-BE(2) IC50 (µM) | hPBMC IC50 (µM) | TR FRET Kd (nM) |
|---|---|---|---|---|
| Q-1195 | 0.002 | | 0.047 | |
| Q-1196 | 0.003 | | 0.052 | |
| Q-1197 | 0.003 | | 0.026 | |
| Q-1198 | 0.001 | | 0.017 | |
| Q-1199 | 0.001 | | 0.029 | |
| Q-1200 | 0.001 | | 0.15 | |
| Q-1201 | 0.001 | | 0.069 | |
| Q-1202 | 0.005 | | 0.26 | |
| Q-1203 | 0.006 | | 0.18 | |
| Q-1204 | 0.001 | | 0.017 | |
| Q-1205 | 0.003 | | 0.035 | |
| Q-1206 | 0.001 | | 0.07 | |
| Q-1207 | 0.001 | | 0.029 | |
| Q-1208 | 0.001 | | 0.061 | |
| Q-1209 | 0.001 | | 0.92 | |
| Q-1210 | 0.002 | | 0.084 | |
| Q-1211 | 0.01 | | 0.16 | |
| Q-1212 | 0.001 | | 0.013 | |
| Q-1213 | 0.003 | | 0.89 | |
| Q-1214 | 0.006 | | 1.0 | |
| Q-1215 | 0.001 | | 0.017 | |
| Q-1216 | 0.001 | | 0.046 | |
| Q-1217 | 0.003 | | 0.27 | |
| Q-1218 | 0.003 | | 0.13 | |
| Q-1219 | 0.001 | | 0.079 | |
| Q-1220 | 0.001 | | 0.022 | |
| Q-1221 | 0.001 | | 0.037 | |
| Q-1222 | 0.001 | | 0.025 | |
| Q-1223 | 0.003 | | 0.024 | |
| Q-1224 | 0.009 | | 0.37 | |
| Q-1225 | 0.001 | | 0.029 | |
| Q-1226 | 0.007 | | 0.41 | |
| Q-1227 | 0.001 | | 0.014 | |
| Q-1228 | 0.001 | | 0.017 | |
| Q-1229 | 0.002 | | 0.1 | |
| Q-1230 | 0.01 | | 0.18 | |
| Q-1231 | 0.003 | | 0.062 | |
| Q-1232 | 0.001 | | 0.056 | |
| Q-1233 | 0.001 | | 0.023 | |
| Q-1234 | 0.002 | | 0.027 | |
| Q-1235 | 0.005 | | 0.018 | |
| Q-1236 | 0.006 | | 0.048 | |
| Q-1237 | 0.003 | | 0.70 | |
| Q-1238 | 0.002 | | 0.079 | |
| Q-1239 | 0.002 | | 0.027 | |
| Q-1240 | 0.001 | | 0.035 | |
| Q-1241 | 0.002 | | 0.02 | |
| Q-1242 | 0.005 | | 0.032 | |
| Q-1243 | 0.02 | | 0.051 | |
| Q-1244 | 0.001 | | 0.036 | |
| Q-1245 | 0.001 | | 0.026 | |
| Q-1246 | 0.004 | | 0.10 | |
| Q-1247 | 0.002 | | 0.15 | |
| Q-1249 | 0.002 | | 0.046 | |
| Q-1250 | 0.001 | | 0.024 | |
| Q-1251 | 0.05 | | | |
| Q-1254 | 0.1 | | 0.87 | |
| Q-1255 | 0.1 | | 0.58 | |
| Q-1256 | 0.03 | | 0.33 | |
| Q-1259 | 0.1 | | 0.36 | |
| Q-1260 | 0.03 | | 0.081 | |
| Q-1263 | 0.1 | | 0.37 | |
| Q-1266 | 0.2 | | | |
| Q-1269 | 0.005 | | 0.053 | |
| Q-1288 | 0.008 | | 0.60 | |
| Q-1289 | 0.002 | | 0.07 | |
| Q-1291 | 0.2 | | 2.4 | |
| Q-1292 | 5.0 | | | |
| Q-1295 | 2.4 | | | |
| Q-1296 | 0.6 | | | |
| Q-1301 | 0.01 | | 0.82 | |
| Q-1305 | 0.1 | | 1.2 | |
| Q-1306 | 0.5 | | | |
| Q-1311 | 5.0 | | | |
| Q-1313 | 5.0 | | | |
| Q-1320 | 0.02 | | | |
| Q-1322 | 0.4 | | | |
| Q-1341 | 5.0 | | | |
| Q-1343 | 0.07 | | | |
| Q-1344 | 0.009 | | 0.32 | |
| Q-1345 | 1.4 | | | |
| Q-1346 | 0.05 | | | |
| Q-1362 | 0.001 | | 0.043 | |
| Q-1365 | 1.0 | | | |
| Q-1483 | 0.03 | | | |
| Q-1535 | 0.001 | | 0.11 | |
| Q-1539 | 0.004 | | 0.78 | |
| Q-1558 | 0.002 | | 0.092 | |
| Q-1560 | 0.8 | | | |
| Q-1563 | 5.0 | | | |
| Q-1564 | 5.0 | | | |
| Q-1565 | 5.0 | | | |
| Q-1581 | 0.004 | | 0.17 | |
| Q-1591 | 0.003 | | 0.11 | |
| Q-1597 | 5.0 | | | |
| Q-1641 | 5.0 | | | |
| Q-1728 | 0.001 | | 0.086 | |
| Q-1794 | 0.002 | | 0.25 | |
| Q-1796 | 0.001 | | 0.26 | |
| Q-1797 | 0.001 | | 0.079 | |
| Q-1798 | 0.002 | | | |
| Q-1799 | 0.001 | | 0.10 | |
| Q-1800 | 0.002 | | | |
| Q-1801 | 0.002 | | | |
| Q-1804 | 0.002 | | | |
| Q-1805 | 0.001 | | 0.13 | |
| Q-1807 | 0.001 | | 0.11 | |
| Q-1814 | 0.002 | | | |
| Q-1815 | 0.002 | | | |
| Q-1818 | 0.001 | | 0.095 | |
| Q-1819 | 0.001 | | 0.091 | |
| Q-1820 | 0.001 | | 0.094 | |
| Q-1821 | 0.001 | | 0.13 | |
| Q-1822 | 0.001 | | 0.12 | |
| Q-1823 | 0.001 | | 0.11 | |
| Q-1824 | 0.003 | | | |
| Q-1825 | 0.002 | | | |
| Q-1826 | 0.002 | | | |
| Q-1827 | 0.001 | | | |
| Q-1829 | 0.002 | | | |
| Q-1830 | 0.002 | | | |
| Q-1831 | 0.003 | | | |
| Q-1832 | 0.003 | | | |
| Q-1833 | 0.001 | | | |
| Q-1834 | 0.001 | | | |
| Q-1835 | 0.004 | | | |
| Q-1836 | 0.001 | | 0.27 | |
| Q-1837 | 0.001 | | | |
| Q-1838 | 0.001 | | 0.17 | |
| Q-1839 | 0.002 | | | |
| Q-1840 | 0.003 | | | |
| Q-1841 | 0.001 | | 0.087 | |
| Q-1842 | 0.001 | | 0.15 | |
| Q-1845 | 0.002 | | | |
| Q-1846 | 0.001 | | 0.17 | |
| Q-1847 | 0.001 | | 0.064 | |
| Q-1848 | 0.001 | | 0.21 | |
| Q-1857 | 0.001 | | 0.15 | |
| Q-1858 | 0.001 | | 0.26 | |
| Q-1859 | 0.001 | | 0.16 | |
| Q-1861 | 0.001 | | 0.098 | |
| Q-1862 | 0.002 | | 0.25 | |
| Q-1864 | 0.004 | | | |
| Q-1866 | 0.002 | | 0.08 | |
| Q-1875 | 0.001 | | 0.11 | |
| Q-1876 | 0.001 | | 0.11 | |
| Q-1882 | 0.002 | | 0.092 | |
| Q-1884 | 0.001 | | 0.084 | |
| Q-1885 | 0.01 | | | |
| Q-1886 | 0.002 | | 0.11 | |
| Q-1889 | 0.001 | | 0.036 | |
| Q-1925 | 0.001 | | 0.17 | |

TABLE 24-continued

| Compound | hTR-FRET IC50 (μM) | SK-N-BE(2) IC50 (μM) | hPBMC IC50 (μM) | TR FRET Kd (nM) |
|---|---|---|---|---|
| Q-1932 | 0.003 | | 2.7 | |
| Q-1984 | 0.001 | | | |
| Q-1985 | 0.002 | | | |
| Q-2007 | 0.001 | | | |
| Q-2008 | 0.002 | | 0.30 | |
| Q-2009 | 0.002 | | 0.37 | |
| Q-2016 | 0.001 | | 0.045 | |
| Q-2017 | 0.002 | | 0.17 | |
| Q-2031 | 0.003 | | | |
| Q-2032 | 0.006 | | | |
| Q-2041 | 0.003 | | | |
| Q-2043 | 0.005 | | | |
| Q-2048 | 0.004 | | | |
| Q-2054 | 0.004 | | | |
| Q-2055 | 0.007 | | | |

Example 955—Behavioral Pharmacology Models

Compounds were tested in standard behavioral pharmacology models for pain in rats as described in the literature (see, e.g., Latremoliere et al., Neuron, 86:1393-1406 (2015); Tegeder et al., Nature Medicine, 12:1269-1277 (2006)). Compounds were administered by oral gavage to rats that had undergone one of two nerve injury surgeries: spared nerve injury to injure two of the three peripheral branches of the sciatic nerve (SNI, Decosterd et al., Pain, 87:149-158 (2000)) or chronic constriction injury of the sciatic nerve (CCI, Bennett et al., Pain, 33:87-107 (1988)). Paw withdrawal thresholds to mechanical stimulation using calibrated von Frey filaments were used as measurement of neuropathic pain-like behaviors. Effect on pain behavior in these models is provided in Table 25.

TABLE 25

| Compound | Model | Dose (mpk) | Dosing Schedule | Behavior Endpoint | Behavior Time Point | Behavior Significant effect |
|---|---|---|---|---|---|---|
| Q-1127 | SNI | 20 | QD 3 days | mechanical | 4 hrs | yes |
| Q-1133 | CCI | 10 | QD 3 days | mechanical | 4 hrs | yes |
| Q-1169 | CCI | 9.5 | QD 3 days | mechanical | 4 hrs | yes |
| Q-1195 | SNI | 15 | QD 3 days | mechanical | 4 hrs | yes |
| Q-1204 | SNI | 10 | QD 3 days | mechanical | 4 hrs | yes |
| Q-1242 | SNI | 10 | QD 3 days | mechanical | 4 hrs | yes |
| Q-1245 | CCI | 9.5 | QD 3 days | mechanical | 4 hrs | yes | mpk = mg per kg
QD 3 days = daily for 3 days

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. A compound of formula V or V', or a pharmaceutically acceptable salt thereof:

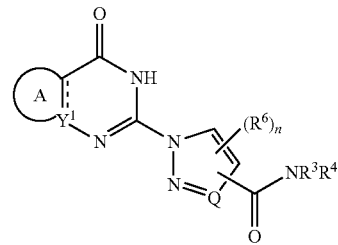

(V)

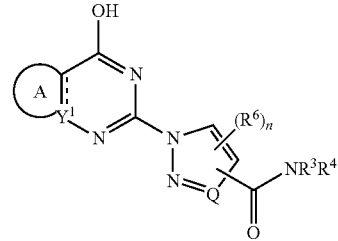

(V')

wherein:
⸺ is a single bond;
$Y^1$ is N;

is a pyrrolyl ring optionally substituted with F, Cl, or $C_{1-3}$alkyl;
n is 0 or 1;
each $R^6$ is selected from the group consisting of $C_{1-5}$alkyl, $C_{3-5}$cycloalkyl, $C_{1-5}$haloalkyl, halo, and benzyl;
Q is CH, $CR^6$, or N;
$R^3$ and $R^4$, taken together with the nitrogen atom to which they are attached form a 3-, 4-, 5-, 6-, or 7-membered monocyclic ring having 1 or 2 heteroatom ring atoms, or 6-, 7-, 8-, 9-, 10-, 11-, 12-, 13-, or 14-membered spiro, fused, and/or bridged polycyclic ring having 1 or 2 heteroatom ring atoms, and the heteroatom ring atoms are selected from nitrogen, oxygen, and sulfur.

2. The compound of claim 1, wherein

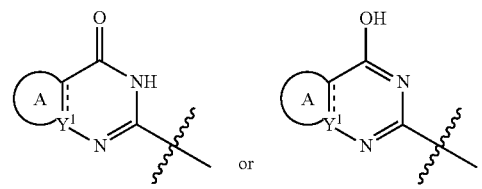

is selected from the group consisting of:

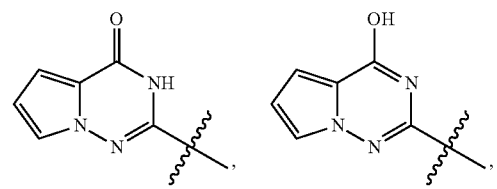

-continued
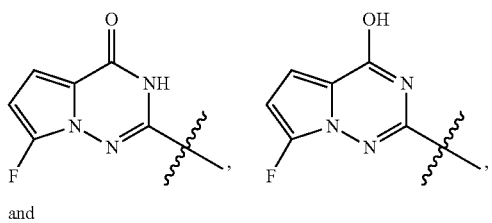
and
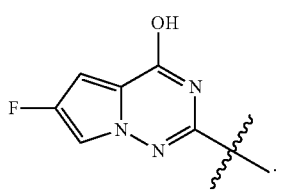
3. The compound of claim 1, wherein
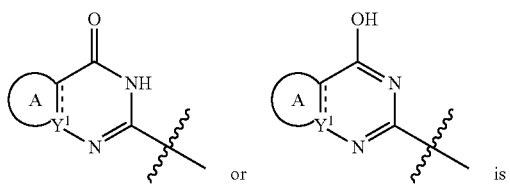
or
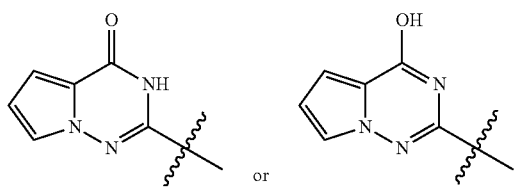
and is optionally substituted with one to four substituents selected from the group consisting of F, Cl, and $C_{1-3}$alkyl.
4. The compound of claim 1, wherein
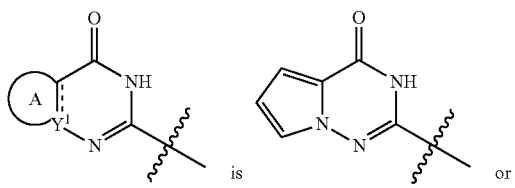
is
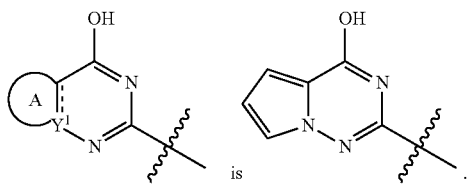
5. The compound of claim 3, wherein
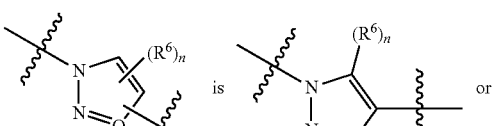
is
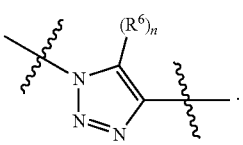
or
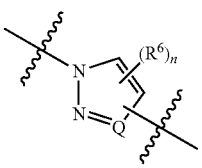
6. The compound of claim 1, wherein
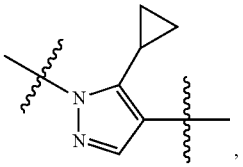
is selected from the group consisting of
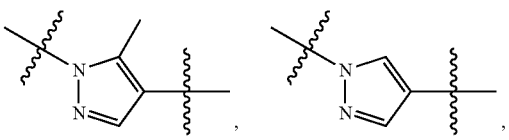
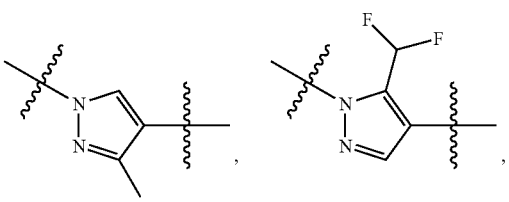
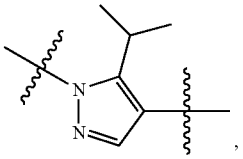
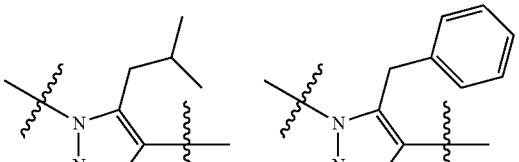

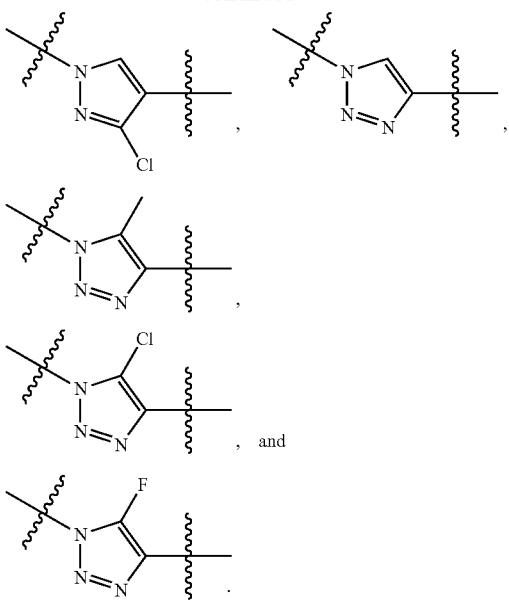

7. The compound of claim 6, wherein

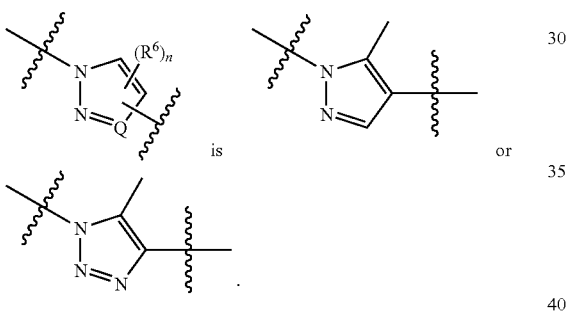

is

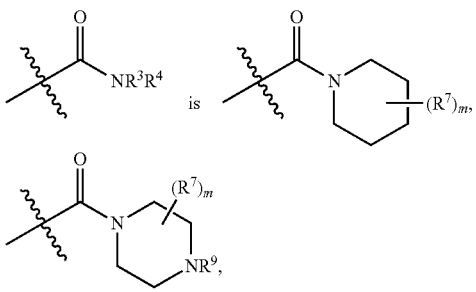

8. The compound of claim 1, wherein $R^3$ and $R^4$, taken together with nitrogen atom to which they are attached form a 3-, 4-, 5-, 6-, or 7-membered ring having 1 or 2 heteroatom ring atoms selected from nitrogen, oxygen, and sulfur.

9. The compound of claim 8, wherein the 3-, 4-, 5-, 6-, or 7-membered ring is piperidinyl, pyrrolidinyl, azetidinyl, piperazinyl, morpholinyl, thiomorpholinyl, aziridinyl, oxaziridinyl, imidazolidinyl, pyrazolidinyl, oxazolidinyl, isoxazolidinyl, thiazolidinyl, isothiazolidinyl, azepanyl, diazepanyl, or diazabicycloheptane.

10. The compound of claim 1, wherein

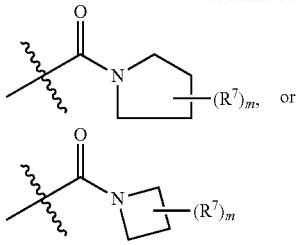

$m$ is 0, 1, 2, or 3;

$R^7$ and $R^9$ are each independently selected from the group consisting of halo, $C_{1-5}$ alkyl, $C_{3-5}$cycloalkyl, heterocycloalkyl, $C_{1-5}$haloalkyl, $C_{1-5}$haloalkylene-OH, $C_{1-5}$alkylene-CN, $C_{1-5}$alkoxy, $C_{1-5}$haloalkoxy, aryloxy, heteroaryloxy, CN, OH, —NHR$^8$, —NR$^8$CO$_2$R$^{8a}$, —SO$_2$R$^8$, —CO$_2$R$^8$, —CONHR$^8$, aryl, and heteroaryl, or two $R^7$ groups, together with the carbon atom(s) to which they are attached, form a 3-, 4-, 5-, 6-, 7-, or 8-membered cycloalkyl, a 3-, 4-, 5-, 6-, 7-, or 8-membered heterocyclic ring, aryl, or a 5- or 6-membered heteroaryl ring; and $R^8$ and $R^{8a}$ are each independently selected from the group consisting of H, $C_{1-5}$alkyl, —$C_{0-5}$alkylene-aryl, and —$C_{0-5}$alkylene-heteroaryl; or one $R^7$ group and $R^9$, together with the atoms to which they are attached, form a 5- or 6-membered heterocyclic ring or 5- or 6-membered heteroaryl ring, and wherein the heterocyclic ring and heteroaryl ring have 1 or 2 heteroatom ring atoms selected from nitrogen, oxygen, and sulfur.

11. The compound of claim 1, wherein

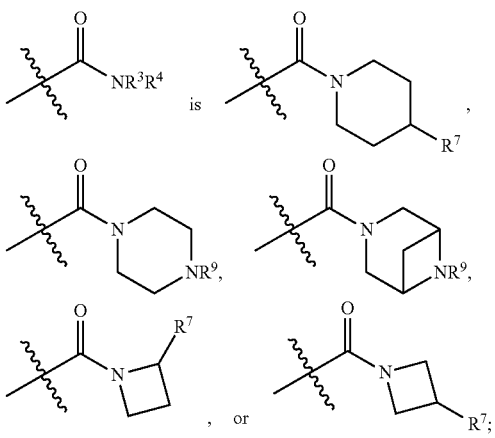

$R^7$ and $R^9$ are each independently selected from the group consisting of halo, $C_{1-5}$alkyl, $C_{3-5}$cycloalkyl, heterocyclic ring, $C_{1-5}$haloalkyl, $C_{1-5}$haloalkylene-OH, $C_{1-5}$alkylene-CN, $C_{1-5}$alkoxy, $C_{1-5}$haloalkoxy, aryloxy, heteroaryloxy, CN, OH, —NHR$^8$, —NR$^8$CO$_2$R$^{8a}$, —SO$_2$R$^8$, —CO$_2$R$^8$, —CONHR$^8$, aryl, and heteroaryl; and $R^8$ and $R^{8a}$ are each independently selected from the group consisting of H, $C_{1-5}$alkyl, —$C_{0-5}$alkylene-aryl, and —$C_{0-5}$alkylene-heteroaryl, and wherein the heterocyclic ring or heteroaryl is a 5- or 6-membered ring having 1 or 2 heteroatom ring atoms selected from nitrogen, oxygen, and sulfur.

12. The compound of claim 11, wherein R⁷ or R⁹ is selected from the group consisting of $C_{3-5}$cycloalkyl, heterocycloalkyl, aryloxy, heteroaryloxy, aryl, and heteroaryl.

13. The compound of claim 12, wherein R⁷ is oxazolyl or pyridinyl, each of which is optionally substituted with CN or F.

14. The compound of claim 13, wherein R⁷ is selected from the group consisting of

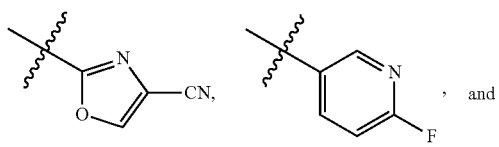

and

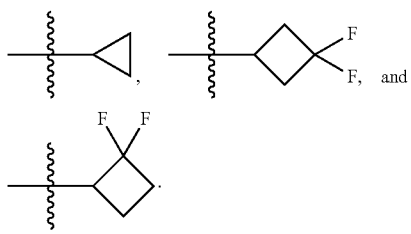

15. The compound of claim 12, wherein R⁹ is $C_{3-5}$cycloalkyl.

16. The compound of claim 15, wherein R⁹ is cyclopropyl or cyclobutyl, each of which is optionally substituted with 1, 2, 3, or 4 F atoms.

17. The compound of claim 16, wherein R⁹ is selected from the group consisting of

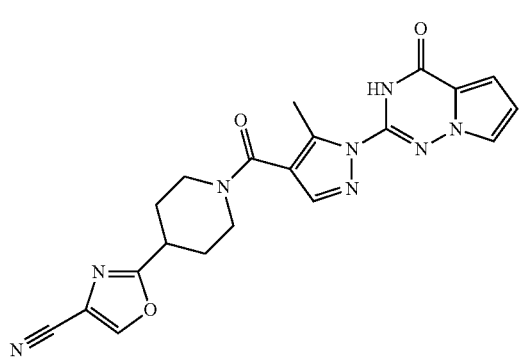

18. The compound of claim 1, wherein the compound is

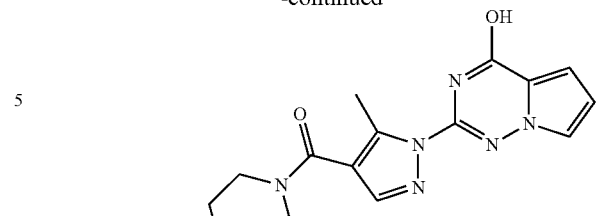

or

-continued

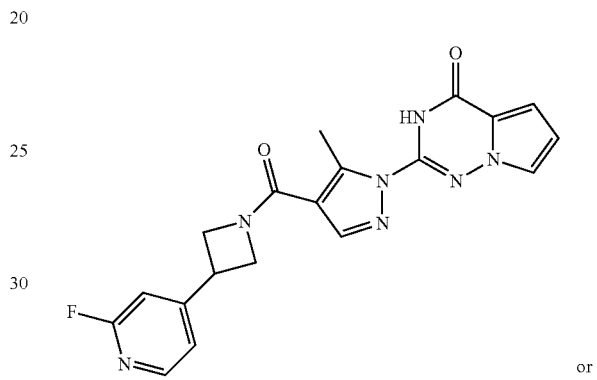

or a pharmaceutically acceptable salt thereof.

19. The compound of claim 1, wherein the compound is

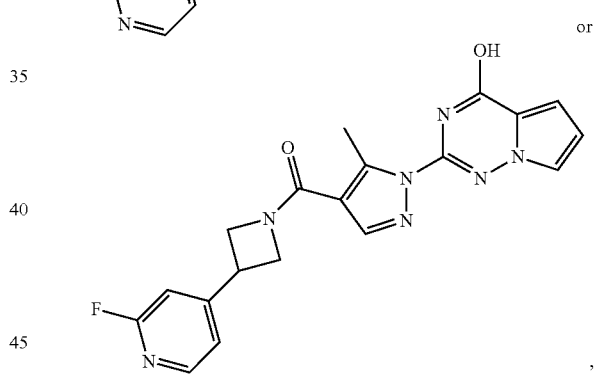

or a pharmaceutically acceptable salt thereof.

20. The compound of claim 1, wherein the compound is

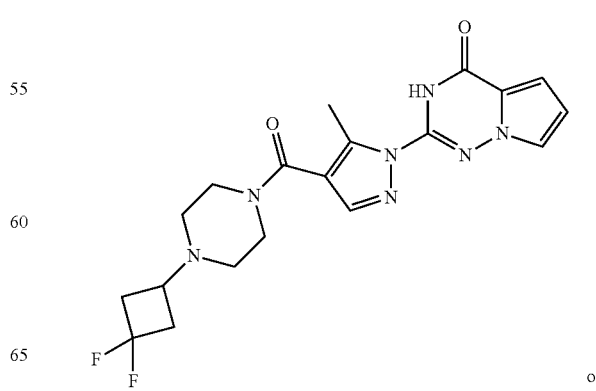

or

831
-continued

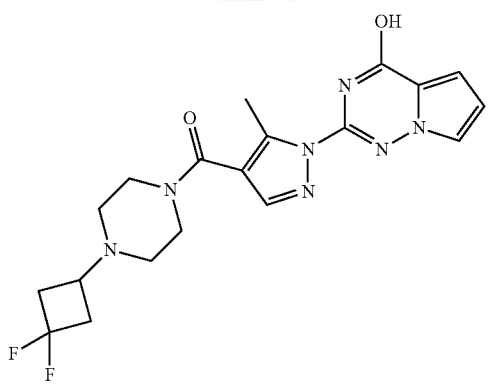

or a pharmaceutically acceptable salt thereof.

21. The compound of claim 1, wherein the compound is

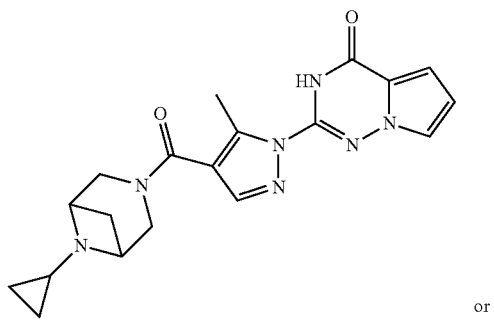

or

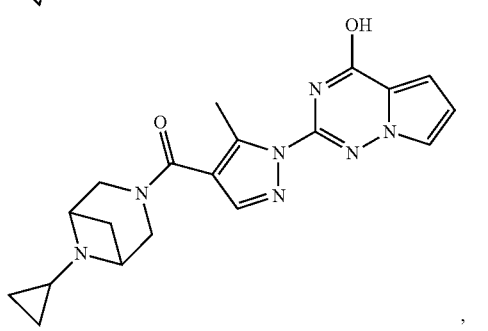

or a pharmaceutically acceptable salt thereof.

22. The compound of claim 1, wherein the compound is

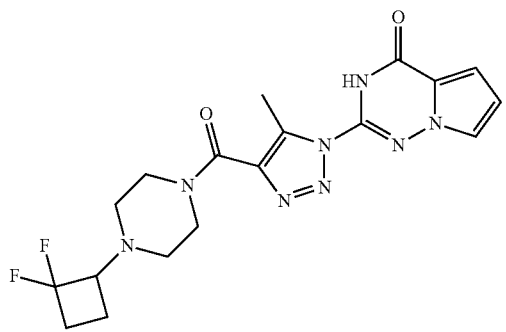

or

832
-continued or a pharmaceutically acceptable salt thereof.

23. The compound of claim 1, wherein the compound is or or a pharmaceutically acceptable salt thereof.

24. The compound of claim 1, wherein the compound is

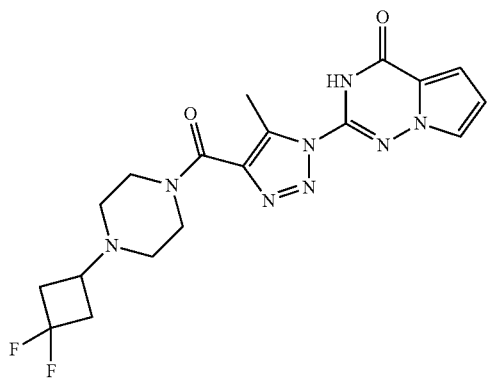

or

-continued

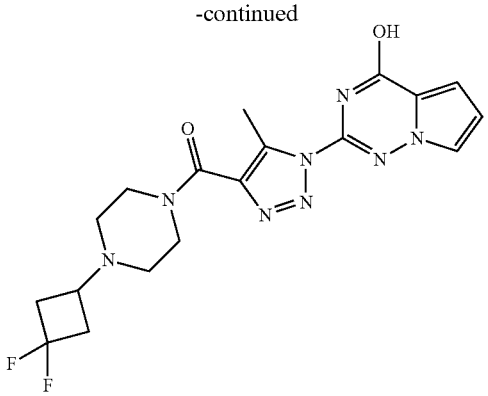

, or a pharmaceutically acceptable salt thereof.

25. A method of treating a subject suffering from pain, comprising administering to the subject a therapeutically effective amount of the compound of claim 1.

26. The compound of claim 3, wherein

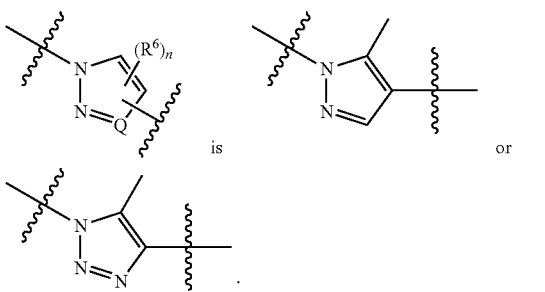

.

27. The compound of claim 7, wherein

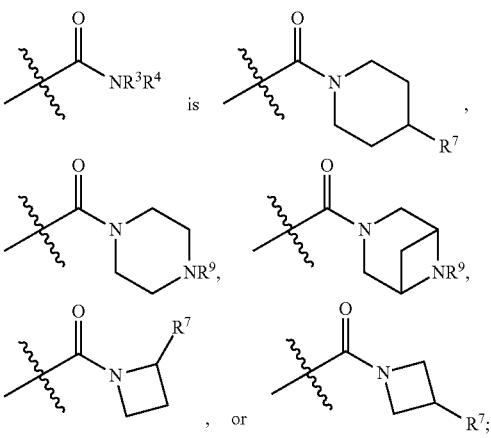

$R^7$ and $R^9$ are each independently selected from the group consisting of halo, $C_{1-5}$ alkyl, $C_{3-5}$cycloalkyl, heterocyclyl ring, $C_{1-5}$haloalkyl, $C_{1-5}$haloalkylene-OH, $C_{1-5}$alkylene-CN, $C_{1-5}$alkoxy, $C_{1-5}$haloalkoxy, aryloxy, heteroaryloxy, CN, OH, —$NHR^8$, —$NR^6CO_2R^{8a}$, —$SO_2R^8$, —$CO_2R^8$, —$CONHR^8$, aryl, and heteroaryl; and $R^8$ and $R^{8a}$ are each independently selected from the group consisting of H, $C_{1-5}$alkyl, —$C_{1-5}$alkylene-aryl, and —$C_{1-5}$alkylene-heteroaryl, and wherein the heterocyclic ring or heteroaryl is a 5- or 6-membered ring having 1 or 2 heteroatom ring atoms selected from nitrogen, oxygen, and sulfur.

* * * * *